United States Patent
Schulze et al.

(10) Patent No.: US 12,227,501 B2
(45) Date of Patent: Feb. 18, 2025

(54) 3-AMINO-2-[2-(ACYLAMINO)PYRIDIN-4-YL]-1,5,6,7-TETRAHYDRO-4H-PYRROLO[3,2-C]PYRIDIN-4-ONE AS CSNK1 INHIBITORS

(71) Applicants: Bayer Aktiengesellschaft, Leverkusen (DE); Dana-Farber Cancer Institute, Inc., Boston, MA (US); The Broad Institute, Inc., Cambridge, MA (US)

(72) Inventors: Volker Schulze, Hohen Neuendorf (DE); Anne Mengel, Berlin (DE); Jens Schröder, Berlin (DE); Adelaide Clara Faria Alvares De Lemos, Berlin (DE); Wilhelm Bone, Berlin (DE); Ulf Bömer, Berlin (DE); Detlev Sülzle, Berlin (DE); Clara Christ, Berlin (DE); Roman Hillig, Berlin (DE); Christian Lechner, Berlin (DE); Steven Corsello, Boston, MA (US); Katarzyna Handing, Framingham, MA (US); Alisha Caliman, Cambridge, MA (US); Ulrike Rauh, Berlin (DE); Stefan Kaulfuss, Berlin (DE); Jérémie Xavier G. Mortier, Berlin (DE)

(73) Assignees: Bayer Aktiengesellschaft, Leverkusen (DE); Dana-Farber Cancer Institute, Inc., Boston, MA (US); The Broad Institute, Inc., Cambridge, MA (US)

(*) Notice: Subject to any disclaimer, the term of this patent is extended or adjusted under 35 U.S.C. 154(b) by 838 days.

(21) Appl. No.: 17/428,730

(22) PCT Filed: Feb. 6, 2020

(86) PCT No.: PCT/EP2020/053020
§ 371 (c)(1),
(2) Date: Aug. 5, 2021

(87) PCT Pub. No.: WO2020/161257
PCT Pub. Date: Aug. 13, 2020

(65) Prior Publication Data
US 2023/0046077 A1  Feb. 16, 2023

Related U.S. Application Data

(60) Provisional application No. 62/802,492, filed on Feb. 17, 2019.

(51) Int. Cl.
C07D 471/04 (2006.01)
A61P 35/00 (2006.01)

(52) U.S. Cl.
CPC ............ C07D 471/04 (2013.01); A61P 35/00 (2018.01)

(58) Field of Classification Search
CPC .................. C07D 471/04; A61P 35/00

USPC ....................................................... 514/278
See application file for complete search history.

(56) References Cited

U.S. PATENT DOCUMENTS

| | | | |
|---|---|---|---|
| 2016/0176871 A1 | 6/2016 | Fink et al. | |
| 2023/0322767 A1 | 10/2023 | Schulze et al. | |
| 2023/0339939 A1 | 10/2023 | Schulze et al. | |
| 2023/0365554 A1 | 11/2023 | Schulze et al. | |
| 2023/0391769 A1 | 12/2023 | Schulze et al. | |

FOREIGN PATENT DOCUMENTS

| | | |
|---|---|---|
| WO | WO-99/20624 A1 | 4/1999 |
| WO | WO-2005/013986 A1 | 2/2005 |
| WO | WO-2007/067506 A2 | 6/2007 |
| WO | WO-2008/132434 A2 | 11/2008 |
| WO | WO-2010/046215 A2 | 4/2010 |
| WO | WO-2010/070237 A1 | 6/2010 |
| WO | WO-2010/070238 A1 | 6/2010 |
| WO | WO-2011/053476 A1 | 5/2011 |
| WO | WO-2015/073763 A1 | 5/2015 |
| WO | WO-2015/195880 A1 | 12/2015 |
| WO | WO-2016/100166 A1 | 6/2016 |
| WO | WO-2016/120196 A1 | 8/2016 |
| WO | WO-2017/079558 A1 | 5/2017 |
| WO | WO-2020/161257 A1 | 8/2020 |

(Continued)

OTHER PUBLICATIONS

Cancer [online], [retrieved on Jul. 6, 2007] Retrieved from the Internet, URL: http://www.nlm.nih.gov/medlineplus/cancer.html (Year: 2007).*

(Continued)

*Primary Examiner* — Kristin A Vajda
(74) *Attorney, Agent, or Firm* — Foley Hoag LLP; David P. J. Halstead D.

(57) ABSTRACT

The present invention relates to compounds of formula (I)

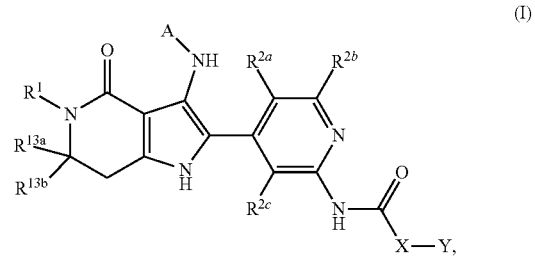

processes for their production and their use as pharmaceuticals. The compounds are inhibitors of Casein kinase 1 alpha and/or delta (CSNK1α and/or β) useful for the treatment of proliferative disorders.

15 Claims, 1 Drawing Sheet

(56) References Cited

FOREIGN PATENT DOCUMENTS

| WO | WO-2022/023337 A1 | 2/2022 |
| WO | WO-2022/023339 A1 | 2/2022 |
| WO | WO-2022/023340 A1 | 2/2022 |
| WO | WO-2022/023341 A1 | 2/2022 |
| WO | WO-2023/147015 A1 | 8/2023 |

OTHER PUBLICATIONS

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

International Search Report For International Application No. PCT/EP2020/053020 dated May 6, 2020.

Bibian, Mathieu, et al. Development of highly selective casein kinase 1delta/1epsilon (CK1delta/epsilon) inhibitors with potent antiproliferative properties. Bioorganic & medicinal chemistry letters, 2013, 23.15: 4374-4380.

Huart, Anne-Sophie, et al. A Casein kinase 1/Checkpoint kinase 1 pyrazolo-pyridine protein kinase inhibitor as novel activator of the p53 pathway. Bioorganic & medicinal chemistry letters, 2013, 23.20: 5578-5585.

International Search Report and Written Opinion for Application No. PCT/US2023/011694 dated Apr. 27, 2023.

International Search Report and Written Opinion for International Application No. PCT/EP2021/070992 dated Nov. 3, 2021.

International Search Report and Written Opinion for International Application No. PCT/EP2021/070994 dated Oct. 27, 2021.

International Search Report and Written Opinion for International Application No. PCT/EP2021/070996 dated Nov. 19, 2021.

International Search Report and Written Opinion for International Application No. PCT/EP2021/070998 dated Oct. 20, 2021.

Jaras, Marcus, et al. Csnk1a1 inhibition has p53-dependent therapeutic efficacy in acute myeloid leukemia. Journal of Experimental Medicine, 2014, 211.4: 605-612. DOI: <10.1084/jem.20131033>. Published: Mar. 10, 2014.

Knippschild, Uwe, et al. The CK1 family: contribution to cellular stress response and its role in carcinogenesis. Frontiers in oncology, 2014, 4: 96. Published: May 19, 2014.

Shanware, Naval P., et al. Non-specific in vivo inhibition of CK1 by the pyridinyl imidazole p38 inhibitors SB 203580 and SB 202190. BMB reports, 2009, 42.3: 142. doi: 10.5483/bmbrep.2009.42.3.142. Published: Mar. 31, 2009.

U.S. Appl. No. 18/018,148, Published.
U.S. Appl. No. 18/018,207, Published.
U.S. Appl. No. 18/018,216, Published.
U.S. Appl. No. 18/018,221, Published.
U.S. Appl. No. 18/833,767, Pending.

* cited by examiner

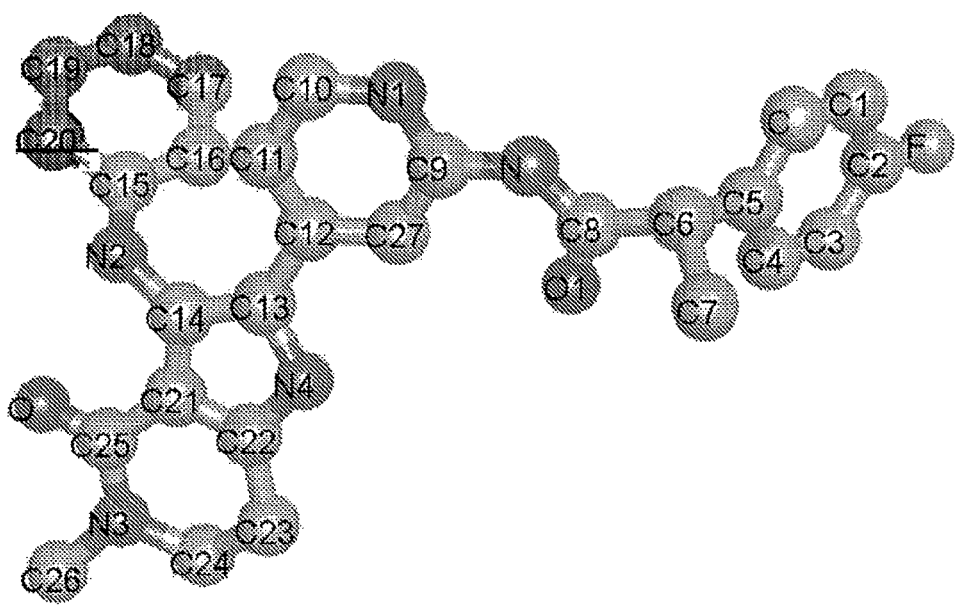

3-AMINO-2-[2-(ACYLAMINO)PYRIDIN-4-YL]-1,5,6,7-TETRAHYDRO-4H-PYRROLO[3,2-C] PYRIDIN-4-ONE AS CSNK1 INHIBITORS

RELATED APPLICATIONS

This application is the U.S. national phase of International Application No. PCT/EP2020/053020, filed Feb. 6, 2020, which claims the benefit of priority to U.S. Provisional Patent Application No. 62/802,492, filed Feb. 7, 2019, both of which are herein incorporated by reference in their entireties.

INTRODUCTION

The invention relates to substituted 3-amino-2-[2-(acylamino)pyridin-4-yl]-1,5,6,7-tetrahydro-4H-pyrrolo[3,2-c]pyridin-4-one compounds, a process for their production and uses thereof.

BACKGROUND OF THE INVENTION

One of the most fundamental characteristics of cancer cells is their ability to sustain chronic proliferation whereas in normal tissues the entry into and progression through the cell division cycle is tightly controlled to ensure a homeostasis of cell number and maintenance of normal tissue function. Loss of proliferation control was emphasized as one of the six hallmarks of cancer [Hanahan D and Weinberg R A, Cell 100, 57, 2000; Hanahan D and Weinberg R A, Cell 144, 646, 2011].

The members of the casein kinase 1 (CSNK1) family are highly conserved and are expressed in many eukaryotes ranging from yeast to humans. Mammalian CSNK1 isoforms (α, β, γ, δ, ε) and their splice variants are involved in diverse cellular processes including membrane trafficking, circadian rhythm, cell cycle progression, chromosome segregation, apoptosis and cellular differentiation. Mutations and deregulation of CSNK1 expression and activity has been linked to proliferative diseases such as cancer (Knippschild, Onkologie 2005; 28:508-514).

CSNK1 substrates are enzymes, transcription factors, splice factors, cytoskeleton proteins, receptors, membrane-associated proteins and cell signaling proteins. Since recognition motifs for CSNK1 are found on most cellular proteins, more than 140 in vitro and in vivo substrates have been reported thus far (Knippschild et al., Front Oncol. 2014 May 19; 4:96). Several known substrates especially of the CSNK1α and δ isoforms are involved in oncogenic signaling pathways as Wnt/β-catenin (β-catenin; dishevelled (DVL); adenomatous polyposis coli (APC); nuclear factor of activated Tcells, cytoplasmic 3 (NFATC3)), p53 (p53; p53/E3 ubiquitin-protein ligase Mdm2 (MDM2)), PI3K/AKT (forkhead box protein O1 (Foxo1)), and death receptor signaling (Fas-associated death domain protein (FADD); BH3-interactive domain death agonist (BID)) (Schittek and Sinnberg Molecular Cancer 2014, 13:231). A distinctive feature of CSNK1 family members is their exclusive need of ATP to phosphorylate their substrates and their independency of other co-factors.

CSNK1α plays a role in the mitotic spindle formation during cell division and in DNA repair mechanisms, and participates in RNA metabolism. Antibodies specific for CSNK1α block cell cycle progression during M phase in mouse oocytes, which indicates that CSNK1α is required for proper cell cycle progression in these cells. CSNK1α can be found at the centrosomes, microtubule asters and the kinetochore. Similarly, CSNK1α regulates apoptotic signaling pathways, however, there seems to be cell type-specific differences. CSNK1α has been shown to have an anti-apoptotic function in the extrinsic apoptosis pathway. Its inhibition increased Fas-induced apoptosis in Hela cells, whereas the overexpression of CSNK1α delayed cell death, caused by the phosphorylation of BID, which prevented the caspase 8 dependent cleavage of BID. In addition, CSNK1α inhibits TRAIL induced apoptosis by modification of the TNF receptor or FADD at the death-inducing signaling complex (DISC). Therefore downregulation of CSNK1α leads to an enhancement of TRAIL-induced cell death. Likewise, CSNK1α promotes cell survival by interacting with the retinoid X receptor (RXR). Downregulation of CSNK1α enhances the apoptotic effect of RXR agonists (Schittek and Sinnberg, Molecular Cancer 2014, 13:231).

Knockdown or downregulation of CSNK1α in the intestinal epithelium of mice, in human colon cancers or in leukemia cells triggers p53 activation. Similarly, one study showed that CSNK1α stably associates with MDM2, stimulates MDM2-p53 binding, and cooperates with MDM2 to inactivate p53. These data suggest that inhibition of CSNK1α activity increases p53 activity. The knockdown of CSNK1α induces p53 transcriptional activity by reducing the inhibitory effect of MDM2 for p53 since MDM2 phosphorylation is necessary for interaction with p53 (Schittek and Sinnberg, Molecular Cancer 2014, 13:231).

Ribosomal protein S6 (RPS6) is a critical component of the 40S ribosomal subunit that mediates translation initiation. RPS6 activity is regulated by phosphorylation by CSNK1α, which phosphorylates serine residue 247, enhancing the phosphorylation of upstream sites (Hutchinson et al., JBC, 2011, 286, 10, 8688). CSNK1α inhibition leads to dramatic reduction in RPS6 phosphorylation and activation of p53, resulting in selective elimination of solid tumor and AML cells. Pharmacological inhibition of CSNK1α in p53 wt colon and lung carcinoma as well as in AML induces p53 accumulation along with apoptosis. Targeting of CSNK1α provides a potential approach to the therapeutic activation of p53 in AML, a disorder predominantly associated with non-mutated p53 (Jaras et al., J. Exp. Med. 2014, 211, 4, 605). CSNK1α is an essential participant in the aberrant NF-kB activity required for ABC DLBCL subtype survival. CSNK1α knockdown is specifically lethal to ABC DLBCL cells (Bidere, Nature, 458, 5 Mar. 2009). Pharmacological inhibition of CSNK1α will specifically kill ABC-DLBCL due to the blocking of the CARD11-Bcl-10-MALT1 complex (CBM complex).

Thus, pharmacological inhibition of CSNK1α represents a new approach for the treatment of proliferative disorders, including solid tumors such as carcinomas, sarcomas, leukaemias and lymphoid malignancies or other disorders, associated with uncontrolled cellular proliferation.

Due to the fact that especially cancer disease as being expressed by uncontrolled proliferative cellular processes in tissues of different organs of the human- or animal body is still not considered to be a controlled disease in that sufficient drug therapies do not already exist, there is a strong need to provide further new therapeutically useful drugs, preferably those inhibiting new targets and providing new therapeutic options.

Therefore, inhibitors of Casein kinase 1 alpha and/or delta represent valuable compounds that in some instances, can complement therapeutic options either as single agents or in combination with other drugs.

WO 2016/120196 discloses 4H-pyrrolo[3,2-c]pyridin-4-one derivatives, which may be useful as Bub1 kinase inhibitors.

SUMMARY OF THE INVENTION

The invention provides compounds that inhibit Casein kinase 1 alpha and/or Casein kinase 1 delta.

It has now been found that compounds of the present invention have surprising and advantageous properties.

In particular, compounds of the present invention have surprisingly been found to effectively inhibit CSNK1A1. In certain embodiments, compounds of the present invention display an $IC_{50}$ of below 100 nM in a CSNK1A1 kinase assay in the presence of 1 μM ATP. Furthermore, in certain embodiments, compounds of the present invention additionally show low inhibition of wild type-EGFR kinase. In certain embodiments, compounds of the present invention are less potent than 600 nM in a wild type-EGFR kinase assay in the presence of 2 mM ATP. In certain embodiments, compounds of the present invention display an $IC_{50}$ below 100 nM in a CSNK1A1 kinase assay in the presence of 1 mM ATP and are less potent than 100 nM in a wild type-EGFR kinase assay in the presence of 2 mM ATP.

In general, reduced or no inhibition of other kinases and specifically reduced or no inhibition of wild type EGFR kinase, in particular in a high ATP assay (e.g. with a concentration of 2 mM ATP), is considered to be relevant in the clinical setting to avoid/reduce unwanted side effects associated with the inhibition of said wild type EGFR kinase, such as, for example, skin rash and GI toxicity.

BRIEF DESCRIPTION OF THE FIGURE

FIG. 1 shows an electron density map of the compound of Example 5. For clarity only the ligand atoms are shown. Carbon atom C6 unambiguously features the (S)-configuration.

DESCRIPTION OF THE INVENTION

In accordance with a first aspect, the invention relates to compounds of formula (I),

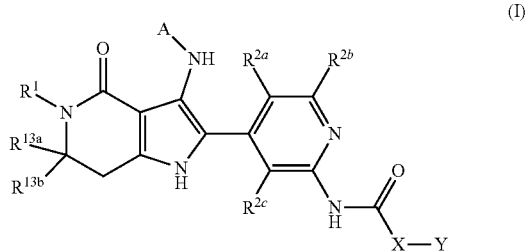

in which:
- $R^1$ represents hydrogen or a group selected from $C_1$-$C_4$-alkyl, $C_3$-$C_6$-cycloalkyl, $C_3$-$C_6$-cycloalkyl-$C_1$-$C_4$-alkyl-, $C_1$-$C_3$-alkoxy-$C_1$-$C_3$-alkyl-, and $C_1$-$C_5$-hydroxyalkyl, wherein said groups are each independently optionally substituted, one or more times, with halogen;
- $R^{2a}$ represents hydrogen, hydroxy, halogen, cyano, —$NH_2$, —NHMe, —$NMe_2$, $C_1$-$C_2$-alkoxy, $C_1$-$C_2$-haloalkyl, or $C_1$-$C_2$-haloalkoxy;
- $R^{2b}$ represents hydrogen, hydroxy, halogen, cyano, —$NH_2$, —$NHR^9$, or —$NMe_2$;
- $R^{2c}$ represents hydrogen, halogen, cyano, —$NMe_2$, $C_1$-$C_2$-alkoxy, or $C_1$-$C_2$-haloalkoxy;
- X represents methylene or ethylene,
  - wherein said methylene and ethylene group are each independently optionally substituted, one or more times, with $R^3$;
- Y represents phenyl or a heteroaryl group,
  - wherein said phenyl and heteroaryl group are each independently optionally substituted, one or more times, with $R^4$;
- $R^3$ represents hydroxy, halogen, cyano, $C_1$-$C_3$-alkyl, $C_1$-$C_3$-alkoxy, $C_1$-$C_3$-haloalkyl, $C_1$-$C_2$-haloalkoxy, $C_3$-$C_4$-cycloalkyl, —$NHR^6$, $R^5O$—$C_1$-$C_3$-alkyl, $R^6R^7N$—$C_1$-$C_5$-alkyl, or $R^6R^7N$—X'—$C(R^{10})(R^{11})$—$C_1$-$C_2$-alkyl-;
- X' represents methylene or ethylene;
- $R^4$ represents hydroxy, halogen, cyano, $C_1$-$C_4$-alkyl, $C_1$-$C_4$-alkoxy, $C_1$-$C_4$-haloalkyl, $C_1$-$C_4$-haloalkoxy, —$NMe_2$, —$CO_2R^{14}$, —$CONR^{15}R^{16}$, or —$SO_2Me$;
- $R^5$ represents hydrogen, $C_1$-$C_2$-alkyl, $C_1$-$C_2$-haloalkyl, or $C_3$-$C_4$-cycloalkyl;
- $R^6$ represents hydrogen, $C_1$-$C_2$-alkyl, $C_1$-$C_2$-haloalkyl, or $C_3$-$C_4$-cycloalkyl;
- $R^7$ represents hydrogen, $C_1$-$C_2$-alkyl, $C_1$-$C_2$-haloalkyl, $C_3$-$C_4$-cycloalkyl, or —$CO_2$—$C_1$-$C_4$-alkyl or
- $R^6$ and $R^7$, together with the nitrogen atom to which they are attached, represent a 4- to 7-membered heterocyclic ring, wherein said heterocyclic ring optionally contains one or more further heteroatoms selected from N, O, S, or groups selected from C(=O), S(=O), and $SO_2$, and is independently optionally substituted, one or more times, with halogen, $C_1$-$C_3$-alkyl, $C_3$-cycloalkyl-$C_1$-$C_2$-alkyl-, —$NH_2$, —$NHR^9$, —$NR^9R^{9a}$, or hydroxy;
- A represents a group selected from the group:

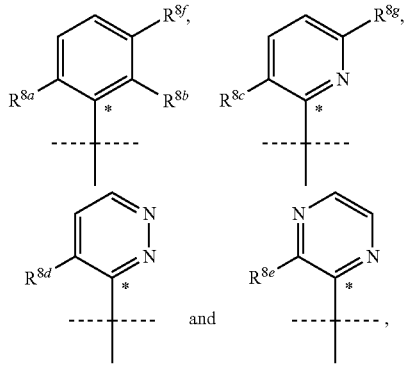

wherein * indicates the point of attachment of said group to the —NH— of formula (I);
- $R^{8a}$ represents hydrogen, hydroxy, halogen, cyano, $C_1$-$C_2$-alkyl, or $C_1$-$C_2$-haloalkyl;
- $R^{8b}$ represents hydrogen, hydroxy, halogen, cyano, $C_1$-$C_2$-alkyl, or $C_1$-$C_2$-haloalkyl;
- $R^{8c}$ represents hydrogen, hydroxy, halogen, cyano, $C_1$-$C_2$-alkyl, or $C_1$-$C_2$-haloalkyl;
- $R^{8d}$ represents hydrogen, hydroxy, halogen, cyano, $C_1$-$C_2$-alkyl, or $C_1$-$C_2$-haloalkyl;
- $R^{8e}$ represents hydrogen, hydroxy, halogen, cyano, $C_1$-$C_2$-alkyl, or $C_1$-$C_2$-haloalkyl;
- $R^{8f}$ represents hydrogen, hydroxy, halogen, cyano, $C_1$-$C_2$-alkyl, or $C_1$-$C_2$-haloalkyl;
- $R^{8g}$ represents hydrogen or halogen;
- $R^9$ represents $C_1$-$C_3$-alkyl or cyclopropyl;
- $R^{9a}$ represents $C_1$-$C_3$-alkyl or cyclopropyl;
- $R^{10}$ represents methyl, halogen, or hydroxy;

$R^{11}$ represents methyl, halogen, or hydroxy;

$R^{13a}$ represents hydrogen, or a group selected from $C_1$-$C_4$-alkyl, $C_1$-$C_4$-haloalkyl, $C_3$-$C_4$-cycloalkyl, $C_3$-$C_6$-cycloalkyl-$C_1$-$C_4$-alkyl- and $C_1$-$C_3$-alkoxy-$C_1$-$C_3$-alkyl-, wherein said groups are each independently optionally substituted, one or more times, with halogen;

$R^{13b}$ represents hydrogen, or a group selected from $C_1$-$C_4$-alkyl, $C_3$-$C_4$-cycloalkyl, $C_3$-$C_6$-cycloalkyl-$C_1$-$C_4$-alkyl- and $C_1$-$C_3$-alkoxy-$C_1$-$C_3$-alkyl-, wherein said groups are each independently optionally substituted, one or more times, with halogen, or, $R^{13a}$ and $R^{13b}$, together with the carbon atom to which they are attached, form a $C_3$-$C_5$-cycloalkyl ring or a 4- to 5-membered heterocyclic ring;

$R^{14}$ represents hydrogen, methyl or ethyl;

$R^{15}$ represents hydrogen, methyl, or ethyl;

$R^{16}$ represents hydrogen, methyl, ethyl, methoxyethyl, or dimethylaminoethyl; or $R^{15}$ and $R^{16}$, together with the nitrogen atom to which they are attached, represent a 5- to 6-membered heterocyclic ring, wherein said heterocyclic ring optionally contains one or two further heteroatoms selected from N, O, S, or groups selected from C(=O), S(=O), and $SO_2$;

or an N-oxide, a salt, a tautomer or a stereoisomer of said compound, or a salt of said N-oxide, tautomer or stereoisomer.

In accordance with an embodiment of the first aspect, the present invention relates to compounds of formula (I) supra, wherein:

$R^1$ represents hydrogen or a group selected from $C_1$-$C_4$-alkyl, $C_3$-$C_6$-cycloalkyl, $C_3$-$C_6$-cycloalkyl-$C_1$-$C_4$-alkyl-, and $C_1$-$C_5$-hydroxyalkyl, wherein said groups are each independently optionally substituted, one or more times with halogen;

$R^{2a}$ represents hydrogen or halogen;

$R^{2b}$ represents hydrogen, halogen, —$NH_2$, or —$NHR^9$;

$R^{2c}$ represents hydrogen or halogen;

X represents methylene, wherein said methylene group is independently optionally substituted, one or more times, with $R^3$;

Y represents phenyl or a pyridyl group, wherein said phenyl and heteroaryl group are each independently optionally substituted, one or more times, with $R^4$;

$R^3$ represents hydroxy, $C_1$-$C_3$-alkyl, $C_1$-$C_3$-haloalkyl, —$NHR^6$, $R^5O$—$C_1$-$C_3$-alkyl, or $R^6R^7N$—$C_1$-$C_5$-alkyl;

$R^4$ represents halogen, $C_1$-$C_4$-alkyl, $C_1$-$C_4$-haloalkyl, methoxy, —$OCF_3$, —$NMe_2$, —$CO_2R^{14}$, —$CONR^{15}R^{16}$, or —$SO_2Me$;

$R^5$ represents hydrogen, methyl, or trifluoromethyl;

$R^6$ represents hydrogen, $C_1$-$C_2$-alkyl, $C_1$-$C_2$-haloalkyl, or $C_3$-$C_4$-cycloalkyl;

$R^7$ represents hydrogen, $C_1$-$C_2$-alkyl, $C_1$-$C_2$-haloalkyl, $C_3$-$C_4$-cycloalkyl, or —$CO_2$-tert-butyl, or $R^6$ and $R^7$, together with the nitrogen atom to which they are attached, represent a 4- to 7-membered heterocyclic ring, wherein said heterocyclic ring optionally contains one or more further heteroatoms selected from N, O and S, or a group C(=O), and is independently optionally substituted, one or more times, with halogen, $C_1$-$C_3$-alkyl, $C_3$-cycloalkyl-$C_1$-$C_2$-alkyl-, —$NH_2$, —$NHR^9$, or —$NR^9R^{9a}$;

A represents a group selected from the group:

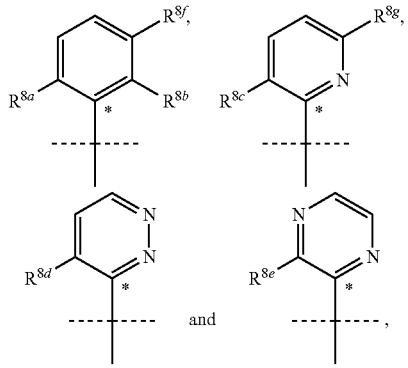

wherein * indicates the point of attachment of said group to the —NH— of formula (I);

$R^{8a}$ represents hydrogen, hydroxy, halogen, or $C_1$-$C_2$-alkyl;

$R^{8b}$ represents hydrogen, hydroxy, halogen, or $C_1$-$C_2$-alkyl;

$R^{8c}$ represents hydrogen, hydroxy, halogen, or $C_1$-$C_2$-alkyl;

$R^{8d}$ represents hydrogen, hydroxy, halogen, or $C_1$-$C_2$-alkyl;

$R^{8e}$ represents hydrogen, hydroxy, halogen, or $C_1$-$C_2$-alkyl;

$R^{8f}$ represents hydrogen, hydroxy, halogen, or $C_1$-$C_2$-alkyl;

$R^{8g}$ represents hydrogen or halogen;

$R^9$ represents $C_1$-$C_3$-alkyl or cyclopropyl;

$R^{9a}$ represents $C_1$-$C_3$-alkyl or cyclopropyl;

$R^{13a}$ represents hydrogen or $C_1$-$C_2$-alkyl, wherein said $C_1$-$C_2$-alkyl is independently optionally substituted, one or more times, with halogen;

$R^{13b}$ represents hydrogen or $C_1$-$C_2$-alkyl, wherein said $C_1$-$C_2$-alkyl is independently optionally substituted, one or more times, with halogen;

$R^{13a}$ and $R^{13b}$, together with the carbon atom to which they are attached, form a $C_3$-$C_5$-cycloalkyl ring;

$R^{14}$ represents hydrogen, methyl or ethyl;

$R^{15}$ represents hydrogen or methyl;

$R^{16}$ represents methyl, ethyl, methoxyethyl, or dimethylaminoethyl; or $R^{15}$ and $R^{16}$, together with the nitrogen atom to which they are attached, represent a 5- to 6-membered heterocyclic ring, wherein said heterocyclic ring optionally contains one or two heteroatoms selected from N, O, S;

or an N-oxide, a salt, a tautomer or a stereoisomer of said compound, or a salt of said N-oxide, tautomer or stereoisomer.

In accordance with an embodiment of the first aspect, the present invention relates to compounds of formula (I) supra, wherein:

$R^1$ represents hydrogen or a group selected from $C_1$-$C_2$-alkyl, cyclopropyl, and cyclopropylmethyl, wherein said $C_1$-$C_2$-alkyl is independently optionally substituted, one or more times, with halogen;

$R^{2a}$ represents hydrogen;

$R^{2b}$ represents hydrogen;

$R^{2c}$ represents hydrogen;

X represents methylene, wherein said methylene group is independently optionally substituted, one or two times, with $R^3$;

Y represents phenyl, wherein said phenyl is independently optionally substituted, one or two times, with $R^4$;

$R^3$ represents $C_1$-$C_3$-alkyl, $C_1$-$C_3$-haloalkyl, $R^5O$—$C_1$-$C_3$-alkyl, or $R^6R^7N$—$C_1$-$C_3$-alkyl;

$R^4$ represents halogen, $C_1$-$C_4$-alkyl, $C_1$-$C_4$-haloalkyl, —$NMe_2$, —$CO_2R^{14}$, —$CONR^{15}R^{16}$, or —$SO_2Me$;

$R^5$ represents hydrogen;

$R^6$ represents hydrogen or $C_1$-$C_2$-alkyl;

$R^7$ represents hydrogen, $C_1$-$C_2$-alkyl, or —$CO_2$-tert-butyl, or $R^6$ and $R^7$, together with the nitrogen atom to which they are attached, represent a 4- to 6-membered heterocyclic ring, wherein said heterocyclic ring optionally contains further heteroatoms selected from N, O and S, and is independently optionally substituted, one or more times, with halogen, $C_1$-$C_3$-alkyl, —$NH_2$, —$NHR^9$, or —$NR^9R^{9a}$;

A represents a group selected from the group:

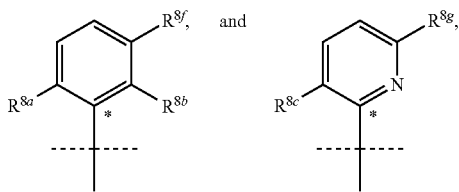

wherein * indicates the point of attachment of said group to the —NH— of formula (I);

$R^{8a}$ represents hydrogen, hydroxy, halogen, or $C_1$-$C_2$-alkyl;

$R^{8b}$ represents hydrogen, hydroxy, halogen, or $C_1$-$C_2$-alkyl;

$R^{8c}$ represents hydrogen, hydroxy, halogen, or $C_1$-$C_2$-alkyl;

$R^{8f}$ represents hydrogen or halogen;

$R^{8g}$ represents hydrogen or halogen;

$R^9$ represents $C_1$-$C_3$-alkyl;

$R^{9a}$ represents $C_1$-$C_3$-alkyl;

$R^{13a}$ represents hydrogen or methyl, wherein said methyl is independently optionally substituted, one or more times, with halogen;

$R^{13b}$ represents hydrogen or methyl, wherein said methyl is independently optionally substituted, one or more times, with halogen, or $R^{13a}$ and $R^{13b}$, together with the carbon atom to which they are attached, form a $C_3$-$C_4$-cycloalkyl ring;

$R^{14}$ represents methyl;

$R^{15}$ represents hydrogen;

$R^{16}$ represents methoxyethyl or dimethylaminoethyl; or $R^{15}$ and $R^{16}$, together with the nitrogen atom to which they are attached, represent a 6-membered heterocyclic ring, wherein said heterocyclic ring optionally contains one or two heteroatoms selected from N, O;

or an N-oxide, a salt, a tautomer or a stereoisomer of said compound, or a salt of said N-oxide, tautomer or stereoisomer.

In accordance with an embodiment of the first aspect, the present invention relates to compounds of formula (I) supra, wherein:

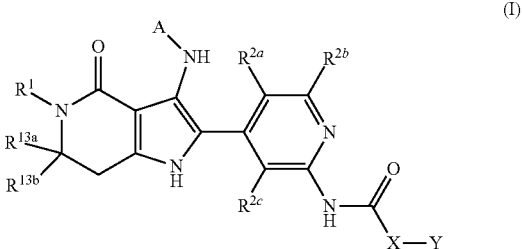

in which:

$R^1$ represents hydrogen or a group selected from $C_1$-$C_4$-alkyl, $C_3$-$C_6$-cycloalkyl, $C_3$-$C_6$-cycloalkyl-$C_1$-$C_4$-alkyl-, $C_1$-$C_3$-alkoxy-$C_1$-$C_3$-alkyl-, and $C_1$-$C_5$-hydroxyalkyl, wherein said groups are each independently optionally substituted, one or more times, with halogen;

$R^{2a}$ represents hydrogen, hydroxy, halogen, cyano, —$NH_2$, —$NHMe$, —$NMe_2$, $C_1$-$C_2$-alkoxy, $C_1$-$C_2$-haloalkyl, or $C_1$-$C_2$-haloalkoxy;

$R^{2b}$ represents hydrogen, hydroxy, halogen, cyano, —$NH_2$, —$NHR^9$, or —$NMe_2$;

$R^{2c}$ represents hydrogen, halogen, cyano, —$NMe_2$, $C_1$-$C_2$-alkoxy, or $C_1$-$C_2$-haloalkoxy;

X represents methylene or ethylene, wherein said methylene and ethylene group are each independently optionally substituted, one or more times, with $R^3$;

Y represents phenyl or a heteroaryl group, wherein said phenyl and heteroaryl group are each independently optionally substituted, one or more times, with $R^4$;

$R^3$ represents hydroxy, halogen, cyano, $C_1$-$C_3$-alkyl, $C_1$-$C_3$-alkoxy, $C_1$-$C_3$-haloalkyl, $C_1$-$C_2$-haloalkoxy, $C_3$-$C_4$-cycloalkyl, —$NHR^6$, $R^5O$—$C_1$-$C_3$-alkyl, $R^6R^7N$—$C_1$-$C_5$-alkyl, or $R^6R^7N$—$X'$—$C(R^{10})(R^{11})$—$C_1$-$C_2$-alkyl-;

X' represents methylene or ethylene;

$R^4$ represents hydroxy, halogen, cyano, $C_1$-$C_4$-alkyl, $C_1$-$C_4$-alkoxy, $C_1$-$C_4$-haloalkyl, or $C_1$-$C_4$-haloalkoxy;

$R^5$ represents hydrogen, $C_1$-$C_2$-alkyl, $C_1$-$C_2$-haloalkyl, or $C_3$-$C_4$-cycloalkyl;

$R^6$ and $R^7$ each independently represent hydrogen, $C_1$-$C_2$-alkyl, $C_1$-$C_2$-haloalkyl, or $C_3$-$C_4$-cycloalkyl, or $R^6$ and $R^7$, together with the nitrogen atom to which they are attached, represent a 4- to 7-membered heterocyclic ring, wherein said heterocyclic ring optionally contains one or more further heteroatoms selected from N, O, S, or groups selected from C(=O), S(=O), and $SO_2$, and is independently optionally substituted, one or more times, with halogen, $C_1$-$C_3$-alkyl, $C_3$-cycloalkyl-$C_1$-$C_2$-alkyl-, —$NH_2$, —$NHR^9$, —$NR^9R^{9a}$, or hydroxy;

A represents a group selected from:

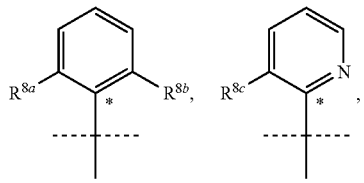

-continued

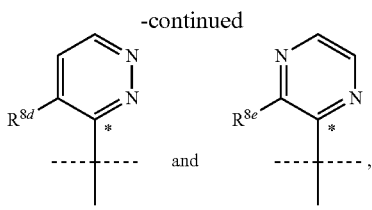

wherein * indicates the point of attachment of said group to the —NH— of formula (I);
$R^{8a}$ represents hydrogen, hydroxy, halogen, cyano, $C_1$-$C_2$-alkyl, or $C_1$-$C_2$-haloalkyl;
$R^{8b}$ represents hydrogen, hydroxy, halogen, cyano, $C_1$-$C_2$-alkyl, or $C_1$-$C_2$-haloalkyl;
$R^{8c}$ represents hydrogen, hydroxy, halogen, cyano, $C_1$-$C_2$-alkyl, or $C_1$-$C_2$-haloalkyl;
$R^{8d}$ represents hydrogen, hydroxy, halogen, cyano, $C_1$-$C_2$-alkyl, or $C_1$-$C_2$-haloalkyl;
$R^{8e}$ represents hydrogen, hydroxy, halogen, cyano, $C_1$-$C_2$-alkyl, or $C_1$-$C_2$-haloalkyl;
$R^9$ and $R^{9a}$ each independently represent $C_1$-$C_3$-alkyl, cyclopropyl, $C_1$-$C_3$-haloalkyl, or halocyclopropyl;
$R^{10}$ represents methyl, halogen, or hydroxy;
$R^{11}$ represents methyl, halogen, or hydroxy;
$R^{13a}$ represents hydrogen, or a group selected from $C_1$-$C_4$-alkyl, $C_3$-$C_4$-cycloalkyl, $C_3$-$C_6$-cycloalkyl-$C_1$-$C_4$-alkyl- and $C_1$-$C_3$-alkoxy-$C_1$-$C_3$-alkyl-, wherein said groups are each independently optionally substituted, one or more times, with halogen;
$R^{13b}$ represents hydrogen, or a group selected from $C_1$-$C_4$-alkyl, $C_3$-$C_4$-cycloalkyl, $C_3$-$C_6$-cycloalkyl-$C_1$-$C_4$-alkyl- and $C_1$-$C_3$-alkoxy-$C_1$-$C_3$-alkyl-, wherein said groups are each independently optionally substituted, one or more times, with halogen, or,
$R^{13a}$ and $R^{13b}$, together with the carbon atom to which they are attached, form a $C_3$-$C_5$-cycloalkyl ring or a 4- to 5-membered heterocyclic ring;
or an N-oxide, a salt, a tautomer, or a stereoisomer of said compound, or a salt of said N-oxide, tautomer or stereoisomer.

In a further embodiment, the invention relates to compounds of formula (I) as described supra, wherein:
$R^1$ represents hydrogen or a group selected from $C_1$-$C_4$-alkyl, $C_3$-$C_6$-cycloalkyl, $C_3$-$C_6$-cycloalkyl-$C_1$-$C_4$-alkyl-, and $C_1$-$C_5$-hydroxyalkyl, wherein said groups are each independently optionally substituted, one or more times, with halogen;
$R^{2a}$ represents hydrogen or halogen;
$R^{2b}$ represents hydrogen, halogen, —$NH_2$, or —$NHR^9$;
$R^{2c}$ represents hydrogen or halogen;
X represents methylene, wherein said methylene group is independently optionally substituted, one or more times, with $R^3$;
Y represents phenyl or a heteroaryl group,
 wherein said phenyl and heteroaryl group are each independently optionally substituted, one or more times, with $R^4$;
$R^3$ represents hydroxy, $C_1$-$C_3$-alkyl, $C_1$-$C_3$-haloalkyl, —$NHR^6$, $R^5O$—$C_1$-$C_3$-alkyl, or $R^6R^7N$—$C_1$-$C_5$-alkyl;
$R^4$ represents halogen, $C_1$-$C_4$-alkyl, or $C_1$-$C_4$-haloalkyl;
$R^5$ represents hydrogen;
$R^6$ and $R^7$ each independently represent hydrogen, $C_1$-$C_2$-alkyl, $C_1$-$C_2$-haloalkyl, or $C_3$-$C_4$-cycloalkyl, or
$R^6$ and $R^7$, together with the nitrogen atom to which they are attached, represent a 4- to 7-membered heterocyclic ring, wherein said heterocyclic ring optionally contains further heteroatoms selected from N, O and S, or groups selected from C(=O), S(=O), and $SO_2$, and is independently optionally substituted, one or more times, with halogen, $C_1$-$C_3$-alkyl, $C_3$-cycloalkyl-$C_1$-$C_2$-alkyl-, —$NH_2$, —$NHR^9$, or —$NR^9R^{9a}$;
A represents a group selected from:

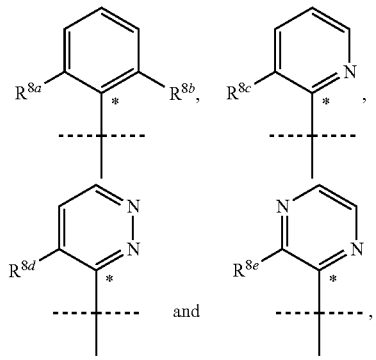

wherein * indicates the point of attachment of said group to the —NH— of formula (I);
$R^{8a}$ represents hydrogen, hydroxy, halogen, or $C_1$-$C_2$-alkyl;
$R^{8b}$ represents hydrogen, hydroxy, halogen, or $C_1$-$C_2$-alkyl;
$R^{8c}$ represents hydrogen, hydroxy, halogen, or $C_1$-$C_2$-alkyl;
$R^{8d}$ represents hydrogen, hydroxy, halogen, or $C_1$-$C_2$-alkyl;
$R^{8e}$ represents hydrogen, hydroxy, halogen, or $C_1$-$C_2$-alkyl;
$R^9$ and $R^{9a}$ each independently represent $C_1$-$C_3$-alkyl or cyclopropyl;
$R^{13a}$ represents hydrogen or $C_1$-$C_2$-alkyl, wherein said $C_1$-$C_2$-alkyl is independently optionally substituted, one or more times, with halogen;
$R^{13b}$ represents hydrogen or $C_1$-$C_2$-alkyl, wherein said $C_1$-$C_2$-alkyl is independently optionally substituted, one or more times, with halogen or;
$R^{13a}$ and $R^{13b}$, together with the carbon atom to which they are attached, form a $C_3$-$C_4$-cycloalkyl ring;
or an N-oxide, a salt, a tautomer, or a stereoisomer of said compound, or a salt of said N-oxide, tautomer or stereoisomer.

In a further embodiment, the invention relates to compounds of formula (I) as described supra, wherein:
$R^1$ represents hydrogen or a group selected from $C_1$-$C_2$-alkyl, cyclopropyl, and cyclopropylmethyl, wherein said $C_1$-$C_2$-alkyl is independently optionally substituted, one or more times, with halogen;
$R^{2a}$ represents hydrogen;
$R^{2b}$ represents hydrogen;
$R^{2c}$ represents hydrogen;
X represents methylene, wherein said methylene group is independently optionally substituted, one or more times, with $R^3$;
Y represents phenyl, wherein said phenyl is independently optionally substituted, one or more times, with $R^4$;
$R^3$ represents $C_1$-$C_3$-alkyl, $C_1$-$C_3$-haloalkyl, $R^5O$—$C_1$-$C_3$-alkyl, or $R^6R^7N$—$C_1$-$C_5$-alkyl;
$R^4$ represents halogen or $C_1$-$C_4$-alkyl;
$R^5$ represents hydrogen;

$R^6$ and $R^7$ each independently represent hydrogen, $C_1$-$C_2$-alkyl, $C_1$-$C_2$-haloalkyl, or $C_3$-$C_4$-cycloalkyl, or $R^6$ and $R^7$, together with the nitrogen atom to which they are attached, represent a 4- to 7-membered heterocyclic ring, wherein said heterocyclic ring optionally contains further heteroatoms selected from N, O and S, and is independently optionally substituted, one or more times, with halogen, $C_1$-$C_3$-alkyl, —$NH_2$, —$NHR^9$, or —$NR^9R^{9a}$;

A represents a group selected from:

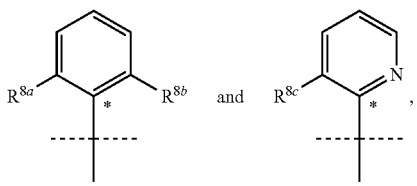

wherein * indicates the point of attachment of said group to the —NH— of formula (I);

$R^{8a}$ represents hydrogen, hydroxy, halogen, or $C_1$-$C_2$-alkyl;

$R^{8b}$ represents hydrogen, hydroxy, halogen, or $C_1$-$C_2$-alkyl;

$R^{8c}$ represents hydrogen, hydroxy, halogen, or $C_1$-$C_2$-alkyl;

$R^9$ and $R^{9a}$ each independently represent $C_1$-$C_3$-alkyl;

$R^{13a}$ represents hydrogen or methyl, wherein said methyl is independently optionally substituted, one or more times, with halogen;

$R^{13b}$ represents hydrogen or methyl, wherein said methyl is independently optionally substituted, one or more times, with halogen;

or an N-oxide, a salt, a tautomer, or a stereoisomer of said compound, or a salt of said N-oxide, tautomer or stereoisomer.

In a further embodiment, the invention relates to compounds of formula (I) as described supra, wherein:

$R^1$ represents methyl;

$R^{2a}$ represents hydrogen;

$R^{2b}$ represents hydrogen;

$R^{2c}$ represents hydrogen;

X—Y represents a group:

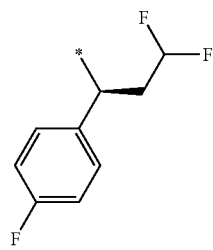 [SMILES: *[C@@H](CC(F)F)c1ccc(F)cc1]

wherein * indicates the point of attachment of said group to the —CO of formula (I);

A represents a group:

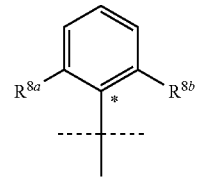

wherein * indicates the point of attachment of said group to the —NH— of formula (I);

$R^{8a}$ represents hydrogen;

$R^{8b}$ represents hydrogen;

$R^{13a}$ represents hydrogen or methyl, wherein said methyl is independently optionally substituted, one or more times, with halogen;

$R^{13b}$ represents hydrogen or methyl, wherein said methyl is independently optionally substituted, one or more times, with halogen, or $R^{13a}$ and $R^{13b}$, together with the carbon atom to which they are attached, form a $C_3$-$C_4$-cycloalkyl ring;

or an N-oxide, a salt, a tautomer, or a stereoisomer of said compound, or a salt of said N-oxide, tautomer or stereoisomer.

One aspect of the invention are compounds of formula (I) as described in the examples, as characterized by their names in the title, as claimed in claim 4, and/or their structures as well as the subcombinations of all residues specifically disclosed in the compounds of the examples.

Another aspect of the present invention are the intermediates used for their synthesis. One special aspect of the invention are intermediates 1-3 or a salt thereof:

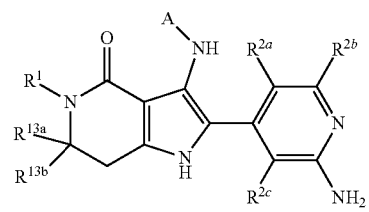

1-3 in which $R^1$, $R^{2a}$, $R^{2b}$, $R^{2c}$, $R^{13a}$, $R^{13b}$ and A are as defined herein for the compound of general formula (I), with the proviso that $R^1$ is not hydrogen or methyl.

Another aspect of the invention relates to the use of intermediates 1-3, or a salt thereof:

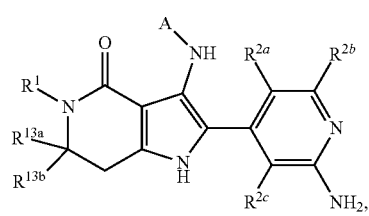

1-3 in which $R^1$, $R^{2a}$, $R^{2b}$, $R^{2c}$, $R^{13a}$, $R^{13b}$ and A are as defined herein for the compound of general formula (I), for preparing a compound of formula (I) as defined herein or an N-oxide, a salt, a tautomer or a stereoisomer of said compound, or a salt of said N-oxide, tautomer or stereoisomer.

Another aspect of the invention relates to the use of any of the intermediates described herein for preparing a compound of formula (I) as defined herein or an N-oxide, a salt, a tautomer or a stereoisomer of said compound, or a salt of said N-oxide, tautomer or stereoisomer.

In further embodiments of the above-mentioned aspects, the invention relates to compounds of formula (I), wherein:
$R^1$ represents hydrogen or a group selected from $C_1$-$C_4$-alkyl, $C_3$—C-cycloalkyl, $C_3$-$C_6$-cycloalkyl-$C_1$-$C_4$-alkyl-, $C_1$-$C_3$-alkoxy-$C_1$-$C_3$-alkyl-, and $C_1$-$C_5$-hydroxyalkyl, wherein said groups are each independently optionally substituted, one or more times, with halogen.

In further embodiments of the above-mentioned aspects, the invention relates to compounds of formula (I), wherein:
$R^1$ represents hydrogen or a group selected from $C_1$-$C_4$-alkyl, $C_3$-$C_6$-cycloalkyl, $C_3$-$C_6$-cycloalkyl-$C_1$-$C_4$-alkyl-, and $C_1$-$C_5$-hydroxyalkyl, wherein said groups are each independently optionally substituted, one or more times, with halogen.

In further embodiments of the above-mentioned aspects, the invention relates to compounds of formula (I), wherein:
$R^1$ represents hydrogen or $C_1$-$C_4$-alkyl, wherein said $C_1$-$C_4$-alkyl is independently optionally substituted, one or more times, with halogen.

In further embodiments of the above-mentioned aspects, the invention relates to compounds of formula (I), wherein:
$R^1$ represents methyl.

In further embodiments of the above-mentioned aspects, the invention relates to compounds of formula (I), wherein:
$R^{2a}$ represents hydrogen, hydroxy, halogen, cyano, —$NH_2$, —NHMe, —$NMe_2$, $C_1$-$C_2$-alkyl, $C_1$-$C_2$-alkoxy, $C_1$-$C_2$-haloalkyl, or $C_1$-$C_2$-haloalkoxy.

In further embodiments of the above-mentioned aspects, the invention relates to compounds of formula (I), wherein:
$R^{2a}$ represents hydrogen or halogen.

In further embodiments of the above-mentioned aspects, the invention relates to compounds of formula (I), wherein:
$R^{2a}$ represents hydrogen.

In further embodiments of the above-mentioned aspects, the invention relates to compounds of formula (I), wherein:
$R^{2b}$ represents hydrogen, hydroxy, halogen, cyano, —$NH_2$, —$NHR^9$, or —$NMe_2$.

In further embodiments of the above-mentioned aspects, the invention relates to compounds of formula (I), wherein:
$R^{2b}$ represents hydrogen, halogen, —$NH_2$, or —$NHR^9$.

In further embodiments of the above-mentioned aspects, the invention relates to compounds of formula (I), wherein:
$R^{2b}$ represents hydrogen.

In further embodiments of the above-mentioned aspects, the invention relates to compounds of formula (I), wherein:
$R^{2c}$ represents hydrogen, halogen, cyano, —$NMe_2$, $C_1$-$C_2$-alkoxy, or $C_1$-$C_2$-haloalkoxy.

In further embodiments of the above-mentioned aspects, the invention relates to compounds of formula (I), wherein:
$R^{2c}$ represents hydrogen or halogen.

In further embodiments of the above-mentioned aspects, the invention relates to compounds of formula (I), wherein:
$R^{2c}$ represents hydrogen.

In further embodiments of the above-mentioned aspects, the invention relates to compounds of formula (I), wherein:
X represents methylene or ethylene,
wherein said methylene and ethylene group are each independently optionally substituted, one or more times, with $R^3$.

In further embodiments of the above-mentioned aspects, the invention relates to compounds of formula (I), wherein:
X represents methylene, wherein said methylene group is independently optionally substituted, one or more times, with $R^3$.

In further embodiments of the above-mentioned aspects, the invention relates to compounds of formula (I), wherein:
Y represents phenyl or a heteroaryl group,
wherein said phenyl and heteroaryl group are each independently optionally substituted, one or more times, with $R^4$.

In further embodiments of the above-mentioned aspects, the invention relates to compounds of formula (I), wherein:
Y represents phenyl, wherein said phenyl is independently optionally substituted, one or more times, with $R^4$.

In further embodiments of the above-mentioned aspects, the invention relates to compounds of formula (I), wherein:
X—Y represents a group:

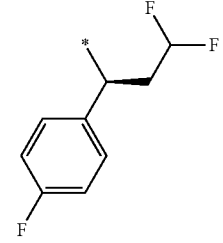 [SMILES: *[C@@H](CC(F)F)c1ccc(F)cc1]

wherein * indicates the point of attachment of said group to the —CO of formula (I).

In further embodiments of the above-mentioned aspects, the invention relates to compounds of formula (I), wherein:
$R^3$ represents hydroxy, halogen, cyano, $C_1$-$C_3$-alkyl, $C_1$-$C_3$-alkoxy, $C_1$-$C_3$-haloalkyl, $C_1$-$C_2$-haloalkoxy, $C_3$-$C_4$-cycloalkyl, —$NHR^6$, $R^5O$—$C_1$-$C_3$-alkyl, $R^6R^7N$—$C_1$-$C_5$-alkyl, or $R^6R^7N$—X'—$C(R^{10})(R^{11})$—$C_1$-$C_2$-alkyl-.

In further embodiments of the above-mentioned aspects, the invention relates to compounds of formula (I), wherein:
$R^3$ represents hydroxy, $C_1$-$C_3$-alkyl, $C_1$-$C_3$-haloalkyl, —$NHR^6$, $R^5O$—$C_1$-$C_3$-alkyl, or $R^6R^7N$—$C_1$-$C_5$-alkyl.

In further embodiments of the above-mentioned aspects, the invention relates to compounds of formula (I), wherein:
$R^3$ represents $C_1$-$C_3$-alkyl, $C_1$-$C_3$-haloalkyl, $R^5O$—$C_1$-$C_3$-alkyl, or $R^6R^7N$—$C_1$-$C_5$-alkyl.

In further embodiments of the above-mentioned aspects, the invention relates to compounds of formula (I), wherein:
$R^3$ represents $R^5O$—$C_1$-$C_3$-alkyl.

In further embodiments of the above-mentioned aspects, the invention relates to compounds of formula (I), wherein:
$R^3$ represents $C_1$-$C_3$-alkyl or $C_1$-$C_3$-haloalkyl.

In further embodiments of the above-mentioned aspects, the invention relates to compounds of formula (I), wherein:
$R^3$ represents $R^6R^7N$—$C_1$-$C_5$-alkyl.

In further embodiments of the above-mentioned aspects, the invention relates to compounds of formula (I), wherein:
X' represents methylene or ethylene.

In further embodiments of the above-mentioned aspects, the invention relates to compounds of formula (I), wherein:
X' represents methylene.

In further embodiments of the above-mentioned aspects, the invention relates to compounds of formula (I), wherein:
$R^4$ represents hydroxy, halogen, cyano, $C_1$-$C_4$-alkyl, $C_1$-$C_4$-alkoxy, $C_1$-$C_4$-haloalkyl, $C_1$-$C_4$-haloalkoxy, —$NMe_2$, —$CO_2R^{14}$, —$CONR^{15}R^{16}$, or —$SO_2Me$.

In further embodiments of the above-mentioned aspects, the invention relates to compounds of formula (I), wherein:
$R^4$ represents hydroxy, halogen, cyano, $C_1$-$C_4$-alkyl, $C_1$-$C_4$-alkoxy, $C_1$-$C_4$-haloalkyl, or $C_1$-$C_4$-haloalkoxy.

In further embodiments of the above-mentioned aspects, the invention relates to compounds of formula (I), wherein:
$R^4$ represents halogen, $C_1$-$C_4$-alkyl, or $C_1$-$C_4$-haloalkyl.

In further embodiments of the above-mentioned aspects, the invention relates to compounds of formula (I), wherein:
$R^4$ represents halogen or $C_1$-$C_4$-alkyl.

In further embodiments of the above-mentioned aspects, the invention relates to compounds of formula (I), wherein:
$R^5$ represents hydrogen, $C_1$-$C_2$-alkyl, $C_1$-$C_2$-haloalkyl, or $C_3$-$C_4$-cycloalkyl.

In further embodiments of the above-mentioned aspects, the invention relates to compounds of formula (I), wherein:
$R^5$ represents hydrogen.

In further embodiments of the above-mentioned aspects, the invention relates to compounds of formula (I), wherein:
$R^6$ represents hydrogen, $C_1$-$C_2$-alkyl, $C_1$-$C_2$-haloalkyl, or $C_3$-$C_4$-cycloalkyl.

In further embodiments of the above-mentioned aspects, the invention relates to compounds of formula (I), wherein:
$R^7$ represents hydrogen, $C_1$-$C_2$-alkyl, $C_1$-$C_2$-haloalkyl, $C_3$-$C_4$-cycloalkyl, or —$CO_2$—$C_1$-$C_4$-alkyl.

In further embodiments of the above-mentioned aspects, the invention relates to compounds of formula (I), wherein:
$R^6$ and $R^7$ each independently represent hydrogen, $C_1$-$C_2$-alkyl, $C_1$-$C_2$-haloalkyl, or $C_3$-$C_4$-cycloalkyl, or
$R^6$ and $R^7$, together with the nitrogen atom to which they are attached, represent a 4- to 7-membered heterocyclic ring, wherein said heterocyclic ring optionally contains further heteroatoms selected from N, O and S, or groups selected from C(═O), S(═O), and $SO_2$, and is independently optionally substituted, one or more times, with halogen, $C_1$-$C_3$-alkyl, $C_3$-cycloalkyl-$C_1$-$C_2$-alkyl-, —$NH_2$, —$NHR^9$, —$NR^9R^{9a}$, or hydroxy.

In further embodiments of the above-mentioned aspects, the invention relates to compounds of formula (I), wherein:
$R^6$ and $R^7$ each independently represent hydrogen, $C_1$-$C_2$-alkyl, $C_1$-$C_2$-haloalkyl, or $C_3$-$C_4$-cycloalkyl, or
$R^6$ and $R^7$, together with the nitrogen atom to which they are attached, represent a 4- to 7-membered heterocyclic ring, wherein said heterocyclic ring optionally contains further heteroatoms selected from N, O and S, or groups selected from C(═O), S(═O), and $SO_2$, and is optionally substituted, one or more times, with halogen, $C_1$-$C_3$-alkyl, $C_3$-cycloalkyl-$C_1$-$C_2$-alkyl-, —$NH_2$, —$NHR^9$, or —$NR^9R^{9a}$.

In further embodiments of the above-mentioned aspects, the invention relates to compounds of formula (I), wherein:
$R^6$ and $R^7$ each independently represent hydrogen, $C_1$-$C_2$-alkyl, $C_1$-$C_2$-haloalkyl, or $C_3$-$C_4$-cycloalkyl, or
$R^6$ and $R^7$, together with the nitrogen atom to which they are attached, represent a 4- to 7-membered heterocyclic ring, wherein said heterocyclic ring optionally contains further heteroatoms selected from N, O and S, or groups selected from C(═O), S(═O), and $SO_2$, and is optionally substituted, one or more times, with $C_1$-$C_3$-alkyl, —$NH_2$, —$NHR^9$, or —$NR^9R^{9a}$.

In further embodiments of the above-mentioned aspects, the invention relates to compounds of formula (I), wherein:
$R^6$ and $R^7$ each independently represent hydrogen, $C_1$-$C_2$-alkyl, $C_1$-$C_2$-haloalkyl, or $C_3$-$C_4$-cycloalkyl.

In further embodiments of the above-mentioned aspects, the invention relates to compounds of formula (I), wherein:

$R^6$ and $R^7$, together with the nitrogen atom they are attached, represent a 4- to 7-membered heterocyclic ring, wherein said heterocyclic ring optionally contains further heteroatoms selected from N, O and S, and is independently optionally substituted, one or more times, with halogen, $C_1$-$C_3$-alkyl, —$NH_2$, —$NHR^9$, or —$NR^9R^{9a}$.

In further embodiments of the above-mentioned aspects, the invention relates to compounds of formula (I), wherein:
A represents a group selected from:

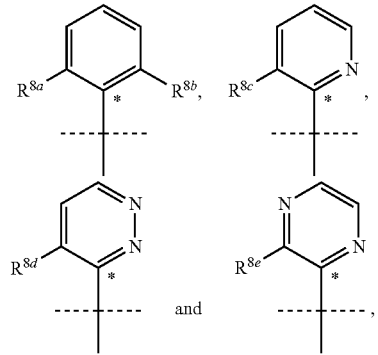

wherein * indicates the point of attachment of said group to the —NH— of formula (I).

In further embodiments of the above-mentioned aspects, the invention relates to compounds of formula (I), wherein:
A represents a group selected from:

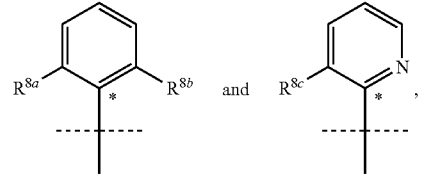

wherein * indicates the point of attachment of said group to the —NH— of formula (I).

In further embodiments of the above-mentioned aspects, the invention relates to compounds of formula (I), wherein:
A represents a group

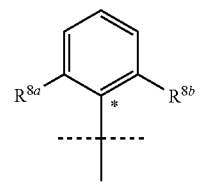

wherein * indicates the point of attachment of said group to the —NH— of formula (I).

In further embodiments of the above-mentioned aspects, the invention relates to compounds of formula (I), wherein:
$R^{8a}$ represents hydrogen, hydroxy, halogen, cyano, $C_1$-$C_2$-alkyl, or $C_1$-$C_2$-haloalkyl.

In further embodiments of the above-mentioned aspects, the invention relates to compounds of formula (I), wherein:

$R^{8a}$ represents hydrogen, hydroxy, halogen, or $C_1$-$C_2$-alkyl.

In further embodiments of the above-mentioned aspects, the invention relates to compounds of formula (I), wherein:
$R^{8a}$ represents hydrogen, halogen, or methyl.

In further embodiments of the above-mentioned aspects, the invention relates to compounds of formula (I), wherein:
$R^{8a}$ represents hydrogen, or halogen.

In further embodiments of the above-mentioned aspects, the invention relates to compounds of formula (I), wherein:
$R^{8a}$ represents hydrogen.

In further embodiments of the above-mentioned aspects, the invention relates to compounds of formula (I), wherein:
$R^{8b}$ represents hydrogen, hydroxy, halogen, cyano, $C_1$-$C_2$-alkyl, or $C_1$-$C_2$-haloalkyl.

In further embodiments of the above-mentioned aspects, the invention relates to compounds of formula (I), wherein:
$R^{8b}$ represents hydrogen, hydroxy, halogen, or $C_1$-$C_2$-alkyl.

In further embodiments of the above-mentioned aspects, the invention relates to compounds of formula (I), wherein:
$R^{8b}$ represents hydrogen, halogen, or methyl.

In further embodiments of the above-mentioned aspects, the invention relates to compounds of formula (I), wherein:
$R^{8b}$ represents hydrogen, or halogen.

In further embodiments of the above-mentioned aspects, the invention relates to compounds of formula (I), wherein:
$R^{8b}$ represents hydrogen.

In further embodiments of the above-mentioned aspects, the invention relates to compounds of formula (I), wherein:
$R^{8c}$ represents hydrogen, hydroxy, halogen, cyano, $C_1$-$C_2$-alkyl, or $C_1$-$C_2$-haloalkyl.

In further embodiments of the above-mentioned aspects, the invention relates to compounds of formula (I), wherein:
$R^{8c}$ represents hydrogen, hydroxy, halogen, or $C_1$-$C_2$-alkyl.

In further embodiments of the above-mentioned aspects, the invention relates to compounds of formula (I), wherein:
$R^{8c}$ represents hydrogen, halogen, or methyl.

In further embodiments of the above-mentioned aspects, the invention relates to compounds of formula (I), wherein:
$R^{8c}$ represents hydrogen, or halogen.

In further embodiments of the above-mentioned aspects, the invention relates to compounds of formula (I), wherein:
$R^{8d}$ represents hydrogen, hydroxy, halogen, cyano, $C_1$-$C_2$-alkyl, or $C_1$-$C_2$-haloalkyl.

In further embodiments of the above-mentioned aspects, the invention relates to compounds of formula (I), wherein:
$R^{8d}$ represents hydrogen, hydroxy, halogen, or $C_1$-$C_2$-alkyl.

In further embodiments of the above-mentioned aspects, the invention relates to compounds of formula (I), wherein:
$R^{8d}$ represents hydrogen, halogen, or methyl.

In further embodiments of the above-mentioned aspects, the invention relates to compounds of formula (I), wherein:
$R^{8d}$ represents hydrogen, or halogen.

In further embodiments of the above-mentioned aspects, the invention relates to compounds of formula (I), wherein:
$R^{8e}$ represents hydrogen, hydroxy, halogen, cyano, $C_1$-$C_2$-alkyl, or $C_1$-$C_2$-haloalkyl.

In further embodiments of the above-mentioned aspects, the invention relates to compounds of formula (I), wherein:
$R^{8e}$ represents hydrogen, hydroxy, halogen, or $C_1$-$C_2$-alkyl.

In further embodiments of the above-mentioned aspects, the invention relates to compounds of formula (I), wherein:
$R^{8e}$ represents hydrogen, halogen, or methyl.

In further embodiments of the above-mentioned aspects, the invention relates to compounds of formula (I), wherein:
$R^{8e}$ represents hydrogen, or halogen.

In further embodiments of the above-mentioned aspects, the invention relates to compounds of formula (I), wherein:
$R^{8f}$ represents hydrogen, hydroxy, halogen, cyano, $C_1$-$C_2$-alkyl, or $C_1$-$C_2$-haloalkyl.

In further embodiments of the above-mentioned aspects, the invention relates to compounds of formula (I), wherein:
$R^{8g}$ represents hydrogen or halogen.

In further embodiments of the above-mentioned aspects, the invention relates to compounds of formula (I), wherein:
$R^{9}$ represents $C_1$-$C_3$-alkyl or cyclopropyl.

In further embodiments of the above-mentioned aspects, the invention relates to compounds of formula (I), wherein:
$R^{9a}$ represents $C_1$-$C_3$-alkyl or cyclopropyl.

In further embodiments of the above-mentioned aspects, the invention relates to compounds of formula (I), wherein:
$R^{9}$ and $R^{9a}$ each independently represent $C_1$-$C_3$-alkyl, cyclopropyl, $C_1$-$C_3$-haloalkyl, or halocyclopropyl.

In further embodiments of the above-mentioned aspects, the invention relates to compounds of formula (I), wherein:
$R^{9}$ and $R^{9a}$ each independently represent $C_1$-$C_3$-alkyl or cyclopropyl.

In further embodiments of the above-mentioned aspects, the invention relates to compounds of formula (I), wherein:
$R^{9}$ and $R^{9a}$ each independently represent $C_1$-$C_3$-alkyl.

In further embodiments of the above-mentioned aspects, the invention relates to compounds of formula (I), wherein:
$R^{10}$ represents methyl, halogen, or hydroxy.

In further embodiments of the above-mentioned aspects, the invention relates to compounds of formula (I), wherein:
$R^{11}$ represents methyl, halogen, or hydroxy.

In further embodiments of the above-mentioned aspects, the invention relates to compounds of formula (I), wherein:
$R^{13a}$ represents hydrogen, or a group selected from $C_1$-$C_4$-alkyl, $C_3$-$C_4$-cycloalkyl, $C_3$-$C_6$-cycloalkyl-$C_1$-$C_4$-alkyl- and $C_1$-$C_3$-alkoxy-$C_1$-$C_3$-alkyl-, wherein said groups are each independently optionally substituted, one or more times, with halogen.

In further embodiments of the above-mentioned aspects, the invention relates to compounds of formula (I), wherein:
$R^{13a}$ represents hydrogen or $C_1$-$C_2$-alkyl, wherein said $C_1$-$C_2$-alkyl is independently optionally substituted, one or more times, with halogen.

In further embodiments of the above-mentioned aspects, the invention relates to compounds of formula (I), wherein:
$R^{13a}$ represents hydrogen or methyl, wherein said methyl is independently optionally substituted, one or more times, with halogen.

In further embodiments of the above-mentioned aspects, the invention relates to compounds of formula (I), wherein:
$R^{13a}$ represents hydrogen.

In further embodiments of the above-mentioned aspects, the invention relates to compounds of formula (I), wherein:
$R^{13a}$ represents hydrogen or methyl, wherein said methyl is independently optionally substituted, one or more times, with halogen.

In further embodiments of the above-mentioned aspects, the invention relates to compounds of formula (I), wherein:
$R^{13b}$ represents hydrogen, or a group selected from $C_1$-$C_4$-alkyl, $C_3$-$C_4$-cycloalkyl, $C_3$-$C_6$-cycloalkyl-$C_1$-$C_4$-alkyl- and $C_1$-$C_3$-alkoxy-$C_1$-$C_3$-alkyl-, wherein said groups are each independently optionally substituted, one or more times, with halogen.

In further embodiments of the above-mentioned aspects, the invention relates to compounds of formula (I), wherein:

$R^{13b}$ represents hydrogen or $C_1$-$C_2$-alkyl, wherein said $C_1$-$C_2$-alkyl is independently optionally substituted, one or more times, with halogen.

In further embodiments of the above-mentioned aspects, the invention relates to compounds of formula (I), wherein:
$R^{13b}$ represents hydrogen or methyl, wherein said methyl is independently optionally substituted, one or more times, with halogen.

In further embodiments of the above-mentioned aspects, the invention relates to compounds of formula (I), wherein:
$R^{13b}$ represents hydrogen.

In further embodiments of the above-mentioned aspects, the invention relates to compounds of formula (I), wherein:
$R^{13a}$ and $R^{13b}$ together with the carbon atom to which they are attached form a $C_3$-$C_5$-cycloalkyl ring or a 4- to 5-membered heterocyclic ring.

In further embodiments of the above-mentioned aspects, the invention relates to compounds of formula (I), wherein:
$R^{13a}$ and $R^{13b}$, together with the carbon atom to which they are attached, form a cyclopropyl ring.

A further aspect of the invention are compounds of formula (I), which are present as their salts.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

In other embodiments of the invention, compounds are defined according to the claims as disclosed in the Claims section wherein the definitions are limited according to the preferred or more preferred definitions as disclosed below or specifically disclosed residues of the exemplified compounds and subcombinations thereof.

In certain embodiments, compounds of the present invention have surprising and advantageous properties.

In particular, compounds of the present invention have surprisingly been found to effectively inhibit Casein kinase 1 alpha and/or delta and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Casein kinase 1 alpha and/or delta, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Definitions

Constituents which are optionally substituted as stated herein, may be substituted, unless otherwise noted, one or more times, independently of one another at any possible position. When any variable occurs more than one time in any constituent, each definition is independent. For example, when in which $R^2$, $R^3$, $R^4$, $R^5$, $R^6$, $R^7$, and/or $R^8$, occur more than one time in any compound of formula (I) each definition of $R^2$, $R^3$, $R^4$, $R^5$, $R^6$, $R^7$, and $R^8$ is independent.

Should a constituent be composed of more than one part, e.g. $C_3$-$C_6$-cycloalkyl-$C_1$-$C_4$-alkyl-, unless stated otherwise, the position of a possible substituent can be at any of these parts at any suitable position (e.g. in the case of a substituted $C_3$-$C_6$-cycloalkyl-$C_1$-$C_4$-alkyl- group, substituents may be present at the $C_3$-$C_6$-cycloalkyl part of the group, at the $C_1$-$C_4$-alkyl part of the group or both). A hyphen at the beginning or at the end of the constituent marks the point of attachment to the rest of the molecule. Should a ring be substituted the substituent could be at any suitable position of the ring, also on a ring nitrogen atom if suitable.

The term "comprising" when used in the specification includes "consisting of".

If it is referred to "as mentioned above" or "mentioned above", "supra" within the description it is referred to any of the disclosures made within the specification in any of the preceding pages.

If it is referred to "as mentioned herein", "described herein", "provided herein" or "stated herein" within the description it is referred to any of the disclosures made within the specification in any of the preceding or subsequent pages.

"suitable" within the sense of the invention means chemically possible to be made by methods within the knowledge of a skilled person.

The terms as mentioned in the present text have preferably the following meanings:

The term "halogen atom", "halo-" or "Hal-" is to be understood as meaning a fluorine, chlorine, bromine or iodine atom, preferably a fluorine, chlorine or bromine atom.

The term "$C_1$-$C_6$-alkyl" is to be understood as meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl or iso-propyl group.

The term "$C_1$-$C_4$-haloalkyl" is to be understood as meaning a linear or branched, saturated, monovalent hydrocarbon group in which the term "$C_1$-$C_4$-alkyl" is defined supra, and in which one or more hydrogen atoms are replaced by a halogen atom, identically or differently, i.e. one halogen atom being independent from another. Particularly, said halogen atom is F. Said $C_1$-$C_4$-haloalkyl group is, for example, —$CF_3$, —$CHF_2$, —$CH_2F$, —$CF_2CF_3$, —$CH_2CH_2F$, —$CH_2CHF_2$, —$CH_2CF_3$, —$CH_2CH_2CF_3$, or —$CH(CH_2F)_2$. Particularly, said group has 1, 2, or 3 carbon atoms ("$C_1$-$C_3$-haloalkyl"). More particularly, said group has 1, or 2 carbon atoms ("$C_1$-$C_2$-haloalkyl").

The term "$C_1$-$C_5$-hydroxyalkyl" means a linear or branched, saturated, monovalent hydrocarbon group in which the term "$C_1$-$C_5$-alkyl" is defined supra, and in which 1 or 2 hydrogen atoms are replaced with a hydroxy group, e.g. a hydroxymethyl, 1-hydroxyethyl, 2-hydroxyethyl, 1,2-di-hydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl or 1-hydroxy-2-methyl-propyl group.

The term "$C_1$-$C_4$-alkoxy" is to be understood as meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy or sec-butoxy group, or an isomer thereof.

The term "$C_1$-$C_4$-haloalkoxy" is to be understood as meaning a linear or branched, saturated, monovalent $C_1$-$C_4$-alkoxy group, as defined supra, in which one or more of the hydrogen atoms are replaced, identically or differently, by a halogen atom. Particularly, said halogen atom is F. Said $C_1$-$C_4$-haloalkoxy group is, for example, —$OCF_3$, —$OCHF_2$, —$OCH_2F$, —$OCF_2CF_3$, or —$OCH_2CF_3$. Particularly, said group has 1, 2, or 3 carbon atoms ("$C_1$-$C_3$-haloalkoxy"). More particularly, said group has 1, or 2 carbon atoms ("$C_1$-$C_2$-haloalkoxy").

The term "$C_3$-$C_6$-cycloalkyl" is to be understood as meaning a saturated, monovalent, mono- or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl, or a bicyclic hydrocarbon ring.

The term "halocyclopropyl" is to be understood as meaning a cyclopropyl group in which one or more hydrogen atoms are replaced by a halogen atom, identically or differently, i.e. one halogen atom being independent from another. Particularly, said halogen atom is F.

The term "4- to 7-membered heterocyclic ring" mean a monocyclic, saturated heterocycle with 4, 5, 6 or 7 ring atoms in total, wherein said heterocyclic ring contains one N atom and optionally one or more heteroatoms from the series N, O and S, or groups from the series C(=O), S(=O), and $SO_2$.

Said heterocyclic ring, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

The term "heteroaryl" means a monovalent, monocyclic, bicyclic or tricyclic aromatic ring having 5, 6, 8, 9, 10, 11, 12, 13 or 14 ring atoms (a "5- to 14-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_6$", as used throughout this text, e.g. in the context of the definition of "$C_1$-$C_6$-alkyl" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$, $C_2$-$C_6$, $C_3$-$C_6$, $C_1$-$C_2$, $C_1$-$C_3$, particularly $C_1$-$C_2$, $C_1$-$C_3$, $C_1$-$C_4$.

The term "$C_1$-$C_4$", as used throughout this text, e.g. in the context of the definition of "$C_1$-$C_4$-alkyl", "$C_1$-$C_4$-haloalkyl", "$C_1$-$C_4$-alkoxy", or "$C_1$-$C_4$-haloalkoxy" is to be understood as meaning an alkyl group having a finite number of carbon atoms of 1 to 4, i.e. 1, 2, 3 or 4 carbon atoms. It is to be understood further that said term "$C_1$-$C_4$" is to be interpreted as any sub-range comprised therein, e.g. $C_1$-$C_4$, $C_2$-$C_4$, $C_3$-$C_4$, $C_1$-$C_2$, $C_1$-$C_3$, particularly $C_1$-$C_2$, $C_1$-$C_3$, $C_1$-$C_4$, in the case of "$C_1$-$C_4$-haloalkyl" or "$C_1$-$C_4$-haloalkoxy" even more particularly $C_1$-$C_2$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The compounds of general formula (I) may exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes of the elements that constitute such a compound.

The term "Isotopic variant of the compound of general formula (I)" is defined as a compound of general formula (I) exhibiting an unnatural proportion of one or more of the isotopes of the elements that constitute such a compound.

The expression "unnatural proportion" is to be understood as meaning a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the disorders specified herein, isotopic variant(s) of the compounds of general formula (I) preferably contain elevated levels of deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses (H. J. Leis et al., Curr. Org. Chem., 1998, 2, 131) in the context of preclinical or clinical studies.

Isotopic variants of the compounds of general formula (I) can generally be prepared by methods known to a person skilled in the art, such as those described in the schemes and/or examples herein, e.g., by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron, 2011, 52, 3865) is a rapid route for incorporation of deuterium. Metal catalysts (i.e. e.g., Pd, Pt, and Rh) in the presence of deuterium gas can be used to directly exchange deuterium for hydrogen in functional groups containing hydrocarbons (J. G. Atkinson et al., U.S. Pat. No. 3,966, 781). A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844, 1989; P. J. Reider et al., J. Org. Chem. 52, 3326-3334, 1987; M. Jarman et al., Carcinogenesis 16(4), 683-688, 1993; J. Atzrodt et al., Angew. Chem., Int. Ed. 2007, 46, 7744; K. Matoishi et al., J. Chem. Soc, Chem. Commun. 2000, 1519-1520; K. Kassahun et al., WO2012/112363.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [A. Streitwieser et al., J. Am. Chem. Soc., 1963, 85, 2759; C. L. Perrin, et al., J. Am. Chem. Soc., 2007, 129, 4490], basicity [C. L. Perrin, et al., J. Am. Chem. Soc., 2003, 125, 15008; C. L. Perrin in Advances in Physical Organic Chemistry, 44, 144; C. L Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (D. J. Kushner et al., Can. J. Physiol. Pharmacol., 1999, 77, 79; A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and/or enhances the formation of a desired metabolite (e.g. Nevirapine: A. M. Sharma et al., Chem. Res. Toxicol., 2013, 26, 410; Uetrecht et al., Chemical Research in Toxicology, 2008, 21, 9, 1862; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels, i.e., reduced peak-trough variation. This could result in lower side effects and/or enhanced efficacy, depending on the particular compound's pharmacokinetic/pharmacodynamic relationship. Indiplon (A. J. Morales et al., Abstract 285, The 15$^{th}$ North American Meeting of the International Society of Xenobiotics, San Diego, CA, Oct. 12-16, 2008), ML-337 (C. J. Wenthur et al., J. Med. Chem., 2013, 56, 5208), and Odanacatib (K. Kassahun et al., WO2012/112363) are examples of this deuterium effect. Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to include also a single compound, salt, polymorph, isomer, hydrate, solvate or the like.

By "stable compound" or "stable structure" is meant a compound that is sufficiently robust to survive isolation to a useful degree of purity from a reaction mixture, and is capable of being subjected to further chemical transformation or, preferably, formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds, (i.e., atropisomers).

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

Separated optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials or optically active catalysts.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

1H-tautomer    2H-tautomer    4H-tautomer

Specifically, the compound of formula (may exist, at least as the following tautomers:

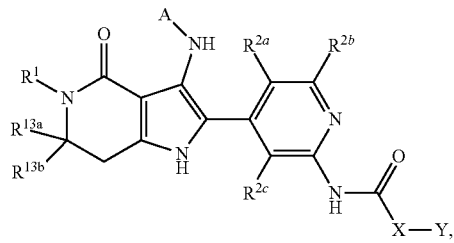

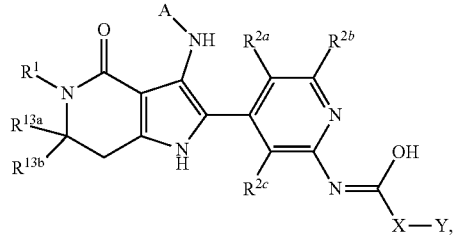

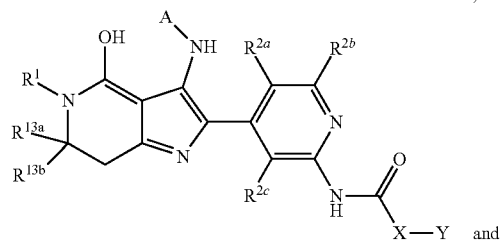

and

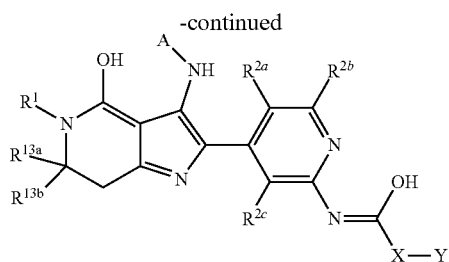

More specifically, when $R^1$ is hydrogen, the compound of formula (I) may exist, at least as the following tautomers:

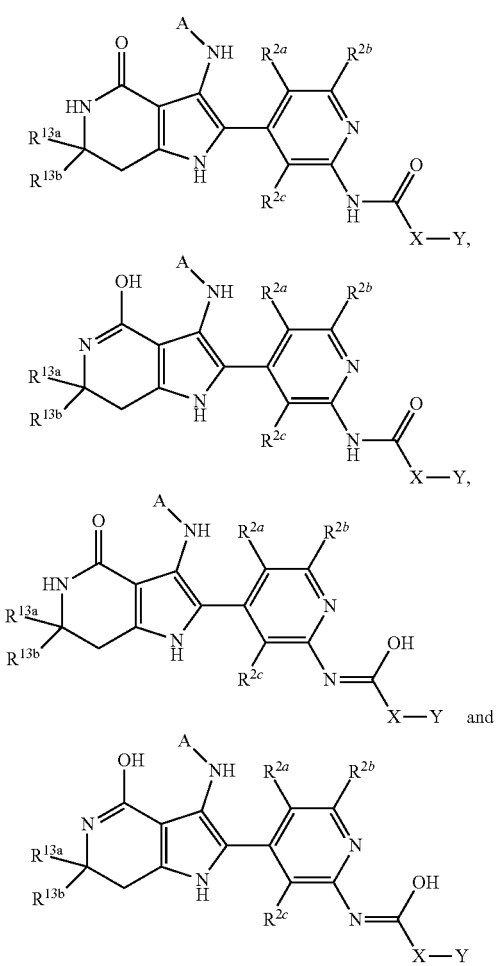

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, preferably water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x $CF_3COOH$", "x $Na^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The salts include water-insoluble and, particularly, water-soluble salts.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxy-ethyl, 1,3-dioxolen-2-onylmethyl esters, e.g. 5-methyl-1,3-dioxolen-2-onylmethyl, and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered. Any such combination of a compound of formula (I) of the present invention with an anti-cancer agent as defined below is an embodiment of the invention.

The term "(chemotherapeutic) anti-cancer agents" includes but is not limited to:

131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, Ionidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, rucaparib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

General Procedures

The compounds according to the invention can be prepared according to the following Schemes 1 through 4.

The schemes and procedures described below illustrate synthetic routes to the compounds of general formula (I) of the invention and are not intended to be limiting. It is obvious to the person skilled in the art that the order of transformations as exemplified in the schemes can be modified in various ways. The order of transformations exemplified in the schemes is therefore not intended to be limiting. In addition, interconversion of any of the substituents $R^1$, $R^{2a}$, $R^{2b}$, $R^{2c}$, $R^{13a}$, $R^{13b}$, A, X, Y, Z and PG can be achieved before and/or after the exemplified transformations. These modifications can be such as the introduction of protecting groups, cleavage of protecting groups, reduction or oxidation of functional groups, dehydrogenation, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art.

Specific examples are described in the subsequent paragraphs.

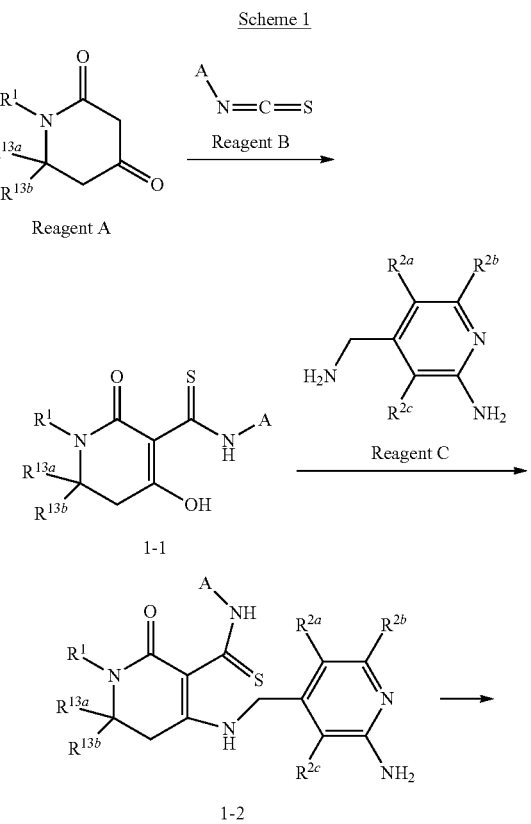

-continued

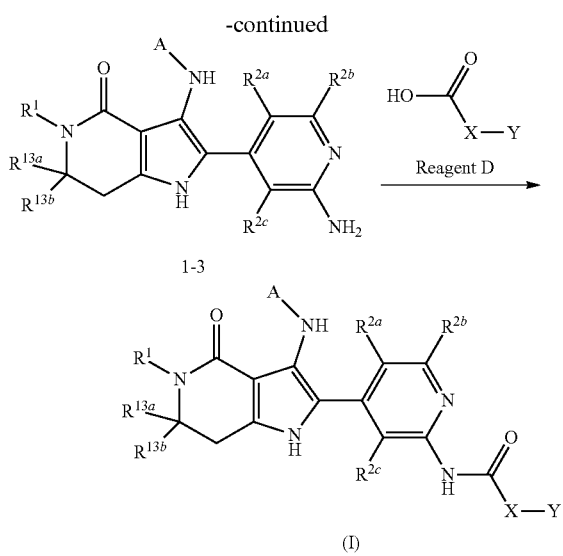

1-3

Scheme 1: Route for the preparation of compounds of general formula (I), wherein $R^1$, $R^{2a}$, $R^{2b}$, $R^{2c}$, $R^{13a}$, $R^{13b}$, A, X and Y have the meaning as given for general formula (I), supra. In addition, interconversion of any of the substituents, $R^1$, $R^{2a}$, $R^{2b}$, $R^{2c}$, $R^{13a}$, $R^{13b}$, A, X and Y can be achieved before and/or after the exemplified transformation.
Reagent A, reagent B, reagent C and reagent D are either commercially available or can be prepared according to procedures available from the public domain, as understandable to the person skilled in the art. Specific examples are described in the subsequent paragraphs.

A suitably substituted piperidine-2,4-dione of general formula (reagent A), such as, for example, N-methyl-piperidine-2,4-dione, can be reacted with a suitably substituted isothiocyanate (reagent B), such as, for example, phenylisothiocyanate, in a suitable solvent system, such as, for example, acetonitrile or THF, in the presence of a suitable base, such as, for example, triethylamine or DBU, at temperatures ranging from −78° C. to +100° C. Preferably the reaction is carried out at 0° C. or +100° C. to furnish compounds of general formula 1-1. Similar reactions have been performed in the literature (D. E. Worrall, J. Am. Chem. Soc., 1940, 62, 675).

Intermediates of general formula 1-1 can be converted to Intermediates of general formula 1-2 by reaction with a suitable amine, such as, for example 4-(aminomethyl)pyridin-2-amine, in a suitable solvent system, such as, for example, ethanol and ethyl acetate or N,N-dimethylacetamide, at a temperature between room temperature and the boiling point of the respective solvents, preferably the reaction is carried out at the boiling point of the respective solvents, whereby the water formed in the reaction can be removed from the reaction by methods known to those skilled in the art, such as, for example, azeotropic removal of water (Dean-Stark conditions) or with molecular sieves, to furnish intermediates of general formula 1-2. Alternatively the reaction can be carried out in a sealed tube or in a microwave oven at a temperature between room temperature and the boiling point of the respective solvents or at a temperature slightly above the boiling point of the respective solvents.

Intermediates of general formula 1-2 are reacted with a base and/or oxidizing reagent, preferably an oxidizing agent, such as, for example hydrogen peroxide, SIBX (stabilized iodoxybenzoic acid or mCPBA, in a suitable solvent system, such as, for example, methanol, in a temperature range from −30° C. to the boiling point of the respective solvent which may contain an acid like for example TFA. Preferably the reaction is carried out at the boiling point of the respective solvent, to furnish intermediates of general formula 1-3.

Intermediates of general formula 1-3 can be subjected to a peptide coupling by reaction with a carboxylic acid of formula Y—X—(=O)OH, in which X and Y are as defined for compounds of general formula (I), in the presence of a peptide coupling reagent, selected from HATU (O-(7-azabenzotriazol-1-yl)-N,N,N',N'-tetramethyluronium hexafluorophosphate), TBTU (O-(benzotriazol-1-yl)-N,N,N',N'-tetramethyluronium tetrafluoroborate), PyBOP (benzotriazol-1-yl-oxytripyrrolidinophosphonium hexafluorophosphate), or T3P (2,4,6-tripropyl-1,3,5,2,4,6-trioxatriphosphinane 2,4,6-trioxide), all of them being well known to the person skilled in the art and all of them being commercially available, in the presence of a base such as a tertiary aliphatic amine of the formula $N(C_1-C_4-alkyl)_3$, or sodium bicarbonate, or potassium carbonate, in an appropriate solvent such as N,N-dimethylformamide, N,N-dimethylacetamide, dimethylsulfoxide, THF, dichloromethane or N-methyl pyrrolidin-2-one in a temperature range from 0° C. to the boiling point of the respective solvent to furnish compounds of general formula (I). Specific examples are described in the Experimental Section.

Scheme 2

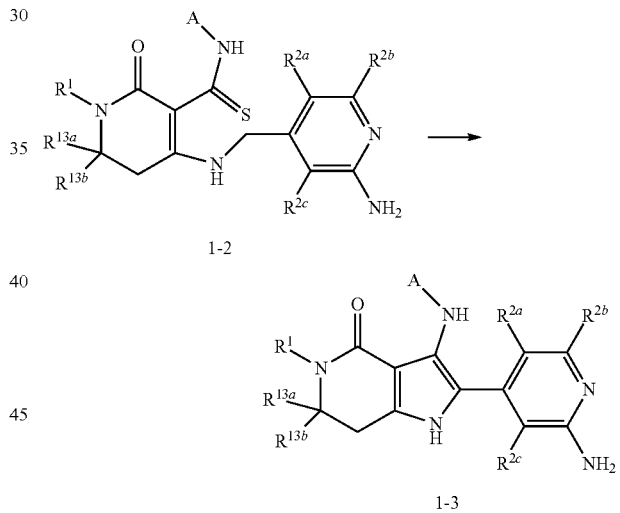

Scheme 2: Route for the preparation of compounds of general formula 1-3, wherein $R^1$, $R^{2a}$, $R^{2b}$, $R^{2c}$, $R^{13a}$, $R^{13b}$ and A have the meaning as given for general formula (I), supra.

Intermediates of general formula 1-2 are reacted under dehydrogenation conditions, such reactions are known (J. H. Hutchinson, et al., J. Med. Chem., 1996, 39, 4583-4591, N. L. Subasinghe, et al., Bioorg. Med. Chem. Lett., 2013, 23, 1063-1069, C. F. Jones, et al., Synlett, 2010, 654-658, M. Noguchi, et al., Bull. Chem. Soc. Japan, 1986, 59, 1355-1362). These conditions can be carried out using, for example, metal catalysis such as, for example, palladium on charcoal, in a suitable solvent system, such as, for example, dimethylacetamide, in a temperature range from 0° C. to 200° C. of the respective solvent, preferably at elevated temperatures, to furnish compounds of general formula 1-3.

Scheme 3

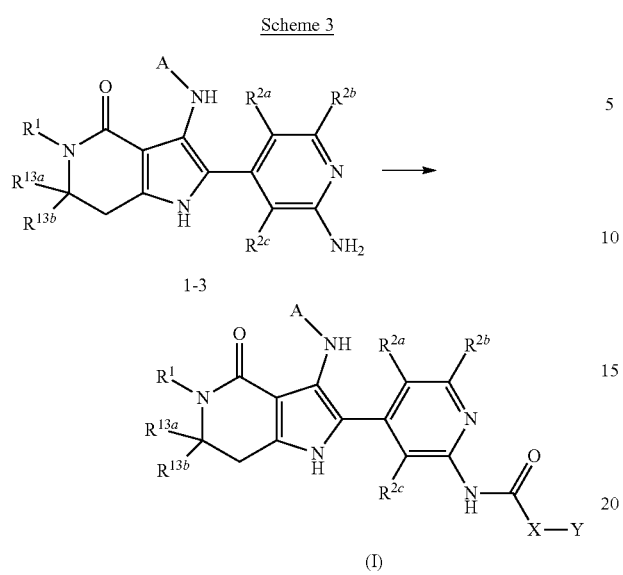

Scheme 3: Route for the preparation of compounds of general formula (I), wherein $R^1$, $R^{2a}$, $R^{2b}$, $R^{2c}$, $R^{13a}$, $R^{13b}$, A, X and Y have the meaning as given for general formula (I), supra. In addition, interconversion of any of the substituents, $R^1$, $R^{2a}$, $R^{2b}$, $R^{2c}$, $R^{13a}$, $R^{13b}$, A, X and Y can be achieved before and/or after the exemplified transformation.

Intermediates of general formula 1-3 are reacted with an acylating reagent, an acylating agent which can be generated in situ, to furnish compounds of general formula (I). These types of reactions are well-known (selected literature examples are: S. Miwatashi, et al., J. Med. Chem., 2005, 48, 5966-5979; J. Zhao, et al., Bioorg. Med. Chem. Lett., 2014, 24, 2802-2806; M. P. Hay, et al., J. Med. Chem., 2010, 53, 787-797; J. M. Keith, et al., Med. Chem. Lett, 2012, 3, 823-827; J. Liang, et al., Eur. J. Med. Chem., 2013, 67, 175-187).

Not-limiting examples of these types of reagents are:
i) carboxylic acids with dehydrating reagents typically used in amide bond formation, such as, for example (HBTU, HATU, PyBOP, BOP, T3P, EDC, DIC, DCC)
ii) acid fluorides, acid chlorides or acid bromides, preferably in the presence of a base
iii) acid anhydrides of the general formulae

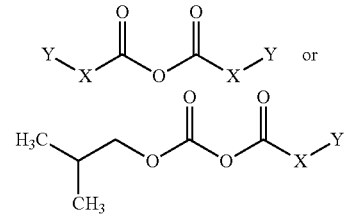

preferably in the presence of a base

Said acylating agent can be in a protected form, containing a protecting group like Boc for example leading to a protected form of compounds of general formula (I) which furnishes compounds of general formula (I) after an additional deprotection step. Further protecting groups are well known to the person skilled in the art. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

Scheme 4

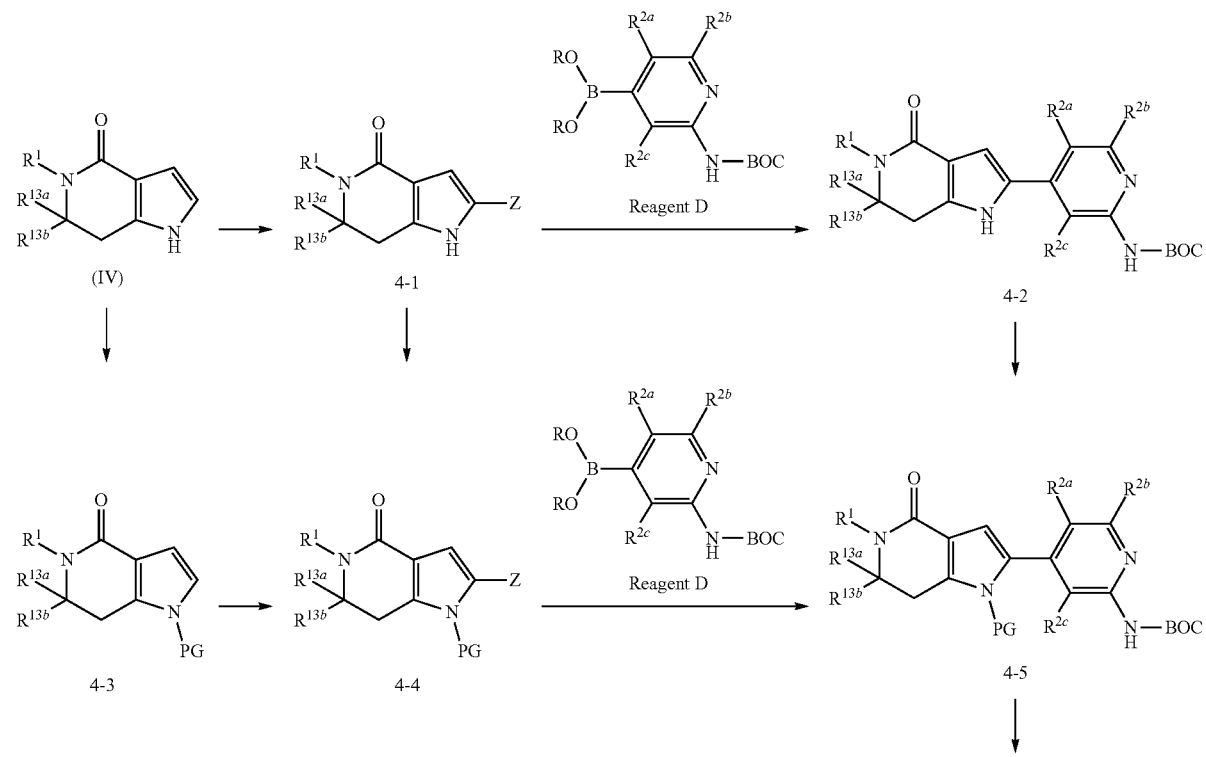

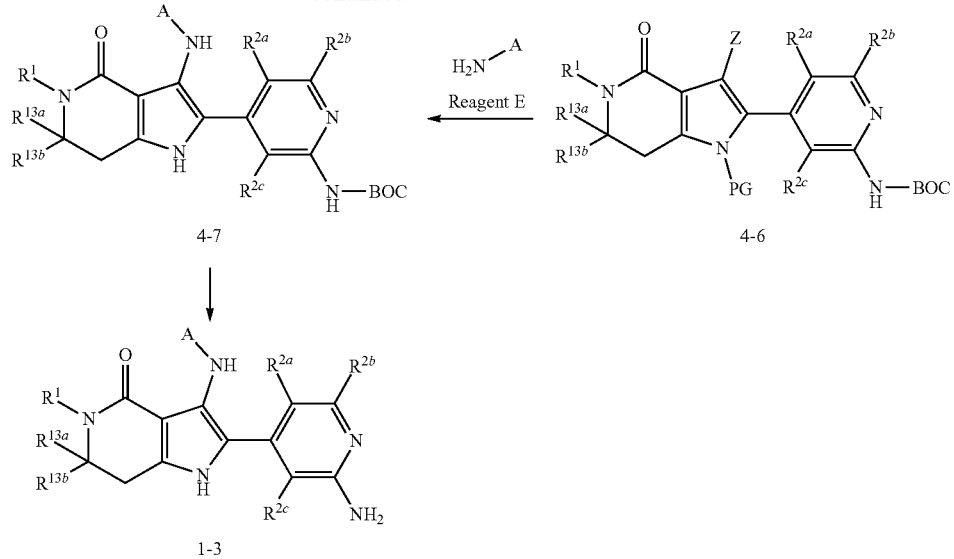

4-7            4-6

1-3

Scheme 4: Route for the preparation of compounds of general formula (I), wherein $R^1$, $R^{2a}$, $R^{2b}$, $R^{2c}$, $R^{13a}$, $R^{13b}$ and A have the meaning as given for general formula (I), supra. BOC represents a Boc-protecting group. PG is a suitable protecting group like for example SEM, Tosyl, paramethoxy-benzyl or Boc. In addition, interconversion of any of the substituents, $R^1$, $R^{2a}$, $R^{2b}$, $R^{2c}$, $R^{13a}$, $R^{13b}$ and A can be achieved before and/or after the exemplified transformation. The R in reagent D can be hydrogen to represent boronic acids or alkyl groups to represent boronic esters, optionally both R groups can be attached to each other to represent, for example, pincacol boronic esters. The substituent Z in the intermediates of general formulae 4-1, 4-4 and 4-6 can be a suitable leaving group, such as, for example, Cl, Br, I, aryl sulfonates such as for example p-toluene sulfonate, or alkyl sulfonates such as for example methane sulfonate or trifluoromethane sulfonate.

These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wutts in Protective Groups in Organic Synthesis, 3rd edition, Wiley 1999). Specific examples are described in the subsequent paragraphs. Intermediates of general formula (IV) are commercially available or are reported in the public domain, see the teachings of, for example, Menichincheri et al., WO2014/72220 A1; Clark et al., J. Heterocyclic Chem., 1993, 30, 829-831; Clark et al., J. Med. Chem., 1993, 36, 2645-2657; Schneller et al., J. Med. Chem., 1978, 21, 990-993.

Intermediates of general formula (IV) or intermediates of the formula 4-3 can be reacted to introduce a substituent Z, which is preferably a halide, such reactions are known to those skilled in the art (see Menichincheri et al., WO2014/72220 A1 (introduction of bromide and iodide); Smith et al., Bioorg. Med. Chem. Lett., 2007, 17, 673-678 (introduction of bromide) Cee et al., WO2014/22752 A1 (introduction of bromide)) to furnish intermediates of the formula 4-1 from formula (IV) or intermediates of the formula 4-4 from formula 4-3.

Intermediates of general formula (IV), of formula 4-1 or of formula 4-2 can be reacted to introduce the PG group, such as, for example, a Tosyl-group or a SEM-group via alkylation under basic conditions (Marchionni et al., WO2009/40399 A1, also see for example T. W. Greene and P. G. M. Wutts in Protective Groups in Organic Synthesis, 3rd edition, Wiley 1999) or a tert-butoxycarbonyl (Boc) group (Kim et al., WO2013/62344 A1; Voss et al., WO2015/22073 A1) to furnish intermediates of the formula 4-3 from general formula (IV) or intermediates of the formula 4-4 from formula 4-1 or intermediates of the formula 4-5 from formula 4-2.

Intermediates of general formula 4-1 or intermediates of the formula 4-4 can be reacted with reagent D to introduce the substituted pyridinyl substituent, using metal-catalyzed reactions, such as, for example, the Suzuki reaction. Such reactions are known to those skilled in the art (WO2007/39740 A2; Cee et al., WO2014/22752 A1; Smith et al., Bioorg. Med. Chem. Lett., 2007, 17, 673-678) and can be used to furnish intermediates of the formula 4-2 from general formula 4-1 or intermediates of the formula 4-5 from formula 4-4.

Intermediates of general formula 4-5 can be reacted with a suitable halogenating reagent, such as, for example, copper (I) bromide and N-bromosuccinimide, preferably N-bromosuccinimide, in a suitable solvent system, such as, for example, acetonitrile, in a temperature range from 0° C. to the boiling point of the respective solvent, preferably the reaction is carried out at room temperature, to furnish general formula 4-6. Similar examples for the bromination of pyrroles have been previously published using lactams (Aiello, E. et al., J. Heterocyclic Chem., 1982, 19, 977-979; Duranti, A. et al., Bioorg. Med. Chem., 2003, 11, 3965-3973).

Intermediates of general formula 4-6 can be reacted with a suitable primary amines, such as, for example, primary aromatic amines and primary amines, preferably primary aromatic amines, such as, for example aniline or 3-aminothiophene, in the presence of a base, such as, for example, lithium bis(trimethylsilyl)amide (LHMDS), in the presence of a catalyst, such as, for example a suitable ligand, preferably 2-(di-tert-butylphosphino)-2',4',6'-triisopropyl-3,6-dimethoxy-1,1'-biphenyl (tBuBrettPhos) and in the presence of a pre-catalyst, such as, for example a palladium pre-catalyst, preferably chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct) in a suitable solvent system, such as, for example, tetrahydrofuran (THF), in a temperature range from 0° C. to the 200° C., preferably the reaction is carried out at 80° C., to furnish compounds of general formula 4-7.

Intermediates of general formula 4-7 can be subjected to reaction conditions for the removal of protecting groups to furnish intermediates of general formula 1-3, such as for example acidic conditions for the removal of a Boc group and TBAF for the removal of a SEM group. A comprehensive overview of conditions for possible protecting groups is outlined for example in T. W. Greene and P. G. M. Wutts in Protective Groups in Organic Synthesis, 3rd edition, Wiley 1999). In general, the PG group can be removed first or the Boc group can be removed first or both protecting groups could be selected in a way that they can be removed simultaneously.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC may be applied. The compounds of the present invention which possess a sufficiently basic or acidic functionality, may result as a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of the compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, free acid, solvate, inclusion complex) of a compound of the present invention as isolated and described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds or optically active catalysts in synthesis or by separating enantiomeric and diasteriomeric mixtures obtained in synthesis.

Enantiomeric and diastereomeric mixtures can be separated into the pure enantiomers and pure diastereomers by methods known to the person skilled in the art. Preferably, diastereomeric mixtures are separated by crystallization, in particular fractional crystallization, or chromatography. Enantiomeric mixtures can be separated e.g. by forming diastereomers with a chiral auxillary agent, resolving the diastereomers obtained and removing the chiral auxillary agent. As chiral auxillary agents, for example, chiral acids can be used to separate enantiomeric bases such as e.g. mandelic acid and chiral bases can be used to separate enantiomeric acids by formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxillary agents. Additionally, diastereomeric complexes or diastereomeric clathrates may be used for separating enantiomeric mixtures. Alternatively, enantiomeric mixtures can be separated using chiral separating columns in chromatography. Another suitable method for the isolation of enantiomers is the enzymatic separation.

One preferred aspect of the invention is the process for the preparation of the compounds of claims 1 to 4 according to the examples as well as the intermediates used for their preparation.

The intermediates used for the synthesis of the compounds of claims of formula (I) as described herein, as well as their use for the synthesis of the compounds of formula (I), are one further aspect of the present invention. Preferred intermediates are the Intermediate Examples as disclosed herein.

Optionally, compounds of the formula (I) can be converted into their salts, or, optionally, salts of the compounds of the formula (I) can be converted into the free compounds. Corresponding processes are customary for the skilled person.

Commercial Utility

As mentioned supra, the compounds of the present invention have surprisingly been found to effectively inhibit Casein kinase 1 alpha and/or delta finally resulting in cell death e.g. apoptosis and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Casein kinase 1 alpha and/or delta, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g. thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumors in said organs and corresponding secondary tumors in distant organs ("tumor metastases"). Haematological tumors can e.g. be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

The term "inappropriate" within the context of the present invention, in particular in the context of "inappropriate cellular immune responses, or inappropriate cellular inflammatory responses", as used herein, is to be understood as preferably meaning a response which is associated with, responsible for, or results in, the pathology of said diseases.

Preferably, the use is in the treatment or prophylaxis of diseases, especially the treatment, wherein the diseases are haematological tumours, solid tumours and/or metastases thereof. Another aspect is the use of a compound of formula (I) for the prophylaxis and/or treatment of cervical tumours, lung tumours (such as lung carcinoma), colon tumours (such as colorectal carcinoma), or lymphoma (such as diffuse large B-cell lymphoma) and/or metastases thereof, especially preferred for the treatment thereof.

Another aspect of the present invention is the use of a compound of formula (I) or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease, wherein such disease is a hyperproliferative disorder or a disorder responsive to induction of cell death e.g. apoptosis. In an embodiment the disease is a haematological tumour, a solid tumour and/or metastases thereof. In another embodiment the disease is a cervical tumour, a lung tumour (such as lung carcinoma), a colon tumour (such as colorectal carcinoma), or a lymphoma (such as diffuse large B-cell lymphoma and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as cancer.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes.

Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels.

These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death, e.g., apoptosis, of such cell types.

Preferably, the diseases of said method are haematological tumours, solid tumour and/or metastases thereof.

The compounds of the present invention can be used in particular in therapy and prevention, e.g., prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haematological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include, but are not limited to acetic acid, citric acid, fumaric acid, hydrochloric acid, nitric acid);

alkalinizing agents (examples include, but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include, but are not limited to powdered cellulose and activated charcoal);

aerosol Propellants (examples include, but are not limited to carbon dioxide, $CCl_2F_2$, $F_2ClC$—$CClF_2$ and $CClF_3$);

air displacement agents—examples include, but are not limited to nitrogen and argon;

antifungal preservatives (examples include, but are not limited to benzoic acid, butylparaben, ethylparaben, methylparaben, propylparaben, sodium benzoate);

antimicrobial preservatives (examples include, but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include, but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include, but are not limited to block polymers, natural and synthetic rubber, polyacrylates, polyurethanes, silicones, polysiloxanes and styrene-butadiene copolymers);

buffering agents (examples include, but are not limited to potassium metaphosphate, dipotassium phosphate, sodium acetate, sodium citrate anhydrous and sodium citrate dihydrate);

carrying agents (examples include, but are not limited to acacia syrup, aromatic syrup, aromatic elixir, cherry syrup, cocoa syrup, orange syrup, corn oil, mineral oil, peanut oil, sesame oil, bacteriostatic sodium chloride injection and bacteriostatic water for injection);

chelating agents (examples include, but are not limited to edetate disodium and edetic acid);

colourants (examples include, but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include, but are not limited to bentonite);

emulsifying agents (examples include, but are not limited to acacia, cetomacrogol, cetyl alcohol, glyceryl monostearate, lecithin, sorbitan monooleate, polyoxyethylene 50 monostearate);

encapsulating agents (examples, include but are not limited to gelatin and cellulose acetate phthalate);

flavourants (examples include, but are not limited to anise oil, cinnamon oil, cocoa, menthol, orange oil, peppermint oil and vanillin);

humectants (examples include, but are not limited to glycerol, propylene glycol and sorbitol);

levigating agents (examples include, but are not limited to mineral oil and glycerin);

oils (examples include, but are not limited to arachis oil, mineral oil, olive oil, peanut oil, sesame oil and vegetable oil);

ointment bases (examples include, but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include, but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include, but are not limited to diethyl phthalate and glycerol);

solvents (examples include, but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include, but are not limited to cetyl alcohol, cetyl esters wax, microcrystalline wax, paraffin, stearyl alcohol, white wax and yellow wax);

suppository bases (examples include, but are not limited to cocoa butter and polyethylene glycols (mixtures));

surfactants (examples include, but are not limited to benzalkonium chloride, nonoxynol 10, oxtoxynol 9, polysorbate 80, sodium lauryl sulfate and sorbitan mono-palmitate);

suspending agents (examples include, but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include, but are not limited to aspartame, dextrose, glycerol, mannitol, propylene glycol, saccharin sodium, sorbitol and sucrose);

tablet anti-adherents (examples include, but are not limited to magnesium stearate and talc);

tablet binders (examples include, but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include, but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include, but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include, but are not limited to dibasic calcium phosphate);

tablet disintegrants (examples include, but are not limited to alginic acid, carboxymethylcellulose calcium, microcrystalline cellulose, polacrillin potassium, crosslinked polyvinylpyrrolidone, sodium alginate, sodium starch glycollate and starch);

tablet qlidants (examples include, but are not limited to colloidal silica, corn starch and talc);

tablet lubricants (examples include, but are not limited to calcium stearate, magnesium stearate, mineral oil, stearic acid and zinc stearate);

tablet/capsule opaquants (examples include, but are not limited to titanium dioxide);

tablet polishing agents (examples include, but are not limited to carnuba wax and white wax);

thickening agents (examples include, but are not limited to beeswax, cetyl alcohol and paraffin);

tonicity agents (examples include, but are not limited to dextrose and sodium chloride);

viscosity increasing agents (examples include, but are not limited to alginic acid, bentonite, carbomers, carboxymethylcellulose sodium, methylcellulose, polyvinyl pyrrolidone, sodium alginate and tragacanth); and wetting agents (examples include, but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. solution: A 5 mg/mL solution of the desired compound of this invention can be made using sterile, injectable water, and the pH is adjusted if necessary. The solution is diluted for administration to 1-2 mg/mL with sterile 5% dextrose and is administered as an i.v. infusion over about 60 minutes.

Lyophilised powder for i.v. administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haematological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (h) as disclosed by the specific examples.

The term "according to" within the experimental section is used in the sense that the procedure referred to is to be used "analogously to".

EXPERIMENTAL PART

Table 1 lists the abbreviations used in this paragraph and in the Intermediates and Examples sections as far as they are not explained within the text body.

TABLE 1

| Abbreviation | Meaning |
|---|---|
| AcOH | acetic acid (ethanoic acid) |
| aq. | aqueous |
| Boc | t-butoxycarbonyl |
| BOP | (benzotriazol-1-yloxy)tris(dimethylamino)phosphonium hexafluorophosphate |
| br | broad |
| CI | chemical ionisation |
| $Cs_2CO_3$ | caesium carbonate |
| d | doublet |
| DAD | diode array detector |
| DBU | 1,8-diazabicyclo(5.4.0)undec-7-ene |
| DCC | N,N'-dicyclohexylcarbodiimide |
| DCM | dichloromethane |
| dd | double-doublet |
| DIC | N,N'-diisopropylcarbodiimide |
| DIPEA | diisopropylethylamine |
| DMA | Dimethylacetamide |
| DMAP | N,N-dimethylpyridin-4-amine |
| DME | 1,2-dimethoxyethane |
| DMF | N,N-dimethylformamide |
| DMSO | dimethyl sulfoxide |
| dt | double-triplet |
| EDC | 1-ethyl-3-(3-dimethylaminopropyl)carbodiimide |
| ELSD | Evaporative Light Scattering Detector |
| EtOAc | ethyl acetate |
| EtOH | ethanol |
| eq. | equivalent |
| ESI | electrospray (ES) ionisation |
| h | hour |
| HATU | 1-[bis(dimethylamino)methylene]-1H-1,2,3-triazolo[4,5-b]pyridinium 3-oxid hexafluorophosphate |
| HBTU | (o-benzotriazole-10yl)-N,N,N',N,-tetramethyluronium hexafluorophosphate |
| HCl | hydrochloric acid |
| HPLC | high performance liquid chromatography |
| $K_2CO_3$ | potassium carbonate |
| LC-MS | liquid chromatography mass spectrometry |
| LDA | Lithium diisopropylamide |
| m | multiplet |
| mCPBA | meta-Chloroperbenzoic acid |
| min | minute |
| MeCN | acetonitrile |
| MeOH | methanol |
| MS | mass spectrometry |

TABLE 1-continued

| Abbreviation | Meaning |
| --- | --- |
| MTBE | methyl-tert-butyl ether |
| NaCl | sodium chloride |
| NaHCO$_3$ | sodium hydrogen carbonate or sodium bicarbonate |
| NMR | nuclear magnetic resonance spectroscopy: chemical shifts (δ) are given in ppm. The chemical shifts were corrected by setting the DMSO signal to 2.50 ppm unless otherwise stated. |
| PDA | Photo Diode Array |
| Pd/C | palladium on activated charcoal |
| PyBOP | (benzotriazol-1-yloxy)tripyrrolidinophosphonium hexafluorophosphate |
| q | quartet |
| r.t. or rt or RT | room temperature |
| Rt | retention time (as measured either with HPLC or UPLC) in minutes |
| s | singlet |
| sat. | saturated |
| SIBX | stabilized 2-iodoxybenzoic acid |
| SM | starting material |
| SQD | Single-Quadrupole-Detector |
| T3P | propylphosphonic anhydride |
| t | triplet |
| td | triple-doublet |
| TEA | triethylamine |
| TFA | trifluoroacetic acid |
| THF | tetrahydrofuran |
| UPLC | ultra performance liquid chromatography |

Other abbreviations have their meanings customary per se to the skilled person.

The various aspects of the invention described in this application are illustrated by the following examples which are not meant to limit the invention in any way.

Specific Experimental Descriptions

NMR peak forms in the following specific experimental descriptions are stated as they appear in the spectra, possible higher order effects have not been considered.

Reactions employing microwave irradiation may be run with a Biotage Initiator® microwave oven optionally equipped with a robotic unit. The reported reaction times employing microwave heating are intended to be understood as fixed reaction times after reaching the indicated reaction temperature.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example pre-packed silica gel cartridges, e.g. from Separtis such as Isolute® Flash silica gel or Isolute® Flash NH$_2$ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula and introduced into reaction vessels through rubber septa. Commercial grade reagents and solvents were used without further purification. The term "concentrated in vacuo" refers to the use of a Buchi rotary evaporator at a minimum pressure of approximately 15 mm of Hg. All temperatures are reported uncorrected in degrees Celsius (° C.). In order that this invention may be better understood, the following examples are set forth. These examples are for the purpose of illustration only, and are not to be construed as limiting the scope of the invention in any manner. All publications mentioned herein are incorporated by reference in their entirety.

Analytical Conditions

UPLC-MS Standard Procedures

UPLC-MS-data given in the subsequent specific experimental descriptions refer (unless otherwise noted) to the following conditions:

Method 1:

| | |
| --- | --- |
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.1% vol. formic acid (99%) B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μL |
| Detection: | DAD scan range 210-400 nm MS ESI+, ESI−, scan range 160-1000 m/z ELSD |

Method 2:

| | |
| --- | --- |
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.2% vol. ammonia (32%) B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μL |
| Detection: | DAD scan range 210-400 nm MS ESI+, ESI−, scan range 160-1000 m/z ELSD |

Preparative HPLC Conditions

"Purification by preparative HPLU" in the subsequent experimental descriptions refers to the following conditions (unless otherwise noted):

Preparative HPLC (Method Acidic):

| System: | Waters Autopurificationsystem: |
| --- | --- |
| | Pump 2545, Sample Manager 2767, |
| | CFO, DAD 2996, ELSD 2424, SQD 3001 |
| Column: | XBridge C18 5 μm 100 × 30 mm |
| Solvent: | A = water + 0.1% vol. formic acid (99%) |
| | B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sufoxide or DMF |
| Injection: | 1 × 2.5 mL |
| Detection: | DAD scan range 210-400 nm |
| | MS ESI+, ESI−, scan range 160-1000 m/z |

Preparative HPLC (Method Basic):

| System: | Waters Autopurificationsystem: |
| --- | --- |
| | Pump 2545, Sample Manager 2767, |
| | CFO, DAD 2996, ELSD 2424, SQD 3001 |
| Column: | XBridge C18 5 μm 100 × 30 mm |
| Solvent: | A = water + 0.2% vol. ammonia (32%) |
| | B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sufoxide or DMF |
| Injection: | 1 × 2.5 mL |
| Detection: | DAD scan range 210-400 nm |
| | MS ESI+, ESI−, scan range 160-1000 m/z |

Flash Column Chromatography Conditions

"Purification by (flash) column chromatography" as stated in the subsequent specific experimental descriptions refers to the use of a Biotage Isolera purification system. For technical specifications see "Biotage product catalogue" on www.biotage.com.

Chemical names were generated using the ACD/Name software from ACD/Labs. In some cases generally accepted names of commercially available reagents were used in place of ACD/Name generated names.

Optical rotations were measured using a JASCO P2000 Polarimeter. Typical, a solution of the compound with a concentration of 1 mg/mL to 15 mg/mL was used for the measurement. The specific rotation $[\alpha]_D$ was calculated according to the following formula:

$$[\alpha]D = \frac{\alpha}{\beta \times d}$$

In this equation, a is the measured rotation in degrees; d is the path length in decimeters and β is the concentration in g/mL.

Experimental Section—Intermediates

Intermediate 1

4-hydroxy-1-methyl-2-oxo-N-phenyl-1,2,5,6-tetrahydropyridine-3-carbothioamide

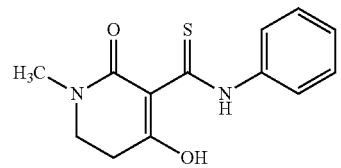 [SMILES: CN1CCC(O)=C(C(=S)Nc2ccccc2)C1=O]

To an ice-cooled mixture of 1-methylpiperidine-2,4-dione (5.00 g, 39.3 mmol) (CAS-RN: 118263-97-1) and isothiocyanatobenzene (4.7 mL, 39 mmol) in acetonitrile (53 mL) was slowly added DBU (9.4 mL, 63 mmol) and the mixture was stirred at r.t. for 16 h. The reaction was poured into ice-water containing concentrated hydrochloric acid (10 mL). The mixture was extracted with ethyl acetate. The organic phase was washed with saturated sodium chloride solution, dried (sodium sulfate), filtered and the solvent was removed in vacuum. Silicagel chromatography (20-60% ethyl acetate/hexane) gave 9.84 g (95% yield) of the title compound as a crude product, that was used without further purification.

LC-MS (Method 1): $R_t$=1.23 min; MS (ESIneg): m/z=253.3 [M−H]−

$^1$H-NMR (400 MHz, DMSO-d6) δ [ppm]: 1.985 (0.63), 1.987 (0.66), 2.667 (0.49), 2.803 (2.63), 2.820 (4.96), 2.838 (2.74), 2.962 (16.00), 3.099 (0.63), 3.332 (9.71), 3.333 (10.46), 3.451 (2.85), 3.469 (5.14), 3.487 (2.64), 5.756 (1.37), 5.758 (1.41), 7.290 (1.30), 7.304 (1.86), 7.309 (1.89), 7.318 (1.34), 7.418 (1.98), 7.440 (7.89), 7.452 (12.48), 14.570 (2.62), 16.485 (4.87).

Intermediate 2

4-{[(2-aminopyridin-4-yl)methyl]amino}-1-methyl-2-oxo-N-phenyl-1,2,5,6-tetrahydropyridine-3-carbothioamide

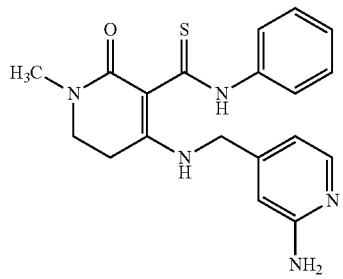 [SMILES: CN1CCC(NCc2ccnc(N)c2)=C(C(=S)Nc2ccccc2)C1=O]

A stirred solution of 4-hydroxy-1-methyl-2-oxo-N-phenyl-1,2,5,6-tetrahydropyridine-3-carbothioamide (10.6 g, 40.6 mmol) and 4-(aminomethyl)pyridin-2-amine (27.0 g, 74% purity, 162 mmol) (CAS-RN: 199296-51-0) in DMA (110 mL) distributed to 8 20-mL-microwave tubes was heated to 130° C. for 1 h. A half-saturated solution of potassium carbonate was added and the mixture was extracted with ethyl acetate. The organic phase was washed with half-saturated sodium chloride solution, dried (sodium sulfate), filtered and the solvent was removed in vacuum. Silicagel chromatography gave a solid that was triturated with a dichloromethane to give 4.10 g (28% yield) of the title compound as a crude product, that was used without further purification.

LC-MS (Method 1): $R_t$=0.83 min; MS (ESIpos): m/z=368.6 [M+H]$^+$ $^1$H-NMR (400 MHz, DMSO-d6) δ [ppm]: 1.154 (0.48), 1.172 (1.01), 1.190 (0.51), 1.988 (1.85), 2.518 (0.93), 2.523 (0.61), 2.716 (1.34), 2.734 (2.54), 2.750 (1.45), 2.935 (13.17), 3.304 (1.58), 3.321 (2.91), 3.333 (16.00), 4.017 (0.40), 4.557 (2.74), 4.572 (2.70), 6.003 (3.82), 6.332 (2.92), 6.402 (1.62), 6.405 (1.48), 6.416 (1.64), 6.419 (1.51), 7.166 (0.75), 7.184 (1.76), 7.203 (1.12), 7.339 (1.92), 7.359 (3.50), 7.373 (0.83), 7.378 (2.63), 7.425 (3.50), 7.443 (2.24), 7.859 (2.41), 7.872 (2.33), 13.631 (0.80), 14.697 (1.88).

Intermediate 3

2-(2-aminopyridin-4-yl)-3-anilino-5-methyl-1,5,6,7-tetrahydro-4H-pyrrolo[3,2-c]pyridin-4-one

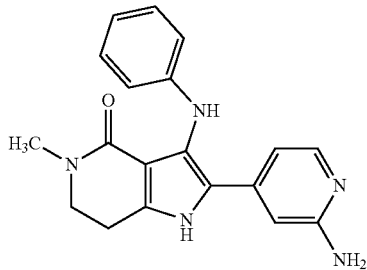 [SMILES: CN1CCc2[nH]c(-c3ccnc(N)c3)c(Nc3ccccc3)c2C1=O]

A stirred solution of 4-{[(2-aminopyridin-4-yl)methyl]amino}-1-methyl-2-oxo-N-phenyl-1,2,5,6-tetrahydropyridine-3-carbothioamide (1.10 g, 2.99 mmol) and hydrogen peroxide (30% in water, 610 μL, 6.0 mmol) in methanol (14 mL) was heated in a microwave tube to 90° C. for 2 h. An aqueous solution of disodium sulfurothioate and a half-saturated solution of potassium carbonate were added and the mixture was extracted with ethyl acetate. The organic phase was washed with half-saturated sodium chloride solution, dried (sodium sulfate), filtered and the solvent was removed in vacuum. Aminophase-silicagel chromatography followed by silicagel chromatography gave 535 mg (54% yield) of the title compound.

LC-MS (Method 1): $R_t$=0.73 min; MS (ESIpos): m/z=334.5 [M+H]$^+$ $^1$H-NMR (400 MHz, DMSO-d6) δ [ppm]: 2.518 (1.58), 2.523 (1.01), 2.853 (16.00), 2.882 (1.57), 2.899 (3.32), 2.916 (1.67), 3.377 (0.59), 3.507 (1.84), 3.524 (3.76), 3.542 (1.64), 5.657 (3.93), 5.759 (7.76), 6.547 (5.28), 6.549 (6.04), 6.568 (3.28), 6.570 (2.79), 6.595 (0.62), 6.597 (1.01), 6.600 (0.63), 6.616 (1.96), 6.634 (1.08), 6.670 (1.91), 6.674 (1.83), 6.684 (1.88), 6.688 (1.78), 7.003 (2.43), 7.022 (3.07), 7.025 (3.05), 7.043 (2.03), 7.223 (3.78), 7.720 (2.48), 7.733 (2.39), 11.520 (1.76).

Intermediate 4

Ethyl N-cyclopropyl-beta-alaninate

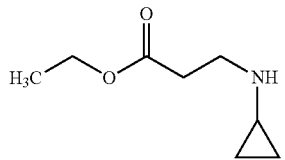

To an ice-cold solution of cyclopropanamine (7.1 mL, 100 mmol) in ethanol (100 mL) was slowly added ethyl prop-2-enoate (11 mL, 100 mmol) and the mixture was stirred at r.t. for 2 h. The solvent was removed in vacuum to give 16.0 g of the title compound as a crude product, that was used for the next step without purification.

Intermediate 5

Ethyl N-cyclopropyl-N-(3-ethoxy-3-oxopropanoyl)-beta-alaninate

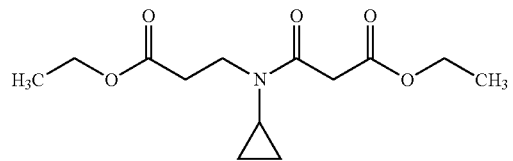 [SMILES: CCOC(=O)CCN(C(=O)CC(=O)OCC)C1CC1]

To an ice-cold solution of ethyl N-cyclopropyl-beta-alaninate (12.9 g, 82.1 mmol) in dichloromethane (83 mL) was added N,N-diisopropylethylamine (16 mL, 90 mmol) and DMAP (1.00 g, 8.21 mmol). Then ethyl 3-chloro-3-oxopropanoate (12 mL, 90 mmol) was added while monitoring that the temperature maintained below 15° C. The mixture was stirred at 0° C. for 30 min and at r.t. for 16 h. A half-saturated solution of ammonium chloride (200 mL) was added, the mixture was stirred for 15 minutes, and the mixture was extracted with dichloromethane. The organic phase was dried (sodium sulfate), filtered and the solvent was removed in vacuum. Silicagel chromatography (20-100% ethyl acetate/hexane) gave 12.1 g of the title compound as a crude product, that was used without further purification.

LC-MS (Method 1): $R_t$=0.94 min; MS (ESIpos): m/z=272.2 [M+H]$^+$

Intermediate 6

Ethyl 1-cyclopropyl-2,4-dioxopiperidine-3-carboxylate

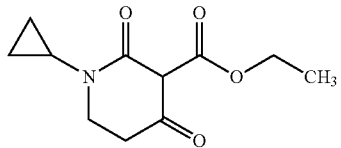 [SMILES: CCOC(=O)C1C(=O)CCN(C2CC2)C1=O]

To an ice-cold solution of sodium ethanolate (solution in ethanol, 17 mL, 21% w/w, 45 mmol) in ethanol (70 mL) was added a solution of ethyl N-cyclopropyl-N-(3-ethoxy-3-oxopropanoyl)-beta-alaninate (11.0 g, 40.5 mmol) in ethanol ethanol (7 mL) while monitoring that the temperature maintained below 5° C. The mixture was stirred at r.t. for 3 h. A solid precipitated, was collected by filtration and was dried in vacuum to give a first crop of the title compound. The remaining solution was concentrated in vacuum. Silicagel chromatography gave a solid that was recrystallized from ethanol to give a second crop of the title compound. Combined yield: 5.11 g (56% yield) of the title compound.

LC-MS (Method 1): $R_t$=0.81 min; MS (ESIpos): m/z=226.3 [M+H]$^+$ $^1$H-NMR (400 MHz, DMSO-d6) δ [ppm]: 0.396 (0.87), 0.409 (2.87), 0.414 (2.92), 0.419 (3.08), 0.424 (3.61), 0.435 (1.28), 0.546 (1.20), 0.557 (2.72), 0.563 (3.61), 0.575 (3.52), 0.580 (2.54), 0.592 (0.85), 1.035 (7.29), 1.052 (13.58), 1.070 (7.43), 1.101 (7.29), 1.119 (16.00), 1.136 (7.44), 1.988 (2.75), 2.003 (4.52), 2.020 (2.92), 2.444 (0.56), 2.454 (1.13), 2.461 (1.38), 2.471 (2.44), 2.482 (1.82), 2.518 (1.63), 2.523 (1.04), 3.027 (2.82), 3.043 (4.41), 3.059 (2.65), 3.404 (1.10), 3.417 (1.20), 3.421 (3.01), 3.435 (3.11), 3.439 (3.27), 3.452 (3.31), 3.457 (1.08), 3.469 (1.04), 3.882 (2.30), 3.899 (7.46), 3.917 (7.35), 3.935 (2.20), 4.350 (2.12), 4.363 (4.19), 4.375 (2.06).

Intermediate 7

1-cyclopropylpiperidine-2,4-dione

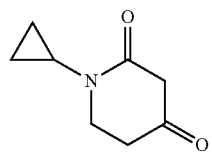 [SMILES: O=C1CCN(C2CC2)C(=O)C1]

To a stirred solution of ethyl 1-cyclopropyl-2,4-dioxopiperidine-3-carboxylate (3.20 g, 14.2 mmol) in dichloromethane (27 mL) was added aqueous hydrochloric acid (27 mL, 2.0 M, 54 mmol). The mixture was stirred at room temperature for 15 min. The mixture was extracted with further dichloromethane. The organic phase was dried (sodium sulfate), filtered and the solvent was removed in vacuum. The residue was dissolved in acetonitrile acetonitrile (36 mL) and water (400 μL) and the mixture was heated to reflux for 1 h. The solvent was removed in vacuum to give 1.81 g (83% yield) of the title compound as crude product that was used for the next step without purification.

LC-MS (Method 1): $R_t$=0.48 min; MS (ESIneg): m/z=152.1 [M−H]$^-$ $^1$H-NMR (400 MHz, DMSO-d6) δ [ppm]: 0.625 (13.33), 0.702 (12.75), 1.232 (0.63), 1.902 (0.77), 2.323 (3.66), 2.327 (4.43), 2.331 (3.66), 2.518 (10.17), 2.523 (7.50), 2.665 (3.03), 2.669 (3.89), 2.673 (3.34), 2.711 (4.56), 3.290 (16.00), 3.498 (10.94), 4.828 (0.86), 10.480 (0.45).

Intermediate 8

1-cyclopropyl-4-hydroxy-2-oxo-N-phenyl-1,2,5,6-tetrahydropyridine-3-carbothioamide

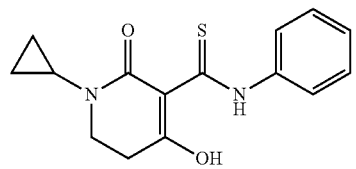 [SMILES: O=C1C(C(=S)Nc2ccccc2)=C(O)CCN1C1CC1]

To solution of 1-cyclopropylpiperidine-2,4-dione (1.80 g, 11.8 mmol) and isothiocyanatobenzene (1.4 mL, 12 mmol) in acetonitrile (16 mL) was slowly added DBU (2.8 mL, 19 mmol) and the mixture was stirred at r.t. for 16 h. The reaction was poured into ice-water containing concentrated hydrochloric acid (20 mL). The mixture was extracted with ethyl acetate. The organic phase was washed with saturated sodium chloride solution, dried (sodium sulfate), filtered and the solvent was removed in vacuum. Silicagel chromatography (20-60% ethyl acetate/hexane) gave 3.11 g (92% yield) of the title compound.

LC-MS (Method 1): $R_t$=1.32 min; MS (ESIpos): m/z=289.2 [M+H]$^+$ $^1$H-NMR (400 MHz, DMSO-d6) δ [ppm]: 0.653 (0.87), 0.674 (4.12), 0.682 (4.20), 0.693 (1.53), 0.709 (0.49), 0.721 (0.49), 0.727 (0.52), 0.747 (1.48), 0.759 (3.24), 0.764 (3.53), 0.777 (3.77), 0.795 (0.94), 0.840 (0.71), 1.987 (0.45), 2.518 (1.09), 2.522 (0.75), 2.615 (0.44), 2.713 (0.64), 2.723 (1.25), 2.731 (1.63), 2.741 (2.84), 2.748 (4.13), 2.765 (6.20), 2.782 (3.26), 3.390 (3.35), 3.407 (6.05), 3.425 (3.02), 3.554 (0.42), 7.275 (0.58), 7.293 (1.49), 7.302 (1.53), 7.308 (2.12), 7.315 (1.78), 7.324 (1.63), 7.389 (0.68), 7.422 (2.06), 7.443 (7.30), 7.453 (8.81), 7.459 (16.00), 7.473 (1.37), 14.529 (3.06), 16.502 (4.17).

Intermediate 9

4-{[(2-aminopyridin-4-yl)methyl]amino}-1-cyclopropyl-2-oxo-N-phenyl-1,2,5,6-tetrahydropyridine-3-carbothioamide

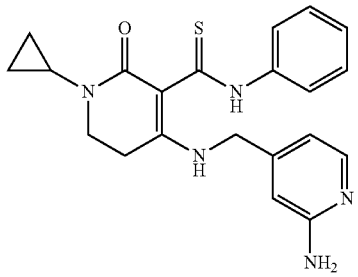 [SMILES: Nc1cc(CNC2=C(C(=S)Nc3ccccc3)C(=O)N(C3CC3)CC2)ccn1]

A stirred solution of 1-cyclopropyl-4-hydroxy-2-oxo-N-phenyl-1,2,5,6-tetrahydropyridine-3-carbothioamide (1.51 g, 5.24 mmol) and 4-(aminomethyl)pyridin-2-amine (2.61 g, 74% purity, 15.7 mmol) (CAS-RN: 199296-51-0) in N,N-dimethylacetamide (15 mL) was heated to 130° C. in a microwave for 1 h. A half-saturated solution of potassium carbonate was added and the mixture was extracted with ethyl acetate. The organic phase was washed with half-saturated sodium chloride solution, dried (sodium sulfate), filtered and the solvent was removed in vacuum. Silicagel chromatography (0-15% ethanol/dichloromethane) gave a solid that was triturated with a dichloromethane to give 396 mg (90% purity, 17% yield) of the title compound.

LC-MS (Method 1): $R_t$=0.89 min; MS (ESIpos): m/z=394.7 [M+H]$^+$ $^1$H-NMR (400 MHz, DMSO-d6) δ [ppm]: 0.610 (1.59), 0.617 (1.63), 0.628 (0.56), 0.699 (0.58), 0.711 (1.36), 0.717 (1.53), 0.729 (1.58), 2.658 (1.04), 2.674 (2.10), 2.690 (1.41), 2.704 (0.90), 2.713 (0.59), 2.722 (0.44), 3.233 (1.19), 3.249 (1.99), 3.266 (1.05), 4.541 (2.21), 4.555 (2.19), 5.755 (16.00), 5.998 (3.38), 6.321 (2.37), 6.393 (1.42), 6.396 (1.27), 6.406 (1.41), 6.409 (1.30), 7.171 (0.65), 7.174 (0.43), 7.189 (1.52), 7.205 (0.57), 7.207 (0.95), 7.210 (0.56), 7.343 (1.64), 7.347 (0.70), 7.363 (2.93), 7.377 (0.67), 7.382 (2.19), 7.433 (2.73), 7.451 (1.75), 7.854 (2.14), 7.866 (2.09), 13.627 (0.64), 14.695 (1.53).

Intermediate 10

2-(2-aminopyridin-4-yl)-3-anilino-5-cyclopropyl-1,5,6,7-tetrahydro-4H-pyrrolo[3,2-c]pyridin-4-one

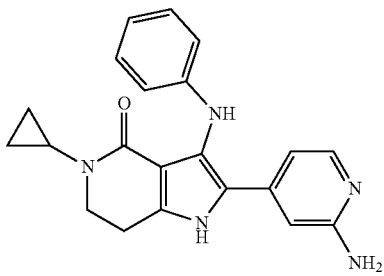 [SMILES: Nc1cc(-c2[nH]c3c(c2Nc2ccccc2)C(=O)N(C2CC2)CC3)ccn1]

A stirred solution of 4-{[(2-aminopyridin-4-yl)methyl]amino}-1-cyclopropyl-2-oxo-N-phenyl-1,2,5,6-tetrahydropyridine-3-carbothioamide (386 mg, 981 μmol) and hydrogen peroxide (30% in water, 200 μL, 2.0 mmol) in methanol (190 mL) was heated to 90° C. in a microwave for 4 h. An aqueous solution of disodium sulfurothioate and a half-saturated solution of potassium carbonate were added and the mixture was extracted with ethyl acetate. The organic phase was dried (sodium sulfate), filtered and the solvent was removed in vacuum. Aminophase-silicagel chromatography (0-25% ethanol/ethyl acetate) gave a solid that was triturated with dichloromethane to give 178 mg (50% yield) of the title compound.

LC-MS (Method 1): $R_t$=0.79 min; MS (ESIpos): m/z=360.7 [M+H]$^+$ $^1$H-NMR (400 MHz, DMSO-d6) δ [ppm]: 0.531 (0.54), 0.544 (1.75), 0.549 (1.93), 0.553 (2.07), 0.559 (2.25), 0.570 (0.78), 0.669 (0.73), 0.681 (1.80), 0.686 (2.16), 0.699 (2.17), 0.717 (0.52), 1.154 (4.57), 1.172 (9.31), 1.190 (4.49), 1.988 (16.00), 2.523 (1.25), 2.533 (1.38), 2.543 (0.79), 2.551 (0.65), 2.818 (1.36), 2.834 (2.89), 2.852 (1.49), 3.486 (1.61), 3.503 (3.19), 3.520 (1.43), 4.000 (1.23), 4.017 (3.70), 4.035 (3.61), 4.053 (1.15), 5.658 (3.97), 5.758 (3.62), 6.535 (2.86), 6.537 (2.93), 6.557 (3.16), 6.576 (3.34), 6.578 (2.72), 6.601 (0.63), 6.604 (0.98), 6.622 (2.04), 6.641 (1.10), 6.658 (2.00), 6.662 (1.85), 6.672 (1.89), 6.676 (1.90), 7.010 (2.53), 7.028 (3.17), 7.031 (3.08), 7.049 (2.05), 7.257 (3.95), 7.717 (2.61), 7.732 (2.49), 11.513 (1.87).

Intermediate 11

4-hydroxy-1-methyl-2-oxo-N-(pyridin-2-yl)-1,2,5,6-tetrahydropyridine-3-carbothioamide

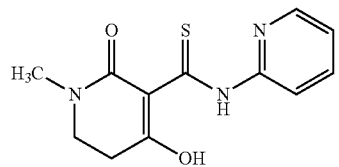 [SMILES: CN1CCC(O)=C(C(=S)Nc2ccccn2)C1=O]

To a stirred solution of 1H-imidazole (535 mg, 7.86 mmol) and di-1H-imidazol-1-ylmethanethione (10.5 g, 59.0 mmol) in THF (75 mL) was added pyridin-2-amine (3.70 g, 39.3 mmol), dissolved in THF (10 mL) at r.t. The mixture was stirred at 60° C. for 2 h and at r.t. for 16 h. To the stirred mixture 1-methylpiperidine-2,4-dione (5.00 g, 39.3 mmol) and trimethylamine (398 mg, 3.9 mmol) were added and the mixture was stirred at 65° C. for 24 h. The reaction mixture was concentrated in vacuum. Silicagel chromatography (20-100% ethyl acetate/hexane) of the residue gave 662 mg (6% yield) of the title compound.

LC-MS (Method 1): $R_t$=1.06 min; MS (ESIpos): m/z=264.6 [M+H]$^+$ $^1$H-NMR (400 MHz, DMSO-d6) δ [ppm]: 1.172 (0.41), 1.987 (0.83), 2.318 (0.49), 2.322 (1.09), 2.326 (1.47), 2.331 (1.11), 2.336 (0.49), 2.518 (5.87), 2.523 (3.75), 2.659 (0.80), 2.664 (1.42), 2.669 (1.91), 2.673 (1.53), 2.678 (0.96), 2.832 (3.08), 2.848 (5.01), 2.865 (3.02), 2.880 (1.32), 2.926 (0.47), 2.972 (16.00), 3.114 (0.78), 3.458 (3.36), 3.475 (5.79), 3.492 (3.36), 3.593 (0.49), 5.759 (0.72), 7.288 (2.17), 7.302 (2.71), 7.885 (1.94), 7.903 (2.97), 7.922 (1.58), 8.289 (3.33), 8.309 (2.69), 8.471 (3.62), 15.045 (2.95), 16.408 (4.11).

Intermediate 12

4-{[(2-aminopyridin-4-yl)methyl]amino}-1-methyl-2-oxo-N-(pyridin-2-yl)-1,2,5,6-tetrahydropyridine-3-carbothioamide

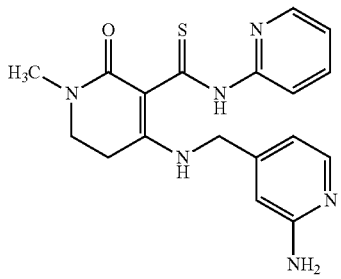

A stirred solution of 4-hydroxy-1-methyl-2-oxo-N-(pyridin-2-yl)-1,2,5,6-tetrahydropyridine-3-carbothioamide (330 g, 1.25 mol) and 4-(aminomethyl)pyridin-2-amine (626 g, 74% purity, 3.76 mol) (CAS-RN: 199296-51-0) in N,N-dimethylacetamide (3.0 mL) was heated to 130° C. in a microwave for 1 h. A half-saturated solution of potassium carbonate was added and the mixture was extracted with ethyl acetate. The organic phase was washed with half-saturated sodium chloride solution, dried (sodium sulfate), filtered and the solvent was removed in vacuum. Aminophase-silicagel chromatography followed by silicagel chromatography (0-15% ethanol/dichloromethane) gave 103 g (22% yield) of the title compound.

LC-MS (Method 1): $R_t$=0.61 min; MS (ESIpos): m/z=369.5 [M+H]$^+$ $^1$H-NMR (400 MHz, DMSO-d6) δ [ppm]: 2.518 (1.34), 2.523 (0.89), 2.745 (1.14), 2.762 (2.20), 2.778 (1.28), 2.946 (15.88), 3.307 (1.38), 3.325 (3.05), 3.331 (16.00), 3.340 (1.60), 4.594 (2.39), 4.609 (2.40), 6.014 (3.22), 6.338 (2.37), 6.415 (1.45), 6.419 (1.45), 6.428 (1.53), 6.432 (1.48), 7.133 (1.09), 7.135 (1.14), 7.145 (1.01), 7.147 (1.13), 7.151 (1.22), 7.154 (1.13), 7.163 (1.17), 7.166 (1.19), 7.752 (0.79), 7.758 (0.81), 7.771 (0.89), 7.773 (1.03), 7.775 (0.99), 7.778 (1.00), 7.792 (0.79), 7.796 (0.80), 7.867 (2.25), 7.880 (2.21), 8.366 (1.05), 8.368 (1.31), 8.370 (1.25), 8.373 (1.22), 8.378 (1.12), 8.380 (1.34), 8.383 (1.13), 8.385 (1.16), 8.422 (1.93), 8.443 (1.77), 13.652 (0.74), 15.060 (1.77).

Intermediate 13

2-(2-aminopyridin-4-yl)-5-methyl-3-[(pyridin-2-yl)amino]-1,5,6,7-tetrahydro-4H-pyrrolo[3,2-c]pyridin-4-one

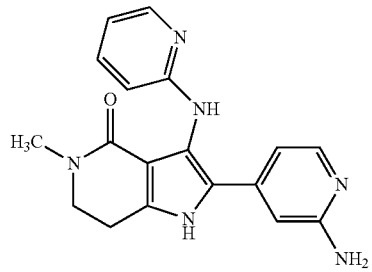 [SMILES: CN1CCc2[nH]c(-c3ccnc(N)c3)c(Nc3ccccn3)c2C1=O]

A stirred solution of 4-{[(2-aminopyridin-4-yl)methyl]amino}-1-methyl-2-oxo-N-(pyridin-2-yl)-1,2,5,6-tetrahydropyridine-3-carbothioamide (99.0 mg, 269 μmol) and hydrogen peroxide (30% in water, 55 μL, 540 μmol) in methanol (2.9 mL) was heated to 90° C. in a microwave for 4 h. An aqueous solution of disodium sulfurothioate and a half-saturated solution of potassium carbonate were added and the mixture was extracted with ethyl acetate. The organic phase was dried (sodium sulfate), filtered and the solvent was removed in vacuum. Silicagel chromatography (0-55% ethanol/ethyl acetate) followed by aminophase-silicagel chromatography gave 21 g (23% yield) of the title compound as a crude product that was used without further purification.

LC-MS (Method 2): $R_t$=0.69 min; MS (ESIpos): m/z=335.4 [M+H]$^+$

Intermediate 14 tert-butyl 5-[(2-chlorophenyl)carbamothioyl]-4-hydroxy-6-oxo-3,6-dihydropyridine-1(2H)-carboxylate

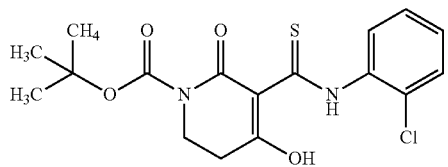 [SMILES: CC(C)(C)OC(=O)N1CCC(O)=C(C(=S)Nc2ccccc2Cl)C1=O]

To solution of tert-butyl 2,4-dioxopiperidine-1-carboxylate (10.0 g, 46.9 mmol) and 1-chloro-2-isothiocyanatobenzene (6.4 mL, 49 mmol) in acetonitrile (200 mL) was slowly added DBU (10 mL, 70 mmol) at 0° C. and the mixture was stirred at r.t. for 16 h. The reaction was poured into an aqueous solution of ammonium chlorid (5 wt %, 300 mL). The mixture was extracted with ethyl acetate. The organic phase was dried (sodium sulfate), filtered and the solvent was removed in vacuum to give 12.5 g (70% purity, 49% yield) of the title compound as a crude product that was used without further purification.

LC-MS (Method 2): $R_t$=0.64 min; MS (ESIneg): m/z=381 [M−H]$^-$ $^1$H-NMR (400 MHz, DMSO-d6) δ [ppm]: 1.442 (16.00), 1.598 (0.47), 1.608 (0.46), 1.618 (0.46), 1.909 (0.59), 2.261 (0.47), 2.275 (0.74), 2.290 (0.49), 2.627 (0.42), 2.653 (0.44), 3.246 (0.60), 3.471 (0.66), 3.535 (0.46), 3.558 (0.50), 3.582 (0.49), 3.597 (0.72), 3.612 (0.45), 7.072 (0.42), 7.076 (0.41), 7.221 (0.40), 7.400 (0.64), 7.404 (0.66), 7.421 (0.60), 7.424 (0.55), 8.177 (0.48), 8.181 (0.48), 8.197 (0.47), 8.201 (0.44), 14.352 (0.78).

Intermediate 15

N-(2-chlorophenyl)-4-hydroxy-2-oxo-1,2,5,6-tetrahydropyridine-3-carbothioamide

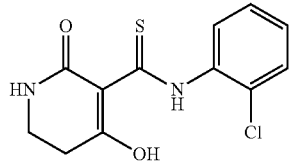 [SMILES: O=C1NCCC(O)=C1C(=S)Nc1ccccc1Cl]

To a stirred solution of tert-butyl 5-[(2-chlorophenyl)carbamothioyl]-4-hydroxy-6-oxo-3,6-dihydropyridine-1 (2H)-carboxylate (12.4 g, 70% purity, 22.7 mmol) in dichloromethane (250 mL) and methanol (100 mL) was added hydrogen chloride in dioxane (57 mL, 4.0 M, 230 mmol) and the mixture was stirred at rt for 16 h. The mixture was poured into ice water and was extracted with a mixture of dichloromethane and methanol (30:1). The organic phase was dried, filtered and the solvent was removed in vacuum to give a solid. The solid was triturated with ethyl acetate to give 5.22 g (81% yield) of the title compound.

LC-MS (Method 1): $R_t$=1.15 min; MS (ESIpos): m/z=283 [M+H]$^+$ $^1$H-NMR (400 MHz, DMSO-d6) δ [ppm]: 2.322 (0.70), 2.326 (0.98), 2.331 (0.70), 2.518 (3.98), 2.522 (2.49), 2.617

(4.53), 2.636 (8.51), 2.654 (5.01), 2.664 (0.95), 2.669 (1.08), 2.673 (0.79), 2.775 (4.04), 2.793 (8.70), 2.810 (4.63), 3.283 (2.80), 3.290 (2.93), 3.301 (5.28), 3.308 (5.17), 3.319 (2.83), 3.415 (2.93), 3.422 (3.21), 3.433 (5.10), 3.441 (4.97), 3.451 (2.81), 3.459 (2.65), 3.565 (1.00), 7.306 (1.37), 7.310 (1.59), 7.325 (3.65), 7.329 (3.63), 7.344 (4.38), 7.348 (4.20), 7.363 (4.09), 7.366 (5.27), 7.369 (4.16), 7.382 (3.99), 7.386 (6.05), 7.389 (5.09), 7.397 (2.88), 7.401 (3.35), 7.403 (2.52), 7.408 (2.04), 7.416 (3.57), 7.420 (3.98), 7.435 (1.75), 7.439 (1.57), 7.562 (4.89), 7.566 (5.17), 7.582 (4.63), 7.587 (7.38), 7.590 (8.75), 7.594 (9.60), 7.610 (7.00), 7.614 (7.87), 8.168 (2.75), 9.365 (2.45), 14.209 (5.81), 14.572 (4.47), 16.420 (16.00), 16.440 (12.66).

Intermediate 16

4-{[(2-aminopyridin-4-yl)methyl]amino}-N-(2-chlorophenyl)-2-oxo-1,2,5,6-tetrahydropyridine-3-carbothioamide

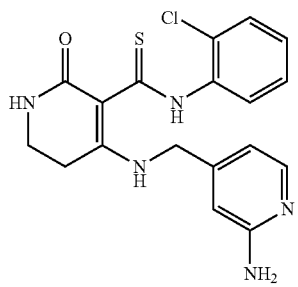 [SMILES: Nc1cc(CNC2=C(C(=S)Nc3ccccc3Cl)C(=O)NCC2)ccn1]

A stirred solution of N-(2-chlorophenyl)-4-hydroxy-2-oxo-1,2,5,6-tetrahydropyridine-3-carbothioamide (3.00 g, 10.6 mmol) and 4-(aminomethyl)pyridin-2-amine (1.83 g, 14.9 mmol) (CAS-RN: 199296-51-0) in ethanol (30 mL) was distributed to two microwave vials and was heated to 100° C. for 16 h. The mixture was cooled to room temperature, and a solid was collected by filtration washed with ethanol and dried in vacuum. The solution was concentrated to 20 mL stirred for 48 h and a second crop of solid was obtained by filtration. Both solids were combined to give 1.37 g (33% yield) of the title compound.

LC-MS (Method 1): $R_t$=0.75 min; MS (ESIpos): m/z=388; 390 [M+H]$^+$ $^1$H-NMR (400 MHz, DMSO-d6) δ [ppm]: 1.036 (0.49), 1.052 (0.91), 1.071 (0.49), 2.327 (1.36), 2.670 (1.71), 2.697 (5.77), 2.713 (10.43), 2.729 (6.47), 3.160 (8.52), 4.565 (11.22), 4.579 (11.24), 6.011 (16.00), 6.341 (11.24), 6.408 (6.57), 6.421 (6.69), 7.226 (2.54), 7.245 (5.85), 7.263 (4.21), 7.313 (3.92), 7.332 (6.16), 7.351 (3.05), 7.506 (6.65), 7.526 (5.85), 7.589 (6.51), 7.608 (5.73), 7.708 (6.93), 7.860 (7.60), 7.872 (7.44), 13.743 (5.10), 14.759 (10.57).

Intermediate 17

2-(2-aminopyridin-4-yl)-3-(2-chloroanilino)-1,5,6,7-tetrahydro-4H-pyrrolo[3,2-c]pyridin-4-one

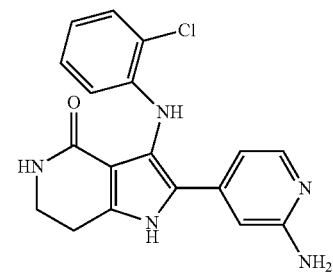 [SMILES: Nc1cc(-c2[nH]c3c(c2Nc2ccccc2Cl)C(=O)NCC3)ccn1]

A stirred solution of 4-{[(2-aminopyridin-4-yl)methyl]amino}-N-(2-chlorophenyl)-2-oxo-1,2,5,6-tetrahydropyridine-3-carbothioamide (1.07 g, 2.76 mmol) and hydrogen peroxide (30% in water, 560 μL, 5.5 mmol) in methanol (16 mL) was distributed to two microwave vials and was heated to 90° C. 2.5 h. Methanol and DMF was added, the mixture was sonicated and undissolved solid material was removed. An aqueous solution of disodium sulfurothioate and a half-saturated solution of potassium carbonate were added to the solution and the mixture was extracted with ethyl acetate. The organic phase was washed with saturated sodium chloride solution, dried (sodium sulfate), filtered and the solvent was removed in vacuum. The residue was triturated with ethyl acetate to give 450 mg (42% yield) of the title compound.

LC-MS (Method 1): $R_t$=0.66 min; MS (ESIpos): m/z=354; 356 [M+H]$^+$ $^1$H-NMR (400 MHz, DMSO-d6) δ [ppm]: 1.154 (2.28), 1.172 (4.54), 1.190 (2.35), 1.987 (8.64), 2.518 (1.69), 2.522 (1.06), 2.669 (0.44), 2.727 (12.72), 2.801 (1.03), 2.818 (2.21), 2.835 (1.18), 2.888 (16.00), 3.370 (0.77), 3.376 (0.83), 3.387 (1.46), 3.393 (1.42), 3.404 (0.74), 3.410 (0.66), 3.999 (0.67), 4.017 (2.04), 4.035 (2.02), 4.053 (0.65), 5.717 (2.85), 6.335 (1.26), 6.339 (1.32), 6.355 (1.35), 6.359 (1.30), 6.451 (2.09), 6.453 (2.14), 6.573 (1.40), 6.577 (1.28), 6.587 (1.40), 6.591 (1.33), 6.656 (0.74), 6.660 (0.73), 6.676 (1.22), 6.679 (1.14), 6.694 (0.88), 6.698 (0.79), 6.916 (0.73), 6.919 (0.72), 6.937 (1.14), 6.954 (0.60), 6.958 (0.56), 7.119 (1.35), 7.320 (4.34), 7.336 (1.53), 7.340 (1.42), 7.734 (1.87), 7.747 (1.79), 7.950 (2.00), 11.644 (1.38).

Intermediate 18

N-[4-(3-anilino-5-methyl-4-oxo-4,5,6,7-tetrahydro-1H-pyrrolo[3,2-c]pyridin-2-yl)pyridin-2-yl]-3-{[tert-butyl(diphenyl)silyl]oxy}-2-(4-fluorophenyl)propanamide

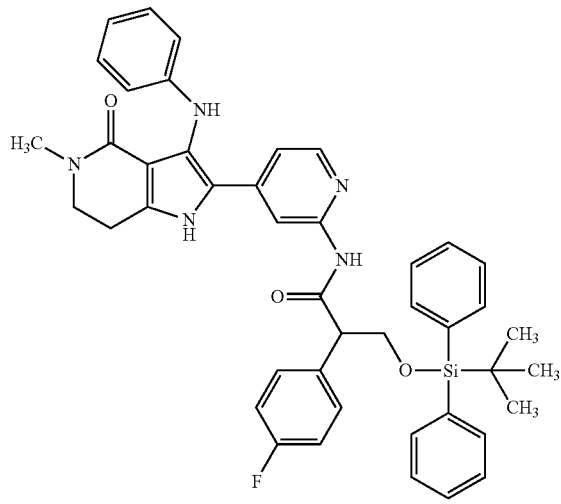 [SMILES: CN1CCc2[nH]c(-c3ccnc(NC(=O)C(CO[Si](c4ccccc4)(c4ccccc4)C(C)(C)C)c4ccc(F)cc4)c3)c(Nc3ccccc3)c2C1=O]

To a stirred solution of 3-{[tert-butyl(diphenyl)silyl]oxy}-2-(4-fluorophenyl)propanoic acid (456 mg, 1.08 mmol) (prepared as described in WO 2013/87579) in DMA (12.0 mL) was added 2-(2-aminopyridin-4-yl)-3-anilino-5-methyl-1,5,6,7-tetrahydro-4H-pyrrolo[3,2-c]pyridin-4-one (see Intermediate 3) (300 mg, 900 μmol), N,N-dimethylpyridin-4-amine (22.0 mg, 180 μmol), N,N-diethylethanamine (630 μL, 4.5 mmol) and T3P (859 mg, 50% purity in ethyl acetate, 1.35 mmol). The mixture was stirred at room temperature for 16 h. An aqueous solution of sodium bicarbonate was added, the mixture was stirred for 15 minutes and the mixture was extracted with ethyl acetate. The organic phase was filtered through a silicone filter and the solvent was removed in vacuum. Silicagel chromatography gave 370 mg (56% yield) of the title compound.

LC-MS (Method 2): $R_t$=1.67 min; MS (ESIpos): m/z=738 [M+H]$^+$ $^1$H-NMR (400 MHz, DMSO-d6) δ [ppm]: 0.859 (0.55), 0.918 (16.00), 1.154 (2.00), 1.172 (4.13), 1.190 (2.07), 1.235 (0.46), 1.987 (6.71), 2.518 (1.02), 2.523 (0.69), 2.865 (6.53), 2.912 (0.57), 2.930 (1.23), 2.947 (0.63), 3.522 (0.68), 3.539 (1.41), 3.558 (0.57), 3.722 (0.51), 3.731 (0.52), 4.000 (0.49), 4.017 (1.49), 4.035 (1.48), 4.053 (0.49), 4.262 (0.62), 4.275 (1.40), 5.758 (1.20), 6.542 (1.27), 6.561 (1.34), 6.563 (1.15), 6.570 (0.43), 6.572 (0.47), 6.590 (0.81), 6.609 (0.44), 6.961 (1.04), 6.979 (1.25), 6.982 (1.23), 7.001 (0.81), 7.124 (0.93), 7.128 (1.08), 7.132 (0.91), 7.141 (1.08), 7.147 (2.16), 7.169 (0.98), 7.324 (0.92), 7.330 (0.44), 7.338 (1.17), 7.347 (0.96), 7.354 (0.72), 7.357 (1.02), 7.360 (1.07), 7.375 (2.88), 7.385 (0.59), 7.390 (1.13), 7.393 (1.47), 7.406 (1.48), 7.410 (0.92), 7.425 (1.52), 7.426 (1.62), 7.430 (0.70), 7.438 (0.59), 7.442 (1.01), 7.445 (1.29), 7.459 (0.99), 7.522 (1.43), 7.526 (1.58), 7.531 (0.45), 7.542 (1.43), 7.546 (0.83), 7.598 (1.46), 7.602 (1.52), 7.607 (0.43), 7.615 (0.62), 7.618 (1.40), 7.622 (0.90), 8.033 (1.07), 8.048 (1.00), 8.254 (0.89), 10.658 (1.08), 11.751 (0.90).

Intermediate 19

Ethyl N-(cyclopropylmethyl)-beta-alaninate

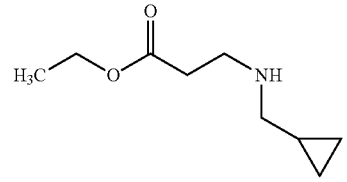

To an ice-cold solution of cyclopropanamine 1-cyclopropylmethanamine (8.7 mL, 100 mmol) in ethanol (100 mL) was slowly added ethyl prop-2-enoate (11 mL, 100 mmol) and the mixture was stirred at 0° C. for 2 h and at r.t. for 15 min. The solvent was removed in vacuum to give 17.1 g of the title compound as a crude product, that was used for the next step without purification.

Intermediate 20

Ethyl N-(cyclopropylmethyl)-N-(3-ethoxy-3-oxopropanoyl)-beta-alaninate

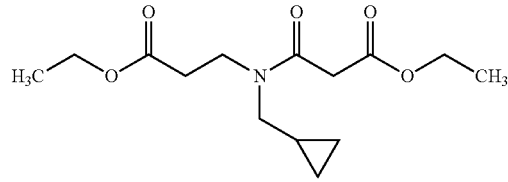 [SMILES: CCOC(=O)CCN(CC1CC1)C(=O)CC(=O)OCC]

To an ice-cold solution of crude ethyl N-(cyclopropylmethyl)-beta-alaninate (17.0 g, 99.3 mmol) in dichloromethane (130 mL) was added N,N-diisopropylethylamine (19 mL, 110 mmol) and DMAP (1.21 g, 9.93 mmol). Then ethyl 3-chloro-3-oxopropanoate (14 mL, 110 mmol) was added while monitoring that the temperature maintained below 15° C. The mixture was stirred at 0° C. for 30 min and at r.t. for 16 h. An aqueous solution of hydrochloric acid (55 mL, 2 M) was added, the mixture was stirred for 15 minutes, and the mixture was extracted with dichloromethane. The organic phase was dried (sodium sulfate), filtered and the solvent was removed in vacuum. Silicagel chromatography gave 4.20 g of the title compound as a crude product, that was used without further purification.

LC-MS (Method 2): $R_t$=1.01 min; MS (ESIpos): m/z=286 [M+H]$^+$ $^1$H-NMR (400 MHz, DMSO-d6) δ [ppm]: 0.199 (1.10), 0.202 (1.02), 0.211 (1.14), 0.214 (1.07), 0.225 (0.65), 0.237 (1.41), 0.241 (1.29), 0.250 (1.47), 0.253 (1.34), 0.264 (0.52), 0.396 (0.40), 0.405 (0.95), 0.410 (1.07), 0.415 (0.53), 0.420 (0.49), 0.425 (1.09), 0.430 (1.02), 0.468 (0.51), 0.478 (1.20), 0.482 (1.34), 0.488 (0.62), 0.494 (0.60), 0.499 (1.36), 0.502 (1.23), 0.513 (0.45), 0.934 (0.63), 0.942 (0.43), 0.946 (0.41), 0.954 (0.64), 1.160 (7.48), 1.165 (6.16), 1.169 (1.80), 1.178 (16.00), 1.183 (13.77), 1.187 (3.35), 1.195 (7.67), 1.201 (6.33), 1.204 (1.65), 1.295 (0.60), 2.518 (1.10), 2.527 (1.86), 2.546 (1.36), 2.619 (0.85), 2.637 (1.36), 2.655 (0.91), 3.150 (1.82), 3.167 (3.91), 3.184 (2.21), 3.347 (1.17), 3.435 (0.50), 3.476 (0.51), 3.492 (6.96), 3.528 (1.20), 3.548 (1.92), 3.554

(5.74), 3.565 (1.55), 3.581 (1.32), 3.599 (0.79), 3.696 (1.47), 4.022 (1.04), 4.040 (3.53), 4.048 (1.32), 4.055 (1.36), 4.058 (4.05), 4.060 (3.46), 4.066 (3.91), 4.072 (3.16), 4.078 (3.15), 4.084 (4.10), 4.090 (3.00), 4.095 (1.25), 4.102 (1.68), 4.108 (0.97), 4.116 (0.48).

Intermediate 21

Ethyl 1-(cyclopropylmethyl)-2,4-dioxopiperidine-3-carboxylate

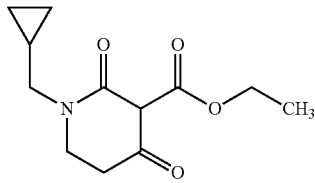 [SMILES: CCOC(=O)C1C(=O)CCN(CC2CC2)C1=O]

To an ice-cold solution of sodium ethanolate (solution in ethanol, 6 mL, 21% w/w, 16 mmol) in ethanol (29 mL) was added a solution of ethyl N-(cyclopropylmethyl)-N-(3-ethoxy-3-oxopropanoyl)-beta-alaninate (4.20 g, 14.7 mmol) in ethanol ethanol (6 mL) while monitoring that the temperature maintained below 5° C. The mixture was stirred at r.t. for 3 h. An aqueous solution of hydrochloric acid (2 M) was added until pH 4 was reached. The mixture was stirred for 5 minutes, and the mixture was extracted with dichloromethane. The organic phase was dried (sodium sulfate), filtered and the solvent was removed in vacuum. Silicagel chromatography gave 2.20 g of the title compound.

LC-MS (Method 1): $R_t$=0.92 min; MS (ESIpos): m/z=240 [M+H]$^+$ $^1$H-NMR (400 MHz, DMSO-d6) δ [ppm]: 0.191 (4.32), 0.203 (4.73), 0.221 (1.83), 0.225 (1.52), 0.233 (1.57), 0.237 (1.54), 0.247 (0.93), 0.406 (1.54), 0.419 (4.32), 0.428 (3.32), 0.438 (4.78), 0.448 (2.47), 0.452 (2.19), 0.464 (0.82), 0.935 (1.31), 0.952 (1.21), 0.972 (0.85), 1.035 (1.05), 1.052 (2.21), 1.070 (0.90), 1.173 (1.11), 1.177 (1.23), 1.183 (1.18), 1.199 (8.18), 1.217 (16.00), 1.234 (8.15), 2.318 (0.51), 2.322 (1.11), 2.326 (1.49), 2.331 (1.11), 2.336 (0.51), 2.518 (6.92), 2.522 (4.42), 2.529 (2.65), 2.544 (1.90), 2.573 (2.83), 2.659 (0.69), 2.664 (1.26), 2.669 (1.67), 2.673 (1.29), 2.678 (0.69), 3.106 (0.41), 3.123 (0.44), 3.172 (3.60), 3.188 (3.55), 3.245 (2.08), 3.262 (2.03), 3.376 (0.51), 3.385 (0.44), 3.394 (0.82), 3.431 (2.42), 3.448 (3.91), 3.464 (2.19), 3.630 (1.21), 3.645 (2.24), 3.660 (1.16), 4.111 (0.49), 4.146 (2.50), 4.164 (6.71), 4.182 (6.56), 4.200 (2.14), 5.758 (1.16).

Intermediate 22

1-(cyclopropylmethyl)piperidine-2,4-dione

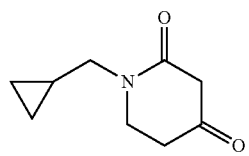 [SMILES: O=C1CCN(CC2CC2)C(=O)C1]

To a stirred solution of ethyl 1-(cyclopropylmethyl)-2,4-dioxopiperidine-3-carboxylate (1.70 g, 7.10 mmol) in dichloromethane (14 mL) was added aqueous hydrochloric acid (14 mL, 2.0 M, 28 mmol). The mixture was stirred at room temperature for 15 min. The mixture was extracted with further dichloromethane. The organic phase was dried (sodium sulfate), filtered and the solvent was removed in vacuum. The residue was dissolved in acetonitrile acetonitrile (20 mL) and water (2.7 mL) and the mixture was heated to reflux for 2 h. The solvent was removed in vacuum to give 1.11 g (93% yield) of the title compound as crude product that was used for the next step without purification.

LC-MS (Method 1): $R_t$=0.60 min; MS (ESIpos): m/z=168 [M+H]$^+$

Intermediate 23

1-(cyclopropylmethyl)-4-hydroxy-2-oxo-N-phenyl-1,2,5,6-tetrahydropyridine-3-carbothioamide

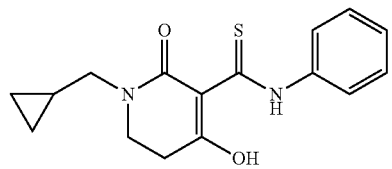 [SMILES: O=C1C(C(=S)Nc2ccccc2)=C(O)CCN1CC1CC1]

To solution of 1-(cyclopropylmethyl)piperidine-2,4-dione (1.44 g, 8.61 mmol) and isothiocyanatobenzene (1.0 mL, 8.6 mmol) in acetonitrile (16 mL) was slowly added DBU (2.1 mL, 14 mmol) and the mixture was stirred at r.t. for 3 h. The reaction was poured into ice-water containing concentrated hydrochloric acid (20 mL, c=4 M). The mixture was extracted with ethyl acetate. The organic phase was washed with saturated sodium chloride solution, dried (sodium sulfate), filtered and the solvent was removed in vacuum. Silicagel chromatography (20-60% ethyl acetate/hexane) gave 2.07 g (79% yield) of the title compound.

LC-MS (Method 1): $R_t$=1.43 min; MS (ESIpos): m/z=303 [M+H]$^+$

1H NMR (400 MHz, DMSO-d6) δ [ppm]: 0.26 (br d, 2H), 0.47 (br d, 2H), 1.04 (br s, 1H), 2.81 (br t, 2H), 3.31 (br d, 2H), 3.55 (br t, 2H), 7.30 (br t, 1H), 7.39-7.51 (m, 4H), 14.54 (br s, 1H), 16.50 (br s, 1H)

Intermediate 24

4-{[(2-aminopyridin-4-yl)methyl]amino}-1-(cyclopropylmethyl)-2-oxo-N-phenyl-1,2,5,6-tetrahydropyridine-3-carbothioamide

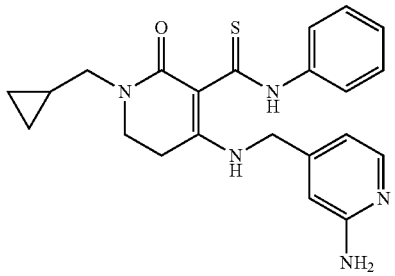 [SMILES: Nc1cc(CNC2=C(C(=S)Nc3ccccc3)C(=O)N(CC3CC3)CC2)ccn1]

A mixture of 1-(cyclopropylmethyl)-4-hydroxy-2-oxo-N-phenyl-1,2,5,6-tetrahydropyridine-3-carbothioamide (2.25 g, 6.78 mmol) and 4-(aminomethyl)pyridin-2-amine (3.34 g, 27.12 mmol) (CAS-RN: 199296-51-0) was melted and heated to 120° C. in a microwave tube for 2 h. A half-saturated solution of potassium carbonate was added and the mixture was extracted with ethyl acetate. The organic phase was washed with half-saturated sodium chloride solution, dried (sodium sulfate), filtered and the solvent was removed in vacuum. Silicagel chromatography (0-15% ethanol/dichloromethane) gave a solid that was triturated with a dichloromethane to give 396 mg (1.87 g) of the title compound.

LC-MS (Method 2): $R_t$=1.21 min; MS (ESIpos): m/z=408 $[M+H]^+$ $^1$H-NMR (400 MHz, DMSO-d6) δ [ppm]: 0.213 (2.30), 0.224 (8.81), 0.228 (8.19), 0.237 (9.25), 0.250 (3.03), 0.415 (3.02), 0.425 (7.65), 0.429 (7.83), 0.434 (4.26), 0.440 (4.13), 0.444 (8.19), 0.449 (7.74), 0.459 (2.53), 0.969 (1.07), 0.988 (2.80), 0.993 (2.22), 1.000 (1.72), 1.006 (2.45), 1.010 (3.33), 1.028 (2.04), 1.766 (2.98), 2.115 (0.41), 2.232 (0.49), 2.475 (1.03), 2.518 (3.34), 2.523 (2.19), 2.701 (4.65), 2.717 (8.59), 2.734 (5.10), 3.269 (11.14), 3.286 (11.05), 3.378 (5.61), 3.394 (9.16), 3.411 (5.05), 3.514 (0.85), 3.552 (8.06), 4.562 (10.36), 4.577 (10.34), 4.991 (0.89), 5.748 (2.44), 5.758 (6.39), 6.010 (16.00), 6.340 (11.32), 6.395 (2.77), 6.398 (2.77), 6.406 (7.14), 6.410 (6.57), 6.420 (7.28), 6.423 (6.80), 6.428 (2.28), 6.432 (1.92), 6.441 (1.81), 6.445 (1.51), 6.449 (0.54), 6.452 (0.79), 6.454 (0.46), 6.467 (0.66), 6.470 (1.28), 6.473 (0.72), 6.488 (0.72), 6.491 (0.41), 6.525 (1.63), 6.528 (1.78), 6.530 (0.98), 6.533 (0.50), 6.542 (0.61), 6.545 (1.07), 6.547 (2.15), 6.549 (1.65), 6.970 (1.56), 6.975 (0.48), 6.989 (1.73), 6.991 (1.66), 7.005 (0.45), 7.010 (1.33), 7.163 (2.06), 7.166 (3.60), 7.169 (2.10), 7.185 (7.96), 7.188 (3.25), 7.200 (2.93), 7.203 (5.17), 7.206 (2.84), 7.335 (1.28), 7.340 (8.70), 7.344 (3.57), 7.360 (14.50), 7.374 (3.37), 7.379 (12.05), 7.383 (2.34), 7.430 (12.89), 7.433 (13.54), 7.450 (9.03), 7.454 (6.92), 7.771 (2.34), 7.782 (2.23), 7.861 (10.46), 7.875 (10.12), 13.610 (2.94), 14.680 (6.19).

Intermediate 25

2-(2-aminopyridin-4-yl)-3-anilino-5-(cyclopropylmethyl)-1,5,6,7-tetrahydro-4H-pyrrolo[3,2-c]pyridin-4-one

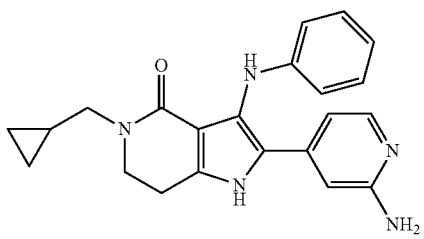 [SMILES: Nc1cc(-c2[nH]c3c(c2Nc2ccccc2)C(=O)N(CC2CC2)CC3)ccn1]

A solution of 4-{[(2-aminopyridin-4-yl)methyl]amino}-1-(cyclopropylmethyl)-2-oxo-N-phenyl-1,2,5,6-tetrahydropyridine-3-carbothioamide (1.76 g, 4.32 mmol) and TFA (670 μL, 8.6 mmol) in methanol (18 mL) was stirred for 15 min. mCPBA (1.94 g, 77% purity, 8.64 mmol) was added and the mixture was heated to 50° C. for 2.5 h. An aqueous solution of sodium bicarbonate was added, and the mixture was extracted with ethyl acetate. The organic phase was dried (sodium sulfate), filtered and the solvent was removed in vacuum. Silicagel chromatography (0-50% ethanol/dichloromethane) gave 545 mg (34% yield) of the title compound.

LC-MS (Method 2): $R_t$=1.02 min; MS (ESIpos): m/z=374 $[M+H]^+$ $^1$H-NMR (400 MHz, DMSO-d6) δ [ppm]: 0.179 (1.63), 0.191 (6.07), 0.194 (5.60), 0.203 (6.43), 0.216 (2.25), 0.394 (2.16), 0.404 (5.28), 0.408 (5.20), 0.414 (3.06), 0.419 (3.01), 0.424 (5.60), 0.428 (5.22), 0.439 (1.99), 0.914 (0.68), 0.926 (1.23), 0.934 (1.25), 0.946 (1.95), 0.958 (1.19), 0.963 (1.17), 0.976 (0.59), 1.035 (1.40), 1.053 (2.59), 1.070 (1.44), 1.137 (0.45), 1.232 (0.64), 2.084 (1.02), 2.118 (0.74), 2.518 (5.88), 2.522 (3.76), 2.881 (3.44), 2.898 (7.38), 2.915 (3.84), 3.212 (8.40), 3.229 (8.42), 3.339 (1.82), 3.411 (0.91), 3.429 (1.08), 3.446 (0.95), 3.463 (0.53), 3.601 (1.02), 3.612 (4.35), 3.629 (8.59), 3.646 (4.05), 3.664 (0.55), 3.738 (1.27), 5.720 (6.15), 5.758 (16.00), 6.400 (0.53), 6.421 (0.45), 6.544 (6.94), 6.546 (7.26), 6.559 (7.81), 6.578 (8.04), 6.581 (6.75), 6.600 (2.50), 6.618 (4.88), 6.636 (2.76), 6.668 (4.67), 6.671 (4.29), 6.682 (4.58), 6.685 (4.46), 7.006 (6.07), 7.024 (7.68), 7.027 (7.49), 7.045 (4.86), 7.074 (0.62), 7.231 (0.42), 7.286 (9.25), 7.501 (1.19), 7.521 (2.38), 7.538 (0.72), 7.542 (1.44), 7.655 (1.21), 7.657 (1.27), 7.663 (1.00), 7.674 (0.72), 7.679 (0.98), 7.683 (0.76), 7.718 (6.28), 7.732 (6.18), 7.873 (1.38), 7.876 (1.91), 7.879 (1.68), 7.888 (1.78), 7.893 (3.65), 7.897 (4.29), 11.543 (4.73).

Intermediate 26

Ethyl N-ethyl-beta-alaninate

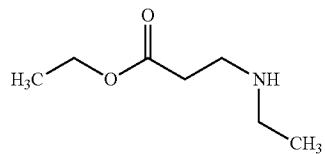

Ethyl prop-2-enoate (11 mL, 100 mmol) was added dropwise to ethanamine (CAS: 75-04-7, 50 mL, 2.0 M in THF, 100 mmol) at 0° C. The reaction mixture was stirred under nitrogen atmosphere overnight at rt. The reaction mixture was concentrated under reduced pressure. The crude product was used without further purification: 8.6 g.

LC-MS (Method 2): $R_t$=0.73 min; MS (ESIpos): m/z=147 $[M+H]^+$ $^1$H-NMR (400 MHz, DMSO-d6) δ [ppm]: 0.894 (0.67), 0.912 (1.50), 0.929 (0.71), 0.952 (5.71), 0.969 (11.97), 0.987 (5.80), 1.154 (7.70), 1.171 (16.00), 1.189 (7.80), 2.342 (0.63), 2.359 (1.56), 2.368 (2.85), 2.377 (1.04), 2.385 (6.63), 2.396 (0.43), 2.402 (3.53), 2.414 (0.69), 2.432 (0.64), 2.463 (1.79), 2.481 (5.51), 2.625 (0.81), 2.642 (1.47), 2.660 (0.66), 2.687 (3.32), 2.705 (6.25), 2.722 (2.66), 4.004 (0.56), 4.014 (2.02), 4.022 (1.78), 4.032 (6.20), 4.040 (1.84), 4.050 (6.19), 4.057 (0.65), 4.067 (1.99).

Intermediate 27

Ethyl N-(3-ethoxy-3-oxopropanoyl)-N-ethyl-beta-alaninate

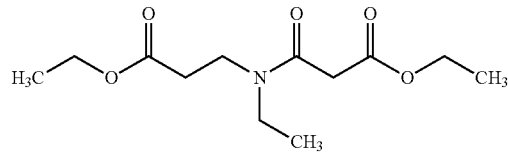 [SMILES: CCOC(=O)CCN(CC)C(=O)CC(=O)OCC]

Ethyl N-ethyl-beta-alaninate (see Intermediate 26, 8.56 g) was dissolved in 56 mL dichloromethane and cooled down to 0° C. Then N,N-diisopropylethylamine (11 mL, 65 mmol) and 4-dimethylaminopyridine (720 mg, 5.90 mmol) were added. Ethyl 3-chloro-3-oxopropanoate (CAS: 36239-09-5, 8.3 mL, 65 mmol) was added dropwise at 15° C. The reaction mixture was stirred under nitrogen atmosphere for 1.5 h at 0° C. and then over night at rt. 200 mL half saturated ammoniumchloride-solution and dichloromethane were added to the reaction mixture. The aqueous layer was extracted with dichloromethane three times. The combined organic layers were washed with brine once, dried over a water resistant filter and concentrated under reduced pressure. The crude product was purified by column chromatography (Biotage, column: 25 g, SI Ultra, hexane/ethyl acetate, 0-100%) to provide the target compound in two batches: 5.9 g (batch 1) and 2.6 g (batch 2):

Batch 1:
LC-MS (Method 1): $R_t$=0.85 min; MS (ESIpos): m/z=259 [M+H]$^+$ $^1$H-NMR (400 MHz, DMSO-d6) δ [ppm]: 0.902 (0.64), 0.920 (1.46), 0.938 (0.67), 0.971 (1.32), 0.989 (3.25), 1.007 (1.47), 1.060 (1.67), 1.078 (3.96), 1.096 (1.72), 1.154 (2.23), 1.161 (7.59), 1.166 (2.98), 1.171 (4.90), 1.179 (16.00), 1.184 (5.92), 1.189 (2.69), 1.197 (7.67), 1.202 (2.83), 2.354 (0.54), 2.372 (1.28), 2.389 (0.69), 2.435 (0.42), 2.453 (0.42), 2.481 (1.22), 2.518 (1.60), 2.522 (0.50), 2.597 (0.72), 2.615 (1.32), 2.632 (0.80), 2.645 (0.60), 2.662 (1.08), 2.680 (0.47), 3.242 (1.16), 3.260 (1.19), 3.269 (0.58), 3.278 (0.51), 3.287 (1.54), 3.305 (1.60), 3.429 (1.07), 3.447 (1.70), 3.462 (6.29), 3.482 (1.29), 3.499 (0.67), 3.526 (4.28), 4.007 (0.59), 4.024 (2.58), 4.042 (4.43), 4.045 (1.25), 4.050 (1.74), 4.060 (3.46), 4.063 (2.57), 4.067 (4.87), 4.078 (1.27), 4.081 (2.24), 4.085 (4.63), 4.099 (0.75), 4.103 (1.43).

Batch 2:
LC-MS (Method 1): $R_t$=0.85 min; MS (ESIpos): m/z=259 [M+H]$^+$ $^1$H-NMR (400 MHz, DMSO-d6) δ [ppm]: 0.972 (1.19), 0.989 (2.77), 1.001 (1.11), 1.006 (1.59), 1.020 (1.46), 1.037 (0.99), 1.052 (0.50), 1.061 (1.59), 1.070 (0.89), 1.078 (3.68), 1.087 (0.53), 1.096 (2.02), 1.113 (1.44), 1.130 (0.73), 1.154 (1.28), 1.161 (7.57), 1.166 (4.01), 1.173 (3.14), 1.179 (16.00), 1.184 (7.80), 1.191 (2.70), 1.197 (8.03), 1.201 (4.11), 1.209 (0.98), 1.986 (0.61), 2.481 (1.24), 2.517 (1.62), 2.523 (0.86), 2.532 (0.73), 2.542 (0.41), 2.551 (0.71), 2.596 (0.65), 2.614 (1.21), 2.632 (0.70), 3.224 (0.47), 3.242 (1.30), 3.260 (1.38), 3.269 (0.74), 3.278 (0.75), 3.287 (1.70), 3.305 (1.98), 3.313 (1.27), 3.429 (1.07), 3.447 (1.71), 3.462 (5.90), 3.481 (1.37), 3.490 (0.43), 3.499 (0.72), 3.526 (3.79), 3.688 (0.41), 3.702 (0.57), 3.710 (0.54), 3.809 (1.19), 3.992 (0.59), 4.009 (0.60), 4.024 (0.94), 4.027 (0.65), 4.036 (0.48), 4.042 (2.69), 4.045 (1.90), 4.049 (2.00), 4.059 (3.12), 4.063 (3.31), 4.068 (4.80), 4.076 (1.94), 4.080 (2.84), 4.085 (4.55), 4.093 (1.47), 4.098 (1.22), 4.103 (1.47), 4.111 (0.48), 4.139 (0.58), 4.157 (0.62), 5.268 (0.59), 5.381 (0.42), 5.756 (1.11).

Intermediate 28

Ethyl 1-ethyl-2,4-dioxopiperidine-3-carboxylate

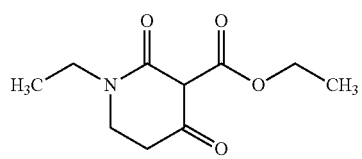

Ethyl N-(3-ethoxy-3-oxopropanoyl)-N-ethyl-beta-alaninate (see Intermediate 27—batch 1 and 2, 8.50 g) was dissolved in 47 mL ethanol and added dropwise to sodium ethanolate (13 mL, 21% purity in ethanol, 36 mmol) under ice bath cooling. It was then stirred over night at rt. The reaction mixture was extracted with dichloromethane and water. The aqueous layer was acidified with 4M hydrochloric acid and extracted with dichloromethane. The combined organic layers were dried with a water resistant filter and concentrated under reduced pressure. The crude product was purified by column chromatography (Biotage, column: 100 g, SI Ultra, ethyl acetate/ethanol, 0-50%) to provide the target compound: 5.0 g, 98% purity.

LC-MS (Method 1): $R_t$=0.75 min; MS (ESIpos): m/z=214 [M+H]$^+$ $^1$H-NMR (400 MHz, DMSO-d6) δ [ppm]: 0.931 (0.62), 0.953 (0.57), 0.971 (1.20), 0.988 (0.98), 1.002 (4.64), 1.019 (9.58), 1.025 (7.34), 1.037 (5.66), 1.043 (9.57), 1.052 (2.64), 1.061 (4.47), 1.069 (1.32), 1.154 (3.32), 1.171 (6.54), 1.189 (4.07), 1.198 (8.30), 1.216 (16.00), 1.233 (7.89), 1.906 (0.67), 1.986 (8.65), 2.322 (0.42), 2.326 (0.62), 2.332 (0.61), 2.349 (0.42), 2.390 (0.50), 2.517 (5.76), 2.522 (2.10), 2.532 (2.92), 2.539 (2.90), 2.558 (3.69), 2.574 (2.36), 2.664 (0.66), 2.669 (0.93), 2.673 (0.82), 2.689 (0.46), 3.231 (0.44), 3.249 (0.88), 3.267 (1.17), 3.280 (1.52), 3.290 (8.74), 3.298 (3.91), 3.363 (11.35), 3.380 (7.64), 3.398 (4.38), 3.416 (1.98), 3.537 (2.39), 3.552 (4.32), 3.567 (2.28), 3.999 (0.61), 4.017 (1.89), 4.027 (1.00), 4.034 (1.93), 4.045 (0.99), 4.052 (0.71), 4.145 (2.71), 4.163 (7.33), 4.181 (7.16), 4.199 (2.38), 4.853 (0.50), 5.756 (7.25).

Intermediate 29

1-ethylpiperidine-2,4-dione

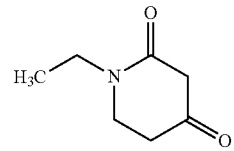

Ethyl-1-ethyl-2,4-dioxopiperidine-3-carboxylate (see Intermediate 28, 250 mg) was dissolved in 2.2 mL dichloromethane and treated with aqueous hydrochloric acid (2.2 mL, 2.0 M, 4.3 mmol). It was stirred for 20 min under argon atmosphere and at rt. The reaction mixture was then filtered through a water resistant filter and concentrated under reduced pressure. The residue was dissolved in acetonitrile, treated with water and was stirred under reflux for 1 hour. The reaction mixture was then filtered through a water resistant filter and was concentrated under reduced pressure to provide the crude product, which was used without further purification: 87 mg.

$^1$H-NMR (400 MHz, DMSO-d6): δ [ppm]=1.04 (t, 3H), 2.51-2.55 (m, 2H), 3.29 (s, 2H), 3.39 (q, 2H), 3.55 (t, 2H).

Intermediate 30

1-ethyl-4-hydroxy-2-oxo-N-phenyl-1,2,5,6-tetrahydropyridine-3-carbothioamide

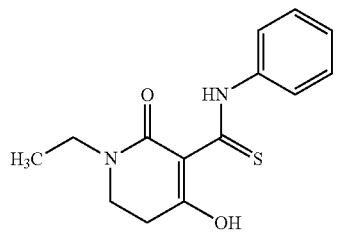 [SMILES: CCN1CCC(O)=C(C(=S)Nc2ccccc2)C1=O]

1-Ethylpiperidine-2,4-dione (see Intermediate 29, 2.40 g) was suspended in 22 mL acetonitrile and treated with isothiocyanatobenzene (1.9 mL, 16 mmol). 1,8-Diazabicyclo[5.4.0]undec-7-ene (3.9 mL, 26 mmol) was slowly added to the mixture at 0° C. and under argon atmosphere. The reaction mixture was stirred under argon atmosphere over night at rt. The reaction mixture was poured into a mixture of ice and hydrochloric acid (4 M). It was extracted with ethyl acetate three times. The combined organic layers were washed with water and brine once, filtered through a water resistant filter and concentrated under reduced pressure to provide the crude product, which was used without further purification: 4.31 g.

LC-MS (Method 2): $R_t$=0.55 min; MS (ESIpos): m/z=277 [M+H]$^+$ $^1$H-NMR (400 MHz, DMSO-d6): δ [ppm]=1.10 (t, 3H), 2.81 (t, 2H), 3.40-3.52 (m, 4H), 7.25-7.50 (m, 6H).—OH not detectable

Intermediate 31

4-{[(2-aminopyridin-4-yl)methyl]amino}-1-ethyl-2-oxo-N-phenyl-1,2,5,6-tetrahydropyridine-3-carbothioamide

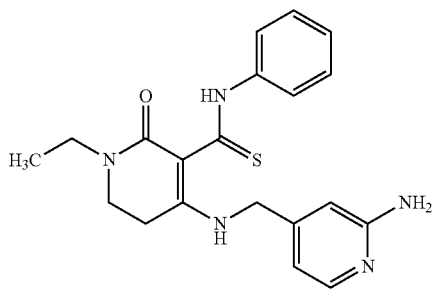 [SMILES: CCN1CCC(NCc2ccnc(N)c2)=C(C(=S)Nc2ccccc2)C1=O]

1-Ethyl-4-hydroxy-2-oxo-N-phenyl-1,2,5,6-tetrahydropyridine-3-carbothioamide (see Intermediate 30, 4.31 g) and 4-(aminomethyl)pyridin-2-amine (3.20 g, 26.0 mmol) were combined and stirred at 100° C. under argon atmosphere for 4.5 h (no solvent was used). The reaction mixture was cooled down to rt and turned very viscous. It was dissolved in dichloromethane and methanol and the crude product was purified by column chromatography (Biotage, column: 100 g, SI Ultra, dichloromethane/ethanol, 0-20%) to provide the target compound in 92% purity: 1.7 g.

LC-MS (Method 2): $R_t$=1.10 min; MS (ESIpos): m/z=382 [M+H]$^+$ $^1$H-NMR (400 MHz, DMSO-d6): δ [ppm]=1.07 (t, 3H), 2.67-2.76 (m, 2H), 3.25-3.30 (m, 2H), 3.44-3.48 (m, 2H), 4.56 (d, 2H), 6.00 (s, 2H), 6.33 (s, 1H), 6.41 (dd, 1H), 7.12-7.25 (m, 1H), 7.28-7.39 (m, 2H), 7.44 (d, 2H), 7.86 (d, 1H), 13.52-13.68 (m, 1H), 14.70 (s, 1H).—contains ethanol

Intermediate 32

2-(2-aminopyridin-4-yl)-3-anilino-5-ethyl-1,5,6,7-tetrahydro-4H-pyrrolo[3,2-c]pyridin-4-one

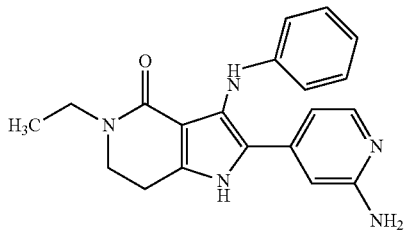 [SMILES: CCN1CCc2[nH]c(-c3ccnc(N)c3)c(Nc3ccccc3)c2C1=O]

4-{[(2-Aminopyridin-4-yl)methyl]amino}-1-ethyl-2-oxo-N-phenyl-1,2,5,6-tetrahydropyridine-3-carbothioamide (see Intermediate 31, 1.70 g) was suspended in 39 mL methanol and treated with trifluoric acid (690 μL, 8.9 mmol). After it was stirred for 5 minutes before 3-chloro-peroxybenzoic acid (1.54 g, 8.91 mmol) was added. The reaction mixture was stirred at 50° C. under argon atmosphere overnight meanwhile methanol evaporated. The reaction mixture was diluted with methanol again, 3-chloro-peroxybenzoic acid (0.77 g, 4.45 mmol) was added and it was stirred again at 50° C. under argon atmosphere overnight. Saturated sodium bicarbonate solution and dichloromethane were added and stirred for 30 min. The organic layer was filtered through a silicone coated filter and concentrated under reduced pressure. The crude product was then diluted with dichloromethane, until a precipitate was formed. Ethanol was added and the undissolved precipitate was filtered off and washed with ethanol and methanol. The filtrate was concentrated under reduced pressure. With adding dichloromethane further precipitate was formed, which was filtered off and washed with ethanol and methanol. The filtrate was concentrated under reduced pressure. The crude product was purified by column chromatography twice (Biotage, column: 100 g, SI Ultra, hexane/ethyl acetate, 0-100% and ethyl acetate/ethanol 0-20% and Biotage, column: 28 g, KP—NH, dichloromethane/ethanol, 0-5%) to provide the target compound in 95% purity: 135 mg.

LC-MS (Method 2): $R_t$=0.91 min; MS (ESIpos): m/z=348 [M+H]$^+$ $^1$H-NMR (400 MHz, DMSO-d6): δ [ppm]=1.04 (t, 3H), 2.88 (t, 2H), 3.35-3.40 (m, 2H), 3.54 (t, 2H), 5.65 (s, 2H), 6.51-6.58 (m, 3H), 6.59-6.64 (m, 1H), 6.67 (dd, 1H), 7.02 (dd, 2H), 7.26 (s, 1H), 7.72 (d, 1H), 11.51 (s, 1H).—contains ethanol

Intermediate 33

4-hydroxy-6,6-dimethyl-2-oxo-N-phenyl-1,2,5,6-tetrahydropyridine-3-carbothioamide

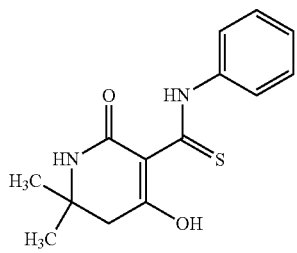 [SMILES: CC1(C)CC(O)=C(C(=S)Nc2ccccc2)C(=O)N1]

6,6-Dimethylpiperidine-2,4-dione (CAS: 5239-39-4, 11.1 g) was suspended in 110 mL acetonitrile and treated with isothiocyanatobenzene (CAS: 103-72-0, 9.4 mL, 79 mmol). The mixture was cooled down to 0° C. and treated slowly with DBU (19 mL, 130 mmol). It was stirred at rt over night. The reaction mixture was poured into a mixture of ice and aqueous hydrogen chloride solution (4 M). The mixture was diluted with ethyl acetate. The undissolved precipitate was filtered off, washed with water and ethyl acetate and dried at 50° C. under vacuo. The filtrate was extracted with ethyl acetate three times. The combined organic layers were washed with water and brine once, filtered through a silicone coated filter and concentrated under reduced pressure to provide the analytically pure target compound, which was used without further purification: 18.8 g LC-MS (Method 2): $R_t$=0.51 min; MS (ESIpos): m/z=277 [M+H]$^+$ $^1$H-NMR (400 MHz, DMSO-d6) δ [ppm]: −4.175 (1.29), −4.167 (1.98), 1.250 (12.42), 1.268 (16.00), 2.518 (0.49), 2.615 (4.84), 2.758 (3.77), 7.251 (0.42), 7.260 (0.44), 7.266 (0.72), 7.273 (0.60), 7.282 (0.80), 7.287 (0.63), 7.304 (0.77), 7.321 (0.52), 7.385 (0.54), 7.400 (0.54), 7.407 (2.57), 7.417 (3.34), 7.423 (7.84), 7.440 (2.00), 7.459 (2.27), 7.464 (2.17), 7.468 (2.34), 7.485 (0.73), 7.490 (0.47), 8.193 (1.08), 9.301 (1.18), 14.226 (1.61), 14.716 (0.98).

Intermediate 34

4-{[(2-aminopyridin-4-yl)methyl]amino}-6,6-dimethyl-2-oxo-N-phenyl-1,2,5,6-tetrahydropyridine-3-carbothioamide

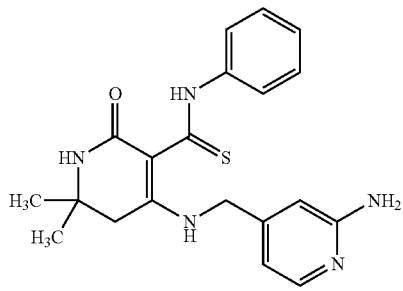 [SMILES: CC1(C)CC(NCc2ccnc(N)c2)=C(C(=S)Nc2ccccc2)C(=O)N1]

4-Hydroxy-6,6-dimethyl-2-oxo-N-phenyl-1,2,5,6-tetrahydropyridine-3-carbothioamide (see Intermediate 33, 8.00 g) and 4-(aminomethyl)pyridin-2-amine (CAS: 199296-51-0, 6.06 g, 49.2 mmol) were combined and it was stirred at 100° C. under argon atmosphere without further solvent. The reaction mixture was cooled down to rt. It was treated with dichloromethane and methanol and sonicated for ~20 min. The formed precipitate was filtered off, washed with dichloromethane and dried at 50° C. under vacuo to provide batch 1 of the target compound: 5.53 g (97% purity). The filtrate was concentrated under reduced pressure, treated with a small amount of dichloromethane. The formed precipitate was filtered off, washed with dichloromethane and dried at 50° C. under vacuo to provide batch 2 of the target compound: 1.84 g (81% purity).

Batch 1:

LC-MS (Method 2): $R_t$=1.01 min; MS (ESIpos): m/z=383 [M+H]$^+$ $^1$H-NMR (400 MHz, DMSO-d6): δ [ppm]=1.15 (s, 6H), 2.67 (s, 2H), 4.59 (d, 2H), 6.00 (s, 2H), 6.34 (s, 1H), 6.41 (dd, 1H), 7.14-7.24 (m, 1H), 7.31-7.40 (m, 2H), 7.42-7.48 (m, 2H), 7.65 (s, 1H), 7.86 (d, 1H), 13.96 (br t, 1H), 14.97 (s, 1H).

Intermediate 35

2-(2-aminopyridin-4-yl)-3-anilino-6,6-dimethyl-1,5,6,7-tetrahydro-4H-pyrrolo[3,2-c]pyridin-4-one

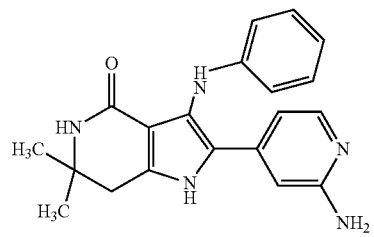 [SMILES: CC1(C)Cc2[nH]c(-c3ccnc(N)c3)c(Nc3ccccc3)c2C(=O)N1]

4-{[(2-Aminopyridin-4-yl)methyl]amino}-6,6-dimethyl-2-oxo-N-phenyl-1,2,5,6-tetrahydropyridine-3-carbothioamide (see Intermediate 34, 1.83 g) was suspended in 42 mL methanol and treated with trifluoroacetic acid (740 μL, 9.6 mmol). It was stirred for 5 minutes, then 3-chloroperoxybenzoic acid (1.66 g, 9.59 mmol) was added and the reaction mixture was stirred at 50° C. under argon atmosphere over night. The reaction mixture was combined with the reaction mixture of another batch (starting from 5.5 g of Intermediate 34). Aqueous saturated sodiumhydrogencarbonate solution was added and it was diluted with dichloromethane. It was extracted with dichloromethane three times. Between both layers a beige precipitate was formed. The precipitate was filtered off. The filtrate was washed with water and brine once, filtered through a silicone coated filter and concentrated under reduced pressure. The residue was treated with a small amount of ethyl acetate and stirred for a few minutes. The unsolved precipitate was filtered off. The precipitate and the crude product were combined and treated with dichloromethane and ethanol, the undissolved precipitate was filtered off and dried at 50° C. under vacuo to provide the target compound in 86% purity: 1.8 g.

LC-MS (Method 2): $R_t$=0.83 min; MS (ESIpos): m/z=348 [M+H]$^+$ $^1$H-NMR (400 MHz, DMSO-d6) δ [ppm]: 1.171 (0.50), 1.215 (10.47), 1.220 (16.00), 1.522 (0.60), 1.778 (0.75), 1.986 (0.85), 2.083 (11.41), 2.477 (5.53), 2.518 (3.79), 2.523 (2.24), 3.833 (14.85), 5.757 (1.64), 6.307 (1.30), 6.865

(1.40), 6.868 (1.60), 6.878 (1.50), 6.882 (1.64), 6.950 (1.55), 6.952 (1.84), 6.956 (1.40), 7.277 (1.05), 7.280 (0.85), 7.296 (1.74), 7.315 (1.35), 7.318 (1.00), 7.410 (0.70), 7.413 (0.85), 7.421 (1.10), 7.424 (1.35), 7.427 (1.35), 7.430 (1.40), 7.439 (0.95), 7.441 (1.30), 7.444 (1.10), 7.448 (0.55), 7.451 (0.50), 7.459 (0.75), 7.462 (0.75), 7.527 (1.40), 7.887 (0.65), 7.899 (1.40), 7.902 (1.30), 7.907 (1.60), 7.918 (1.60), 7.929 (1.10), 7.936 (0.70), 8.042 (1.35), 8.044 (1.40), 8.055 (1.45), 8.057 (1.40), 13.777 (0.70), 13.939 (0.45).

Intermediate 36

Ethyl N-(2-hydroxy-2-methylpropyl)-beta-alaninate

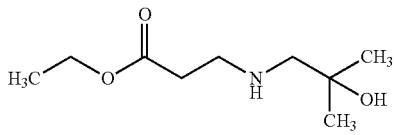

1-Amino-2-methylpropan-2-ol (CAS: 2854-16-2, 9.3 mL, 100 mmol) was dissolved in 100 mL ethanol and cooled down to 0° C. Then ethyl prop-2-enoate (CAS: 140-88-5, 11 mL, 100 mmol) was added and it was stirred at rt for 2 hours under argon atmosphere. The reaction mixture was concentrated under reduced pressure to provide the crude product which was used without further purification: 18.5 g.

Intermediate 37

Ethyl N-(3-ethoxy-3-oxopropanoyl)-N-(2-hydroxy-2-methylpropyl)-beta-alaninate

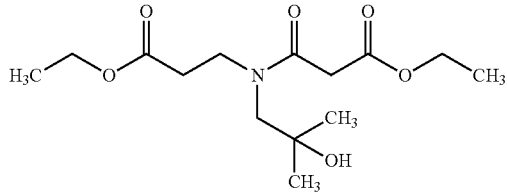 [SMILES: CCOC(=O)CCN(CC(C)(C)O)C(=O)CC(=O)OCC]

Ethyl-N-(2-hydroxy-2-methylpropyl)-beta-alaninate (see Intermediate 36, 17.4 g) was dissolved in 94 mL dichloromethane and cooled down to 0° C. Then N,N-diisopropylethylamine (18 mL, 100 mmol) and the 4-dimethyl-aminopyridine (1.13 g, 9.22 mmol) were added. Subsequently ethyl 3-chloro-3-oxopropanoate (CAS: 36239-09-5, 13 mL, 100 mmol) was added dropwise. It was stirred at 0° C. for 1.5 hours and at room temperature over night. Aqueous half concentrated ammonium chloride solution was added and the reaction mixture was diluted with dichloromethane. It was stirred for a few minutes, filtered through a silicone coated filter and concentrated under reduced pressure. The crude product was purified by flash chromatography three times (Biotage, 100 g column, silica ultra; hexane/ethyl acetate 0%-100%/ethyl acetate/ethanol 0%-20%), (Biotage, 50 g column, silica ultra; hexane/ethyl acetate 0%-100%/ ethyl acetate/ethanol 0%-20%) and (Biotage, 50 g column, silica ultra; hexane/ethyl acetate 0%-100%/ethyl acetate/ ethanol 0%-20%) to provide the target compound in 88% purity: 5.8 g.

LC-MS (Method 2): $R_t$=0.83 min; MS (ESIpos): m/z=305 $[M+H]^+$ $^1$H-NMR (400 MHz, DMSO-d6) δ [ppm]: 1.018 (0.67), 1.043 (13.62), 1.097 (16.00), 1.152 (4.33), 1.158 (5.01), 1.161 (4.69), 1.163 (4.37), 1.169 (9.33), 1.176 (10.86), 1.178 (9.66), 1.180 (8.83), 1.187 (4.52), 1.194 (5.11), 1.196 (4.67), 1.198 (4.22), 2.518 (1.43), 2.522 (1.80), 2.539 (1.92), 2.558 (1.28), 2.643 (0.86), 2.662 (1.15), 2.681 (0.92), 3.236 (4.18), 3.269 (3.02), 3.554 (13.39), 3.574 (1.84), 3.592 (1.13), 3.701 (0.82), 3.720 (1.03), 3.739 (0.77), 4.017 (1.15), 4.034 (5.13), 4.042 (0.49), 4.052 (8.52), 4.070 (6.23), 4.073 (3.80), 4.088 (1.82), 4.091 (3.27), 4.109 (0.98), 4.533 (3.59), 4.678 (4.10), 5.758 (0.57).

Intermediate 38

Ethyl-1-(2-hydroxy-2-methylpropyl)-2,4-dioxopiperidine-3-carboxylate

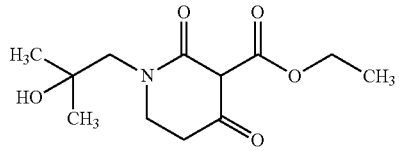 [SMILES: CCOC(=O)C1C(=O)CCN(CC(C)(C)O)C1=O]

Sodium ethylat solution in ethanol (4.9 mL, 21% purity, 21 mmol) was cooled down with an ice bath and treated dropwise with ethyl N-(3-ethoxy-3-oxopropanoyl)-N-(2-hydroxy-2-methylpropyl)-beta-alaninate (see Intermediate 37, 5.79 g), dissolved in 28 mL ethanol. It was stirred at this temperature for 30 minutes and at rt over night under argon atmosphere. The reaction mixture was diluted with dichloromethane and the pH was adjusted to 1 by the addition of aqueous hydrochloric acid (4 M). It was stirred for a few minutes, filtered through a silicone coated filter and concentrated under reduced pressure. The crude product was purified by flash chromatography (Biotage, 25 g column, silica ultra; ethyl acetate/ethanol 0%-20%) to provide the analytically pure target compound: 3.2 g.

LC-MS (Method 2): $R_t$=0.74 min; MS (ESIpos): m/z=258 $[M+H]^+$ $^1$H-NMR (400 MHz, DMSO-d6) δ [ppm]: 1.035 (2.68), 1.042 (3.17), 1.052 (8.33), 1.056 (16.00), 1.066 (3.03), 1.070 (3.25), 1.085 (1.52), 1.097 (3.40), 1.151 (1.05), 1.157 (1.03), 1.160 (1.02), 1.161 (1.02), 1.167 (2.12), 1.175 (2.12), 1.177 (1.96), 1.179 (1.91), 1.186 (1.44), 1.196 (4.22), 1.206 (0.59), 1.213 (7.27), 1.231 (3.51), 2.518 (1.06), 2.522 (0.82), 2.539 (0.54), 2.551 (0.79), 2.557 (0.69), 2.568 (1.37), 2.584 (0.78), 2.659 (0.40), 3.235 (1.34), 3.249 (4.13), 3.269 (1.32), 3.307 (1.47), 3.327 (2.15), 3.367 (4.66), 3.378 (4.52), 3.401 (3.62), 3.410 (3.53), 3.428 (4.18), 3.435 (1.81), 3.445 (3.69), 3.463 (1.65), 3.468 (0.97), 3.475 (0.86), 3.495 (1.54), 3.513 (2.23), 3.530 (1.32), 3.553 (2.88), 3.573 (0.62), 3.591 (0.43), 3.721 (0.43), 4.033 (1.00), 4.051 (1.61), 4.069 (1.20), 4.072 (0.80), 4.087 (0.52), 4.090 (0.75), 4.103 (0.44), 4.106 (0.51), 4.121 (0.42), 4.123 (0.43), 4.148 (0.98), 4.165 (3.03), 4.183 (3.01), 4.201 (0.94), 4.719 (0.80).

Intermediate 39

1-(2-hydroxy-2-methylpropyl)piperidine-2,4-dione

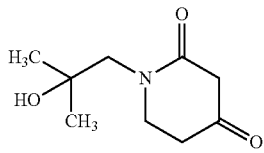

Ethyl-1-(2-hydroxy-2-methylpropyl)-2,4-dioxopiperidine-3-carboxylate (see Intermediate 38, 3.24 g) was dissolved in 24 mL dichloromethane and treated with the aqueous hydrochloric acid (24 mL, 2.0 M). It was stirred 20 min at rt under argon atmosphere. The reaction mixture was filtered through a silicone coated filter and concentrated under reduced pressure. The crude product was dissolved in acetonitrile and treated with 3.4 mL water. It was stirred under reflux for 1 hour. The reaction mixture was concentrated under reduced pressure to provide the crude product, which was used without further purification: 2.1 g.

$^1$H-NMR (400 MHz, DMSO-d6): δ [ppm]=1.07 (s, 6H), 2.51-2.53 (m, 2H), 3.33 (s, 2H), 3.37 (s, 2H), 3.72 (t, 2H), 4.51 (s, 1H).

Intermediate 40

4-hydroxy-1-(2-hydroxy-2-methylpropyl)-2-oxo-N-phenyl-1,2,5,6-tetrahydropyridine-3-carbothioamide

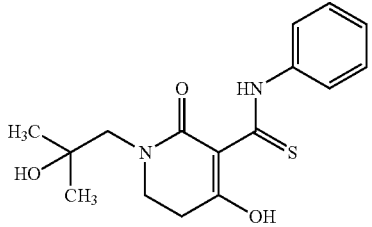 [SMILES: CC(C)(O)CN1CCC(O)=C(C(=S)Nc2ccccc2)C1=O]

1-(2-Hydroxy-2-methylpropyl)piperidine-2,4-dione (see Intermediate 39, 120 mg) was suspended in 870 μL acetonitrile and treated with isothiocyanatobenzene (77 μL, 650 μmol). The mixture was cooled down to 0° C. and treated slowly with the DBU (150 μL, 1.0 mmol). It was stirred at rt over night under argon atmosphere. The reaction mixture was poured into a mixture of ice and aqueous hydrochloric acid (4 M) and diluted with ethyl acetate and water. It was stirred for a few minutes, filtered through a silicone coated filter and concentrated under reduced pressure. The crude product was purified by HPLC chromatography under basic conditions to provide the target compound in 80% purity: 110 mg.

LC-MS (Method 2): $R_t$=0.51 min; MS (ESIpos): m/z=321 [M+H]$^+$ $^1$H-NMR (400 MHz, DMSO-d6): δ [ppm]=1.11 (s, 6H), 2.80 (t, 2H), 3.38 (s, 2H), 3.61 (t, 2H), 4.58 (s, 1H), 7.19-7.51 (m, 5H), 14.46 (s, 1H), 16.49 (s, 1H).

Intermediate 41

4-{[(2-aminopyridin-4-yl)methyl]amino}-1-(2-hydroxy-2-methylpropyl)-2-oxo-N-phenyl-1,2,5,6-tetrahydropyridine-3-carbothioamide

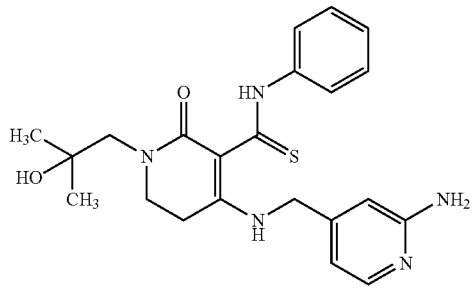 [SMILES: CC(C)(O)CN1CCC(NCc2ccnc(N)c2)=C(C(=S)Nc2ccccc2)C1=O]

4-Hydroxy-1-(2-hydroxy-2-methylpropyl)-2-oxo-N-phenyl-1,2,5,6-tetrahydropyridine-3-carbothioamide (see Intermediate 40, 110 mg) and 4-(aminomethyl)pyridin-2-amine (CAS: 199296-51-0, 71.9 mg, 584 μmol) were combined and it was stirred at 100° C. under argon atmosphere without further solvent. The reaction mixture was cooled down to rt and turned very thick. It was dissolved with dichloromethane and methanol. The crude product was purified by flash chromatography (Biotage, 10 g column, silica ultra; dichloromethane/ethanol 0%-20%) to provide the target compound with 81% purity: 38 mg.

LC-MS (Method 2): $R_t$=1.04 min; MS (ESIpos): m/z=427 [M+H]$^+$

1H-NMR (400 MHz, DMSO-d6): δ [ppm]=1.09 (s, 6H), 2.51-2.54 (m, 2H), 2.69-2.76 (m, 2H), 3.37 (s, 2H), 3.46 (br t, 2H), 4.52 (s, 1H), 4.57 (d, 2H), 6.01 (s, 2H), 6.34 (s, 1H), 6.42 (dd, 1H), 7.11-7.22 (m, 1H), 7.32-7.39 (m, 2H), 7.41-7.47 (m, 2H), 7.87 (d, 1H), 13.59 (br s, 1H), 14.56 (s, 1H).

Intermediate 42

2-(2-aminopyridin-4-yl)-3-anilino-5-(2-hydroxy-2-methylpropyl)-1,5,6,7-tetrahydro-4H-pyrrolo[3,2-c]pyridin-4-one

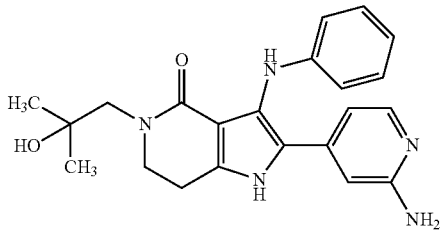 [SMILES: CC(C)(O)CN1CCc2[nH]c(-c3ccnc(N)c3)c(Nc3ccccc3)c2C1=O]

4-{[(2-Aminopyridin-4-yl)methyl]amino}-1-(2-hydroxy-2-methylpropyl)-2-oxo-N-phenyl-1,2,5,6-tetrahydropyridine-3-carbothioamide (see Intermediate 41, 1.85 g) was suspended in 38 mL methanol and treated with the trifluoric acid (670 μL, 8.7 mmol). It was stirred for 5 minutes, then the 3-chloroperoxybenzoic acid (1.50 g, 8.69 mmol) was added and it was stirred at 50° C. under argon atmosphere over night. Aqueous saturated sodium hydrogencarbonate solution was added and methanol was removed under vacuo.

The crude solution was diluted with dichloromethane. Between both layers a beige precipitate was formed. It was filtered off, treated with ethyl acetate and stirred for a few minutes. The undissolved precipitate was filtered off. The filtrate was purified by flash chromatography (Biotage, 28 g column, aminophase; dichloromethane/ethanol 0%-10%) to provide the target compound in 90% purity: 386 mg.

LC-MS (Method 2): $R_t$=0.85 min; MS (ESIpos): m/z=393 [M+H]$^+$ $^1$H-NMR (400 MHz, DMSO-d6) δ [ppm]: 1.036 (1.21), 1.054 (2.49), 1.071 (16.00), 2.518 (1.35), 2.523 (0.91), 2.860 (0.86), 2.877 (1.78), 2.894 (0.95), 3.279 (3.54), 3.423 (0.47), 3.436 (0.49), 3.441 (0.46), 3.453 (0.46), 3.680 (0.98), 3.697 (1.90), 3.714 (0.91), 4.358 (0.63), 4.526 (5.23), 5.659 (2.67), 6.539 (1.97), 6.541 (2.06), 6.556 (2.24), 6.575 (2.32), 6.578 (1.95), 6.589 (0.47), 6.592 (0.69), 6.610 (1.40), 6.628 (0.76), 6.661 (1.34), 6.665 (1.27), 6.675 (1.29), 6.679 (1.28), 6.998 (1.68), 7.017 (2.11), 7.019 (2.09), 7.038 (1.39), 7.275 (2.75), 7.718 (1.80), 7.732 (1.76), 11.546 (1.46).

Intermediate 43

N-(2-fluorophenyl)-4-hydroxy-1-methyl-2-oxo-1,2,5,6-tetrahydropyridine-3-carbothioamide

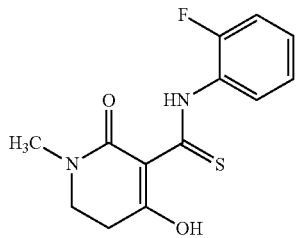 [SMILES: CN1CCC(O)=C(C(=S)Nc2ccccc2F)C1=O]

1-Methylpiperidine-2,4-dione (250 mg, 1.97 mmol) and 1-fluoro-2-isothiocyanatobenzene (301 mg, 1.97 mmol) were dissolved in 10 mL acetonitrile and cooled down to 0° C. DBU (470 µL, 3.1 mmol) was added and the reaction mixture was stirred over night at rt. The reaction mixture was cooled down to 0° C., the pH was adjusted to pH3 by the addition of aqueous hydrochloric acid (4 M) and water was added. The aqueous layer was extracted with ethyl acetate. The organic layer was washed with brine, filtered through a silicone coated filter and concentrated under reduced pressure. The crude product was purified by column chromatography (Biotage 25 g silica ultra column, Gradient: 0-100% hexan/ethyl acetated) to provide the target compound in 93% purity: 718 mg.

LC-MS (Method 2): $R_t$=0.47 min; MS (ESIpos): m/z=281 [M+H]$^+$ $^1$H-NMR (400 MHz, DMSO-d6) δ [ppm]: 2.518 (1.50), 2.523 (0.94), 2.664 (0.50), 2.669 (0.62), 2.673 (0.57), 2.678 (0.49), 2.827 (1.89), 2.846 (3.77), 2.863 (2.05), 2.947 (0.42), 2.964 (16.00), 3.110 (0.95), 3.464 (2.39), 3.482 (4.39), 3.500 (2.12), 7.247 (0.81), 7.252 (0.90), 7.267 (1.53), 7.287 (1.00), 7.331 (0.74), 7.348 (1.78), 7.351 (1.65), 7.359 (1.32), 7.377 (2.56), 7.391 (0.76), 7.623 (0.90), 7.643 (1.56), 7.662 (0.76), 14.476 (2.11), 16.411 (5.07).

Intermediate 44

4-{[(2-aminopyridin-4-yl)methyl]amino}-N-(2-fluorophenyl)-1-methyl-2-oxo-1,2,5,6-tetrahydropyridine-3-carbothioamide

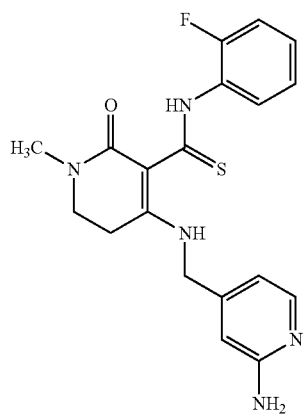 [SMILES: CN1CCC(NCc2ccnc(N)c2)=C(C(=S)Nc2ccccc2F)C1=O]

N-(2-Fluorophenyl)-4-hydroxy-1-methyl-2-oxo-1,2,5,6-tetrahydropyridine-3-carbothioamide (see Intermediate 43, 550 mg, 1.96 mmol), 4-(aminomethyl)pyridin-2-amine (435 mg, 3.53 mmol) and 4.6 mL N,N-dimethylacetamide were combined in microwave vial. The reaction mixture stirred for 2 h at 120° C. under a nitrogen atmosphere. It was extracted with ethyl acetate and brine twice. The combined organic layers were filtered trough a silicone coated filter and were concentrated under reduced pressure. The crude product was purified by column chromatography twice (Biotage, column: 25 g silica ultra, gradient: 0-15% dichloromethane/ethanol) (Biotage, column: 10 g Snap Ultra, gradient: 0-10% dichloromethane/ethanol) to provide the target compound in 99% purity: 238 mg.

LC-MS (Method 2): $R_t$=1.02 min; MS (ESIpos): m/z=386 [M+H]$^+$ $^1$H-NMR (400 MHz, DMSO-d6) δ [ppm]: 1.035 (1.19), 1.052 (2.67), 1.070 (1.34), 1.956 (0.88), 2.327 (0.86), 2.331 (0.63), 2.518 (3.41), 2.523 (2.11), 2.669 (0.88), 2.673 (0.65), 2.740 (1.19), 2.757 (2.31), 2.774 (1.33), 2.781 (1.05), 2.938 (16.00), 3.317 (1.91), 3.350 (1.31), 3.422 (0.55), 3.435 (0.57), 3.440 (0.54), 3.452 (0.55), 4.355 (0.69), 4.569 (2.45), 4.585 (2.42), 6.004 (3.36), 6.331 (2.45), 6.400 (1.51), 6.404 (1.36), 6.413 (1.50), 6.417 (1.40), 7.164 (0.52), 7.171 (0.42), 7.177 (0.74), 7.186 (0.94), 7.193 (0.55), 7.197 (0.76), 7.206 (0.97), 7.246 (2.08), 7.248 (2.22), 7.257 (1.29), 7.262 (1.43), 7.266 (1.17), 7.269 (1.26), 7.277 (1.66), 7.279 (1.50), 7.623 (0.77), 7.645 (1.22), 7.662 (0.69), 7.857 (2.20), 7.870 (2.16), 13.656 (0.43), 13.669 (0.79), 13.683 (0.40), 14.584 (2.10).

Intermediate 45

2-(2-aminopyridin-4-yl)-3-(2-fluoroanilino)-5-methyl-1,5,6,7-tetrahydro-4H-pyrrolo[3,2-c]pyridin-4-one

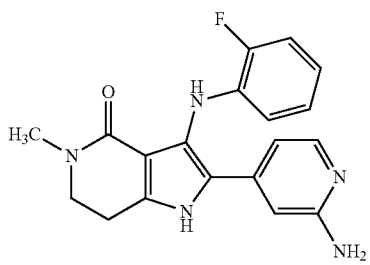 [SMILES: CN1CCc2[nH]c(-c3ccnc(N)c3)c(Nc3ccccc3F)c2C1=O]

4-{[(2-Aminopyridin-4-yl)methyl]amino}-N-(2-fluorophenyl)-1-methyl-2-oxo-1,2,5,6-tetrahydropyridine-3-carbothioamide (see Intermediate 44, 238 mg) was suspended in 5.5 mL methanol and treated with trifluoric acid (95 µl, 1.2 mmol). After it was stirred for 5 minutes 3-chloroperoxybenzoid acid (181 mg, 1.05 mmol) was added. The mixture was stirred at 50° C. under argon atmosphere over night. Aqueous saturated sodium hydrogencarbonate solution was added and diluted with dichloromethane. It was stirred for 30 minutes. The organic layer was filtered through a silicone coated filter and concentrated under reduced pressure. The crude product was purified by HPLC under basic conditions to provide the target compound in 90% purity: 59 mg.

LC-MS (Method 2): $R_t$=0.86 min; MS (ESIpos): m/z=553 [M+H]$^+$ $^1$H-NMR (400 MHz, DMSO-d6) δ [ppm]: 2.518 (4.24), 2.522 (2.74), 2.673 (0.84), 2.858 (16.00), 2.892 (1.42), 2.909 (3.01), 2.927 (1.52), 3.311 (1.40), 3.336 (1.52), 3.377 (1.13), 3.382 (1.52), 3.518 (1.80), 3.535 (3.59), 3.552 (1.57), 5.736 (2.71), 5.758 (0.52), 6.280 (0.63), 6.284 (0.71), 6.304 (1.21), 6.323 (0.67), 6.327 (0.65), 6.507 (2.28), 6.509 (2.34), 6.637 (0.44), 6.646 (2.23), 6.649 (2.17), 6.660 (2.05), 6.663 (2.07), 6.668 (0.63), 6.676 (0.59), 6.680 (0.48), 6.763 (0.81), 6.767 (0.84), 6.786 (1.30), 6.802 (0.63), 7.080 (0.79), 7.084 (0.82), 7.100 (0.81), 7.104 (0.77), 7.110 (0.86), 7.114 (0.82), 7.130 (0.73), 7.134 (0.71), 7.271 (1.80), 7.276 (1.80), 7.755 (1.92), 7.768 (1.84), 8.150 (5.53), 11.605 (1.55).

Intermediate 46

Ethyl 4-chloro-2-cyano-2-phenylbutanoate

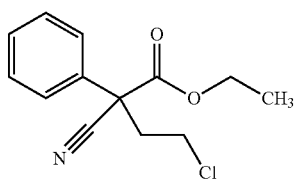 [SMILES: CCOC(=O)C(C#N)(CCCl)c1ccccc1]

To a stirred solution of potassium 2-methylpropan-2-olate (7.2 g, 63 mmol) in DMF (60 mL) was added ethyl cyano(phenyl)acetate (7.3 ml, 42 mmol) with water bath cooling within 1 h. The mixture was stirred at room temperature for 0.5 h. 1-bromo-2-chloroethane (5.3 ml, 63 mmol) was added and the mixture was stirred at room temperature for 16 h. An aqueous solution of ammonium chloride was added and the mixture was extracted with MTBE. The organic phase was washed with saturated sodium chloride solution, dried (sodium sulfate), filtered and the solvent was removed in vacuum. Silicagel chromatography gave 5.04 g (43% yield) of the title compound.

LC-MS (Method 1): $R_t$=1.27 min; MS (ESIpos): m/z=251 [M+H]$^+$ $^1$H NMR (400 MHz, DMSO-d$_6$) δ [ppm]: 1.16 (t, 3H), 2.70 (dt, 1H), 2.93 (dt, 1H), 3.68 (dd, 2H), 4.14-4.31 (m, 2H), 7.38-7.60 (m, 5H).

Intermediate 47

4-chloro-2-phenylbutanenitrile

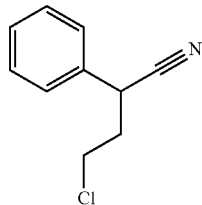 [SMILES: N#CC(CCCl)c1ccccc1]

To a stirred solution of ethyl 4-chloro-2-cyano-2-phenylbutanoate (7.25 g, 28.8 mmol) in methanol (40 mL) was added a half-saturated aqueous solution of potassium carbonate (8 mL) at 0° C. and the mixture was stirred at 0° C. for 3.5 h. Hydrochloric acid was added until pH 3 was reached, then an aqueous solution of sodium bicarbonate was added until pH 7 was reached and the mixture was extracted with MTBE. The organic phase was washed with saturated sodium chloride solution, dried (sodium sulfate), filtered and the solvent was removed in vacuum. Silicagel chromatography gave 3.95 g (76% yield) of the title compound.

LC-MS (Method 1): $R_t$=1.15 min; MS (ESIpos): m/z=221/223 [M+CH$_3$CO]$^+$ $^1$H NMR (400 MHz, DMSO-d$_6$) δ ppm: 2.22-2.33 (m, 1H), 2.42 (ddt, 1H), 3.57-3.72 (m, 2H), 4.36 (dd, 1H), 7.32-7.50 (m, 4H).

Intermediate 48

4-iodo-2-phenylbutanenitrile

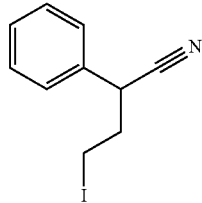 [SMILES: N#CC(CCI)c1ccccc1]

To a stirred solution of 4-chloro-2-phenylbutanenitrile (1.15 g, 6.40 mmol) in acetone (15 mL) was added sodium iodide (1.58 g, 10.6 mmol) and the mixture was stirred at reflux for 48 h. The mixture was filtered and the solvent was removed in vacuum. Water was added and the mixture was extracted with MTBE. The organic phase was dried (sodium sulfate), filtered and the solvent was removed in vacuum. Silicagel chromatography gave 1.53 g (88% yield) of the title compound.

LC-MS (Method 1): $R_t$=1.24 min; MS (ESIpos): m/z=272 [M+H]$^+$ $^1$H-NMR (400 MHz, DMSO-d6) δ [ppm]:

$^1$H NMR (400 MHz, DMSO-$d_6$) δ ppm: 2.27-2.38 (m, 1H), 2.39-2.48 (m, 1H), 3.11-3.28 (m, 2H), 4.27 (dd, 1H), 7.32-7.50 (m, 4H)

Intermediate 49

4-(morpholin-4-yl)-2-phenylbutanenitrile

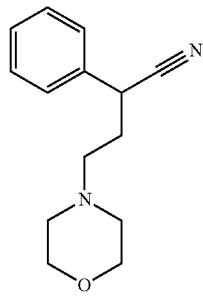 [SMILES: N#CC(CCN1CCOCC1)c1ccccc1]

To a stirred solution of morpholine (490 µl, 5.6 mmol) in dichloromethane (12 mL) in a sealed tube was added sodium hydrogen carbonate (948 mg, 11.3 mmol) and a solution of 4-iodo-2-phenylbutanenitrile (1.53 g, 5.64 mmol) in dichloromethane (5 mL) and the mixture was stirred at 45° C. for 16 h. Dichloromethane (35 mL) was added, the mixture was filtered and the solvent was removed in vacuum. Silicagel chromatography gave 739 mg (57% yield) of the title compound.

LC-MS (Method 1): $R_t$=0.48 min; MS (ESIpos): m/z=231 [M+H]$^+$ $^1$H-NMR (400 MHz, DMSO-d6) δ [ppm]: 1.89-2.14 (m, 2H), 2.20-2.41 (m, 6H), 3.50-3.64 (m, 4H), 4.23 (dd, 1H), 7.27-7.47 (m, 5H).

Intermediate 50 propyl-4-(morpholin-4-yl)-2-phenylbutanoate

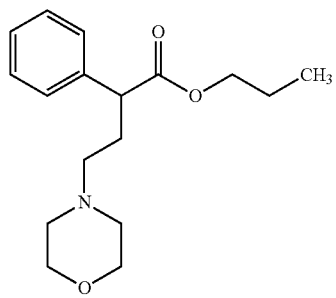 [SMILES: CCCOC(=O)C(CCN1CCOCC1)c1ccccc1]

To a stirred solution of 4-(morpholin-4-yl)-2-phenylbutanenitrile (370 mg, 1.61 mmol) in propan-1-ol (8.0 ml, 130 mmol) (10 mL) in a sealed tube was added conc. sulfuric acid (1.0 ml, 19 mmol) and the mixture was stirred at 130° C. for 3 h. The mixture was added to an aqueous solution of sodium bicarbonate and the mixture was extracted with dichloromethane. The organic phase was washed with saturated sodium chloride solution, dried (sodium sulfate), filtered and the solvent was removed in vacuum to give 457 mg (91% yield) of the title compound, that was used without further purification.

LC-MS (Method 2): $R_t$=1.23 min; MS (ESIpos): m/z=292 [M+H]$^+$ $^1$H NMR (400 MHz, DMSO-$d_6$) δ [ppm]: 0.78 (t, 3H), 1.51 (sxt, 2H), 1.68-1.81 (m, 1H), 2.13-2.39 (m, 7H), 3.54 (t, 4H), 3.68 (t, 1H), 3.88-4.04 (m, 2H), 7.20-7.44 (m, 5H).

Intermediate 51

4-(morpholin-4-yl)-2-phenylbutanoic acid

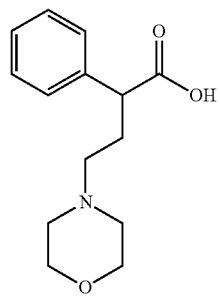 [SMILES: O=C(O)C(CCN1CCOCC1)c1ccccc1]

To a stirred solution of propyl-4-(morpholin-4-yl)-2-phenylbutanoate (425 mg, 1.46 mmol) in propan-1-ol (15 mL) sodium hydroxide (175 mg, 4.38 mmol) dissolved in water (3 mL) was added and the mixture was stirred at 50° C. for 2.5 h. Water was added and the mixture was extracted with dichloromethane. The aqueous phase was filtered and the water was removed in vacuum. Toluene was added to the residue and the solvent was removed in vacuum to give 652 mg (approx. 50% purity) of the title compound as a crude product that was used for the next reaction without purification.

LC-MS (Method 1): $R_t$=0.45 min; MS (ESIpos): m/z=250 [M+H]$^+$ $^1$H NMR (400 MHz, DEUTERIUM OXIDE) δ ppm: 2.07-2.23 (m, 1H), 2.30-2.47 (m, 1H), 2.78-3.19 (m, 4H), 3.32-3.48 (m, 2H), 3.61-3.76 (m, 3H), 3.91-4.07 (m, 2H), 7.22-7.45 (m, 5H)

Intermediate 52

Ethyl 2-cyano-4,4-difluoro-2-phenylbutanoate

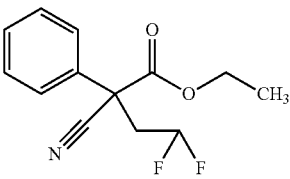 [SMILES: CCOC(=O)C(C#N)(CC(F)F)c1ccccc1]

To a stirred solution of potassium 2-methylpropan-2-olate (1.78 ml, 16 mmol) in DMF (13 mL) was added ethyl cyano(phenyl)acetate (1.8 ml, 11 mmol) portionwise with water bath cooling. The mixture was stirred at room temperature for 0.5 h. 2,2-difluoroethyl trifluoromethanesulfonate (2.1 ml, 16 mmol) was added and the mixture was stirred at room temperature for 16 h. An aqueous solution of ammonium chloride was added and the mixture was extracted with ethyl acetate. The organic phase was washed with saturated sodium chloride solution, dried (sodium sulfate), filtered and the solvent was removed in vacuum. Silicagel chromatography gave 2.02 g (75% yield) of the title compound.

LC-MS (Method 2): $R_t$=1.19 min; MS (ESIpos): m/z=271 $[M+H_2O]^+$ $^1$H-NMR (400 MHz, DMSO-d6) δ [ppm]: 1.15 (t, 3H), 2.89-3.05 (m, 1H), 3.06-3.21 (m, 1H), 4.13-4.31 (m, 2H), 6.03-6.37 (m, 1H), 7.39-7.64 (m, 5H).

Intermediate 53

4,4-difluoro-2-phenylbutanenitrile

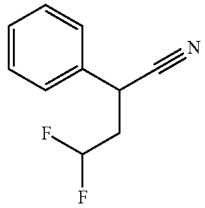 [SMILES: N#CC(CC(F)F)c1ccccc1]

To a stirred solution of ethyl 2-cyano-4,4-difluoro-2-phenylbutanoate (2.00 g, 7.90 mmol) in methanol (13 mL) was added a half-saturated aqueous solution of potassium carbonate (2.6 mL) at 0° C. and the mixture was stirred at 0° C. for 3 h. Hydrochloric acid was added until pH 3 was reached, then an aqueous solution of sodium bicarbonate was added until pH 7 was reached and the mixture was extracted with dichloromethane. The organic phase was washed with saturated sodium chloride solution, dried (sodium sulfate), filtered and the solvent was removed in vacuum to give 1.4 g of the title compound as a crude product that was used without purification.

LC-MS (Method 2): $R_t$=1.05 min; MS (ESIpos): m/z=271

$^1$H-NMR (400 MHz, DMSO-d6) δ [ppm]: 2.35-2.47 (m, 1H), 2.56-2.76 (m, 1H), 4.48 (dd, J=9.38, 5.58 Hz, 1H), 6.14 (tt, J=55.50, 4.31 Hz, 1H), 7.32-7.50 (m, 5H).

Intermediate 54 propyl-4,4-difluoro-2-phenylbutanoate

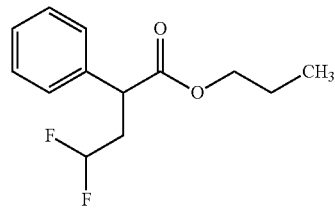 [SMILES: CCCOC(=O)C(CC(F)F)c1ccccc1]

To a stirred solution of 4,4-difluoro-2-phenylbutanenitrile (1.30 g, 7.17 mmol) in propan-1-ol (20 ml, 270 mmol) (20 mL) in a sealed tube was added conc. sulfuric acid (3.8 ml, 72 mmol) and the mixture was stirred at 120° C. for 3 h. Water was added and the mixture was extracted with ethyl acetate. The organic phase was washed with saturated sodium chloride solution, dried (sodium sulfate), filtered and the solvent was removed in vacuum to give 920 mg (53% yield) of the title compound.

LC-MS (Method 2): $R_t$=1.34 min; MS (ESIpos): m/z=243 $[M+H]^+$ $^1$H-NMR (400 MHz, DMSO-d6) δ [ppm]: 0.733 (7.03), 0.752 (16.00), 0.770 (7.37), 1.455 (0.59), 1.472 (1.54), 1.474 (1.76), 1.490 (3.65), 1.508 (3.11), 1.525 (1.65), 2.218 (0.60), 2.228 (0.49), 2.232 (0.57), 2.261 (0.50), 2.265 (0.58), 2.269 (0.44), 2.275 (0.49), 2.279 (0.41), 2.634 (0.47), 2.645 (0.49), 2.656 (0.50), 2.669 (0.70), 2.682 (0.42), 2.692 (0.43), 2.704 (0.43), 3.330 (6.98), 3.846 (1.23), 3.860 (1.33), 3.868 (1.30), 3.882 (1.15), 3.958 (4.38), 3.974 (9.07), 3.990 (4.15), 5.879 (0.49), 5.891 (0.79), 5.902 (0.45), 6.020 (0.93), 6.031 (1.57), 6.043 (0.93), 6.161 (0.42), 6.172 (0.76), 6.183 (0.45), 7.269 (0.41), 7.274 (0.79), 7.279 (0.48), 7.282 (0.47), 7.291 (2.13), 7.293 (0.84), 7.298 (0.96), 7.300 (0.79), 7.305 (1.09), 7.308 (1.57), 7.312 (2.32), 7.317 (2.16), 7.321 (1.26), 7.325 (0.76), 7.333 (7.63), 7.339 (8.69), 7.348 (0.86), 7.354 (2.75), 7.357 (3.46), 7.362 (1.44), 7.372 (0.44), 7.376 (1.16), 7.379 (0.67).

Intermediate 55

4,4-difluoro-2-phenylbutanoic acid

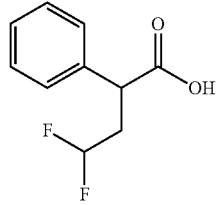 [SMILES: O=C(O)C(CC(F)F)c1ccccc1]

To a stirred solution of propyl 4,4-difluoro-2-phenylbutanoate (915 mg, 3.78 mmol) in ethanol (33 mL) was added an aqueous solution of sodium hydroxide (3.8 ml, c=2.0 M, 7.6 mmol) and the mixture was stirred at room temperature for 2 h. Hydrochloric acid was added until pH 3 was reached and the mixture was extracted with ethyl acetate. The organic phase was dried (sodium sulfate), filtered and the solvent was removed in vacuum to give 730 mg (97% yield) of the title compound as a crude product that was used for the next reaction without purification.

LC-MS (Method 2): $R_t$=0.49 min; MS (ESIneg): m/z=199 $[M-H]^-$ $^1$H-NMR (400 MHz, DMSO-d6) δ [ppm]: 2.10-2.28 (m, 1H), 2.54-2.73 (m, 1H), 3.73 (dd, 1H), 6.00 (tt, 1H), 7.23-7.40 (m, 5H), 12.67 (br s, 1H).

Intermediate 56

Ethyl N-benzyl-beta-alaninate

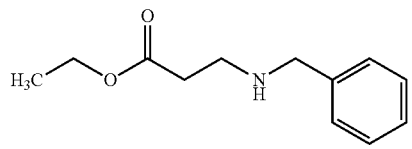

1-Phenylmethanamine (CAS: 100-46-9, 1.1 mL, 10 mmol) was dissolved in 10 mL ethanol and treated with ethyl prop-2-enoate (CAS: 140-88-5, 1.1 mL, 10 mmol). It was stirred at rt under argon atmosphere for 2 hours. The reaction mixture was concentrated under reduced pressure to provide the crude product, which was used without further purification: 2.1 g, 86% purity.

LC-MS (Method 2): $R_t$=1.02 min; MS (ESIpos): m/z=209 [M+H]$^+$ $^1$H-NMR (400 MHz, DMSO-d6) δ [ppm]: 1.149 (7.59), 1.167 (16.00), 1.185 (7.45), 2.126 (0.40), 2.408 (2.39), 2.416 (0.55), 2.426 (6.09), 2.442 (3.14), 2.683 (2.95), 2.699 (5.39), 2.717 (2.24), 3.336 (2.57), 3.700 (0.48), 4.014 (2.17), 4.032 (6.62), 4.049 (6.43), 4.067 (1.98), 7.195 (0.54), 7.198 (0.74), 7.200 (0.54), 7.205 (0.56), 7.208 (1.45), 7.216 (0.75), 7.219 (1.13), 7.222 (0.86), 7.230 (0.83), 7.271 (0.53), 7.274 (0.42), 7.279 (0.44), 7.284 (0.59), 7.293 (8.94), 7.304 (13.16), 7.315 (0.45).

Intermediate 57

Ethyl N-benzyl-N-(2,2,2-trifluoroethyl)-beta-alaninate

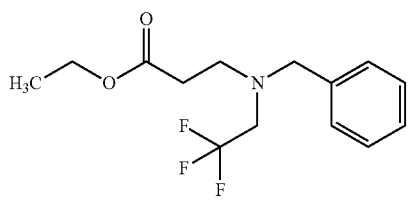 [SMILES: CCOC(=O)CCN(Cc1ccccc1)CC(F)(F)F]

Ethyl N-benzyl-beta-alaninate (see Intermediate 56, 2.00 g) was dissolved in 37 mL DMF and treated with N,N-diisopropylethylamine (3.7 mL, 22 mmol) and 2,2,2-trifluoroethyl trifluoromethanesulfonate (1.5 mL, 11 mmol). It was stirred at rt under argon atmosphere. Further 2,2,2-trifluoroethyl trifluoromethanesulfonate (1.5 mL, 11 mmol) was added and it was stirred at rt for 2 days. The reaction mixture was diluted with water and dichloromethane. The aqueous layer was extracted with dichloromethane three times. The combined organic layers were washed with water and brine once, filtered through a silicone coated filter and concentrated under reduced pressure. The crude product was purified by flash chromatography (25 g column, silica; hexane/ethyl acetate 0%-80%) to provide the target compound in 95% purity: 2.2 g.

LC-MS (Method 2): $R_t$=1.40 min; MS (ESIpos): m/z=291 [M+H]$^+$ $^1$H-NMR (400 MHz, DMSO-d6) δ [ppm]: 1.126 (7.40), 1.144 (16.00), 1.154 (0.66), 1.161 (7.44), 1.172 (0.88), 1.986 (1.56), 2.456 (2.35), 2.474 (5.05), 2.481 (0.74), 2.828 (2.19), 2.846 (3.84), 2.863 (1.81), 3.256 (1.23), 3.281 (3.61), 3.306 (3.48), 3.763 (7.62), 3.987 (2.06), 4.005 (6.29), 4.017 (0.61), 4.023 (6.11), 4.035 (0.46), 4.041 (1.96), 7.238 (0.61), 7.247 (0.46), 7.255 (1.73), 7.261 (0.67), 7.266 (0.60), 7.272 (1.06), 7.275 (1.14), 7.285 (1.76), 7.294 (0.77), 7.301 (5.45), 7.306 (3.34), 7.311 (4.44), 7.313 (4.78), 7.318 (1.34), 7.327 (2.86), 7.329 (3.40), 7.332 (1.58), 7.344 (0.45), 7.348 (1.05), 7.351 (0.63).

Intermediate 58

Ethyl N-(2,2,2-trifluoroethyl)-beta-alaninate

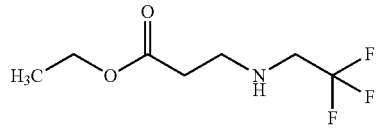

Ethyl N-benzyl-N-(2,2,2-trifluoroethyl)-beta-alaninate (see Intermediate 57, 1.67 g) was dissolved in 5.8 mL ethanol and treated with Palladium (10%) on activated carbon (104 mg, 10% purity, 97.9 µmol). Then ammonium formiate (763 mg, 12.1 mmol) was added portion wise and it was stirred at 50° C. for 1 hour. The reaction mixture was evacuated and air flushed. Then further Palladium (10%) on activated carbon (123 mg, 10% purity, 115 µmol) was added followed by ammonium formiate (763 mg, 12.1 mmol). The reaction mixture was stirred at 65° C. over night. The catalyst was filtered off over celite and washed with ethanol. The filtrate was concentrated under reduced pressure at maximum of 166 mbar to provide the crude product which was used without further purification: 1.4 g.

$^1$H-NMR (400 MHz, DMSO-d6) δ [ppm]: 1.035 (3.83), 1.052 (8.47), 1.070 (3.66), 1.156 (7.36), 1.173 (16.00), 1.191 (7.84), 2.402 (3.69), 2.419 (7.81), 2.436 (3.97), 2.518 (0.54), 2.820 (1.64), 3.183 (0.40), 3.207 (1.08), 3.226 (1.08), 3.405 (0.61), 3.417 (0.69), 3.422 (1.94), 3.435 (1.99), 3.440 (1.88), 3.452 (1.92), 3.457 (0.64), 3.469 (0.58), 4.021 (2.28), 4.039 (6.94), 4.056 (6.78), 4.074 (2.13), 4.346 (1.42), 4.358 (2.74), 4.371 (1.32).

Intermediate 59

Ethyl N-(3-ethoxy-3-oxopropanoyl)-N-(2,2,2-trifluoroethyl)-beta-alaninate

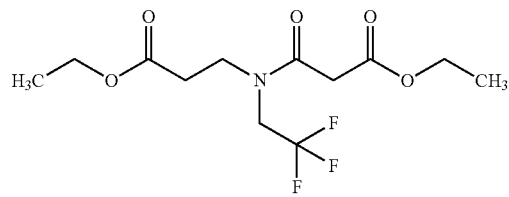 [SMILES: CCOC(=O)CCN(CC(F)(F)F)C(=O)CC(=O)OCC]

Ethyl N-(2,2,2-trifluoroethyl)-beta-alaninate (see Intermediate 58, 1.15 g) was dissolved in 5.9 mL dichloromethane and cooled down to 0° C. Then N,N-diisopropylethylamine (1.1 mL, 6.4 mmol) and N,N-Dimethylpyridin-4-amine (70.5 mg, 577 µmol) were added. Subsequently ethyl 3-chloro-3-oxopropanoate (800 µL, 6.4 mmol) was added, while the temperature stayed under 13° C. It was stirred at 0° C. for 1.5 hours and at rt over night. Half concentrated ammonium chloride solution was added and the reaction mixture was diluted with dichloromethane. It was stirred for a few minutes, filtered through a silicone coated filter and concentrated under reduced pressure. The crude product was purified by flash chromatography (10 g column, silica ULTRA; hexane/ethyl acetate 0%-100%) to provide the desired target compound in 87% purity: 1.6 g.

LC-MS (Method 2): $R_t$=1.03 min; MS (ESIpos): m/z=315 [M+H]$^+$ $^1$H-NMR (400 MHz, DMSO-d6) δ [ppm]: 1.156 (2.52), 1.160 (4.59), 1.163 (7.14), 1.169 (8.20), 1.175 (5.50), 1.178 (9.77), 1.181 (14.58), 1.187 (16.00), 1.192 (3.55), 1.195 (5.32), 1.199 (7.45), 1.204 (7.57), 2.403 (0.65), 2.421 (1.50), 2.437 (0.78), 2.518 (0.65), 2.523 (0.42), 2.539 (1.22), 2.556 (2.02), 2.575 (1.34), 2.680 (1.66), 2.698 (2.48), 2.717 (1.78), 2.809 (0.55), 2.826 (1.02), 2.843 (0.46), 3.207 (1.18), 3.232 (1.09), 3.475 (1.97), 3.537 (1.34), 3.546 (6.78), 3.555 (2.15), 3.573 (1.18), 3.613 (1.58), 3.632 (2.30), 3.649 (1.43), 3.680 (10.44), 4.022 (0.59), 4.033 (1.11), 4.040 (1.73), 4.048 (2.27), 4.052 (3.91), 4.057 (2.03), 4.066 (6.37), 4.069 (5.90), 4.075 (1.37), 4.085 (8.02), 4.088 (5.03), 4.098 (2.44), 4.103 (5.77), 4.116 (1.78), 4.121 (1.65), 4.133 (0.53), 4.153 (0.85), 4.177 (2.46), 4.201 (2.37), 4.225 (0.79), 4.321 (0.49), 4.343 (1.42), 4.366 (1.35), 4.389 (0.43).

Intermediate 60

Ethyl 2,4-dioxo-1-(2,2,2-trifluoroethyl)piperidine-3-carboxylate

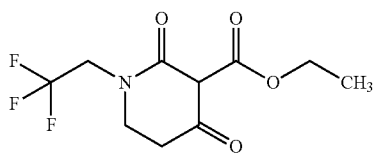 [SMILES: CCOC(=O)C1C(=O)CCN(CC(F)(F)F)C1=O]

Sodium ethoxide solution in ethanol (1.3 mL, 21% purity, 5.5 mmol) was cooled down with an ice bath and was treated dropwise with ethyl N-(3-ethoxy-3-oxopropanoyl)-N-(2,2,2-trifluoroethyl)-beta-alaninate (see Intermediate 59, 1.57 g) dissolved in 3.7 mL ethanol. The reaction mixture was stirred at this temperature for 30 minutes and at room temperature over night under argon atmosphere. The reaction mixture was diluted with dichloromethane and the pH was adjusted to 1 by addition of aqueous hydrochloric acid (4 M). It was stirred for a few minutes, filtered through a silicone coated filter and concentrated under reduced pressure. The crude product was purified by flash chromatography (25 g column, silica; ethyl acetate/ethanol 0%-20%) to provide the target compound: 592 mg.

$^1$H-NMR (400 MHz, DMSO-d6) δ [ppm]: 1.156 (0.56), 1.168 (0.75), 1.177 (0.58), 1.180 (0.71), 1.186 (1.23), 1.202 (7.69), 1.220 (16.00), 1.237 (7.59), 2.399 (1.41), 2.416 (2.92), 2.433 (1.50), 2.518 (1.19), 2.522 (0.76), 2.535 (2.23), 2.550 (4.12), 2.565 (2.28), 2.639 (2.78), 2.656 (5.71), 2.673 (3.23), 3.335 (9.59), 3.357 (1.02), 3.436 (1.54), 3.453 (3.12), 3.463 (9.76), 3.471 (2.09), 3.478 (3.03), 3.495 (5.41), 3.513 (2.63), 3.713 (1.75), 3.728 (3.25), 3.743 (1.63), 4.047 (0.98), 4.071 (2.71), 4.085 (0.56), 4.096 (2.73), 4.107 (1.54), 4.115 (0.74), 4.120 (1.25), 4.132 (4.04), 4.157 (5.21), 4.175 (7.75), 4.193 (7.15), 4.211 (2.36), 4.222 (1.15), 4.246 (3.12), 4.271 (3.01), 4.295 (0.96), 4.951 (3.53), 10.764 (0.53).

Intermediate 61

1-(2,2,2-trifluoroethyl)piperidine-2,4-dione

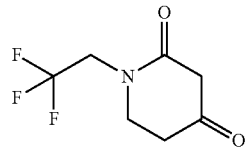 [SMILES: O=C1CCN(CC(F)(F)F)C(=O)C1]

Ethyl 2,4-dioxo-1-(2,2,2-trifluoroethyl)piperidine-3-carboxylate (see Intermediate 60, 590 mg) was dissolved in 4.3 mL dichloromethane and treated with aqueous hydrochloric acid (4.2 mL, 2.0 M, 8.3 mmol). The reaction mixture was stirred 20 min at rt under argon atmosphere. The reaction mixture was filtered through a silicone coated filter and concentrated under reduced pressure. The crude product was dissolved in 5.8 mL acetonitrile and treated with 600 μL water. It was stirred under reflux for 1 hour under argon atmosphere. The reaction mixture was concentrated under reduced pressure to provide the target compound, which was used without further purification: 428 mg, 75% purity.

LC-MS (Method 1): $R_t$=0.59 min; MS (ESIpos): m/z=196 [M+H]$^+$ $^1$H-NMR (400 MHz, DMSO-d6) δ [ppm]: 1.169 (0.73), 1.174 (0.65), 1.177 (0.43), 1.180 (0.61), 1.187 (1.36), 1.204 (0.69), 2.399 (2.49), 2.416 (5.08), 2.434 (2.71), 2.518 (3.26), 2.523 (2.35), 2.535 (3.79), 2.550 (7.01), 2.565 (3.82), 3.436 (2.68), 3.453 (5.46), 3.463 (16.00), 3.470 (3.39), 3.713 (3.13), 3.728 (5.85), 3.743 (2.96), 4.047 (1.56), 4.057 (0.41), 4.072 (4.36), 4.085 (0.77), 4.096 (4.23), 4.121 (1.45), 4.223 (1.78), 4.247 (5.13), 4.271 (4.94), 4.296 (1.59), 4.950 (5.96), 10.764 (2.74).

Intermediate 62

4-hydroxy-2-oxo-N-phenyl-1-(2,2,2-trifluoroethyl)-1,2,5,6-tetrahydropyridine-3-carbothioamide

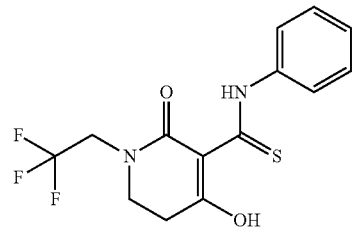 [SMILES: O=C1C(C(=S)Nc2ccccc2)=C(O)CCN1CC(F)(F)F]

1-(2,2,2-Trifluoroethyl)piperidine-2,4-dione (see Intermediate 61, 428 mg) was suspended in 3 mL acetonitrile and treated with isothiocyanatobenzene (260 μL, 2.2 mmol). The mixture was cooled down to 0° C. and treated slowly with DBU (520 μL, 3.5 mmol). The reaction mixture was stirred at rt over night. The reaction mixture was poured into a mixture of ice and aqueous hydrochloric acid (4 M). The aqueous layer was extracted with ethyl acetate thrice. The combined organic layers were washed with water and brine once, filtered through a silicone coated filter and concen-

Intermediate 63

4-{[(2-aminopyridin-4-yl)methyl]amino}-2-oxo-N-phenyl-1-(2,2,2-trifluoroethyl)-1,2,5,6-tetrahydro-pyridine-3-carbothioamide

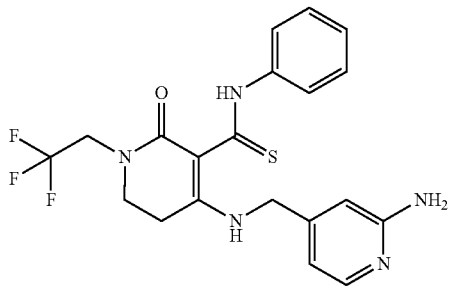 [SMILES: Nc1cc(CNC2=C(C(=S)Nc3ccccc3)C(=O)N(CC(F)(F)F)CC2)ccn1]

4-Hydroxy-2-oxo-N-phenyl-1-(2,2,2-trifluoroethyl)-1,2,5,6-tetrahydropyridine-3-carbothioamide (see Intermediate 62, 740 mg) and 4-(aminomethyl)pyridin-2-amine (469 mg, 3.81 mmol) were combined and stirred at 100° C. for 2 h under argon atmosphere without further solvent. The reaction mixture was cooled down to rt and turned very thick. It was dissolved in dichloromethane and methanol. The crude product was purified by flash chromatography (25 g column, silica ULTRA; dichloromethane/ethanol 0%-20% ethanol) to provide the target compound in 96% purity: 98 mg.

LC-MS (Method 2): $R_t$=1.18 min; MS (ESIpos): m/z=436 [M+H]$^+$ $^1$H-NMR (400 MHz, DMSO-d6) δ [ppm]: 1.232 (0.41), 2.331 (0.77), 2.518 (4.52), 2.522 (2.74), 2.530 (0.86), 2.548 (0.45), 2.673 (0.81), 2.762 (4.35), 2.778 (7.80), 2.794 (4.65), 3.160 (0.86), 3.172 (0.90), 3.452 (4.91), 3.468 (8.16), 3.483 (4.52), 3.513 (0.43), 3.834 (0.62), 3.849 (0.62), 4.216 (0.62), 4.244 (2.33), 4.268 (5.98), 4.292 (5.66), 4.316 (1.89), 4.578 (9.98), 4.593 (9.85), 5.758 (4.13), 5.925 (0.79), 6.017 (16.00), 6.104 (0.58), 6.341 (11.55), 6.411 (6.85), 6.414 (6.15), 6.424 (6.79), 6.427 (6.28), 7.165 (0.66), 7.184 (2.46), 7.188 (3.58), 7.191 (2.14), 7.206 (7.11), 7.221 (2.83), 7.224 (4.58), 7.227 (2.68), 7.239 (0.49), 7.255 (0.58), 7.275 (0.66), 7.294 (0.51), 7.351 (6.70), 7.371 (13.36), 7.389 (10.95), 7.421 (12.62), 7.440 (6.90), 7.775 (0.49), 7.790 (0.49), 7.864 (10.24), 7.878 (9.92), 13.621 (2.55), 14.093 (5.68).

Intermediate 64

2-(2-aminopyridin-4-yl)-3-anilino-5-(2,2,2-trifluoroethyl)-1,5,6,7-tetrahydro-4H-pyrrolo[3,2-c]pyridin-4-one

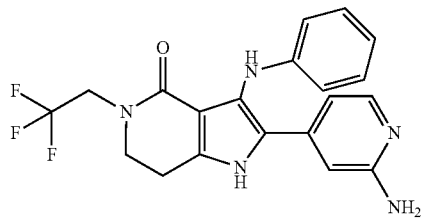 [SMILES: Nc1cc(-c2[nH]c3c(c2Nc2ccccc2)C(=O)N(CC(F)(F)F)CC3)ccn1]

4-{[(2-Aminopyridin-4-yl)methyl]amino}-2-oxo-N-phenyl-1-(2,2,2-trifluoroethyl)-1,2,5,6-tetrahydropyridine-3-carbothioamide (see Intermediate 63, 100 mg) was suspended in 2.0 mL methanol and treated with trifluoric acid (35 µL, 460 µmol). The reaction mixture was stirred for 5 minutes, then 3-chloroperoxybenzoic acid (113 mg, 70% purity, 459 µmol) was added and it was stirred at 90° C. under argon atmosphere in a sealed vessel for 2 hours. Saturated sodium hydrogencarbonate solution was added and the methanol was removed under vacuo. The crude product was diluted with dichloromethane. It was stirred for a few minutes, filtered through a silicone coated filter and concentrated under reduced pressure. This crude product was combined with a further batch of the same reaction starting with 4-{[(2-Aminopyridin-4-yl)methyl]amino}-2-oxo-N-phenyl-1-(2,2,2-trifluoroethyl)-1,2,5,6-tetrahydropyridine-3-carbothioamide (see Intermediate 63, 100 mg) and purified by flash chromatography (11 g column, aminophase; dichloromethane/ethanol 0%-5%) to provide the target compound in 91% purity: 74 mg.

LC-MS (Method 2): $R_t$=1.01 min; MS (ESIpos): m/z=403 [M+H]$^+$ $^1$H-NMR (400 MHz, DMSO-d6) δ [ppm]: 0.905 (0.45), 2.518 (1.61), 2.522 (1.04), 2.917 (1.67), 2.935 (3.56), 2.952 (1.86), 3.663 (1.79), 3.680 (3.57), 3.697 (1.71), 4.140 (0.86), 4.165 (2.45), 4.189 (2.29), 4.213 (0.72), 5.702 (4.68), 5.758 (16.00), 6.551 (4.14), 6.570 (4.53), 6.573 (4.14), 6.577 (4.86), 6.580 (5.19), 6.598 (2.59), 6.613 (0.96), 6.616 (1.36), 6.694 (2.40), 6.698 (2.31), 6.708 (2.46), 6.711 (2.35), 6.998 (3.20), 7.016 (3.91), 7.019 (3.86), 7.037 (2.57), 7.180 (5.02), 7.739 (3.19), 7.752 (3.09), 11.692 (2.37).

Intermediate 65

4-(dimethylamino)-2-phenylbutanenitrile

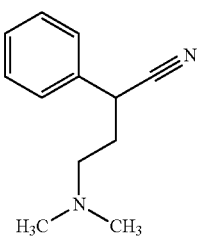

---

Previous page content (col 95):

trated under reduced pressure to provide the crude product, which was used without further purification: 748 mg, 97% purity.

LC-MS (Method 2): $R_t$=0.59 min; MS (ESIpos): m/z=331 [M+H]$^+$ $^1$H-NMR (400 MHz, DMSO-d6) δ [ppm]: -4.196 (0.90), 2.083 (3.90), 2.518 (1.04), 2.523 (0.65), 2.845 (1.82), 2.862 (3.58), 2.879 (1.97), 3.454 (0.44), 3.464 (0.41), 3.470 (0.52), 3.596 (1.98), 3.613 (3.60), 3.631 (1.85), 4.277 (0.93), 4.301 (2.63), 4.324 (2.54), 4.348 (0.86), 7.299 (0.60), 7.310 (1.41), 7.321 (2.12), 7.330 (1.61), 7.342 (1.08), 7.424 (0.58), 7.447 (11.04), 7.458 (16.00), 13.851 (1.84).

To a stirred solution of N-methylmethanamine (solution in THF; 3.0 ml, 2.0 M, 6.0 mmol) in dichloromethane (15 mL) in a sealed tube was added sodium hydrogen carbonate (1.00 g, 12.0 mmol) and a solution of 4-iodo-2-phenylbutanenitrile (Intermediate 48) (1.62 g, 5.98 mmol) in dichloromethane (5 mL) and the mixture was stirred at 45° C. for 64 h. Further N-methylmethanamine (solution in THF; 3.0 ml, 2.0 M, 6.0 mmol) and sodium hydrogen carbonate (1.00 g, 12.0 mmol) was added and the mixture was stirred at 50° C. for 16 h. Dichloromethane was added, the mixture was filtered and the solvent was removed in vacuum. Aminophase-silicagel chromatography gave 789 mg (56% yield) of the title compound.

LC-MS (Method 2): $R_t$=1.02 min; MS (ESIpos): m/z=188 [M+H]$^+$ $^1$H NMR (400 MHz, DMSO-d$_6$) δ [ppm]: 1.87-2.08 (m, 2H), 2.13 (s, 6H), 2.20 (ddd, 1H), 2.28-2.38 (m, 1H), 4.21 (dd, 1H), 7.24-7.51 (m, 5H).

Intermediate 66

4-(dimethylamino)-2-phenylbutanoic acid-hydrogen chloride salt

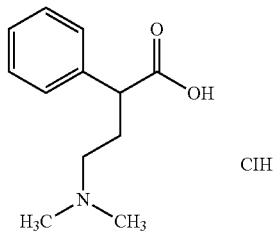

To a stirred solution of sodium hydroxide (489 mg, 12.2 mmol) in water (1 mL) was added 4-(dimethylamino)-2-phenylbutanenitrile (720 mg, 3.82 mmol) and the mixture was stirred at 105° C. for 2 h. Water was added and the mixture was extracted with a mixture of chloroform and methanol (9:1). Hydrochloric acid was added to the aqueous phase until pH 1 was reached. The aqueous phase was filtered and the water was removed in vacuum. Toluene was added to the residue and the solvent was removed in vacuum to give 1.17 g (approx. 50% purity) of the title compound as a crude product that was used for the next reaction without purification.

$^1$H NMR (400 MHz, DEUTERIUM OXIDE) δ [ppm]: 2.12 (dddd, 1H), 2.35 (dddd, 1H), 2.73 (s, 3H), 2.75 (s, 3H), 2.85 (td, 1H), 3.07 (td, 1H), 3.66 (dd, 1H), 7.19-7.44 (m, 5H).

Intermediate 67

4-hydroxy-2-oxo-N-phenyl-6-(trifluoromethyl)-1,2,5,6-tetrahydropyridine-3-carbothioamide (Racemate)

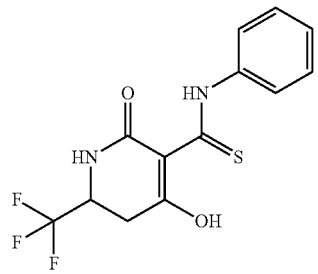 [SMILES: O=C1NC(C(F)(F)F)CC(O)=C1C(=S)Nc1ccccc1]

6-(Trifluoromethyl)piperidine-2,4-dione (250 mg, 1.38 mmol; CAS-RN: [1552231-27-2]) and isothiocyanatobenzene (110 μL, 1.4 mmol; CAS-RN: [103-72-0]) were dissolved in 10 mL acetonitrile and cooled down to 0° C. DBU (330 μL, 2.2 mmol; CAS-RN: [6674-22-2]) was added and the reaction mixture was stirred over night at rt. The reaction mixture was cooled down to 0° C. and the pH was adjusted to pH3 by addition of hydrochloric acid (4N). Water and ethyl acetate were added. The organic layer was extracted with brine, dried by filtering through a silicone coated filter and concentrated under reduced pressure. The crude product was purified by flash chromatography (Biotage 25 g silica ultra column: Gradient: 0-60% hexane/ethyl acetate) to provide the target compound in 94% purity: 780 mg.

LC-MS (Method 1): $R_t$=1.26 min; MS (ESIpos): m/z=317 [M+H]$^+$ $^1$H-NMR (400 MHz, DMSO-d6): δ [ppm]=2.55-2.80 (m, 1H), 3.36-3.70 (m, 1H), 4.25-4.73 (m, 1H), 7.32 (br t, 1H), 7.37-7.55 (m, 4H), 8.88 (br d, 1H), 13.80-14.27 (m, 1H), 16.59-17.34 (m, 1H).

Intermediate 68

4-{[(2-aminopyridin-4-yl)methyl]amino}-2-oxo-N-phenyl-6-(trifluoromethyl)-1,2,5,6-tetrahydropyridine-3-carbothioamide (Racemate)

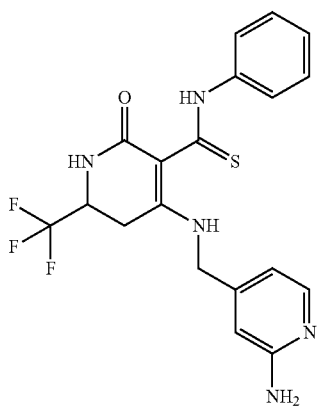 [SMILES: Nc1cc(CNC2=C(C(=S)Nc3ccccc3)C(=O)NC(C(F)(F)F)C2)ccn1]

4-Hydroxy-2-oxo-N-phenyl-6-(trifluoromethyl)-1,2,5,6-tetrahydropyridine-3-carbothioamide (see Intermediate 67, 440 mg), 4-(aminomethyl)pyridin-2-amine (308 mg, 2.50 mmol; CAS-RN: [199296-51-0]) were dissolved in 4.6 mL DMA in a microwave vial. Nitrogen was bubbled through and the reaction mixture was stirred for 2 h at 120° C. Ethyl acetate and brine were added and the aqueous layer was extracted with ethyl acetate twice. The collected organic layers were filtered trough a silicone coated filter and concentrated under reduced pressure. The crude product was purified by chromatography (Biotage 25 g silica ultra column, Gradient: 0-15% dichloromethane/ethanol) to provide the target compound in 88% purity: 630 mg.

LC-MS (Method 2): $R_t$=1.02 min; MS (ESIpos): m/z=422 [M+H]$^+$ $^1$H-NMR (400 MHz, DMSO-d6): δ [ppm]=2.90 (br s, 1H), 3.21 (dd, 1H), 4.19-4.30 (m, 1H), 4.61 (br d, 2H), 6.01 (s, 2H), 6.34 (s, 1H), 6.41 (dd, 1H), 7.17-7.24 (m, 1H), 7.30-7.46 (m, 4H), 7.87 (d, 1H), 8.31 (d, 1H), 14.01 (br s, 1H), 14.48 (s, 1H).—contains DMA and ethanol Intermediate 69

2-(2-aminopyridin-4-yl)-3-anilino-6-(trifluoromethyl)-1,5,6,7-tetrahydro-4H-pyrrolo[3,2-c]pyridin-4-one (Racemate)

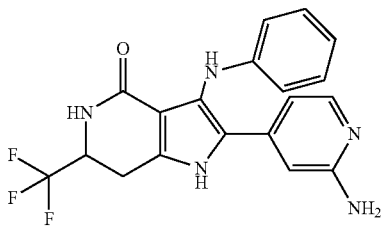 [SMILES: Nc1cc(-c2[nH]c3c(c2Nc2ccccc2)C(=O)NC(C(F)(F)F)C3)ccn1]

4-{[(2-Aminopyridin-4-yl)methyl]amino}-2-oxo-N-phenyl-6-(trifluoromethyl)-1,2,5,6-tetrahydropyridine-3-carbothioamide (Racemate) (see Intermediate 68, 190 mg) was dissolved in 2.2 mL methanol and treated with the hydrogen peroxide (92 μL, 0.902 mmol, 30%). It was stirred at 90° C. for 2 hours in the microwave reactor under argon atmosphere. The reaction mixture was combined with another batch of the reaction with Intermediate 68 (200 mg) and saturated sodium thiosulfate solution, half concentrated potassium carbonate solution, dichloromethan and water were added. It was stirred for a few minutes, filtered through a silicone coated filter and concentrated under reduced pressure. The crude product was purified by HPLC chromatography under basic conditions to provide the target compound in 84% purity: 24 mg.

LC-MS (Method 2): $R_t$=0.86 min; MS (ESIpos): m/z=389 [M+H]$^+$ $^1$H-NMR (400 MHz, DMSO-d6) δ [ppm]=2.99 (dd, 1H), 3.36-3.42 (m, 1H), 4.26-4.45 (m, 1H), 5.70 (s, 2H), 6.49-6.63 (m, 4H), 6.68 (dd, 1H), 7.01 (dd, 2H), 7.15 (s, 1H), 7.65-7.81 (m, 2H), 11.66 (br s, 1H).

Intermediate 70

4-hydroxy-1,6,6-trimethyl-2-oxo-N-phenyl-1,2,5,6-tetrahydropyridine-3-carbothioamide

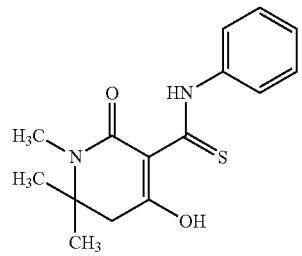 [SMILES: CN1C(=O)C(C(=S)Nc2ccccc2)=C(O)CC1(C)C]

1,6,6-Trimethylpiperidine-2,4-dione (660 mg, CAS-RN: [118263-86-8], EP 278742) was suspended in 5.7 mL acetonitrile and treated with isothiocyanatobenzene (510 μL, 4.3 mmol). The mixture was cooled down to 0° C. and treated slowly with DBU (1.0 mL, 6.8 mmol). After complete addition the ice bath was removed and the mixture was stirred at rt overnight. The reaction mixture was poured into a mixture of ice and hydrochloric acid (4 M). This aqueous mixture was extracted with ethyl acetate twice. The combined organic layers were filtered using a water resistant filter and concentrated under reduced pressure to provide the 87% pure target compound, which was used without further purification: 1.27 g LC-MS (Method 2): $R_t$=0.66 min; MS (ESIpos): m/z=291 [M+H]$^+$ $^1$H-NMR (400 MHz, DMSO-d6) δ [ppm]: 1.138 (0.44), 1.156 (0.87), 1.173 (0.47), 1.274 (0.68), 1.299 (16.00), 1.316 (2.37), 1.376 (2.13), 1.907 (1.94), 1.959 (1.48), 1.987 (0.50), 2.518 (0.60), 2.684 (0.78), 2.818 (5.85), 2.860 (1.51), 2.901 (0.59), 2.913 (12.96), 2.952 (0.69), 3.047 (1.51), 4.017 (0.44), 7.254 (0.42), 7.273 (0.63), 7.275 (0.66), 7.288 (0.58), 7.293 (0.61), 7.305 (0.96), 7.322 (0.71), 7.326 (0.48), 7.405 (1.17), 7.416 (0.90), 7.420 (1.07), 7.425 (0.52), 7.436 (1.35), 7.441 (2.40), 7.449 (0.48), 7.454 (0.92), 7.459 (2.62), 7.467 (2.53), 7.470 (2.69), 7.487 (0.99), 7.492 (0.62), 14.664 (1.00), 16.548 (3.38).

Intermediate 71

4-{[(2-aminopyridin-4-yl)methyl]amino}-1,6,6-trimethyl-2-oxo-N-phenyl-1,2,5,6-tetrahydropyridine-3-carbothioamide

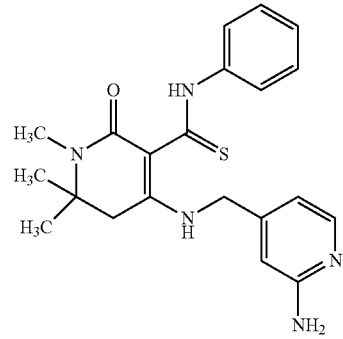 [SMILES: CN1C(=O)C(C(=S)Nc2ccccc2)=C(NCc2ccnc(N)c2)CC1(C)C]

4-Hydroxy-1,6,6-trimethyl-2-oxo-N-phenyl-1,2,5,6-tetrahydropyridine-3-carbothioamide (see Intermediate 70, 470 mg) and 4-(aminomethyl)pyridin-2-amine (339 mg, CAS-RN: [199296-51-0]) were combined and stirred at 100° C. under argon for 2 h. The reaction mixture was cooled down to rt and turned very thick. It was treated with dichloromethane and sonicated for approximately 20 min. The formed precipitate was filtered off, washed with dichloromethane and dried at 50° C. under vacuum. The filtrate was purified by flash chromatography (28 g column, aminophase; ethyl acetate/ethanol 0%-10%). The product containing fractions were combined, concentrated under reduced pressure, treated with ethanol and sonicated. The undissolved precipitate was filtered off, washed with ethanol and dried at 50° C. under vacuum to provide the 94% pure target compound: 214 mg.

LC-MS (Method 2): $R_t$=1.13 min; MS (ESIpos): m/z=396 [M+H]$^+$ $^1$H-NMR (400 MHz, DMSO-d6) δ [ppm]=1.20 (s, 6H), 2.73 (s, 2H), 2.87 (s, 3H), 4.59 (d, 2H), 6.00 (s, 2H), 6.34 (s, 1H), 6.42 (dd, 1H), 7.13-7.23 (m, 1H), 7.31-7.40 (m, 2H), 7.45 (d, 2H), 7.87 (d, 1H), 13.71-13.94 (m, 1H), 14.87 (s, 1H).

Intermediate 72

2-(2-aminopyridin-4-yl)-3-anilino-5,6,6-trimethyl-1,5,6,7-tetrahydro-4H-pyrrolo[3,2-c]pyridin-4-one

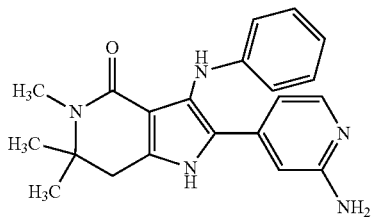 [SMILES: CN1C(=O)c2c([nH]c(-c3ccnc(N)c3)c2Nc2ccccc2)CC1(C)C]

4-{[(2-Aminopyridin-4-yl)methyl]amino}-1,6,6-trimethyl-2-oxo-N-phenyl-1,2,5,6-tetrahydropyridine-3-carbothioamide (see Intermediate 71, 20.0 mg) was suspended in 200 μL methanol and treated with the TFA (7.8 μL, 100 μmol). It was stirred for 5 minutes, then 3-chloroperoxybenzoic acid (24.9 mg, 70% purity, 101 μmol) was added and the reaction mixture was stirred at 90° C. under argon atmosphere over night in a sealed vessel. The reaction mixture was quenched with saturated sodium hydrogen carbonate solution and extracted with ethyl acetate three times. It was washed with water and brine once, filtered through a silicone coated filter and concentrated under reduced pressure. The crude product was purified by HPLC chromatography under basic conditions to provide the target compound in 95% purity: 8 mg.

LC-MS (Method 2): $R_t$=0.93 min; MS (ESIpos): m/z=362 [M+H]$^+$ $^1$H-NMR (400 MHz, DMSO-d6) δ [ppm]=1.28 (s, 6H), 2.73-2.82 (m, 3H), 2.86 (s, 2H), 5.67 (br s, 2H), 6.47-6.64 (m, 4H), 6.69 (br d, 1H), 7.02 (t, 2H), 7.27 (s, 1H), 7.73 (br s, 1H), 11.50 (s, 1H).

Intermediate 73

N-(2-fluorophenyl)-4-hydroxy-1,6,6-trimethyl-2-oxo-1,2,5,6-tetrahydropyridine-3-carbothioamide

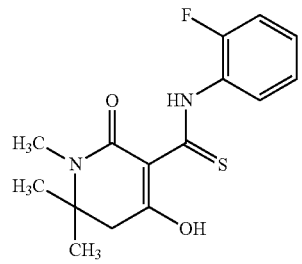

1,6,6-Trimethylpiperidine-2,4-dione (760 mg, CAS-RN: [118263-86-8], EP 278742) was suspended in 6.4 mL acetonitrile and treated with 1-fluoro-2-isothiocyanatobenzene (600 μL, 4.9 mmol). The mixture was cooled down to 0° C. and treated slowly with DBU (1.2 mL, 7.8 mmol). After complete addition the ice bath was removed and the mixture was stirred at rt for 2 hours. The reaction mixture was poured into a mixture of ice and hydrochloric acid (4 M). This aqueous mixture was extracted with ethyl acetate twice. The combined organic layers were filtered using a water resistant filter and concentrated under reduced pressure to provide the crude product in 97% purity, which was used without further purification: 1.5 g.

LC-MS (Method 1): $R_t$=1.37 min; MS (ESIpos): m/z=309 [M+H]$^+$ $^1$H-NMR (400 MHz, DMSO-d6) δ [ppm]]=1.30 (s, 6H), 2.85 (s, 2H), 2.91 (s, 3H), 7.20-7.29 (m, 1H), 7.31-7.41 (m, 2H), 7.65-7.73 (m, 1H), 14.58 (s, 1H), 16.47 (s, 1H).

Intermediate 74

4-{[(2-aminopyridin-4-yl)methyl]amino}-N-(2-fluorophenyl)-1,6,6-trimethyl-2-oxo-1,2,5,6-tetrahydropyridine-3-carbothioamide

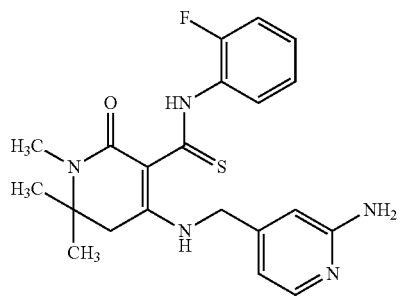 [SMILES: CN1C(=O)C(C(=S)Nc2ccccc2F)=C(NCc2ccnc(N)c2)CC1(C)C]

N-(2-fluorophenyl)-4-hydroxy-1,6,6-trimethyl-2-oxo-1,2,5,6-tetrahydropyridine-3-carbothioamide (see Intermediate 73, 396 mg) and 4-(aminomethyl)pyridin-2-amine (269 mg, 2.18 mmol) were combined and the mixture was stirred at 100° C. under nitrogen atmosphere without further solvent for 2 hours. The reaction mixture was cooled and diluted with dichloromethane. A yellow precipitate was filtered off under vacuum. The filter cake was dried in a vacuum drying oven to provide the target compound in 80% purity, which was used without further purification: 237 mg.

LC-MS (Method 2): $R_t$=1.14 min; MS (ESIpos): m/z=414 [M+H]$^+$ $^1$H-NMR (400 MHz, DMSO-d6) δ [ppm]: 1.209 (16.00), 1.234 (0.43), 1.241 (0.50), 1.263 (0.59), 2.518 (0.91), 2.523 (0.67), 2.755 (4.79), 2.874 (14.35), 3.364 (0.49), 3.502 (0.70), 3.680 (4.05), 4.271 (0.53), 4.285 (0.52), 4.600 (2.26), 4.615 (2.26), 5.758 (0.43), 5.863 (0.89), 5.890 (1.66), 6.008 (3.31), 6.155 (0.72), 6.305 (0.69), 6.344 (2.45), 6.380 (0.42), 6.399 (1.55), 6.401 (1.57), 6.409 (1.79), 6.413 (1.71), 6.422 (1.54), 6.426 (1.42), 6.474 (0.87), 6.477 (0.79), 6.487 (0.85), 6.490 (0.80), 6.849 (0.61), 6.866 (0.44), 6.880 (0.44), 7.162 (0.56), 7.174 (0.67), 7.177 (0.55), 7.185 (0.93), 7.189 (0.46), 7.195 (0.72), 7.205 (0.95), 7.247 (2.05), 7.256 (1.51), 7.259 (1.53), 7.263 (1.07), 7.270 (1.21), 7.275 (1.48), 7.278 (1.49), 7.670 (0.82), 7.689 (1.23), 7.691 (1.19), 7.710 (0.70), 7.799 (0.61), 7.811 (0.57), 7.830 (1.24), 7.842 (1.21), 7.861 (2.14), 7.874 (2.11), 7.996 (0.44), 7.998 (0.44), 8.010 (0.43), 8.012 (0.43), 13.838 (0.42), 13.853 (0.78), 14.775 (1.43).

Intermediate 75

2-(2-aminopyridin-4-yl)-3-(2-fluoroanilino)-5,6,6-trimethyl-1,5,6,7-tetrahydro-4H-pyrrolo[3,2-c]pyridin-4-one

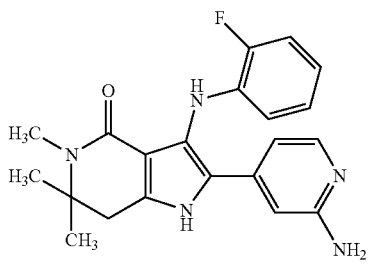 [SMILES: CN1C(=O)c2c([nH]c(-c3ccnc(N)c3)c2Nc2ccccc2F)CC1(C)C]

4-{[(2-Aminopyridin-4-yl)methyl]amino}-N-(2-fluorophenyl)-1,6,6-trimethyl-2-oxo-1,2,5,6-tetrahydropyridine-3-carbothioamide (see Intermediate 74, 522 mg) was suspended in 5.1 mL methanol. Adding TFA (190 μL, 2.5 mmol) gave a clear solution. It was stirred 5 min. at rt. 2.5 mL methanol was added to receive a stirrable suspension. Then 3-chloroperoxybenzoic acid (622 mg, 70% purity, 2.52 mmol) was added. Immediately the mixture changed into a clear solution. It was stirred at 90° C. in a sealed vessel for 2 hours. After cooling down to rt there was a beige precipitate in the reaction mixture. It was filtered off under vacuum and washed with methanol. To the filtrate aqueous saturated sodium hydrogencarbonate solution was added and it was diluted with dichloromethane. The layers were separated and the organic layer was dried using a water resistant filter. The clear filtrate was concentrated under reduced pressure and purified by flash chromatography (28 g amino column, gradient dichloromethane/ethanol 2-25%). The filter cake (82% purity) and the product containing fractions (74% purity) were combined to provide the target compound: 287 mg.

LC-MS (Method 2): $R_t$=0.98 min; MS (ESIpos): m/z=380 [M+H]$^+$

Intermediate 76

4-hydroxy-1-(2-methoxyethyl)-2-oxo-N-phenyl-1,2,5,6-tetrahydropyridine-3-carbothioamide

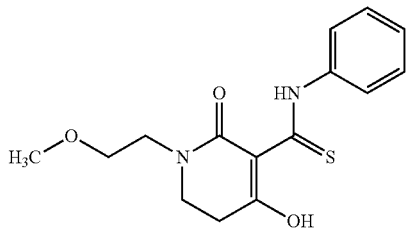 [SMILES: COCCN1CCC(O)=C(C(=S)Nc2ccccc2)C1=O]

1-(2-Methoxyethyl)piperidine-2,4-dione (940 mg, CAS-RN: [1508972-60-8], VCS 307781601, Journal of Medicinal Chemistry (2017), 60, 3438-3450) was suspended in 7.2 mL acetonitrile and treated with isothiocyanatobenzene (660 μL, 5.5 mmol). The mixture was cooled down to 0° C. and treated slowly with DBU (1.3 mL, 8.8 mmol). After complete addition the ice bath was removed and the mixture was stirred at rt for 2 hours. The reaction mixture was poured into a mixture of ice and hydrochloric acid (4 M). This aqueous mixture was extracted with ethyl acetate twice. The combined organic layers were filtered using a water resistant filter and concentrated under reduced pressure to provide the crude product in 87% purity, which was used without further purification: 1.3 g.

LC-MS (Method 1): $R_t$=1.29 min; MS (ESIpos): m/z=307 [M+H]$^+$ $^1$H-NMR (400 MHz, DMSO-d6) δ [ppm]=2.78 (t, 2H), 3.27 (s, 3H), 3.47-3.54 (m, 4H), 3.55-3.61 (m, 2H), 7.25-7.34 (m, 1H), 7.40-7.53 (m, 4H), 14.43 (s, 1H), 16.48 (s, 1H).

Intermediate 77

4-{[(2-aminopyridin-4-yl)methyl]amino}-1-(2-methoxyethyl)-2-oxo-N-phenyl-1,2,5,6-tetrahydropyridine-3-carbothioamide

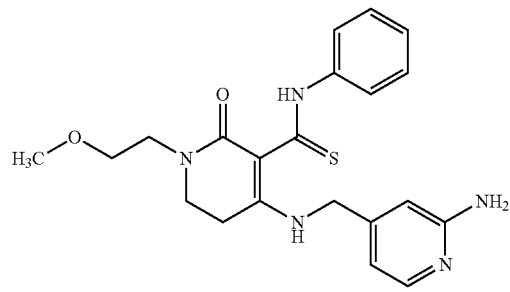 [SMILES: COCCN1CCC(NCc2ccnc(N)c2)=C(C(=S)Nc2ccccc2)C1=O]

4-hydroxy-1-(2-methoxyethyl)-2-oxo-N-phenyl-1,2,5,6-tetrahydropyridine-3-carbothioamide (see Intermediate 76, 630 mg) and 4-(aminomethyl)pyridin-2-amine (431 mg, 3.50 mmol) were combined and the reaction mixture was stirred at 100° C. under nitrogen atmosphere without further solvent for 5 hours. The reaction mixture was cooled and diluted with dichloromethane. After 10 min. of sonification a precipitate was filtered off under vacuum. The filter cake was dried in a vacuum drying oven, the clear filtrate was concentrated under reduced pressure. The filtrate was purified by flash chromatography (25 g silica ultra column, gradient dichloromethane/ethanol 0-20%) to provide the analytically pure target compound: 262 mg LC-MS (Method 2): $R_t$=1.07 min; MS (ESIneg): m/z=412 [M+H]⁻

¹H-NMR (400 MHz, DMSO-d6) δ [ppm]=2.69 (t, 2H), 3.25 (s, 3H), 3.34-3.39 (m, 2H), 3.42-3.50 (m, 2H), 3.52-3.60 (m, 2H), 4.56 (d, 2H), 6.01 (s, 2H), 6.33 (s, 1H), 6.41 (dd, 1H), 7.14-7.24 (m, 1H), 7.29-7.39 (m, 2H), 7.42-7.49 (m, 2H), 7.87 (d, 1H), 13.59 (br s, 1H), 14.58 (s, 1H).

Intermediate 78

2-(2-aminopyridin-4-yl)-3-anilino-5-(2-methoxyethyl)-1,5,6,7-tetrahydro-4H-pyrrolo[3,2-c]pyridin-4-one

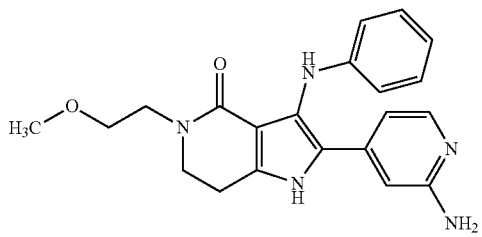 [SMILES: COCCN1CCc2[nH]c(-c3ccnc(N)c3)c(Nc3ccccc3)c2C1=O]

4-{[(2-aminopyridin-4-yl)methyl]amino}-1-(2-methoxyethyl)-2-oxo-N-phenyl-1,2,5,6-tetrahydropyridine-3-carbothioamide (see Intermediate 77, 255 mg) was suspended in 2.5 mL methanol. Adding TFA (95 μL, 1.2 mmol) gave a clear solution. It was stirred 5 min. at rt. Suddenly the mixture got solid. 2.5 mL methanol must be added to receive a stirrable suspension. Then 3-chloroperoxybenzoic acid (306 mg, 70% purity, 1.24 mmol) was added. Immediately the mixture changed into a clear solution. It was stirred at 90° C. in a sealed vessel for 2 hours. To the reaction mixture saturated sodium hydrogencarbonate solution was added and it was diluted with dichloromethane. The layers were separated and the organic layer was dried using a water resistant filter. The clear filtrate was concentrated under reduced pressure. The crude product was dissolved in dichloromethane. A white precipitate was formed and filtered off. The filtrate was purified by flash chromatography (11 g snap amino column, gradient dichloromethane/ethanol 0-20%) to provide the target compound in 98% purity: 62 mg.

LC-MS (Method 2): $R_t$=0.87 min; MS (ESIpos): m/z=378 [M+H]⁺

¹H-NMR (400 MHz, DMSO-d6) δ [ppm]=2.86 (t, 2H), 3.24 (s, 3H), 3.39-3.45 (m, 2H), 3.46-3.53 (m, 2H), 3.60 (t, 2H), 5.66 (s, 2H), 6.50-6.58 (m, 3H), 6.59-6.65 (m, 1H), 6.67 (dd, 1H), 6.96-7.09 (m, 2H), 7.24 (s, 1H), 7.72 (d, 1H), 11.53 (s, 1H).—contains dichloromethane Intermediate 79

8-hydroxy-6-oxo-N-phenyl-5-azaspiro[3.5]non-7-ene-7-carbothioamide

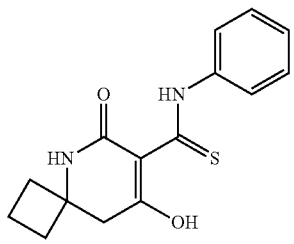 [SMILES: O=C1NC2(CCC2)CC(O)=C1C(=S)Nc1ccccc1]

5-Azaspiro[3.5]nonane-6,8-dione (2.00 g, 13.1 mmol, CAS-RN: [No 1105665-46-0]) was suspended in 17 mL acetonitrile and treated with isothiocyanatobenzene (1.6 mL, 13 mmol). The mixture was cooled down to 0° C. and treated slowly with DBU (3.1 mL, 21 mmol). After complete addition the ice bath was removed and the mixture was stirred at rt overnight. The mixture was acidified using aqueous hydrochloric acid (4 M) and ethyl acetate was added. The layers were separated and the organic layer was washed with water once, filtered using a water resistant filter and concentrated under reduced pressure to provide the analytically pure target compound: 3.6 g.

LC-MS (Method 2): $R_t$=0.55 min; MS (ESIpos): m/z=289 [M+H]⁺

¹H-NMR (400 MHz, DMSO-d6) δ [ppm]=1.75 (br dd, 2H), 2.05 (tt, 2H), 2.12-2.29 (m, 2H), 2.79-3.04 (m, 2H), 7.22-7.34 (m, 1H), 7.38-7.42 (m, 2H), 7.43-7.49 (m, 2H), 8.16-9.81 (m, 1H), 13.89-14.72 (m, 1H), 16.27-16.85 (m, 1H).

Intermediate 80

8-{[(2-aminopyridin-4-yl)methyl]amino}-6-oxo-N-phenyl-5-azaspiro[3.5]non-7-ene-7-carbothioamide

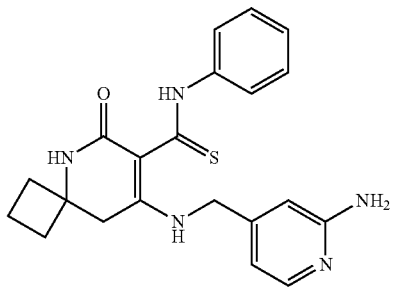 [SMILES: Nc1cc(CNC2=C(C(=S)Nc3ccccc3)C(=O)NC3(CCC3)C2)ccn1]

8-hydroxy-6-oxo-N-phenyl-5-azaspiro[3.5]non-7-ene-7-carbothioamide (see Intermediate 79, 3.62 g) and 4-(aminomethyl)pyridin-2-amine (2.63 g, 21.3 mmol) were combined and the mixture was stirred at 100° C. for 2 h under nitrogen atmosphere without further solvent in a sealed vessel in a heating block. The reaction mixture was cooled and diluted with dichloromethane. A beige precipitate was filtered off under vacuum. The filter cake was dried in a vacuum drying oven, the clear filtrate was concentrated under reduced pressure. The gritty filter cake was grinded, diluted with dichloromethane and stirred for 4 days. The precipitate was filtered off under vacuum. The filter cake was dried in a vacuum drying oven to provide the target compound in 74% purity: 4.0 g.

LC-MS (Method 2): $R_t$=1.03 min; MS (ESIpos): m/z=394 [M+H]$^+$ $^1$H-NMR (400 MHz, DMSO-d6) δ [ppm]=1.46-1.67 (m, 2H), 1.83-1.95 (m, 2H), 2.01-2.12 (m, 2H), 2.86 (s, 2H), 4.63 (br d, 2H), 6.02 (s, 2H), 6.38 (s, 1H), 6.42-6.46 (m, 1H), 7.14-7.24 (m, 1H), 7.27-7.38 (m, 2H), 7.40-7.49 (m, 2H), 7.88 (d, 1H), 8.08 (s, 1H), 13.91 (br d, 1H), 14.83 (s, 1H).

Intermediate 81

2'-(2-aminopyridin-4-yl)-3'-anilino-1',7'-dihydrospiro[cyclobutane-1,6'-pyrrolo[3,2-c]pyridin]-4'(5'H)-one

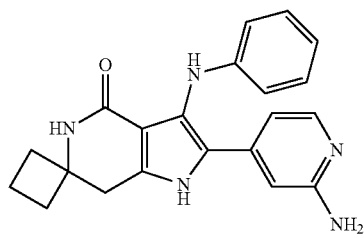 [SMILES: Nc1cc(-c2[nH]c3c(c2Nc2ccccc2)C(=O)NC2(CCC2)C3)ccn1]

8-{[(2-aminopyridin-4-yl)methyl]amino}-6-oxo-N-phenyl-5-azaspiro[3.5]non-7-ene-7-carbothioamide (see Intermediate 80, 4.10 g) was suspended in 42 mL methanol. Adding TFA (1.6 mL, 21 mmol) gave a clear solution. It was stirred 5 min. at rt. Then 3-chloroperoxybenzoic acid (5.14 g, 70% purity, 20.8 mmol) was added. It was stirred at 90° C. in a sealed vessel for 2 hours (in two portions). To the reaction mixture aqueous saturated sodium hydrogencarbonate solution was added and it was diluted with dichloromethane. The layers were separated and the organic layer was dried using a water resistant filter. The clear filtrate was concentrated under reduced pressure. The crude product was purified by flash chromatography (55 g amino column, gradient dichloromethane/ethanol 2-25%) to provide the target compound in 92% purity: 1.2 g.

LC-MS (Method 2): $R_t$=0.83 min; MS (ESIpos): m/z=360 [M+H]$^+$ $^1$H-NMR (400 MHz, DMSO-d6) δ [ppm]=1.66-1.81 (m, 2H), 1.97-2.06 (m, 2H), 2.07-2.17 (m, 2H), 2.97 (s, 2H), 5.66 (s, 2H), 6.50-6.58 (m, 3H), 6.58-6.64 (m, 1H), 6.67 (dd, 1H), 6.95-7.07 (m, 2H), 7.18 (s, 1H), 7.46 (s, 1H), 7.73 (d, 1H), 11.56 (s, 1H).

Intermediate 82

5-(dimethylamino)-2-phenylpentanoic acid hydrogen chloride salt (Racemate), CAS-RN: [1199781-00-4], (=Free Base)

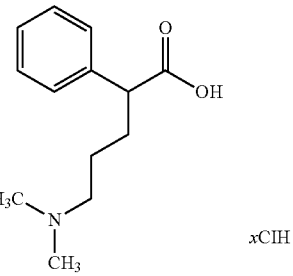

To a stirred solution of sodium hydroxide (151 mg, 3.76 mmol) in water (5 mL) in a sealed tube was added 5-(dimethylamino)-2-phenylpentanenitrile (Racemate) (238 mg, 1.18 mmol, CAS-RN: [10404-34-9], Organic Reactions (Hoboken, NJ, United States), 31, No pp. given; 1984) and the mixture was stirred at 100° C. for 16 h. Water (5 mL) was added and the mixture was extracted with chloroform and methanol (10:1). A solution of hydrogen chloride in dioxane (1.0 mL, 4.0 M, 4.0 mmol) was added to the aqueous phase and the mixture was concentrated in vacuum to give a solid. Toluene was added and the solvent was removed in vacuum to give 535 mg (purity approx. 50%) of the title compound as a crude product that was used without purification.

$^1$H-NMR (400 MHz, DEUTERIUM OXIDE) δ [ppm]: 1.549 (0.56), 1.563 (0.69), 1.576 (0.53), 1.589 (0.53), 1.603 (0.50), 1.616 (0.42), 1.630 (0.74), 1.644 (0.57), 1.655 (0.48), 1.662 (0.41), 1.808 (0.74), 1.820 (0.68), 1.828 (0.53), 1.833 (0.65), 1.842 (0.47), 2.004 (0.50), 2.007 (0.48), 2.016 (0.44), 2.021 (0.56), 2.030 (0.81), 2.033 (0.55), 2.037 (0.47), 2.040 (0.43), 2.047 (0.47), 2.744 (16.00), 2.756 (15.89), 3.026 (0.85), 3.041 (0.84), 3.052 (1.22), 3.069 (1.27), 3.080 (0.83), 3.086 (0.42), 3.095 (0.79), 3.662 (1.22), 3.679 (1.52), 3.684 (1.43), 3.701 (1.16), 7.307 (0.63), 7.316 (2.59), 7.320 (1.43), 7.328 (3.02), 7.334 (5.10), 7.336 (4.07), 7.344 (2.36), 7.347 (1.50), 7.349 (0.86), 7.352 (0.54), 7.371 (3.34), 7.378 (0.55), 7.381 (1.01), 7.386 (2.02), 7.389 (2.27), 7.393 (1.62), 7.404 (0.63), 7.408 (0.96), 7.411 (0.64).

Intermediate 83

N-(2-fluorophenyl)-4-hydroxy-6,6-dimethyl-2-oxo-1,2,5,6-tetrahydropyridine-3-carbothioamide

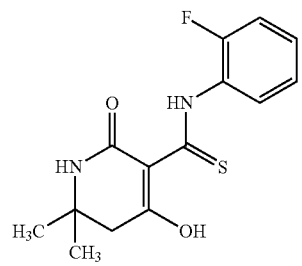 [SMILES: CC1(C)CC(O)=C(C(=S)Nc2ccccc2F)C(=O)N1]

6,6-Dimethylpiperidine-2,4-dione (3.00 g, CAS-RN: [5239-39-4]) and 1-fluoro-2-isothiocyanatobenzene (2.6 mL, 21 mmol) were dissolved in 25 mL acetonitrile and cooled to 0° C. DBU (5.1 mL, 34 mmol) was added and the reaction mixture was stirred at rt for 20 h. The reaction mixture was poured into a mixture of ice and hydrochloric acid (2 M), it was extracted with ethyl acetate three times. The combined organic layers were dried with sodium sulfate, filtered and concentrated under reduced pressure to provide the target compound in 93% purity which was used without further purification: 8.1 g.

LC-MS (Method 2): $R_f$=1.23 min; MS (ESIpos): m/z=295 [M+H]$^+$ $^1$H-NMR (400 MHz, DMSO-d6) δ [ppm]: 1.172 (0.40), 1.190 (0.42), 1.216 (0.82), 1.221 (1.22), 1.252 (10.06), 1.272 (16.00), 1.988 (0.73), 2.518 (2.57), 2.523 (1.67), 2.631 (4.77), 2.784 (2.64), 7.214 (0.40), 7.221 (0.48), 7.236 (0.80), 7.240 (0.65), 7.252 (0.67), 7.256 (0.74), 7.268 (0.54), 7.316 (1.09), 7.321 (1.30), 7.337 (1.79), 7.347 (1.29), 7.352 (1.01), 7.373 (0.91), 7.377 (0.93), 7.646 (0.51), 7.666 (0.99), 7.692 (0.63), 8.229 (0.79), 9.385 (1.15), 14.046 (1.66), 14.621 (0.90), 16.402 (4.45), 16.473 (2.19).

Intermediate 84

4-{[(2-aminopyridin-4-yl)methyl]amino}-N-(2-fluorophenyl)-6,6-dimethyl-2-oxo-1,2,5,6-tetrahydropyridine-3-carbothioamide

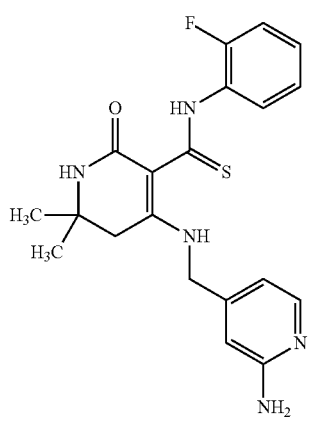 [SMILES: CC1(C)CC(NCc2ccnc(N)c2)=C(C(=S)Nc2ccccc2F)C(=O)N1]

N-(2-fluorophenyl)-4-hydroxy-6,6-dimethyl-2-oxo-1,2,5,6-tetrahydropyridine-3-carbothioamide (see Intermediate 83, 8.12 g) and 4-(aminomethyl)pyridin-2-amine (5.78 g, 46.9 mmol) were combined and the mixture was stirred at 100° C. for 3 h under nitrogen atmosphere without further solvent in a sealed vessel in a heating block. The reaction mixture was cooled to 60° C. and diluted with dichloromethane and sonicated for 20 min. A precipitate was filtered off under vacuum. The filter cake was dried in a vacuum drying oven and purified by flash chromatography (Isolera: 50 g ULTRA column, gradient: hexane/ethyl acetate/ethanol) to provide the analytically pure target compound: 2.3 g.

LC-MS (Method 2): $R_f$=1.00 min; MS (ESIpos): m/z=401 [M+H]$^+$ $^1$H-NMR (400 MHz, DMSO-d6) δ [ppm]=1.16 (s, 6H), 2.69 (s, 2H), 4.60 (d, 2H), 6.01 (s, 2H), 6.34 (s, 1H), 6.41 (dd, 1H), 7.11-7.22 (m, 1H), 7.23-7.30 (m, 2H), 7.62-7.73 (m, 2H), 7.87 (d, 1H), 13.94 (br t, 1H), 14.86 (s, 1H).

Intermediate 85

2-(2-aminopyridin-4-yl)-3-(2-fluoroanilino)-6,6-dimethyl-1,5,6,7-tetrahydro-4H-pyrrolo[3,2-c]pyridin-4-one

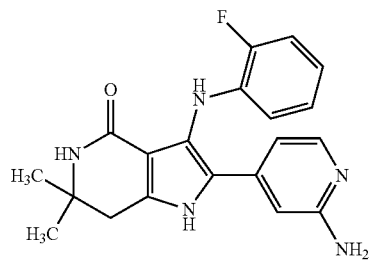 [SMILES: CC1(C)Cc2[nH]c(-c3ccnc(N)c3)c(Nc3ccccc3F)c2C(=O)N1]

A suspension of 4-{[(2-aminopyridin-4-yl)methyl]amino}-N-(2-fluorophenyl)-6,6-dimethyl-2-oxo-1,2,5,6-tetrahydropyridine-3-carbothioamide (see Intermediate 84, 2.28 g) in methanol (50 mL) and TFA (0.880 mL, 2 eq; CAS-RN: [76-05-1]) was treated with mCPBA (1.97 g, 2 eq, CAS-RN: [937-14-4]) and stirred for 21 h at 60° C. under an atmosphere of nitrogen. After cooling the pH of the reaction mixture was adjusted to 9 by treatment with a solution of Sodium hydrogencarbonate, three times extracted with dichloromethane/methanol, the combined organic layers were dried with sodium sulfate, filtered and concentrated under reduced pressure to provide the crude title compound. After chromatographic purification (Biotage, 50 g Ultra, gradient: hexane/dichloromethane/ethanol) the title compound (0.376 g) was obtained.

Intermediate 86 tert-butyl 5-[(2-chloro-3-fluorophenyl)carbamothioyl]-4-hydroxy-6-oxo-3,6-dihydropyridine-1(2H)-carboxylate

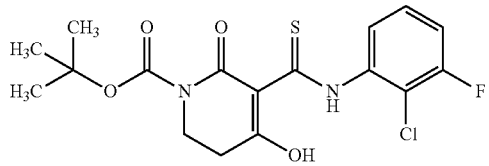 [SMILES: CC(C)(C)OC(=O)N1CCC(O)=C(C(=S)Nc2cccc(F)c2Cl)C1=O]

A solution of tert-butyl-2,4-dioxopiperidine-1-carboxylate (5.50 g, 25.8 mmol) CAS-RN: [845267-78-9] and 2-chloro-1-fluoro-3-isothiocyanatobenzene (4.84 g, 1 eq., CAS-RN: [364363-52-0], WO 2001072960) in acetonitrile 100 mL was treated under a controlled atmosphere of argon at 0° C. with DBU (5.8 mL, 1.5 eq) and stirred for 0.5 h at 0° C. and further 18 h at 25° C. Then the reaction mixture was quenched with ethyl acetate/ethanol (500 mL, 9:1) treated with ammonium chloride-sol (5% in water, 150 mL,) extracted with ethyl acetate/ethanol (150 mL, 9:1), the combined organic phases were washed with brine (30 mL), dried with sodium sulfate and concentrated under reduced pressure. The crude product was triturated with ethyl acetate (400 mL) filtered, twice washed with ethyl acetate (10 mL) and dried, One obtained the title compound (5.87 g, UPLC=96%, NMR=ok) as the beige solid.

Intermediate 87

N-(2-chloro-3-fluorophenyl)-4-hydroxy-2-oxo-1,2,5,6-tetrahydropyridine-3-carbothioamide

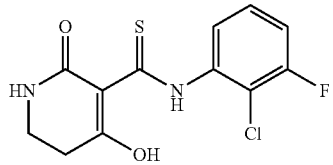 [SMILES: O=C1NCCC(O)=C1C(=S)Nc1cccc(F)c1Cl]

A solution of tert-butyl 5-[(2-chloro-3-fluorophenyl)carbamothioyl]-4-hydroxy-6-oxo-3,6-dihydropyridine-1(2H)-carboxylate (see Intermediate 86, 5.87 g, 14.6 mmol) in dichloromethane (150 mL) and methanol (75 mL) was treated with HCl (37 mL, 10 eq., 4.0 M in dioxane) and stirred for 23 h r.t. Then the reaction mixture was quenched by the addition of ice (200 g), extracted with dichloromethane/methanol (85:15, 500 mL) twice, washed with brine (100 mL) dried over sodium sulfate concentrated under reduced pressure, triturated with dichloromethane (80 mL) filtered and washed with dichloromethane (6 mL) twice. One obtained the title compound (3.05 g, UPLC 95%, NMR ok) as a beige solid. Concentration and tituration of the mother liquor gave another 0.67 g, UPLC 80%, NMR 90% of the desired product.

LC-MS (Method 1): $R_t$=1.13 min; MS (ESIpos): m/z=301 [M+H]$^+$ $^1$H-NMR (400 MHz, DMSO-d6) δ [ppm]: 2.323 (0.86), 2.327 (1.26), 2.332 (0.90), 2.457 (0.44), 2.461 (0.52), 2.466 (0.52), 2.471 (0.52), 2.518 (4.03), 2.523 (3.21), 2.627 (3.86), 2.645 (7.29), 2.663 (4.75), 2.669 (1.81), 2.673 (1.05), 2.678 (0.46), 2.786 (2.98), 2.804 (6.40), 2.822 (3.38), 3.288 (2.06), 3.295 (2.23), 3.306 (3.93), 3.313 (3.97), 3.422 (2.54), 3.429 (2.67), 3.440 (4.39), 3.447 (4.24), 3.458 (2.44), 3.465 (2.23), 7.354 (1.03), 7.359 (1.18), 7.375 (2.77), 7.380 (2.73), 7.397 (2.56), 7.401 (4.35), 7.411 (1.36), 7.416 (2.92), 7.421 (4.47), 7.432 (2.48), 7.435 (3.82), 7.442 (4.12), 7.452 (4.39), 7.461 (8.90), 7.468 (8.38), 7.477 (1.99), 7.484 (1.55), 8.206 (2.06), 9.427 (2.10), 14.262 (5.08), 14.661 (3.61), 16.315 (16.00), 16.374 (10.56).

Intermediate 88

4-{[(2-aminopyridin-4-yl)methyl]amino}-N-(2-chloro-3-fluorophenyl)-2-oxo-1,2,5,6-tetrahydropyridine-3-carbothioamide

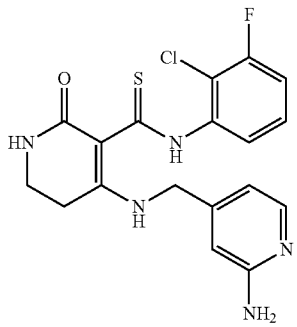 [SMILES: Nc1cc(CNC2=C(C(=S)Nc3cccc(F)c3Cl)C(=O)NCC2)ccn1]

A solution of N-(2-chloro-3-fluorophenyl)-4-hydroxy-2-oxo-1,2,5,6-tetrahydropyridine-3-carbothioamide (see Intermediate 87, 0.5 g, 1.66 mmol) and 4-(aminomethyl)pyridin-2-amine (287 mg, 1.4 eq.) in DMA (6 mL) was purged with nitrogen and stirred 2.8 h at 120° C. 2 h. After removal of the solvent under vacuum the product was triturated with ethanol (6 mL), filtered, washed with ethanol (1 mL) twice and dried. One obtained the title compound (0.320 g, H-NMR-purity ~75%) as a beige solid.

LC-MS (Method 1): $R_t$=0.76 min; MS (ESIpos): m/z=406 [M+H]$^+$

1H-NMR (DMSO-d6) Shift: 14.89 (s, 1H), 13.69-13.76 (m, 1H), 7.87 (d, 1H), 7.76 (br s, 1H), 7.45-7.48 (m, 1H), 7.37 (m, 1H), 7.25-7.32 (m, 1H), 6.41 (m, 1H), 6.34 (s, 1H), 6.01 (s, 2H), 4.58 (d, 2H), 3.17 (m, 2H), 2.73 (m, 2H).

Intermediate 89

2-(2-aminopyridin-4-yl)-3-(2-chloro-3-fluoroanilino)-1,5,6,7-tetrahydro-4H-pyrrolo[3,2-c]pyridin-4-one

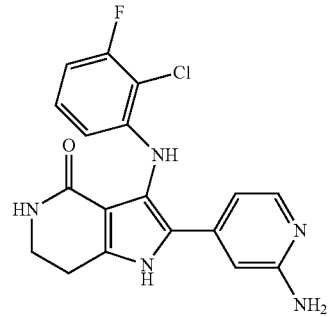 [SMILES: Nc1cc(-c2[nH]c3c(c2Nc2cccc(F)c2Cl)C(=O)NCC3)ccn1]

A solution of 4-{[(2-aminopyridin-4-yl)methyl]amino}-N-(2-chloro-3-fluorophenyl)-2-oxo-1,2,5,6-tetrahydropyridine-3-carbothioamide (see Intermediate 88, 0.540 g, 1.33 mmol) in methanol (8 mL) was treated with hydrogen peroxide (0.270 mL, 30% purity, 2.0 eq.) and stirred for 2 h at 90° C. Then sodium thiosulfate-sol. (2 mL, halfconc.) and K2CO3 (3 g in water, 40 mL) was added, stirred for 15 min at r.t., after addition of ethyl acetate (300 mL) the mixture was stirred for 40 min, the organic phase was washed with brine (30 mL) and dried over sodium sulfate. One obtained the crude product (0.360 g) which was chromatographically purified over an NH-column (50 g), trituration with ethyl acetate (1.5 mL, ultrasonic bath, 15 min), filtration and drying gave the title compound (0.117 g) as a beige solid as well as a second batch from the mother liquor (97 mg).

LC-MS (Method 1): $R_t$=0.68 min; MS (ESIpos): m/z=372 [M+H]$^+$

1H-NMR (DMSO-d6) Shift: 11.68 (s, 1H), 7.77 (d, 1H), 7.40 (s, 1H), 7.10 (s, 1H), 6.96 (d, 1H), 6.65 (m, 1H), 6.62 (m, 1H), 6.46 (br s, 1H), 6.16 (d, 1H), 5.75 (s, 2H), 3.36-3.42 (m, 2H), 2.82 (m, 2H).

Intermediate 90

Ethyl-3-[(3-ethoxy-3-oxopropanoyl)(methyl)amino]butanoate (Racemate)

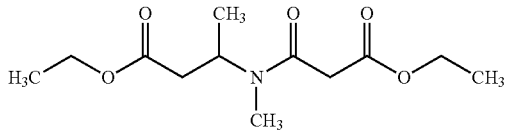 [SMILES: CCOC(=O)CC(=O)N(C)C(C)CC(=O)OCC]

A solution of ethyl-3-(methylamino)butanoate (13.5 g, 87.4 mmol; CAS-RN: [68384-70-3], VCS 201657) in DMC (116 mL) placed in a three neck round bottom flask, cooled to 0° C., N,N-diisopropylethylamine (17 mL, 1.1 eq.; CAS-RN: [7087-68-5]) and 4-dimethylaminopyridine (1.07 g, 0.1 eq.; CAS-RN: [1122-58-3]) was added. Then ethyl 3-chloro-3-oxopropanoate (12 mL, 1.1 eq.) was slowly added so that the temperature of the reaction was kept below 15° C., stirred for 0.5 h at 0° C. and for 18 h at r.t. Then HCl (2 M, 55 mL) was added, stirred for 15 min, extracted with dichloromethane, dried over sodium sulfate, concentrated under reduced pressure and purified by column chromatography (340 g Si-Biotage, gradient: ethyl acetate/hexane) 50-100% One obtained the title compound (4.6 g, ~70% purity).

LC-MS (Method 2): $R_t$=0.86 min; MS (ESIpos): m/z=260 [M+H]$^+$ $^1$H NMR (DMSO-d$_6$) δ: 4.81 (sxm, 1H), 4.05-4.11 (m, 4H), 3.47 (d, 1H), 3.41 (d, 1H), 2.77 (s, 3H), 2.47 (d, 2H), 1.17-1.21 (m, 6H), 1.06 (d, 3H).

Intermediate 91

Ethyl 4-hydroxy-1,2-dimethyl-6-oxo-2,3-dihydropyridine-5-carboxylate (Racemate)

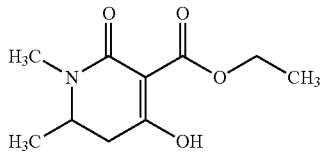

A solution of sodium ethylate (7.3 mL, 21% purity, 1.1 eq.) was treated at 0° C. with a solution of ethyl 3-[(3-ethoxy-3-oxopropanoyl)(methyl)amino]butanoate (Racemate) (see Intermediate 90, 4.60 g, 17.7 mmol) in ethanol (35 mL), in a dropwise manner so that the temperature was kept below 5° C. and stirred for 18 h at r.t. Then the reaction mixture was adjusted to pH4 by the addition of HCl (2M in water) extracted with dichloromethane dried, concentrated under reduced pressure and purified by chromatography (Si-Biotage 100 g, gradient: ethyl acetate/hexane 20-100%). One obtained the title compound (2.78 g).

LC-MS (Method 1): $R_t$=0.76 min; MS (ESIpos): m/z=214 [M+H]$^+$

1H-NMR (DMSO-d6) Shift: 12.51 (br s, 1H), 4.18 (q, 2H), 3.60 (br s, 1H), 2.99 (br s, 2H), 2.82 (br s, 3H), 1.22 (m, 3H), 1.12 (t, 3H).

Intermediate 92

1,6-dimethylpiperidine-2,4-dione (Racemate), CAS-RN: [209901-13-3], #1, WO 9829412

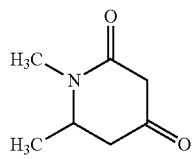

A solution of ethyl 4-hydroxy-1,2-dimethyl-6-oxo-2,3-dihydropyridine-5-carboxylate (Racemate) (see Intermediate 91, 2.77 g, 13.0 mmol) in dichloromethane (20 mL) was treated with HCl (20 mL, 2.0 M, CAS-RN: [7647-01-0]), stirred for 15 min at r.t. Then the reaction mixture was extracted with dichloromethane, the organic phases were dried, concentrated under reduced pressure, solved in acetonitrile (30 mL) and water (4 mL), stirred for 2 h at reflux and concentrated under vacuum. One obtained the title compound (1.72 g).

LC-MS (Method 1): $R_t$=0.45 min; MS (ESIneg): m/z=140 [M−H]$^−$

1H-NMR (DMSO-d$_6$) Shift: 3.78 (qd, 1H), 3.28 (d, 1H), 3.21 (d, 1H), 2.92 (s, 3H), 2.91 (m, 1H), 2.38 (m, 1H), 1.14 (d, 3H); keto- (78%) & enol-tautomer (22%): 10.33 (s, 1H), 4.86 (d, 1H), 3.56 (qd, 1H), 2.70-2.78 (m, 4H), 1.98-2.05 (m, 1H), 1.10 (d, 3H).

Intermediate 93

4-hydroxy-1,6-dimethyl-2-oxo-N-phenyl-1,2,5,6-tetrahydropyridine-3-carbothioamide (Racemate)

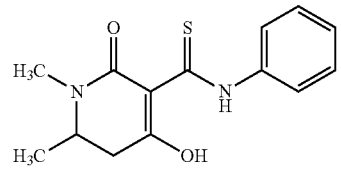 [SMILES: CC1CC(O)=C(C(=S)Nc2ccccc2)C(=O)N1C]

A solution of 1,6-dimethylpiperidine-2,4-dione (Racemate) (see Intermediate 92, 1.72 g, 12.1 mmol, CAS-RN: [209901-13-3], WO 9829412) and isothiocyanatobenzene (1.5 mL, 1 eq.; CAS-RN: [103-72-0]) in acetonitrile (19 mL), was cooled with ice, treated with DBU (2.9 mL, 1.6 eq.; CAS-RN: [6674-22-2]) stirred for 16 h at r.t. Then the reaction was quenched in ice/water/HCl (4 mL, 4 M) extracted with ethyl acetate, washed with brine, dried over sodium sulfat and concentrated under reduced pressure. After purification by Si-Biotage column (50 g, gradient: ethyl acetate/hexane, 20-40%) one obtained the title compound (3.02 g, ~90% purity).

LC-MS (Method 2): $R_t$=0.55 min; MS (ESIpos): m/z=277 [M+H]$^+$ $^1$H-NMR (400 MHz, DMSO-d6) δ [ppm]: 1.154 (0.76), 1.172 (1.57), 1.189 (7.47), 1.206 (6.80), 1.987 (2.75), 2.432 (1.22), 2.437 (1.20), 2.475 (1.43), 2.480 (1.60), 2.958 (16.00), 3.112 (1.50), 3.260 (0.97), 3.278 (1.07), 3.303 (0.90), 3.321 (1.02), 3.331 (5.57), 3.686 (0.55), 3.692 (0.60), 3.703 (0.83), 3.708 (0.82), 3.719 (0.58), 3.725 (0.51), 4.017

(0.60), 4.035 (0.60), 5.758 (1.94), 7.282 (0.47), 7.286 (0.67), 7.290 (0.47), 7.303 (1.28), 7.316 (0.53), 7.321 (0.92), 7.325 (0.61), 7.402 (1.22), 7.414 (1.03), 7.419 (1.47), 7.440 (3.22), 7.457 (4.51), 7.462 (4.08), 7.465 (4.36), 7.483 (1.27), 7.487 (0.86), 14.614 (1.50), 16.539 (4.83), 17.312 (0.52); tautomers (5:1).

Intermediate 94

4-{[(2-aminopyridin-4-yl)methyl]amino}-1,6-dimethyl-2-oxo-N-phenyl-1,2,5,6-tetrahydropyridine-3-carbothioamide (Racemate)

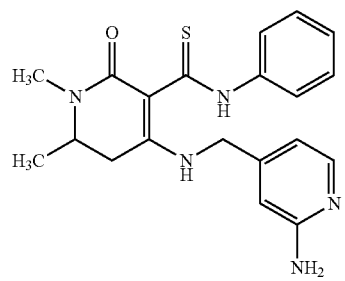 [SMILES: CC1CC(NCc2ccnc(N)c2)=C(C(=S)Nc2ccccc2)C(=O)N1C]

A mixture of 4-hydroxy-1,6-dimethyl-2-oxo-N-phenyl-1,2,5,6-tetrahydropyridine-3-carbothioamide (Racemate) (see Intermediate 93, 2.80 g, 10.1 mmol) and 4-(aminomethyl)pyridin-2-amine (4.99 g, 4 eq.) was heated to 120° C. in a microwave for 1 h. The crude product was taken-up in dichloromethane/methanol (120 mL/24 mL) and purified by chromatography on silicagel (100 g, dichloromethane/ethanol 0-30%) gave a solid that was triturated with dichloromethane to give 2.5 g (90% purity) of the title compound.

LC-MS (Method 2): $R_t$=1.06 min; MS (ESIpos): m/z=381 [M–H]$^+$ $^1$H-NMR (400 MHz, DMSO-d$_6$) δ [ppm]: 1.058 (5.22), 1.075 (5.23), 1.154 (0.67), 1.172 (1.26), 1.190 (0.60), 1.988 (2.36), 2.518 (0.95), 2.523 (0.67), 2.661 (0.79), 2.668 (0.93), 2.703 (1.05), 2.709 (1.04), 2.841 (0.80), 2.857 (0.87), 2.883 (0.64), 2.899 (0.74), 2.914 (16.00), 3.571 (0.49), 3.578 (0.49), 3.587 (0.70), 3.594 (0.67), 3.603 (0.48), 3.610 (0.40), 4.018 (0.52), 4.035 (0.52), 4.571 (2.44), 4.586 (2.46), 6.004 (3.59), 6.340 (2.60), 6.403 (1.55), 6.406 (1.45), 6.416 (1.57), 6.419 (1.46), 7.161 (0.43), 7.164 (0.80), 7.167 (0.48), 7.183 (1.85), 7.198 (0.66), 7.201 (1.19), 7.204 (0.65), 7.338 (2.03), 7.343 (0.80), 7.358 (3.37), 7.372 (0.78), 7.377 (2.62), 7.438 (3.16), 7.440 (3.25), 7.459 (2.31), 7.462 (1.70), 7.858 (2.32), 7.873 (2.33), 13.820 (0.72), 14.807 (1.79).

Intermediate 95

2-(2-aminopyridin-4-yl)-3-anilino-5,6-dimethyl-1,5,6,7-tetrahydro-4H-pyrrolo[3,2-c]pyridin-4-one (Racemate)

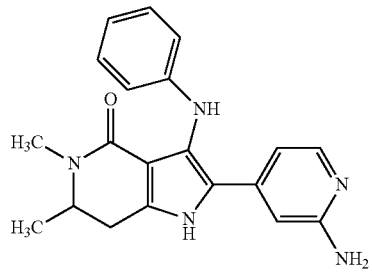 [SMILES: CC1Cc2[nH]c(-c3ccnc(N)c3)c(Nc3ccccc3)c2C(=O)N1C]

A solution of 4-{[(2-aminopyridin-4-yl)methyl]amino}-1,6-dimethyl-2-oxo-N-phenyl-1,2484,5,6-tetrahydropyridine-3-carbothioamide (Racemate) (see Intermediate 94, 2.40 g, 6.29 mmol) in methanol (26 mL) was treated with TFA (0.970 mL, 2 eq.; CAS-RN: [76-05-1]) stirred for 5 min at r.t., cautiously mCPBA (2.82 g, 77% purity, 2 eq.) was added and stirred for 4 h at 50° C. Then an aqueous solution of NaHCO$_3$— (100 mL, half-concentrated) was added, extracted with dichloromethane, dried and concentrated under reduced pressure and purified by chromatography on silicagel. (Si-Biotage column, 50 g, gradient: One obtained the title compound (0.71 g):

LC-MS (Method 2): $R_t$=0.88 min; MS (ESIneg): m/z=346 [M–H]$^-$

1H-NMR (400 MHz, DMSO-d$_6$) 0 ppm 1.16 (d, 3H), 2.64 (dd, 1H), 2.85 (s, 3H), 3.20 (dd, 1H), 3.73-3.86 (m, 1H), 5.68 (s, 2H), 6.52-6.58 (m, 3H), 6.58-6.64 (m, 1H), 6.68 (dd, 1H), 6.98-7.07 (m, 2H), 7.24 (s, 1H), 7.72 (d, 1H), 11.51 (s, 1H).

Intermediate 96

(+)-2-(2-aminopyridin-4-yl)-3-anilino-5,6-dimethyl-1,5,6,7-tetrahydro-4H-pyrrolo[3,2-c]pyridin-4-one (Enantiomer 1)

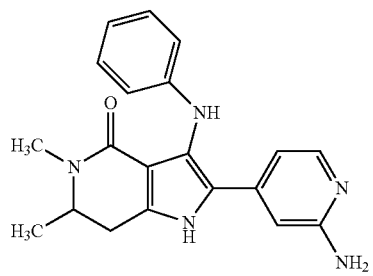 [SMILES: CC1Cc2[nH]c(-c3ccnc(N)c3)c(Nc3ccccc3)c2C(=O)N1C]

The racemic compound (Intermediate 95, 344 mg) was separated into enantiomers by preparative chiral HPLC to give enantiomer 1 (160 mg, 98.4% ee, see Intermediate 96) and enantiomer 2 (175 mg, 96.3% ee, see Intermediate 97). Preparative Chiral HPLC Method:
Instrument: Sepiatec: Prep SFC100; Column: Chiralpak IG 5μ 250×30 mm; eluent A: carbon dioxide; eluent B: methanol+0.2 vol % aqueous ammonia (32%); isocratic: 40% B; flow: 100 mL/min; temperature: 40° C.; BPR: 150 bar; UV: 254 nm;

Analytical Chiral HPLC Method:

Instrument: Agilent: 1260, Aurora SFC-Modul; Column: Chiralpak IG 5μ 100×4.6 mm; eluent A: carbondioxide; eluent B: methanol+0.2 vol % aqueous ammonia (32%); isocratic: 40% B; flow: 4 mL/min; temperature: 37.5° C.; BPR: 100 bar; UV: 254 nm;

Analytical Chiral HPLC (method see Intermediate 96): $R_t$=2.01 min.

$[a]_D$=+33.4° (from solution in DMSO, c=3.8 mg/mL)

¹H-NMR (400 MHz, DMSO-d₆) δ [ppm]: 1.147 (5.67), 1.164 (5.74), 1.233 (0.98), 2.074 (12.55), 2.084 (1.30), 2.326 (0.51), 2.518 (2.14), 2.522 (1.38), 2.539 (0.41), 2.610 (0.99), 2.616 (1.02), 2.651 (1.16), 2.658 (1.16), 2.664 (0.51), 2.669 (0.59), 2.673 (0.44), 2.845 (16.00), 3.169 (0.82), 3.185 (0.97), 3.209 (0.82), 3.226 (0.79), 3.769 (0.50), 3.775 (0.56), 3.785 (0.80), 3.791 (0.78), 3.802 (0.56), 3.807 (0.48), 5.647 (3.72), 6.543 (5.51), 6.562 (3.23), 6.564 (2.65), 6.590 (0.59), 6.592 (0.97), 6.611 (1.94), 6.628 (1.07), 6.668 (1.67), 6.672 (1.58), 6.682 (1.68), 6.686 (1.60), 7.003 (2.38), 7.022 (2.98), 7.025 (2.93), 7.043 (1.97), 7.228 (3.83), 7.718 (1.93), 7.731 (1.84), 11.496 (1.77).

Intermediate 97

(−)-2-(2-aminopyridin-4-yl)-3-anilino-5,6-dimethyl-1,5,6,7-tetrahydro-4H-pyrrolo[3,2-c]pyridin-4-one (Enantiomer 2)

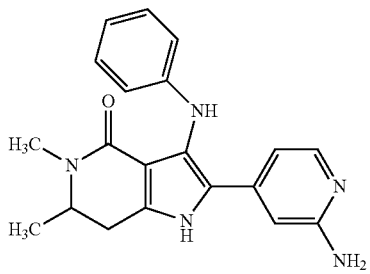 [SMILES: CC1Cc2[nH]c(-c3ccnc(N)c3)c(Nc3ccccc3)c2C(=O)N1C]

For the preparation of the racemic title compound see Intermediate 95. Separation of enantiomers by preparative chiral HPLC (method see Intermediate 96) gave the title compound (175 mg).

Analytical Chiral HPLC (method see Intermediate 96): $R_t$=3.35 min.

$[a]_D$=−45.6° (from solution in DMSO, c=2.3 mg/mL)

¹H-NMR (400 MHz, DMSO-d₆) δ [ppm]: 1.150 (4.90), 1.166 (4.93), 1.233 (0.98), 2.326 (0.43), 2.518 (1.86), 2.522 (1.19), 2.539 (16.00), 2.627 (0.87), 2.633 (0.89), 2.668 (1.42), 2.674 (1.23), 2.853 (14.49), 2.994 (0.49), 3.186 (0.74), 3.203 (0.89), 3.228 (0.78), 3.244 (0.78), 3.376 (0.49), 3.783 (0.45), 3.789 (0.51), 3.799 (0.70), 3.805 (0.70), 3.815 (0.50), 3.821 (0.43), 5.758 (2.08), 6.133 (0.99), 6.564 (2.72), 6.583 (2.95), 6.586 (2.48), 6.597 (2.04), 6.620 (0.86), 6.639 (1.73), 6.657 (0.97), 6.748 (1.16), 6.751 (1.14), 6.762 (1.22), 6.766 (1.18), 7.023 (2.13), 7.041 (2.64), 7.045 (2.56), 7.063 (1.73), 7.346 (2.81), 7.726 (1.38), 7.740 (1.33), 8.137 (0.85), 11.629 (1.40).

Intermediate 98

N-(2-fluorophenyl)-4-hydroxy-1,6-dimethyl-2-oxo-1,2,5,6-tetrahydropyridine-3-carbothioamide (Racemate)

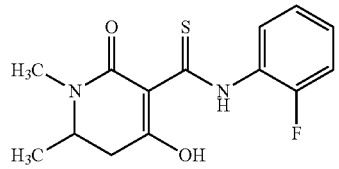 [SMILES: CC1CC(O)=C(C(=S)Nc2ccccc2F)C(=O)N1C]

A solution of 1,6-dimethylpiperidine-2,4-dione (Racemate) (see Intermediate 92, 1.10 g, 7.79 mmol; CAS-RN: [209901-13-3], WO 9829412) and 1-fluoro-2-isothiocyanatobenzene (1.19 g, 1 eq.) in acetonitrile (20 mL) cooled with ice was treated with DBU (1.9 mL, 1.6 eq.), stirred for 16 h at r.t. Then the reaction was quenched in ice/water/HCl (4 mL, 4M) extracted with ethyl acetate, washed with brine, dried over sodium sulfat and concentrated under reduced pressure. After purification by Si-Biotage column (100 g, gradient: ethyl acetate/hexane, 20-40%) one obtained the title compound (1.82 g, ~95% purity)

LC-MS (Method 2): $R_t$=0.57 min; MS (ESIpos): m/z=295 [M+H]⁺

¹H-NMR (400 MHz, DMSO-d₆) δ [ppm]: 1.192 (5.13), 1.200 (1.43), 1.209 (5.29), 1.217 (1.26), 2.459 (1.00), 2.465 (1.05), 2.518 (1.50), 2.523 (1.00), 2.961 (16.00), 3.122 (2.49), 3.285 (0.74), 3.302 (0.84), 3.345 (0.89), 3.699 (0.40), 3.705 (0.46), 3.716 (0.61), 3.722 (0.62), 3.733 (0.43), 7.245 (0.46), 7.251 (0.64), 7.260 (0.43), 7.266 (0.82), 7.270 (0.72), 7.280 (0.42), 7.282 (0.48), 7.287 (0.68), 7.339 (0.43), 7.348 (1.09), 7.353 (0.98), 7.358 (0.93), 7.362 (0.70), 7.374 (1.71), 7.379 (1.54), 7.389 (0.49), 7.393 (0.46), 7.659 (0.51), 7.663 (0.53), 7.679 (0.97), 7.682 (0.94), 7.698 (0.48), 7.702 (0.46), 14.521 (1.28), 16.455 (4.39), 17.128 (1.02) tautomers (5:1).

Intermediate 99

4-{[(2-aminopyridin-4-yl)methyl]amino}-N-(2-fluorophenyl)-1,6-dimethyl-2-oxo-1,2,5,6-tetrahydropyridine-3-carbothioamide (Racemate)

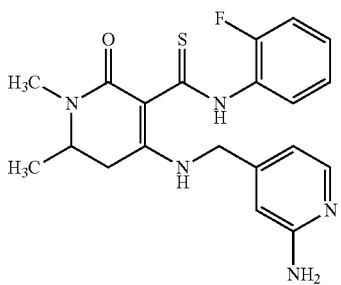 [SMILES: CC1CC(NCc2ccnc(N)c2)=C(C(=S)Nc2ccccc2F)C(=O)N1C]

A mixture of N-(2-fluorophenyl)-4-hydroxy-1,6-dimethyl-2-oxo-1,2,5,6-tetrahydropyridine-3-carbothioamide (Racemate) (see Intermediate 98, 0.200 g, 0.679 mmol) and 4-(aminomethyl)pyridin-2-amine (0.165 g, 2 eq.) was heated to 120° C. in a microwave for 2 h. The crude product was taken-up in dichloromethane/methanol (4 mL/1 mL) and purified by chromatography on silicagel (50 g, a) hexane/ethyl acetate 0-60%; b) ethyl acetate/methanol) gave (0.149 g, 95% purity) the title compound as a beige solid.

The formation of a less polar by-product: 3-(1,3-benzothiazol-2-yl)-4-hydroxy-1,6-dimethyl-5,6-dihydropyridin-2(1H)-one (as tautomers, 3:2) was observed under those conditions.

LC-MS (Method 2): $R_t$=1.08 min; MS (ESIpos): m/z=400 $[M+H]^+$ $^1$H-NMR (400 MHz, DMSO-$d_6$) δ [ppm]: 0.798 (0.42), 0.815 (0.45), 0.822 (0.45), 0.905 (0.51), 1.061 (5.07), 1.078 (5.12), 2.518 (1.03), 2.523 (0.67), 2.680 (0.74), 2.687 (0.73), 2.722 (1.06), 2.729 (1.04), 2.868 (0.79), 2.883 (0.93), 2.916 (16.00), 3.584 (0.43), 3.591 (0.48), 3.600 (0.68), 3.607 (0.65), 3.616 (0.48), 4.584 (2.45), 4.598 (2.45), 5.758 (6.09), 6.006 (3.57), 6.340 (2.51), 6.401 (1.56), 6.404 (1.40), 6.414 (1.56), 6.418 (1.42), 7.163 (0.54), 7.174 (0.66), 7.185 (0.97), 7.190 (0.45), 7.195 (0.80), 7.205 (1.01), 7.247 (2.18), 7.256 (1.63), 7.259 (1.59), 7.263 (1.11), 7.270 (1.31), 7.275 (1.59), 7.278 (1.58), 7.663 (0.79), 7.682 (1.29), 7.684 (1.28), 7.702 (0.72), 7.858 (2.32), 7.871 (2.25), 13.820 (0.45), 13.834 (0.84), 13.848 (0.43), 14.697 (2.43).

Intermediate 100

2-(2-aminopyridin-4-yl)-3-(2-fluoroanilino)-5,6-dimethyl-1,5,6,7-tetrahydro-4H-pyrrolo[3,2-c]pyridin-4-one (Racemate)

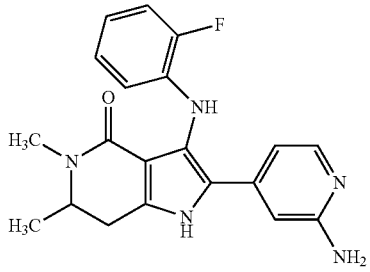 [SMILES: CC1Cc2[nH]c(-c3ccnc(N)c3)c(Nc3ccccc3F)c2C(=O)N1C]

A suspension of 4-{[(2-aminopyridin-4-yl)methyl]amino}-N-(2-fluorophenyl)-1,6-dimethyl-2-oxo-1,2,5,6-tetrahydropyridine-3-carbothioamide (Racemate) (see Intermediate 99, 0.5 g, 1.25 mmol) in methanol (11 mL) was treated with hydrogen peroxide (0.26 mL, 30% purity, 2 eq.) stirred 2 h at 90° C. in the microwave, further hydrogen peroxide (0.12 mL, 30% purity) was added and stirred for 75 min at 90° C. Then the mixture was concentrated under reduced pressure, solved in dichloromethane/methanol (4 mL/1 mL) and purified by chromatography (NH-column, 55 g, ethyl acetate/ethanol 0-25%). One obtained the title compound (0.261 g, 95% purity).

LC-MS (Method 2): $R_t$=0.92 min; MS (ESIpos): m/z=366 $[M+H]^+$ $^1$H-NMR (400 MHz, DMSO-$d_6$) δ [ppm]: 1.151 (5.41), 1.154 (6.76), 1.168 (5.49), 1.172 (10.61), 1.190 (4.64), 1.988 (16.00), 2.327 (0.43), 2.518 (1.93), 2.522 (1.20), 2.620 (0.96), 2.625 (0.98), 2.661 (1.24), 2.667 (1.30), 2.673 (0.48), 2.851 (14.15), 3.179 (0.78), 3.195 (0.91), 3.220 (0.78), 3.237 (0.75), 3.782 (0.49), 3.788 (0.56), 3.798 (0.78), 3.804 (0.77), 3.815 (0.56), 3.821 (0.48), 4.000 (1.25), 4.017 (3.79), 4.035 (3.76), 4.053 (1.21), 5.705 (3.76), 6.282 (0.65), 6.286 (0.71), 6.306 (1.30), 6.325 (0.71), 6.329 (0.69), 6.501 (2.64), 6.503 (2.74), 6.634 (0.48), 6.642 (2.44), 6.646 (2.32), 6.656 (2.43), 6.660 (2.34), 6.672 (0.51), 6.676 (0.46), 6.770 (0.91), 6.788 (1.38), 6.805 (0.61), 7.078 (0.81), 7.081 (0.83), 7.098 (0.80), 7.102 (0.81), 7.108 (0.85), 7.112 (0.82), 7.128 (0.76), 7.131 (0.71), 7.261 (1.96), 7.265 (1.95), 7.754 (2.35), 7.768 (2.25), 11.575 (1.75).

Intermediate 101

(+)-2-(2-aminopyridin-4-yl)-3-(2-fluoroanilino)-5,6-dimethyl-1,5,6,7-tetrahydro-4H-pyrrolo[3,2-c]pyridin-4-one (Enantiomer 1)

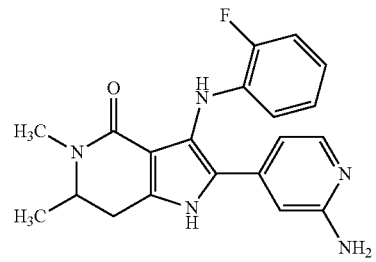 [SMILES: CC1Cc2[nH]c(-c3ccnc(N)c3)c(Nc3ccccc3F)c2C(=O)N1C]

The racemic compound (Intermediate 100, 680 mg) was separated into enantiomers by preparative chiral HPLC to give enantiomer 1 (260 mg, 100% ee, see Intermediate 101) and enantiomer 2 (307 mg, 98.8% ee, see Intermediate 102).

Preparative Chiral HPLC Method:
Instrument: PrepCon Labomatic HPLC; Column: YMC Cellulose SC 5µ, 250×30; eluent A: hexane+0.1 vol % diethylamine; eluent B: ethanol+0.1 vol % diethylamine; isocratic: 80% A+20% B; flow: 50 mL/min; temperature: 25° C.; UV: 254 nm;

Analytical Chiral HPLC Method:
Instrument: Waters Alliance 2695; Column: YMC Cellulose SC 3µ, 100×4.6; eluent A: hexane+0.1 vol % diethylamine; eluent B: ethanol; isocratic: 80% A+20% B; flow: 1.4 mL/min; temperature: 25° C.; UV: 254 nm;

Analytical Chiral HPLC (method see Intermediate 101): $R_t$=3.42 min.

$[α]_D$=+50.1° (from solution in DMSO, c=2.1 mg/mL)

$^1$H-NMR (400 MHz, DMSO-$d_6$): δ [ppm]=11.58 (s, 1H), 7.76 (d, 1H), 7.26 (d, 1H), 7.11 (ddd, 1H), 6.83-6.76 (m, 1H), 6.69-6.61 (m, 2H), 6.50 (d, 1H), 6.35-6.27 (m, 1H), 5.71 (s, 2H), 3.80 (quind, 1H), 3.21 (dd, 1H), 2.85 (s, 3H), 2.64 (dd, 1H), 1.16 (d, 3H)

Intermediate 102

(−)-2-(2-aminopyridin-4-yl)-3-(2-fluoroanilino)-5,6-dimethyl-1,5,6,7-tetrahydro-4H-pyrrolo[3,2-c]pyridin-4-one (Enantiomer 2)

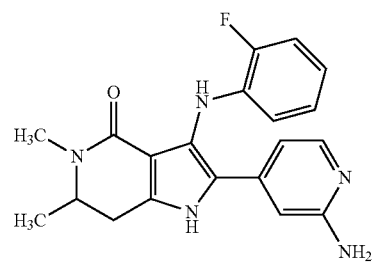 [SMILES: CC1Cc2[nH]c(-c3ccnc(N)c3)c(Nc3ccccc3F)c2C(=O)N1C]

For the preparation of the racemic title compound see Intermediate 100. Separation of enantiomers by preparative chiral HPLC (method see Intermediate 101) gave the title compound (307 mg).

Analytical Chiral HPLC (method see Intermediate 101): $R_t$=4.87 min.

$[\alpha]_D$=−52.5° (from solution in DMSO, c=2.0 mg/mL)

$^1$H-NMR (400 MHz, DMSO-$d_6$) δ [ppm]: 1.138 (0.43), 1.151 (5.54), 1.168 (5.57), 1.233 (0.45), 2.075 (0.50), 2.518 (1.59), 2.523 (1.07), 2.539 (3.32), 2.620 (0.97), 2.626 (1.01), 2.661 (1.26), 2.667 (1.34), 2.673 (0.45), 2.728 (1.25), 2.851 (16.00), 2.865 (0.46), 2.888 (1.56), 3.179 (0.82), 3.195 (0.95), 3.220 (0.83), 3.237 (0.79), 3.377 (0.44), 3.782 (0.50), 3.788 (0.56), 3.798 (0.80), 3.804 (0.79), 3.815 (0.57), 3.821 (0.49), 5.707 (3.80), 6.283 (0.68), 6.287 (0.75), 6.306 (1.34), 6.325 (0.73), 6.329 (0.73), 6.502 (2.67), 6.504 (2.78), 6.634 (0.45), 6.642 (2.45), 6.646 (2.28), 6.656 (2.58), 6.660 (2.41), 6.672 (0.57), 6.676 (0.50), 6.770 (0.97), 6.789 (1.43), 6.806 (0.63), 6.808 (0.62), 7.078 (0.84), 7.082 (0.86), 7.098 (0.85), 7.102 (0.83), 7.109 (0.90), 7.112 (0.89), 7.128 (0.79), 7.132 (0.75), 7.261 (2.00), 7.266 (2.03), 7.754 (2.39), 7.768 (2.31), 11.576 (1.82).

Intermediate 103

N-(2-chloro-3-fluorophenyl)-4-hydroxy-6,6-dimethyl-2-oxo-1,2,5,6-tetrahydropyridine-3-carbothioamide

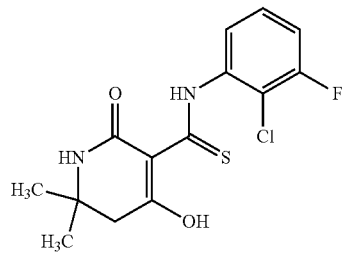 [SMILES: CC1(C)CC(O)=C(C(=S)Nc2cccc(F)c2Cl)C(=O)N1]

6,6-Dimethylpiperidine-2,4-dione (1.98 g, 14.0 mmol, CAS-No 5239-39-4) was suspended in 18 mL acetonitrile and treated with the 2-chloro-1-fluoro-3-isothiocyanatobenzene (2.63 g, 14.0 mmol, CAS-No 364363-52-0, WO 2001072960). The mixture was cooled down to 0° C. and treated slowly with DBU (3.3 mL, 22 mmol). After complete addition the ice bath was removed and the mixture was stirred at rt for 2 hours. The reaction mixture was poured into a mixture of ice and hydrochloric acid (4 M) and it was diluted with ethyl acetate. The layers were separated and the formed precipitate was filtered off under vacuum. It was dried in a vacuum drying oven for 1 hour to provide the first batch of the analytically pure target compound: 2.8 g. The aqueous filtrate was extracted with ethyl acetate. The combined organic layers were filtered using a water resistant filter and concentrated under reduced pressure. The crude product was diluted with dichloromethane and again product precipitated. It was filtered off under vacuum and dried in a vacuum drying oven for 1 hour to provide the second batch of the analytically pure target compound: 702 mg.

LC-MS of batch 1:

LC-MS (Method 2): $R_t$=0.55 min; MS (ESIpos): m/z=329 [M+H]$^+$

NMR of batch 1:

$^1$H-NMR (400 MHz, DMSO-$d_6$) δ [ppm]=1.22-1.35 (m, 6H), 2.60-2.87 (m, 2H), 7.20-7.57 (m, 3H), 8.13-9.55 (m, 1H), 13.97-15.00 (m, 1H), 16.18-16.55 (m, 1H).

Intermediate 104

4-{[(2-aminopyridin-4-yl)methyl]amino}-N-(2-chloro-3-fluorophenyl)-6,6-dimethyl-2-oxo-1,2,5,6-tetrahydropyridine-3-carbothioamide

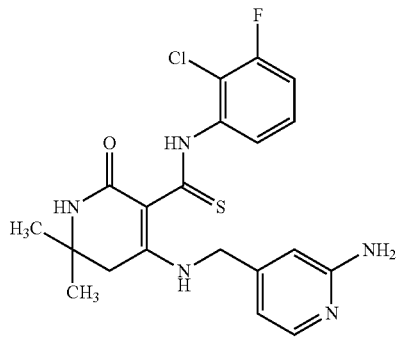 [SMILES: CC1(C)CC(NCc2ccnc(N)c2)=C(C(=S)Nc2cccc(F)c2Cl)C(=O)N1]

N-(2-chloro-3-fluorophenyl)-4-hydroxy-6,6-dimethyl-2-oxo-1,2,5,6-tetrahydropyridine-3-carbothioamide (see Intermediate 103, 3.49 g) and 4-(aminomethyl)pyridin-2-amine (2.22 g, 18.0 mmol) were combined and the mixture was stirred at 100° C. under nitrogen atmosphere for 1 h without further solvent. The reaction mixture was cooled to 60° C. and diluted with dichloromethane. A precipitate was filtered off under vacuum. The filter cake (fc1) was dried in a vacuum drying oven, the clear filtrate was concentrated under reduced pressure. The filtrate was diluted with dichloromethane. Again a precipitate was formed and filtered off under vacuum (fc2). The filter cake (fc1) was diluted with dichloromethane and some drops of ethanol. A precipitate was formed and filtered off under vacuum (fc3). The filter cakes (fc2) and (fc3) were combined to provide the target compound in 95% purity: 1.6 g.

The combined filtrates were purified by flash chromatography (100 g ultra column, gradient dichloromethane/ethanol 1-25%) to provide the second batch of the analytically pure target compound: 0.81 g.

LC-MS of batch 1: LC-MS (Method 2): $R_t$=1.06 min; MS (ESIpos): m/z=434 [M+H]$^+$ LC-MS of batch 2: LC-MS (Method 2): $R_t$=1.05 min; MS (ESIpos): m/z=434 [M+H]$^+$ NMR of batch 1:

$^1$H-NMR (400 MHz, DMSO-d6) δ [ppm]=1.16 (s, 6H), 2.71 (s, 2H), 4.61 (d, 2H), 6.01 (s, 2H), 6.34 (s, 1H), 6.41 (dd, 1H), 7.21-7.31 (m, 1H), 7.37 (td, 1H), 7.50 (d, 1H), 7.73 (s, 1H), 7.87 (d, 1H), 13.92 (t, 1H), 15.09 (s, 1H).

Intermediate 105

2-(2-aminopyridin-4-yl)-3-(2-chloro-3-fluoroanilino)-6,6-dimethyl-1,5,6,7-tetrahydro-4H-pyrrolo[3,2-c]pyridin-4-one

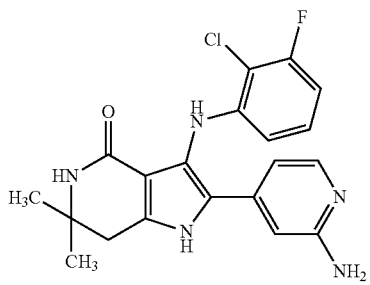 [SMILES: CC1(C)Cc2[nH]c(-c3ccnc(N)c3)c(Nc3cccc(F)c3Cl)c2C(=O)N1]

4-{[(2-Aminopyridin-4-yl)methyl]amino}-N-(2-chloro-3-fluorophenyl)-6,6-dimethyl-2-oxo-1,2,5,6-tetrahydropyridine-3-carbothioamide (see Intermediate 104, 1.55 g) was suspended in 14 mL methanol. TFA (550 µL, 7.1 mmol) was added. It was stirred for 3 min. at rt. Then 3-chloroperoxybenzoic acid (1.76 g, 70% purity, 7.14 mmol) was added and the mixture was heated at 90° C. in a sealed vessel for 2 hours. To the reaction mixture aqueous saturated sodium hydrogencarbonate solution was added and it was diluted with dichloromethane. The layers were separated and the organic layer was dried using a water resistant filter. The clear filtrate was concentrated under reduced pressure. The crude product was purified by flash chromatography (55 g amino column, gradient: dichloromethane/ethanol 2-25%) to provide the target compound in 96% purity: 0.76 g.

LC-MS (Method 2): $R_t$=0.91 min; MS (ESIpos): m/z=400 [M+H]$^+$ $^1$H-NMR (400 MHz, DMSO-d6) δ [ppm]=1.26 (s, 6H), 2.78 (s, 2H), 5.74 (s, 2H), 6.12-6.20 (m, 1H), 6.46 (d, 1H), 6.59-6.70 (m, 2H), 6.96 (td, 1H), 7.01 (s, 1H), 7.38 (s, 1H), 7.77 (d, 1H), 11.63 (s, 1H).—contains ethanol.

Intermediate 106

4-hydroxy-6,6-dimethyl-N-(2-methylphenyl)-2-oxo-1,2,5,6-tetrahydropyridine-3-carbothioamide

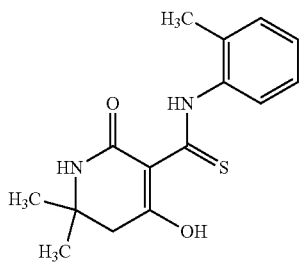 [SMILES: Cc1ccccc1NC(=S)C1=C(O)CC(C)(C)NC1=O]

6,6-Dimethylpiperidine-2,4-dione (750 mg, 5.31 mmol) was suspended in 7.2 mL acetonitrile and treated with 1-isothiocyanato-2-methylbenzene (710 µL, 5.3 mmol). The mixture was cooled down to 0° C. and treated slowly with DBU (1.3 mL, 8.5 mmol). It was stirred at rt over night. The reaction mixture was poured into a mixture of ice and hydrochloric acid (4 M). A white precipitate was formed. The undissolved precipitate was filtered off, washed with water and dried at 50° C. under vacuum over night to provide the analytically pure target compound: 1.5 g.

LC-MS (Method 2): $R_t$=0.56 min; MS (ESIpos): m/z=291 [M+H]$^+$ $^1$H-NMR (400 MHz, DMSO-d$_6$) δ [ppm]=1.26 (d, 6H), 2.16 (d, 3H), 2.58-2.81 (m, 2H), 7.10-7.43 (m, 4H), 8.02-9.41 (m, 1H), 13.72-14.52 (m, 1H), 16.59 (d, 1H).

Intermediate 107

4-{[(2-aminopyridin-4-yl)methyl]amino}-6,6-dimethyl-N-(2-methylphenyl)-2-oxo-1,2,5,6-tetrahydropyridine-3-carbothioamide

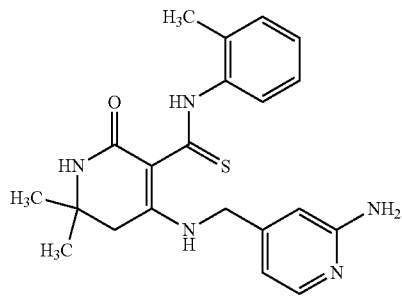 [SMILES: Cc1ccccc1NC(=S)C1=C(NCc2ccnc(N)c2)CC(C)(C)NC1=O]

4-Hydroxy-6,6-dimethyl-N-(2-methylphenyl)-2-oxo-1,2,5,6-tetrahydropyridine-3-carbothioamide (see Intermediate 106, 1.50 g) and 4-(aminomethyl)pyridin-2-amine (1.08 g, 8.76 mmol) were combined and it was stirred at 100° C. under nitrogen atmosphere without further solvent in a sealed vessel for 4 h. The reaction mixture was cooled down to 60° C. and dichloromethane was carefully added to the hot vial and it was sonicated for 10 min. 5 mL Methanol were added and it was sonicated again for 10 min. The precipitate was filtered off, washed with dichloromethane and dried at 50° C. under vacuum to provide the target compound in 95% purity: 1.4 g.

LC-MS (Method 2): $R_t$=1.03 min; MS (ESIpos): m/z=396 [M+H]$^+$ $^1$H-NMR (400 MHz, DMSO-d6) δ [ppm]=1.16 (s, 6H), 2.16 (s, 3H), 2.67 (s, 2H), 4.57 (d, 2H), 6.00 (s, 2H), 6.35 (s, 1H), 6.41 (dd, 1H), 7.09-7.22 (m, 2H), 7.23-7.33 (m, 2H), 7.61 (s, 1H), 7.86 (d, 1H), 13.95 (br t, 1H), 14.61 (s, 1H).

Intermediate 108

2-(2-aminopyridin-4-yl)-6,6-dimethyl-3-(2-methylanilino)-1,5,6,7-tetrahydro-4H-pyrrolo[3,2-c]pyridin-4-one

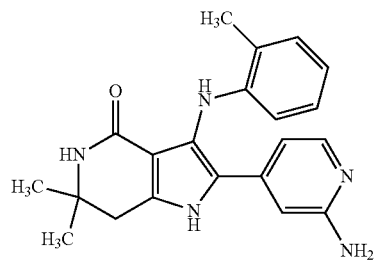 [SMILES: Cc1ccccc1Nc1c(-c2ccnc(N)c2)[nH]c2c1C(=O)NC(C)(C)C2]

The reaction was performed in 2 portions. 4-{[(2-Aminopyridin-4-yl)methyl]amino}-6,6-dimethyl-N-(2-methylphenyl)-2-oxo-1,2,5,6-tetrahydropyridine-3-carbothioamide (see Intermediate 107, 1.36 g) was suspended in 21 mL methanol and treated with TFA (530 µL, 6.9 mmol). It was stirred for 5 minutes, then 3-chloroperoxybenzoic acid (1.53 g, 70% purity, 6.19 mmol) was added and it was stirred at 90° C. under argon atmosphere for 2 hours. To the reaction mixture aqueous saturated sodium hydrogencarbonate solution was added and the layers were separated. The aqueous layer was extracted with dichloromethane three times. The combined organic layers were washed with water and brine once, filtered through a silicone coated filter and concentrated under reduced pressure. The crude product was treated with dichloromethane. MTBE was added and the undissolved precipitate was filtered off. The residue and the filtrate were combined and purified by flash chromatography (28 g column, aminophase; dichloromethane/ethanol 0%-20% ethanol) to provide the target compound in 81% purity: 388 mg.

LC-MS (Method 2): $R_t$=0.88 min; MS (ESIpos): m/z=362 [M+H]$^+$ $^1$H-NMR (400 MHz, DMSO-d6) δ [ppm]=1.26 (s, 6H), 2.30 (s, 3H), 2.78 (s, 2H), 5.66 (s, 2H), 6.26 (d, 1H), 6.49 (d, 1H), 6.55-6.65 (m, 2H), 6.78-6.86 (m, 1H), 6.97 (s, 1H), 7.01-7.10 (m, 2H), 7.70 (d, 1H), 11.50 (s, 1H).—contains ethanol.

Intermediate 109 methyl 4,4-difluoro-2-[4-(methylsulfonyl)phenyl]butanoate (Racemate)

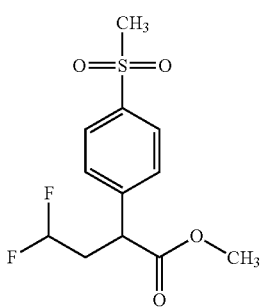

Methyl [4-(methylsulfonyl)phenyl]acetate (32.2 g, 141 mmol, CAS-Rn: [300355-18-4]) was added to a 28% solution of LDA in THF:heptane:ethylbenzene (100 mL) in THF (500 mL) at −20° C. and stirred for 1 h. Then a solution of 2,2-difluoroethyl trifluoromethanesulfonate (60.4 g, 282 mmol) in THF (200 mL) was added dropwise at −20° C. and the resulting mixture was stirred for 24 h at rt. Then an aqueous solution of ammonium chloride was added and the mixture was extracted with ethyl acetate. The combined organic layers were evaporated in vacuum. The crude product was purified by column chromatography on silica gel (Hexane:ethyl acetate 4:1) to give 4.2 g of the target compound as white semi-solid.

Intermediate 110

4,4-difluoro-2-[4-(methylsulfonyl)phenyl]butanoic acid (Racemate)

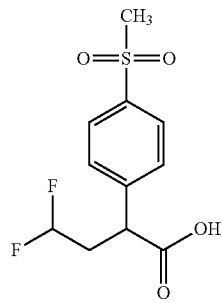

Lithiumhydroxide monohydrate (1.21 g, 28.8 mmol) was added to a solution of methyl 4,4-difluoro-2-[4-(methylsulfonyl)phenyl]butanoate (Racemate) (4.2 g) in methanol (50 mL). The resulting mixture was stirred overnight at rt. The reaction mixture was concentrated under reduced pressure and the residue was taken up in water (30 mL). The resulting solution was acidified with hydrochloric acid (5N) to pH-2 and extracted with MTBE. The combined organic extracts were dried over sodium sulfate and concentrated in vacuum to give 3.73 g of the target compound (13.4 mmol, 93% yield).

$^1$H-NMR (400 MHz, DMSO-d6): δ [ppm]=2.19-2.37 (m, 1H), 2.59-2.77 (m, 1H), 3.22 (s, 3H), 3.93 (t, 1H), 6.05 (tt, 1H), 7.59-7.64 (m, 2H), 7.88-7.93 (m, 2H), 12.89 (br s, 1H).

Intermediate 111

N-(4-chloro-3-fluorophenyl)-4-hydroxy-6,6-dimethyl-2-oxo-1,2,5,6-tetrahydropyridine-3-carbothioamide

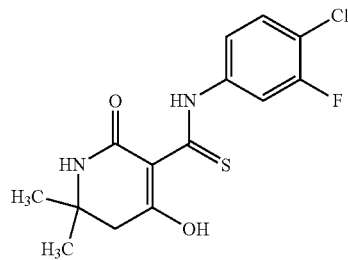 [SMILES: CC1(C)CC(O)=C(C(=S)Nc2ccc(Cl)c(F)c2)C(=O)N1]

6,6-Dimethylpiperidine-2,4-dione (1.64 g, 11.6 mmol) was suspended in 16 mL acetonitrile and treated with 1-chloro-2-fluoro-4-isothiocyanatobenzene (2.18 g, 11.6 mmol, CAS-RN: [597545-17-0]). The mixture was cooled down to 0° C. and treated slowly with DBU (2.8 mL, 19 mmol). It was stirred at rt over night. The reaction mixture was poured into a mixture of ice and hydrochloric acid (4 M). The undissolved precipitate was filtered off, washed with water and dried at 50° C. under vacuum over night to the provide target compound in 97% purity: 3.3 g. The filtrate was discarded.

LC-MS (Method 2): $R_t$=0.63 min; MS (ESIpos): m/z=329 [M+H]$^+$ $^1$H-NMR (400 MHz, DMSO-d6) δ [ppm]=1.16-1.37 (m, 6H), 2.58-2.89 (m, 2H), 7.17-7.82 (m, 3H), 8.19-9.56 (m, 1H), 14.22-14.98 (m, 1H), 16.27-16.45 (m, 1H).

Intermediate 112

4-{[(2-aminopyridin-4-yl)methyl]amino}-N-(4-chloro-3-fluorophenyl)-6,6-dimethyl-2-oxo-1,2,5,6-tetrahydropyridine-3-carbothioamide

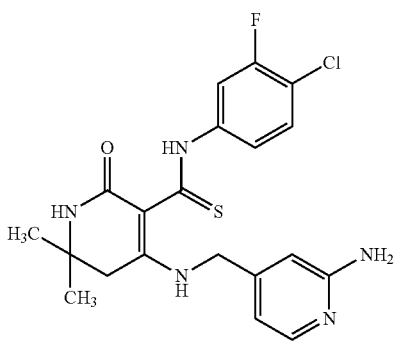 [SMILES: CC1(C)CC(NCc2ccnc(N)c2)=C(C(=S)Nc2ccc(Cl)c(F)c2)C(=O)N1]

N-(4-chloro-3-fluorophenyl)-4-hydroxy-6,6-dimethyl-2-oxo-1,2,5,6-tetrahydropyridine-3-carbothioamide (see Intermediate 111, 2.73 g) and 4-(aminomethyl)pyridin-2-amine (1.74 g, 14.1 mmol) were combined and stirred at 100° C. for 30 min under nitrogen atmosphere without addition of any further solvent. The reaction mixture was diluted with dichloromethane. A yellow precipitate was filtered off under vacuum. The filter cake was dried in a vacuum drying oven to provide the target compound in 96% purity: 1.3 g. The clear filtrate was concentrated under reduced pressure and combined with another batch (starting from N-(4-chloro-3-fluorophenyl)-4-hydroxy-6,6-dimethyl-2-oxo-1,2,5,6-tetrahydropyridine-3-carbothioamide (see Intermediate 111, 0.5 g). Adding dichloromethane gave a beige precipitate. It was filtered off and dried under vacuum to provide a second batch of the target compound in 92% purity: 840 mg.

Analytical data of batch 1:
LC-MS (Method 2): R$_t$=1.17 min; MS (ESIpos): m/z=434 [M+H]$^+$ $^1$H-NMR (400 MHz, DMSO-d6) δ [ppm]: 1.149 (16.00), 1.198 (0.51), 2.518 (0.78), 2.522 (0.53), 2.690 (4.21), 3.744 (0.68), 4.606 (2.15), 4.621 (2.12), 6.010 (3.36), 6.335 (2.37), 6.403 (1.55), 6.406 (1.34), 6.416 (1.44), 6.419 (1.36), 7.231 (0.82), 7.233 (0.92), 7.236 (0.91), 7.240 (0.87), 7.253 (0.96), 7.255 (1.02), 7.258 (1.06), 7.261 (0.99), 7.530 (1.57), 7.551 (2.74), 7.572 (1.31), 7.763 (2.30), 7.788 (1.47), 7.794 (1.36), 7.817 (1.39), 7.823 (1.36), 7.863 (2.18), 7.876 (2.11), 13.871 (0.43), 13.886 (0.81), 15.274 (1.72).

Intermediate 113

2-(2-aminopyridin-4-yl)-3-(4-chloro-3-fluoroanilino)-6,6-dimethyl-1,5,6,7-tetrahydro-4H-pyrrolo[3,2-c]pyridin-4-one

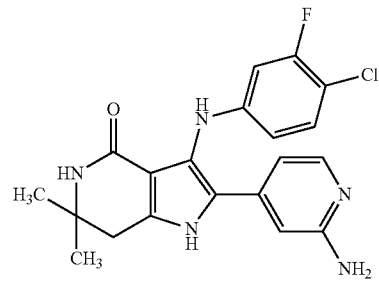 [SMILES: CC1(C)Cc2[nH]c(-c3ccnc(N)c3)c(Nc3ccc(Cl)c(F)c3)c2C(=O)N1]

4-{[(2-Aminopyridin-4-yl)methyl]amino}-N-(4-chloro-3-fluorophenyl)-6,6-dimethyl-2-oxo-1,2,5,6-tetrahydropyridine-3-carbothioamide (see Intermediate 112, 1.62 g) was suspended in 15 mL methanol. Addition of TFA (580 μL, 7.5 mmol) gave a clear solution. It was stirred 5 min at rt. 2.5 mL methanol was added to receive a stirrable suspension. Then 3-chloroperoxybenzoic acid (1.84 g, 70% purity, 7.47 mmol) was added. It was stirred at 90° C. in a sealed vessel for 2 hours. To the reaction mixture aqueous saturated sodium hydrogencarbonate solution and dichloromethane were added. The layers were separated and the organic layer was dried using a water resistant filter. The clear filtrate was concentrated under reduced pressure. The crude product was purified by flash chromatography (55 g amino column, gradient dichloromethane/ethanol 2-25%) to provide the target compound in 90% purity: 635 mg.

LC-MS (Method 2): R$_t$=0.94 min; MS (ESIpos): m/z=400 [M+H]$^+$ $^1$H-NMR (400 MHz, DMSO-d6) 0 [ppm]=1.25 (s, 6H), 2.77 (s, 2H), 5.74 (s, 2H), 6.34-6.46 (m, 2H), 6.55 (s, 1H), 6.68 (dd, 1H), 6.92 (s, 1H), 7.15 (t, 1H), 7.67 (s, 1H), 7.79 (d, 1H), 11.59 (s, 1H)

Intermediate 114

N-{4-[3-(4-chloro-3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide

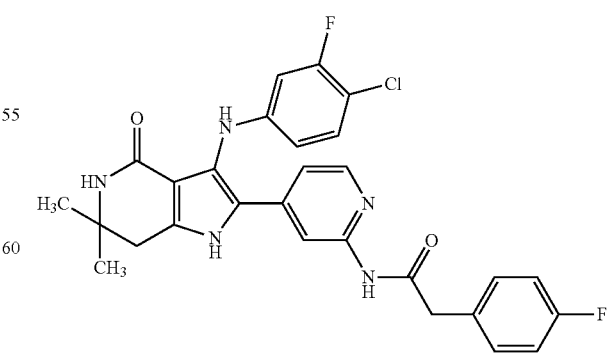

2-(2-Aminopyridin-4-yl)-3-(4-chloro-3-fluoroanilino)-6,6-dimethyl-1,5,6,7-tetrahydro-4H-pyrrolo[3,2-c]pyridin-4- one (see Intermediate 113, 235 mg), (4-fluorophenyl)acetic acid (181 mg, 1.18 mmol), N,N-diisopropylethylamine (610 µL, 3.5 mmol) and PyBOP (1.53 g, 2.94 mmol) were dissolved in 3.4 mL N,N-dimethylacetamide and stirred at rt under nitrogen atmosphere overnight. To the reaction mixture saturated aqueous sodium hydrogencarbonate solution and dichloromethane were added. The layers were separated and the aqueous layer was extracted with dichloromethane twice. The combined organic layers were dried using a water resistant filter. The clear filtrate was concentrated under reduced pressure. The crude product was purified by HPLC under basic conditions to provide the target compound in 95% purity: 85 mg.

LC-MS (Method 2): $R_t$=1.20 min; MS (ESIpos): m/z=536 [M+H]$^+$ $^1$H-NMR (400 MHz, DMSO-d6) δ [ppm]=1.25 (s, 6H), 2.78 (s, 2H), 3.69 (s, 2H), 6.32-6.48 (m, 2H), 6.98 (s, 1H), 7.07-7.24 (m, 4H), 7.29-7.42 (m, 2H), 7.77 (s, 1H), 8.14 (d, 1H), 8.20 (s, 1H), 10.59 (s, 1H), 11.80 (s, 1H).

Intermediate 115

N-{4-[3-(4-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl) butanamide (Racemate)

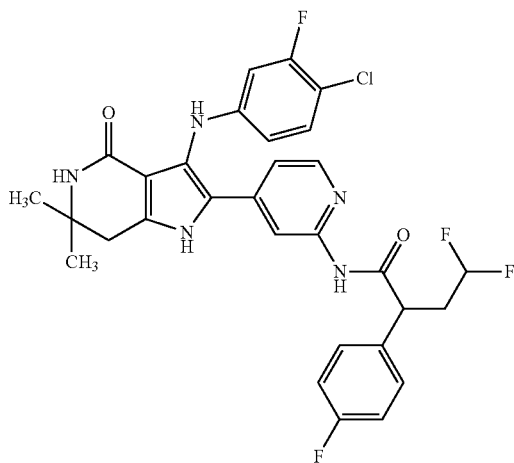 [SMILES: CC1(C)Cc2[nH]c(-c3ccnc(NC(=O)C(CC(F)F)c4ccc(F)cc4)c3)c(Nc3ccc(Cl)c(F)c3)c2C(=O)N1]

2-(2-Aminopyridin-4-yl)-3-(4-chloro-3-fluoroanilino)-6,6-dimethyl-1,5,6,7-tetrahydro-4H-pyrrolo[3,2-c]pyridin-4-one (see Intermediate 113, 400 mg), 4,4-difluoro-2-(4-fluorophenyl)butanoic acid (Racemate) (437 mg, 2.00 mmol), N,N-diisopropylethylamine (1.0 mL, 6.0 mmol) and PyBOP (2.60 g, 5.00 mmol) were dissolved in 5.8 mL N,N-dimethylacetamide and stirred at rt under nitrogen atmosphere over night. To the reaction mixture saturated aqueous sodium hydrogencarbonate solution and dichloromethane were added. The layers were separated and the aqueous layer was extracted with dichloromethane twice. The combined organic layers were dried using a water resistant filter. The clear filtrate was concentrated under reduced pressure. The crude product was purified by HPLC under basic conditions to provide the first batch of the target compound in 99% purity: 297 mg and a second batch in 91% purity: 104 mg.

Analytical data of batch 1:

LC-MS (Method 2): $R_t$=1.27 min; MS (ESIpos): m/z=600 [M+H]$^+$ $^1$H-NMR (400 MHz, DMSO-d6) δ [ppm]=1.26 (s, 6H), 2.12-2.26 (m, 1H), 2.59-2.74 (m, 1H), 2.80 (s, 2H), 4.15 (br dd, 1H), 5.75-6.16 (m, 1H), 6.36 (dd, 1H), 6.43 (dd, 1H), 7.01 (s, 1H), 7.08-7.24 (m, 4H), 7.39-7.52 (m, 2H), 7.78 (s, 1H), 8.12 (d, 1H), 8.17 (s, 1H), 10.66 (s, 1H), 11.81 (s, 1H).

Intermediate 116

N-{4-[3-(4-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl) butanamide (Enantiomer 1)

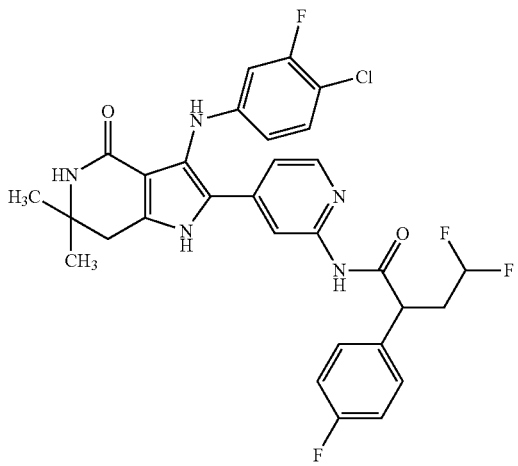 [SMILES: CC1(C)Cc2[nH]c(-c3ccnc(NC(=O)C(CC(F)F)c4ccc(F)cc4)c3)c(Nc3ccc(Cl)c(F)c3)c2C(=O)N1]

The racemic compound (see Intermediate 115, 384 mg) was separated into enantiomers by preparative chiral HPLC to give enantiomer 1 (170 mg, 100% ee, see Intermediate 116) and enantiomer 2 (185 mg, 98% ee, see Intermediate 117).

Preparative Chiral HPLC Method:

Instrument: PrepCon Labomatic HPLC; Column: YMC Amylose SA 5µ, 250×30; eluent A: hexane+0.1 vol % diethylamine; eluent B: ethanol+0.1 vol % diethylamine; isocratic: 60% A+40% B; flow: 60 mL/min; temperature: 25° C.; UV: 254 nm.

Analytical Chiral HPLC Method:

Instrument: Waters Alliance 2695; Column: YMC Amylose SA 3µ, 100×4.6; eluent A: hexane+0.1 vol % diethylamine; eluent B: ethanol; isocratic: 60% A+40% B; flow: 1.4 mL/min; temperature: 25° C.; UV: 254 nm.

Analytical Chiral HPLC (method see Intermediate 116): $R_t$=5.09 min.

LC-MS (Method 2): $R_t$=1.30 min; MS (ESIpos): m/z=600 [M+H]$^+$ $^1$H-NMR (400 MHz, DMSO-d6) δ [ppm]=1.26 (s, 6H), 2.05-2.25 (m, 1H), 2.56-2.75 (m, 1H), 2.80 (s, 2H), 4.15 (dd, 1H), 5.78-6.15 (m, 1H), 6.27-6.50 (m, 2H), 7.01 (s, 1H), 7.07-7.26 (m, 4H), 7.37-7.48 (m, 2H), 7.78 (s, 1H), 8.12 (d, 1H), 8.17 (s, 1H), 10.66 (s, 1H), 11.81 (s, 1H).

Intermediate 117

N-{4-[3-(4-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl)butanamide (Enantiomer 2)

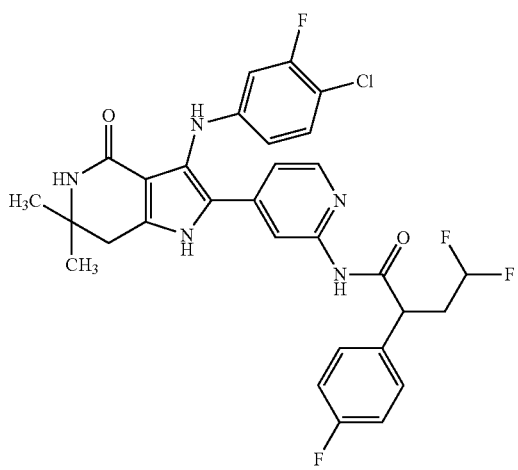 [SMILES: CC1(C)Cc2[nH]c(-c3ccnc(NC(=O)C(CC(F)F)c4ccc(F)cc4)c3)c(Nc3ccc(Cl)c(F)c3)c2C(=O)N1]

For the preparation of the racemic title compound see Intermediate 115. Separation of enantiomers by preparative chiral HPLC (method see Intermediate 116) gave the title compound (185 mg).

Analytical Chiral HPLC (method see Intermediate 116): $R_t$=6.35 min.

LC-MS (Method 2): $R_t$=1.30 min; MS (ESIpos): m/z=600 [M+H]$^+$ $^1$H-NMR (400 MHz, DMSO-d6) δ [ppm]=1.26 (s, 6H), 2.08-2.29 (m, 1H), 2.67 (dt, 1H), 2.80 (s, 2H), 4.15 (dd, 1H), 5.77-6.14 (m, 1H), 6.36 (dd, 1H), 6.44 (dd, 1H), 7.01 (s, 1H), 7.06-7.24 (m, 4H), 7.35-7.50 (m, 2H), 7.78 (s, 1H), 8.12 (d, 1H), 8.17 (s, 1H), 10.67 (s, 1H), 11.81 (s, 1H).

Intermediate 118

N-(2-chloro-3-fluorophenyl)-8-hydroxy-6-oxo-5-azaspiro[3.5]non-7-ene-7-carbothioamide

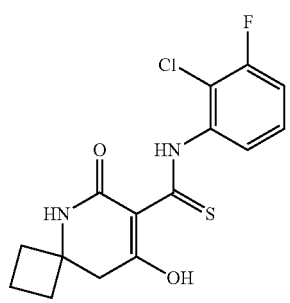 [SMILES: O=C1NC2(CCC2)CC(O)=C1C(=S)Nc1cccc(F)c1Cl]

5-Azaspiro[3.5]nonane-6,8-dione (1.50 g, 9.79 mmol, CAS-RN: [1105665-46-0]) was suspended in 13 mL acetonitrile and treated with 2-chloro-1-fluoro-3-isothiocyanatobenzene (1.84 g, 9.79 mmol). The mixture was cooled down to 0° C. and treated slowly with DBU (2.3 ml, 16 mmol). After complete addition the ice bath was removed and the mixture was stirred at rt for 2 hours. The mixture was diluted with ethyl acetate and acidified using aqueous hydrochloric acid (4 M). The layers were separated and the aqueous layer was extracted with ethyl acetate once, filtered using a water resistant filter and concentrated under reduced pressure to provide the crude product in 90% purity which was used without further purification: 2.34 g LC-MS (Method 2): $R_t$=0.57 min; MS (ESIpos): m/z=341 [M+H]$^+$ $^1$H-NMR (400 MHz, DMSO-d6) δ [ppm]=1.61-1.86 (m, 2H), 2.01-2.11 (m, 2H), 2.13-2.31 (m, 2H), 2.83-3.07 (m, 2H), 7.34-7.55 (m, 3H), 8.63-9.94 (m, 1H), 14.08-14.80 (m, 1H), 16.39 (d, 1H).

Intermediate 119

8-{[(2-aminopyridin-4-yl)methyl]amino}-N-(2-chloro-3-fluorophenyl)-6-oxo-5-azaspiro[3.5]non-7-ene-7-carbothioamide

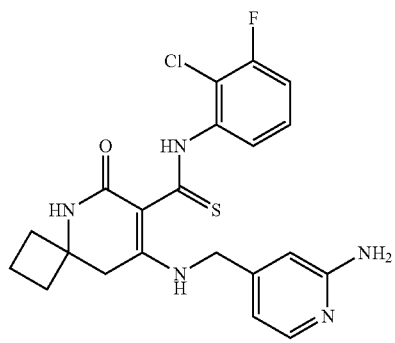 [SMILES: Nc1cc(CNC2=C(C(=S)Nc3cccc(F)c3Cl)C(=O)NC3(CCC3)C2)ccn1]

N-(2-Chloro-3-fluorophenyl)-8-hydroxy-6-oxo-5-azaspiro[3.5]non-7-ene-7-carbothioamide (see Intermediate 118, 2.00 g) and 4-(aminomethyl)pyridin-2-amine (1.23 g, 9.98 mmol) were combined and the mixture was stirred at 100° C. under nitrogen atmosphere without further addition of solvent in a sealed vessel in a heating block for 1 hour. The reaction mixture was diluted with a mixture of dichloromethane and methanol. Sonification gave a yellow precipitate. It was filtered off under vacuum. The filter cake was dried in a vacuum drying oven to provide the target compound in 98% purity: 1.38 g.

LC-MS (Method 2): $R_t$=1.11 min; MS (ESIpos): m/z=446 [M+H]$^+$ $^1$H-NMR (400 MHz, DMSO-d6) δ [ppm]=1.41-1.70 (m, 2H), 1.83-1.96 (m, 2H), 2.02-2.15 (m, 2H), 2.91 (s, 2H), 4.65 (d, 2H), 6.03 (s, 2H), 6.39 (s, 1H), 6.46 (dd, 1H), 7.21-7.32 (m, 1H), 7.37 (td, 1H), 7.48 (d, 1H), 7.88 (d, 1H), 8.16 (s, 1H), 13.88 (t, 1H), 14.95 (s, 1H)

Intermediate 120

2'-(2-aminopyridin-4-yl)-3'-(2-chloro-3-fluoroanilino)-1',7'-dihydrospiro[cyclobutane-1,6'-pyrrolo[3,2-c]pyridin]-4'(5'H)-one

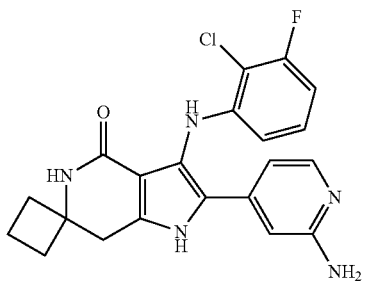 [SMILES: Nc1cc(-c2[nH]c3c(c2Nc2cccc(F)c2Cl)C(=O)NC2(CCC2)C3)ccn1]

8-{[(2-Aminopyridin-4-yl)methyl]amino}-N-(2-chloro-3-fluorophenyl)-6-oxo-5-azaspiro[3.5]non-7-ene-7-carbothioamide (see Intermediate 119, 1.38 g) was suspended in 13 mL methanol. Addition of TFA (480 µL, 6.2 mmol) gave a clear solution. It was stirred 5 min. at rt. Then 3-chloroperoxybenzoic acid (1.53 g, 70% purity, 6.19 mmol) was added. It was stirred at 90° C. in a sealed vessel for 2 hours. To the reaction mixture aqueous saturated sodium hydrogencarbonate solution and dichloromethane were added. The precipitate was filtered off and dried under vacuum to provide the target compound in 90% purity: 610 mg. The layers were separated and the organic layer was dried using a water resistant filter. The clear filtrate was concentrated under reduced pressure. The crude product was purified by flash chromatography (28 g amino column, gradient dichloromethane/ethanol 2-10%) to provide a second batch of the target compound in 79% purity: 104 mg.

Analytical data of batch 1:

LC-MS (Method 2): $R_t$=0.95 min; MS (ESIpos): m/z=412 [M+H]$^+$ $^1$H-NMR (400 MHz, DMSO-d6) δ [ppm]=1.66-1.80 (m, 2H), 1.97-2.20 (m, 4H), 2.99 (s, 2H), 5.70-5.81 (m, 2H), 6.14 (d, 1H), 6.48 (d, 1H), 6.59-6.71 (m, 2H), 6.95 (td, 1H), 7.36-7.43 (m, 1H), 7.46-7.55 (m, 1H), 7.77 (d, 1H), 11.77 (s, 1H).—minor impurities in the aromatic range.

Intermediate 121

N-(6-fluoropyridin-2-yl)-4-hydroxy-6,6-dimethyl-2-oxo-1,2,5,6-tetrahydropyridine-3-carbothioamide

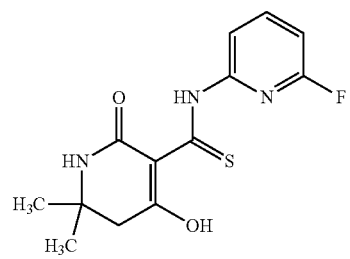 [SMILES: CC1(C)CC(O)=C(C(=S)Nc2cccc(F)n2)C(=O)N1]

6,6-Dimethylpiperidine-2,4-dione (20 mg, 1.77 mmol) was suspended in 7.3 mL acetonitrile and treated with 2-fluoro-6-isothiocyanatopyridine (273 mg, 1.77 mmol, CAS-RN: [1103425-73-5]). The mixture was cooled down to 0° C. and treated slowly with DBU (1.02 mL, 2.8 mmol). It was stirred at rt over night. The reaction mixture was poured into a mixture of ice and hydrochloric acid (4 M). The undissolved precipitate was filtered off, washed with water and dried at 50° C. under vacuum over night to provide the target compound in 97% purity: 277 mg.

LC-MS (Method 2): $R_t$=0.47 min; MS (ESIpos): m/z=296 [M+H]$^+$ $^1$H-NMR (400 MHz, DMSO-d6) δ [ppm]=1.14-1.33 (m, 6H), 2.61-2.89 (m, 2H), 6.99-7.15 (m, 1H), 7.97-8.15 (m, 1H), 8.22-8.31 (m, 1H), 8.32-9.64 (m, 1H), 14.63-15.48 (m, 1H), 16.21-16.57 (m, 1H).

Intermediate 122

4-{[(2-aminopyridin-4-yl)methyl]amino}-N-(6-fluoropyridin-2-yl)-6,6-dimethyl-2-oxo-1,2,5,6-tetrahydropyridine-3-carbothioamide

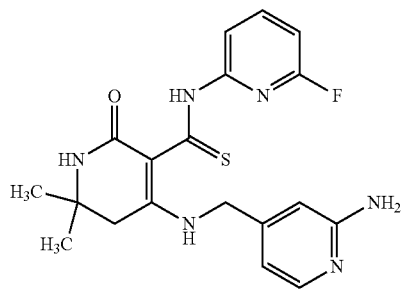 [SMILES: CC1(C)CC(NCc2ccnc(N)c2)=C(C(=S)Nc2cccc(F)n2)C(=O)N1]

N-(6-Fluoropyridin-2-yl)-4-hydroxy-6,6-dimethyl-2-oxo-1,2,5,6-tetrahydropyridine-3-carbothioamide (see Intermediate 121, 1.36 g) and 4-(aminomethyl)pyridin-2-amine (966 mg, 7.84 mmol) were combined and stirred at 100° C. for 2 h under nitrogen atmosphere without further solvent addition. Dichloromethane was carefully added to the hot vial and it was sonicated for 10 min. The precipitate was filtered off, washed with dichloromethane and dried at 50° C. under vacuum to provide the target compound in 87% purity: 752 mg.

LC-MS (Method 2): $R_t$=0.97 min; MS (ESIpos): m/z=401 [M+H]$^+$

Intermediate 123

2-(2-aminopyridin-4-yl)-3-[(6-fluoropyridin-2-yl)amino]-6,6-dimethyl-1,5,6,7-tetrahydro-4H-pyrrolo[3,2-c]pyridin-4-one

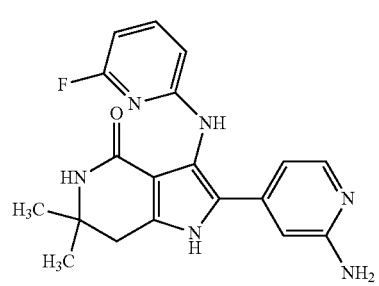 [SMILES: CC1(C)Cc2[nH]c(-c3ccnc(N)c3)c(Nc3cccc(F)n3)c2C(=O)N1]

4-{[(2-Aminopyridin-4-yl)methyl]amino}-N-(6-fluoro-pyridin-2-yl)-6,6-dimethyl-2-oxo-1,2,5,6-tetrahydropyridine-3-carbothioamide (see Intermediate 122, 752 mg) was suspended in 11 mL methanol and treated with TFA (290 µl, 3.8 mmol). It was stirred for 5 minutes, then 3-chloroperoxybenzoic acid (833 mg, 70% purity, 3.38 mmol) was added and it was stirred at 90° C. under nitrogen atmosphere for 2 hours. To the reaction mixture aqueous, saturated sodium hydrogencarbontae solution and dichloromethane were added. The aqueous layer was extracted with dichloromethane three times. The combined organic layers were washed with water and brine once, filtered through a silicone coated filter and concentrated under reduced pressure. A beige precipitate was formed. It was filtered off, washed with water and dichloromethane and dried at 50° C. under vacuum to provide the target compound in 90% purity: 294 mg.

LC-MS (Method 2): R$_t$=0.75 min; MS (ESIpos): m/z=367 [M+H]$^+$ $^1$H-NMR (400 MHz, DMSO-d6) δ [ppm]=1.25 (s, 6H), 2.77 (s, 2H), 5.76 (d, 2H), 6.12 (br d, 1H), 6.17 (dd, 1H), 6.57 (d, 1H), 6.71 (dd, 1H), 6.87 (s, 1H), 7.42-7.52 (m, 1H), 7.79 (d, 1H), 8.08 (s, 1H), 11.58 (s, 1H).

Intermediate 124

N-(3-fluoro-2-methylphenyl)-4-hydroxy-6,6-dimethyl-2-oxo-1,2,5,6-tetrahydropyridine-3-carbothioamide

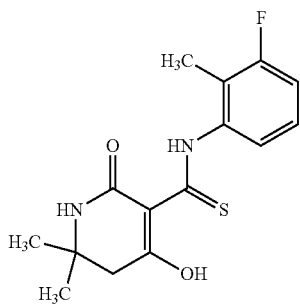 [SMILES: Cc1c(F)cccc1NC(=S)C1=C(O)CC(C)(C)NC1=O]

6,6-Dimethylpiperidine-2,4-dione (422 mg, 2.99 mmol) was suspended in 4 mL acetonitrile and treated with 1-fluoro-3-isothiocyanato-2-methylbenzene (500 mg, 2.99 mmol, CAS-RN: [363179-58-2]). The mixture was cooled down to 0° C., treated with the DBU (710 µL, 4.8 mmol) and stirred at rt over night. The reaction mixture was poured into a mixture of ice and hydrochloric acid (4 M). The undissolved precipitate was filtered off, washed with water and dried at 50° C. under vacuum over night to provide the analytically pure target compound: 897 mg.

LC-MS (Method 2): R$_t$=0.57 min; MS (ESIpos): m/z=309 [M+H]$^+$ $^1$H-NMR (400 MHz, DMSO-d6) δ [ppm]=1.27 (d, 6H), 2.06 (t, 3H), 2.60-2.84 (m, 2H), 7.06-7.21 (m, 2H), 7.23-7.39 (m, 1H), 8.07-9.44 (m, 1H), 13.84-14.59 (m, 1H), 16.39-16.60 (m, 1H).

Intermediate 125

4-{[(2-aminopyridin-4-yl)methyl]amino}-N-(3-fluoro-2-methylphenyl)-6,6-dimethyl-2-oxo-1,2,5,6-tetrahydropyridine-3-carbothioamide

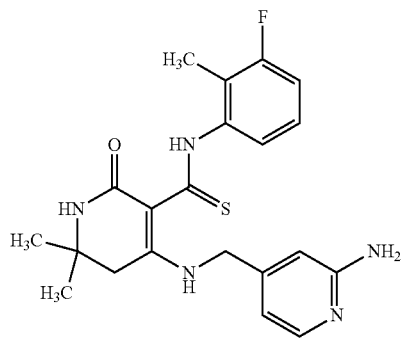 [SMILES: Cc1c(F)cccc1NC(=S)C1=C(NCc2ccnc(N)c2)CC(C)(C)NC1=O]

N-(3-Fluoro-2-methylphenyl)-4-hydroxy-6,6-dimethyl-2-oxo-1,2,5,6-tetrahydropyridine-3-carbothioamide (see Intermediate 124, 1.82 g) and 4-(aminomethyl)pyridin-2-amine (1.24 g, 10.0 mmol) were combined and stirred at 100° C. for 2 h under nitrogen atmosphere without further solvent addition. Dichloromethane was added to the hot flask and it was sonicated for 20 min. The formed precipitate was filtered off, washed with dichloromethane and dried at 50° C. under vacuum to provide batch 1 of the target compound in 80% purity: 817 mg. The filtrate was concentrated under reduced pressure, treated with a ethanol and MTBE and sonicated for 20 minutes. The undissolved precipitate was filtered of to provide batch 2 of the analytically pure target compound: 947 mg.

Analytical data for batch 1:

LC-MS (Method 2): R$_t$=1.07 min; MS (ESIpos): m/z=414 [M+H]$^+$ $^1$H-NMR (400 MHz, DMSO-d6) δ [ppm]=1.16 (s, 6H), 2.06 (d, 3H), 2.69 (s, 2H), 4.58 (d, 2H), 6.00 (s, 2H), 6.34 (s, 1H), 6.41 (dd, 1H), 7.02-7.08 (m, 1H), 7.12 (d, 1H), 7.18-7.27 (m, 1H), 7.66 (s, 1H), 7.86 (d, 1H), 13.91 (br t, 1H), 14.71 (s, 1H).—minor impurities in the aromatic range.

Intermediate 126

2-(2-aminopyridin-4-yl)-3-(3-fluoro-2-methyl-anilino)-6,6-dimethyl-1,5,6,7-tetrahydro-4H-pyrrolo[3,2-c]pyridin-4-one

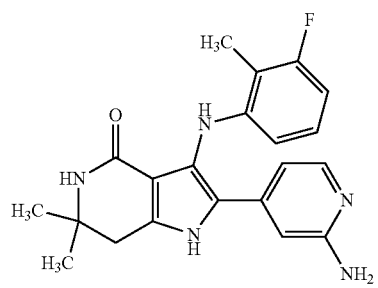 [SMILES: Cc1c(F)cccc1Nc1c(-c2ccnc(N)c2)[nH]c2c1C(=O)NC(C)(C)C2]

4-{[(2-Aminopyridin-4-yl)methyl]amino}-N-(3-fluoro-2-methylphenyl)-6,6-dimethyl-2-oxo-1,2,5,6-tetrahydropyridine-3-carbothioamide (see Intermediate 125, 1.76 g) was suspended in 26 mL methanol and treated with TFA (660 μL, 8.5 mmol). It was stirred for 5 minutes, then 3-chloroperoxybenzoic acid (1.89 g, 70% purity, 7.68 mmol) was added and it was stirred at 90° C. under nitrogen atmosphere for 2 hours. To the reaction mixture aqueous saturated sodium hydrogencarbonate solution was added. It was extracted with dichloromethane three times, washed with water and brine once, filtered through a silicone coated filter and concentrated under reduced pressure. The crude product was purified by flash chromatography (28 g column, aminophase; dichloromethane/ethanol 0%-20%). The target compound containing fractions were combined, concentrated under reduced pressure and purified by HPLC under basic conditions to provide the target compound in 90% purity: 123 mg.

LC-MS (Method 2): $R_t$=0.89 min; MS (ESIpos): m/z=381 [M+H]$^+$ $^1$H-NMR (400 MHz, DMSO-d6) δ [ppm]=1.26 (s, 6H), 2.19 (d, 3H), 2.78 (s, 2H), 5.68 (s, 2H), 6.08 (d, 1H), 6.45 (t, 1H), 6.50 (d, 1H), 6.62 (dd, 1H), 6.76-6.87 (m, 1H), 7.00 (d, 2H), 7.73 (d, 1H), 11.54 (s, 1H).

Intermediate 127

3-[(tert-butoxycarbonyl)amino]-2-(4-fluorophenyl) propanoic acid (Racemate)

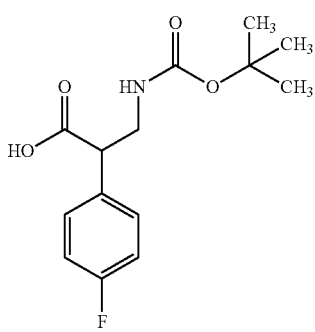 [SMILES: CC(C)(C)OC(=O)NCC(C(=O)O)c1ccc(F)cc1]

3-Amino-2-(4-fluorophenyl)propanoic acid hydrogen chloride salt (Racemate) (500 mg) was suspended in aqueous sodium hydroxide solution (1.3 ml, 2.0 M, 2.6 mmol). The mixture was stirred for 10 minutes until it reached rt, then di-tert-butyl dicarbonate (551 mg, 2.53 mmol) dissolved in 3.7 mL THF was added dropwise. The reaction mixture was stirred at rt over night under nitrogen atmosphere. THF was removed under reduced pressure, the residue was diluted with dichloromethane and water. The layers were separated and the aqueous layer was extracted with dichloromethane three times. The combined organic layers were filtered through a silicone coated filter and concentrated under reduced pressure to provide the crude product in 88% purity: 296 mg. The crude product was used without further purification:

$^1$H-NMR (400 MHz, DMSO-d6) δ [ppm]=1.32 (s, 9H), 3.22 (ddd, 1H), 3.42 (ddd, 1H), 3.75 (t, 1H), 6.86 (br t, 1H), 7.11-7.21 (m, 2H), 7.23-7.36 (m, 2H), 12.33-12.70 (m, 1H).

Intermediate 128

8-hydroxy-N-(2-methylphenyl)-6-oxo-5-azaspiro [3.5]non-7-ene-7-carbothioamide

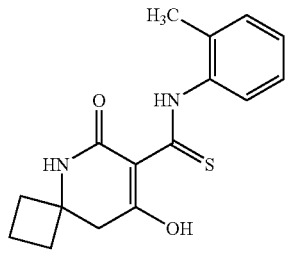 [SMILES: Cc1ccccc1NC(=S)C1=C(O)CC2(CCC2)NC1=O]

5-Azaspiro[3.5]nonane-6,8-dione (1.50 g, 9.79 mmol, CAS-RN: [1105665-46-0]) was suspended in 13 mL acetonitrile and treated with 1-isothiocyanato-2-methylbenzene (1.3 mL, 9.8 mmol). The mixture was cooled down to 0° C. and treated slowly with DBU (2.3 ml, 16 mmol). It was stirred at rt over night. The reaction mixture was poured into a mixture of ice and aqueous hydrochloric acid (4 M). The undissolved precipitate was filtered off, washed with water and dried at 50° C. under vacuum over night to provide the analytically pure target compound: 3.0 g.

LC-MS (Method 2): $R_t$=0.59 min; MS (ESIpos): m/z=303 [M+H]$^+$ $^1$H-NMR (400 MHz, DMSO-d6) δ [ppm]=1.60-1.90 (m, 2H), 1.98-2.11 (m, 2H), 2.13-2.29 (m, 5H), 2.78-3.06 (m, 2H), 7.12-7.43 (m, 4H), 8.42-9.84 (m, 1H), 13.80-14.43 (m, 1H), 16.43-16.80 (m, 1H).

Intermediate 129

8-{[(2-aminopyridin-4-yl)methyl]amino}-N-(2-methylphenyl)-6-oxo-5-azaspiro[3.5]non-7-ene-7-carbothioamide

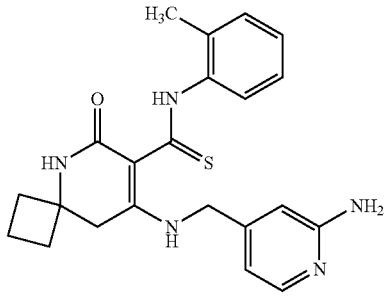 [SMILES: Cc1ccccc1NC(=S)C1=C(NCc2ccnc(N)c2)CC2(CCC2)NC1=O]

8-Hydroxy-N-(2-methylphenyl)-6-oxo-5-azaspiro[3.5] non-7-ene-7-carbothioamide (see Intermediate 128, 3.02 g) and 4-(aminomethyl)pyridin-2-amine (1.84 g, 15.0 mmol) were suspended in 16 mL dry DME in a sealed vessel. At 0° C. N,O-Bis-(trimethylsiliyl)-acetamide (5.0 ml, 20 mmol) was added dropwise. It was stirred at 80° C. in a sealed vessel under nitrogen atmosphere for 3 hours. The reaction mixture was diluted with ethyl acetate and the undissolved precipitate was filtered off, washed with ethyl acetate and dried at 50° C. under vacuum to provide the analytically pure target compound as first batch: 2.1 g.

The filtrate was concentrated under reduced pressure and suspended in dichloromethane and diluted with MTBE. The undissolved precipitate was filtered off to provide the target compound as second batch in 99% purity: 1.1 g.

Analytical data for the first batch:

LC-MS (Method 2): $R_t$=1.04 min; MS (ESIpos): m/z=408 [M+H]$^+$ $^1$H-NMR (400 MHz, DMSO-d6) δ [ppm]=1.42-1.55 (m, 1H), 1.56-1.70 (m, 1H), 1.84-1.96 (m, 2H), 2.00-2.13 (m, 2H), 2.15 (s, 3H), 2.87 (s, 2H), 4.61 (d, 2H), 6.02 (s, 2H), 6.39 (s, 1H), 6.45 (dd, 1H), 7.07-7.22 (m, 2H), 7.23-7.31 (m, 2H), 7.88 (d, 1H), 8.04 (s, 1H), 13.91 (br t, 1H), 14.50 (s, 1H).

Intermediate 130

2'-(2-aminopyridin-4-yl)-3'-(2-methylanilino)-1',7'-dihydrospiro[cyclobutane-1,6'-pyrrolo[3,2-c]pyridin]-4'(5'H)-one

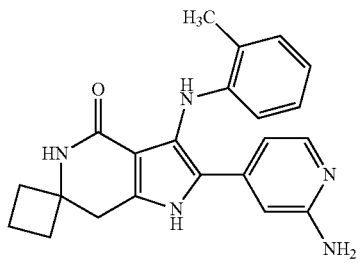 [SMILES: Cc1ccccc1Nc1c(-c2ccnc(N)c2)[nH]c2c1C(=O)NC1(CCC1)C2]

8-{[(2-Aminopyridin-4-yl)methyl]amino}-N-(2-methylphenyl)-6-oxo-5-azaspiro[3.5]non-7-ene-7-carbothioamide (see Intermediate 129, 1.05 g) was suspended in 12 mL methanol and treated with hydrogenperoxide (530 μL, 30% purity, 5.2 mmol). It was stirred at 90° C. for 2 hours in the microwave reactor under nitrogen atmosphere. The reaction mixture was combined with the reaction mixture of a batch starting from 8-{[(2-Aminopyridin-4-yl)methyl]amino}-N-(2-methylphenyl)-6-oxo-5-azaspiro[3.5]non-7-ene-7-carbothioamide (see Intermediate 129, 2.07 g). Aqueous saturated sodiumthiosulfate solution, aqueous half concentrated potassiumcarbonate solution and dichloromethane were added. It was stirred for a few minutes. Between both layers a beige precipitate was formed. It was filtered off, washed with water and dichloromethane and dried at 50° C. under vacuum. The organic layer of the filtrate was filtered through a silicone coated filter and concentrated under reduced pressure. The residue was suspended in ethanol and dichloromethane and the undissolved precipitate was filtered off to provide the target compound as batch 1 in 85% purity: 213 mg. The filtrate was combined with the crude product and purified by flash chromatography (28 g column, aminophase; dichloromethane/ethanol 0%-100%) to provide the target compound in 86% purity as batch 2: 1.3 g.

Analytical data of batch 2:

LC-MS (Method 2): $R_t$=0.89 min; MS (ESIpos): m/z=375 [M+H]$^+$ $^1$H-NMR (400 MHz, DMSO-d6) δ [ppm]=1.66-1.80 (m, 2H), 1.94-2.08 (m, 2H), 2.07-2.19 (m, 2H), 2.30 (s, 3H), 2.98 (s, 2H), 5.66 (s, 2H), 6.24 (d, 1H), 6.48 (d, 1H), 6.55-6.64 (m, 2H), 6.76-6.86 (m, 1H), 6.95 (s, 1H), 7.06 (d, 1H), 7.51 (s, 1H), 7.71 (d, 1H), 11.57 (s, 1H).—contains ethanol.

Intermediate 131

7-hydroxy-5-oxo-N-phenyl-4-azaspiro[2.5]oct-6-ene-6-carbothioamide

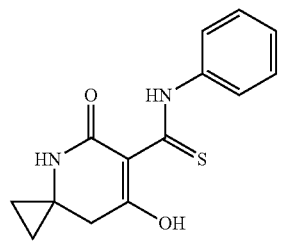 [SMILES: O=C1NC2(CC2)CC(O)=C1C(=S)Nc1ccccc1]

4-Azaspiro[2.5]octane-5,7-dione (1.00 g, 7.19 mmol, CAS-RN: [1105663-34-0]) was suspended in 11 mL acetonitrile and treated with isothiocyanatobenzene (860 μL, 7.2 mmol). The reaction mixture was cooled down to 0° C. and treated slowly with DBU (1.7 mL, 11 mmol) and was stirred at rt over night. The reaction mixture was poured into a mixture of ice and aqueous hydrochloric acid (4 M). The undissolved precipitate was filtered off, washed with water and dried at 50° C. under vacuo over night to provide the target compound in 79% purity: 1.91 g. The filtrate was discarded.

LC-MS (Method 2): $R_t$=0.47 min; MS (ESIpos): m/z=275 [M+H]$^+$ $^1$H-NMR (400 MHz, DMSO-d6) δ [ppm]=0.67-0.94 (m, 4H), 2.61-2.90 (m, 2H), 7.21-7.51 (m, 5H), 8.18-9.63 (m, 1H), 14.16-14.74 (m, 1H), 16.62 (d, 1H).

Intermediate 132

7-{[(2-aminopyridin-4-yl)methyl]amino}-5-oxo-N-phenyl-4-azaspiro[2.5]oct-6-ene-6-carbothioamide

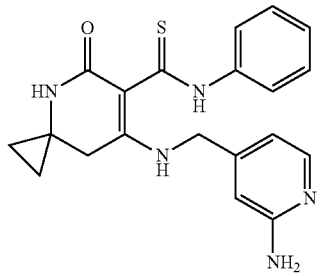 [SMILES: Nc1cc(CNC2=C(C(=S)Nc3ccccc3)C(=O)NC3(CC3)C2)ccn1]

7-Hydroxy-5-oxo-N-phenyl-4-azaspiro[2.5]oct-6-ene-6-carbothioamide (see Intermediate 131, 1.91 g, 79% purity) and 4-(aminomethyl)pyridin-2-amine (1.02 g, 8.25 mmol) were dissolved in 8.6 mL dry DME in a sealed vessel. At 0° C. N,O-Bis-(trimethylsiliyl)-acetamide (2.7 mL, 11 mmol; CAS-RN: [10416-59-8]) was added dropwise. It was stirred at 80° C. in a sealed vessel under nitrogen atmosphere overnight. The reaction mixture was diluted with ethyl acetate. The undissolved precipitate was filtered off to provide the analytically pure target compound. The filtrate was diluted with dichloromethane and treated with MTBE. The undissolved precipitate was filtered off to provide the target compound in 98% purity. Both filter cakes were combined: 1.87 g.

LC-MS (Method 2): $R_t$=0.95 min; MS (ESIpos): m/z=380 [M+H]$^+$ $^1$H-NMR (400 MHz, DMSO-d6) δ [ppm]=0.52-0.62 (m, 2H), 0.69-0.78 (m, 2H), 2.71 (s, 2H), 4.53 (d, 2H), 6.02 (s, 2H), 6.33 (s, 1H), 6.39 (dd, 1H), 7.14-7.24 (m, 1H), 7.32-7.40 (m, 2H), 7.40-7.48 (m, 2H), 7.83-7.93 (m, 2H), 13.83 (br t, 1H), 14.76 (s, 1H).

Intermediate 133

2'-(2-aminopyridin-4-yl)-3'-anilino-1',7'-dihydrospiro[cyclopropane-1,6'-pyrrolo[3,2-c]pyridin]-4' (5'H)-one

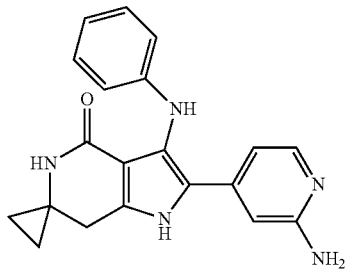 [SMILES: Nc1cc(-c2[nH]c3c(c2Nc2ccccc2)C(=O)NC2(CC2)C3)ccn1]

7-{[(2-Aminopyridin-4-yl)methyl]amino}-5-oxo-N-phenyl-4-azaspiro[2.5]oct-6-ene-6-carbothioamide (see Intermediate 132, 1.91 g) was suspended in 31 mL methanol and treated with trifluoric acid (780 μL, 10 mmol; CAS-RN: [76-05-1]). It was stirred for 5 minutes, then 3-chloroperoxybenzoic acid (2.23 g, 70% purity, 9.06 mmol) was added, the vessel was sealed and stirred at 80° C. for 2 hours under nitrogen atmosphere. To the reaction mixture aqueous saturated sodiumhydrogencarbonate solution was added. An undissolved precipitate was formed and filtered off. The filtrate was extracted with dichloromethane three times. The combined organic layers were filtered through a silicone coated filter and concentrated under reduced pressure. The crude product was purified by flash chromatography (55 g column, aminophase, ethyl acetate/ethanol 0%-20%) to provide the target compound in 87% purity which was combined with the filter cake: 934 mg.

LC-MS (Method 2): $R_t$=0.78 min; MS (ESIpos): m/z=346 [M+H]$^+$ $^1$H-NMR (400 MHz, DMSO-d6) δ [ppm]=0.62-0.79 (m, 4H), 2.80 (s, 2H), 5.66 (s, 2H), 6.53-6.65 (m, 4H), 6.68 (br d, 1H), 7.03 (br t, 2H), 7.19 (br d, 2H), 7.73 (d, 1H), 11.22-11.89 (m, 1H).

Intermediate 134

N-(2,5-difluorophenyl)-4-hydroxy-1-methyl-2-oxo-1,2,5,6-tetrahydropyridine-3-carbothioamide

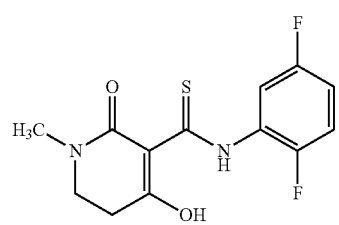 [SMILES: CN1CCC(O)=C(C(=S)Nc2cc(F)ccc2F)C1=O]

To a solution of 1-methylpiperidine-2,4-dione (2.23 g, 17.5 mmol) and 1,4-difluoro-2-isothiocyanatobenzene (3.00 g, 17.5 mmol, CAS-RN: [206559-57-1]) in acetonitrile (30 mL) was added 1,8-diazabicyclo(5.4.0)undec-7-ene (4.00 g, 2.63 mmol) dropwise below 5° C. The mixture was stirred at 25° C. for 5 hours. The mixture was separated and the water phase was extracted with dichloromethane. The combined organic phase was washed with brine, dried over anhydrous sodium sulfate, filtered and concentrated to give a residue. The residue was purified by column chromatography (200-300 mesh, petroleum ether:ethyl acetate=30:1 then 5:1) to give N-(2,5-difluorophenyl)-4-hydroxy-1-methyl-2-oxo-1,2,5,6-tetrahydropyridine-3-carbothioamide (1.35 g) as yellow oil.

$^1$H NMR (400 MHz, CDCl$_3$): δ [ppm]=14.53 (s, 1H), 7.79-7.75 (m, 1H), 7.15-7.09 (m, 1H), 6.98-6.92 (m, 1H), 3.47 (t, 2H), 3.07 (s, 3H), 2.82 (t, 2H).

Intermediate 135

4-{[(2-aminopyridin-4-yl)methyl]amino}-N-(2,5-difluorophenyl)-1-methyl-2-oxo-1,2,5,6-tetrahydropyridine-3-carbothioamide

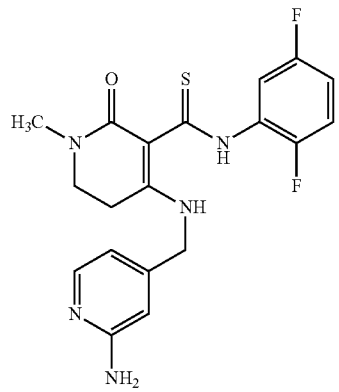 [SMILES: CN1CCC(NCc2ccnc(N)c2)=C(C(=S)Nc2cc(F)ccc2F)C1=O]

A mixture of N-(2,5-difluorophenyl)-4-hydroxy-1-methyl-2-oxo-1,2,5,6-tetrahydropyridine-3-carbothioamide (1.00 g, see Intermediate 134), 4-(aminomethyl)pyridin-2-amine (413 mg, 3.35 mmol), 4A molecular sieve and trimethylsilyl (1Z)—N-(trimethylsilyl)ethanimidate (2.05 g, 10.1 mmol) was dissolved in 10 mL DME and stirred at 80° C. for 5 hours under nitrogen. The mixture was filtered and the filtrate was concentrated by evaporation in vacuum. The residue was purified by preparative-TLC (ethyl acetate/methanol=10/1) to afford 4-{[(2-aminopyridin-4-yl)methyl]amino}-N-(2,5-difluorophenyl)-1-methyl-2-oxo-1,2,5,6-tetrahydropyridine-3-carbothioamide (800 mg) as a yellow solid.

LC-MS (Method C): $R_t$=0.68 min; MS (ESIpos): m/z=404.2 [M+H]$^+$

Method C: 5-95AB, Shimadzu

Instrument: SHIMADZU LCMS-2020 SingleQuad; Column: Chromolith@Flash RP-18E 25-2 MM; eluent A: water+0.0375 vol % trifluoroacetic acid, eluent B: acetonitrile+0.01875 vol % trifluoroacetic acid; gradient: 0-0.8 min, 5-95% B, 0.8-1.2 min 95% B; flow 1.5 mL/min; temperature: 50° C.; PDA: 220 nm & 254 nm.

Intermediate 136

2-(2-aminopyridin-4-yl)-3-(2,5-difluoroanilino)-5-methyl-1,5,6,7-tetrahydro-4H-pyrrolo[3,2-c]pyridin-4-one

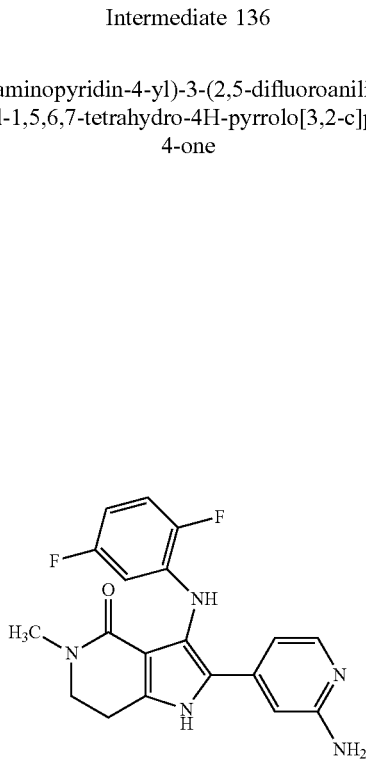

To a solution of 4-{[(2-aminopyridin-4-yl)methyl]amino}-N-(2,5-difluorophenyl)-1-methyl-2-oxo-1,2,5,6-tetrahydropyridine-3-carbothioamide (700 mg, Intermediate 135) in ethanol (10 mL) was added trifluoroacetic acid (197.8 mg, 1.735 mmol) and the mixture was stirred at rt for 5 minutes. Then hydrogen peroxide (393 mg, 3.47 mmol) was added and the reaction mixture was heated to 100° C. and stirred at the same temperature for 16 hours. The reaction mixture was concentrated in vacuum to give a residue. The residue was purified by preparative TLC (petroleum ether:ethyl acetate=0:1) to give 2-(2-aminopyridin-4-yl)-3-(2,5-difluoroanilino)-5-methyl-1,5,6,7-tetrahydro-4H-pyrrolo[3,2-c]pyridin-4-one (120 mg) as a yellow oil.

LC-MS (Method C, see Intermediate 135): $R_t$=0.69 min; MS (ESIpos): m/z=370 [M+H]$^+$ $^1$H NMR (400 MHz, DMSO-d$_6$): δ [ppm]=11.83 (s, 1H), 7.83 (d, 1H), 7.54 (s, 1H), 7.17-7.12 (m, 1H), 6.84-6.74 (m, 1H), 6.61 (s, 1H), 6.51-6.29 (m, 3H), 6.05-5.94 (m, 1H), 3.56 (t, 2H), 2.94 (t, 2H), 2.91 (s, 3H).

Intermediate 137 tert-butyl 4-[4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoyl]piperazine-1-carboxylate

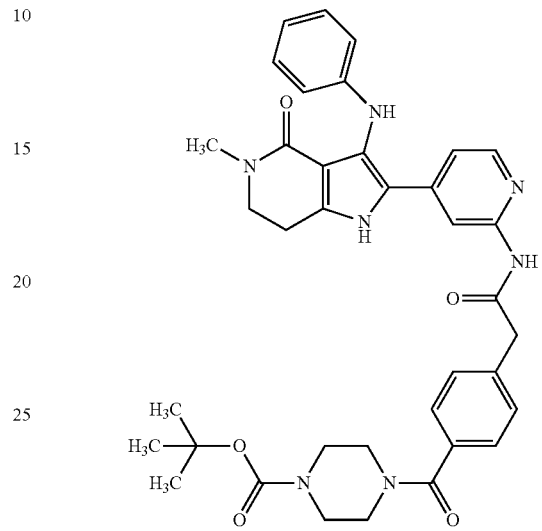

A solution of 4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoic acid (see Example 151, 498 mg, 1.00 mmol) in DMF (53 mL) was treated with potassium carbonate (347 mg, 2.51 mmol), tert-butyl piperazine-1-carboxylate (206 mg, 1.10 mmol), and HATU (1.15 g, 3.01 mmol), and stirred for 5 h at r.t. Then water was added, and the mixture was extracted with ethyl acetate. The organic phase was washed with saturated sodium chloride solution, dried (sodium sulfate), filtered, and concentrated under reduced pressure to give a solid that was triturated with a mixture of dichloromethane and ethanol to give 546 mg of the title compound.

LC-MS (§ OA01a02): $R_t$=1.06 min; MS (ESIneg): m/z=662 [M−H]$^−$ $^1$H-NMR (400 MHz, DMSO-d$_6$): δ [ppm]=11.73 (s, 1H), 10.62 (s, 1H), 8.19 (s, 1H), 8.05 (d, 1H), 7.44-7.34 (m, 5H), 7.13 (dd, 1H), 7.01 (t, 2H), 6.62 (t, 1H), 6.58-6.53 (m, 2H), 4.54-4.22 (m, 2H), 3.75 (s, 2H), 3.66-3.46 (m, 6H), 2.94-2.90 (m, 2H), 2.86 (s, 3H), 1.40 (s, 9H) (2H not detected).

Intermediate 138

2-(2-chloropyridin-4-yl)-5-methyl-1,5,6,7-tetrahydro-4H-pyrrolo[3,2-c]pyridin-4-one

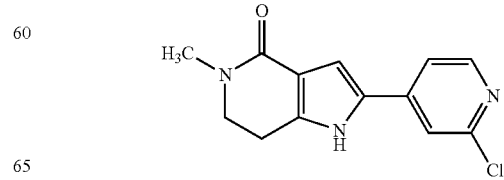

To a solution of 1-methylpiperidine-2,4-dione (813 mg, 6.40 mmol) in ethanol (10 mL) was added ammonium acetate (1.31 g, 17.1 mmol) at rt. The mixture was stirred at 25° C. for 0.75 hours. Then 2-bromo-1-(2-chloropyridin-4-yl)ethan-1-one (1.00 g, 4.26 mmol, CAS-RN: [23794-16-3]) was added into the mixture at 25° C. The mixture was stirred at 25° C. for 16 hours. The reaction mixture was concentrated in vacuum to give a residue. The residue was purified by flash silica gel chromatography (ethyl acetate/methanol=10/1) to give 2-(2-chloropyridin-4-yl)-5-methyl-1,5,6,7-tetrahydro-4H-pyrrolo[3,2-c]pyridin-4-one (560 mg) as a yellow solid.

$^1$H NMR (400 MHz, DMSO-d$_6$): δ [ppm]=11.99 (s, 1H), 8.29 (d, 1H), 7.75 (d, 1H), 7.64 (dd, 1.6 Hz, 1H), 7.15 (d, 1H), 3.56 (t, 2H), 2.94 (t, 2H), 2.92 (s, 3H).

Intermediate 139

2-(4-fluorophenyl)-N-[4-(5-methyl-4-oxo-4,5,6,7-tetrahydro-1H-pyrrolo[3,2-c]pyridin-2-yl)pyridin-2-yl]acetamide

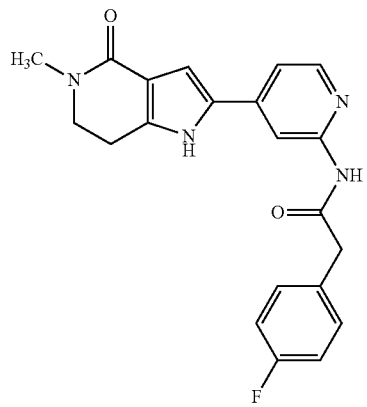 [SMILES: CN1CCc2[nH]c(-c3ccnc(NC(=O)Cc4ccc(F)cc4)c3)cc2C1=O]

To a mixture of 2-(2-chloropyridin-4-yl)-5-methyl-1,5,6,7-tetrahydro-4H-pyrrolo[3,2-c]pyridin-4-one (950 mg, Intermediate 138) and 2-(4-fluorophenyl)acetamide (612 mg, 3.99 mmol, CAS-RN: [332-29-6]) in dioxane (19 mL) were added palladium(II) acetate (40.7 mg, 181 μmol), 9,9-dimethyl-4,5-bis(diphenylphosphino)xanthene (210 mg, 363 μmol) and cesium carbonate (1.77 g, 5.44 mmol) in one portion at rt. The reaction mixture was stirred at 100° C. for 16 hours under nitrogen atmosphere. The reaction mixture was adjusted to pH-3 with hydrochloric acid (2 M in water). The mixture was extracted with ethyl acetate and the combined organic layers were washed with brine, dried over anhydrous sodium sulfate, filtered and concentrated in vacuum. The residue was purified by silica gel chromatography (petroleum ether/ethyl acetate=0/1) to give 2-(4-fluorophenyl)-N-[4-(5-methyl-4-oxo-4,5,6,7-tetrahydro-1H-pyrrolo[3,2-c]pyridin-2-yl)pyridin-2-yl]acetamide (600 mg) as yellow oil.

LC-MS (Method C, see Intermediate 135): R$_t$=0.77 min; MS (ESIpos): m/z=379 [M+H]$^+$ $^1$H NMR (400 MHz, DMSO-d$_6$): δ [ppm]=11.92 (s, 1H), 10.65 (s, 1H), 8.25-8.20 (m, 2H), 7.41-7.37 (m, 2H), 7.35-7.25 (m, 2H), 7.19-7.07 (m, 3H), 6.84 (d, J=2.4 Hz, 1H), 3.73 (s, 2H), 3.58-3.50 (m, 2H), 2.93-2.86 (m, 5H)

Intermediate 140

N-[4-(3-bromo-5-methyl-4-oxo-4,5,6,7-tetrahydro-1H-pyrrolo[3,2-c]pyridin-2-yl)pyridin-2-yl]-2-(4-fluorophenyl)acetamide

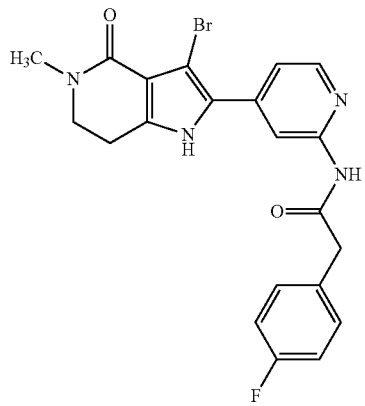 [SMILES: CN1CCc2[nH]c(-c3ccnc(NC(=O)Cc4ccc(F)cc4)c3)c(Br)c2C1=O]

A solution of 2-(4-fluorophenyl)-N-[4-(5-methyl-4-oxo-4,5,6,7-tetrahydro-1H-pyrrolo[3,2-c]pyridin-2-yl)pyridin-2-yl]acetamide (500 mg, Intermediate 139) in N,N-dimethylformamide (5.0 mL) was added N-bromosuccinimide (235 mg, 1.32 mmol) at 25° C. The mixture was stirred at room temperature for 0.5 hour. Saturated aqueous sodium thiosulfate was added at 25° C. The mixture was stirred at 25° C. for another 0.5 hour. The mixture was extracted with ethyl acetate and the combined organic layers were washed with brine, dried over anhydrous sodium sulfate, filtered and concentrated in vacuum. The residue was purified by silica gel chromatography (100-200 mesh silica gel, dichloromethane/methanol=10/1) to give N-[4-(3-bromo-5-methyl-4-oxo-4,5,6,7-tetrahydro-1H-pyrrolo[3,2-c]pyridin-2-yl)pyridin-2-yl]-2-(4-fluorophenyl)acetamide (450 mg) as a gray solid.

$^1$H NMR (400 MHz, DMSO-d$_6$): δ [ppm]=12.13 (s, 1H), 10.76 (s, 1H), 8.53 (s, 1H), 8.34 (d, 1H), 7.46-7.32 (m, 3H), 7.20-7.07 (m, 2H), 3.77-3.71 (m, 2H), 3.56-3.47 (m, 2H), 2.94-2.88 (m, 5H).

Intermediate 141

Ethyl [1-(methylamino)cyclobutyl]acetate

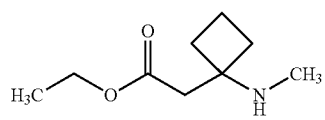

Methane amine (3.4 mL, 33% purity in ethanol, 27 mmol) was cooled down with an ice bath and treated dropwise with ethyl cyclobutylideneacetate (CAS-RN: [27741-65-7], 3.80 g, 27.1 mmol), dissolved in 4.4 mL ethanol. The reaction mixture was stirred at rt over night under Argon atmosphere. The reaction mixture was concentrated under reduced pressure. The crude product was used without further purification: 4.3 g.

Intermediate 142

Ethyl 3-{[1-(2-ethoxy-2-oxoethyl)cyclobutyl](methyl)amino}-3-oxopropanoate

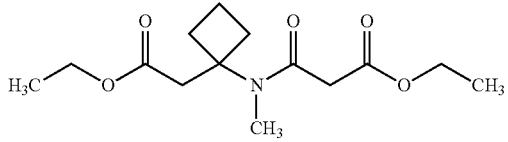 [SMILES: CCOC(=O)CC(=O)N(C)C1(CC(=O)OCC)CCC1]

Ethyl [1-(methylamino)cyclobutyl]acetate (see Intermediate 141, 4.31 g), was dissolved in 26 mL dichloromethane and cooled down to 0° C. Then N,N-diisopropylethylamine (4.8 ml, 28 mmol) and DMAP (307 mg, 2.52 mmol) were added. Subsequently ethyl 3-chloro-3-oxopropanoate (3.5 ml, 28 mmol) was added. The reaction mixture was stirred at 0° C. for 1.5 h at rt over night. Half concentrated ammonium chloride solution and dichloromethane were added to the reaction mixture. It was stirred for a few minutes, filtered through a silicone coated filter and concentrated under reduced pressure. The crude product was combined with the crude product of another batch starting from ethyl [1-(methylamino)cyclobutyl]acetate (see BRAL818-2, 5.0 g) and purified by flash chromatography (Isolera, Biotage, 50 g column silica ULTRA; hexane/ethyl acetate 12%-100%, collection mode: collect all fractions) to provide the target compound in 46% purity: 3.7 g, which was used without further purification.

LC-MS (Method 2): $R_t$=0.96 min; MS (ESIpos): m/z=286 [M+H]$^+$

Intermediate 143

Ethyl 5-methyl-6,8-dioxo-5-azaspiro[3.5]nonane-7-carboxylate (Racemate)

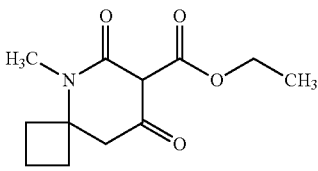 [SMILES: CCOC(=O)C1C(=O)CC2(CCC2)N(C)C1=O]

Sodium ethoxide (1.5 mL, 21% in ethanol, 6.6 mmol) was cooled down with an ice bath and treated dropwise with ethyl 3-{[1-(2-ethoxy-2-oxoethyl)cyclobutyl](methyl)amino}-3-oxopropanoate (see Intermediate 142, 3.70 g, 46% purity), dissolved in 8.7 mL ethanol. The reaction mixture was stirred at 0° C. for 30 minutes, then further 20 mL ethanol were added and the reaction mixture was stirred at rt over night under Argon atmosphere. The reaction mixture was diluted with dichloromethane and the pH was adjusted to 1 by addition of hydrochloric acid (4 M). It was stirred for a few minutes, filtered through a silicone coated filter and concentrated under reduced pressure to provide the target compound, which was used without further purification: 3.0 g.

LC-MS (Method 1): $R_t$=0.93 min; MS (ESIpos): m/z=241 [M+H]$^+$

Intermediate 144

5-methyl-5-azaspiro[3.5]nonane-6,8-dione

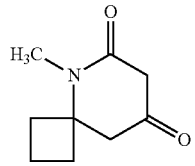

5-Methyl-6,8-dioxo-5-azaspiro[3.5]nonane-7-carboxylate (Racemate) (see Intermediate 143, 1.43 g) was dissolved in 12 mL dichloromethane and treated with hydrochloric acid (11 mL, 2.0 M, 23 mmol). It was stirred 20 min at rt under Argon atmosphere. The reaction mixture was filtered through a silicone coated filter and concentrated under reduced pressure. The crude intermediate was dissolved in 16 mL acetonitrile and treated with 1.6 mL water. It was stirred under reflux for 1 hour under Argon atmosphere. The reaction mixture was concentrated under reduced pressure. The crude product was purified by flash chromatography (50 g column, silica ULTRA; ethyl acetate/ethanol 0%-20% ethanol) to provide the analytically pure target compound: 1.4 g.

LC-MS (Method 1): $R_t$=0.62 min; MS (ESIpos): m/z=168 [M+H]$^+$ $^1$H-NMR (400 MHz, DMSO-d6) δ [ppm]: 1.680 (0.52), 1.688 (0.64), 1.705 (1.27), 1.714 (0.89), 1.716 (0.82), 1.723 (1.46), 1.730 (1.41), 1.732 (1.64), 1.741 (1.01), 1.744 (0.91), 1.748 (1.65), 1.753 (0.70), 1.757 (0.76), 1.768 (0.95), 1.792 (0.47), 1.796 (0.41), 1.819 (0.67), 1.831 (0.60), 1.837 (0.56), 1.844 (0.62), 1.851 (0.54), 1.870 (0.49), 1.876 (0.93), 1.883 (1.19), 1.891 (1.16), 1.900 (1.21), 1.902 (1.34), 1.907 (1.37), 1.909 (1.30), 1.917 (1.07), 1.927 (1.04), 1.931 (0.52), 1.934 (0.66), 2.370 (0.73), 2.376 (0.64), 2.394 (0.63), 2.401 (0.70), 2.518 (0.48), 2.527 (1.78), 2.534 (1.49), 2.552 (1.58), 2.558 (1.70), 2.582 (4.03), 2.856 (12.03), 3.001 (16.00), 3.334 (10.32), 4.884 (2.27), 10.439 (1.29).

Intermediate 145

8-hydroxy-5-methyl-6-oxo-N-phenyl-5-azaspiro[3.5]non-7-ene-7-carbothioamide

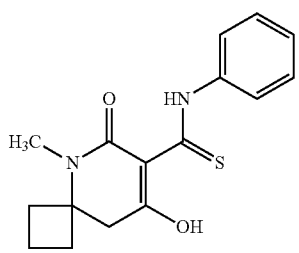 [SMILES: CN1C(=O)C(C(=S)Nc2ccccc2)=C(O)CC12CCC2]

5-Methyl-5-azaspiro[3.5]nonane-6,8-dione (see Intermediate 144, 675 mg) was suspended in 5.4 mL acetonitrile and treated with isothiocyanatobenzene (480 μL, 4.0 mmol). The mixture was cooled down to 0° C. and treated slowly DBU (960 μL, 6.5 mmol). It was stirred ar rt over night. The reaction mixture was poured into a mixture of ice and hydrochloric acid (4 M). The precipitate was filtered off, washed with water and dried at 50° C. under vacuo to provide the analytically pure target compound: 1.1 g.

LC-MS (Method 2): $R_t$=0.66 min; MS (ESIpos): m/z=303 [M+H]$^+$ $^1$H-NMR (400 MHz, DMSO-d6) δ [ppm]=1.64-1.88 (m, 2H), 1.94 (dtd, 2H), 2.51-2.57 (m, 2H), 3.06 (s, 5H), 7.23-7.36 (m, 1H), 7.38-7.54 (m, 4H), 14.48 (s, 1H), 16.55 (s, 1H).

Intermediate 146

8-{[(2-aminopyridin-4-yl)methyl]amino}-5-methyl-6-oxo-N-phenyl-5-azaspiro[3.5]non-7-ene-7-carbothioamide

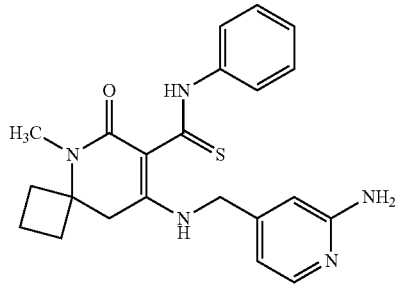 [SMILES: CN1C(=O)C(C(=S)Nc2ccccc2)=C(NCc2ccnc(N)c2)CC12CCC2]

8-Hydroxy-5-methyl-6-oxo-N-phenyl-5-azaspiro[3.5]non-7-ene-7-carbothioamide (see Intermediate 145, 1.01 g) and 4-(aminomethyl)pyridin-2-amine (615 mg, 4.99 mmol) were suspended in 5.2 mL dry DME. At 0° C. N,O-bis(trimethylsilyl)acetamide (1.7 mL, 6.7 mmol) was added dropwise. The reaction mixture was stirred at 80° C. in a sealed vessel under nitrogen atmosphere over night. The reaction mixture was diluted with ethyl acetate and stirred for 20 minutes. The undissolved precipitate was filtered off, washed with ethyl acetate and dried at 50° C. under vacuo to provide the target compound in 98% purity: 698 mg.

LC-MS (Method 2): $R_t$=1.18 min; MS (ESIpos): m/z=408 [M+H]$^+$ $^1$H-NMR (400 MHz, DMSO-d6) δ [ppm]=1.38-1.54 (m, 1H), 1.57-1.69 (m, 1H), 1.75-1.87 (m, 2H), 2.34-2.46 (m, 2H), 2.93 (s, 2H), 3.00 (s, 3H), 4.64 (d, 2H), 6.02 (s, 2H), 6.40 (s, 1H), 6.47 (dd, 1H), 7.12-7.24 (m, 1H), 7.31-7.40 (m, 2H), 7.41-7.51 (m, 2H), 7.88 (d, 1H), 13.65-13.92 (m, 1H), 14.68 (s, 1H).

Intermediate 147

2'-(2-aminopyridin-4-yl)-3'-anilino-5'-methyl-1',7'-dihydrospiro[cyclobutane-1,6'-pyrrolo[3,2-c]pyridin]-4'(5'H)-one

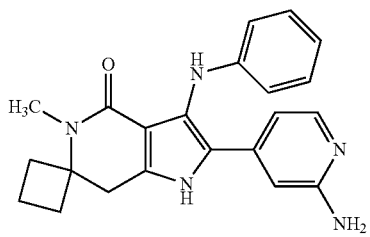 [SMILES: CN1C(=O)c2c([nH]c(-c3ccnc(N)c3)c2Nc2ccccc2)CC12CCC2]

The reaction was performed in 2 portions. 8-{[(2-Aminopyridin-4-yl)methyl]amino}-5-methyl-6-oxo-N-phenyl-5-azaspiro[3.5]non-7-ene-7-carbothioamide (see Intermediate 146, 2.35 g) was suspended in 28 mL methanol and treated with hydrogenperoxide (1.2 mL, 30% purity, 12 mmol). The reaction mixture was stirred at 90° C. for 2 hours in the microwave reactor under nitrogen atmosphere. The reaction mixture was combined with another batch starting from 8-{[(2-aminopyridin-4-yl)methyl]amino}-5-methyl-6-oxo-N-phenyl-5-azaspiro[3.5]non-7-ene-7-carbothioamide (see Intermediate 146, 689 mg). To the reaction mixture aqueous saturated sodium thiosulfate, aqueous half concentrated potassium carbonate and dichloromethane were added. The layers were separated and the aqueous layer was extracted with dichloromethane three times. The combined organic layers were washed with water and brine, filtered through a silicone coated filter and concentrated under reduced pressure. The crude product was purified by flash chromatography (28 g column, aminophase; dichloromethane/ethanol 0%-20%) to provide the target compound in 81% purity: 562 mg.

LC-MS (Method 2): $R_t$=0.99 min; MS (ESIpos): m/z=375 [M+H]$^+$ $^1$H-NMR (400 MHz, DMSO-d6) δ [ppm]=1.72-1.85 (m, 2H), 1.92 (br dd, 2H), 2.37-2.48 (m, 2H), 2.95 (s, 3H), 3.10 (s, 2H), 5.67 (s, 2H), 6.47-6.57 (m, 3H), 6.61 (t, 1H), 6.68 (dd, 1H), 7.02 (dd, 2H), 7.23 (s, 1H), 7.73 (d, 1H), 11.57 (s, 1H).—contains ethanol.

Intermediate 148

Ethyl 3-{[1-(2-ethoxy-2-oxoethyl)cyclopropyl](methyl)amino}-3-oxopropanoate

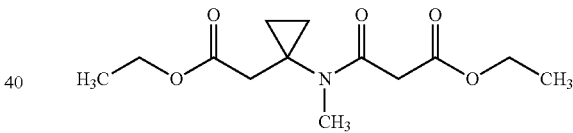

ethyl [1-(methylamino)cyclopropyl]acetate (5.00 g, 31.8 mmol) was dissolved in 32 mL dichloromethane and cooled down to 0° C. Then the N,N-diisopropylethylamine (6.1 ml, 35 mmol) and DMAP (389 mg, 3.18 mmol) were added. Subsequently ethyl 3-chloro-3-oxopropanoate (4.4 mL, 35 mmol) was added. The reaction mixture was stirred at 0° C. for 1.5 hours and at rt over night under nitrogen atmosphere. To the reaction mixture half concentrated aqueous ammoniumchloride solution and dichloromethane was added. The aqueous layer was extracted with dichloromethane three times. The combined organic layers were filtered through a silicone coated filter and concentrated under reduced pressure. The crude product was purified by flash chromatography (50 g column, silica ULTRA; hexane/ethyl acetate 12%-100%) to provide the target compound in 45% purity, which was used without further purification: 2.7 g.

LC-MS (Method 1): $R_t$=0.87 min; MS (ESIpos): m/z=272 [M+H]$^+$ $^1$H-NMR (400 MHz, DMSO-d6) δ [ppm]: 0.782 (1.12), 0.788 (1.22), 0.808 (1.03), 0.812 (1.25), 0.818 (1.20), 0.855 (0.43), 0.868 (0.52), 0.987 (0.45), 1.113 (0.95), 1.133 (1.13), 1.156 (3.18), 1.166 (6.99), 1.169 (6.26), 1.174 (5.91), 1.183 (14.29), 1.187 (12.08), 1.192 (3.19), 1.201 (6.98), 1.205 (5.81), 1.988 (1.92), 2.412 (0.58), 2.450 (0.92), 2.518 (0.63), 2.523 (0.44), 2.705 (0.80), 2.743 (0.53), 2.795 (16.00), 2.900 (8.53), 3.398 (5.04), 3.521 (0.40), 3.559 (1.32), 3.636 (1.30), 4.003 (0.77), 4.018 (0.64), 4.021 (2.30), 4.036 (0.73), 4.040 (2.47), 4.044 (1.94), 4.052 (1.93), 4.057 (1.32), 4.062 (5.37), 4.070 (5.31), 4.079 (5.23), 4.088 (5.14), 4.097 (1.71), 4.105 (1.59).

Intermediate 149

Ethyl 4-methyl-5,7-dioxo-4-azaspiro[2.5]octane-6-carboxylate (Racemate)

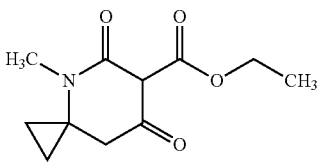 [SMILES: CCOC(=O)C1C(=O)CC2(CC2)N(C)C1=O]

Sodium ethoxide solution (2.6 mL, 21% purity in ethanol, 11 mmol) was cooled down with an ice bath and treated drop wise with ethyl 3-{[1-(2-ethoxy-2-oxoethyl)cyclopropyl](methyl)amino}-3-oxopropanoate (see Intermediate 148, 2.70 g), dissolved in 14 mL ethanol. It was stirred at this temperature for 30 minutes and at rt over night under nitrogen atmosphere. The reaction mixture was diluted with dichloromethane and the pH was adjusted to 1 by addition of hydrochloric acid (4 M). The reaction mixture was stirred for a few minutes, filtered through a silicone coated filter and concentrated under reduced pressure to provide the target compound in 94% purity: 2.2 g.

LC-MS (Method 1): $R_t$=0.83 min; MS (ESIpos): m/z=226 [M+H]$^+$ $^1$H-NMR (400 MHz, DMSO-d6) δ [ppm]: 0.658 (1.76), 0.672 (5.52), 0.674 (5.48), 0.689 (2.15), 0.781 (1.12), 0.787 (1.49), 0.801 (1.45), 0.805 (1.62), 0.807 (1.55), 0.818 (1.71), 0.838 (0.47), 0.855 (0.47), 0.867 (0.53), 0.967 (0.54), 1.018 (3.40), 1.035 (1.97), 1.052 (2.46), 1.070 (1.24), 1.082 (0.54), 1.095 (1.06), 1.099 (1.14), 1.113 (1.02), 1.133 (0.91), 1.156 (2.19), 1.165 (5.39), 1.168 (4.95), 1.174 (4.79), 1.183 (10.62), 1.186 (9.21), 1.192 (3.91), 1.201 (5.58), 1.204 (4.91), 1.211 (8.24), 1.229 (16.00), 1.247 (7.56), 2.044 (0.73), 2.412 (0.41), 2.430 (0.43), 2.450 (0.59), 2.470 (2.76), 2.518 (1.61), 2.522 (1.35), 2.544 (2.43), 2.560 (1.58), 2.662 (4.71), 2.703 (0.83), 2.720 (0.48), 2.744 (1.41), 2.751 (4.66), 2.770 (2.57), 2.795 (9.66), 2.798 (5.11), 2.822 (0.63), 2.836 (0.50), 2.864 (0.53), 2.900 (5.03), 2.908 (1.97), 3.300 (1.17), 3.397 (2.91), 3.426 (0.43), 3.461 (2.47), 3.559 (0.78), 3.635 (0.75), 4.003 (0.54), 4.021 (1.62), 4.031 (0.44), 4.039 (1.99), 4.043 (1.33), 4.048 (0.77), 4.052 (1.27), 4.057 (1.85), 4.061 (3.35), 4.069 (3.20), 4.074 (1.52), 4.079 (3.33), 4.087 (3.06), 4.091 (0.78), 4.097 (1.37), 4.105 (1.03), 4.115 (0.44), 4.137 (0.70), 4.155 (0.73), 4.168 (2.15), 4.186 (6.14), 4.204 (6.04), 4.221 (1.93), 4.732 (0.77).

Intermediate 150

4-methyl-4-azaspiro[2.5]octane-5,7-dione

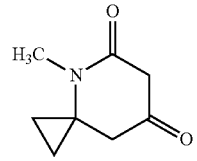

Ethyl 4-methyl-5,7-dioxo-4-azaspiro[2.5]octane-6-carboxylate (Racemate) (see Intermediate 149, 7.70 g) was dissolved in 66 mL dichloromethane and treated with aqueous hydrochloric acid (64 mL, 2.0 M, 130 mmol). The reaction mixture was stirred for 20 minutes at rt under nitrogen atmosphere. The reaction mixture was filtered through a water resistant filter and concentrated under reduced pressure. The residue was dissolved in 90 mL acetonitrile and treated with 9.2 mL water. The reaction mixture was stirred under reflux for 1 hour at 100° C. under nitrogen atmosphere. The crude product was concentrated under vacuo. The crude product was purified by flash chromatography (50 g column, silica gel ULTRA; ethyl acetate/ethanol 0%-20%) to provide the target compound in 88% purity: 2.4 g.

LC-MS (Method 1): $R_t$=0.50 min; MS (ESIpos): m/z=154 [M+H]$^+$ $^1$H-NMR (400 MHz, DMSO-d6) δ [ppm]=0.77-0.85 (m, 2H), 1.06-1.13 (m, 2H), 2.47 (s, 2H), 2.75 (s, 3H), 3.46 (s, 2H).

Intermediate 151

7-hydroxy-4-methyl-5-oxo-N-phenyl-4-azaspiro[2.5]oct-6-ene-6-carbothioamide

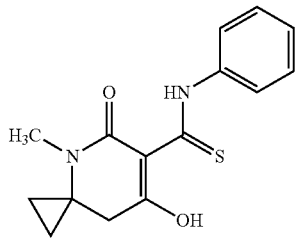 [SMILES: CN1C(=O)C(C(=S)Nc2ccccc2)=C(O)CC12CC2]

4-Methyl-4-azaspiro[2.5]octane-5,7-dione (see Intermediate 150, 500 mg) was suspended in 5.3 mL acetonitrile and treated with isothiocyanatobenzene (390 μL, 3.3 mmol). The mixture was cooled down to 0° C. and treated slowly with DBU (780 μL, 5.2 mmol). It was stirred at rt over night. The reaction mixture was poured into a mixture of ice and hydrochlorid acid and diluted with ethyl acetate, stirred and extracted with ethyl acetate two times. The combined organic layers were dried using a silicon coated filter und concentrated under reduced pressure to provide the target compound in 81% purity, which was used without further purification: 1.08 g.

LC-MS (Method 2): $R_t$=0.55 min; MS (ESIpos): m/z=289 [M+H]$^+$

¹H-NMR (400 MHz, DMSO-d6) δ [ppm]=0.72-0.83 (m, 2H), 1.10-1.15 (m, 2H), 2.79 (s, 4H), 7.24-7.37 (m, 1H), 7.38-7.55 (m, 5H), 14.39 (s, 1H), 16.54 (s, 1H).

Intermediate 152

7-{[(2-aminopyridin-4-yl)methyl]amino}-4-methyl-5-oxo-N-phenyl-4-azaspiro[2.5]oct-6-ene-6-carbothioamide

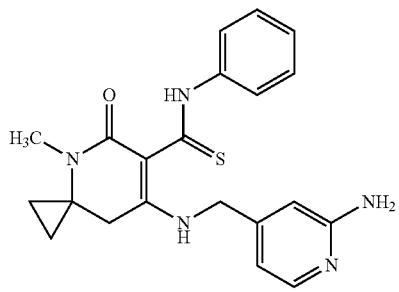 [SMILES: CN1C(=O)C(C(=S)Nc2ccccc2)=C(NCc2ccnc(N)c2)CC12CC2]

7-Hydroxy-4-methyl-5-oxo-N-phenyl-4-azaspiro[2.5]oct-6-ene-6-carbothioamide (see Intermediate 151, 1.08 g) and 4-(aminomethyl)pyridin-2-amine (692 mg, 5.62 mmol) were suspended in 5.8 mL dry DME in a sealed vessel. At 0° C. N,O-Bis-(trimethylsiliyl)-acetamide (1.9 ml, 7.5 mmol) was added drop wise. It was stirred at 80° C. in a sealed vessel under nitrogen atmosphere. The reaction mixture was diluted with ethyl acetate and stirred for 20 minutes. The undissolved precipitate was filtered off, washed with ethyl acetate and dried at 50° C. under vacuo to provide batch 1 of the target compound in 99% purity: 620 mg.

LC-MS (Method 2): $R_t$=1.13 min; MS (ESIpos): m/z=394 [M+H]$^+$

¹H-NMR (400 MHz, DMSO-d6) δ [ppm]=0.59-0.68 (m, 2H), 0.98-1.08 (m, 2H), 2.69 (s, 2H), 2.76 (s, 3H), 4.52 (d, 2H), 6.01 (s, 2H), 6.32 (s, 1H), 6.39 (dd, 1H), 7.16-7.24 (m, 1H), 7.33-7.41 (m, 2H), 7.42-7.49 (m, 2H), 7.86 (d, 1H), 13.64 (br s, 1H), 14.54 (s, 1H).

Intermediate 153

2'-(2-aminopyridin-4-yl)-3'-anilino-5'-methyl-1',7'-dihydrospiro[cyclopropane-1,6'-pyrrolo[3,2-c]pyridin]-4'(5'H)-one

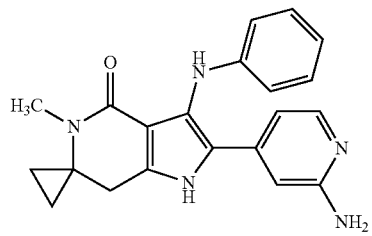 [SMILES: CN1C(=O)c2c([nH]c(-c3ccnc(N)c3)c2Nc2ccccc2)CC12CC2]

7-{[(2-Aminopyridin-4-yl)methyl]amino}-4-methyl-5-oxo-N-phenyl-4-azaspiro[2.5]oct-6-ene-6-carbothioamide (see Intermediate 152, 545 mg) was suspended in 6.6 mL methanol and treated with aqueous hydrogenperoxide solution (280 μL, 30% purity, 2.8 mmol). The reaction mixture was stirred at 90° C. for 2 hours in the microwave reactor under nitrogen atmosphere. To the reaction mixture aqueous saturated sodium thiosulfate, aqueous half concentrated potassium carbonate solution and dichloromethane were added. The layers were separated and the aqueous layer was extracted dichloromethane three times. The combined organic layers were washed with water and brine, filtered through a silicone coated filter and concentrated under reduced pressure. The crude product was purified by HPLC to provide the target compound in 78% purity: 139 mg.

LC-MS (Method 2): $R_t$=0.94 min; MS (ESIpos): m/z=361 [M+H]$^+$

¹H-NMR (400 MHz, DMSO-d6): δ [ppm]=0.67-0.80 (m, 2H), 1.01-1.09 (m, 2H), 2.67 (s, 3H), 2.80 (s, 2H), 5.68 (s, 2H), 6.51-6.65 (m, 4H), 6.69 (dd, 1H), 7.03 (dd, 2H), 7.26 (s, 1H), 7.73 (d, 1H), 11.54 (s, 1H).

Experimental Section—Examples

Example 1

N-[4-(3-anilino-5-methyl-4-oxo-4,5,6,7-tetrahydro-1H-pyrrolo[3,2-c]pyridin-2-yl)pyridin-2-yl]-2-(4-fluorophenyl)acetamide

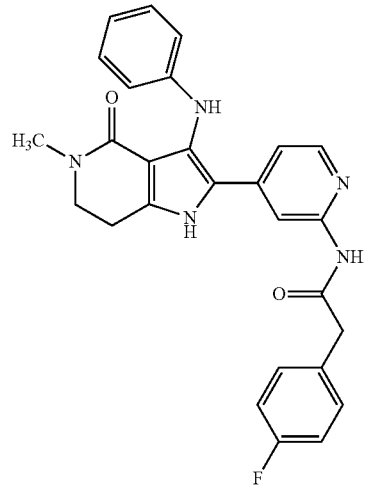 [SMILES: CN1CCc2[nH]c(-c3ccnc(NC(=O)Cc4ccc(F)cc4)c3)c(Nc3ccccc3)c2C1=O]

To a stirred solution of 2-(2-aminopyridin-4-yl)-3-anilino-5-methyl-1,5,6,7-tetrahydro-4H-pyrrolo[3,2-c]pyridin-4-one (Intermediate 3) (100 mg, 300 μmol) in DMF (2.0 mL) was added N,N-diisopropylethylamine (310 μL, 1.8 mmol), (4-fluorophenyl)acetic acid (69.4 mg, 450 μmol) and HATU (228 mg, 600 μmol). The mixture was stirred at 60° C. for 4 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography followed by amino-phase-silicagel chromatography gave 30.0 mg (21% yield) of the title compound.

LC-MS (Method 1): $R_t$=1.03 min; MS (ESIpos): m/z=470 [M+H]$^+$

¹H-NMR (400 MHz, DMSO-d6) δ [ppm]: 2.331 (0.42), 2.518 (2.32), 2.523 (1.57), 2.673 (0.46), 2.820 (0.40), 2.856 (16.00), 2.888 (1.60), 2.905 (3.38), 2.922 (1.71), 2.998 (0.45), 3.509 (1.88), 3.526 (3.83), 3.544 (1.71), 3.687 (6.65), 5.759 (0.75), 6.539 (3.19), 6.558 (3.36), 6.560 (2.76), 6.597 (0.98), 6.616 (2.05), 6.634 (1.11), 6.991 (2.55), 7.009 (3.22), 7.011 (3.12), 7.030 (1.98), 7.117 (2.11), 7.122 (2.16), 7.129 (3.10), 7.135 (2.72), 7.145 (1.12), 7.151 (4.71), 7.157 (1.11), 7.168 (0.90), 7.174 (2.87), 7.336 (2.48), 7.342 (1.25), 7.353 (5.47), 7.367 (0.99), 7.372 (1.97), 8.037 (2.67), 8.051 (2.55), 8.184 (2.38), 10.561 (2.94), 11.731 (1.90).

Example 2

N-[4-(3-anilino-5-methyl-4-oxo-4,5,6,7-tetrahydro-1H-pyrrolo[3,2-c]pyridin-2-yl)pyridin-2-yl]-2-phenylacetamide

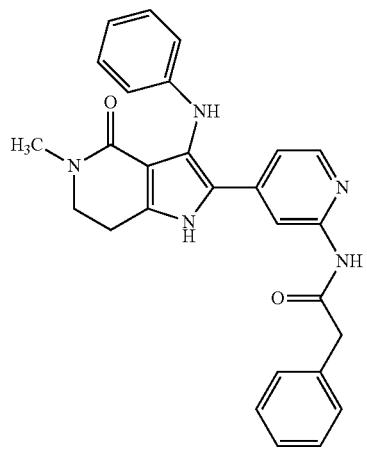

To a stirred solution of 2-(2-aminopyridin-4-yl)-3-anilino-5-methyl-1,5,6,7-tetrahydro-4H-pyrrolo[3,2-c]pyridin-4-one (Intermediate 3) (78.0 mg, 234 µmol) in DMF (1.6 mL) was added N,N-diisopropylethylamine (240 µL, 1.4 mmol), phenylacetic acid (79.6 mg, 585 µmol) and HATU (267 mg, 702 µmol). The mixture was stirred at 60° C. for 16 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave a solid that was triturated with a mixture of dichloromethane and hexane to give 31.0 mg (26% yield) of the title compound.

LC-MS (Method 1): $R_t$=1.00 min; MS (ESIneg): m/z=450 [M−H]⁻

¹H-NMR (400 MHz, DMSO-d6) δ [ppm]: 2.518 (3.13), 2.522 (1.92), 2.855 (16.00), 2.886 (1.63), 2.903 (3.45), 2.921 (1.76), 3.378 (0.72), 3.507 (1.91), 3.525 (3.92), 3.542 (1.76), 3.692 (8.49), 3.712 (0.52), 6.540 (3.25), 6.559 (3.51), 6.597 (1.00), 6.616 (2.06), 6.634 (1.11), 6.991 (2.56), 7.010 (3.36), 7.012 (3.30), 7.031 (2.09), 7.114 (2.00), 7.118 (1.99), 7.127 (1.97), 7.132 (1.94), 7.230 (0.60), 7.236 (0.74), 7.243 (1.33), 7.249 (0.95), 7.252 (0.99), 7.257 (1.06), 7.264 (0.95), 7.298 (0.75), 7.301 (0.68), 7.305 (0.64), 7.320 (6.43), 7.324 (6.55), 7.332 (11.85), 7.341 (1.47), 7.351 (4.24), 8.035 (2.78), 8.049 (2.65), 8.190 (2.53), 10.554 (3.10), 11.729 (2.12).

Example 3

N-[4-(3-anilino-5-methyl-4-oxo-4,5,6,7-tetrahydro-1H-pyrrolo[3,2-c]pyridin-2-yl)pyridin-2-yl]-2-(4-fluoro-3-methylphenyl)acetamide

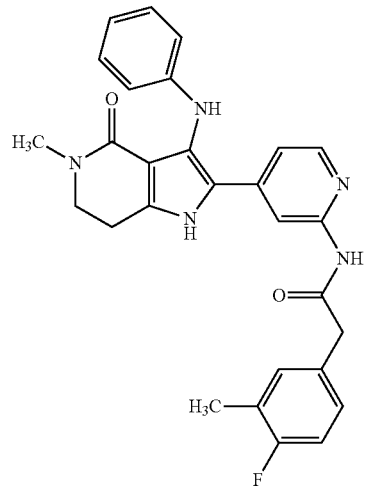 [SMILES: Cc1cc(CC(=O)Nc2cc(-c3[nH]c4c(c3Nc3ccccc3)C(=O)N(C)CC4)ccn2)ccc1F]

To a stirred solution of 2-(2-aminopyridin-4-yl)-3-anilino-5-methyl-1,5,6,7-tetrahydro-4H-pyrrolo[3,2-c]pyridin-4-one (Intermediate 3) (78.0 mg, 234 µmol) in DMF (1.6 mL) was added N,N-diisopropylethylamine (240 µL, 1.4 mmol), (4-fluoro-3-methylphenyl)acetic acid (98.4 mg, 585 µmol) and HATU (267 mg, 702 µmol). The mixture was stirred at 60° C. for 16 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography followed by preparative reverse phase HPLC (gradient of water and acetonitrile containing aqueous ammonia as additive) gave 39.0 mg (90% purity, 34% yield) of the title compound after lyophilisation.

LC-MS (Method 1): $R_t$=1.08 min; MS (ESIneg): m/z=482.4 [M−H]⁻

¹H-NMR (400 MHz, DMSO-d6) δ [ppm]: 2.217 (7.53), 2.221 (7.46), 2.518 (1.88), 2.523 (1.41), 2.857 (16.00), 2.889 (1.50), 2.907 (3.28), 2.924 (1.64), 3.509 (1.82), 3.527 (3.69), 3.544 (1.63), 3.641 (6.36), 5.759 (0.65), 6.537 (2.58), 6.540 (3.13), 6.559 (3.32), 6.561 (2.71), 6.593 (0.62), 6.596 (0.98), 6.614 (2.04), 6.630 (0.74), 6.632 (1.10), 6.990 (2.55), 7.008 (3.15), 7.011 (3.06), 7.029 (2.00), 7.052 (1.11), 7.073 (1.87), 7.076 (1.28), 7.098 (1.72), 7.116 (1.97), 7.119 (1.92), 7.129 (1.93), 7.133 (1.92), 7.142 (0.70), 7.147 (0.79), 7.154 (0.77), 7.161 (1.01), 7.167 (0.57), 7.175 (0.44), 7.181 (0.49), 7.214 (1.10), 7.219 (0.98), 7.233 (1.11), 7.238 (0.96), 7.351 (3.93), 8.034 (2.51), 8.048 (2.41), 8.189 (2.27), 10.535 (2.83), 11.730 (1.83).

Example 4

N-[4-(3-anilino-5-methyl-4-oxo-4,5,6,7-tetrahydro-1H-pyrrolo[3,2-c]pyridin-2-yl)pyridin-2-yl]-2-(4-fluorophenyl)propanamide

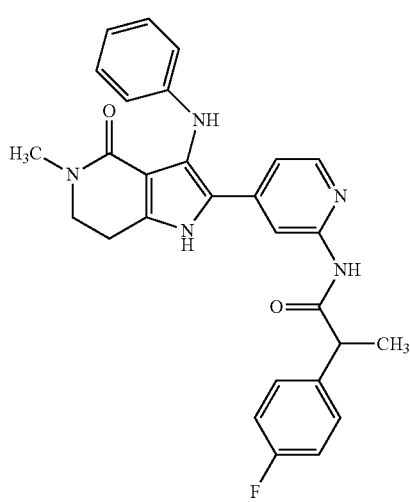

To a stirred solution of 2-(2-aminopyridin-4-yl)-3-anilino-5-methyl-1,5,6,7-tetrahydro-4H-pyrrolo[3,2-c]pyridin-4-one (Intermediate 3) (10.0 g, 30.0 mmol) in DMA (200 mL) was added N,N-diisopropylethylamine (31 mL, 180 mmol), racemic 2-(4-fluorophenyl)propanoic acid (10.1 g, 60.0 mmol) and PyBOP (46.8 g, 90.0 mmol). The mixture was stirred at r.t. for 24 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave a solid that was triturated with a dichloromethane and then with ethanol to give 11.9 g (82% yield) of the title compound.

LC-MS (Method 1): $R_t$=1.04 min; MS (ESIneg): m/z=482.5 [M−H]$^-$ $^1$H-NMR (400 MHz, DMSO-d6) δ [ppm] 1.39 (d, 3H), 2.86 (s, 3H), 2.92 (t, 2H), 3.54 (t, 2H), 4.01 (q, 1H), 6.52-6.58 (m, 2H), 6.61 (t, 1H), 7.01 (dd, 2H), 7.06-7.24 (m, 3H), 7.31-7.50 (m, 3H), 8.02 (d, 1H), 8.20 (d, 1H), 10.50 (s, 1H), 11.74 (s, 1H).

Example 5

(2S)—N-[4-(3-anilino-5-methyl-4-oxo-4,5,6,7-tetrahydro-1H-pyrrolo[3,2-c]pyridin-2-yl)pyridin-2-yl]-2-(4-fluorophenyl)propanamide (Stereoisomer 1)

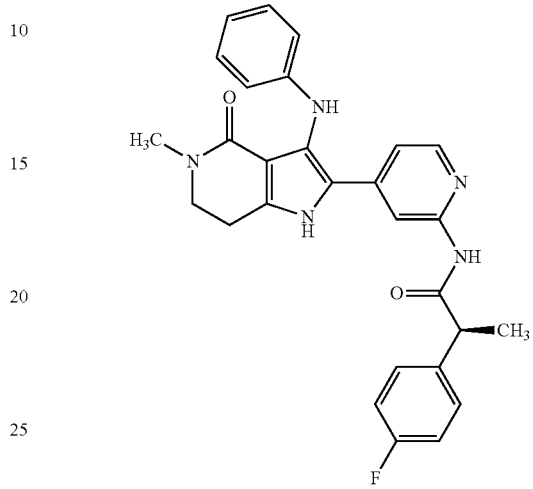

Racemic N-[4-(3-anilino-5-methyl-4-oxo-4,5,6,7-tetrahydro-1H-pyrrolo[3,2-c]pyridin-2-yl)pyridin-2-yl]-2-(4-fluorophenyl)propanamide (2.22 g, 4.58 mmol) was separated into the single stereoisomers (Example 5 and Example 6) via preparative, chiral HPLC.

Instrument: Labomatic HD5000, Labocord-5000; Gilson GX-241, Labcol Vario 4000, Column: Chiralpak IA 5μ 250×30 mm;

Eluent: Methanol+0.1 Vol-% diethylamine (99%)/Ethanol 50:50%;

Flow: 40.0 mL/min;

Detection: UV: 254 nm

Injected solution: 2210 mg racemic N-[4-(3-anilino-5-methyl-4-oxo-4,5,6,7-tetrahydro-1H-pyrrolo[3,2-c]pyridin-2-yl)pyridin-2-yl]-2-(4-fluorophenyl)propanamide dissolved in 22 mL DMSO Injected volume: 22×1 mL.

Analytical Chiral HPLC Method 1:

Instrument: Agilent 1260 HPLC; Column: Chiralpak IA 3μ 100×4.6; Eluent A: Methanol+0.1% diethylamin; Eluent B: Ethanol; isokratic: 50% A+50% B; Flow: 1.4 mL/min; Temperature: 25° C.;

UV: 254 nm;

| | Retention time in min | e.e. [%] | yield | Optical rotation [α]$_D$ |
|---|---|---|---|---|
| Example 5 Stereoisomer 1 Peak 1; (2S)-Enantiomer | 5.6-7.7 | >99.8% | 1.07 g | +165.8° (from solution in DMSO, c = 2.2 mg/mL) |
| Example 6 Stereoisomer 2 Peak 2; (2R)-Enantiomer | 9.0-14.3 | 98.8% | 996 mg | −178.4° (from solution in DMSO, c = 13.2 mg/mL) |

Isolated Stereoisomer 1: 1.07 g

Analytical Chiral HPLC (Method 1): $R_t$=2.20 min (e.e.: >99.8%)

$[a]_D$=+165.8° (from solution in DMSO, c=2.2 mg/mL)

LC-MS (Method 1): $R_t$=1.07 min; MS (ESIneg): m/z=482.5 [M−H]⁻

¹H-NMR (400 MHz, DMSO-d6) δ [ppm]: 1.376 (6.33), 1.394 (6.55), 2.518 (1.71), 2.523 (1.11), 2.863 (16.00), 2.903 (1.59), 2.920 (3.45), 2.938 (1.75), 3.385 (0.46), 3.518 (1.95), 3.535 (3.99), 3.553 (1.72), 3.998 (1.36), 4.015 (1.33), 5.758 (14.38), 6.538 (3.29), 6.558 (3.46), 6.560 (2.90), 6.594 (1.01), 6.613 (2.12), 6.631 (1.14), 6.988 (2.61), 7.007 (3.30), 7.009 (3.27), 7.027 (2.05), 7.103 (2.07), 7.108 (2.00), 7.117 (1.96), 7.121 (2.10), 7.133 (2.41), 7.138 (0.85), 7.149 (0.97), 7.155 (5.04), 7.161 (1.08), 7.172 (0.85), 7.177 (2.73), 7.369 (4.17), 7.390 (2.44), 7.395 (1.05), 7.404 (2.70), 7.412 (2.39), 7.421 (0.95), 7.426 (2.10), 8.009 (2.77), 8.024 (2.63), 8.201 (2.63), 10.498 (3.03), 11.740 (1.69).

Example 6

(2R)—N-[4-(3-anilino-5-methyl-4-oxo-4,5,6,7-tetrahydro-1H-pyrrolo[3,2-c]pyridin-2-yl)pyridin-2-yl]-2-(4-fluorophenyl)propanamide (Stereoisomer 2)

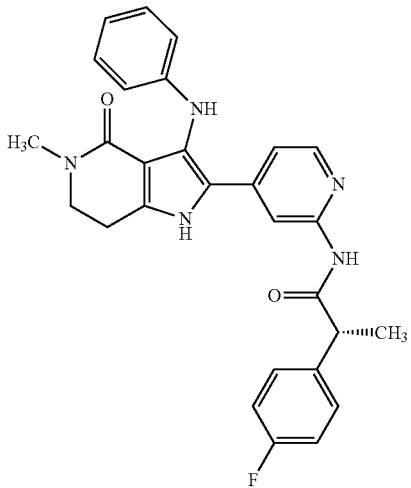 [SMILES: C[C@@H](C(=O)Nc1cc(-c2[nH]c3c(c2Nc2ccccc2)C(=O)N(C)CC3)ccn1)c1ccc(F)cc1]

Obtained Stereoisomer 2: 996 mg

Analytical Chiral HPLC (Method 1): $R_t$=4.16 min (e.e.: 98.8%)

$[a]_D$=−178.4° (from solution in DMSO, c=2.1 mg/mL)

LC-MS (Method 1): $R_t$=1.04 min; MS (ESIneg): m/z=482.4 [M−H]⁻

¹H-NMR (400 MHz, DMSO-d6) δ [ppm]: 1.036 (0.61), 1.054 (1.28), 1.071 (0.59), 1.378 (6.48), 1.395 (6.62), 2.518 (0.61), 2.539 (1.18), 2.863 (16.00), 2.903 (1.69), 2.921 (3.61), 2.938 (1.86), 3.518 (2.02), 3.535 (4.13), 3.552 (1.81), 3.983 (0.42), 4.000 (1.43), 4.017 (1.41), 4.034 (0.40), 5.758 (4.10), 6.541 (3.48), 6.560 (3.64), 6.595 (1.04), 6.613 (2.16), 6.632 (1.17), 6.989 (2.54), 7.008 (3.44), 7.010 (3.47), 7.029 (2.11), 7.106 (1.98), 7.110 (1.99), 7.120 (1.97), 7.124 (2.18), 7.133 (2.33), 7.138 (0.88), 7.150 (1.07), 7.155 (4.90), 7.161 (1.10), 7.173 (0.89), 7.178 (2.76), 7.372 (4.38), 7.384 (0.43), 7.392 (2.49), 7.397 (1.15), 7.405 (2.76), 7.414 (2.52), 7.423 (0.98), 7.428 (2.17), 8.012 (2.93), 8.025 (2.78), 8.204 (2.86), 10.500 (3.25), 11.742 (1.78).

Example 7

N-[4-(3-anilino-5-cyclopropyl-4-oxo-4,5,6,7-tetrahydro-1H-pyrrolo[3,2-c]pyridin-2-yl)pyridin-2-yl]-2-(4-fluorophenyl)acetamide

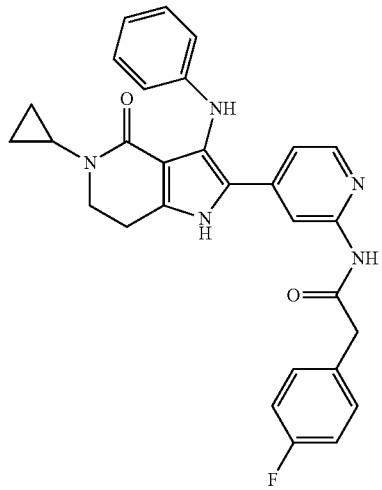 [SMILES: O=C(Cc1ccc(F)cc1)Nc1cc(-c2[nH]c3c(c2Nc2ccccc2)C(=O)N(C2CC2)CC3)ccn1]

To a stirred solution of 2-(2-aminopyridin-4-yl)-3-anilino-5-cyclopropyl-1,5,6,7-tetrahydro-4H-pyrrolo[3,2-c]pyridin-4-one (see Intermediate 3) (70.0 mg, 195 μmol) in DMF (1.3 mL) was added N,N-diisopropylethylamine (200 μL, 1.2 mmol), (4-fluorophenyl)acetic acid (75.0 mg, 487 μmol) and HATU (222 mg, 584 μmol). The mixture was stirred at 60° C. for 2 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave a solid that was triturated with dichloromethane to give 30.0 mg (31% yield) of the title compound.

LC-MS (Method 1): $R_t$=1.08 min; MS (ESIpos): m/z=496.8 [M+H]⁺

¹H-NMR (400 MHz, DMSO-d6) δ [ppm]: 0.535 (1.33), 0.547 (4.35), 0.553 (4.82), 0.556 (5.12), 0.563 (5.63), 0.573 (1.88), 0.669 (1.71), 0.681 (4.41), 0.686 (5.20), 0.699 (5.27), 0.717 (1.24), 2.518 (5.14), 2.522 (4.95), 2.530 (2.33), 2.540 (3.43), 2.550 (2.01), 2.557 (1.67), 2.567 (0.73), 2.673 (0.92), 2.825 (3.30), 2.842 (7.00), 2.858 (3.64), 3.487 (3.90), 3.504 (7.73), 3.521 (3.58), 3.686 (16.00), 3.708 (0.54), 6.545 (7.63), 6.564 (8.05), 6.566 (6.75), 6.604 (2.31), 6.622 (4.90), 6.641 (2.68), 6.996 (6.08), 7.015 (7.67), 7.017 (7.65), 7.036 (4.80), 7.101 (4.73), 7.105 (4.76), 7.114 (4.67), 7.119 (4.99), 7.128 (5.68), 7.133 (2.08), 7.144 (2.46), 7.150 (11.80), 7.155 (2.68), 7.167 (2.08), 7.172 (6.92), 7.180 (0.86), 7.327 (0.71), 7.334 (5.55), 7.340 (2.46), 7.348 (6.30), 7.356 (5.53), 7.365 (2.18), 7.370 (4.93), 7.388 (9.64), 8.033 (6.40), 8.047 (6.19), 8.176 (5.76), 10.559 (7.15), 11.721 (4.48).

Example 8

N-[4-(3-anilino-5-cyclopropyl-4-oxo-4,5,6,7-tetra-hydro-1H-pyrrolo[3,2-c]pyridin-2-yl)pyridin-2-yl]-2-(4-fluorophenyl)propanamide

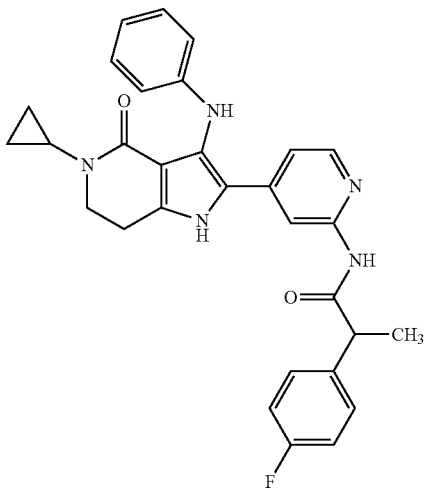 [SMILES: CC(C(=O)Nc1cc(-c2[nH]c3c(c2Nc2ccccc2)C(=O)N(C2CC2)CC3)ccn1)c1ccc(F)cc1]

To a stirred solution of 2-(2-aminopyridin-4-yl)-3-anilino-5-cyclopropyl-1,5,6,7-tetrahydro-4H-pyrrolo[3,2-c]pyridin-4-one (see Intermediate 3) (80.0 mg, 223 µmol) in DMF (1.8 mL) was added N,N-diisopropylethylamine (230 µL, 1.3 mmol), racemic 2-(4-fluorophenyl)propanoic acid (93.6 mg, 556 µmol) and HATU (254 mg, 668 µmol). The mixture was stirred at 60° C. for 16 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Aminophase-silicagel chromatography gave a solid that was triturated with dichloromethane to give 15.0 mg (13% yield) of the title compound.

LC-MS (Method 1): $R_t$=1.13 min; MS (ESIneg): m/z=508 [M−H]⁻

¹H-NMR (400 MHz, DMSO-d6) δ [ppm]: 0.541 (1.44), 0.554 (4.53), 0.559 (5.07), 0.563 (5.37), 0.569 (5.97), 0.580 (2.10), 0.674 (1.74), 0.686 (4.71), 0.691 (5.34), 0.704 (5.55), 0.722 (1.29), 1.154 (0.87), 1.172 (1.80), 1.190 (0.90), 1.230 (0.42), 1.239 (0.42), 1.375 (15.67), 1.392 (16.00), 1.987 (3.12), 2.336 (0.57), 2.518 (8.08), 2.522 (5.10), 2.528 (2.31), 2.536 (2.58), 2.545 (3.81), 2.555 (2.22), 2.563 (1.83), 2.572 (0.81), 2.678 (0.60), 2.839 (3.42), 2.857 (7.35), 2.873 (3.81), 3.497 (4.08), 3.514 (8.14), 3.531 (3.72), 3.978 (0.96), 3.996 (3.36), 4.014 (3.30), 4.031 (0.96), 4.034 (1.05), 5.758 (1.32), 6.544 (8.08), 6.563 (8.56), 6.566 (7.17), 6.601 (2.52), 6.619 (5.07), 6.637 (2.79), 6.994 (6.21), 7.012 (7.95), 7.015 (8.05), 7.033 (5.19), 7.086 (4.98), 7.090 (5.04), 7.100 (4.83), 7.103 (5.01), 7.124 (0.57), 7.131 (5.85), 7.137 (2.07), 7.148 (2.40), 7.154 (12.01), 7.159 (2.55), 7.171 (2.07), 7.176 (6.90), 7.184 (0.84), 7.380 (0.75), 7.388 (6.09), 7.393 (3.06), 7.403 (15.91), 7.410 (6.99), 7.419 (2.46), 7.424 (5.34), 8.005 (6.66), 8.019 (6.54), 8.191 (6.51), 10.498 (7.41), 11.730 (5.04).

Example 9

N-[4-(3-anilino-4-oxo-4,5,6,7-tetrahydro-1H-pyrrolo[3,2-c]pyridin-2-yl)pyridin-2-yl]-2-(4-fluorophenyl)propanamide

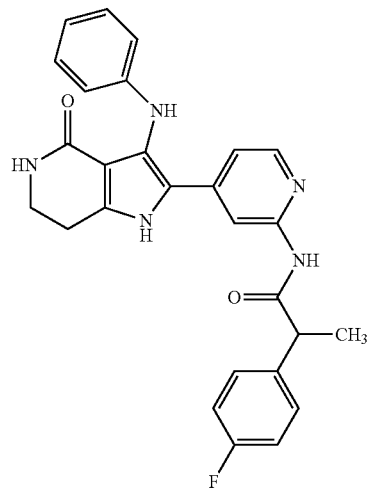 [SMILES: CC(C(=O)Nc1cc(-c2[nH]c3c(c2Nc2ccccc2)C(=O)NCC3)ccn1)c1ccc(F)cc1]

To a stirred solution of 2-(2-aminopyridin-4-yl)-3-anilino-1,5,6,7-tetrahydro-4H-pyrrolo[3,2-c]pyridin-4-one (WO 2016120196) (115 mg, 360 µmol) in DMA (2.4 mL) was added N,N-diisopropylethylamine (380 µL, 2.2 mmol), racemic 2-(4-fluorophenyl)propanoic acid (121 mg, 720 µmol) and PyBOP (562 mg, 1.08 mmol). The mixture was stirred at r.t. for 16 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave a solid that was triturated with a dichloromethane to give 47.0 mg (27% yield) of the title compound.

LC-MS (Method 1): $R_t$=1.00 min; MS (ESIpos): m/z=470 [M+H]⁺

¹H-NMR (400 MHz, DMSO-d6) δ [ppm]: 1.232 (0.54), 1.378 (15.90), 1.395 (16.00), 1.988 (0.68), 2.084 (2.13), 2.518 (8.19), 2.523 (5.18), 2.810 (3.48), 2.827 (7.68), 2.844 (3.92), 3.159 (1.15), 3.172 (1.08), 3.365 (2.67), 3.371 (2.91), 3.382 (5.11), 3.388 (5.04), 3.399 (2.50), 3.405 (2.33), 3.981 (0.95), 3.998 (3.42), 4.015 (3.55), 4.033 (1.18), 4.651 (0.44), 4.667 (0.47), 6.546 (8.02), 6.565 (8.39), 6.589 (2.40), 6.607 (5.04), 6.625 (2.77), 6.987 (6.49), 7.006 (8.19), 7.008 (8.05), 7.027 (5.07), 7.101 (7.44), 7.105 (9.07), 7.114 (6.90), 7.118 (5.62), 7.133 (5.99), 7.138 (2.81), 7.150 (2.47), 7.155 (11.91), 7.173 (2.13), 7.178 (6.63), 7.186 (0.85), 7.250 (0.51), 7.271 (0.64), 7.290 (0.54), 7.324 (10.22), 7.384 (0.74), 7.392 (5.89), 7.397 (2.60), 7.405 (6.70), 7.414 (6.05), 7.423 (2.74), 7.428 (5.45), 7.445 (0.51), 7.509 (0.68), 7.527 (0.58), 8.008 (6.80), 8.022 (6.49), 8.043 (0.51), 8.196 (6.43), 8.271 (0.47), 8.285 (0.47), 10.497 (7.68), 10.726 (0.51), 11.751 (5.45), 12.640 (0.64).

Example 10

N-[4-(3-anilino-4-oxo-4,5,6,7-tetrahydro-1H-pyrrolo[3,2-c]pyridin-2-yl)pyridin-2-yl]-2-(4-fluorophenyl)propanamide (Stereoisomer 1)

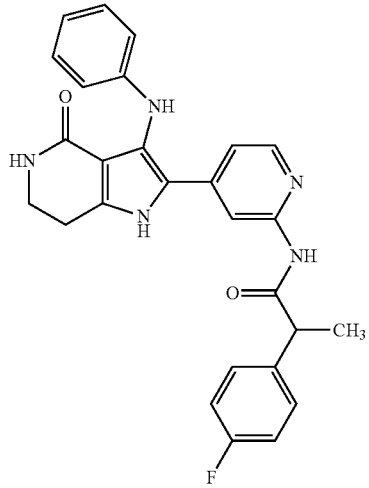 [SMILES: CC(C(=O)Nc1cc(-c2[nH]c3c(c2Nc2ccccc2)C(=O)NCC3)ccn1)c1ccc(F)cc1]

Racemic N-[4-(3-anilino-4-oxo-4,5,6,7-tetrahydro-1H-pyrrolo[3,2-c]pyridin-2-yl)pyridin-2-yl]-2-(4-fluorophenyl)propanamide (45.0 mg, 95.8 µmol) was separated into the single stereoisomers (Example 10 and Example 11) via preparative, chiral HPLC.

Instrument: PrepCon Labomatic HPLC,

Column: YMC Amylose SA 5µ 250×30;

Eluent: Eluent A: Hexan+0.1% diethylamin; Eluent B: Ethanol; Isokratic: 50% A+50% B;

Flow: 40.0 mL/min;

Temperature: 25° C.

Detection: UV: 254 nm

Injected solution: 45 mg racemic N-[4-(3-anilino-4-oxo-4,5,6,7-tetrahydro-1H-pyrrolo[3,2-c]pyridin-2-yl)pyridin-2-yl]-2-(4-fluorophenyl)propanamide dissolved in 2 mL dichlormethane/methanol 1:1

Injected volume: 2×1 mL.

Analytical Chiral HPLC Method 2:

Instrument: Waters Alliance 2695; Column: YMC Amylose SA 3µ 100×4.6; Eluent A: Hexan+0.1% diethylamin; Eluent B: Ethanol; Isokratic: 50% A+50% B; Flow: 1.4 mL/min; Temperature: 25° C.; UV: 254 nm;

|  | Retention time in min | e.e. [%] | yield | Optical rotation $[\alpha]_D$ |
| --- | --- | --- | --- | --- |
| Example 10 Stereoisomer 1 Peak 1 | 8.9-11.2 | >99.8% | 17 mg | +173.3° (from solution in DMSO, c = 2.3 mg/mL) |
| Example 11 Stereoisomer 2 Peak 2 | 13.8-17.1 | 99.2% | 18 mg | −131.1° (from solution in DMSO, c = 2.5 mg/mL) |

Isolated Isomer 1: 17 mg (38% yield)

Analytical Chiral HPLC (Method 2): $R_t$=2.77 min (e.e.: >99.8%)

$[\alpha]_D$=+173.3° (from solution in DMSO, c=2.3 mg/mL)

LC-MS (Method 1): $R_t$=0.97 min; MS (ESIneg): m/z=468.5 [M−H]$^-$ $^1$H-NMR (400 MHz, DMSO-d6) δ [ppm]: 1.035 (0.49), 1.052 (0.94), 1.070 (0.52), 1.108 (16.00), 1.232 (0.47), 1.377 (6.52), 1.395 (6.72), 2.083 (0.61), 2.522 (1.20), 2.539 (2.89), 2.810 (1.57), 2.827 (3.38), 2.844 (1.79), 3.365 (1.26), 3.371 (1.36), 3.382 (2.35), 3.388 (2.33), 3.399 (1.21), 3.405 (1.14), 3.981 (0.43), 3.999 (1.46), 4.016 (1.45), 4.033 (0.43), 4.192 (1.38), 6.547 (3.57), 6.566 (3.73), 6.589 (1.06), 6.607 (2.17), 6.625 (1.19), 6.987 (2.61), 7.006 (3.56), 7.008 (3.56), 7.027 (2.15), 7.101 (3.00), 7.106 (3.35), 7.115 (3.27), 7.119 (2.65), 7.133 (2.39), 7.138 (0.98), 7.156 (4.90), 7.173 (0.96), 7.178 (2.76), 7.327 (4.38), 7.392 (2.52), 7.397 (1.21), 7.406 (2.87), 7.414 (2.58), 7.422 (1.07), 7.428 (2.19), 8.009 (2.73), 8.022 (2.64), 8.199 (2.94), 10.499 (3.31), 11.753 (2.43).

Example 11

N-[4-(3-anilino-4-oxo-4,5,6,7-tetrahydro-1H-pyrrolo[3,2-c]pyridin-2-yl)pyridin-2-yl]-2-(4-fluorophenyl)propanamide (Stereoisomer 2)

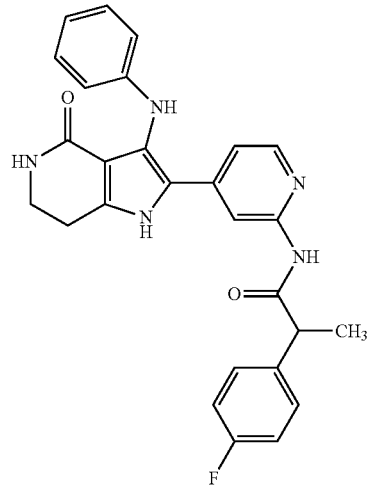 [SMILES: CC(C(=O)Nc1cc(-c2[nH]c3c(c2Nc2ccccc2)C(=O)NCC3)ccn1)c1ccc(F)cc1]

Obtained Isomer 2: 18.0 mg (38% yield)

Analytical Chiral HPLC (Method 2): $R_t$=4.23 min (e.e.: 99.2%)

$[\alpha]_D$=−131.1° (from solution in DMSO, c=2.5 mg/mL)

LC-MS (Method 1): $R_t$=0.97 min; MS (ESIneg): m/z=468.5 [M−H]$^-$ $^1$H-NMR (400 MHz, DMSO-d6) δ [ppm]: 1.035 (0.74), 1.052 (1.46), 1.070 (0.80), 1.108 (16.00), 1.134 (0.53), 1.152 (1.04), 1.170 (0.56), 1.232 (0.73), 1.377 (7.02), 1.395 (7.16), 2.083 (0.57), 2.327 (0.53), 2.522 (1.49), 2.539 (0.49), 2.664 (0.41), 2.669 (0.56), 2.673 (0.41), 2.810 (1.67), 2.827 (3.59), 2.844 (1.86), 3.365 (1.32), 3.371 (1.41), 3.382 (2.48), 3.388 (2.43), 3.398 (1.25), 3.405 (1.24), 3.980 (0.46), 3.998 (1.55), 4.016 (1.54), 4.033 (0.44), 4.191 (1.55), 4.358 (0.42), 6.547 (3.72), 6.566 (3.96), 6.589 (1.10), 6.607 (2.29), 6.625 (1.24), 6.987 (2.79), 7.006 (3.78), 7.027 (2.25), 7.101 (3.21), 7.105 (3.64), 7.115 (3.38), 7.119 (2.70), 7.134 (2.56), 7.139 (0.98), 7.156 (5.28), 7.178 (2.94), 7.326 (4.72), 7.392 (2.70), 7.397 (1.25), 7.406 (3.04), 7.414 (2.73), 7.422 (1.10), 7.427 (2.29), 8.008 (2.95), 8.022 (2.79), 8.198 (3.10), 10.499 (3.50), 11.752 (2.62).

Example 12

2-(4-fluorophenyl)-N-(4-{5-methyl-4-oxo-3-[(pyridin-2-yl)amino]-4,5,6,7-tetrahydro-1H-pyrrolo[3,2-c]pyridin-2-yl}pyridin-2-yl)acetamide

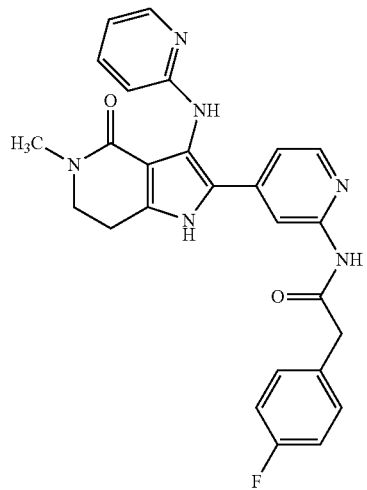 [SMILES: CN1CCc2[nH]c(-c3ccnc(NC(=O)Cc4ccc(F)cc4)c3)c(Nc3ccccn3)c2C1=O]

To a stirred solution of 2-(2-aminopyridin-4-yl)-5-methyl-3-[(pyridin-2-yl)amino]-1,5,6,7-tetrahydro-4H-pyrrolo[3,2-c]pyridin-4-one (see Intermediate 13) (19.0 mg, 56.8 μmol) in DMF (0.5 mL) was added N,N-diisopropylethylamine (59 μL, 340 μmol), (4-fluorophenyl)acetic acid (21.9 mg, 142 μmol) and HATU (75.6 mg, 199 μmol). The mixture was stirred at 60° C. for 16 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography followed by aminophase-silicagel chromatography gave 7.00 mg (24% yield) of the title compound.

LC-MS (Method 2): $R_t$=0.98 min; MS (ESIneg): m/z=469 [M−H]$^−$ $^1$H-NMR (400 MHz, DMSO-d6) δ [ppm]: 2.331 (0.50), 2.518 (2.52), 2.523 (1.63), 2.673 (0.55), 2.845 (16.00), 2.884 (1.62), 2.902 (3.44), 2.919 (1.75), 3.361 (1.37), 3.506 (1.93), 3.523 (3.92), 3.540 (1.74), 3.683 (6.78), 3.707 (0.67), 5.759 (8.37), 6.273 (1.86), 6.294 (1.88), 6.373 (0.44), 6.553 (1.32), 6.555 (1.33), 6.565 (1.27), 6.568 (1.46), 6.571 (1.49), 6.573 (1.23), 6.583 (1.28), 6.585 (1.20), 7.127 (2.37), 7.133 (1.02), 7.144 (1.10), 7.150 (4.93), 7.155 (1.45), 7.167 (0.96), 7.172 (2.89), 7.180 (2.34), 7.184 (2.07), 7.193 (1.98), 7.197 (1.97), 7.311 (0.99), 7.316 (1.07), 7.321 (0.52), 7.333 (3.86), 7.347 (3.22), 7.355 (3.22), 7.363 (1.16), 7.369 (2.21), 7.377 (0.47), 7.826 (4.63), 7.936 (1.43), 7.939 (1.46), 7.949 (1.41), 7.952 (1.38), 8.079 (2.73), 8.094 (2.56), 8.173 (2.71), 10.577 (3.06), 11.743 (1.98).

Example 13

N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)acetamide

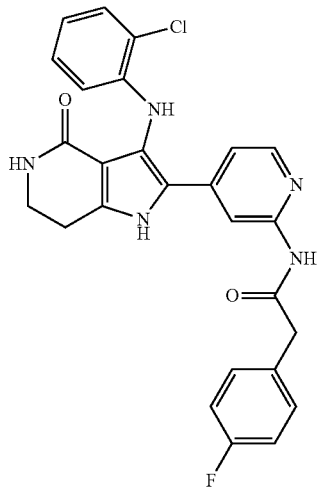 [SMILES: O=C(Cc1ccc(F)cc1)Nc1cc(-c2[nH]c3c(c2Nc2ccccc2Cl)C(=O)NCC3)ccn1]

To a stirred solution of 2-(2-aminopyridin-4-yl)-3-(2-chloroanilino)-1,5,6,7-tetrahydro-4H-pyrrolo[3,2-c]pyridin-4-one (see Intermediate 17) (120 mg, 339 μmol) in DMA (3.0 mL) was added N,N-diisopropylethylamine (350 μL, 2.0 mmol), (4-fluorophenyl)acetic acid (140 μL, 680 μmol) and HATU (645 mg, 1.70 mmol). The mixture was stirred at 60° C. for 30 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography followed by preparative reverse phase HPLC (gradient of water and acetonitrile containing ammonia as additive) gave a solid that was triturated with ethyl acetate to give 8.50 mg (5% yield) of the title compound.

LC-MS (Method 1): $R_t$=1.00 min; MS (ESIpos): m/z=490 [M+H]$^+$ $^1$H-NMR (400 MHz, DMSO-d6) δ [ppm]: 1.154 (0.77), 1.172 (1.50), 1.189 (0.74), 1.231 (0.42), 1.987 (2.93), 2.133 (0.50), 2.331 (1.11), 2.518 (6.84), 2.522 (4.33), 2.673 (1.16), 2.811 (3.67), 2.828 (7.60), 2.844 (3.96), 3.373 (2.80), 3.379 (3.17), 3.390 (5.25), 3.396 (5.07), 3.407 (2.64), 3.413 (2.32), 3.679 (16.00), 3.701 (0.53), 4.017 (0.63), 4.035 (0.66), 6.291 (4.33), 6.295 (4.38), 6.312 (4.41), 6.316 (4.33), 6.648 (2.38), 6.652 (2.43), 6.667 (4.17), 6.671 (4.09), 6.686 (2.85), 6.690 (2.67), 6.876 (2.51), 6.879 (2.56), 6.897 (3.93), 6.915 (2.01), 6.918 (1.87), 6.994 (4.65), 6.999 (4.54), 7.008 (4.46), 7.012 (4.62), 7.123 (0.66), 7.131 (5.57), 7.136 (2.19), 7.147 (2.72), 7.153 (11.72), 7.159 (3.35), 7.176 (10.01), 7.322 (6.05), 7.325 (6.84), 7.329 (6.81), 7.334 (3.27), 7.342 (11.27), 7.345 (9.19), 7.350 (6.02), 7.359 (2.69), 7.365 (4.83), 7.398 (10.14), 8.062 (6.47), 8.075 (6.23), 8.159 (5.78), 10.575 (7.29), 11.855 (5.41).

Example 14

N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)propanamide

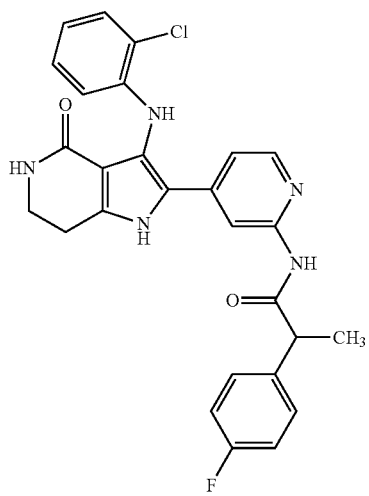 [SMILES: CC(C(=O)Nc1cc(-c2[nH]c3c(c2Nc2ccccc2Cl)C(=O)NCC3)ccn1)c1ccc(F)cc1]

To a stirred solution of 2-(2-aminopyridin-4-yl)-3-(2-chloroanilino)-1,5,6,7-tetrahydro-4H-pyrrolo[3,2-c]pyridin-4-one (see Intermediate 17) (361 mg, 1020 µmol) in DMA (13 mL) was added N,N-diisopropylethylamine (1048 µL), 2-(4-fluorophenyl)propanoic acid (343 mg, 2.40 mmol) and PyBOP (2.65 g, 5.10 mmol). The mixture was stirred at room temperature for 96 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave a solid that was triturated with ethyl acetate to give 233 mg of the title compound.

LC-MS (Method 1): $R_t$=1.06 min; MS (ESIpos): m/z=504 [M+H]$^+$ $^1$H NMR (400 MHz, DMSO-d$_6$) δ ppm: 1.38 (d, 3H), 2.84 (t, 2H), 3.40 (td, 2H), 4.00 (q, 1H), 6.29 (dd, 1H), 6.66 (td, 1H), 6.85-6.93 (m, 1H), 6.99 (dd, 1H), 7.10-7.22 (m, 3H), 7.34 (dd, 1H), 7.37-7.44 (m, 3H), 8.04 (d, 1H), 8.18 (s, 1H), 10.51 (s, 1H), 11.86 (s, 1H).

Example 15

N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)propanamide (Stereoisomer 1)

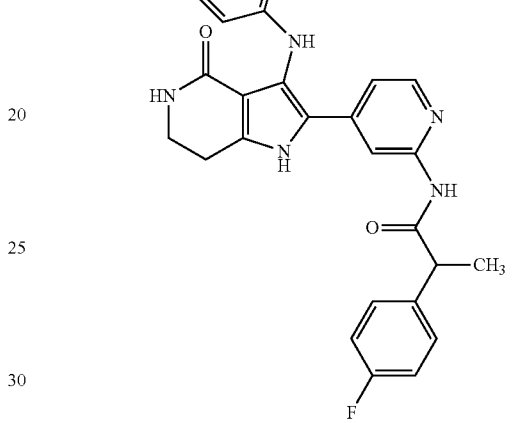

Racemic N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)propanamide (230 mg) was separated into the single stereoisomers (Example 15 and Example 16) via preparative, chiral HPLC.

Instrument: Labomatic HD5000, Labocord-5000; Gilson GX-241, Labcol Vario 4000,

Column: Cellulose SB 5µ 250×30 mm;

Eluent: Eluent A: Hexan+0.1 vol % diethylamine; Eluent B: Ethanol; Isokratic: 75% A+25% B;

Flow: 50.0 mL/min;

Temperature: 25° C.

Detection: UV: 254 nm

Injected solution: 230 mg racemic N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)propanamide in 12 mL dichlormethane/trifluoroethanol 1:1

Analytical Chiral HPLC Method 3:

Instrument: Agilent HPLC 1260; Column: Cellulose SB 3µ 100×4.6 mm; Eluent A: Hexan+0.1 vol % diethylamine; Eluent B: Ethanol; Gradient: 20%-50% B in 7 minutes; Flow: 1.4 mL/min;

Temperature: 25° C.; Detection:DAD: 254 nm.

| | Retention time in min | e.e. [%] | yield | Optical rotation [α]$_D$ |
|---|---|---|---|---|
| Example 15 Stereoisomer 1 Peak 1 | 8.0-7.6 | >99.9% | 80 mg | -147.9 ° (from solution in DMSO, c = 5.47 mg/mL) |

-continued

|  | Retention time in min | e.e. [%] | yield | Optical rotation [α]$_D$ |
|---|---|---|---|---|
| Example 16 Stereoisomer 2 Peak 2 | 8.0-11.0 | 99.9% | 77 mg | +143.8° (from solution in DMSO, c = 5.78 mg/mL) |

Isolated Isomer 1: 80 mg

Analytical Chiral HPLC (Method 3): R$_t$=2.22 min (e.e.: >99.9%)

[a]$_D$=−147.9° (from solution in DMSO, c=5.47 mg/mL)

LC-MS (Method 1): R$_t$=1.08 min; MS (ESIpos): m/z=504.5; 506.3 [M+H]$^+$ $^1$H NMR (400 MHz, DMSO-d$_6$) 0 ppm: 1.38 (d, 3H), 2.84 (t, 2H), 3.40 (td, 2H), 4.00 (q, 1H), 6.29 (dd, 1H), 6.66 (td, 1H), 6.86-6.92 (m, 1H), 6.99 (dd, 1H), 7.11-7.21 (m, 3H), 7.34 (dd, 1H), 7.37-7.44 (m, 3H), 8.04 (d, 1H), 8.18 (d, 1H), 10.51 (s, 1H), 11.86 (s, 1H).

Example 16

N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)propanamide (Stereoisomer 2)

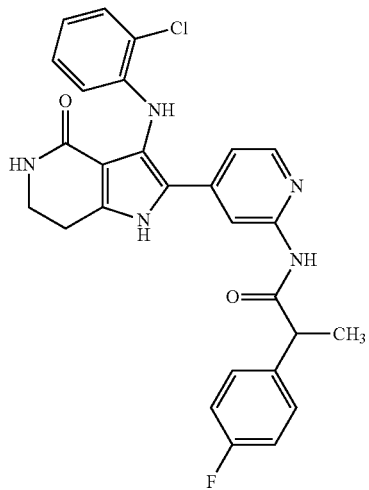 [SMILES: CC(C(=O)Nc1cc(-c2[nH]c3c(c2Nc2ccccc2Cl)C(=O)NCC3)ccn1)c1ccc(F)cc1]

Obtained Stereoisomer 2: 77 mg

Analytical Chiral HPLC (Method 3): R$_t$=2.97 min (e.e.: >99.9%)

[a]$_D$=+143.8° (from solution in DMSO, c=5.78 mg/mL)

LC-MS (Method 1): R$_t$=1.07 min; MS (ESIpos): m/z=504.6; 506.3 [M+H]$^+$ $^1$H NMR (400 MHz, DMSO-d$_6$) δ ppm: 1.38 (d, 3H), 2.84 (t, 2H), 3.40 (td, 2H), 4.00 (q, 1H), 6.29 (dd, 1H), 6.66 (td, 1H), 6.85-6.92 (m, 1H), 6.99 (dd, 1H), 7.11-7.21 (m, 3H), 7.34 (dd, 1H), 7.37-7.43 (m, 3H), 8.04 (d, 1H), 8.18 (s, 1H), 10.51 (s, 1H), 11.86 (s, 1H).

Example 17

N-[4-(3-anilino-5-methyl-4-oxo-4,5,6,7-tetrahydro-1H-pyrrolo[3,2-c]pyridin-2-yl)pyridin-2-yl]-2-(4-fluorophenyl)-3-hydroxypropanamide

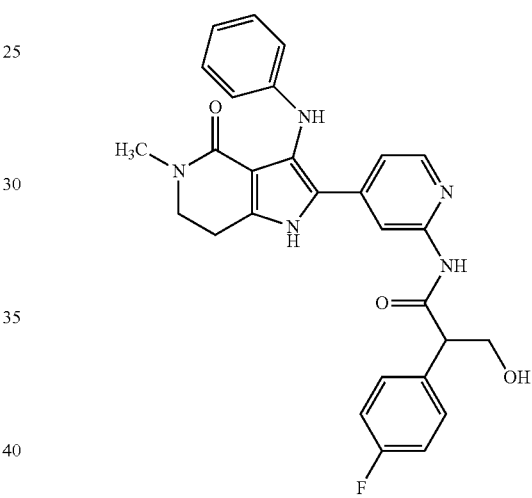

To a stirred solution of N-[4-(3-anilino-5-methyl-4-oxo-4,5,6,7-tetrahydro-1H-pyrrolo[3,2-c]pyridin-2-yl)pyridin-2-yl]-3-{[tert-butyl(diphenyl)silyl]oxy}-2-(4-fluorophenyl) propanamide (see Intermediate 18) (370 mg, 501 μmol). in THF (40 mL), was added tetra-n-butylammoniumfluorid (1.3 mL, c=1.0 M in THF, 1.3 mmol) and the mixture was stirred at rt for 1 h. Water was added and the mixture was extracted with MTBE. The combined organic phases were dried (sodium sulfate), filtered and the solvent was removed in vacuum. Silicagel chromatography gave 195 mg (74% yield) of the title compound.

LC-MS (Method 2): R$_t$=1.04 min; MS (ESIpos): m/z=500 [M+H]$^+$ $^1$H NMR (400 MHz, DMSO-d$_6$) δ ppm: 2.86 (s, 3H), 2.93 (t, 2H), 3.50-3.59 (m, 3H), 3.95-4.11 (m, 2H), 4.95 (t, 1H), 6.53-6.57 (m, 2H), 6.61 (t, 1H), 7.01 (dd, 2H), 7.08-7.21 (m, 3H), 7.34-7.43 (m, 3H), 8.02 (d, 1H), 8.25 (s, 1H), 10.53 (s, 1H), 11.76 (s, 1H)

Example 18

N-[4-(3-anilino-5-methyl-4-oxo-4,5,6,7-tetrahydro-1H-pyrrolo[3,2-c]pyridin-2-yl)pyridin-2-yl]-2-(4-fluorophenyl)-3-hydroxypropanamide (Stereoisomer 1)

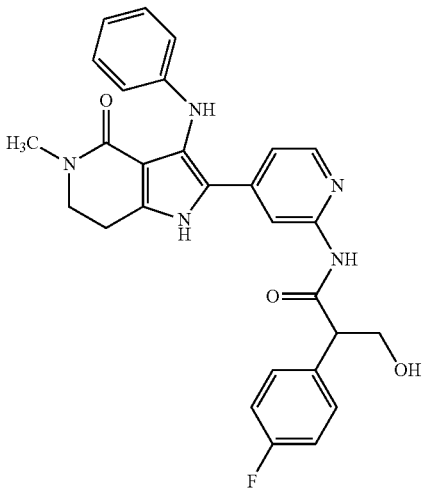 [SMILES: CN1CCc2[nH]c(-c3ccnc(NC(=O)C(CO)c4ccc(F)cc4)c3)c(Nc3ccccc3)c2C1=O]

Racemic N-[4-(3-anilino-5-methyl-4-oxo-4,5,6,7-tetrahydro-1H-pyrrolo[3,2-c]pyridin-2-yl)pyridin-2-yl]-2-(4-fluorophenyl)-3-hydroxypropanamide (195 mg) was separated into the single stereoisomers (Example 18 and Example 19) via preparative, chiral HPLC.

Instrument: Labomatic HD5000, Labocord-5000; Gilson GX-241, Labcol Vario 4000,

Column: Cellulose SB 5μ 250×30 mm;

Eluent: Eluent A: Hexan+0.1 vol % diethylamine; Eluent B: Ethanol; Isokratic: 75% A+25% B;

Flow: 50.0 mL/min;

Temperature: 25° C.

Detection: UV: 254 nm

Injected solution: 195 mg racemic N-[4-(3-anilino-5-methyl-4-oxo-4,5,6,7-tetrahydro-1H-pyrrolo[3,2-c]pyridin-2-yl)pyridin-2-yl]-2-(4-fluorophenyl)-3-hydroxypropanamide in 12 mL dichlormethane/methanol 1:1

Analytical Chiral HPLC Method 4:

Instrument: Agilent HPLC 1260; Column: Cellulose SB 3μ 100×4.6 mm; Eluent A: Hexan+0.1 vol % diethylamine; Eluent B: Ethanol; Isokratic: 75% A+25% B; Flow: 1.4 mL/min; Temperature: 25° C.; Detection:DAD: 254 nm.

|  | Retention time in min | e.e. [%] | yield | Optical rotation $[\alpha]_D$ |
|---|---|---|---|---|
| Example 18 Stereoisomer 1 Peak 1 | 5.1-7.5 | >99.9% | 72 mg | -111.9° (from solution in DMSO, c = 4.09 mg/mL) |
| Example 19 Stereoisomer 2 Peak 2 | 9.2-12.5 | 99.8% | 81 mg | +93.9° (from solution in DMSO, c = 4.0 mg/mL) |

Isolated Isomer 1: 72 mg

Analytical Chiral HPLC (Method 4): $R_t$=2.25 min (e.e.: >99.9%)

$[\alpha]_D$=−111.9° (from solution in DMSO, c=4.09 mg/mL)

LC-MS (Method 2): $R_t$=1.06 min; MS (ESIpos): m/z=500.5 [M+H]$^+$ $^1$H NMR (400 MHz, DMSO-$d_6$) δ ppm: 2.86 (s, 3H), 2.93 (t, 2H), 3.50-3.61 (m, 3H), 3.95-4.09 (m, 2H), 4.95 (t, 1H), 6.53-6.57 (m, 2H), 6.61 (t, 1H), 7.01 (dd, 2H), 7.11 (dd, 1H), 7.13-7.19 (m, 2H), 7.36-7.42 (m, 3H), 8.02 (d, 1H), 8.25 (s, 1H), 10.53 (s, 1H), 11.76 (s, 1H).

Example 19

N-[4-(3-anilino-5-methyl-4-oxo-4,5,6,7-tetrahydro-1H-pyrrolo[3,2-c]pyridin-2-yl)pyridin-2-yl]-2-(4-fluorophenyl)-3-hydroxypropanamide (Stereoisomer 2)

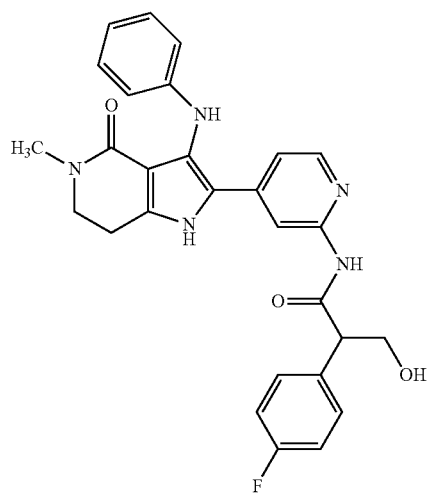 [SMILES: CN1CCc2[nH]c(-c3ccnc(NC(=O)C(CO)c4ccc(F)cc4)c3)c(Nc3ccccc3)c2C1=O]

Obtained Stereoisomer 2 after chiral HPLC: 81 mg

Analytical Chiral HPLC (Method 4): $R_t$=3.09 min (e.e.: 99.8%)

The oily material was further purified using silicagel chromatography followed by preparative reverse phase HPLC (gradient of water and acetonitrile containing ammonia as additive) to give 50 mg of the title compound as a solid.

$[\alpha]_D$=+93.9° (from solution in DMSO, c=4.0 mg/mL)

LC-MS (Method 2): $R_t$=1.05 min; MS (ESIpos): m/z=500 [M+H]$^+$ $^1$H NMR (400 MHz, DMSO-$d_6$) δ ppm: 2.86 (s, 3H), 2.93 (t, 2H), 3.50-3.58 (m, 3H), 3.97-4.08 (m, 2H), 4.95 (t, 1H), 6.53-6.57 (m, 2H), 6.58-6.64 (m, 1H), 6.97-7.05 (m, 2H), 7.11 (dd, 1H), 7.12-7.20 (m, 2H), 7.35-7.43 (m, 3H), 8.01 (d, 1H), 8.25 (s, 1H), 10.53 (s, 1H), 11.75 (s, 1H).

Example 20

N-{4-[3-anilino-5-(cyclopropylmethyl)-4-oxo-4,5,6,7-tetrahydro-1H-pyrrolo[3,2-c]pyridin-2-yl]pyridin-2-yl}-2-(4-fluorophenyl)acetamide

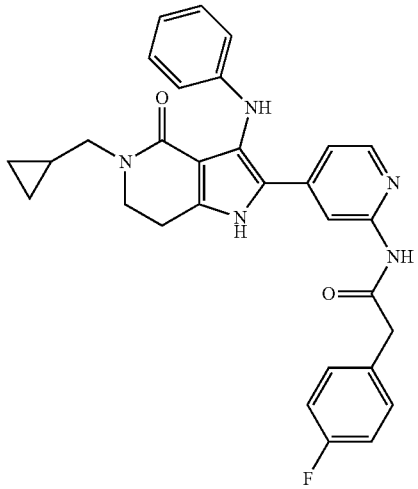 [SMILES: O=C(Cc1ccc(F)cc1)Nc1cc(-c2[nH]c3c(c2Nc2ccccc2)C(=O)N(CC2CC2)CC3)ccn1]

To a stirred solution of 2-(2-aminopyridin-4-yl)-3-anilino-5-(cyclopropylmethyl)-1,5,6,7-tetrahydro-4H-pyrrolo[3,2-c]pyridin-4-one (see Intermediate 25) (100 mg, 268 µmol) in DMA (2.0 mL) was added N,N-diisopropylethylamine (280 µL, 1.6 mmol), (4-fluorophenyl)acetic acid (82.5 mg, 536 µmol) and PyBOP (418 mg, 803 µmol). The mixture was stirred at room temperature for 16 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum.

Silicagel chromatography followed by preparative reverse phase HPLC (gradient of water and acetonitrile containing ammonia as additive) gave 35.0 mg (23% yield) of the title compound.

LC-MS (Method 2): $R_t$=1.26 min; MS (ESIpos): m/z=510 [M+H]$^+$ $^1$H NMR (400 MHz, DMSO-d6) δ [ppm]: 0.16-0.24 (m, 2H), 0.37-0.47 (m, 2H), 0.89-1.02 (m, 1H), 2.90 (t, 2H), 3.22 (d, 2H), 3.63 (t, 2H), 3.69 (s, 2H), 6.54-6.58 (m, 2H), 6.62 (t, 1H), 7.01 (dd, 2H), 7.09-7.19 (m, 3H), 7.33-7.38 (m, 2H), 7.40 (s, 1H), 8.04 (d, 1H), 8.18 (s, 1H), 10.56 (s, 1H), 11.74 (s, 1H).

Example 21

N-[4-(3-anilino-5-ethyl-4-oxo-4,5,6,7-tetrahydro-1H-pyrrolo[3,2-c]pyridin-2-yl)pyridin-2-yl]-2-(4-fluorophenyl)propanamide

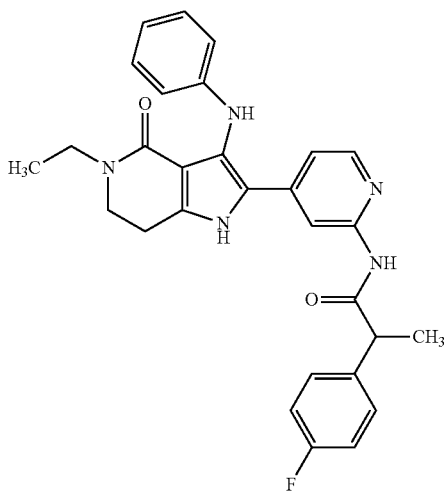 [SMILES: CCN1CCc2[nH]c(-c3ccnc(NC(=O)C(C)c4ccc(F)cc4)c3)c(Nc3ccccc3)c2C1=O]

2-(2-Aminopyridin-4-yl)-3-anilino-5-ethyl-1,5,6,7-tetrahydro-4H-pyrrolo[3,2-c]pyridin-4-one (see Intermediate 32, 135 mg) was diluted in 2.1 mL N,N-dimethylacetamide. 2-(4-fluorophenyl)propanoic acid (CAS: 75908-73-5, 124 mg, 738 µmol), N,N-diisopropylethylamine (390 µL, 2.2 mmol) and (Benzotriazol-1-yloxy)tripyrrolidinophosphonium hexafluorophosphate (576 mg, 1.11 mmol) were added and stirred over night at rt under nitrogen atmosphere. Further (Benzotriazol-1-yloxy)tripyrrolidinophosphonium hexafluorophosphate (288 mg, 554 µmol) and 2-(4-fluorophenyl)propanoic acid (124 mg, 738 µmol) were added to the reaction mixture and stirred again overnight under the same conditions. The reaction mixture was diluted with saturated sodium bicarbonate solution and ethyl acetate. The organic layer was extracted with water three times, filtered through a water resistant filter and concentrated under reduced pressure. The crude product was purified by HPLC under basic conditions to provide the target compound in 95% purity: 72 mg.

LC-MS (Method 2): $R_t$=1.25 min; MS (ESIpos): m/z=498 [M+H]$^+$ $^1$H-NMR (400 MHz, DMSO-d6): δ [ppm]=1.04 (t, 3H), 1.38 (d, 3H), 2.90 (t, 2H), 3.36-3.41 (m, 2H), 3.55 (t, 2H), 4.00 (q, 1H), 6.55 (dd, 2H), 6.61 (t, 1H), 7.01 (dd, 2H), 7.09 (dd, 1H), 7.12-7.21 (m, 2H), 7.36-7.47 (m, 3H), 8.00 (d, 1H), 8.20 (s, 1H), 10.48 (s, 1H), 11.60-11.89 (m, 1H).

Example 22

N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)acetamide

Example 23

N-{4-[3-anilino-5-(2-hydroxy-2-methylpropyl)-4-oxo-4,5,6,7-tetrahydro-1H-pyrrolo[3,2-c]pyridin-2-yl]pyridin-2-yl}-2-(4-fluorophenyl)acetamide

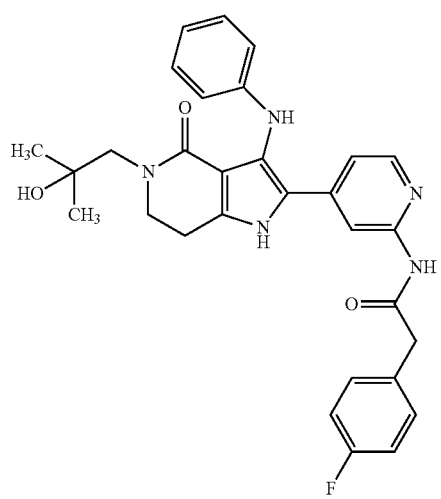

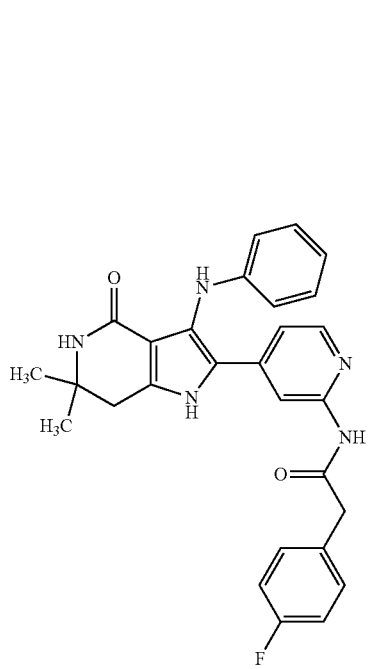 [SMILES: CC1(C)Cc2[nH]c(-c3ccnc(NC(=O)Cc4ccc(F)cc4)c3)c(Nc3ccccc3)c2C(=O)N1]

2-(2-Aminopyridin-4-yl)-3-anilino-6,6-dimethyl-1,5,6,7-tetrahydro-4H-pyrrolo[3,2-c]pyridin-4-one (see Intermediate 35, 250 mg), (4-fluorophenyl)acetic acid (CAS: 405-50-5, 166 mg, 1.08 mmol), HATU (410 mg, 1.08 mmol) and N,N-diisopropylethylamine (380 µL, 2.2 mmol) were dissolved in 5.5 mL DMF and stirred at 60° C. over night under argon atmosphere and at 100° C. for 1 day. Aqueous saturated sodium hydrogencarbonate solution was added and diluted with ethyl acetate. It was stirred for a few minutes, filtered through a silicone coated filter and concentrated under reduced pressure. The crude product was purified by flash chromatography (25 g column, silica Ultra; ethyl acetate/ethanol 0%-20%) and HPLC to provide the target compound in two batches: batch 1 (21 mg, 85% purity) and batch 2 (15 mg, 87% purity).

Batch 1:

LC-MS (Method 2): $R_t$=1.12 min; MS (ESIpos): m/z=485 [M+H]$^+$

1H-NMR (400 MHz, DMSO-d6): δ [ppm]=1.25 (s, 6H), 2.77 (s, 2H), 3.69 (s, 2H), 6.53-6.58 (m, 2H), 6.58-6.65 (m, 1H), 6.94-7.06 (m, 3H), 7.09-7.20 (m, 3H), 7.30-7.40 (m, 3H), 8.04 (d, 1H), 8.16 (s, 1H), 10.55 (s, 1H), 11.69 (s, 1H).

2-(2-Aminopyridin-4-yl)-3-anilino-5-(2-hydroxy-2-methylpropyl)-1,5,6,7-tetrahydro-4H-pyrrolo[3,2-c]pyridin-4-one (Intermediate 42, 186 mg) was dissolved in 2.5 mL N,N-dimethylacetamide. (4-Fluorophenyl)acetic acid (131 mg, 853 µmol), N,N-diisopropylethylamine (450 µL, 2.6 mmol) and PyBOP (666 mg, 1.28 mmol) were added and stirred over night at room temperature under nitrogen atmosphere. Further PyBOP (333 mg, 0.64 mmol) and (4-fluorophenyl)acetic acid (131 mg, 853 µmol) were added to the reaction mixture. It was stirred under the same conditions over three days. The reaction mixture was diluted with aqueous saturated sodium hydrogencarbonate solution and ethyl acetate. The organic layer was extracted three times with water, filtered through a water resistant filter and concentrated under reduced pressure. The crude product was further purified by column chromatography (Biotage, column: 28 g KP—NH, dichloromethane/ethanol, gradient: 0-10%) to provide the target compound in 94% purity: 87 mg LC-MS (Method 2): $R_t$=1.13 min; MS (ESIpos): m/z=528 [M+H]$^+$ 1H-NMR (400 MHz, DMSO-d6) δ [ppm]: 1.067 (16.00), 2.518 (3.30), 2.523 (2.14), 2.865 (0.94), 2.883 (1.96), 2.899 (1.07), 3.282 (3.79), 3.299 (0.40), 3.373 (0.40), 3.687 (5.44), 3.698 (2.41), 3.715 (1.07), 4.524 (4.99), 6.545 (2.41), 6.564 (2.54), 6.593 (0.76), 6.611 (1.52), 6.629 (0.85), 6.985 (1.87), 7.003 (2.36), 7.006 (2.32), 7.025 (1.52), 7.101 (1.43), 7.105 (1.47), 7.115 (1.47), 7.119 (1.47), 7.129 (1.78), 7.135 (0.67), 7.146 (0.80), 7.152 (3.74), 7.157 (0.80), 7.169 (0.67), 7.174 (2.18), 7.337 (1.78), 7.343 (0.80), 7.351 (2.01), 7.359 (1.74), 7.367 (0.67), 7.373 (1.52), 7.402 (2.99), 8.034 (2.01), 8.048 (1.92), 8.181 (1.78), 10.557 (2.27), 11.753 (1.43).

Example 24

N-{4-[3-anilino-5-(2-hydroxy-2-methylpropyl)-4-oxo-4,5,6,7-tetrahydro-1H-pyrrolo[3,2-c]pyridin-2-yl]pyridin-2-yl}-2-(4-fluorophenyl)propanamide

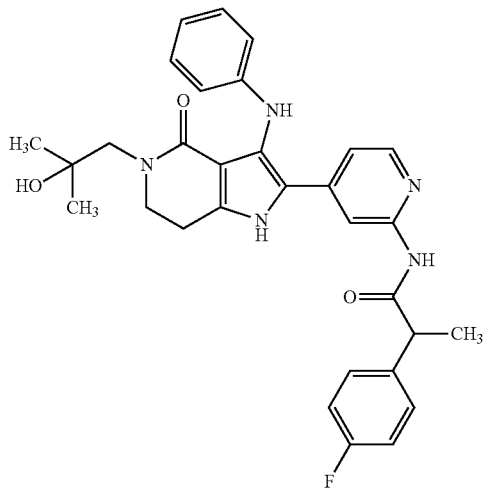 [SMILES: CC(C(=O)Nc1cc(-c2[nH]c3c(c2Nc2ccccc2)C(=O)N(CC(C)(C)O)CC3)ccn1)c1ccc(F)cc1]

2-(2-Aminopyridin-4-yl)-3-anilino-5-(2-hydroxy-2-methylpropyl)-1,5,6,7-tetrahydro-4H-pyrrolo[3,2-c]pyridin-4-one (see Intermediate 42, 201 mg) was dissolved in 2.7 mL N,N-dimethylacetamide. 2-(4-Fluorophenyl)propanoic acid (155 mg, 922 μmol), N,N-diisopropylethylamine (480 μL, 2.8 mmol) and PyBOP (720 mg, 1.38 mmol) were added and stirred over night at room temperature under nitrogen atmosphere. Further PyBOP (350 mg, 0.69 mmol) and 2-(4-fluorophenyl)propanoic acid (155 mg, 922 μmol) were added to the reaction mixture. It was stirred under the same conditions over three days. The reaction mixture was diluted with aqueous saturated sodium hydrogencarbonate solution and ethyl acetate. The organic layer was extracted three times with water, filtered through a water resistant filter and concentrated under reduced pressure. The crude product was purified by HPLC under basic conditions to provide the target compound in 93% purity: 52 mg.

LC-MS (Method 2): $R_t$=1.19 min; MS (ESIpos): m/z=542 [M+H]$^+$ $^1$H-NMR (400 MHz, DMSO-d6) δ [ppm]: 1.072 (16.00), 1.376 (4.56), 1.394 (4.73), 2.518 (7.14), 2.523 (4.56), 2.880 (0.95), 2.897 (1.98), 2.913 (1.03), 3.288 (3.70), 3.307 (1.03), 3.381 (0.69), 3.389 (0.52), 3.690 (1.12), 3.707 (2.15), 3.724 (1.03), 3.996 (1.03), 4.014 (0.95), 4.531 (4.22), 5.757 (1.20), 6.545 (2.41), 6.564 (2.58), 6.590 (0.77), 6.608 (1.46), 6.626 (0.86), 6.983 (1.89), 7.001 (2.49), 7.022 (1.55), 7.086 (1.46), 7.090 (1.46), 7.100 (1.38), 7.103 (1.38), 7.133 (1.81), 7.138 (0.69), 7.155 (3.70), 7.178 (1.98), 7.391 (1.81), 7.397 (0.86), 7.405 (2.15), 7.416 (3.35), 7.427 (1.72), 8.007 (1.98), 8.020 (1.89), 8.194 (1.98), 10.494 (2.15), 11.761 (1.46).

Example 25

N-[4-(3-anilino-5-ethyl-4-oxo-4,5,6,7-tetrahydro-1H-pyrrolo[3,2-c]pyridin-2-yl)pyridin-2-yl]-2-(4-fluorophenyl)propanamide (Enantiomer 1)

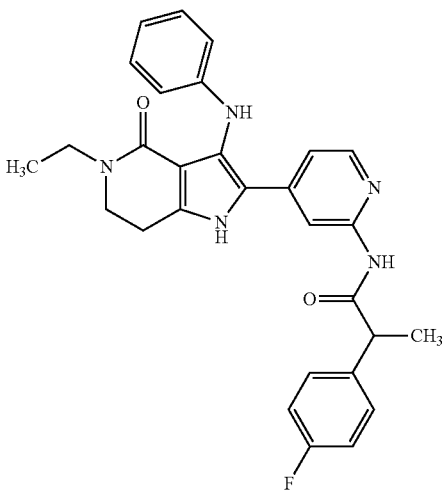 [SMILES: CCN1CCc2[nH]c(-c3ccnc(NC(=O)C(C)c4ccc(F)cc4)c3)c(Nc3ccccc3)c2C1=O]

The racemic compound (Example 21, 62 mg) was separated into enantiomers by preparative chiral HPLC to give enantiomer 1 (26 mg, see Example 25) and enantiomer 2 (23 mg, see Example 26).

Preparative Chiral HPLC Method:

Instrument: Labomatic HD5000, Labocord-5000; Gilson GX-241, Labcol Vario 4000, Column: Cellulose SB 5μ 250×30 mm; Eluent A: Hexane+0.1 Vol-% Diethylamine (99%); Eluent B: 2-Propanol; Gradient: 20-50% B in 20 min; Flow 50.0 mL/min; UV 254 nm Analytical Chiral HPLC Method:

Instrument: Agilent HPLC 1260; Column: Cellulose SB 3μ 100×4.6 mm; Eluent A: Hexane+0.1 Vol-% Diethylamine (99%); Eluent B: 2-Propanol; Isokratic: 80% A+20% B; Flow 1.4 mL/min; Temperature: 25° C.; DAD 254 nm.

Analytical Chiral HPLC (method see Example 25): $R_t$=1.91 min.

$^1$H-NMR (400 MHz, DMSO-d6) δ [ppm]: 1.021 (0.71), 1.038 (1.62), 1.056 (0.74), 1.137 (0.80), 1.154 (1.69), 1.173 (0.85), 1.376 (1.36), 1.394 (1.40), 2.518 (0.98), 2.523 (0.63), 2.539 (16.00), 2.903 (0.82), 2.920 (0.59), 3.365 (0.64), 3.383 (0.57), 3.532 (0.40), 3.549 (0.81), 6.542 (0.70), 6.561 (0.74), 6.614 (0.43), 6.989 (0.53), 7.008 (0.70), 7.010 (0.70), 7.029 (0.42), 7.090 (0.40), 7.103 (0.40), 7.133 (0.47), 7.155 (0.98), 7.178 (0.56), 7.390 (0.51), 7.404 (0.73), 7.409 (1.09), 7.425 (0.46), 8.004 (0.58), 8.018 (0.56), 8.191 (0.59), 10.497 (0.63), 11.730 (0.48).

Example 26

N-[4-(3-anilino-5-ethyl-4-oxo-4,5,6,7-tetrahydro-1H-pyrrolo[3,2-c]pyridin-2-yl)pyridin-2-yl]-2-(4-fluorophenyl)propanamide (Enantiomer 2)

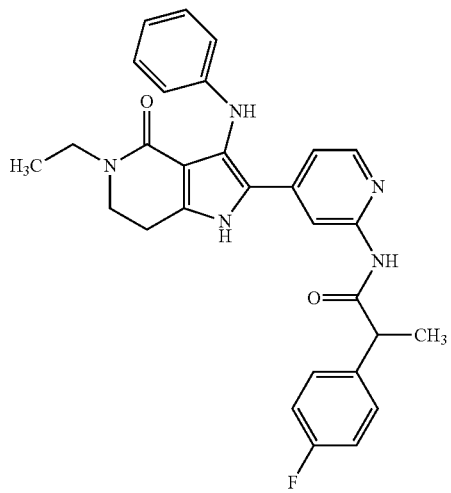 [SMILES: CCN1CCc2[nH]c(-c3ccnc(NC(=O)C(C)c4ccc(F)cc4)c3)c(Nc3ccccc3)c2C1=O]

For the preparation of the racemic title compound see Example 25. Separation of enantiomers by preparative chiral HPLC (method see Example 25) gave the title compound (23 mg).

Analytical Chiral HPLC (method see Example 25): $R_t$=2.94 min.

$^1$H-NMR (400 MHz, DMSO-d6) δ [ppm]: 0.743 (1.15), 0.762 (1.15), 0.776 (2.45), 0.795 (4.58), 0.814 (2.74), 0.819 (1.66), 0.836 (1.95), 0.844 (1.26), 0.851 (1.19), 0.862 (1.59), 0.880 (0.83), 0.929 (0.43), 0.968 (0.47), 0.973 (0.58), 1.006 (4.29), 1.021 (7.03), 1.038 (16.00), 1.056 (7.32), 1.084 (4.22), 1.095 (1.01), 1.100 (1.01), 1.112 (1.51), 1.131 (1.91), 1.153 (3.46), 1.179 (1.84), 1.196 (1.30), 1.204 (1.23), 1.233 (4.65), 1.259 (5.23), 1.285 (0.97), 1.304 (0.72), 1.376 (13.23), 1.394 (13.87), 1.422 (1.48), 1.425 (1.41), 1.440 (1.23), 1.444 (1.23), 1.459 (0.65), 1.527 (0.54), 1.538 (0.50), 1.543 (0.50), 1.593 (0.43), 1.610 (0.43), 2.332 (1.51), 2.336 (0.68), 2.518 (8.18), 2.523 (5.19), 2.539 (0.50), 2.886 (3.06), 2.903 (6.63), 2.920 (3.42), 3.365 (5.48), 3.383 (5.23), 3.401 (1.62), 3.532 (3.82), 3.549 (7.71), 3.566 (3.46), 3.979 (0.83), 3.996 (2.77), 4.014 (2.74), 4.031 (0.79), 6.541 (6.59), 6.561 (6.99), 6.596 (2.02), 6.614 (4.18), 6.632 (2.23), 6.989 (5.12), 7.008 (6.67), 7.010 (6.70), 7.029 (4.11), 7.084 (3.86), 7.089 (3.89), 7.098 (3.78), 7.102 (3.93), 7.133 (4.54), 7.138 (1.73), 7.150 (2.05), 7.155 (9.66), 7.161 (2.27), 7.173 (1.73), 7.178 (5.48), 7.185 (0.76), 7.390 (4.97), 7.395 (2.38), 7.409 (11.24), 7.420 (2.27), 7.426 (4.32), 8.004 (5.62), 8.017 (5.33), 8.193 (5.41), 10.495 (6.27), 10.514 (1.51), 10.635 (0.58), 10.851 (1.44), 11.728 (4.40).

Example 27

N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propanamide

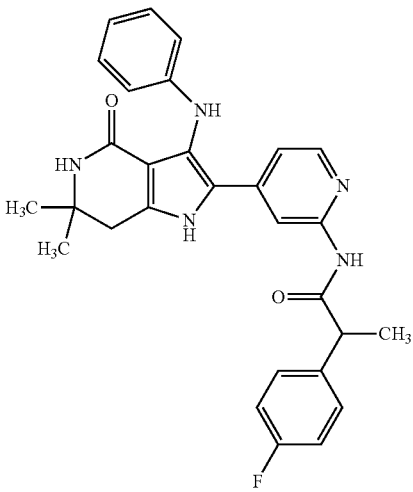 [SMILES: CC(C(=O)Nc1cc(-c2[nH]c3c(c2Nc2ccccc2)C(=O)NC(C)(C)C3)ccn1)c1ccc(F)cc1]

2-(2-Aminopyridin-4-yl)-3-anilino-6,6-dimethyl-1,5,6,7-tetrahydro-4H-pyrrolo[3,2-c]pyridin-4-one (see Intermediate 35, 110 mg, 71% purity) was diluted in 1.3 mL N,N-dimethylacetamide. 2-(4-Fluorophenyl)propanoic acid (75.6 mg, 450 µmol), N,N-diisopropylethylamine (230 µl, 1.3 mmol) and PyBOP (351 mg, 674 µmol) were added and stirred over night at rt under nitrogen atmosphere. The reaction mixture was diluted with saturated aqueous sodium hydrogencarbonate solution and ethyl acetate. The organic layer was extracted with water three times, filtered through a water resistant filter and concentrated under reduced pressure. The crude product was purified by HPLC under basic conditions twice to provide the target compound in 81% purity: 20 mg.

LC-MS (Method 2): $R_t$=1.19 min; MS (ESIpos): m/z=498 [M+H]$^+$ $^1$H-NMR (400 MHz, DMSO-d6) δ [ppm]: 1.232 (0.74), 1.256 (10.02), 1.284 (0.44), 1.375 (3.60), 1.393 (3.59), 1.955 (11.84), 2.331 (0.56), 2.518 (3.33), 2.522 (2.05), 2.673 (0.56), 2.781 (12.67), 2.941 (16.00), 3.997 (0.76), 4.015 (0.74), 6.545 (1.90), 6.564 (1.99), 6.566 (1.69), 6.583 (0.62), 6.601 (1.18), 6.619 (0.66), 6.986 (1.48), 7.004 (2.01), 7.007 (2.07), 7.015 (2.89), 7.025 (1.44), 7.039 (1.77), 7.101 (0.94), 7.105 (0.96), 7.114 (0.95), 7.118 (0.98), 7.133 (1.57), 7.143 (3.10), 7.155 (2.97), 7.172 (0.54), 7.177 (1.58), 7.270 (2.60), 7.338 (1.10), 7.389 (1.38), 7.395 (0.63), 7.403 (1.54), 7.411 (1.39), 7.420 (0.55), 7.425 (1.20), 8.005 (1.35), 8.019 (1.30), 8.175 (1.18), 10.504 (0.78), 11.715 (1.06).

Example 28

N-[4-(3-anilino-5-ethyl-4-oxo-4,5,6,7-tetrahydro-1H-pyrrolo[3,2-c]pyridin-2-yl)pyridin-2-yl]-2-(4-fluorophenyl)acetamide

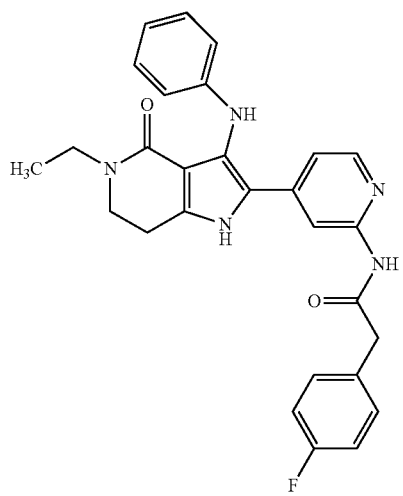 [SMILES: CCN1CCc2[nH]c(-c3ccnc(NC(=O)Cc4ccc(F)cc4)c3)c(Nc3ccccc3)c2C1=O]

2-(2-Aminopyridin-4-yl)-3-anilino-5-ethyl-1,5,6,7-tetrahydro-4H-pyrrolo[3,2-c]pyridin-4-one (see Intermediate 32, 22.0 mg, 87% purity) was dissolved in 320 µL N,N-dimethylacetamide. (4-Fluorophenyl)acetic acid (17.0 mg, 110 µmol), N,N-diisopropylethylamine (58 µl, 330 µmol) and PyBOP (86.0 mg, 165 µmol) were added and stirred over night at rt under nitrogen atmosphere. The reaction mixture was diluted with aqueous saturated sodium hydrogen carbonate solution and ethyl acetate. The organic layer was extracted with water thrice, filtered through a water resistant filter and concentrated under reduced pressure. The crude product was purified by column chromatography (Biotage, column: 11 g KP—NH, dichloromethane/ethanol, gradient: 0-10%) and by HPLC to provide the 87% pure target compound: 6.4 mg.

LC-MS (Method 2): $R_t$=1.18 min; MS (ESIpos): m/z=484 [M+H]$^+$ $^1$H-NMR (400 MHz, DMSO-d6) δ [ppm]: 1.012 (5.26), 1.030 (12.44), 1.048 (5.44), 1.171 (0.51), 1.229 (0.57), 2.518 (3.65), 2.523 (2.51), 2.534 (0.69), 2.538 (0.69), 2.871 (2.48), 2.888 (5.35), 2.905 (2.75), 3.299 (0.63), 3.319 (0.81), 3.374 (5.38), 3.389 (2.12), 3.520 (3.02), 3.537 (6.07), 3.554 (2.72), 3.685 (11.04), 3.708 (0.54), 6.540 (5.32), 6.559 (5.68), 6.596 (1.64), 6.615 (3.41), 6.633 (1.88), 6.989 (4.19), 7.008 (5.38), 7.010 (5.35), 7.029 (3.47), 7.111 (3.41), 7.116 (3.29), 7.126 (5.95), 7.143 (1.94), 7.148 (8.34), 7.154 (2.15), 7.166 (1.67), 7.171 (4.87), 7.178 (0.90), 7.264 (16.00), 7.325 (1.08), 7.333 (4.37), 7.338 (2.27), 7.347 (4.81), 7.354 (4.07), 7.363 (1.79), 7.369 (3.53), 7.388 (6.85), 8.031 (3.86), 8.045 (3.62), 8.172 (3.89), 10.554 (4.67), 11.754 (1.35).

Example 29

N-{4-[3-(2-fluoroanilino)-5-methyl-4-oxo-4,5,6,7-tetrahydro-1H-pyrrolo[3,2-c]pyridin-2-yl]pyridin-2-yl}-2-(4-fluorophenyl)propanamide

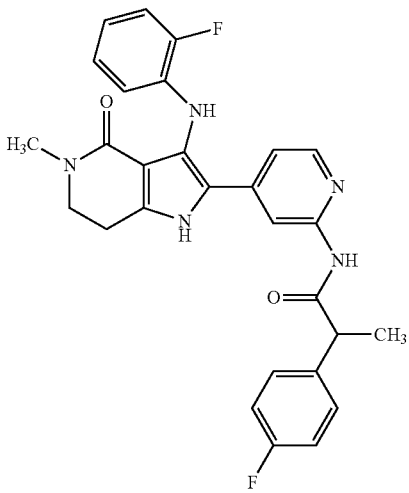 [SMILES: CC(C(=O)Nc1cc(-c2[nH]c3c(c2Nc2ccccc2F)C(=O)N(C)CC3)ccn1)c1ccc(F)cc1]

2-(2-Aminopyridin-4-yl)-3-(2-fluoroanilino)-5-methyl-1,5,6,7-tetrahydro-4H-pyrrolo[3,2-c]pyridin-4-one (see Intermediate 45, 63.0 mg) was dissolved in 1 mL N,N-dimethylacetamide. 2-(4-Fluorophenyl)propanoic acid (60.3 mg, 359 µmol), N,N-diisopropylethylamine (190 µL, 1.1 mmol) and PyBOP (280 mg, 538 µmol) were added and stirred over night at rt under nitrogen atmosphere. The reaction mixture was diluted with aqueous saturated sodium hydrogencarbonate solution and ethyl acetate. The organic layer was extracted with water three times, filtered through a water resistant filter and concentrated under reduced pressure. The crude product was purified by HPLC under basic conditions to provide the target compound in 90% purity: 18 mg.

LC-MS (Method 2): $R_t$=1.22 min; MS (ESIpos): m/z=503 [M+H]$^+$ $^1$H-NMR (400 MHz, DMSO-d6): δ [ppm]=1.37 (d, 3H), 2.87 (s, 3H), 2.93 (t, 2H), 3.55 (t, 2H), 3.99 (q, 1H), 6.13-6.29 (m, 1H), 6.58-6.69 (m, 1H), 6.70-6.78 (m, 1H), 7.05-7.22 (m, 4H), 7.34-7.44 (m, 3H), 8.06 (d, 1H), 8.20 (d, 1H), 10.51 (s, 1H), 11.82 (s, 1H).

Example 30

N-[4-(3-anilino-5-methyl-4-oxo-4,5,6,7-tetrahydro-1H-pyrrolo[3,2-c]pyridin-2-yl)pyridin-2-yl]-4-(morpholin-4-yl)-2-phenylbutanamide

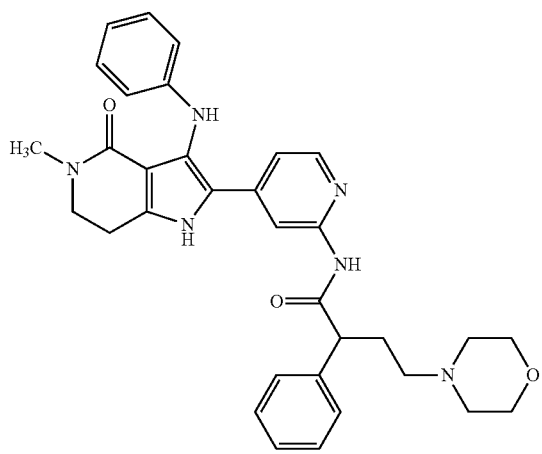 [SMILES: CN1CCc2[nH]c(-c3ccnc(NC(=O)C(CCN4CCOCC4)c4ccccc4)c3)c(Nc3ccccc3)c2C1=O]

To a stirred suspension of 4-[3-carboxy-3-phenylpropyl]morpholin-4-ium chloride (216 mg, approx. 50% purity, 378 µmol); (see Intermediate 51) in DMA (6 mL) was added 2-(2-aminopyridin-4-yl)-3-anilino-5-methyl-1,5,6,7-tetrahydro-4H-pyrrolo[3,2-c]pyridin-4-one (see Intermediate 3) (105 mg, 315 µmol), N,N-dimethylpyridin-4-amine (7.70 mg, 63.0 µmol), N-ethyl-N-(propan-2-yl)propan-2-amine (330 µl, 1.9 mmol) and T3P (370 µl, 50% w/w in ethyl acetate, 630 µmol). The mixture was stirred at 120° C. for 16 h. The solution was concentrated in vacuum. An aqueous solution of sodium bicarbonate was added and the mixture was extracted with dichloromethane. The organic phase was filtered through a silicone filter and the solvent was removed in vacuum. Aminophase-silicagel chromatography followed by silicagel chromatography and preparative reverse phase HPLC (gradient of acetonitrile and water containing formic acid as additive) gave 75.0 mg of the title compound.

LC-MS (Method 2): $R_t$=1.14 min; MS (ESIpos): m/z=565 [M+H]$^+$ $^1$H-NMR (400 MHz, DMSO-d6) δ [ppm]: 1.65-1.82 (m, 1H), 2.15-2.39 (m, 7H), 2.86 (s, 3H), 2.92 (t, 2H), 3.44-3.59 (m, 6H), 3.85-3.98 (m, 1H), 6.51-6.57 (m, 2H), 6.60 (t, 1H), 7.00 (dd, 2H), 7.10 (dd, 1H), 7.19-7.26 (m, 1H), 7.31 (t, 2H), 7.35-7.43 (m, 3H), 8.01 (d, 1H), 8.22 (s, 1H), 10.47 (s, 1H), 11.72 (s, 1H).

Example 31

N-[4-(3-anilino-5-methyl-4-oxo-4,5,6,7-tetrahydro-1H-pyrrolo[3,2-c]pyridin-2-yl)pyridin-2-yl]-4-(morpholin-4-yl)-2-phenylbutanamide, (Stereoisomer 1)

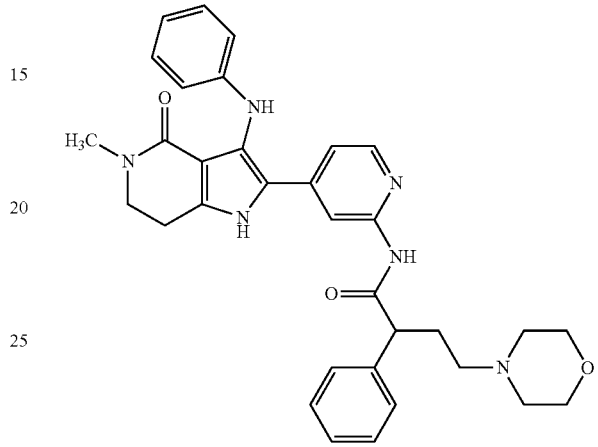

Racemic N-[4-(3-anilino-5-methyl-4-oxo-4,5,6,7-tetrahydro-1H-pyrrolo[3,2-c]pyridin-2-yl)pyridin-2-yl]-4-(morpholin-4-yl)-2-phenylbutanamide (62 mg) was separated into the single stereoisomers (Example 31 and Example 32) via preparative, chiral HPLC.

Instrument: Sepiatec: Prep SFC100;
Column: Chiralpak IA 5µ 250×30 mm;
Eluent: Eluent A: $C_{O2}$; Eluent B: 2-Propanol+0.2% Diethylamin (99%); Isokratic: 35% B;
Flow: 100 ml/min;
Temperature: 40° C.;
BPR: 150 bar;
Detection: UV: 254 nm;
Injected solution: 62 mg racemic N-[4-(3-anilino-5-methyl-4-oxo-4,5,6,7-tetrahydro-1H-pyrrolo[3,2-c]pyridin-2-yl)pyridin-2-yl]-4-(morpholin-4-yl)-2-phenylbutanamide in 1 mL Dichlormethane/Aceton/DMSO=1:1:0.2
Analytical Chiral HPLC Method 5
Instrument: Agilent: 1260, Aurora SFC-Modul;
Column: Chiralpak IA 5µ 100×4.6 mm;
Eluent: Eluent A: $CO_2$; Eluent B: 2-Propanol+0.2% Diethylamin (99%); Isokratic: 35% B;
Flow: 4 ml/min;
Temperature: 37.5° C.;
BPR: 100 bar;
Detection: UV: 254 nm;

|  | Retention time in min | e.e. [%] | yield |
|---|---|---|---|
| Example 31 Stereoisomer 1 Peak 1 | 9.3-11.5 | >99.9% | Crude product: 39 mg |
| Example 32 Stereoisomer 2 Peak 2 | 16.9-20.3 | >99.9% | Crude Product: 39 mg |

The crude product of Peak 1 (Stereoisomer 1) was triturated with hexane/ethyl acetate (4:1) to give 12.5 mg of the title compound (Stereoisomer 1).

Analytical Chiral HPLC (Method 5): $R_t$=2.3 min (e.e.: >99.9%)

$[α]_D$=132.4° (from solution in DMSO, c=2.22 mg/mL)

LC-MS (Method 2): $R_t$=1.14 min; MS (ESIneg): m/z=563 [M−H]⁻

¹H NMR (400 MHz, DMSO-d6) δ [ppm]: 1.68-1.82 (m, 1H), 2.16-2.40 (m, 7H), 2.86 (s, 3H), 2.92 (t, 2H), 3.44-3.59 (m, 6H), 3.86-3.97 (m, 1H), 6.52-6.57 (m, 2H), 6.60 (t, 1H), 6.97-7.04 (m, 2H), 7.10 (dd, 1H), 7.20-7.26 (m, 1H), 7.31 (t, 2H), 7.35-7.42 (m, 3H), 8.01 (d, 1H), 8.21 (s, 1H), 10.47 (s, 1H), 11.72 (s, 1H)

Example 32

N-[4-(3-anilino-5-methyl-4-oxo-4,5,6,7-tetrahydro-1H-pyrrolo[3,2-c]pyridin-2-yl)pyridin-2-yl]-4-(morpholin-4-yl)-2-phenylbutanamide, (Stereoisomer 2)

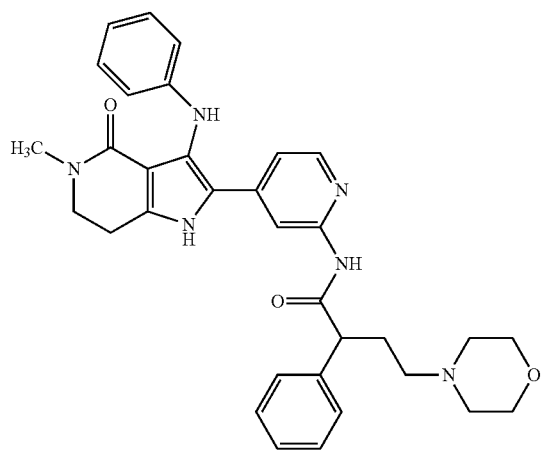 [SMILES: CN1CCc2[nH]c(-c3ccnc(NC(=O)C(CCN4CCOCC4)c4ccccc4)c3)c(Nc3ccccc3)c2C1=O]

The crude product of Peak 2 (Stereoisomer 2) was triturated with hexane/ethyl acetate (4:1) to give 12.2 mg of the title compound (Stereoisomer 2).

Analytical Chiral HPLC (Method 5): $R_t$=4.01 min (e.e.: >99.9%)

$[α]_D$=−120.1° (from solution in DMSO, c=2.20 mg/mL)

LC-MS (Method 2): $R_t$=1.13 min; MS (ESIpos): m/z=565 [M+H]⁺

¹H-NMR (400 MHz, DMSO-d6) δ [ppm]: 0.698 (0.66), 0.832 (0.72), 0.837 (0.48), 0.853 (0.58), 0.859 (0.61), 1.108 (2.30), 1.154 (0.77), 1.172 (1.27), 1.190 (0.64), 1.232 (1.19), 1.294 (0.40), 1.733 (0.61), 1.746 (0.48), 1.988 (2.23), 2.239 (1.75), 2.268 (1.70), 2.282 (1.59), 2.318 (1.72), 2.323 (2.28), 2.327 (2.68), 2.331 (2.09), 2.336 (1.35), 2.518 (7.07), 2.523 (4.50), 2.660 (0.50), 2.665 (1.14), 2.669 (1.59), 2.673 (1.14), 2.678 (0.50), 2.863 (16.00), 2.903 (1.48), 2.921 (3.21), 2.938 (1.67), 3.386 (0.74), 3.494 (4.29), 3.504 (2.75), 3.518 (2.30), 3.535 (3.95), 3.553 (1.67), 3.898 (0.66), 3.918 (0.95), 3.932 (0.56), 4.018 (0.48), 4.035 (0.45), 6.535 (3.23), 6.554 (3.42), 6.557 (2.86), 6.584 (0.98), 6.602 (2.04), 6.621 (1.09), 6.981 (2.57), 6.999 (3.23), 7.002 (3.18), 7.020 (2.01), 7.087 (1.85), 7.091 (1.77), 7.101 (1.77), 7.105 (1.83), 7.208 (0.69), 7.221 (0.56), 7.227 (1.88), 7.232 (0.74), 7.245 (1.43), 7.293 (2.17), 7.312 (3.84), 7.331 (2.09), 7.369 (4.03), 7.386 (3.79), 7.403 (2.62), 7.407 (1.88), 8.004 (2.49), 8.018 (2.36), 8.214 (2.41), 10.472 (2.60), 11.719 (2.25).

Example 33

N-[4-(3-anilino-5-methyl-4-oxo-4,5,6,7-tetrahydro-1H-pyrrolo[3,2-c]pyridin-2-yl)pyridin-2-yl]-4,4-difluoro-2-phenylbutanamide

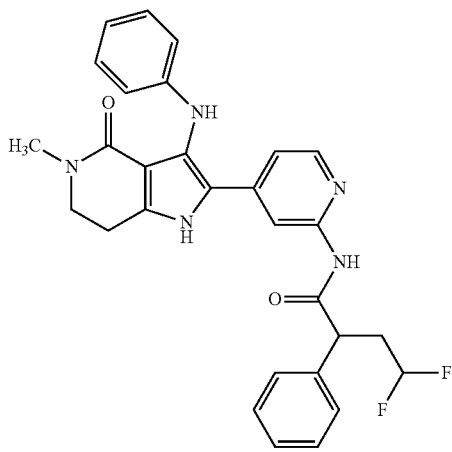 [SMILES: CN1CCc2[nH]c(-c3ccnc(NC(=O)C(CC(F)F)c4ccccc4)c3)c(Nc3ccccc3)c2C1=O]

To a stirred solution of 2-(2-aminopyridin-4-yl)-3-anilino-5-methyl-1,5,6,7-tetrahydro-4H-pyrrolo[3,2-c]pyridin-4-one (200 mg, 600 µmol) (see Intermediate 3) in DMA (2 mL) was added 4,4-difluoro-2-phenylbutanoic acid (360 mg, 1.80 mmol) (see Intermediate 55), N,N-diisopropylethylamine (630 µl, 3.6 mmol) and PyBOP (936 mg, 1.80 mmol). The mixture was stirred at room temperature for 16 h. An aqueous solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Aminophase-silicagel chromatography followed by preparative reverse phase HPLC (gradient of water and acetonitrile containing ammonia as additive) gave 161 mg (69% yield) of the title compound.

LC-MS (Method 2): $R_t$=1.22 min; MS (ESIpos): m/z=516 [M+H]⁺

¹H NMR (400 MHz, DMSO-d6) δ [ppm]: 2.11-2.29 (m, 1H), 2.62-2.80 (m, 1H), 2.87 (s, 3H), 2.93 (t, 2H), 3.54 (t, 2H), 4.14 (dd, 1H), 5.94 (tt, 1H), 6.52-6.57 (m, 2H), 6.61 (t, 1H), 7.01 (dd, 2H), 7.13 (dd, 1H), 7.23-7.30 (m, 1H), 7.32-7.45 (m, 5H), 8.02 (d, 1H), 8.18 (s, 1H), 10.62 (s, 1H), 11.74 (s, 1H)

Example 34

N-[4-(3-anilino-5-methyl-4-oxo-4,5,6,7-tetrahydro-1H-pyrrolo[3,2-c]pyridin-2-yl)pyridin-2-yl]-4,4-difluoro-2-phenylbutanamide, (Stereoisomer 1)

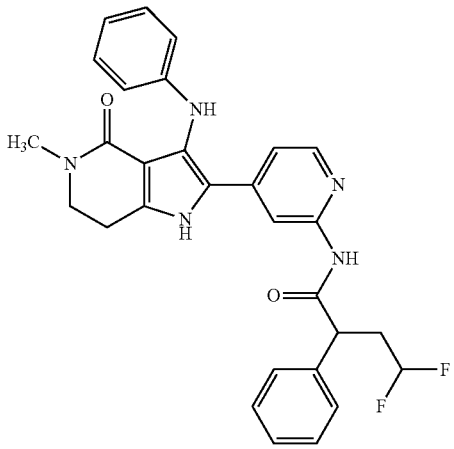 [SMILES: CN1CCc2[nH]c(-c3ccnc(NC(=O)C(CC(F)F)c4ccccc4)c3)c(Nc3ccccc3)c2C1=O]

Racemic N-[4-(3-anilino-5-methyl-4-oxo-4,5,6,7-tetrahydro-1H-pyrrolo[3,2-c]pyridin-2-yl)pyridin-2-yl]-4,4-difluoro-2-phenylbutanamide (150 mg, 291 µmol) was separated into the single stereoisomers (Example 34 and Example 35) via preparative, chiral HPLC.

Instrument: Sepiatec: Prep SFC100;
Column: Chiralpak IA 5µ 250×30 mm;
Eluent: eluent A: $CO_2$; eluent B: 2-propanol+0.4 vol % diethylamin; isocratic: 35% B;
Flow: 100 ml/min;
Temperature: 40° C.;
BPR: 150 bar;
Detection: UV: 280 nm;
Injected solution: 62 mg racemic N-[4-(3-anilino-5-methyl-4-oxo-4,5,6,7-tetrahydro-1H-pyrrolo[3,2-c]pyridin-2-yl)pyridin-2-yl]-4-(morpholin-4-yl)-2-phenylbutanamide in 1 mL Dichlormethane/Aceton/DMSO=1:1:0.2

Analytical Chiral HPLC Method 6
Instrument: Agilent: 1260, Aurora SFC-Modul;
Column: Chiralpak IA 5µ 100×4.6 mm;
Eluent: eluent A: $C_{O2}$; eluent B: 2-propanol+0.2% vol % diethylamin; isokratic: 35% B;
Flow: 4 ml/min;
Temperature: 37.5° C.;
BPR: 100 bar;
Detection: UV: 280 nm;

| | Retention time in min | e.e. [%] | yield | Optical rotation $[\alpha]_D$ |
|---|---|---|---|---|
| Example 34 Stereoisomer 1 Peak 1 | 10.0-11.5 | 98.1% | 34 mg | 132.4° (from solution in DMSO, c = 2.22 mg/mL) |
| Example 35 Stereoisomer 2 Peak 2 | 12.8-15.0 | 96.0% | 44 mg | −196.4° (from solution in DMSO, c = 2.9 mg/mL) |

Isolated Stereoisomer 1: 34 mg

Analytical Chiral HPLC (Method 6): $R_t$=2.15 min (e.e.: 98.1%)

$[a]_D$=212.8° (from solution in DMSO, c=3.7 mg/mL)

LC-MS (Method 2): $R_t$=1.21 min; MS (ESIpos): m/z=516 $[M+H]^+$ $^1$H NMR (400 MHz, DMSO-$d_6$) δ [ppm]: 2.11-2.30 (m, 1H), 2.62-2.80 (m, 1H), 2.86 (s, 3H), 2.93 (t, 2H), 3.54 (t, 2H), 4.14 (dd, 1H), 5.95 (tt, 1H), 6.52-6.57 (m, 2H), 6.61 (t, 1H), 6.97-7.05 (m, 2H), 7.13 (dd, 1H), 7.24-7.30 (m, 1H), 7.31-7.44 (m, 5H), 8.02 (d, 1H), 8.18 (s, 1H), 10.62 (s, 1H), 11.74 (s, 1H).

Example 35

N-[4-(3-anilino-5-methyl-4-oxo-4,5,6,7-tetrahydro-1H-pyrrolo[3,2-c]pyridin-2-yl)pyridin-2-yl]-4,4-difluoro-2-phenylbutanamide, (Stereoisomer 2)

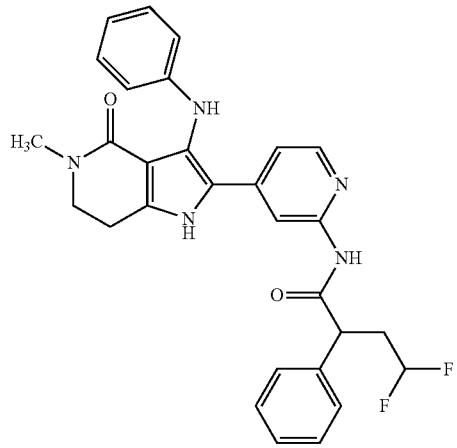 [SMILES: CN1CCc2[nH]c(-c3ccnc(NC(=O)C(CC(F)F)c4ccccc4)c3)c(Nc3ccccc3)c2C1=O]

Isolated Stereoisomer 2: 44 mg

Analytical Chiral HPLC (Method 6): $R_t$=3.03 min (e.e.: 96.0%)

$[a]_D$=−196.4° (from solution in DMSO, c=2.9 mg/mL)

LC-MS (Method 2): $R_t$=1.21 min; MS (ESIpos): m/z=516 $[M+H]^+$ $^1$H NMR (400 MHz, DMSO-$d_6$) δ [ppm]: 2.11-2.29 (m, 1H), 2.62-2.80 (m, 1H), 2.86 (s, 3H), 2.93 (t, 2H), 3.54 (t, 2H), 4.14 (dd, 1H), 5.94 (tt, 1H), 6.55 (d, 2H), 6.61 (t, 1H), 6.97-7.05 (m, 2H), 7.13 (dd, 1H), 7.24-7.30 (m, 1H), 7.31-7.45 (m, 5H), 8.02 (d, 1H), 8.18 (s, 1H), 10.62 (s, 1H), 11.74 (s, 1H)

Example 36

N-{4-[3-anilino-4-oxo-5-(2,2,2-trifluoroethyl)-4,5,6,7-tetrahydro-1H-pyrrolo[3,2-c]pyridin-2-yl]pyridin-2-yl}-2-(4-fluorophenyl)acetamide

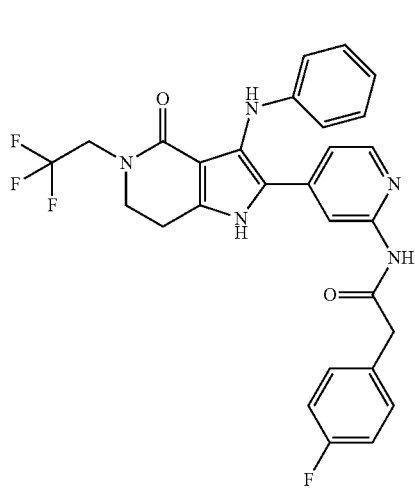 [SMILES: O=C(Cc1ccc(F)cc1)Nc1cc(-c2[nH]c3c(c2Nc2ccccc2)C(=O)N(CC(F)(F)F)CC3)ccn1]

2-(2-Aminopyridin-4-yl)-3-anilino-5-(2,2,2-trifluoroethyl)-1,5,6,7-tetrahydro-4H-pyrrolo[3,2-c]pyridin-4-one (see Intermediate 64, 75 mg), (4-fluorophenyl)acetic acid (57.6 mg, 374 μmol), PyBOP (486 mg, 934 μmol) and N,N-diisopropylethylamine (200 μL, 1.1 mmol) were dissolved in 1.2 mL N,N-dimethylacetamide and stirred at rt over night under argon atmosphere. Aqueous saturated sodium hydrogencarbonate solution was added and the reaction mixture was diluted with dichloromethane and water. The aqueous layer was extracted with dichloromethane three times. The combined organic layers were washed with water three times and with brine once, filtered through a silicone coated filter and concentrated under reduced pressure. The crude product was combined with another batch starting from Intermediate 64 (70 mg) and purified by flash chromatography (11 g column, aminophase; dichloromethane/ethanol 0%-5%) and HPLC under basic condition. The residue was treated with methyl tertbutylether and was sonicated. The undissolved precipitate was filtered off, washed with MTBE and dried at 50° C. under vacuo to provide the target compound in 92% purity: 49 mg LC-MS (Method 2): $R_t$=1.27 min; MS (ESIpos): m/z=539 $[M+H]^+$ 1H-NMR (400 MHz, DMSO-d6): δ [ppm]=2.94 (s, 2H), 3.62-3.73 (m, 4H), 4.18 (br d, 2H), 6.55 (d, 2H), 6.60 (t, 1H), 6.96-7.06 (m, 2H), 7.10-7.20 (m, 3H), 7.31 (s, 1H), 7.33-7.41 (m, 2H), 8.07 (d, 1H), 8.21 (s, 1H), 10.58 (s, 1H), 11.90 (s, 1H).

Example 37

N-{4-[3-anilino-4-oxo-5-(2,2,2-trifluoroethyl)-4,5,6,7-tetrahydro-1H-pyrrolo[3,2-c]pyridin-2-yl]pyridin-2-yl}-2-(4-fluorophenyl)propanamide

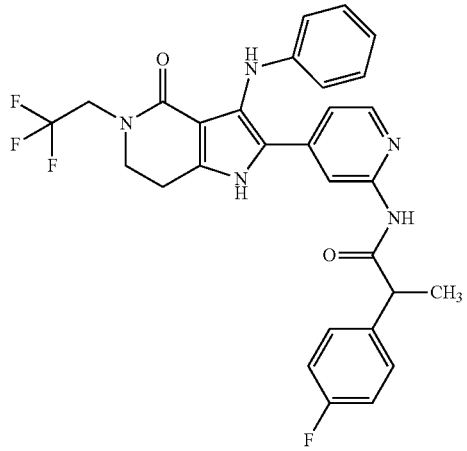 [SMILES: CC(C(=O)Nc1cc(-c2[nH]c3c(c2Nc2ccccc2)C(=O)N(CC(F)(F)F)CC3)ccn1)c1ccc(F)cc1]

2-(2-Aminopyridin-4-yl)-3-anilino-5-(2,2,2-trifluoroethyl)-1,5,6,7-tetrahydro-4H-pyrrolo[3,2-c]pyridin-4-one (see Intermediate 64, 75.0 mg), 2-(4-fluorophenyl)propanoic acid (62.8 mg, 374 μmol), PYBOP (486 mg, 934 μmol) and N,N-diisopropylethylamine (200 μl, 1.1 mmol) were dissolved in 1.2 mL N,N-dimethylacetamide and the reaction mixture was stirred at rt over night under argon atmosphere. Aqueous saturated sodium hydrogencarbonate solution were added and the reaction mixture was diluted with dichloromethane and water. It was stirred for a few minutes, filtered through a silicone coated filter and concentrated under reduced pressure. The crude product was purified by flash chromatography (11 g column, aminophase; dichloromethane/ethanol 0%-5%) and HPLC under basic conditions to provide the target compound in 84% purity: 34 mg.

LC-MS (Method 2): $R_t$=1.32 min; MS (ESIpos): m/z=553 $[M+H]^+$

1H-NMR (400 MHz, DMSO-d6): δ [ppm]=1.39 (d, 3H), 2.95 (t, 2H), 3.69 (t, 2H), 3.97-4.07 (m, 1H), 4.19 (q, 2H), 6.48-6.69 (m, 3H), 6.94-7.07 (m, 2H), 7.11-7.22 (m, 3H), 7.32 (s, 1H), 7.37-7.51 (m, 2H), 8.04 (d, 1H), 8.22 (d, 1H), 10.52 (s, 1H), 11.91 (s, 1H).

Example 38

N-[4-(3-anilino-5-methyl-4-oxo-4,5,6,7-tetrahydro-1H-pyrrolo[3,2-c]pyridin-2-yl)pyridin-2-yl]-4-(dimethylamino)-2-phenylbutanamide

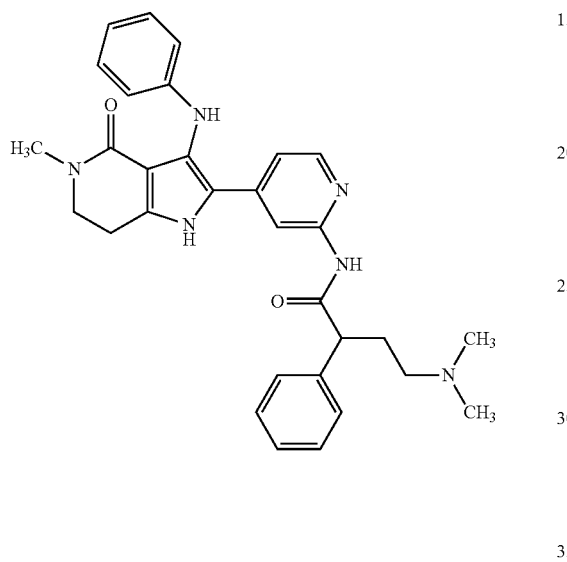

To a stirred suspension of 4-(dimethylamino)-2-phenylbutanoic acid hydrogen chloride salt (see Intermediate 66, 351 mg, approx. 50% purity, approx. 720 μmol) in DMA (12 mL) was added molecular sives (4 Å; 200 mg) and the mixture was stirred for 3 h. The mixture was filtered through a syringe filter and 2-(2-aminopyridin-4-yl)-3-anilino-5-methyl-1,5,6,7-tetrahydro-4H-pyrrolo[3,2-c]pyridin-4-one (120 mg, 360 μmol) (see Intermediate 3), N,N-dimethylpyridin-4-amine (17.6 mg, 144 μmol), N-ethyl-N-(propan-2-yl)propan-2-amine (750 μl, 4.3 mmol) and T3P (860 μl, 50% w/w in ethyl acetate, 1.4 mmol) were added. The mixture was stirred at 120° C. for 16 h. Water was added, the mixture was stirred for 15 min and the solution was concentrated in vacuum. An aqueous solution of potassium carbonate was added and the mixture was extracted with a mixture of chloroform and methanol (10:1). The organic phase was filtered through a silicone filter and the solvent was removed in vacuum. Aminophase-silicagel chromatography followed by preparative reverse phase HPLC (gradient of water and acetonitrile containing ammonium hydroxide as additive) gave 10.0 mg (5% yield) of the title compound.

LC-MS (Method 2): $R_t$=1.17 min; MS (ESIneg): m/z=521 [M−H]$^-$ $^1$H-NMR (400 MHz, DMSO-d6) δ [ppm]: 1.71-1.82 (m, 1H), 2.06-2.25 (m, 9H), 2.86 (s, 3H), 2.93 (t, 2H), 3.54 (t, 2H), 3.86-3.97 (m, 1H), 6.52-6.57 (m, 2H), 6.58-6.64 (m, 1H), 7.01 (dd, 2H), 7.11 (dd, 1H), 7.20-7.26 (m, 1H), 7.28-7.34 (m, 2H), 7.35-7.43 (m, 3H), 8.01 (d, 1H), 8.21 (d, 1H), 10.46 (s, 1H), 11.73 (s, 1H).

Example 39

N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propanamide (Enantiomer 1)

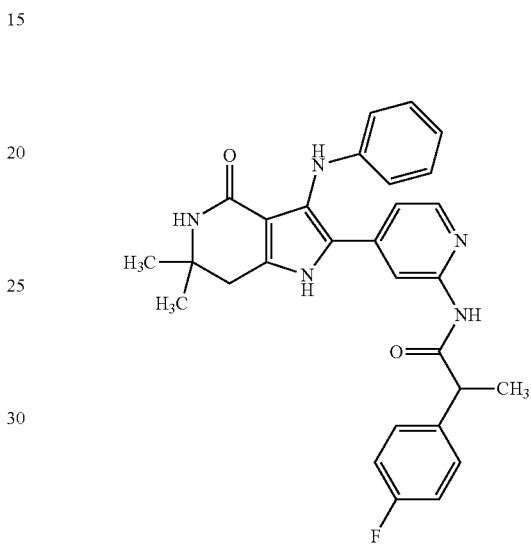

The racemic compound (Example 27, 110 mg) was separated into enantiomers by preparative chiral HPLC to give enantiomer 1 (15 mg, >99.9% ee after dual separation, see Example 39) and enantiomer 2 (31 mg after further purification, >99.9% ee, see Example 40).

Preparative Chiral HPLC Method:

Instrument: PrepCon Labomatic HPLC; Column: YMC Cellulose SB 5p, 250×30; eluent A: hexane+0.1 vol % diethylamine; eluent B: ethanol; gradient: 0-5 min 15-40% B; flow: 50 mL/min; temperature: 35° C.; UV: 280 nm;

Analytical Chiral HPLC Method:

Instrument: Waters Alliance 2695; Column: YMC Cellulose SB 3μ, 100×4.6; eluent A: hexane+0.1 vol % diethylamine; eluent B: ethanol; gradient: 0-7 min 20-50% B; flow: 1.4 mL/min; temperature: 25° C.; UV: 280 nm;

Analytical Chiral HPLC (method see Example 39): $R_t$=1.77 min.

$^1$H-NMR (400 MHz, DMSO-d6) δ [ppm]=1.26 (s, 6H), 1.39 (d, 3H), 2.78 (s, 2H), 4.01 (q, 1H), 6.51-6.67 (m, 3H), 6.96-7.06 (m, 3H), 7.07-7.20 (m, 3H), 7.34 (s, 1H), 7.41 (dd, 2H), 8.01 (d, 1H), 8.18 (s, 1H), 10.50 (s, 1H), 11.70 (s, 1H).

Example 40

(+)-N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propanamide (Enantiomer 2)

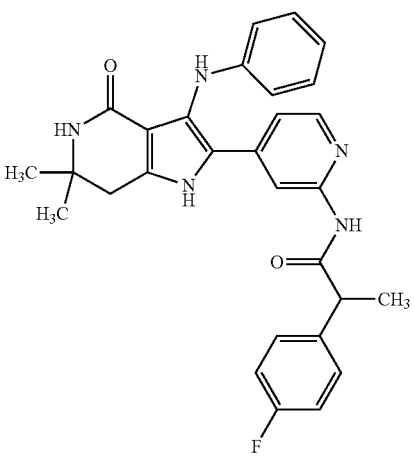 [SMILES: CC(C(=O)Nc1cc(-c2[nH]c3c(c2Nc2ccccc2)C(=O)NC(C)(C)C3)ccn1)c1ccc(F)cc1]

For the separation of the racemic title compound see Example 39. For further purification Enantiomer 2 (see Example 40) was dissolved in dichloromethane and treated with saturated ammonium chloride solution. It was stirred intensively for 5 minutes, the organic layer was filtered through a silicone coated filter and concentrated under reduced pressure to provide the target compound: 31 mg.

Analytical Chiral HPLC (method see Example 39): $R_t$=2.30 min.

$[a]_D$=+145.5° (from solution in methanol, c=4.7 mg/mL)

LC-MS (Method 1): $R_t$=1.08 min; MS (ESIpos): m/z=499 [M+H]$^+$ $^1$H-NMR (400 MHz, DMSO-d6) δ [ppm]=1.26 (s, 6H), 1.39 (d, 3H), 2.78 (s, 2H), 4.01 (q, 1H), 6.48-6.65 (m, 3H), 6.97-7.06 (m, 3H), 7.08-7.21 (m, 3H), 7.33 (s, 1H), 7.38-7.46 (m, 2H), 8.01 (d, 1H), 8.18 (s, 1H), 10.49 (s, 1H), 11.70 (s, 1H).

Example 41

(−)-N-{4-[3-(2-fluoroanilino)-5-methyl-4-oxo-4,5,6,7-tetrahydro-1H-pyrrolo[3,2-c]pyridin-2-yl]pyridin-2-yl}-2-(4-fluorophenyl)propanamide (Enantiomer 1)

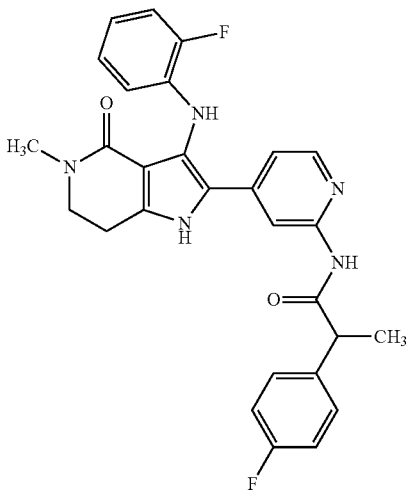 [SMILES: CC(C(=O)Nc1cc(-c2[nH]c3c(c2Nc2ccccc2F)C(=O)N(C)CC3)ccn1)c1ccc(F)cc1]

The racemic compound (see Example 29, 82 mg) was separated into enantiomers by preparative chiral HPLC to give enantiomer 1 (40 mg, 100% ee, see Example 41) and enantiomer 2 (33 mg, 100% ee, see Example 42).

Preparative Chiral HPLC Method:

Instrument: PrepCon Labomatic HPLC; Column: YMC Cellulose SB 5μ, 250×30; eluent A: hexane+0.1 vol % diethylamine; eluent B: ethanol; isocratic: 90% A+10% B; flow: 50 mL/min; temperature: 25° C.; UV: 254 nm.

Analytical Chiral HPLC Method:

Instrument: Waters Alliance 2695; Column: YMC Cellulose SB 3μ, 100×4.6; eluent A: hexane+0.1 vol % diethylamine; eluent B: ethanol; isocratic: 90% A+10% B; flow: 1.4 mL/min; temperature: 25° C.; UV: 254 nm.

Analytical Chiral HPLC (method see Example 41): $R_t$=3.45 min.

$[a]_D$=−149.3° (from solution in methanol, c=3.5 mg/mL)

$^1$H-NMR (400 MHz, DMSO-d6) δ [ppm]=1.37 (d, 3H), 2.87 (s, 3H), 2.93 (t, 2H), 3.55 (t, 2H), 3.99 (q, 1H), 6.19-6.31 (m, 1H), 6.65 (ddd, 1H), 6.71-6.78 (m, 1H), 7.04-7.23 (m, 4H), 7.34-7.46 (m, 3H), 8.06 (d, 1H), 8.20 (d, 1H), 10.51 (s, 1H), 11.82 (s, 1H).

Example 42

N-{4-[3-(2-fluoroanilino)-5-methyl-4-oxo-4,5,6,7-tetrahydro-1H-pyrrolo[3,2-c]pyridin-2-yl]pyridin-2-yl}-2-(4-fluorophenyl)propanamide (Enantiomer 2)

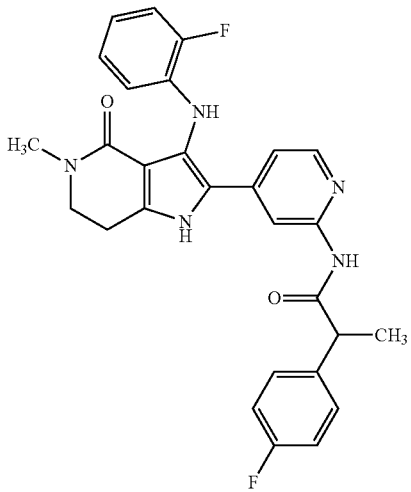 [SMILES: CC(C(=O)Nc1cc(-c2[nH]c3c(c2Nc2ccccc2F)C(=O)N(C)CC3)ccn1)c1ccc(F)cc1]

For the preparation of the racemic title compound see Example 29. Separation of enantiomers by preparative chiral HPLC (method see Example 41) gave the title compound (33 mg).

Analytical Chiral HPLC (method see Example 41): $R_t$=6.05 min.

$^1$H-NMR (400 MHz, DMSO-d6) δ [ppm]=1.37 (d, 3H), 2.87 (s, 3H), 2.93 (t, 2H), 3.55 (t, 2H), 3.99 (d, 1H), 6.16-6.29 (m, 1H), 6.60-6.68 (m, 1H), 6.70-6.79 (m, 1H), 7.05-7.22 (m, 4H), 7.35-7.44 (m, 3H), 8.06 (d, 1H), 8.20 (d, 1H), 10.51 (s, 1H), 11.82 (s, 1H).

Example 43

N-{4-[3-anilino-4-oxo-6-(trifluoromethyl)-4,5,6,7-tetrahydro-1H-pyrrolo[3,2-c]pyridin-2-yl]pyridin-2-yl}-2-(4-fluorophenyl)acetamide (Racemate)

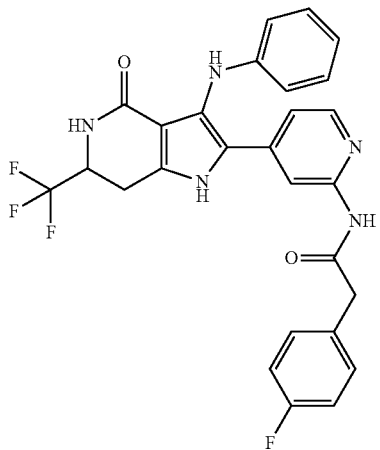 [SMILES: O=C(Cc1ccc(F)cc1)Nc1cc(-c2[nH]c3c(c2Nc2ccccc2)C(=O)NC(C(F)(F)F)C3)ccn1]

2-(2-Aminopyridin-4-yl)-3-anilino-6-(trifluoromethyl)-1,5,6,7-tetrahydro-4H-pyrrolo[3,2-c]pyridin-4-one (Racemate) (see Intermediate 69, 24.0 mg), (4-fluorophenyl)acetic acid (19.1 mg, 124 µmol), PyBOP (161 mg, 310 µmol; CAS-RN: [128625-52-5]) and N,N-diisopropylethylamine (65 µL, 370 µmol) were dissolved in 410 µL DMF and were stirred at rt over night under argon atmosphere. 4-Fluorophenyl)acetic acid (19.1 mg, 124 µmol) and N,N-diisopropylethylamine (65 µL, 370 µmol) were added and it was stirred at rt for 2 days. To the reaction mixture aqueous saturated sodium hydrogencarbonate solution was added and it was diluted with dichloromethane and water. The layers were separated. The aqueous layer was extracted with dichloromethane three times. The combined organic layers were washed with water three times and with brine once, filtered through a silicone coated filter and concentrated under reduced pressure. The crude product was purified by HPLC under basic conditions to provide the target compound in 82% purity: 8 mg.

LC-MS (Method 2): $R_t$=1.14 min; MS (ESIpos): m/z=524 $[M+H]^+$ $^1$H-NMR (400 MHz, DMSO-d6) δ [ppm]=3.01 (dd, 1H), 3.36-3.41 (m, 1H), 3.70 (s, 2H), 4.36-4.42 (m, 1H), 6.49-6.55 (m, 2H), 6.57-6.63 (m, 1H), 7.00 (dd, 2H), 7.11-7.21 (m, 3H), 7.28 (s, 1H), 7.31-7.41 (m, 2H), 7.79 (d, 1H), 8.07 (d, 1H), 8.19 (s, 1H), 10.60 (s, 1H), 11.84 (s, 1H).—contains ethanol.

Example 44

N-[4-(3-anilino-5,6,6-trimethyl-4-oxo-4,5,6,7-tetrahydro-1H-pyrrolo[3,2-c]pyridin-2-yl)pyridin-2-yl]-2-(4-fluorophenyl)acetamide

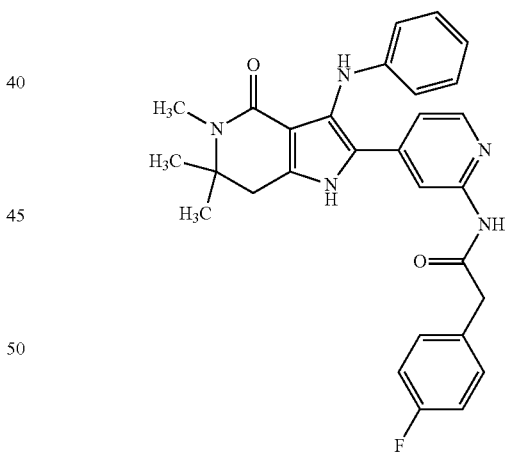

2-(2-Aminopyridin-4-yl)-3-anilino-5,6,6-trimethyl-1,5,6,7-tetrahydro-4H-pyrrolo[3,2-c]pyridin-4-one (see Intermediate 72, 14.0 mg), (4-fluorophenyl)acetic acid (11.9 mg, 77.5 µmol), PyBOP (101 mg, 194 µmol) and N,N-diisopropylethylamine (40 µL, 230 µmol) were dissolved in in 220 µL DMF and were stirred at rt under argon atmosphere over night. To the reaction mixture aqueous saturated sodium hydrogencarbonate solution was added and it was diluted with dichloromethane and water. The layers were separated. The aqueous layer was extracted with dichloromethane three times. The combined organic layers were washed with water three times and with brine once, filtered through a silicone coated filter and concentrated under reduced pressure. The crude product was purified by HPLC under basic conditions to provide the target compound in 92% purity: 3 mg.

LC-MS (Method 2): R$_t$=1.22 min; MS (ESIpos): m/z=498 [M+H]$^+$ $^1$H-NMR (400 MHz, DMSO-d6) δ [ppm]=1.28 (s, 6H), 2.80 (s, 3H), 2.86 (s, 2H), 3.69 (s, 2H), 6.55 (dd, 2H), 6.58-6.65 (m, 1H), 6.95-7.06 (m, 2H), 7.09-7.21 (m, 3H), 7.30-7.48 (m, 3H), 8.04 (br d, 1H), 8.17 (s, 1H), 10.57 (s, 1H), 11.71 (s, 1H).

Example 45

4,4-difluoro-N-{4-[3-(2-fluoroanilino)-5,6,6-trimethyl-4-oxo-4,5,6,7-tetrahydro-1H-pyrrolo[3,2-c]pyridin-2-yl]pyridin-2-yl}-2-(4-fluorophenyl)butanamide (Racemate)

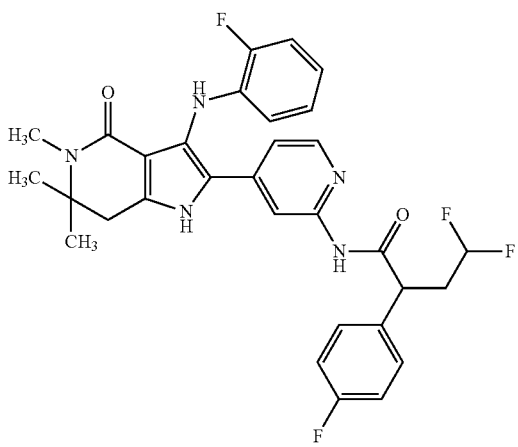 [SMILES: CN1C(=O)c2c([nH]c(-c3ccnc(NC(=O)C(CC(F)F)c4ccc(F)cc4)c3)c2Nc2ccccc2F)CC1(C)C]

2-(2-Aminopyridin-4-yl)-3-(2-fluoroanilino)-5,6,6-trimethyl-1,5,6,7-tetrahydro-4H-pyrrolo[3,2-c]pyridin-4-one (see Intermediate 75, 285 mg), 4,4-difluoro-2-(4-fluorophenyl)butanoic acid (Racemate) (328 mg, 1.50 mmol, CAS-RN: [1538957-14-0], VCS 1835354), PyBOP (1.95 g, 3.76 mmol) and (780 µL, 4.5 mmol; CAS-RN: [7087-68-5]) were dissolved in 4.4 mL DMF and stirred at rt under nitrogen atmosphere overnight. To the reaction mixture aqueous saturated sodium hydrogencarbonate solution was added and it was diluted with dichloromethane. The layers were separated and the aqueous layer was extracted with dichloromethane twice. The combined organic layers were dried using a water resistant filter. The clear filtrate was concentrated under reduced pressure. The crude product was purified by HPLC under basic conditions to provide the target compound in 93% purity: 187 mg.

LC-MS (Method 2): R$_t$=1.33 min; MS (ESIpos): m/z=580 [M+H]$^+$ $^1$H-NMR (400 MHz, DMSO-d6) δ [ppm]=1.30 (d, 6H), 2.10-2.28 (m, 1H), 2.57-2.75 (m, 1H), 2.82 (s, 3H), 2.90 (s, 2H), 4.13 (dd, 1H), 5.73-6.12 (m, 1H), 6.19-6.30 (m, 1H), 6.58-6.67 (m, 1H), 6.69-6.79 (m, 1H), 7.06-7.25 (m, 4H), 7.36-7.52 (m, 3H), 8.07 (d, 1H), 8.15 (s, 1H), 10.64 (s, 1H), 11.79 (s, 1H).

Example 46

4,4-difluoro-N-{4-[3-(2-fluoroanilino)-5,6,6-trimethyl-4-oxo-4,5,6,7-tetrahydro-1H-pyrrolo[3,2-c]pyridin-2-yl]pyridin-2-yl}-2-(4-fluorophenyl)butanamide (Enantiomer 1)

The racemic compound (see Example 45, 82 mg) was separated into enantiomers by preparative chiral HPLC to give enantiomer 1 (70 mg, 100% ee, see Example 46) and enantiomer 2 (67 mg, 98.2% ee, see Example 47).

Preparative Chiral HPLC Method:

Instrument: Sepiatec: Prep SFC100; Column: Chiralpak IA 5µ 250×30 mm; eluent A: carbon dioxide; eluent B: ethanol+0.2 vol % aqueous ammonia (32%); isocratic: 20% B; flow: 100 mL/min; temperature: 40° C.; BPR: 150 bar; UV: 254 nm.

Analytical Chiral HPLC Method:

Instrument: Agilent: 1260, Aurora SFC-Modul; Column: Chiralpak IA 5µ 100×4.6 mm; eluent A: carbon dioxide; eluent B: ethanol+0.2 vol % aqueous ammonia (32%); isocratic: 20% B; flow: 4 mL/min; temperature: 37.5° C.; BPR: 100 bar; UV: 254 nm Analytical Chiral HPLC (method see Example 46): R$_t$=3.24 min.

$^1$H-NMR (400 MHz, DMSO-d6) δ [ppm]=1.30 (s, 6H), 2.23-2.42 (m, 1H), 2.61-2.76 (m, 1H), 2.82 (s, 3H), 2.90 (s, 2H), 4.13 (br dd, 1H), 5.75-6.11 (m, 1H), 6.19-6.29 (m, 1H), 6.58-6.67 (m, 1H), 6.68-6.78 (m, 1H), 7.06-7.26 (m, 4H), 7.37-7.55 (m, 3H), 8.07 (d, 1H), 8.15 (s, 1H), 10.64 (s, 1H), 11.79 (s, 1H).—minor impurities in the aliphatic range.

Example 47

4,4-difluoro-N-{4-[3-(2-fluoroanilino)-5,6,6-trimethyl-4-oxo-4,5,6,7-tetrahydro-1H-pyrrolo[3,2-c]pyridin-2-yl]pyridin-2-yl}-2-(4-fluorophenyl)butanamide (Enantiomer 2)

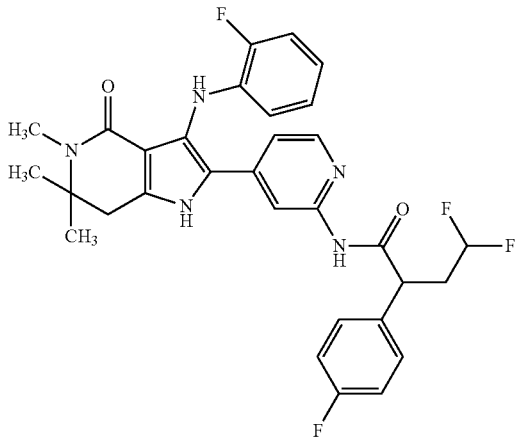 [SMILES: CN1C(=O)c2c([nH]c(-c3ccnc(NC(=O)C(CC(F)F)c4ccc(F)cc4)c3)c2Nc2ccccc2F)CC1(C)C]

For the preparation of the racemic title compound see Example 45. Separation of enantiomers by preparative chiral HPLC (method see Example 46) gave the title compound (67 mg).

Analytical Chiral HPLC (method see Example 41): $R_t$=4.52 min.

$^1$H-NMR (400 MHz, DMSO-d6) δ [ppm]=1.29 (s, 6H), 2.26-2.44 (m, 1H), 2.56-2.76 (m, 1H), 2.82 (s, 3H), 2.87-2.93 (m, 2H), 4.13 (dd, 1H), 5.74-6.12 (m, 1H), 6.19-6.27 (m, 1H), 6.59-6.68 (m, 1H), 6.70-6.77 (m, 1H), 7.07-7.26 (m, 4H), 7.37-7.50 (m, 3H), 8.07 (d, 1H), 8.15 (s, 1H), 10.64 (s, 1H), 11.79 (s, 1H).—minor impurities in the aliphatic range.

Example 48

N-[4-(3-anilino-6,6-dimethyl-4-oxo-4,5,6,7-tetrahydro-1H-pyrrolo[3,2-c]pyridin-2-yl)pyridin-2-yl]-4,4-difluoro-2-(4-fluorophenyl)butanamide (Racemate)

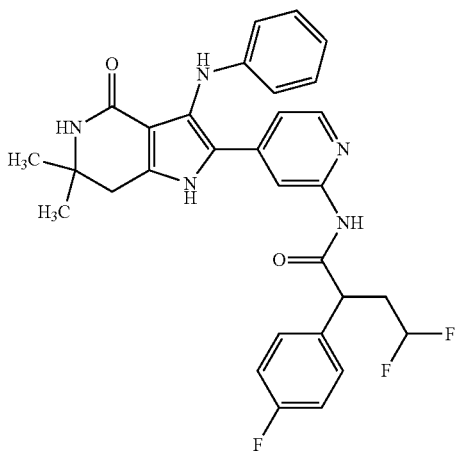 [SMILES: CC1(C)Cc2[nH]c(-c3ccnc(NC(=O)C(CC(F)F)c4ccc(F)cc4)c3)c(Nc3ccccc3)c2C(=O)N1]

2-(2-Aminopyridin-4-yl)-3-anilino-6,6-dimethyl-1,5,6,7-tetrahydro-4H-pyrrolo[3,2-c]pyridin-4-one (see Intermediate 35, 30.0 mg), 4,4-difluoro-2-(4-fluorophenyl)butanoic acid (Racemate) (37.7 mg, 173 µmol, CAS-RN: [1538957-14-0], VCS 1835354), PyBOP (225 mg, 432 µmol) and N,N-diisopropylethylamine (90 µL, 520 µmol; CAS-RN: [7087-68-5]) were dissolved in 0.5 mL DMF and stirred at rt under argon atmosphere over night. To the reaction mixture aqueous saturated sodium hydrogencarbonate solution was added and it was diluted with dichloromethane and water. The layers were separated. The aqueous layer was extracted with dichloromethane three times. The combined organic layers were washed with water three times and with brine once, filtered through a silicone coated filter and concentrated under reduced pressure. The crude product was purified by HPLC under basic conditions to provide the target compound in 94% purity: 9 mg.

LC-MS (Method 2): $R_t$=1.21 min; MS (ESIpos): m/z=548 [M+H]$^+$ $^1$H-NMR (400 MHz, DMSO-d6) δ [ppm]=1.26 (s, 6H), 2.11-2.29 (m, 1H), 2.58-2.75 (m, 1H), 2.79 (s, 2H), 4.14 (dd, 1H), 5.75-6.15 (m, 1H), 6.47-6.57 (m, 2H), 6.57-6.64 (m, 1H), 7.00 (dd, 2H), 7.05 (s, 1H), 7.13 (dd, 1H), 7.15-7.26 (m, 2H), 7.35 (s, 1H), 7.39-7.54 (m, 2H), 8.02 (d, 1H), 8.14 (s, 1H), 10.63 (s, 1H), 11.71 (s, 1H).—contains ethanol.

Example 49

(+)-N-[4-(3-anilino-6,6-dimethyl-4-oxo-4,5,6,7-tetrahydro-1H-pyrrolo[3,2-c]pyridin-2-yl)pyridin-2-yl]-4,4-difluoro-2-(4-fluorophenyl)butanamide (Enantiomer 1)

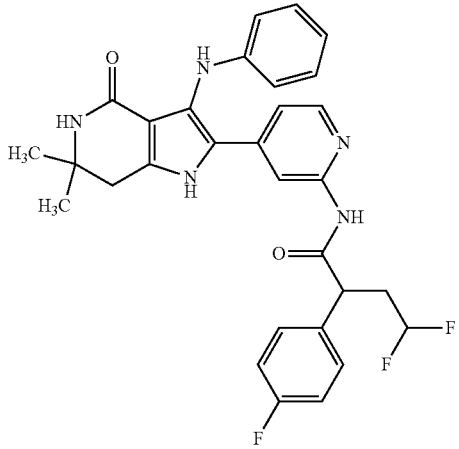 [SMILES: CC1(C)Cc2[nH]c(-c3ccnc(NC(=O)C(CC(F)F)c4ccc(F)cc4)c3)c(Nc3ccccc3)c2C(=O)N1]

The racemic compound (Example 48, 85 mg) was separated into enantiomers by preparative chiral HPLC to give enantiomer 1 (33 mg, 99.6% ee, see Example 49) and enantiomer 2 (45 mg, 97.2% ee, see Example 50).

Preparative Chiral HPLC Method:

Instrument: Sepiatec: Prep SFC100; Column: Chiralpak IA 5µ 250×30 mm; eluent A: carbon dioxide; eluent B: ethanol+0.2 vol % aqueous ammonia (32%); isocratic: 30% B; flow: 100 mL/min; temperature: 40° C.; BPR: 150 bar; UV: 254 nm;

Analytical Chiral HPLC Method:

Instrument: Agilent: 1260, Aurora SFC-Modul; Column: Chiralpak IA 5µ 100×4.6 mm; eluent A: carbon dioxide;

eluent B: ethanol+0.2 vol % aqueous ammonia (32%); isocratic: 30% B; flow: 4 mL/min; temperature: 37.5° C.; BPR: 100 bar; UV: 254 nm;

Analytical Chiral HPLC (method see Example 49): $R_t$=3.21 min.

$[α]_D$=+177.2° (from solution in methanol, c=1.8 mg/mL)

$^1$H-NMR (400 MHz, DMSO-d6) δ [ppm]: 1.256 (3.38), 2.522 (0.45), 2.539 (16.00), 2.789 (1.13), 3.356 (0.57), 6.537 (0.62), 6.556 (0.66), 6.981 (0.47), 7.000 (0.62), 7.039 (0.62), 7.158 (0.41), 7.180 (0.84), 7.202 (0.47), 7.337 (0.78), 7.417 (0.41), 7.430 (0.47), 7.438 (0.43), 8.012 (0.43), 8.026 (0.41), 8.142 (0.45), 10.620 (0.51).

Example 50

N-[4-(3-anilino-6,6-dimethyl-4-oxo-4,5,6,7-tetrahydro-1H-pyrrolo[3,2-c]pyridin-2-yl)pyridin-2-yl]-4,4-difluoro-2-(4-fluorophenyl)butanamide (Enantiomer 2)

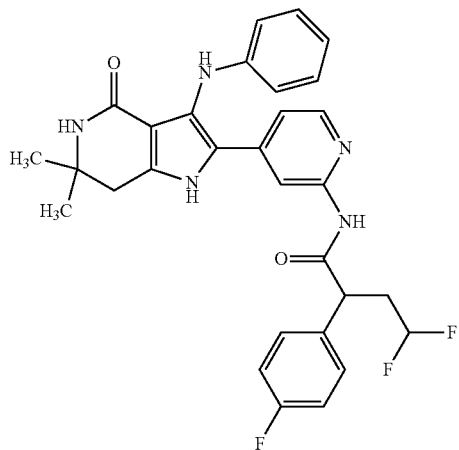

For the preparation of the racemic title compound see Example 48. Separation of enantiomers by preparative chiral HPLC (method see Example 49) gave the title compound (45 mg).

Analytical Chiral HPLC (method see Example 49): $R_t$=4.21 min.

$^1$H-NMR (400 MHz, DMSO-d6) δ [ppm]: 1.256 (4.66), 2.522 (0.67), 2.539 (16.00), 2.789 (1.55), 3.347 (0.60), 6.537 (0.86), 6.556 (0.91), 6.598 (0.53), 6.981 (0.65), 7.000 (0.86), 7.021 (0.55), 7.039 (0.86), 7.118 (0.50), 7.122 (0.50), 7.131 (0.48), 7.135 (0.48), 7.158 (0.55), 7.180 (1.17), 7.202 (0.65), 7.337 (1.05), 7.417 (0.57), 7.430 (0.67), 7.438 (0.60), 7.452 (0.50), 8.012 (0.69), 8.026 (0.65), 8.142 (0.65), 10.620 (0.74), 11.709 (0.55).

Example 51

N-[4-(3-anilino-6,6-dimethyl-4-oxo-4,5,6,7-tetrahydro-1H-pyrrolo[3,2-c]pyridin-2-yl)pyridin-2-yl]-2-(pyridin-4-yl)acetamide

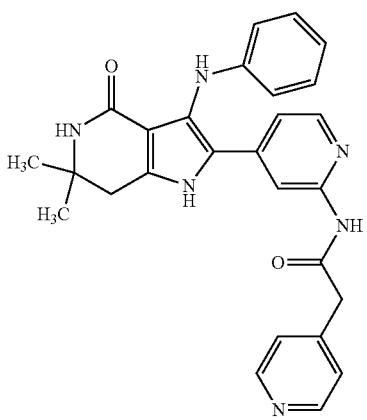 [SMILES: CC1(C)Cc2[nH]c(-c3ccnc(NC(=O)Cc4ccncc4)c3)c(Nc3ccccc3)c2C(=O)N1]

2-(2-Aminopyridin-4-yl)-3-anilino-6,6-dimethyl-1,5,6,7-tetrahydro-4H-pyrrolo[3,2-c]pyridin-4-one (see Intermediate 35, 100 mg), (pyridin-4-yl)acetic acid (158 mg, 1.15 mmol), PyBOP (749 mg, 1.44 mmol) and N,N-diisopropylethylamine (300 µL, 1.7 mmol) were dissolved in 1.7 mL DMF and stirred at rt under argon atmosphere over night. To the reaction mixture aqueous saturated sodium hydrogencarbonate solution was added and it was diluted with dichloromethane and water. The layers were separated. The aqueous layer was extracted with dichloromethane three times. The combined organic layers were washed with water three times and with brine once, filtered through a silicone coated filter and concentrated under reduced pressure. The crude product was purified by flash chromatography (28 g column, aminophase; hexane/ethyl acetate 0%-100%/ethyl acetate/ethanol 0%-20%). The product containing fraction was treated with dichloromethane and the undissolved precipitate was filtered off. The residue was purified by HPLC under basic conditions to provide the analytically pure target compound: 11 mg.

LC-MS (Method 1): $R_t$=0.71 min; MS (ESIpos): m/z=467 [M+H]$^+$ $^1$H-NMR (400 MHz, DMSO-d6) δ [ppm]=1.25 (s, 6H), 2.77 (s, 2H), 3.75 (s, 2H), 6.49-6.57 (m, 2H), 6.61 (t, 1H), 7.01 (dd, 3H), 7.13 (dd, 1H), 7.29-7.40 (m, 3H), 8.05 (d, 1H), 8.15 (s, 1H), 8.47-8.56 (m, 2H), 10.65 (s, 1H), 11.69 (s, 1H).

Example 52

N-[4-(3-anilino-6,6-dimethyl-4-oxo-4,5,6,7-tetra-hydro-1H-pyrrolo[3,2-c]pyridin-2-yl)pyridin-2-yl]-2-(pyridin-3-yl)acetamide

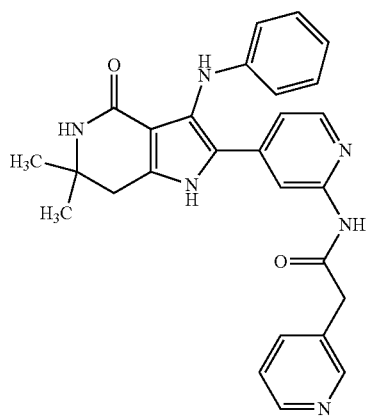 [SMILES: CC1(C)Cc2[nH]c(-c3ccnc(NC(=O)Cc4cccnc4)c3)c(Nc3ccccc3)c2C(=O)N1]

2-(2-Aminopyridin-4-yl)-3-anilino-6,6-dimethyl-1,5,6,7-tetrahydro-4H-pyrrolo[3,2-c]pyridin-4-one (see Intermediate 35, 30.0 mg), (pyridin-3-yl)acetic acid (23.7 mg, 173 µmol), PyBOP (225 mg, 432 µmol) and N,N-diisopropylethylamine (90 µL, 520 µmol) were dissolved in 0.5 mL DMF and it was stirred at rt under argon atmosphere over night. (Pyridin-3-yl)acetic acid (23.7 mg, 173 µmol) and N,N-diisopropylethylamine (90 µL, 520 µmol) were added and it was stirred at rt for 2 days. (Pyridin-3-yl)acetic acid (23.7 mg, 173 µmol), PyBOP (225 mg, 432 µmol) and N,N-diisopropylethylamine (90 µL, 520 µmol) were added and it was stirred at rt over night. To the reaction mixture aqueous saturated sodium hydrogencarbonate solution was added and it was diluted with dichloromethane and water. The layers were separated. The aqueous layer was extracted with dichloromethane three times. The combined organic layers were washed with water three times and with brine once, filtered through a silicone coated filter and concentrated under reduced pressure. The crude product was purified by HPLC under basic conditions. The product containing fractions were combined and treated with dichloromethane. The undissolved precipitate was filtered off to provide the target compound in 98% purity: 10 mg.

LC-MS (Method 1): $R_t$=0.71 min; MS (ESIpos): m/z=467 [M+H]$^+$ $^1$H-NMR (400 MHz, DMSO-d6) δ [ppm]=1.25 (s, 6H), 2.77 (s, 2H), 3.75 (s, 2H), 6.55 (d, 2H), 6.60 (t, 1H), 6.94-7.08 (m, 3H), 7.12 (dd, 1H), 7.33 (s, 1H), 7.36 (dd, 1H), 7.72 (br d, 1H), 8.05 (d, 1H), 8.16 (s, 1H), 8.46 (br d, 1H), 8.52 (br s, 1H), 10.64 (s, 1H), 11.69 (br s, 1H).—contains 1,1',1''-phosphoryltripyrrolidine.

Example 53

N-{4-[3-anilino-5-(2-methoxyethyl)-4-oxo-4,5,6,7-tetrahydro-1H-pyrrolo[3,2-c]pyridin-2-yl]pyridin-2-yl}-2-(4-fluorophenyl)acetamide

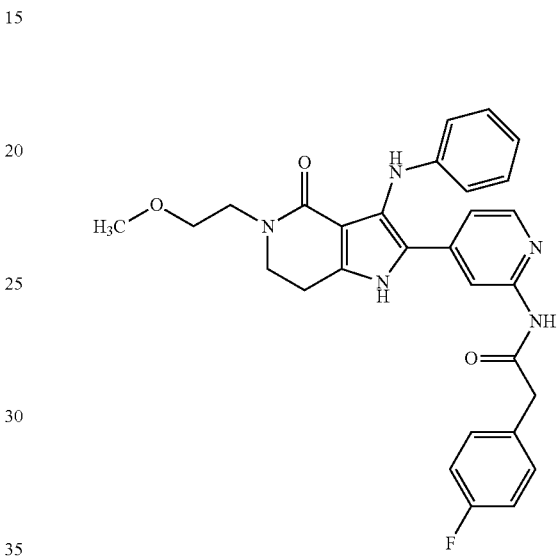

2-(2-Aminopyridin-4-yl)-3-anilino-5-(2-methoxyethyl)-1,5,6,7-tetrahydro-4H-pyrrolo[3,2-c]pyridin-4-one (see Intermediate 78, 60.0 mg), (4-fluorophenyl)acetic acid (49.0 mg, 318 µmol), PyBOP (414 mg, 795 µmol) and N,N-diisopropylethylamine (170 µL, 950 µmol) were combined and stirred at rt under nitrogen atmosphere overnight. To the reaction mixture saturated aqueous sodium hydrogencarbonate solution was added and it was diluted with dichloromethane. The layers were separated and the aqueous layer was extracted with dichloromethane twice. The combined organic layers were dried using a water resistant filter. The clear filtrate was concentrated under reduced pressure The crude product was purified by HPLC under basic conditions to provide the target compound in 85% purity: 29 mg.

LC-MS (Method 2): $R_t$=1.16 min; MS (ESIpos): m/z=514 [M+H]$^+$ $^1$H-NMR (400 MHz, DMSO-d6) δ [ppm]=2.87 (t, 2H), 3.23 (s, 3H), 3.38-3.46 (m, 2H), 3.46-3.53 (m, 2H), 3.60 (t, 2H), 3.69 (s, 2H), 6.55 (d, 2H), 6.62 (t, 1H), 6.96-7.07 (m, 2H), 7.08-7.20 (m, 3H), 7.29-7.41 (m, 3H), 8.04 (d, 1H), 8.18 (s, 1H), 10.56 (s, 1H), 11.74 (s, 1H).

Example 54

N-[4-(3'-anilino-4'-oxo-1',4',5',7'-tetrahydrospiro[cyclobutane-1,6'-pyrrolo[3,2-c]pyridin]-2'-yl)pyridin-2-yl]-4,4-difluoro-2-(4-fluorophenyl)butanamide (Racemate)

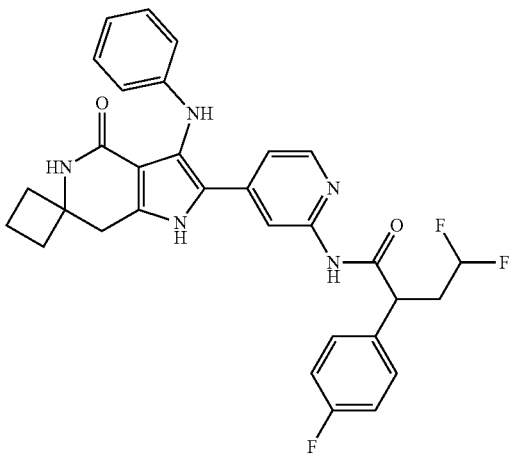 [SMILES: O=C1NC2(CCC2)Cc2[nH]c(-c3ccnc(NC(=O)C(CC(F)F)c4ccc(F)cc4)c3)c(Nc3ccccc3)c21]

2'-(2-Aminopyridin-4-yl)-3'-anilino-1',7'-dihydrospiro[cyclobutane-1,6'-pyrrolo[3,2-c]pyridin]-4'(5'H)-one (see Intermediate 81, 400 mg), 4,4-difluoro-2-(4-fluorophenyl)butanoic acid (Racemate) (486 mg, 2.23 mmol, CAS-RN: [1538957-14-0], VCS 1835354), O-(Benzotriazol-1-yl)-N,N,N—,N-tetramethyluronium-hexafluorophosphate (928 mg, 2.45 mmol; CAS-RN: [94790-37-1]) and cesium fluoride (676 mg, 4.45 mmol) were dissolved in 5.3 mL N-methylpyrrolidone and it was stirred at 35° C. under nitrogen atmosphere overnight. To the reaction mixture saturated aqueous sodium hydrogencarbonate solution was added and it was diluted with dichloromethane. The layers were separated and the aqueous layer was extracted with dichloromethane twice. The combined organic layers were dried using a water resistant filter. The clear filtrate was concentrated under reduced pressure. The crude product was purified by flash chromatography (10 g silica ultra column, gradient dichloromethane/ethanol 0-10%). The product containing fractions were combined, concentrated and purified by HPLC to provide the target compound in 90% purity: 340 mg.

LC-MS (Method 2): $R_t$=1.23 min; MS (ESIpos): m/z=560 [M+H]$^+$ $^1$H-NMR (400 MHz, DMSO-d6) δ [ppm]=1.65-1.80 (m, 2H), 1.94-2.29 (m, 5H), 2.57-2.79 (m, 1H), 3.00 (s, 2H), 4.15 (dd, 1H), 5.77-6.13 (m, 1H), 6.50-6.56 (m, 2H), 6.60 (t, 1H), 6.95-7.04 (m, 2H), 7.12 (dd, 1H), 7.15-7.25 (m, 2H), 7.33 (s, 1H), 7.41-7.50 (m, 2H), 7.54 (s, 1H), 8.02 (d, 1H), 8.16 (s, 1H), 10.64 (s, 1H), 11.78 (s, 1H).

Example 55

(+)-N-[4-(3'-anilino-4'-oxo-1',4',5',7'-tetrahydrospiro[cyclobutane-1,6'-pyrrolo[3,2-c]pyridin]-2'-yl)pyridin-2-yl]-4,4-difluoro-2-(4-fluorophenyl)butanamide (Enantiomer 1)

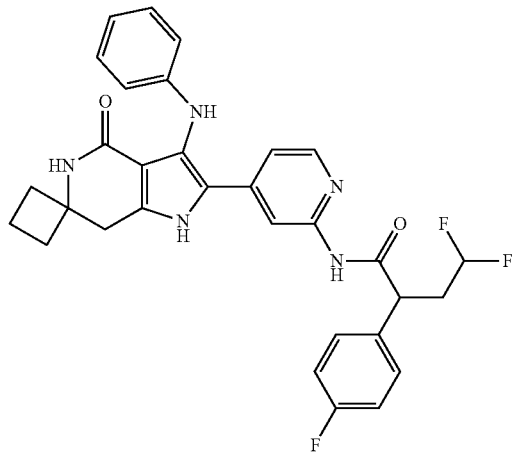 [SMILES: O=C1NC2(CCC2)Cc2[nH]c(-c3ccnc(NC(=O)C(CC(F)F)c4ccc(F)cc4)c3)c(Nc3ccccc3)c21]

The racemic compound (Example 54, 526 mg) was separated into enantiomers by preparative chiral HPLC to give enantiomer 1 (250 mg, 100% ee, see Example 55) and enantiomer 2 (240 mg, 98.9% ee, see Example 56).

Preparative Chiral HPLC Method:

Instrument: PrepCon Labomatic HPLC; Column: YMC Amylose SA 10μ, 250×50; eluent A: hexane+0.1 vol % diethylamine; eluent B: ethanol+0.1 vol % diethylamine; isocratic: 70% A+30% B; flow: 100 mL/min; temperature: 25° C.; UV: 254 nm;

Analytical Chiral HPLC Method:

Instrument: Waters Alliance 2695; Column: YMC Amylose SA 3μ, 100×4.6; eluent A: hexane+0.1 vol % diethylamine; eluent B: ethanol; isocratic: 70% A+30% B; flow: 1.4 mL/min; temperature: 25° C.; UV: 254 nm;

Analytical Chiral HPLC (method see Example 55): $R_t$=4.71 min.

$[α]_D$=+125.9° (from solution in DMSO, c=11 mg/mL)

LC-MS (Method 2): $R_t$=1.23 min; MS (ESIpos): m/z=561 [M+H]$^+$ $^1$H-NMR (400 MHz, DMSO-d6) δ [ppm]=1.64-1.79 (m, 2H), 1.96-2.28 (m, 5H), 2.61-2.81 (m, 1H), 3.00 (s, 2H), 4.15 (br dd, 1H), 5.78-6.15 (m, 1H), 6.54 (d, 2H), 6.60 (t, 1H), 7.00 (t, 2H), 7.12 (dd, 1H), 7.19 (t, 2H), 7.33 (s, 1H), 7.44 (dd, 2H), 7.53 (s, 1H), 8.02 (d, 1H), 8.16 (s, 1H), 10.64 (s, 1H), 11.78 (s, 1H).—minor impurities in the aliphatic range.

Example 56

(−)-N-[4-(3'-anilino-4'-oxo-1',4',5',7'-tetrahydrospiro[cyclobutane-1,6'-pyrrolo[3,2-c]pyridin]-2'-yl)pyridin-2-yl]-4,4-difluoro-2-(4-fluorophenyl)butanamide (Enantiomer 2)

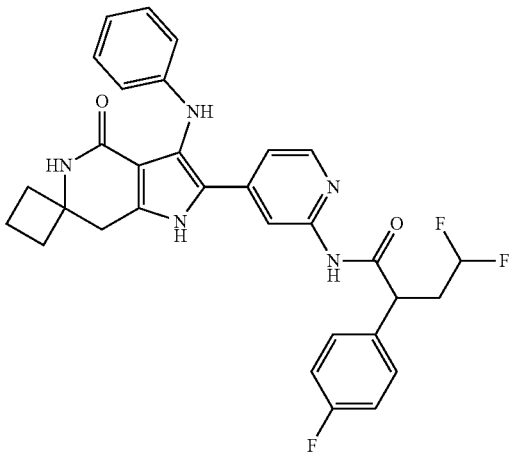 [SMILES: O=C1NC2(CCC2)Cc2[nH]c(-c3ccnc(NC(=O)C(CC(F)F)c4ccc(F)cc4)c3)c(Nc3ccccc3)c21]

For the preparation of the racemic title compound see Example 54. Separation of enantiomers by preparative chiral HPLC (method see Example 55) gave the title compound (240 mg).

Analytical Chiral HPLC (method see Example 55): $R_t$=6.62 min.

$[\alpha]_D$=−109.7° (from solution in DMSO, c=11.5 mg/mL)

LC-MS (Method 2): $R_t$=1.22 min; MS (ESIneg): m/z=561 [M−H]⁻

¹H-NMR (400 MHz, DMSO-d6) δ [ppm]=1.66-1.81 (m, 2H), 1.97-2.28 (m, 5H), 2.60-2.76 (m, 1H), 3.00 (s, 2H), 4.15 (dd, 1H), 5.77-6.18 (m, 1H), 6.49-6.56 (m, 2H), 6.57-6.65 (m, 1H), 7.00 (dd, 2H), 7.12 (dd, 1H), 7.14-7.25 (m, 2H), 7.33 (s, 1H), 7.41-7.49 (m, 2H), 7.53 (s, 1H), 8.03 (d, 1H), 8.16 (s, 1H), 10.64 (s, 1H), 11.78 (s, 1H).—minor impurities in the aliphatic range.

Example 57

N-[4-(3'-anilino-4'-oxo-1',4',5',7'-tetrahydrospiro[cyclobutane-1,6'-pyrrolo[3,2-c]pyridin]-2'-yl)pyridin-2-yl]-2-(4-fluorophenyl)acetamide

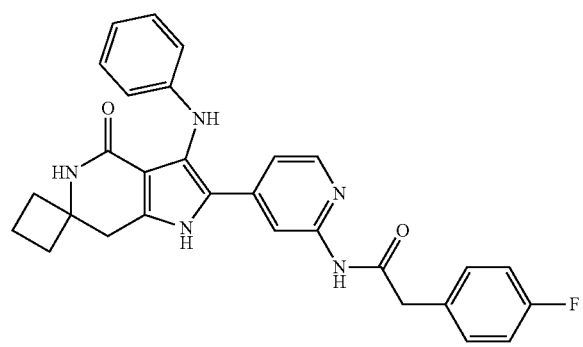 [SMILES: O=C(Cc1ccc(F)cc1)Nc1cc(-c2[nH]c3c(c2Nc2ccccc2)C(=O)NC2(CCC2)C3)ccn1]

2'-(2-Aminopyridin-4-yl)-3'-anilino-1',7'-dihydrospiro[cyclobutane-1,6'-pyrrolo[3,2-c]pyridin]-4'(5'H)-one (see Intermediate 81, 200 mg), (4-fluorophenyl)acetic acid (172 mg, 1.11 mmol), HBTU (464 mg, 1.22 mmol; CAS-RN: [94790-37-1]) and 4-methyl-morpholine (240 μL, 2.2 mmol; CAS-RN: [109-02-4]) were dissolved in 2.1 mL DMF and it was stirred at 35° C. under nitrogen atmosphere overnight. To the reaction mixture saturated aqueous sodium hydrogencarbonate solution was added and it was diluted with dichloromethane. The layers were separated and the aqueous layer was extracted with dichloromethane twice. The combined organic layers were dried using a water resistant filter. The clear filtrate was concentrated under reduced pressure. The crude product was purified by HPLC under basic conditions in two portions to provide the target compound in 90% purity: 28 mg.

LC-MS (Method 2): $R_t$=1.15 min; MS (ESIpos): m/z=496 [M+H]⁺

¹H-NMR (400 MHz, DMSO-d6) δ [ppm]=1.64-1.79 (m, 2H), 1.96-2.06 (m, 2H), 2.06-2.19 (m, 2H), 2.98 (s, 2H), 3.69 (s, 2H), 6.51-6.56 (m, 2H), 6.60 (t, 1H), 6.96-7.06 (m, 2H), 7.08-7.21 (m, 3H), 7.31 (s, 1H), 7.32-7.41 (m, 2H), 7.52 (s, 1H), 8.04 (d, 1H), 8.18 (s, 1H), 10.57 (s, 1H), 11.77 (s, 1H).

Example 58

N-[4-(3-anilino-5-methyl-4-oxo-4,5,6,7-tetrahydro-1H-pyrrolo[3,2-c]pyridin-2-yl)pyridin-2-yl]-5-(dimethylamino)-2-phenylpentanamide (Racemate)

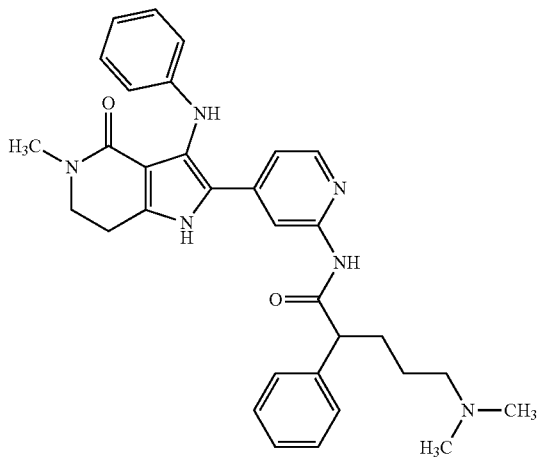

To a solution of (rac)-5-(dimethylamino)-2-phenylpentanoic acid hydrogen chloride (see Intermediate 82; 557 mg, approx. 50% purity, 1.08 mmol) in DMA (12.0 mL) was added molecular sives (4 A, 30 mg) and the mixture was kept for 16 h. The solution was transferred to a new flask, N,N-diisopropylethylamine (1.1 ml, 6.5 mmol), DMAP (26.4 mg, 216 μmol), 2-(2-aminopyridin-4-yl)-3-anilino-5-methyl-1,5,6,7-tetrahydro-4H-pyrrolo[3,2-c]pyridin-4-one (see Intermediate 3,180 mg, 540 μmol) and T3P (1.3 ml, 50% in ethyl acetate, 2.2 mmol) were added and the mixture was stirred at 120° C. for 4 h. An aqueous solution of potassium carbonate was added, the mixture was stirred for 5 minutes and the mixture was extracted with dichloromethane. The organic phase was dried (sodium sulfate), filtered and the solvent was removed in vacuum. Aminophase-silicagel chromatography followed by preparative reverse phase HPLC (gradient of water and acetonitrile containing ammonia as additive) gave 280 mg of the title compound.

LC-MS (Method 2): $R_t$=1.21 min; MS (ESIneg): m/z=535 [M−H]$^-$ $^1$H NMR (400 MHz, DMSO-$d_6$) δ ppm 1.23-1.43 (m, 2H), 1.66 (ddt, 1H), 1.99-2.09 (m, 7H), 2.19 (t, 2H), 2.86 (s, 3H), 2.92 (t, 2H), 3.54 (t, 2H), 3.86 (dd, 1H), 6.55 (d, 2H), 6.60 (t, 1H), 6.97-7.04 (m, 2H), 7.11 (dd, 1H), 7.20-7.26 (m, 1H), 7.28-7.35 (m, 2H), 7.35-7.41 (m, 3H), 8.01 (d, 1H), 8.21 (s, 1H), 10.49 (s, 1H), 11.73 (s, 1H).

Example 59

(−)-N-[4-(3-anilino-5-methyl-4-oxo-4,5,6,7-tetrahydro-1H-pyrrolo[3,2-c]pyridin-2-yl)pyridin-2-yl]-5-(dimethylamino)-2-phenylpentanamide (Enantiomer 1)

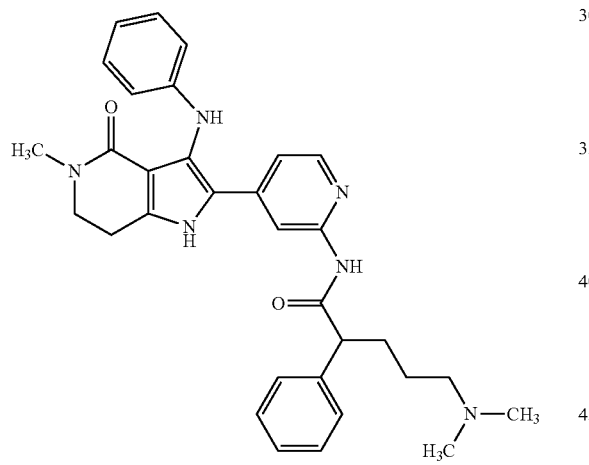

The racemic compound (Example 58, 280 mg) was separated into enantiomers by preparative chiral HPLC to give enantiomer 1 (90 mg, 98.4% ee, see Example 59) and enantiomer 2 (70 mg, 98.6% ee, see Example 60).

Preparative Chiral HPLC Method:

Instrument: PrepCon Labomatic HPLC; Column: YMC Cellulose SC 10μ, 250×50; eluent A: hexane+0.1 vol % diethylamine; eluent B: ethanol; isocratic: 90% A+10% B; flow: 140 mL/min; temperature: 25° C.; UV: 280 nm;

Analytical Chiral HPLC Method:

Instrument: Waters Alliance 2695; Column: YMC Cellulose SB 3μ, 100×4.6; eluent A: hexane+0.1 vol % diethylamine; eluent B: ethanol; isocratic: 90% A+10% B; flow: 1.4 mL/min; temperature: 25° C.; UV: 280 nm;

Analytical Chiral HPLC (method see Example 59): $R_t$=3.65 min.

$[a]_D$=+−143.9° (from solution in DMSO, c=2.1 mg/mL)

LC-MS (Method 2): $R_t$=1.23 min; MS (ESIneg): m/z=535 [M−H]$^-$ $^1$H-NMR (400 MHz, DMSO-$d_6$) δ [ppm]=1.26 (s, 2H), 1.59-1.74 (m, 1H), 1.93-2.15 (m, 7H), 2.22 (t, 2H), 2.86 (s, 3H), 2.92 (t, 2H), 3.54 (t, 2H), 3.81-3.90 (m, 1H), 6.50-6.66 (m, 3H), 7.00 (dd, 2H), 7.11 (dd, 1H), 7.20-7.27 (m, 1H), 7.28-7.42 (m, 5H), 8.01 (d, 1H), 8.21 (s, 1H), 10.49 (s, 1H), 11.73 (s, 1H).

Example 60

(+)-N-[4-(3-anilino-5-methyl-4-oxo-4,5,6,7-tetrahydro-1H-pyrrolo[3,2-c]pyridin-2-yl)pyridin-2-yl]-5-(dimethylamino)-2-phenylpentanamide (Enantiomer 2)

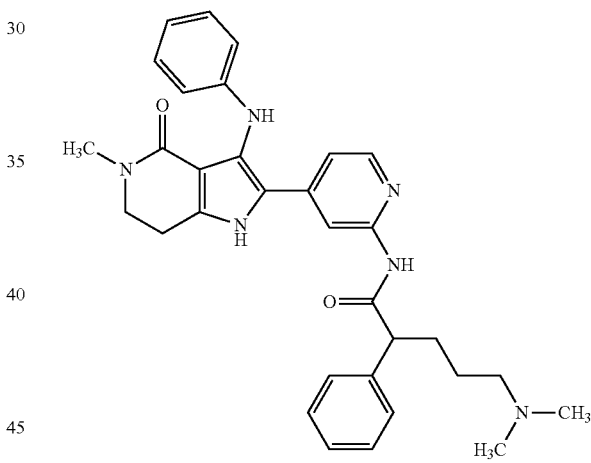

For the preparation of the racemic title compound see Example 58. Separation of enantiomers by preparative chiral HPLC (method see Example 59) gave the title compound (70 mg).

Analytical Chiral HPLC (method see Example 59): $R_t$=5.08 min.

$[a]_D$=+127.9° (from solution in DMSO, c=2.2 mg/mL)

LC-MS (Method 2): $R_t$=1.23 min; MS (ESIneg): m/z=535 [M−H]$^-$ $^1$H-NMR (400 MHz, DMSO-$d_6$) δ [ppm]=1.22-1.41 (m, 2H), 1.59-1.72 (m, 1H), 1.95-2.11 (m, 7H), 2.20 (t, 2H), 2.86 (s, 3H), 2.92 (t, 2H), 3.54 (t, 2H), 3.86 (dd, 1H), 6.52-6.64 (m, 3H), 6.97-7.04 (m, 2H), 7.11 (dd, 1H), 7.20-7.27 (m, 1H), 7.28-7.41 (m, 5H), 8.01 (d, 1H), 8.21 (s, 1H), 10.49 (s, 1H), 11.74 (s, 1H).

Example 61

N-[4-(3-anilino-5-methyl-4-oxo-4,5,6,7-tetrahydro-1H-pyrrolo[3,2-c]pyridin-2-yl)pyridin-2-yl]-4,4-difluoro-2-(4-fluorophenyl)butanamide (Racemate)

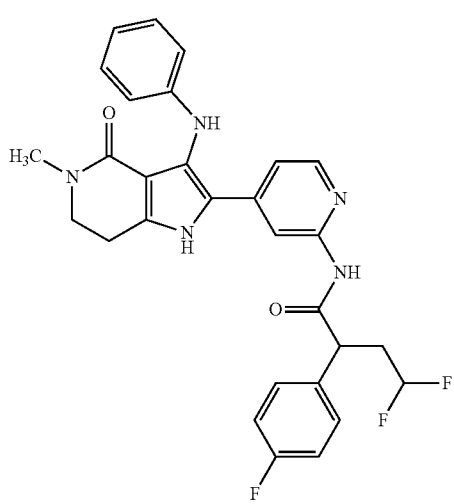 [SMILES: CN1CCc2[nH]c(-c3ccnc(NC(=O)C(CC(F)F)c4ccc(F)cc4)c3)c(Nc3ccccc3)c2C1=O]

To a stirred solution of 2-(2-aminopyridin-4-yl)-3-anilino-5-methyl-1,5,6,7-tetrahydro-4H-pyrrolo[3,2-c]pyridin-4-one (see Intermediate 3, 200 mg, 600 µmol) in DMA (1.0 mL) was added N,N-diisopropylethylamine (630 µl, 3.6 mmol; CAS-RN: [7087-68-5]), (rac)-4,4-difluoro-2-(4-fluorophenyl)butanoic acid (see Intermediate 102, 327 mg, 1.50 mmol) and PyBOP (937 mg, 1.80 mmol; CAS-RN: [128625-52-5]). The mixture was stirred at r.t. for 16 h. An aqueous solution of sodium bicarbonate was added, the mixture was stirred for 5 minutes and the mixture was extracted with ethyl acetate. The organic phase was washed with saturated sodium chloride solution, dried (sodium sulfate), filtered and the solvent was removed in vacuum. Silicagel chromatography followed by aminophase-silicagel chromatography gave a solid that was triturated with a mixture of dichloromethane and hexane to give 198 mg (56% yield) of the title compound.

LC-MS (Method 2): $R_t$=1.24 min; MS (ESIpos): m/z=534 [M+H]$^+$ $^1$H NMR (400 MHz, DMSO-d$_6$) δ ppm 2.10-2.29 (m, 1H), 2.58-2.78 (m, 1H), 2.87 (s, 3H), 2.93 (t, 2H), 3.54 (t, 2H), 4.14 (dd, 1H), 5.93 (tt, 1H), 6.54 (dd, 2H), 6.61 (t, 1H), 7.01 (dd, 2H), 7.13 (dd, 1H), 7.15-7.22 (m, 2H), 7.39 (s, 1H), 7.41-7.47 (m, 2H), 8.03 (d, 1H), 8.16 (s, 1H), 10.63 (s, 1H), 11.74 (s, 1H).

Example 62

(−)-N-[4-(3-anilino-5-methyl-4-oxo-4,5,6,7-tetrahydro-1H-pyrrolo[3,2-c]pyridin-2-yl)pyridin-2-yl]-4,4-difluoro-2-(4-fluorophenyl)butanamide (Enantiomer 1)

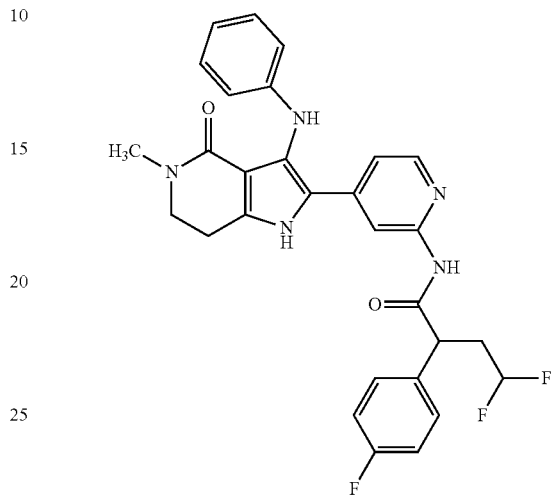

The racemic compound (Example 61, 190 mg) was separated into enantiomers by preparative chiral HPLC to give enantiomer 1 (75 mg, 98.8% ee, see Example 62) and enantiomer 2 (76 mg, 99.3% ee, see Example 63).

Preparative Chiral HPLC Method:
Instrument: PrepCon Labomatic HPLC; Column: YMC Cellulose SB 5µ, 250×30; eluent A: methyl tert-butyl ether+0.1 vol % diethylamine; eluent B: acetonitrile; gradient: 0-7 min 5-45% B; flow: 60 mL/min; temperature: 30° C.; UV: 280 nm;

Analytical Chiral HPLC Method:
Instrument: Waters Alliance 2695; Column: YMC Cellulose SB 3µ, 100×4.6; eluent A: methyl tert-butyl ether+0.1 vol % diethylamine; eluent B: acetonitrile; gradient: 0-7 min 2-60% B; flow: 1.4 mL/min; temperature: 25° C.; UV: 280 nm;

Analytical Chiral HPLC (method see Example 62): $R_t$=2.48 min.

$[α]_D$=−186.7° (from solution in DMSO, c=3.3 mg/mL)

LC-MS (Method 2): $R_t$=1.23 min; MS (ESIpos): m/z=534 [M+H]$^+$ $^1$H-NMR (400 MHz, DMSO-d$_6$) δ [ppm]: 1.138 (0.88), 1.151 (0.46), 2.074 (0.51), 2.323 (0.46), 2.327 (0.65), 2.331 (0.47), 2.518 (3.19), 2.523 (2.07), 2.540 (0.46), 2.665 (0.75), 2.669 (0.86), 2.674 (0.72), 2.865 (16.00), 2.910 (1.54), 2.928 (3.26), 2.945 (1.68), 3.523 (1.81), 3.540 (3.82), 3.557 (1.66), 4.127 (0.65), 4.141 (0.75), 4.149 (0.75), 4.163 (0.61), 5.810 (0.56), 5.939 (0.50), 5.950 (1.15), 5.962 (0.53), 6.091 (0.51), 6.534 (3.09), 6.553 (3.26), 6.556 (2.76), 6.592 (0.98), 6.611 (2.00), 6.629 (1.09), 6.986 (2.43), 7.004 (3.06), 7.007 (3.04), 7.026 (2.00), 7.124 (1.92), 7.129 (1.96), 7.138 (1.89), 7.142 (1.95), 7.162 (2.11), 7.167 (0.76), 7.184 (4.42), 7.201 (0.77), 7.207 (2.41), 7.387 (3.94), 7.421 (2.13), 7.427 (1.01), 7.435 (2.39), 7.443 (2.22), 7.452 (0.87), 7.457 (1.90), 8.021 (2.60), 8.034 (2.51), 8.161 (2.30), 10.633 (2.81), 11.738 (2.15).

Example 63

(+)-N-[4-(3-anilino-5-methyl-4-oxo-4,5,6,7-tetra-hydro-1H-pyrrolo[3,2-c]pyridin-2-yl)pyridin-2-yl]-4,4-difluoro-2-(4-fluorophenyl)butanamide (Enantiomer 2)

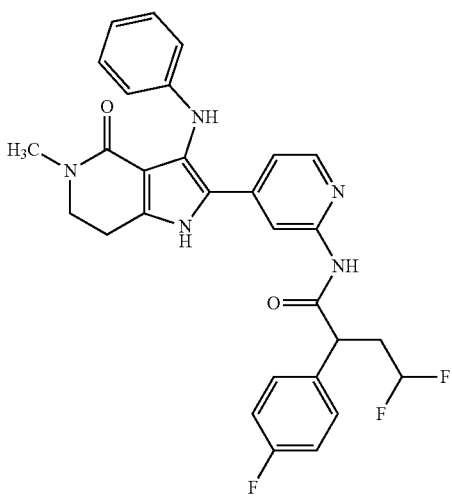 [SMILES: CN1CCc2[nH]c(-c3ccnc(NC(=O)C(CC(F)F)c4ccc(F)cc4)c3)c(Nc3ccccc3)c2C1=O]

For the preparation of the racemic title compound see Example 61. Separation of enantiomers by preparative chiral HPLC (method see Example 62) gave the title compound (76 mg).

Analytical Chiral HPLC (method see Example 62): $R_t$=2.83 min.

$[\alpha]_D$=+180.4° (from solution in DMSO, c=2.8 mg/mL)

LC-MS (Method 2): $R_t$=1.23 min; MS (ESIpos): m/z=534 $[M+H]^+$ $^1$H-NMR (400 MHz, DMSO-$d_6$): δ [ppm]=11.74 (s, 1H), 10.63 (s, 1H), 8.16 (s, 1H), 8.03 (d, 1H), 7.48-7.40 (m, 2H), 7.39 (s, 1H), 7.22-7.15 (m, 2H), 7.13 (dd, 1H), 7.04-6.97 (m, 2H), 6.61 (t, 1H), 6.54 (d, 2H), 6.12-5.78 (m, 1H), 4.15 (dd, 1H), 3.54 (t, 2H), 2.93 (t, 2H), 2.87 (s, 3H), 2.78-2.59 (m, 1H), 2.29-2.10 (m, 1H).

Example 64

N-[4-(3-anilino-5-methyl-4-oxo-4,5,6,7-tetrahydro-1H-pyrrolo[3,2-c]pyridin-2-yl)pyridin-2-yl]-2-(pyridin-4-yl)acetamide

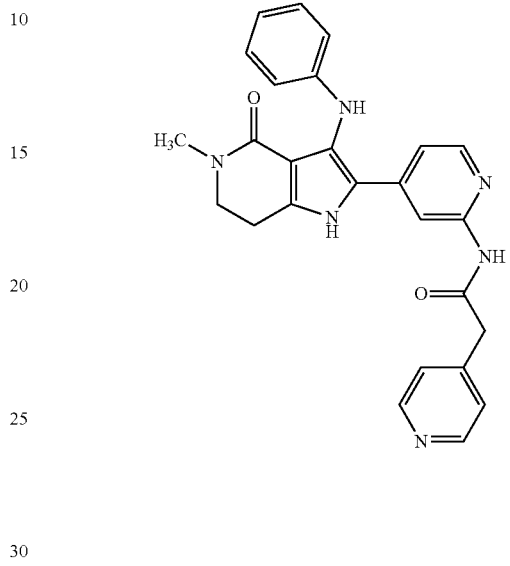

To a stirred solution of 2-(2-aminopyridin-4-yl)-3-anilino-5-methyl-1,5,6,7-tetrahydro-4H-pyrrolo[3,2-c]pyridin-4-one (see Intermediate 3, 100 mg, 300 μmol) in DMA (0.65 mL) was added N,N-diisopropylethylamine (370 μl, 2.1 mmol; CAS-RN: [7087-68-5]), (pyridin-4-yl)acetic acid-hydrogen chloride (1/1) (156 mg, 900 μmol) and PyBOP (468 mg, 900 μmol; CAS-RN: [128625-52-5]). The mixture was stirred at r.t. for 16 h. An aqueous solution of sodium bicarbonate was added, the mixture was stirred for 5 minutes and the mixture was extracted with ethyl acetate. The organic phase was washed with saturated sodium chloride solution, dried (sodium sulfate), filtered and the solvent was removed in vacuum. Aminophase-silicagel chromatography followed by silicagel chromatography (Gradient: MeOH/CH2Cl2, 0-9% MeOH) gave a solid that was triturated with ethanol to give 87.0 mg (58% yield) of the title compound.

LC-MS (Method 2): $R_t$=0.92 min; MS (ESIpos): m/z=453 $[M+H]^+$ $^1$H-NMR (400 MHz, DMSO-$d_6$) δ [ppm]: 1.036 (6.27), 1.053 (12.41), 1.071 (6.81), 2.518 (1.58), 2.523 (1.01), 2.857 (16.00), 2.891 (1.49), 2.908 (3.23), 2.925 (1.62), 3.406 (0.89), 3.418 (0.97), 3.423 (3.18), 3.435 (3.23), 3.440 (2.91), 3.453 (3.03), 3.457 (1.01), 3.470 (0.98), 3.510 (1.81), 3.528 (3.67), 3.545 (1.64), 3.755 (7.02), 4.345 (2.02), 4.357 (3.87), 4.370 (1.82), 5.758 (1.88), 6.540 (3.09), 6.559 (3.26), 6.561 (2.71), 6.598 (0.59), 6.601 (0.96), 6.619 (1.98), 6.637 (1.07), 6.991 (2.44), 7.010 (3.02), 7.012 (3.05), 7.031 (2.03), 7.133 (2.00), 7.138 (1.98), 7.147 (1.88), 7.151 (2.00), 7.314 (4.14), 7.317 (2.54), 7.324 (2.54), 7.329 (4.35), 7.363 (3.89), 8.052 (2.62), 8.066 (2.50), 8.175 (2.04), 8.502 (5.37), 8.506 (3.32), 8.513 (3.21), 8.516 (5.42), 10.652 (2.78), 11.730 (1.90).

Example 65

N-[4-(3-anilino-5-methyl-4-oxo-4,5,6,7-tetrahydro-1H-pyrrolo[3,2-c]pyridin-2-yl)pyridin-2-yl]-2-[4-(methanesulfonyl)phenyl]acetamide

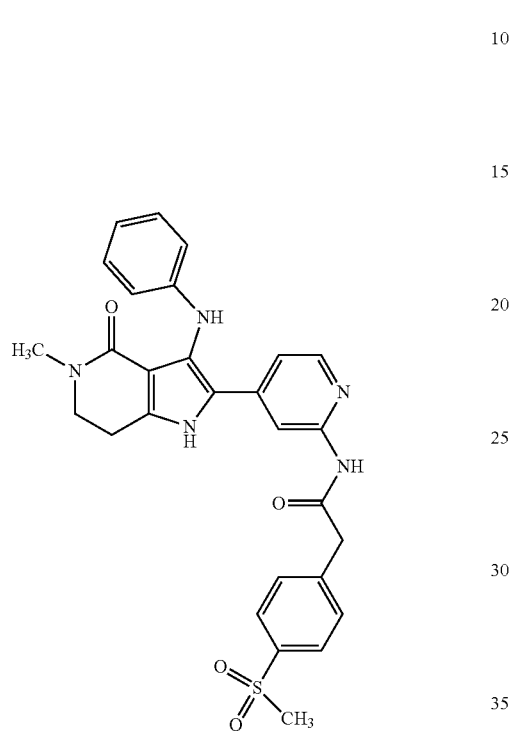

To a stirred solution of 2-(2-aminopyridin-4-yl)-3-anilino-5-methyl-1,5,6,7-tetrahydro-4H-pyrrolo[3,2-c]pyridin-4-one (see Intermediate 3, 120 mg, 360 µmol) in DMA (4.0 mL) was added N,N-diisopropylethylamine (380 µl, 2.2 mmol), [4-(methanesulfonyl)phenyl]acetic acid (154 mg, 720 µmol) and PyBOP [(937 mg, 1.80 mmol). The mixture was stirred at r.t. for 16 h. An aqueous solution of sodium bicarbonate was added, the mixture was stirred for 5 minutes and the mixture was extracted with ethyl acetate. The organic phase was washed with saturated sodium chloride solution, dried (sodium sulfate), filtered and the solvent was removed in vacuum. Silicagel chromatography followed by preparative reverse phase HPLC (gradient of water and acetonitrile containing ammonium hydroxide as additive) gave a solid that was triturated with ethyl acetatene to give 38.2 mg (19% yield) of the title compound.

LC-MS (Method 2): $R_t$=0.98 min; MS (ESIpos): m/z=530 [M+H]$^+$ $^1$H-NMR (400 MHz, DMSO-d$_6$) δ [ppm]=2.86 (s, 3H), 2.90 (t, 2H), 3.20 (s, 3H), 3.53 (t, 2H), 3.84 (s, 2H), 6.52-6.57 (m, 2H), 6.59-6.66 (m, 1H), 7.01 (dd, 2H), 7.14 (dd, 1H), 7.36 (s, 1H), 7.59 (d, 2H), 7.85-7.93 (m, 2H), 8.06 (d, 1H), 8.18 (s, 1H), 10.67 (s, 1H), 11.72 (s, 1H).

Example 66

N-[4-(3-anilino-5-methyl-4-oxo-4,5,6,7-tetrahydro-1H-pyrrolo[3,2-c]pyridin-2-yl)pyridin-2-yl]-2-[4-(trifluoromethyl)phenyl]acetamide

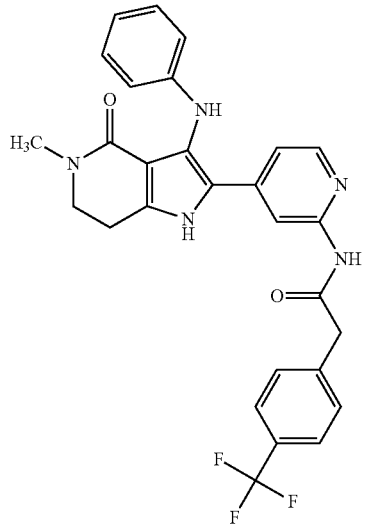 [SMILES: CN1CCc2[nH]c(-c3ccnc(NC(=O)Cc4ccc(C(F)(F)F)cc4)c3)c(Nc3ccccc3)c2C1=O]

To a stirred solution of 2-(2-aminopyridin-4-yl)-3-anilino-5-methyl-1,5,6,7-tetrahydro-4H-pyrrolo[3,2-c]pyridin-4-one (see Intermediate 3, 120 mg, 360 µmol) in DMA (4.0 mL) was added N,N-diisopropylethylamine (380 µl, 2.2 mmol), [4-(trifluoromethyl)phenyl]acetic acid (147 mg, 720 µmol) and PyBOP (937 mg, 1.80 mmol). The mixture was stirred at r.t. for 16 h. An aqueous solution of sodium bicarbonate was added, the mixture was stirred for 5 minutes and the mixture was extracted with ethyl acetate. The organic phase was washed with saturated sodium chloride solution, dried (sodium sulfate), filtered and the solvent was removed in vacuum. Silicagel chromatography followed by preparative reverse phase HPLC (gradient of water and acetonitrile containing ammonium hydroxide as additive) gave a solid that was triturated with ethyl acetatene to give 45.1 mg (23% yield) of the title compound.

LC-MS (Method 2): $R_t$=1.25 min; MS (ESIpos): m/z=520 [M+H]$^+$ $^1$H-NMR (400 MHz, DMSO-d$_6$) δ [ppm]: 1.154 (1.00), 1.173 (2.06), 1.190 (1.07), 1.988 (4.18), 2.084 (0.44), 2.518 (1.58), 2.523 (1.06), 2.856 (16.00), 2.887 (1.49), 2.904 (3.22), 2.922 (1.62), 3.378 (0.47), 3.508 (1.81), 3.525 (3.72), 3.543 (1.65), 3.821 (5.51), 4.017 (0.85), 4.036 (0.85), 6.537 (3.07), 6.556 (3.23), 6.559 (2.69), 6.592 (0.97), 6.610 (2.04), 6.628 (1.09), 6.986 (2.52), 7.005 (3.09), 7.007 (3.05), 7.026 (1.97), 7.127 (1.99), 7.131 (1.97), 7.141 (1.90), 7.145 (1.98), 7.357 (3.93), 7.539 (2.52), 7.559 (3.17), 7.692 (3.51), 7.712 (2.73), 8.048 (2.64), 8.063 (2.53), 8.176 (2.12), 10.649 (2.88), 11.721 (1.99).

Example 67

N-[4-(3-anilino-5-methyl-4-oxo-4,5,6,7-tetrahydro-1H-pyrrolo[3,2-c]pyridin-2-yl)pyridin-2-yl]-2-(pyridin-3-yl)acetamide

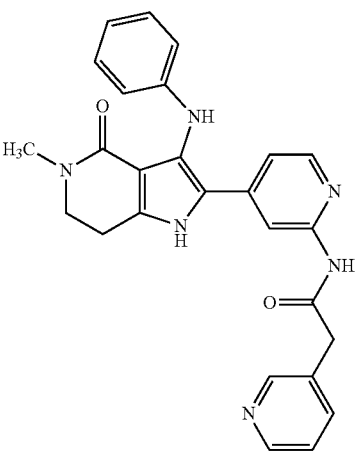 [SMILES: CN1CCc2[nH]c(-c3ccnc(NC(=O)Cc4cccnc4)c3)c(Nc3ccccc3)c2C1=O]

To a stirred solution of 2-(2-aminopyridin-4-yl)-3-anilino-5-methyl-1,5,6,7-tetrahydro-4H-pyrrolo[3,2-c]pyridin-4-one (see Intermediate 3, 100 mg, 300 µmol) in DMA (0.65 mL) was added N,N-diisopropylethylamine (370 µl, 2.1 mmol; CAS-RN: [7087-68-5]), (pyridin-3-yl)acetic acid (123 mg, 900 µmol) and PyBOP (468 mg, 900 µmol; CAS-RN: [128625-52-5]). The mixture was stirred at r.t. for 40 h. An aqueous solution of sodium bicarbonate was added, the mixture was stirred for 5 minutes and the mixture was extracted with ethyl acetate. The organic phase was washed with saturated sodium chloride solution, dried (sodium sulfate), filtered and the solvent was removed in vacuum. Preparative reverse phase HPLC (gradient of water and acetonitrile containing ammonium hydroxide as additive) gave a solid that was triturated with dichloromethane to give 6.0 mg (4% yield) of the title compound.

LC-MS (Method 2): $R_t$=0.92 min; MS (ESIpos): m/z=453 [M+H]$^+$ $^1$H-NMR (400 MHz, DMSO-d$_6$): δ [ppm]=11.72 (s, 1H), 10.65 (s, 1H), 8.52 (d, 1H), 8.46 (dd, 1H), 8.18 (s, 1H), 8.05 (d, 1H), 7.72 (dt, 1H), 7.39-7.33 (m, 2H), 7.13 (dd, 1H), 7.05-6.96 (m, 2H), 6.61 (t, 1H), 6.58-6.51 (m, 2H), 3.75 (s, 2H), 3.53 (t, 2H), 2.90 (t, 2H), 2.86 (s, 3H).

Example 68

N-[4-(3-anilino-5-methyl-4-oxo-4,5,6,7-tetrahydro-1H-pyrrolo[3,2-c]pyridin-2-yl)pyridin-2-yl]-2-(4-methylphenyl)acetamide

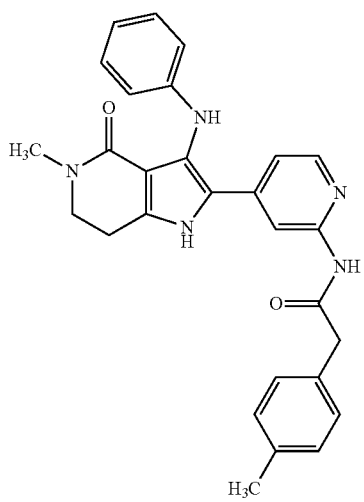 [SMILES: Cc1ccc(CC(=O)Nc2cc(-c3[nH]c4c(c3Nc3ccccc3)C(=O)N(C)CC4)ccn2)cc1]

To a stirred solution of 2-(2-aminopyridin-4-yl)-3-anilino-5-methyl-1,5,6,7-tetrahydro-4H-pyrrolo[3,2-c]pyridin-4-one (see Intermediate 3, 100 mg, 300 µmol) in DMA (0.65 mL) was added N,N-diisopropylethylamine (370 µl, 2.1 mmol; CAS-RN: [7087-68-5]), (4-methylphenyl)acetic acid (135 mg, 900 µmol) and PyBOP (468 mg, 900 µmol; CAS-RN: [128625-52-5]). The mixture was stirred at r.t. for 72 h. An aqueous solution of sodium bicarbonate was added, the mixture was stirred for 5 minutes and the mixture was extracted with ethyl acetate. The organic phase was washed with saturated sodium chloride solution, dried (sodium sulfate), filtered and the solvent was removed in vacuum. Preparative reverse phase HPLC (gradient of water and acetonitrile containing ammonium hydroxide as additive) gave a solid that was triturated with a mixture of dichloromethane and hexane to give 34.0 mg (22% yield) of the title compound.

LC-MS (Method 2): $R_t$=1.11 min; MS (ESIneg): m/z=464 [M−H]$^−$ $^1$H-NMR (400 MHz, DMSO-d$_6$): δ [ppm]=11.77-11.67 (m, 1H), 10.50 (s, 1H), 8.18 (d, 1H), 8.08-8.00 (m, 1H), 7.35 (s, 1H), 7.24-7.19 (m, 2H), 7.15-7.09 (m, 3H), 7.01 (dd, 2H), 6.62 (t, 1H), 6.55 (dd, 2H), 3.63 (s, 2H), 3.53 (t, 2H), 2.90 (t, 2H), 2.86 (s, 3H), 2.27 (s, 3H).

Example 69

N-[4-(3-anilino-5-methyl-4-oxo-4,5,6,7-tetrahydro-1H-pyrrolo[3,2-c]pyridin-2-yl)pyridin-2-yl]-2-[3-(methanesulfonyl)phenyl]acetamide

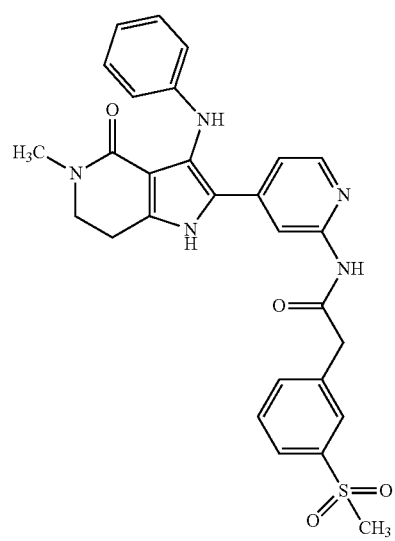 [SMILES: CN1CCc2[nH]c(-c3ccnc(NC(=O)Cc4cccc(S(C)(=O)=O)c4)c3)c(Nc3ccccc3)c2C1=O]

To a stirred solution of 2-(2-aminopyridin-4-yl)-3-anilino-5-methyl-1,5,6,7-tetrahydro-4H-pyrrolo[3,2-c]pyridin-4-one (see Intermediate 3, 120 mg, 360 µmol) in DMA (4.0 mL) was added N,N-diisopropylethylamine (380 µl, 2.2 mmol), [3-(methanesulfonyl)phenyl]acetic acid (154 mg, 720 µmol) and PyBOP (937 mg, 1.80 mmol). The mixture was stirred at r.t. for 24 h. An aqueous solution of sodium bicarbonate was added, the mixture was stirred for 5 minutes and the mixture was extracted with ethyl acetate. The organic phase was washed with saturated sodium chloride solution, dried (sodium sulfate), filtered and the solvent was removed in vacuum. Silicagel chromatography followed by preparative reverse phase HPLC (gradient of water and acetonitrile containing ammonium hydroxide as additive) gave a solid that was triturated with ethyl acetatene to give 40.7 mg (19% yield) of the title compound.

LC-MS (Method 2): $R_t$=0.99 min; MS (ESIpos): m/z=530 [M+H]$^+$ $^1$H-NMR (400 MHz, DMSO-d$_6$) δ [ppm]: 1.154 (2.90), 1.172 (5.84), 1.190 (2.76), 1.988 (10.34), 2.518 (1.37), 2.523 (0.95), 2.854 (11.93), 2.886 (1.16), 2.903 (2.50), 2.921 (1.24), 3.221 (16.00), 3.377 (0.61), 3.507 (1.40), 3.524 (2.87), 3.541 (1.28), 3.855 (4.66), 4.000 (0.76), 4.017 (2.29), 4.035 (2.22), 4.053 (0.71), 6.539 (2.43), 6.558 (2.58), 6.560 (2.16), 6.594 (0.76), 6.612 (1.60), 6.630 (0.88), 6.988 (1.95), 7.007 (2.41), 7.009 (2.43), 7.028 (1.54), 7.124 (1.54), 7.128 (1.44), 7.137 (1.40), 7.142 (1.53), 7.353 (3.02), 7.606 (0.78), 7.625 (2.19), 7.644 (1.71), 7.667 (0.92), 7.670 (1.65), 7.674 (1.10), 7.686 (0.57), 7.690 (0.82), 7.693 (0.48), 7.823 (0.86), 7.827 (1.31), 7.831 (0.98), 7.842 (0.72), 7.847 (1.10), 7.850 (0.76), 7.930 (1.32), 7.934 (2.14), 7.938 (1.24), 8.047 (1.93), 8.061 (1.88), 8.195 (1.67), 10.677 (2.25), 11.730 (1.59).

Example 70

N-[4-(3-anilino-5-methyl-4-oxo-4,5,6,7-tetrahydro-1H-pyrrolo[3,2-c]pyridin-2-yl)pyridin-2-yl]-2-(3-methylphenyl)acetamide

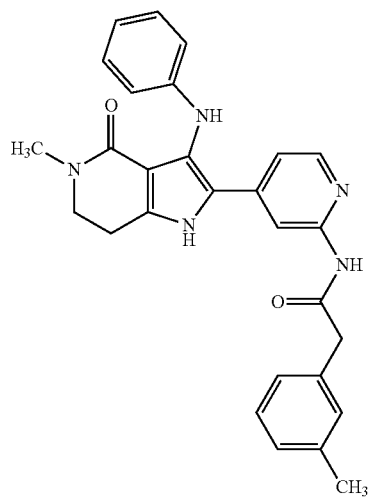 [SMILES: Cc1cccc(CC(=O)Nc2cc(-c3[nH]c4c(c3Nc3ccccc3)C(=O)N(C)CC4)ccn2)c1]

A solution of 2-(2-aminopyridin-4-yl)-3-anilino-5-methyl-1,5,6,7-tetrahydro-4H-pyrrolo[3,2-c]pyridin-4-one (see Intermediate 3, 100 mg, 0.30 mmol, 1 eq) in DMA (2 mL) was treated with N,N-diisopropylethylamine (0.370 mL, 7 eq; CAS-RN: [7087-68-5]), (3-methylphenyl)acetic acid (135 mg, 3 eq), and benzotriazol-1-yloxytripyrrolidinophosphonium hexafluorophosphate (0.468 g, 3 eq; CAS-RN: [128625-52-5]), and stirred for 22 h at r.t. An aqueous solution of sodium bicarbonate was added, the mixture was stirred for 5 minutes and the mixture was extracted with ethyl acetate. The organic phase was washed with saturated sodium chloride solution, dried (sodium sulfate), filtered and the solvent was removed in vacuum. Column chromatography (column NH-Biotage, 11 g, gradient: ethanol/dichloromethane 0-12%), followed by HPLC gave the title compound (70 mg) as a yellow solid.

LC-MS (Method 2): $R_t$=1.19 min; MS (ESIpos): m/z=467 [M+H]$^+$ $^1$H NMR (400 MHz, DMSO-d6) δ ppm 2.29 (s, 3H) 2.86 (s, 3H) 2.88-2.95 (m, 2H) 3.49-3.57 (m, 3H) 3.65 (s, 2H) 6.55 (d, 2H) 6.58-6.65 (m, 1H) 6.98-7.08 (m, 3H) 7.09-7.24 (m, 4H) 7.32-7.38 (m, 1H) 8.02-8.06 (m, 1H) 8.18-8.21 (m, 1H) 10.43-10.62 (m, 1H) 11.58-11.85 (m, 1H).

Example 71

N-[4-(3-anilino-5-methyl-4-oxo-4,5,6,7-tetrahydro-1H-pyrrolo[3,2-c]pyridin-2-yl)pyridin-2-yl]-2-(2-methylphenyl)acetamide

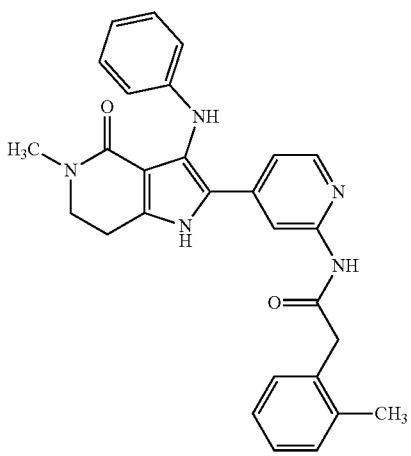

A solution of 2-(2-aminopyridin-4-yl)-3-anilino-5-methyl-1,5,6,7-tetrahydro-4H-pyrrolo[3,2-c]pyridin-4-one (see Intermediate 3, 100 mg, 0.30 mmol, 1 eq) in DMA (2 mL) was treated with N,N-diisopropylethylamine (0.370 mL, 7 eq; CAS-RN: [7087-68-5]), (2-methylphenyl)acetic acid (135 mg, 3 eq), and benzotriazol-1-yloxytripyrrolidinophosphonium hexafluorophosphate (0.468 g, 3 eq; CAS-RN: [128625-52-5]), and stirred for 22 h at r.t. Then a sodium bicarbonate solution in water was added, extracted with ethyl acetate. The organic phase was washed with saturated sodium chloride solution, dried over sodium sulfate, concentrated under reduced pressure, and purified by column chromatography (column NH-Biotage, 28 g, and silica gel, 25 g, gradient: ethanol/dichloromethane 0-12%), and triturated with hexane to give 98 mg of the title compound as a beige solid.

LC-MS (Method 2): $R_t$=1.18 min; MS (ESIpos): m/z=467 [M+H]$^+$ $^1$H NMR (400 MHz, DMSO-d$_6$) δ ppm 2.28 (s, 3H) 2.85 (s, 3H) 2.90 (t, 2H) 3.52 (t, 2H) 3.74 (s, 2H) 6.55 (d, 2H) 6.62 (t, 1H) 7.01 (t, 2H) 7.09-7.18 (m, 4H) 7.19-7.27 (m, 1H) 7.35 (s, 1H) 8.05 (d, 1H) 8.20 (s, 1H) 10.51 (s, 1H) 11.73 (s, 1H).

Example 72

N-[4-(3-anilino-5-methyl-4-oxo-4,5,6,7-tetrahydro-1H-pyrrolo[3,2-c]pyridin-2-yl)pyridin-2-yl]-2-(pyridin-4-yl)propanamide (Racemate)

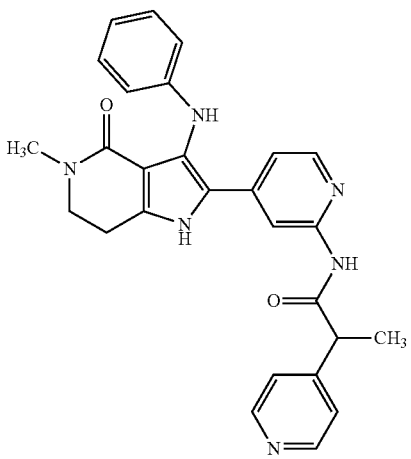 [SMILES: CC(C(=O)Nc1cc(-c2[nH]c3c(c2Nc2ccccc2)C(=O)N(C)CC3)ccn1)c1ccncc1]

A solution of 2-(2-aminopyridin-4-yl)-3-anilino-5-methyl-1,5,6,7-tetrahydro-4H-pyrrolo[3,2-c]pyridin-4-one (see Intermediate 3, 200 mg, 0.60 mmol, 1 eq) in DMA (4 mL) was treated with N,N-diisopropylethylamine (0.73 mL, 7 eq; CAS-RN: [7087-68-5]), sodium 2-(pyridin-4-yl)propanoate (Racemate) (312 mg, 3 eq), and benzotriazol-1-yloxytripyrrolidinophosphonium hexafluorophosphate (0.937 g, 3 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried over sodium sulfate, concentrated under reduced pressure, and purified by column chromatography (column NH-Biotage, 28 g, and silica gel, 25 g, gradient: ethanol/dichloromethane 0-12%), and triturated with dichloromethane to give 104 mg of the title compound as a light yellow solid.

LC-MS (Method 2): $R_t$=0.97 min; MS (ESIpos): m/z=467 [M+H]$^+$ $^1$H NMR (400 MHz, DMSO-d$_6$) δ ppm 1.41 (d, 3H) 2.86 (s, 3H) 2.92 (t, 2H) 3.54 (t, 2H) 4.02 (q, 1H) 6.55 (d, 2H) 6.62 (t, 1H) 7.01 (dd, 2H) 7.09-7.17 (m, 1H) 7.31-7.43 (m, 3H) 8.04 (d, 1H) 8.19 (s, 1H) 8.46-8.54 (m, 2H) 10.61 (s, 1H) 11.74 (s, 1H).

Example 73

(+)-N-[4-(3-anilino-5-methyl-4-oxo-4,5,6,7-tetrahydro-1H-pyrrolo[3,2-c]pyridin-2-yl)pyridin-2-yl]-2-(pyridin-4-yl)propanamide (Enantiomer 1)

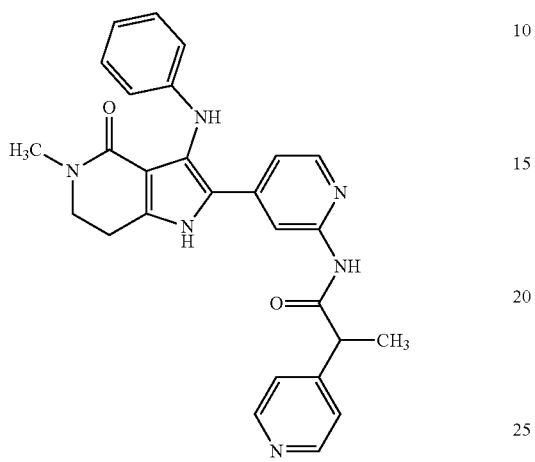

The racemic compound (Example 72, 77 mg) was separated into enantiomers by preparative chiral HPLC to give enantiomer 1 (30 mg, 98.4% ee, see Example 73) and enantiomer 2 (35 mg, 96.4% ee, see Example 74).

Preparative Chiral HPLC Method:

Instrument: PrepCon Labomatic HPLC; Column: YMC Cellulose SB 5μ, 250×30; eluent A: methyl tert-butyl ether+0.1 vol % diethylamine; eluent B: acetonitrile; gradient: 0-7 min 5-45% B; flow: 60 mL/min; temperature: 30° C.; UV: 280 nm;

Analytical Chiral HPLC Method:

Instrument: Waters Alliance 2695; Column: YMC Cellulose SB 3μ, 100×4.6; eluent A: methyl tert-butyl ether+0.1 vol % diethylamine; eluent B: acetonitrile; gradient: 0-7 min 2-60% B; flow: 1.4 mL/min; temperature: 25° C.; UV: 280 nm;

Analytical Chiral HPLC (method see Example 73): $R_t$=3.23 min.

$[a]_D$=+126.3° (from solution in DMSO, c=1.2 mg/mL)

LC-MS (Method 2): $R_t$=0.96 min; MS (ESIpos): m/z=468 [M+H]+

$^1$H-NMR (400 MHz, DMSO-$d_6$) δ [ppm]: 1.402 (1.95), 1.420 (1.97), 2.521 (0.80), 2.525 (0.54), 2.542 (16.00), 2.866 (4.72), 2.906 (0.45), 2.924 (0.98), 2.941 (0.51), 3.522 (0.56), 3.539 (1.17), 3.557 (0.48), 6.542 (0.94), 6.561 (0.99), 6.563 (0.82), 6.619 (0.59), 6.991 (0.75), 7.009 (0.95), 7.012 (0.92), 7.030 (0.58), 7.124 (0.57), 7.128 (0.57), 7.137 (0.57), 7.141 (0.56), 7.350 (1.21), 7.354 (0.75), 7.361 (0.78), 7.365 (1.23), 7.382 (1.20), 8.030 (0.78), 8.044 (0.75), 8.186 (0.71), 8.507 (0.98), 8.510 (0.68), 8.522 (0.93), 10.606 (0.86), 11.742 (0.59).

Example 74

N-[4-(3-anilino-5-methyl-4-oxo-4,5,6,7-tetrahydro-1H-pyrrolo[3,2-c]pyridin-2-yl)pyridin-2-yl]-2-(pyridin-4-yl)propanamide (Enantiomer 2)

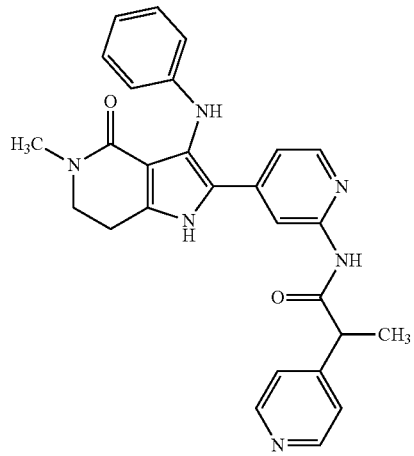 [SMILES: CC(C(=O)Nc1cc(-c2[nH]c3c(c2Nc2ccccc2)C(=O)N(C)CC3)ccn1)c1ccncc1]

For the preparation of the racemic title compound see Example 72. Separation of enantiomers by preparative chiral HPLC (method see Example 73) gave the title compound (35 mg( ) Analytical Chiral HPLC (method see Example 73): $R_t$=4.77 min.

LC-MS (Method 2): $R_t$=0.96 min; MS (ESIpos): m/z=468 [M+H]+

$^1$H-NMR (400 MHz, DMSO-$d_6$) δ [ppm]=1.399 (0.83), 1.417 (0.86), 2.083 (7.98), 2.539 (16.00), 2.864 (1.98), 2.921 (0.42), 3.537 (0.49), 6.540 (0.40), 6.559 (0.43), 7.007 (0.40), 7.009 (0.40), 7.348 (0.48), 7.363 (0.50), 7.380 (0.53).

Example 75

N-[4-(3-anilino-5-methyl-4-oxo-4,5,6,7-tetrahydro-1H-pyrrolo[3,2-c]pyridin-2-yl)pyridin-2-yl]-2-(4-fluorophenyl)butanamide (Racemate)

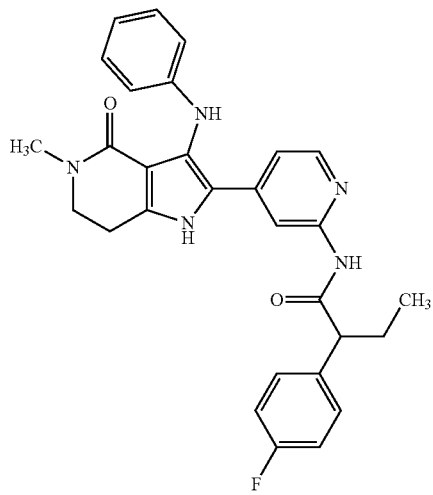 [SMILES: CCC(C(=O)Nc1cc(-c2[nH]c3c(c2Nc2ccccc2)C(=O)N(C)CC3)ccn1)c1ccc(F)cc1]

A solution of 2-(2-aminopyridin-4-yl)-3-anilino-5-methyl-1,5,6,7-tetrahydro-4H-pyrrolo[3,2-c]pyridin-4-one (see Intermediate 3, 800 mg, 2.4 mmol, 1 eq) in DMA (15 mL) was treated with N,N-diisopropylethylamine (3.3 mL, 8 eq; CAS-RN: [7087-68-5]), 2-(4-fluorophenyl)butanoic acid (Racemate) (1.31 g, 3 eq), and benzotriazol-1-yloxytripyrrolidinophosphonium hexafluorophosphate (4.37 g, 3.5 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column silica gel, 25 g, gradient: ethanol/dichloromethane 0-12%, and NH-Biotage, 28 g, gradient: ethanol/dichloromethane 0-15%), and triturated with dichloromethane to give 1.2 g of the title compound as an orange solid.

LC-MS (Method 2): $R_t$=1.11 min; MS (ESIneg): m/z=498 [M−H]$^+$ $^1$H-NMR (400 MHz, DMSO-d$_6$) δ [ppm]=11.74 (br s, 1H), 10.51 (s, 1H), 8.20 (s, 1H), 8.02 (d, 1H), 7.45-7.33 (m, 3H), 7.22-7.08 (m, 3H), 7.05-6.94 (m, 2H), 6.61 (t, 1H), 6.55 (d, 2H), 3.76 (dd, 1H), 3.54 (t, 2H), 2.92 (t, 2H), 2.86 (s, 3H), 2.10-1.94 (m, 1H), 1.66 (dquin, 1H), 0.83 (t, 3H).

Example 76

(−)-N-[4-(3-anilino-5-methyl-4-oxo-4,5,6,7-tetrahydro-1H-pyrrolo[3,2-c]pyridin-2-yl)pyridin-2-yl]-2-(4-fluorophenyl)butanamide (Enantiomer 1)

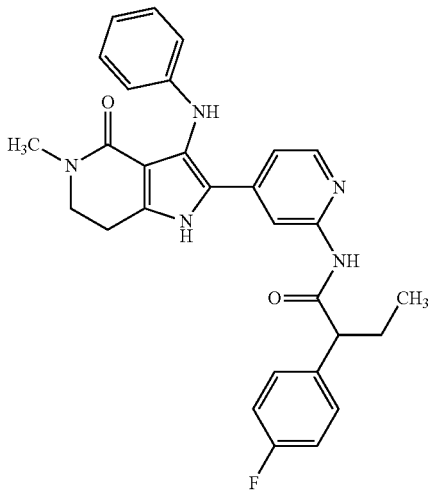 [SMILES: CCC(C(=O)Nc1cc(-c2[nH]c3c(c2Nc2ccccc2)C(=O)N(C)CC3)ccn1)c1ccc(F)cc1]

The racemic compound (Example 75, 1.2 g) was separated into enantiomers by preparative chiral HPLC to give enantiomer 1 (575 mg, 97% ee, see Example 76) and enantiomer 2 (490 mg, 100% ee, see Example 77). Enantiomer 1 was further purified: The compound was dissolved in ethyl acetate/hexane (50 mL, 3:1) and extracted with water three times. The combined organic layers were dried over sodium sulfate and concentrated under vacuum. The compound was titurated with hexane and further purified by chromatography three times (one Si-column and two NH-columns). The resulting compound was titurated with ethanol to provide the 14 mg of the target compound.

Preparative Chiral HPLC Method:
Instrument: PrepCon Labomatic HPLC; Column: YMC Cellulose SB 5µ, 250×30; eluent A: methyl tert-butyl ether+0.1 vol % diethylamine; eluent B: acetonitrile; isocratic: 90% A+10% B; flow: 50 mL/min; temperature: 25° C.; UV: 254 nm;

Analytical Chiral HPLC Method:
Instrument: Waters Alliance 2695; Column: YMC Cellulose SB 3µ, 100×4.6; eluent A: methyl tert-butyl ether+0.1 vol % diethylamine; eluent B: acetonitrile; isocratic: 90% A+10% B; flow: 1.4 mL/min; temperature: 25° C.; UV: 254 nm;

Analytical Chiral HPLC (method see Example 76): $R_t$=1.84 min.

[α]$_D$=−159° (from solution in DMSO, c=1.9 mg/mL)

LC-MS (Method 2): $R_t$=1.28 min; MS (ESIpos): m/z=498 [M+H]$^+$ $^1$H-NMR (400 MHz, DMSO-d$_6$) δ [ppm]=0.83 (t, 3H), 1.66 (dquin, 1H), 1.95-2.10 (m, 1H), 2.86 (s, 3H), 2.92 (t, 2H), 3.54 (t, 2H), 3.76 (dd, 1H), 6.52-6.57 (m, 2H), 6.58-6.64 (m, 1H), 7.00 (dd, 2H), 7.09-7.19 (m, 3H), 7.35-7.44 (m, 3H), 8.02 (d, 1H), 8.20 (d, 1H), 10.51 (s, 1H), 11.74 (s, 1H).

Example 77

(+)-N-[4-(3-anilino-5-methyl-4-oxo-4,5,6,7-tetrahydro-1H-pyrrolo[3,2-c]pyridin-2-yl)pyridin-2-yl]-2-(4-fluorophenyl)butanamide (Enantiomer 2)

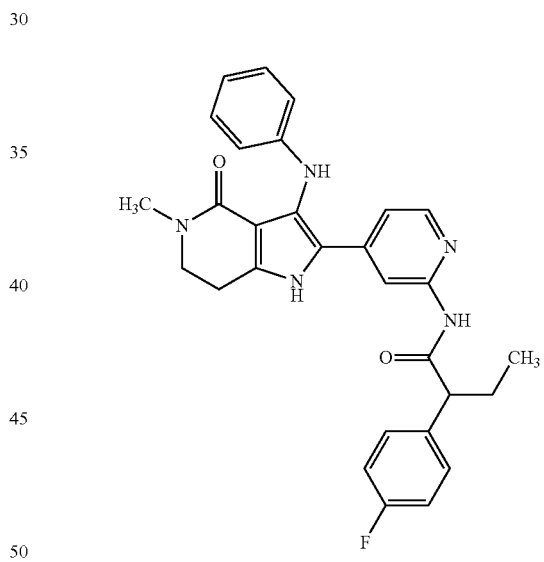

For the preparation of the racemic title compound see Example 75. Separation of enantiomers by preparative chiral HPLC (method see Example 75.) gave the title compound (490 mg), which was further purified: The compound was dissolved in ethyl acetate/hexane (3:1) and extracted with water three times. The combined organic layers were dried over sodium sulfate, concentrated in vacuum and triturated with hexane to provide 235 mg of the target compound.

Analytical Chiral HPLC (method see Example 75): $R_t$=3.07 min.

[α]$_D$=+169° (from solution in DMSO, c=2 mg/mL)

LC-MS (Method 2): $R_t$=1.25 min; MS (ESIpos): m/z=498 [M+H]$^+$ $^1$H-NMR (400 MHz, DMSO-d$_6$) δ [ppm]: 0.83 (t, 3H), 1.58-1.76 (m, 1H), 1.96-2.11 (m, 1H), 2.86 (s, 3H), 2.93 (t, 2H), 3.54 (t, 2H), 3.76 (dd, 1H), 6.52-6.57 (m, 2H), 6.61 (t, 1H), 7.01 (dd, 2H), 7.09-7.22 (m, 3H), 7.35-7.45 (m, 3H), 8.02 (d, 1H), 8.21 (s, 1H), 10.52 (s, 1H), 11.74 (s, 1H).

Example 78

N-[4-(3-anilino-5-methyl-4-oxo-4,5,6,7-tetrahydro-1H-pyrrolo[3,2-c]pyridin-2-yl)pyridin-2-yl]-2-[4-(difluoromethyl)phenyl]acetamide

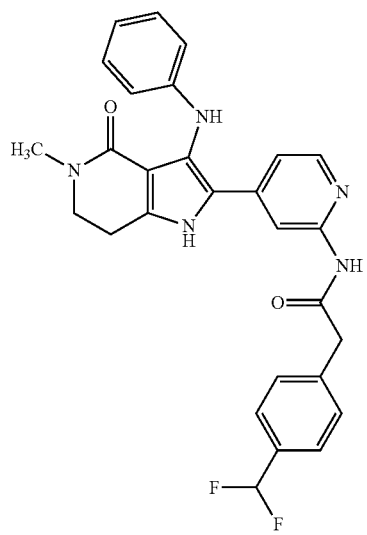 [SMILES: CN1CCc2[nH]c(-c3ccnc(NC(=O)Cc4ccc(C(F)F)cc4)c3)c(Nc3ccccc3)c2C1=O]

A solution of 2-(2-aminopyridin-4-yl)-3-anilino-5-methyl-1,5,6,7-tetrahydro-4H-pyrrolo[3,2-c]pyridin-4-one (see Intermediate 3, 100 mg, 0.30 mmol, 1 eq) in DMA (2 mL) was treated with N,N-diisopropylethylamine (0.37 mL, 7 eq; CAS-RN: [7087-68-5]), [4-(difluoromethyl)phenyl]acetic acid (0.168 g, 3 eq), and benzotriazol-1-yloxytripyrrolidinophosphonium hexafluorophosphate (0.468 g, 3 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column silica gel, 25 g, and NH-Biotage, 28 g, gradient: ethanol/dichloromethane 0-15%), and triturated with dichloromethane to give 14 mg of the title compound as a light yellow solid.

LC-MS (Method 2): $R_t$=1.14 min; MS (ESIpos): m/z=502 [M+H]$^+$ $^1$H-NMR (400 MHz, DMSO-d$_6$): δ [ppm]=11.72 (s, 1H), 10.61 (s, 1H), 8.17 (s, 1H), 8.05 (d, 1H), 7.56-7.50 (m, 2H), 7.49-7.42 (m, 2H), 7.35 (s, 1H), 7.19-6.85 (m, 4H), 6.65-6.58 (m, 1H), 6.58-6.52 (m, 2H), 3.77 (s, 2H), 3.53 (t, 2H), 2.90 (t, 2H), 2.86 (s, 3H).

Example 79

N-[4-(3-anilino-5-methyl-4-oxo-4,5,6,7-tetrahydro-1H-pyrrolo[3,2-c]pyridin-2-yl)pyridin-2-yl]-2-(4-chlorophenyl)propanamide (Racemate)

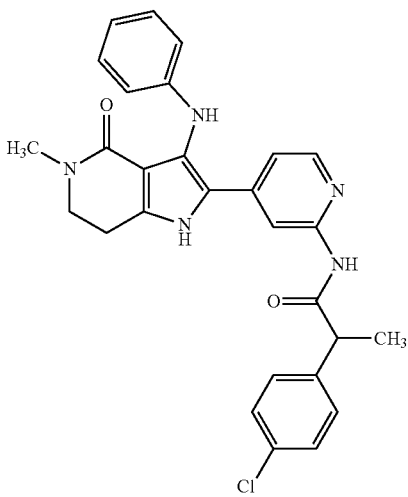 [SMILES: CC(C(=O)Nc1cc(-c2[nH]c3c(c2Nc2ccccc2)C(=O)N(C)CC3)ccn1)c1ccc(Cl)cc1]

A solution of 2-(2-aminopyridin-4-yl)-3-anilino-5-methyl-1,5,6,7-tetrahydro-4H-pyrrolo[3,2-c]pyridin-4-one (see Intermediate 3, 200 mg, 0.60 mmol, 1 eq) in DMA (4 mL) was treated with N,N-diisopropylethylamine (0.73 mL, 7 eq; CAS-RN: [7087-68-5]), 2-(4-chlorophenyl)propanoic acid (Racemate) (332 mg, 3 eq), and benzotriazol-1-yloxytripyrrolidinophosphonium hexafluorophosphate (0.937 g, 3 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure. A solid precipitated and was collected to give 178 mg of the title compound as a light yellow solid.

LC-MS (Method 2): $R_t$=1.26 min; MS (ESIpos): m/z=500 [M+H]$^+$ $^1$H-NMR (400 MHz, DMSO-d$_6$) δ [ppm]: 1.376 (1.53), 1.394 (1.54), 2.083 (16.00), 2.863 (3.87), 2.903 (0.42), 2.921 (0.86), 2.938 (0.45), 3.518 (0.49), 3.535 (0.99), 3.553 (0.42), 6.539 (0.87), 6.558 (0.92), 6.611 (0.53), 6.987 (0.64), 7.006 (0.84), 7.008 (0.85), 7.027 (0.53), 7.107 (0.50), 7.112 (0.48), 7.121 (0.50), 7.125 (0.52), 7.372 (1.06), 7.394 (8.09), 8.013 (0.69), 8.026 (0.65), 8.192 (0.65), 10.522 (0.77), 11.741 (0.50).

Example 80

(−)-N-[4-(3-anilino-5-methyl-4-oxo-4,5,6,7-tetra-hydro-1H-pyrrolo[3,2-c]pyridin-2-yl)pyridin-2-yl]-2-(4-chlorophenyl)propanamide (Enantiomer 1)

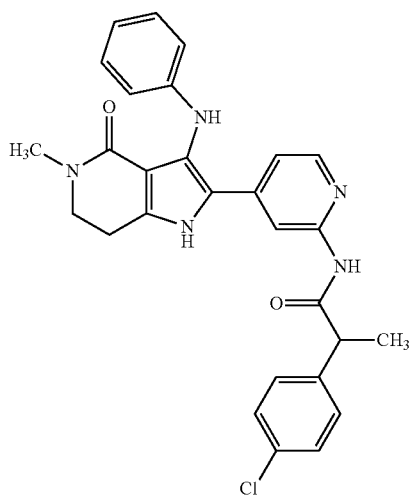 [SMILES: CC(C(=O)Nc1cc(-c2[nH]c3c(c2Nc2ccccc2)C(=O)N(C)CC3)ccn1)c1ccc(Cl)cc1]

The racemic compound (Example 79, 149 mg) was separated into enantiomers by preparative chiral HPLC to give enantiomer 1 (63 mg, 100% ee, see Example 80) and enantiomer 2 (65 mg, 98.1% ee, see Example 81).
Preparative Chiral HPLC Method:
Instrument: PrepCon Labomatic HPLC; Column: YMC Cellulose SB 5µ, 250×30; eluent A: hexane+0.1 vol % diethylamine; eluent B: ethanol+0.1 vol % diethylamine; isocratic: 70% A+30% B; flow: 40 mL/min; temperature: 25° C.; UV: 254 nm;
Analytical Chiral HPLC Method:
Instrument: Waters Alliance 2695; Column: YMC Cellulose SB 3µ, 100×4.6; eluent A: hexane+0.1 vol % diethylamine; eluent B: ethanol; isocratic: 70% A+30% B; flow: 1.4 mL/min; temperature: 25° C.; UV: 254 nm;
Analytical Chiral HPLC (method see Example 80): $R_t$=1.62 min.

$[a]_D$=−192.1° (from solution in DMSO, c=1.3 mg/mL)
$^1$H-NMR (400 MHz, DMSO-$d_6$) δ [ppm]: 1.055 (0.71), 1.135 (1.02), 1.153 (2.23), 1.171 (1.08), 1.378 (2.99), 1.395 (3.06), 2.520 (0.68), 2.525 (0.49), 2.542 (1.57), 2.865 (8.01), 2.906 (0.87), 2.911 (1.14), 2.923 (1.71), 2.929 (1.11), 2.940 (0.85), 3.521 (0.95), 3.538 (1.92), 3.556 (0.81), 3.997 (0.74), 4.015 (0.72), 5.761 (1.47), 6.540 (1.59), 6.559 (1.66), 6.561 (1.36), 6.595 (0.50), 6.613 (1.02), 6.631 (0.54), 6.990 (1.29), 7.008 (1.60), 7.011 (1.54), 7.029 (0.99), 7.108 (1.02), 7.112 (0.93), 7.122 (0.93), 7.126 (0.96), 7.373 (2.09), 7.396 (16.00), 8.014 (1.27), 8.028 (1.19), 8.192 (1.24), 10.523 (1.46), 11.739 (0.99).

Example 81

(+)-N-[4-(3-anilino-5-methyl-4-oxo-4,5,6,7-tetra-hydro-1H-pyrrolo[3,2-c]pyridin-2-yl)pyridin-2-yl]-2-(4-chlorophenyl)propanamide (Enantiomer 2)

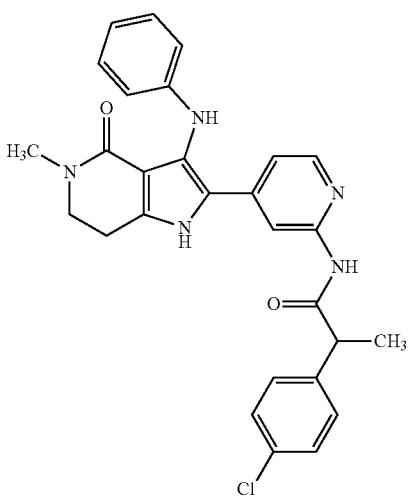 [SMILES: CC(C(=O)Nc1cc(-c2[nH]c3c(c2Nc2ccccc2)C(=O)N(C)CC3)ccn1)c1ccc(Cl)cc1]

For the preparation of the racemic title compound see Example 79. Separation of enantiomers by preparative chiral HPLC (method see Example 80) gave the title compound (65 mg).

Analytical Chiral HPLC (method Example 80): $R_t$=3.04 min.

$[a]_D$=+145.0° (from solution in DMSO, c=1.5 mg/mL)

LC-MS (Method 2): $R_t$=1.22 min; MS (ESIpos): m/z=500 [M+H]$^+$ $^1$H-NMR (400 MHz, DMSO-$d_6$) δ [ppm]: 0.852 (0.51), 1.054 (0.52), 1.139 (0.69), 1.154 (0.69), 1.172 (0.47), 1.237 (1.24), 1.378 (3.76), 1.395 (3.82), 2.085 (1.10), 2.540 (16.00), 2.865 (7.61), 2.910 (1.73), 2.926 (2.64), 2.941 (1.57), 2.995 (0.53), 3.522 (1.94), 3.539 (2.87), 3.556 (1.59), 3.704 (0.74), 3.992 (1.00), 4.010 (0.97), 5.760 (0.89), 6.543 (2.56), 6.563 (2.74), 6.598 (0.80), 6.616 (1.39), 6.634 (0.85), 6.992 (1.64), 7.011 (2.66), 7.030 (1.38), 7.122 (1.25), 7.136 (1.32), 7.351 (0.84), 7.394 (11.57), 8.019 (1.48), 8.032 (1.40), 8.155 (1.32), 10.569 (0.95), 11.759 (1.54).

Example 82

N-[4-(3-anilino-5-methyl-4-oxo-4,5,6,7-tetrahydro-1H-pyrrolo[3,2-c]pyridin-2-yl)pyridin-2-yl]-2-(2,4-difluorophenyl)acetamide

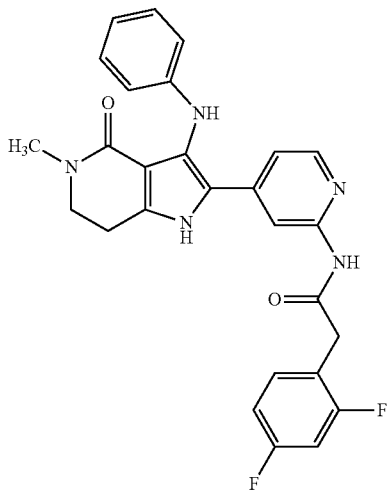 [SMILES: CN1CCc2[nH]c(-c3ccnc(NC(=O)Cc4ccc(F)cc4F)c3)c(Nc3ccccc3)c2C1=O]

A solution of 2-(2-aminopyridin-4-yl)-3-anilino-5-methyl-1,5,6,7-tetrahydro-4H-pyrrolo[3,2-c]pyridin-4-one (see Intermediate 3, 0.1 g, 0.30 mmol, 1 eq) in DMA (2 mL) was treated with N,N-diisopropylethylamine (0.37 mL, 7 eq; CAS-RN: [7087-68-5]), (2,4-difluorophenyl)acetic acid (0.155 g, 3 eq), and benzotriazol-1-yloxytripyrrolidinophosphonium hexafluorophosphate (0.468 g, 3 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column NH-Biotage, 28 g, and silica gel, 25 g, gradient: ethanol/dichloromethane 0-12%), and triturated with dichloromethane to give 61 mg of the title compound as a light yellow solid.

LC-MS (Method 2): $R_t$=1.11 min; MS (ESIpos): m/z=488 [M+H]$^+$ $^1$H-NMR (400 MHz, DMSO-d$_6$) δ [ppm]: 0.000 (5.32), 1.234 (0.77), 1.957 (1.62), 2.325 (0.65), 2.329 (0.88), 2.334 (0.64), 2.520 (3.63), 2.525 (2.34), 2.542 (0.70), 2.667 (0.68), 2.671 (0.91), 2.676 (0.65), 2.783 (1.57), 2.856 (16.00), 2.884 (1.78), 2.901 (3.60), 2.918 (1.81), 2.944 (2.18), 3.379 (0.59), 3.426 (1.38), 3.509 (2.04), 3.526 (4.02), 3.543 (1.80), 3.785 (5.58), 5.761 (0.86), 6.543 (3.43), 6.562 (3.61), 6.605 (1.04), 6.624 (2.13), 6.642 (1.15), 6.997 (2.86), 7.016 (3.58), 7.018 (3.57), 7.037 (2.31), 7.047 (0.91), 7.062 (1.24), 7.068 (1.36), 7.083 (0.70), 7.089 (0.71), 7.125 (2.10), 7.129 (2.03), 7.139 (2.03), 7.143 (1.97), 7.196 (1.01), 7.203 (1.01), 7.220 (1.30), 7.227 (1.24), 7.245 (0.85), 7.251 (0.80), 7.355 (4.22), 7.366 (0.48), 7.391 (0.76), 7.408 (0.94), 7.412 (1.38), 7.429 (1.42), 7.451 (0.67), 8.045 (2.84), 8.059 (2.68), 8.194 (2.16), 10.612 (3.05), 11.734 (2.21).

Example 83

N-[4-(3-anilino-5-methyl-4-oxo-4,5,6,7-tetrahydro-1H-pyrrolo[3,2-c]pyridin-2-yl)pyridin-2-yl]-2-(3,4-difluorophenyl)acetamide

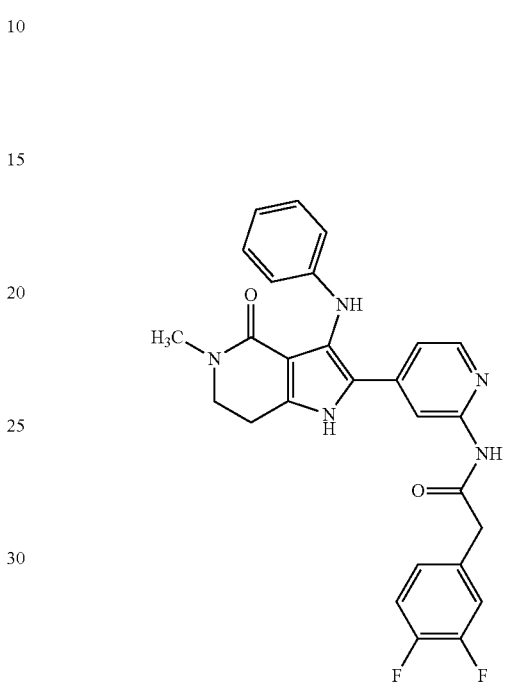

A solution of 2-(2-aminopyridin-4-yl)-3-anilino-5-methyl-1,5,6,7-tetrahydro-4H-pyrrolo[3,2-c]pyridin-4-one (see Intermediate 3, 0.1 g, 0.30 mmol, 1 eq) in DMA (2 mL) was treated with N,N-diisopropylethylamine (0.37 mL, 7 eq; CAS-RN: [7087-68-5]), (3,4-difluorophenyl)acetic acid (155 mg, 3 eq), and benzotriazol-1-yloxytripyrrolidinophosphonium hexafluorophosphate (0.468 g, 3 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column silica gel, 25 g, gradient: ethanol/dichloromethane 0-12%). to give 47 mg of the title compound.

LC-MS (Method 2): $R_t$=1.12 min; MS (ESIpos): m/z=488 [M+H]$^+$ $^1$H-NMR (400 MHz, DMSO-d$_6$) δ [ppm]: 1.140 (0.44), 1.958 (11.42), 2.521 (1.00), 2.525 (0.60), 2.784 (10.78), 2.860 (5.54), 2.894 (0.62), 2.911 (1.20), 2.929 (0.66), 2.944 (16.00), 3.513 (0.68), 3.531 (1.35), 3.548 (0.63), 3.714 (2.32), 6.541 (1.14), 6.560 (1.20), 6.615 (0.74), 6.633 (0.41), 6.990 (0.89), 7.008 (1.12), 7.011 (1.13), 7.030 (0.73), 7.128 (0.72), 7.132 (0.76), 7.142 (0.87), 7.146 (0.91), 7.361 (1.70), 7.376 (0.84), 7.382 (0.63), 7.403 (0.72), 8.047 (0.93), 8.061 (0.91), 8.180 (0.79), 10.581 (1.05), 11.734 (0.73).

Example 84

N-[4-(3-anilino-5-methyl-4-oxo-4,5,6,7-tetrahydro-1H-pyrrolo[3,2-c]pyridin-2-yl)pyridin-2-yl]-2-[4-(dimethylamino)phenyl]acetamide

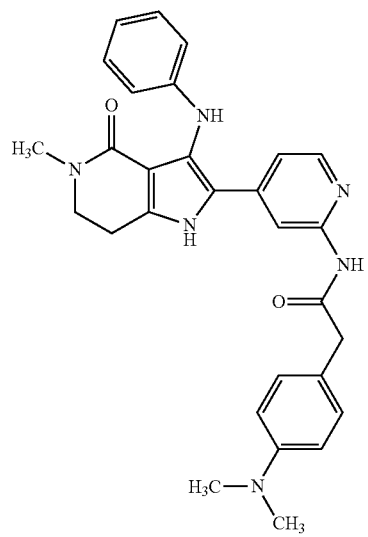 [SMILES: CN1CCc2[nH]c(-c3ccnc(NC(=O)Cc4ccc(N(C)C)cc4)c3)c(Nc3ccccc3)c2C1=O]

A solution of 2-(2-aminopyridin-4-yl)-3-anilino-5-methyl-1,5,6,7-tetrahydro-4H-pyrrolo[3,2-c]pyridin-4-one (see Intermediate 3, 0.1 g, 0.30 mmol, 1 eq) in DMA (2 mL) was treated with N,N-diisopropylethylamine (0.37 mL, 7 eq; CAS-RN: [7087-68-5]), [4-(dimethylamino)phenyl]-acetic acid (161 mg, 3 eq), and benzotriazol-1-yloxytripyrrolidinophosphonium hexafluorophosphate (0.468 g, 3 eq; CAS-RN: [128625-52-5]), and stirred for 18 h at r.t. 0

Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column silica gel, 25 g, gradient: ethanol/dichloromethane 0-12%), and triturated with hexane to give 85 mg of the title compound as a yellow solid.

LC-MS (Method 2): $R_t$=1.14 min; MS (ESIpos): m/z=495 [M+H]$^+$ $^1$H NMR (400 MHz, DMSO-d$_6$) δ ppm 2.85 (s, 6H) 2.86 (s, 3H) 2.91 (t, 2H) 3.54 (s, 4H) 6.53-6.58 (m, 2H) 6.61 (t, 1H) 6.66-6.70 (m, 2H) 7.01 (dd, 2H) 7.11 (dd, 1H) 7.15 (d, 2H) 7.35 (s, 1H) 8.03 (d, 1H) 8.19 (s, 1H) 10.39 (s, 1H) 11.73 (s, 1H)).

Example 85

N-[4-(3-anilino-5-methyl-4-oxo-4,5,6,7-tetrahydro-1H-pyrrolo[3,2-c]pyridin-2-yl)pyridin-2-yl]-2-(2-methylpyridin-4-yl)acetamide

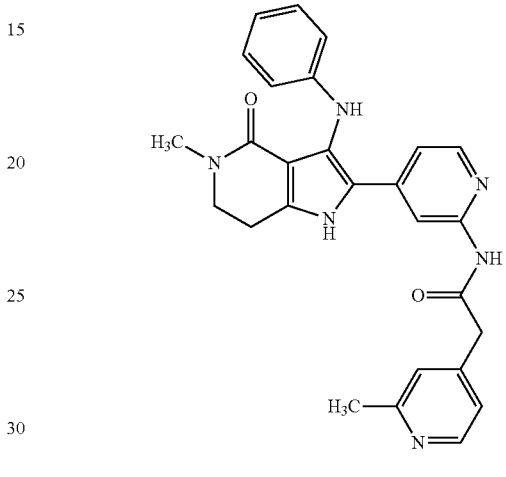

A solution of 2-(2-aminopyridin-4-yl)-3-anilino-5-methyl-1,5,6,7-tetrahydro-4H-pyrrolo[3,2-c]pyridin-4-one (see Intermediate 3, 0.1 g, 0.30 mmol, 1 eq) in DMA (0.65 mL) was treated with N,N-diisopropylethylamine (0.37 mL, 7 eq; CAS-RN: [7087-68-5]), (2-methylpyridin-4-yl)acetic acid (181 mg, 4 eq, CAS-RN: [114919-75-4], Bioorganic & Medicinal Chemistry Letters, 12, 3329-3332; 2002]), and benzotriazol-1-yloxytripyrrolidinophosphonium hexafluorophosphate (0.468 g, 3 eq; CAS-RN: [128625-52-5]), and stirred for 21 h at r.t.

Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column silica gel, 25 g, gradient: ethanol/dichloromethane 0-10%), and triturated with dichloromethane to give 32 mg of the title compound.

LC-MS (Method 2): $R_t$=0.91 min; MS (ESIpos): m/z=467 [M+H]$^+$ $^1$H-NMR (400 MHz, DMSO-d$_6$) δ [ppm]: 2.450 (16.00), 2.520 (1.41), 2.525 (0.91), 2.860 (14.39), 2.894 (1.53), 2.911 (3.24), 2.928 (1.63), 3.513 (1.83), 3.530 (3.66), 3.548 (1.60), 3.705 (6.71), 5.761 (8.69), 6.543 (3.08), 6.562 (3.25), 6.600 (0.92), 6.617 (1.92), 6.636 (1.05), 6.992 (2.40), 7.011 (3.07), 7.013 (3.02), 7.032 (1.88), 7.117 (1.50), 7.132 (2.93), 7.136 (2.00), 7.146 (1.85), 7.149 (1.82), 7.187 (2.78), 7.362 (3.81), 8.051 (2.59), 8.064 (2.45), 8.183 (2.15), 8.363 (2.39), 8.376 (2.29), 10.633 (2.82), 11.735 (1.99).

Example 86

N-{4-[3-(2-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide

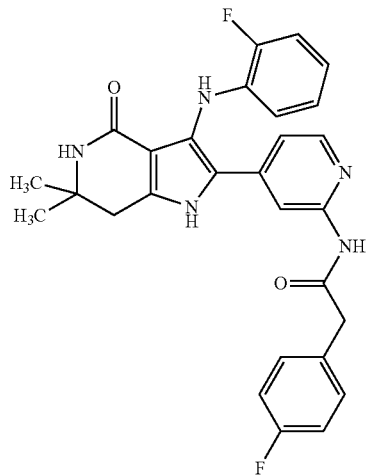 [SMILES: CC1(C)Cc2[nH]c(-c3ccnc(NC(=O)Cc4ccc(F)cc4)c3)c(Nc3ccccc3F)c2C(=O)N1]

A mixture of 2-(2-aminopyridin-4-yl)-3-(2-fluoroanilino)-6,6-dimethyl-1,5,6,7-tetrahydro-4H-pyrrolo[3,2-c]pyridin-4-one (Intermediate 85, 50 mg, 0.137 mmol, 1 eq), DMA (1.2 mL), benzotriazol-1-yloxytripyrrolidinophosphonium hexafluorophosphate (0.356 g, 5 eq; CAS-RN: [128625-52-5]), and N,N-diisopropylethylamine (0.140 mL, 6 eq; CAS-RN: [7087-68-5]), was stirred for 15 h at r.t., further (4-fluorophenyl)acetic acid (42.2 mg, 2 eq), benzotriazol-1-yloxytripyrrolidinophosphonium hexafluorophosphate (246 mg, 3 eq), and N,N-diisopropylethylamine (0.07 mL, 3 eq) were added, and stirring was continued for 30 h at 40° C. Then a sodium bicarbonate solution in water was added, and the mixture was extracted with dichloromethane. The organic phase was dried (sodium sulfate), filtered, concentrated under reduced pressure, and purified by column chromatography (column, 28 g, NH-Biotage, and column Biotage 25 g Ultra, gradient: hexane/ethyl acetate/ethanol) to give 17 mg of the title compound.

LC-MS (Method 2): $R_t$=1.16 min; MS (ESIpos): m/z=502 [M+H]$^+$ $^1$H-NMR (400 MHz, DMSO-d$_6$) δ [ppm]: 0.000 (0.45), 1.184 (0.62), 1.218 (0.72), 1.235 (1.23), 1.253 (0.70), 1.317 (16.00), 1.362 (0.60), 1.774 (0.88), 1.782 (0.90), 1.791 (2.38), 1.799 (0.91), 1.807 (0.92), 2.050 (1.93), 2.581 (2.02), 2.586 (1.28), 2.846 (4.93), 3.051 (0.61), 3.061 (0.94), 3.068 (1.69), 3.078 (1.67), 3.084 (0.90), 3.094 (0.59), 3.353 (1.01), 3.738 (5.22), 4.080 (0.46), 4.098 (0.45), 5.822 (5.26), 6.315 (0.62), 6.319 (0.68), 6.338 (1.19), 6.357 (0.62), 6.361 (0.64), 6.691 (0.67), 6.695 (0.67), 6.703 (0.67), 6.707 (0.67), 6.714 (0.49), 6.722 (0.46), 6.726 (0.43), 6.794 (0.83), 6.813 (1.25), 6.832 (0.54), 7.138 (0.77), 7.141 (0.81), 7.153 (1.83), 7.158 (2.67), 7.164 (3.38), 7.167 (3.43), 7.171 (2.66), 7.192 (2.43), 7.197 (0.84), 7.208 (0.87), 7.214 (3.90), 7.220 (0.95), 7.231 (0.73), 7.236 (2.26), 7.337 (1.97), 7.341 (2.02), 7.386 (1.86), 7.391 (0.90), 7.400 (2.14), 7.408 (1.97), 7.416 (0.80), 7.422 (1.59), 8.143 (2.17), 8.156 (2.08), 8.228 (1.94), 10.633 (2.41), 11.837 (1.80).

Example 87

N-{4-[3-(2-chloro-3-fluoroanilino)-4-oxo-4,5,6,7-tetrahydro-1H-pyrrolo[3,2-c]pyridin-2-yl]pyridin-2-yl}-2-(4-fluorophenyl)acetamide

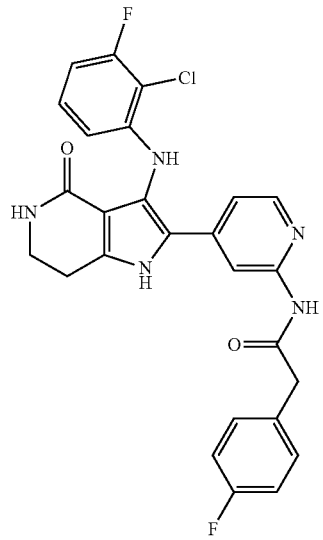 [SMILES: O=C(Cc1ccc(F)cc1)Nc1cc(-c2[nH]c3c(c2Nc2cccc(F)c2Cl)C(=O)NCC3)ccn1]

A solution of 2-(2-aminopyridin-4-yl)-3-(2-chloro-3-fluoroanilino)-1,5,6,7-tetrahydro-4H-pyrrolo[3,2-c]pyridin-4-one (Intermediate 89, 95 mg, 0.256 mmol, 1 eq) in DMA (1 mL) was treated with N,N-diisopropylethylamine (0.26 mL, 6 eq; CAS-RN: [7087-68-5]), (4-fluorophenyl)acetic acid (78.8 mg, 2 eq), and HATU (0.468 g, 5 eq), stirred for 10 h at 60° C. Then a sodium bicarbonate solution in water was added, and the mixture was extracted with ethyl acetate. The organic phase was washed with saturated sodium chloride solution, dried (sodium sulfate), filtered, concentrated under reduced pressure. Silicagel chromatography followed by preparative RP-18 reverse phase HPLC (gradient of water and acetonitrile containing trifluoroacetic acid as additive) gave 15 mg of the title compound.

LC-MS (Method 1): $R_t$=1.04 min; MS (ESIpos): m/z=508 [M+H]$^+$ $^1$H-NMR (400 MHz, DMSO-d$_6$) δ [ppm]: 1.231 (0.43), 1.987 (0.50), 2.518 (4.67), 2.523 (3.21), 2.678 (0.41), 2.814 (3.44), 2.832 (7.47), 2.848 (3.85), 3.372 (2.64), 3.378 (2.80), 3.389 (5.03), 3.394 (4.85), 3.406 (2.44), 3.412 (2.23), 3.670 (16.00), 6.110 (4.55), 6.131 (4.57), 6.613 (2.25), 6.616 (2.32), 6.636 (4.14), 6.656 (2.59), 6.659 (2.48), 6.884 (1.96), 6.900 (2.23), 6.905 (3.66), 6.920 (3.66), 6.925 (1.91), 6.941 (1.66), 7.077 (4.80), 7.081 (4.87), 7.091 (4.80), 7.095 (4.73), 7.115 (0.61), 7.122 (5.67), 7.128 (2.21), 7.139 (2.78), 7.145 (13.18), 7.150 (5.19), 7.155 (5.35), 7.161 (4.64), 7.167 (7.94), 7.174 (1.00), 7.312 (0.71), 7.319 (5.94), 7.325 (2.46), 7.333 (6.60), 7.341 (5.51), 7.350 (2.16), 7.355 (4.80), 7.363 (0.52), 7.476 (11.13), 8.107 (6.74), 8.121 (6.55), 8.156 (5.85), 10.577 (7.76), 11.891 (5.39).

Example 88

N-{4-[3-anilino-5,6-dimethyl-4-oxo-4,5,6,7-tetra-hydro-1H-pyrrolo[3,2-c]pyridin-2-yl]pyridin-2-yl}-2-(4-fluorophenyl)acetamide (Racemate)

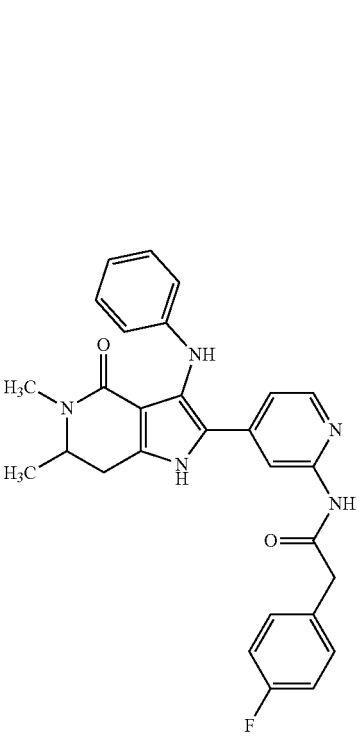

A solution of 2-(2-aminopyridin-4-yl)-3-anilino-5,6-dimethyl-1,5,6,7-tetrahydro-4H-pyrrolo[3,2-c]pyridin-4-one (Racemate) (Intermediate 95, 0.16 g, 0.461 mmol, 1 eq) in DMA (1 mL) was treated with N,N-diisopropylethylamine (0.48 mL, 6 eq; CAS-RN: [7087-68-5]), (4-fluorophenyl) acetic acid (78.8 mg, 2 eq), and benzotriazol-1-yloxytripyrrolidinophosphonium hexafluorophosphate (0.719 g, 3 eq; CAS-RN: [128625-52-5]) and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column NH-Biotage, 28 g and silicagel, 25 g, gradient dichloromethane/methanol, 0-25%) to give 105 mg of the title compound.

LC-MS (Method 2): $R_t$=1.17 min; MS (ESIpos): m/z=484 [M+H]$^+$ $^1$H-NMR (400 MHz, DMSO-d$_6$) δ ppm 1.15 (d, 3H), 2.65 (dd, 1H), 2.85 (s, 3H), 3.19 (dd, 1H), 3.69 (s, 2H), 3.74-3.85 (m, 1H), 6.54 (dd, 2H), 6.58-6.65 (m, 1H), 7.01 (dd, 2H), 7.10-7.20 (m, 3H), 7.31-7.40 (m, 3H), 8.04 (d, 1H), 8.17 (s, 1H), 10.56 (s, 1H), 11.71 (s, 1H).

Example 89

(+)-N-{4-[3-anilino-5,6-dimethyl-4-oxo-4,5,6,7-tetrahydro-1H-pyrrolo[3,2-c]pyridin-2-yl]pyridin-2-yl}-2-(4-fluorophenyl)acetamide (Enantiomer 1)

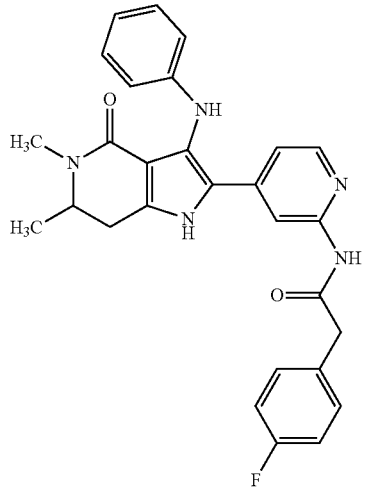 [SMILES: CC1Cc2[nH]c(-c3ccnc(NC(=O)Cc4ccc(F)cc4)c3)c(Nc3ccccc3)c2C(=O)N1C]

The racemic compound (Example 88, 98 mg) was separated into enantiomers by preparative chiral HPLC to give enantiomer 1 (33 mg, 100% ee, see Example 89) and enantiomer 2 (37 mg, 100% ee, see Example 90).

Preparative Chiral HPLC Method:

Instrument: PrepCon Labomatic HPLC; Column: YMC Cellulose SC 5μ, 250×30; eluent A: hexane+0.1 vol % diethylamine; eluent B: ethanol; isocratic: 80% A+20% B; flow: 50 mL/min; temperature: 25° C.; UV: 254 nm;

Analytical Chiral HPLC Method:

Instrument: Waters Alliance 2695; Column: YMC Cellulose SC 3μ, 100×4.6; eluent A: hexane+0.1 vol % diethylamine; eluent B: ethanol; isocratic: 80% A+20% B; flow: 1.4 mL/min; temperature: 25° C.; UV: 254 nm;

Analytical Chiral HPLC (method see Example 89): $R_t$=2.55 min.

[a]$_D$=+14.3° (from solution in DMSO, c=1.8 mg/mL)

LC-MS (Method 2): $R_t$=1.17 min; MS (ESIpos): m/z=484 [M+H]$^+$ $^1$H-NMR (400 MHz, DMSO-d$_6$) δ [ppm]: 0.795 (0.46), 1.036 (0.73), 1.053 (1.55), 1.071 (0.80), 1.084 (0.65), 1.137 (6.26), 1.142 (6.12), 1.155 (13.60), 1.158 (6.89), 1.173 (5.48), 1.232 (0.44), 1.260 (0.85), 2.518 (1.19), 2.523 (0.85), 2.630 (1.04), 2.635 (1.09), 2.670 (1.40), 2.677 (1.31), 2.850 (16.00), 2.872 (0.40), 2.883 (0.46), 2.901 (1.35), 2.917 (1.49), 2.919 (1.75), 2.932 (1.71), 2.950 (1.29), 3.166 (2.88), 3.184 (1.06), 3.209 (0.92), 3.225 (0.84), 3.289 (0.53), 3.412 (0.81), 3.429 (1.36), 3.447 (1.42), 3.464 (1.06), 3.775 (0.59), 3.780 (0.65), 3.791 (0.89), 3.797 (0.89), 3.808 (0.64), 3.813 (0.58), 6.537 (2.84), 6.539 (3.54), 6.558 (3.65), 6.561 (3.00), 6.595 (0.67), 6.597 (1.06), 6.616 (2.17), 6.634 (1.15), 6.994 (2.81), 7.012 (3.36), 7.015 (3.24), 7.029 (0.80), 7.033 (2.20), 7.127 (2.19), 7.130 (3.80), 7.135 (1.25), 7.141 (2.00), 7.145 (2.55), 7.152 (5.33), 7.158 (1.08), 7.169 (0.95), 7.175 (2.97), 7.336 (2.50), 7.341 (1.18), 7.350 (2.88), 7.358 (2.70), 7.367 (1.59), 7.372 (2.95), 8.038 (2.76), 8.053 (2.58), 8.151 (2.12), 10.600 (1.75), 11.729 (1.97).

Example 90

(−)-N-{4-[3-anilino-5,6-dimethyl-4-oxo-4,5,6,7-tetrahydro-1H-pyrrolo[3,2-c]pyridin-2-yl]pyridin-2-yl}-2-(4-fluorophenyl)acetamide (Enantiomer 2)

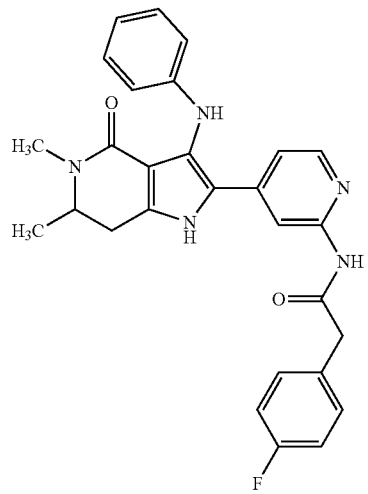

For the preparation of the racemic title compound see Example 88. Separation of enantiomers by preparative chiral HPLC (method see Example 89) gave the title compound (37 mg).

Analytical Chiral HPLC (method see Example 89): $R_t$=3.43 min.

$[a]_D$=−18.0° (from solution in DMSO, c=1.5 mg/mL)

LC-MS (Method 2): $R_t$=1.17 min; MS (ESIpos): m/z=484 [M+H]⁺

¹H-NMR (400 MHz, DMSO-d₆) δ [ppm]=0.776 (0.55), 0.795 (1.42), 0.814 (0.91), 0.820 (0.46), 0.837 (0.49), 0.862 (0.56), 1.006 (1.19), 1.035 (0.80), 1.085 (1.74), 1.114 (0.49), 1.132 (1.25), 1.142 (5.52), 1.150 (1.42), 1.158 (5.50), 1.232 (0.54), 1.260 (2.14), 2.518 (0.90), 2.523 (0.62), 2.627 (0.99), 2.632 (1.04), 2.668 (1.32), 2.673 (1.31), 2.849 (16.00), 3.164 (0.81), 3.181 (0.98), 3.205 (0.83), 3.222 (0.76), 3.688 (6.38), 3.772 (0.52), 3.778 (0.58), 3.789 (0.81), 3.794 (0.81), 3.805 (0.57), 3.811 (0.50), 6.533 (2.56), 6.535 (3.13), 6.554 (3.31), 6.557 (2.72), 6.591 (0.60), 6.594 (0.99), 6.611 (2.00), 6.630 (1.11), 6.991 (2.50), 7.009 (3.09), 7.012 (3.03), 7.030 (2.06), 7.117 (2.03), 7.120 (2.14), 7.130 (4.14), 7.134 (2.70), 7.146 (1.04), 7.151 (4.84), 7.158 (1.01), 7.169 (0.87), 7.174 (3.01), 7.338 (2.40), 7.343 (1.10), 7.355 (5.22), 7.368 (0.92), 7.373 (1.97), 8.035 (2.66), 8.050 (2.45), 8.177 (2.26), 10.518 (0.45), 10.559 (2.92), 10.854 (0.64), 11.709 (1.78).

Example 91

(+)-(2RS)—N-{4-[(6R*)-3-anilino-5,6-dimethyl-4-oxo-4,5,6,7-tetrahydro-1H-pyrrolo[3,2-c]pyridin-2-yl]pyridin-2-yl}-2-(4-fluorophenyl)propanamide (2 Stereoisomers #1)

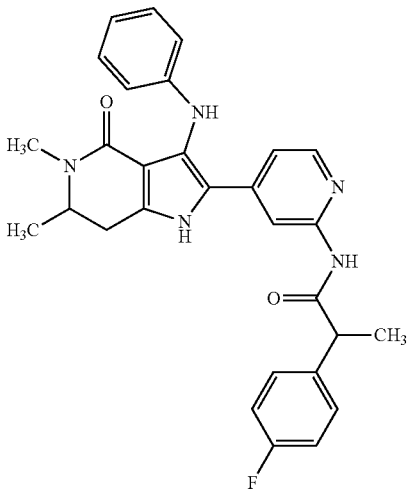 [SMILES: CC(C(=O)Nc1cc(-c2[nH]c3c(c2Nc2ccccc2)C(=O)N(C)C(C)C3)ccn1)c1ccc(F)cc1]

A solution of (+)-2-(2-aminopyridin-4-yl)-3-anilino-5,6-dimethyl-1,5,6,7-tetrahydro-4H-pyrrolo[3,2-c]pyridin-4-one (Enantiomer 1) (see Intermediate 96, 0.155 g, 0.446 mmol, 1 eq) in DMA (0.97 mL) was treated with N,N-diisopropylethylamine (0.47 mL, 6 eq; CAS-RN: [7087-68-5]), 2-(4-fluorophenyl)propanoic acid (Racemate) (0.225 g, 2 eq), and benzotriazol-1-yloxytripyrrolidinophosphonium hexafluorophosphate (0.697 g, 3 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column NH-Biotage, 28 g and silicagel, 25 g, gradient dichloromethane/methanol, 0-25%) to give 157 mg of the title compound.

$[a]_D$=+14.2° (from solution in DMSO, c=3.1 mg/mL)

LC-MS (Method 2): $R_t$=1.24 min; MS (ESIpos): m/z=498 [M+H]⁺

¹H-NMR (400 MHz, DMSO-d₆) δ [ppm]: 1.147 (3.81), 1.152 (3.96), 1.164 (4.01), 1.169 (3.76), 1.190 (0.49), 1.230 (0.45), 1.375 (4.20), 1.378 (4.38), 1.392 (4.37), 1.395 (4.29), 1.987 (1.35), 2.326 (0.50), 2.518 (1.89), 2.522 (1.28), 2.643 (1.04), 2.649 (1.08), 2.664 (0.45), 2.669 (0.61), 2.673 (0.54), 2.684 (1.28), 2.690 (1.16), 2.848 (2.43), 2.855 (16.00), 3.177 (0.64), 3.189 (0.71), 3.193 (0.71), 3.214 (0.60), 3.219 (0.66), 3.235 (0.60), 3.688 (0.54), 3.782 (0.60), 3.788 (0.71), 3.798 (0.94), 3.804 (0.95), 3.815 (0.66), 3.820 (0.58), 3.980 (0.41), 3.997 (1.45), 4.015 (1.45), 4.034 (0.53), 5.758 (15.20), 6.532 (3.44), 6.534 (3.04), 6.553 (3.74), 6.588 (0.75), 6.591 (0.78), 6.606 (1.61), 6.609 (1.62), 6.624 (0.91), 6.627 (0.88), 6.988 (2.41), 7.008 (3.53), 7.027 (1.96), 7.099 (1.38), 7.102 (1.87), 7.106 (1.40), 7.113 (1.43), 7.116 (1.95), 7.119 (1.51), 7.132 (1.81), 7.134 (2.00), 7.154 (3.73), 7.156 (3.73), 7.176 (2.14), 7.178 (1.89), 7.354 (0.62), 7.363 (2.53), 7.370 (2.54), 7.383 (1.45), 7.388 (0.73), 7.397 (2.76), 7.404 (1.63), 7.411 (1.74), 7.419 (2.47), 7.428 (0.57), 7.433 (1.19), 8.009 (2.10), 8.010 (1.74), 8.021 (1.99), 8.189 (1.51), 8.196 (1.51), 10.492 (1.89), 10.500 (1.88), 11.712 (1.46), 11.720 (1.41).

Example 92

(+)-N-{4-[3-anilino-5,6-dimethyl-4-oxo-4,5,6,7-tetrahydro-1H-pyrrolo[3,2-c]pyridin-2-yl]pyridin-2-yl}-2-(4-fluorophenyl)propanamide (Single Stereoisomer 1)

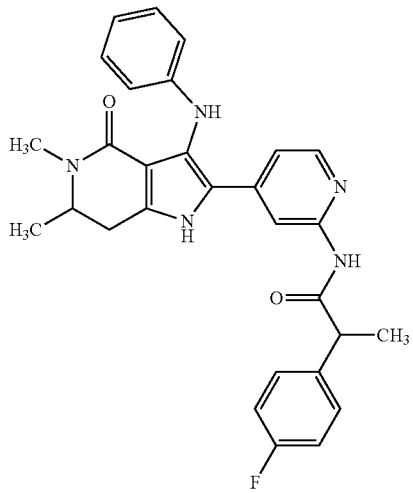 [SMILES: CC(C(=O)Nc1cc(-c2[nH]c3c(c2Nc2ccccc2)C(=O)N(C)C(C)C3)ccn1)c1ccc(F)cc1]

The mixture of two stereoisomers #1 (Example 91, 150 mg) was separated into the single stereoisomers by preparative chiral HPLC to give stereoisomer 1 (51 mg, 100% ee, see Example 92) and stereoisomer 2 (39 mg, 98.8% ee, see Example 93).
Preparative Chiral HPLC Method:
Instrument: Sepiatec: Prep SFC100; Column: Chiralpak IA 5μ 250×30 mm; eluent A: carbon dioxide; eluent B: ethanol+0.2 vol % aqueous ammonia (32%); isocratic: 35% B; flow: 100 mL/min; temperature: 40° C.; BPR: 150 bar; UV: 280 nm;
Analytical Chiral HPLC Method:
Instrument: Agilent: 1260, Aurora SFC-Modul; Column: Chiralpak IA 5μ 100×4.6 mm; Eluent A: carbon dioxide; Eluent B: ethanol+0.2 Vol-% aqueous ammonia (32%); isocratic: 35% B; flow: 4 mL/min; temperature: 37.5° C.; BPR: 100 bar; UV: 280 nm;
Analytical Chiral HPLC (method see Example 92): $R_t$=2.34 min.
[a]$_D$=+172.9° (from solution in DMSO, c=1.6 mg/mL)
LC-MS (Method 2): $R_t$=1.24 min; MS (ESIpos): m/z=498 [M+H]$^+$
$^1$H-NMR (400 MHz, DMSO-d$_6$) δ [ppm]: 0.797 (0.82), 0.802 (0.44), 0.813 (0.88), 0.820 (0.93), 0.825 (0.41), 0.839 (0.60), 0.850 (0.44), 0.857 (0.47), 0.885 (0.50), 0.903 (0.92), 0.922 (0.48), 1.118 (0.42), 1.133 (0.59), 1.147 (5.72), 1.163 (5.86), 1.178 (0.46), 1.379 (6.31), 1.397 (6.45), 2.518 (0.83), 2.523 (0.52), 2.539 (0.42), 2.645 (1.05), 2.650 (1.09), 2.686 (1.25), 2.692 (1.17), 2.855 (16.00), 3.178 (0.86), 3.194 (1.05), 3.219 (0.89), 3.235 (0.82), 3.781 (0.56), 3.787 (0.63), 3.798 (0.88), 3.803 (0.86), 3.814 (0.61), 3.819 (0.54), 3.981 (0.41), 3.998 (1.38), 4.016 (1.36), 6.533 (3.28), 6.553 (3.49), 6.588 (1.01), 6.606 (2.08), 6.625 (1.13), 6.988 (2.56), 7.006 (3.31), 7.008 (3.27), 7.027 (2.08), 7.102 (2.00), 7.106 (1.93), 7.115 (1.89), 7.119 (2.03), 7.134 (2.33), 7.140 (0.83), 7.151 (1.04), 7.157 (4.84), 7.162 (1.03), 7.174 (0.87), 7.179 (2.73), 7.365 (4.18), 7.399 (2.46), 7.404 (1.10), 7.412 (2.71), 7.421 (2.43), 7.429 (0.94), 7.435 (2.08), 8.008 (2.71), 8.021 (2.61), 8.202 (2.66), 10.502 (3.07), 11.724 (1.84).

Example 93

(−)-N-{4-[3-anilino-5,6-dimethyl-4-oxo-4,5,6,7-tetrahydro-1H-pyrrolo[3,2-c]pyridin-2-yl]pyridin-2-yl}-2-(4-fluorophenyl)propanamide (Single Stereoisomer 2)

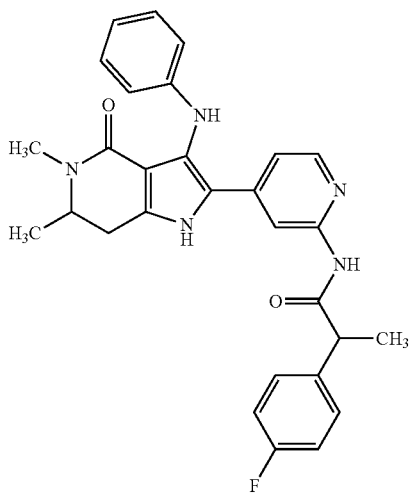 [SMILES: CC(C(=O)Nc1cc(-c2[nH]c3c(c2Nc2ccccc2)C(=O)N(C)C(C)C3)ccn1)c1ccc(F)cc1]

For the preparation of the mixture of two stereoisomers #1 see Example 91. Separation of the mixture of two stereoisomers #1 by preparative chiral HPLC (method see Example 92) gave the title compound (39 mg).

Analytical Chiral HPLC (method see Example 92): $R_t$=3.91 min.
[a]$_D$=−135.2° (from solution in DMSO, c=1.2 mg/mL)
LC-MS (Method 2): $R_t$=1.23 min; MS (ESIpos): m/z=498 [M+H]$^+$
$^1$H-NMR (400 MHz, DMSO-d$_6$) δ [ppm]=0.797 (0.94), 0.802 (0.49), 0.814 (1.06), 0.820 (1.08), 0.839 (0.62), 0.886 (0.63), 0.904 (1.08), 0.922 (0.57), 1.139 (1.01), 1.152 (5.53), 1.169 (5.57), 1.375 (6.29), 1.393 (6.28), 2.518 (0.76), 2.523 (0.50), 2.644 (1.01), 2.649 (1.06), 2.685 (1.22), 2.691 (1.11), 2.856 (16.00), 3.173 (0.82), 3.189 (1.00), 3.214 (0.84), 3.231 (0.77), 3.781 (0.53), 3.787 (0.59), 3.798 (0.84), 3.803 (0.83), 3.814 (0.59), 3.820 (0.51), 3.999 (1.31), 4.017 (1.29), 6.536 (3.22), 6.555 (3.39), 6.558 (2.82), 6.592 (0.97), 6.610 (2.07), 6.628 (1.13), 6.989 (2.50), 7.008 (3.18), 7.010 (3.12), 7.029 (2.07), 7.104 (2.05), 7.109 (1.95), 7.117 (1.91), 7.122 (2.12), 7.132 (2.43), 7.137 (0.81), 7.148 (0.96), 7.154 (5.02), 7.160 (0.98), 7.171 (0.84), 7.176 (2.70), 7.372 (4.12), 7.384 (2.50), 7.390 (1.07), 7.398 (2.67), 7.406 (2.38), 7.414 (0.90), 7.420 (2.09), 8.010 (2.68), 8.024 (2.57), 8.190 (2.49), 8.192 (2.51), 10.494 (3.00), 11.714 (1.89).

Example 94

(−)-(2RS)—N-{4-[(6R*)-3-anilino-5,6-dimethyl-4-oxo-4,5,6,7-tetrahydro-1H-pyrrolo[3,2-c]pyridin-2-yl]pyridin-2-yl}-2-(4-fluorophenyl)propanamide (2 Stereoisomers #2)

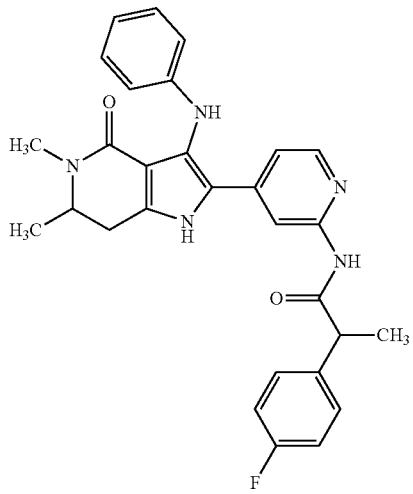 [SMILES: CC(C(=O)Nc1cc(-c2[nH]c3c(c2Nc2ccccc2)C(=O)N(C)C(C)C3)ccn1)c1ccc(F)cc1]

A solution of (−)-2-(2-aminopyridin-4-yl)-3-anilino-5,6-dimethyl-1,5,6,7-tetrahydro-4H-pyrrolo[3,2-c]pyridin-4-one (Enantiomer 2) (see Intermediate 97, 0.170 g, 0.489 mmol, 1 eq) in DMA (1.1 mL) was treated with N,N-diisopropylethylamine (0.51 mL, 6 eq; CAS-RN: [7087-68-5]), 2-(4-fluorophenyl)propanoic acid (Racemate) (0.247 g, 2 eq), and benzotriazol-1-yloxytripyrrolidinophosphonium hexafluorophosphate (0.764 g, 3 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column NH-Biotage, 28 g and silicagel, 25 g, gradient dichloromethane/methanol, 0-25%) to give 124 mg of the title compound.

$[\alpha]_D$=−21.8° (from solution in DMSO, c=3.7 mg/mL)

LC-MS (Method 2): $R_t$=1.24 min; MS (ESIpos): m/z=498 [M+H]$^+$ $^1$H-NMR (400 MHz, DMSO-$d_6$) δ [ppm]: 1.147 (2.63), 1.152 (2.72), 1.164 (2.78), 1.169 (2.60), 1.375 (2.87), 1.378 (3.01), 1.392 (3.05), 1.395 (2.99), 2.518 (1.52), 2.522 (1.01), 2.643 (0.73), 2.649 (0.75), 2.669 (0.44), 2.684 (0.87), 2.690 (0.80), 2.848 (1.53), 2.855 (11.00), 3.178 (0.44), 3.189 (0.49), 3.193 (0.49), 3.218 (0.46), 3.235 (0.43), 3.782 (0.42), 3.788 (0.48), 3.798 (0.65), 3.804 (0.66), 3.815 (0.46), 3.821 (0.40), 3.997 (1.01), 4.015 (1.00), 5.758 (16.00), 6.532 (2.36), 6.534 (2.06), 6.553 (2.55), 6.588 (0.52), 6.591 (0.54), 6.606 (1.11), 6.609 (1.12), 6.624 (0.63), 6.627 (0.62), 6.988 (1.66), 7.007 (2.44), 7.027 (1.36), 7.099 (0.95), 7.102 (1.29), 7.106 (0.97), 7.113 (0.97), 7.116 (1.34), 7.119 (1.06), 7.134 (1.36), 7.154 (2.53), 7.156 (2.60), 7.176 (1.48), 7.178 (1.34), 7.362 (1.73), 7.370 (1.73), 7.383 (1.00), 7.388 (0.51), 7.397 (1.92), 7.404 (1.16), 7.411 (1.21), 7.419 (1.73), 7.428 (0.42), 7.433 (0.84), 8.009 (1.45), 8.021 (1.38), 8.189 (1.04), 8.196 (1.06), 10.492 (1.29), 10.499 (1.31), 11.712 (0.99), 11.720 (0.99).

Example 95

(−)-N-{4-[3-anilino-5,6-dimethyl-4-oxo-4,5,6,7-tetrahydro-1H-pyrrolo[3,2-c]pyridin-2-yl]pyridin-2-yl}-2-(4-fluorophenyl)propanamide (Single Stereoisomer 3)

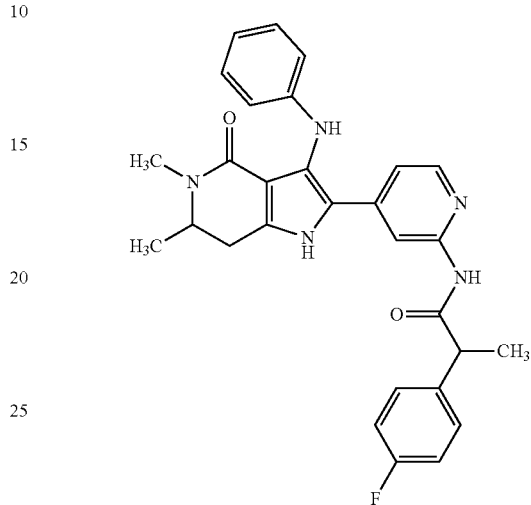

The mixture of two stereoisomers #2 (Example 94, 117 mg) was separated into the single stereoisomers by preparative chiral HPLC to give stereoisomer 3 (33 mg, >99.9% ee, see Example 95) and stereoisomer 4 (34 mg, 92.6% ee, see Example 96).

Preparative Chiral HPLC Method:

Instrument: PrepCon Labomatic HPLC; Column: YMC Cellulose SB 10µ, 250×50; eluent A: hexane+0.1 vol % diethylamine; eluent B: ethanol; gradient; flow: 150 mL/min; temperature: 25° C.; UV: 254 nm;

Analytical Chiral HPLC Method:

Instrument: Waters Alliance 2695; Column: YMC Cellulose SB 3µ, 100×4.6; eluent A: hexane+0.1 vol % diethylamine; eluent B: ethanol; gradient; flow: 1.4 mL/min; temperature: 25° C.; UV: 254 nm;

Analytical Chiral HPLC (method see Example 95): $R_t$=2.81 min.

$[\alpha]_D$=−177.3° (from solution in DMSO, c=3.3 mg/mL)

LC-MS (Method 2): $R_t$=1.22 min; MS (ESIpos): m/z=498 [M+H]$^+$ $^1$H-NMR (400 MHz, DMSO-$d_6$) δ [ppm]: 0.832 (0.62), 0.852 (0.56), 1.148 (2.98), 1.164 (2.98), 1.232 (1.30), 1.353 (0.68), 1.378 (3.29), 1.395 (3.97), 2.337 (1.18), 2.518 (16.00), 2.523 (10.73), 2.649 (0.56), 2.674 (2.67), 2.679 (1.24), 2.685 (0.68), 2.855 (8.74), 3.178 (0.43), 3.194 (0.50), 3.219 (0.43), 3.235 (0.43), 3.800 (0.43), 3.996 (0.68), 4.014 (0.74), 6.531 (1.74), 6.550 (1.80), 6.587 (0.56), 6.606 (1.12), 6.624 (0.62), 6.987 (1.36), 7.005 (1.67), 7.026 (1.12), 7.098 (1.05), 7.103 (1.05), 7.112 (0.99), 7.116 (1.12), 7.135 (1.30), 7.157 (2.73), 7.179 (1.49), 7.362 (1.92), 7.397 (1.30), 7.411 (1.43), 7.419 (1.30), 7.433 (1.12), 8.006 (1.43), 8.021 (1.36), 8.196 (1.30), 10.499 (1.43), 11.720 (1.12).

Example 96

(+)-N-{4-[3-anilino-5,6-dimethyl-4-oxo-4,5,6,7-tetrahydro-1H-pyrrolo[3,2-c]pyridin-2-yl]pyridin-2-yl}-2-(4-fluorophenyl)propanamide (Single Stereoisomer 4)

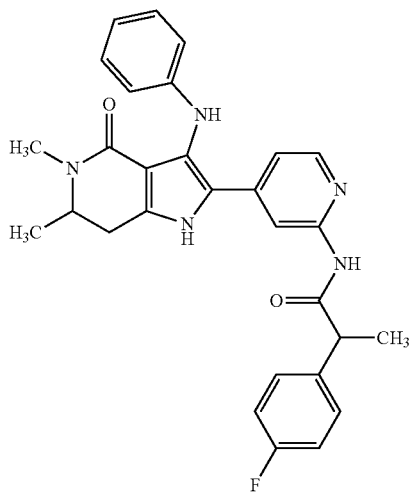 [SMILES: CC(C(=O)Nc1cc(-c2[nH]c3c(c2Nc2ccccc2)C(=O)N(C)C(C)C3)ccn1)c1ccc(F)cc1]

For the preparation of the mixture of two stereoisomers #2 see Example 94. Separation of the mixture of two stereoisomers #2 by preparative chiral HPLC (method see Example 95) gave the title compound (34 mg).

Analytical Chiral HPLC (method see Example 95): $R_t$=2.81 min.

$[a]_D$=+117.5° (from solution in DMSO, c=2.8 mg/mL)

LC-MS (Method 2): $R_t$=1.22 min; MS (ESIpos): m/z=498 [M+H]$^+$ $^1$H-NMR (400 MHz, DMSO-d$_6$) δ [ppm]=0.831 (0.54), 0.852 (0.49), 1.153 (5.91), 1.169 (5.69), 1.232 (1.30), 1.259 (0.49), 1.353 (0.71), 1.374 (6.40), 1.392 (6.62), 2.337 (1.03), 2.518 (13.56), 2.523 (9.11), 2.642 (1.03), 2.648 (1.08), 2.679 (1.30), 2.684 (1.30), 2.689 (1.14), 2.856 (16.00), 3.173 (0.81), 3.189 (0.98), 3.214 (0.87), 3.231 (0.81), 3.789 (0.65), 3.800 (0.92), 3.817 (0.60), 3.996 (1.36), 4.014 (1.36), 6.533 (3.36), 6.552 (3.58), 6.592 (0.98), 6.609 (2.06), 6.628 (1.14), 6.988 (2.60), 7.007 (3.36), 7.028 (2.12), 7.101 (2.01), 7.105 (2.01), 7.115 (2.01), 7.119 (2.12), 7.132 (2.44), 7.154 (5.10), 7.176 (2.77), 7.369 (3.96), 7.382 (2.44), 7.388 (1.08), 7.396 (2.77), 7.404 (2.44), 7.412 (0.98), 7.418 (2.17), 8.010 (2.71), 8.024 (2.60), 8.186 (2.49), 10.491 (2.87), 11.711 (2.17).

Example 97

N-{4-[3-anilino-5,6-dimethyl-4-oxo-4,5,6,7-tetrahydro-1H-pyrrolo[3,2-c]pyridin-2-yl]pyridin-2-yl}-2-(pyridin-4-yl)acetamide (Racemate)

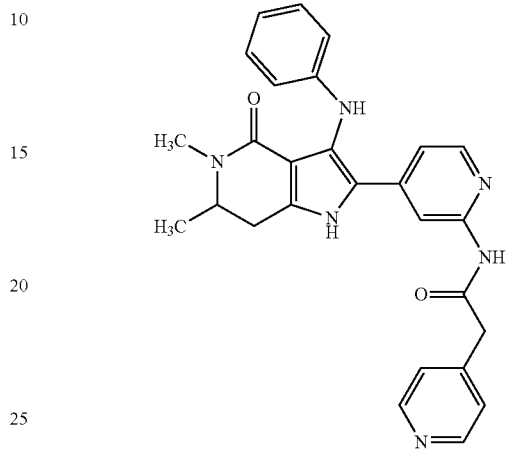

A solution of 2-(2-aminopyridin-4-yl)-3-anilino-5,6-dimethyl-1,5,6,7-tetrahydro-4H-pyrrolo[3,2-c]pyridin-4-one (Racemate) (see Intermediate 95, 0.237 g, 0.682 mmol, 1 eq) in DMA (10 mL) was treated with N,N-diisopropylethylamine (0.83 mL, 7 eq; CAS-RN: [7087-68-5]), (pyridin-4-yl)acetic acid×hydrogen chloride (1/1) (0.355 g, 2 eq), and benzotriazol-1-yloxytripyrrolidinophosphonium hexafluorophosphate (1.06 g, 3 eq; CAS-RN: [128625-52-5]), and stirred for 72 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure. Silicagel chromatography (column silicagel, 50 g, gradient ethyl acetate/ethanol), followed by preparative reverse phase HPLC (gradient of water and acetonitrile containing ammonium hydroxide as additive) gave a solid that was triturated with ethyl acetate to give 99 mg of the title compound.

LC-MS (Method 2): $R_t$=0.96 min; MS (ESIneg): m/z=465 [M−H]$^-$ $^1$H-NMR (400 MHz, DMSO-d$_6$) δ [ppm]: 1.142 (5.67), 1.154 (3.59), 1.159 (5.84), 1.172 (4.48), 1.190 (2.19), 1.727 (0.52), 1.988 (7.73), 2.327 (0.41), 2.518 (1.56), 2.523 (1.03), 2.628 (1.05), 2.634 (1.10), 2.669 (1.64), 2.675 (1.43), 2.850 (16.00), 3.168 (0.85), 3.184 (1.04), 3.209 (0.88), 3.226 (0.81), 3.757 (7.43), 3.775 (0.76), 3.780 (0.69), 3.791 (0.91), 3.796 (0.88), 3.808 (0.62), 3.813 (0.54), 3.999 (0.55), 4.017 (1.64), 4.035 (1.58), 4.053 (0.52), 5.759 (0.70), 6.535 (3.35), 6.554 (3.55), 6.557 (2.91), 6.596 (1.02), 6.614 (2.14), 6.633 (1.16), 6.991 (2.69), 7.010 (3.37), 7.012 (3.26), 7.030 (2.11), 7.132 (2.07), 7.136 (2.05), 7.146 (2.00), 7.150 (2.05), 7.319 (4.17), 7.322 (2.69), 7.329 (2.79), 7.333 (4.25), 7.365 (3.78), 8.050 (2.83), 8.064 (2.65), 8.165 (2.23), 8.505 (4.52), 8.509 (2.87), 8.516 (2.83), 8.520 (4.46), 10.652 (3.00), 11.710 (2.17).

Example 98

(+)-N-{4-[(6R*)-3-anilino-5,6-dimethyl-4-oxo-4,5,6,7-tetrahydro-1H-pyrrolo[3,2-c]pyridin-2-yl]pyridin-2-yl}-2-(pyridin-4-yl)acetamide (Enantiomer 1)

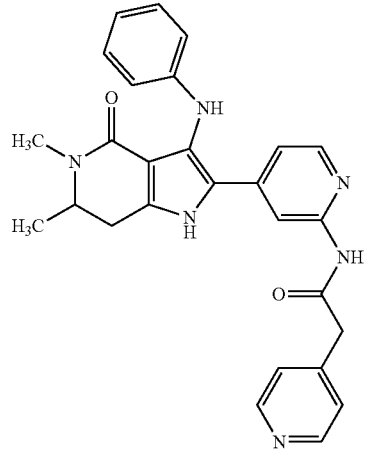 [SMILES: CC1Cc2[nH]c(-c3ccnc(NC(=O)Cc4ccncc4)c3)c(Nc3ccccc3)c2C(=O)N1C]

The racemic compound (Example 97, 89 mg) was separated into enantiomers by preparative chiral HPLC to give enantiomer 1 (27 mg, >99.9% ee, see Example 98) and enantiomer 2 (27 mg, >99.9% ee, see Example 99).
Preparative Chiral HPLC Method:
Instrument: PrepCon Labomatic HPLC; Column: YMC Cellulose SC 10μ, 250×50; eluent A: hexane+0.1 vol % diethylamine; eluent B: ethanol; isocratic: 70% A+30% B; flow: 185 mL/min; temperature: 25° C.; UV: 280 nm;
Analytical Chiral HPLC Method:
Instrument: Waters Alliance 2695; Column: YMC Cellulose SC 3μ, 100×4.6; eluent A: hexane+0.1 vol % diethylamine; eluent B: ethanol; isocratic: 70% A+30% B; flow: 1.4 mL/min; temperature: 25° C.; UV: 280 nm;
Analytical Chiral HPLC (method see Example 65): $R_t$=3.39 min.

$[a]_D$=+33.2° (from solution in DMSO, c=2.0 mg/mL)
$^1$H-NMR (400 MHz, DMSO-d$_6$) δ [ppm]: $^1$H-NMR (400 MHz, DMSO-d6) δ [ppm]: 0.831 (0.77), 0.837 (0.54), 0.854 (0.66), 0.858 (0.96), 1.144 (5.66), 1.159 (5.80), 1.239 (0.57), 2.323 (0.60), 2.327 (0.86), 2.332 (0.60), 2.518 (3.11), 2.523 (2.11), 2.628 (1.02), 2.634 (1.07), 2.660 (0.42), 2.665 (0.92), 2.669 (2.09), 2.674 (1.70), 2.850 (16.00), 3.167 (0.87), 3.184 (1.06), 3.209 (0.89), 3.226 (0.82), 3.755 (7.28), 3.775 (0.63), 3.781 (0.66), 3.791 (0.95), 3.797 (0.87), 3.808 (0.63), 3.813 (0.53), 5.759 (3.80), 6.535 (3.28), 6.554 (3.47), 6.556 (2.85), 6.594 (0.69), 6.596 (1.06), 6.615 (2.12), 6.632 (1.15), 6.991 (2.56), 7.009 (3.24), 7.012 (3.12), 7.026 (0.90), 7.031 (2.12), 7.131 (2.08), 7.135 (2.02), 7.144 (2.01), 7.148 (2.01), 7.314 (4.27), 7.317 (2.64), 7.324 (2.64), 7.329 (4.28), 7.363 (4.15), 8.049 (2.74), 8.064 (2.62), 8.164 (2.15), 8.502 (4.63), 8.506 (2.84), 8.513 (2.79), 8.517 (4.51), 10.648 (2.97), 11.707 (2.09).

Example 99

(−)-N-{4-[(6S*)-3-anilino-5,6-dimethyl-4-oxo-4,5,6,7-tetrahydro-1H-pyrrolo[3,2-c]pyridin-2-yl]pyridin-2-yl}-2-(pyridin-4-yl)acetamide (Enantiomer 2)

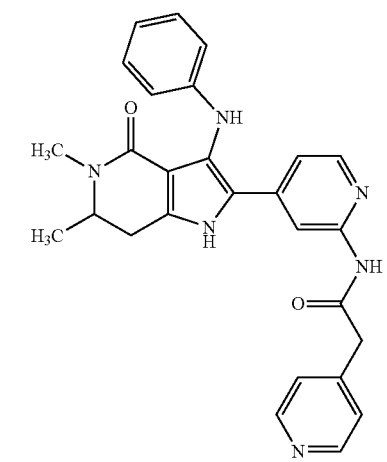 [SMILES: CC1Cc2[nH]c(-c3ccnc(NC(=O)Cc4ccncc4)c3)c(Nc3ccccc3)c2C(=O)N1C]

For the preparation of the racemic title compound see Example 97. Separation of enantiomers by preparative chiral HPLC (method see Example 98) gave the title compound (27 mg).

Analytical Chiral HPLC (method see Example 98): $R_t$=4.80 min.

$[a]_D$=−22.0° (from solution in DMSO, c=2.0 mg/mL)
$^1$H-NMR (400 MHz, DMSO-d$_6$) δ [ppm]=0.858 (0.43), 1.143 (5.78), 1.159 (5.92), 2.323 (0.56), 2.327 (0.80), 2.332 (0.56), 2.518 (3.50), 2.523 (2.32), 2.540 (3.70), 2.628 (1.05), 2.634 (1.11), 2.669 (2.07), 2.674 (1.72), 2.850 (16.00), 3.167 (0.87), 3.184 (1.05), 3.209 (0.89), 3.225 (0.83), 3.755 (7.53), 3.775 (0.68), 3.781 (0.69), 3.791 (0.97), 3.797 (0.91), 3.808 (0.64), 3.814 (0.56), 5.759 (0.61), 6.535 (3.43), 6.554 (3.63), 6.596 (1.08), 6.615 (2.16), 6.632 (1.17), 6.991 (2.63), 7.010 (3.36), 7.012 (3.28), 7.031 (2.15), 7.131 (2.06), 7.135 (2.02), 7.144 (2.00), 7.148 (2.06), 7.314 (4.02), 7.317 (2.70), 7.325 (2.76), 7.329 (4.15), 7.363 (4.24), 8.050 (2.76), 8.064 (2.66), 8.165 (2.26), 8.503 (3.47), 8.506 (2.56), 8.517 (3.38), 10.648 (3.06), 11.707 (2.18).

Example 100

N-{4-[3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)acetamide (Racemate)

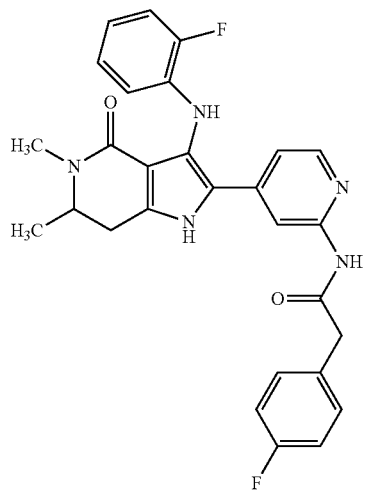

A solution of (2-(2-aminopyridin-4-yl)-3-(2-fluoroanilino)-5,6-dimethyl-1,5,6,7-tetrahydro-4H-pyrrolo[3,2-c]pyridin-4-one (Racemate) (see Intermediate 100, 80 mg, 0.219 mmol, 1 eq) in DMA (3 mL) was treated with N,N-diisopropylethylamine (0.27 mL, 7 eq; CAS-RN: [7087-68-5]), (4-fluorophenyl)acetic acid (101 mg, 3 eq), and benzotriazol-1-yloxytripyrrolidinophosphonium hexafluorophosphate (0.342 g, 3 eq; CAS-RN: [128625-52-5]), was stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column silica gel, 25 g, gradient dichloromethane/methanol, 0-25%) to give 98 mg of the title compound.

LC-MS (Method 2): $R_t$=1.20 min; MS (ESIpos): m/z=502 [M+H]$^+$ $^1$H-NMR (400 MHz, DMSO-d$_6$) δ [ppm]: 1.148 (3.67), 1.154 (4.59), 1.164 (3.72), 1.173 (8.65), 1.190 (4.33), 1.988 (16.00), 2.327 (0.44), 2.518 (1.84), 2.523 (1.23), 2.635 (0.63), 2.641 (0.66), 2.669 (0.52), 2.677 (0.87), 2.682 (0.73), 2.854 (10.39), 3.178 (0.51), 3.194 (0.64), 3.219 (0.57), 3.236 (0.52), 3.675 (3.90), 3.804 (0.53), 3.810 (0.52), 4.000 (1.16), 4.017 (3.46), 4.035 (3.36), 4.053 (1.06), 6.235 (0.45), 6.238 (0.49), 6.257 (0.89), 6.277 (0.50), 6.281 (0.49), 6.632 (0.51), 6.637 (0.50), 6.644 (0.50), 6.649 (0.50), 6.651 (0.47), 6.725 (0.60), 6.728 (0.65), 6.746 (0.93), 6.763 (0.40), 7.078 (0.62), 7.082 (0.63), 7.093 (1.39), 7.097 (1.64), 7.102 (0.84), 7.106 (1.57), 7.110 (1.97), 7.120 (0.43), 7.128 (2.11), 7.133 (1.07), 7.144 (0.70), 7.150 (3.18), 7.156 (0.66), 7.167 (0.58), 7.173 (1.89), 7.322 (1.56), 7.328 (0.72), 7.336 (1.95), 7.344 (2.70), 7.352 (0.79), 7.358 (1.31), 8.081 (1.65), 8.095 (1.60), 8.174 (1.39), 10.570 (1.69), 11.789 (1.29).

Example 101

(+)-N-{4-[3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)acetamide (Enantiomer 1)

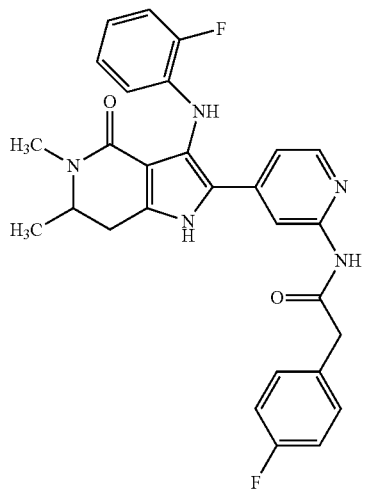 [SMILES: CC1Cc2[nH]c(-c3ccnc(NC(=O)Cc4ccc(F)cc4)c3)c(Nc3ccccc3F)c2C(=O)N1C]

The racemic compound (Example 100, 89 mg) was separated into enantiomers by preparative chiral HPLC to give enantiomer 1 (17 mg, 98.5% ee, see Example 101) and enantiomer 2 (12 mg, 100% ee, see Example 102).

Preparative Chiral HPLC Method:

Instrument: PrepCon Labomatic HPLC; Column: YMC Cellulose SC 5μ, 250×30; eluent A: methyl tert-butyl ether+0.1 vol % diethylamine; eluent B: ethanol; isocratic: 90% A+10% B; flow: 50 LI/min; temperature: 25° C.; UV: 280 nm;

Analytical Chiral HPLC Method:

Instrument: Waters Alliance 2695; Column: YMC Cellulose SC 3μ, 100×4.6; eluent A: methyl tert-butyl ether+0.1 vol % diethylamine; eluent B: ethanol; isocratic: 90% A+10% B; flow: 1.4 mL/min; temperature: 25° C.; UV: 280 nm;

Analytical Chiral HPLC (method see Example 101): $R_t$=1.42 min.

[a]$_D$=+51.3° (from solution in DMSO, c=1.7 mg/mL)

$^1$H-NMR (400 MHz, DMSO-d$_6$) δ [ppm]: 0.000 (1.13), 0.897 (0.42), 0.914 (0.61), 1.212 (7.16), 1.227 (7.41), 1.296 (3.00), 1.323 (0.83), 2.391 (0.90), 2.699 (1.44), 2.704 (1.50), 2.740 (2.08), 2.918 (16.00), 3.241 (1.11), 3.258 (1.28), 3.282 (1.08), 3.299 (1.04), 3.739 (8.14), 3.856 (0.89), 3.867 (1.22), 3.872 (1.22), 3.883 (0.87), 5.823 (3.31), 6.301 (1.01), 6.320 (1.94), 6.341 (1.04), 6.680 (0.52), 6.696 (1.19), 6.712 (1.23), 6.727 (0.79), 6.790 (1.41), 6.809 (2.09), 6.827 (0.90), 7.145 (1.35), 7.156 (2.59), 7.160 (2.98), 7.173 (3.59), 7.191 (3.56), 7.213 (5.26), 7.236 (3.05), 7.386 (2.94), 7.407 (6.21), 7.422 (2.67), 8.145 (3.11), 8.158 (3.01), 8.239 (3.35), 10.633 (3.80), 11.852 (2.88).

Example 102

(−)-N-{4-[3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)acetamide (Enantiomer 2)

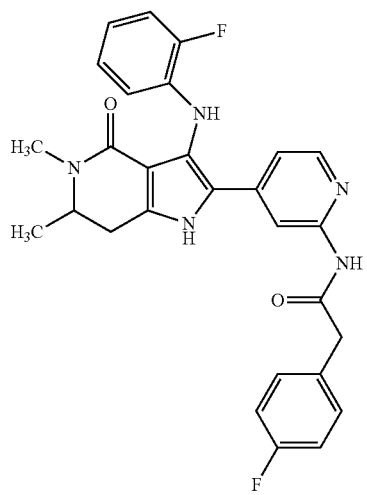 [SMILES: CC1Cc2[nH]c(-c3ccnc(NC(=O)Cc4ccc(F)cc4)c3)c(Nc3ccccc3F)c2C(=O)N1C]

For the preparation of the racemic title compound see Example 100. Separation of enantiomers by preparative chiral HPLC (method see Example 101) gave the title compound (12 mg).

Analytical Chiral HPLC (method see Example 101): $R_t$=2.13 min.

$[α]_D$=−34.1° (from solution in DMSO, c=2.0 mg/mL)

$^1$H-NMR (400 MHz, DMSO-$d_6$) δ [ppm]=0.764 (0.79), 0.781 (0.76), 0.794 (0.66), 0.833 (0.51), 0.851 (0.84), 0.862 (0.45), 1.006 (0.41), 1.084 (0.62), 1.147 (6.60), 1.164 (7.28), 1.232 (4.62), 1.259 (1.15), 2.322 (0.61), 2.326 (0.84), 2.331 (0.61), 2.518 (3.58), 2.522 (2.34), 2.635 (1.11), 2.640 (1.14), 2.664 (0.73), 2.669 (1.03), 2.676 (1.57), 2.682 (1.33), 2.853 (16.00), 3.178 (0.89), 3.194 (1.07), 3.219 (0.91), 3.235 (0.84), 3.378 (0.45), 3.675 (6.72), 3.787 (0.60), 3.792 (0.66), 3.803 (0.93), 3.809 (0.92), 3.820 (0.65), 3.825 (0.58), 5.759 (1.96), 6.233 (0.76), 6.237 (0.84), 6.257 (1.53), 6.276 (0.84), 6.279 (0.83), 6.616 (0.42), 6.625 (0.46), 6.632 (0.89), 6.636 (0.88), 6.644 (0.89), 6.648 (0.89), 6.655 (0.65), 6.663 (0.64), 6.667 (0.57), 6.727 (1.11), 6.746 (1.63), 6.763 (0.70), 7.078 (1.02), 7.082 (1.06), 7.091 (2.17), 7.096 (2.40), 7.105 (2.49), 7.109 (3.01), 7.120 (0.58), 7.127 (3.24), 7.132 (1.73), 7.144 (1.22), 7.150 (4.97), 7.155 (1.25), 7.167 (0.99), 7.172 (2.97), 7.322 (2.57), 7.327 (1.29), 7.336 (3.36), 7.344 (4.78), 7.358 (2.29), 8.082 (2.78), 8.095 (2.68), 8.174 (2.56), 10.571 (3.18), 11.789 (2.28).

Example 103

(+)-(2RS)-4,4-difluoro-N-{4-[(6R*)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide (2 Stereoisomers #1)

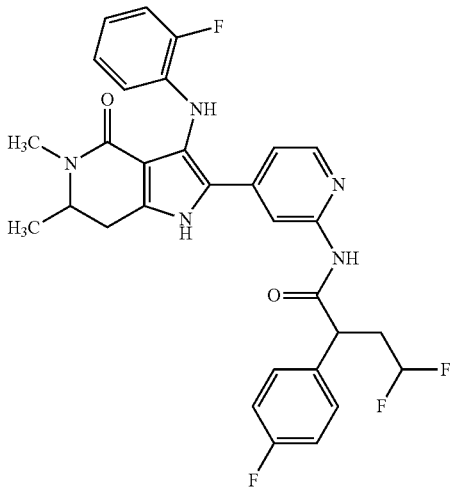 [SMILES: CC1Cc2[nH]c(-c3ccnc(NC(=O)C(CC(F)F)c4ccc(F)cc4)c3)c(Nc3ccccc3F)c2C(=O)N1C]

A solution of (+)-2-(2-aminopyridin-4-yl)-3-(2-fluoroanilino)-5,6-dimethyl-1,5,6,7-tetrahydro-4H-pyrrolo[3,2-c]pyridin-4-one (Enantiomer 1) (see Intermediate 101, 40 mg, 0.109 mmol, 1 eq) in DMA (2.33 mL) was treated with N,N-diisopropylethylamine (0.20 mL, 6 eq; CAS-RN: [7087-68-5]), 4,4-difluoro-2-(4-fluorophenyl)butanoic acid (Racemate) (47.8 mg, 2 eq, CAS 1538957-14-0, VCS 1835354, #3), and benzotriazol-1-yloxytripyrrolidinophosphonium hexafluorophosphate (0.285 g, 5 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column silica gel, 50 g, gradient dichloromethane/ethanol, 0-10%) to give 42 mg of the title compound.

$[α]_D$=+29.9° (from solution in DMSO, c=2.1 mg/mL)

LC-MS (Method 2): $R_t$=1.28 min; MS (ESIpos): m/z=566 $[M+H]^+$ $^1$H-NMR (400 MHz, DMSO-$d_6$) δ [ppm]: 1.220 (6.58), 1.238 (12.52), 1.255 (4.54), 1.298 (0.81), 2.053 (16.00), 2.388 (0.71), 2.392 (1.01), 2.396 (0.72), 2.583 (3.72), 2.588 (2.56), 2.725 (1.26), 2.729 (1.53), 2.734 (1.45), 2.738 (0.98), 2.743 (0.54), 2.767 (1.03), 2.928 (10.26), 3.262 (0.47), 3.278 (0.54), 3.303 (0.45), 3.316 (0.44), 3.866 (0.44), 3.871 (0.49), 3.881 (0.69), 3.887 (0.71), 3.898 (0.49), 3.903 (0.44), 4.065 (1.16), 4.082 (3.45), 4.100 (3.35), 4.118 (1.06), 4.180 (0.45), 4.199 (0.56), 4.215 (0.44), 5.983 (0.47), 6.018 (0.50), 6.270 (0.57), 6.274 (0.62), 6.294 (1.14), 6.313 (0.64), 6.317 (0.62), 6.694 (0.59), 6.709 (0.62), 6.724 (0.42), 6.770 (0.49), 6.775 (0.49), 6.778 (0.49), 6.790 (0.71), 6.795 (0.69), 7.150 (0.40), 7.153 (0.45), 7.157 (0.47), 7.161 (0.49), 7.171 (1.56), 7.173 (1.67), 7.183 (1.68), 7.187 (1.72), 7.199 (0.44), 7.203 (0.45), 7.207 (0.42), 7.211 (0.40), 7.225 (1.60), 7.247 (3.42), 7.269 (1.90), 7.436 (1.19), 7.441 (1.26), 7.448 (1.38), 7.463 (1.09), 7.471 (1.08), 7.479 (1.30), 7.484 (1.21), 7.492 (1.13), 7.500 (0.98), 7.514 (0.86), 8.129 (2.09), 8.143 (1.92), 8.214 (1.35), 10.698 (1.28), 10.711 (1.30), 11.860 (1.04), 11.871 (1.06).

Example 104

(−)-4,4-difluoro-N-{4-[3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide (Enantiomer 1)

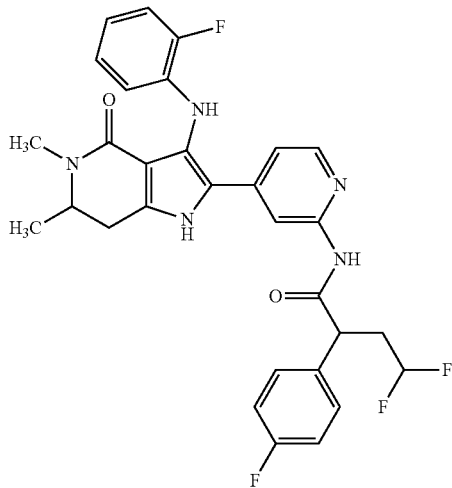 [SMILES: CC1Cc2[nH]c(-c3ccnc(NC(=O)C(CC(F)F)c4ccc(F)cc4)c3)c(Nc3ccccc3F)c2C(=O)N1C]

The mixture of two stereoisomers #1 (Example 103, 205 mg) was separated into the single stereoisomers by preparative chiral HPLC to give stereoisomer 1 (16 mg, 100% ee, see Example 104) and stereoisomer 2 (14 mg, 100% ee, see Example 105).
Preparative Chiral HPLC Method:
Instrument: PrepCon Labomatic HPLC; Column: YMC Cellulose SB 5μ, 250×30; eluent A: methyl tert-butyl ether+ 0.1 vol % diethylamine; eluent B: ethanol; gradient: 0-10 min 2-8% B; flow: 50 mL/min; temperature: 25° C.; UV: 254 nm;
Analytical Chiral HPLC Method:
Instrument: Waters Alliance 2695; Column: YMC Cellulose SB 3μ, 100×4.6; eluent A: methyl tert-butyl ether+0.1 vol % diethylamine; eluent B: ethanol; gradient: 0-7 min 2-60% B; flow: 1.4 mL/min; temperature: 25° C.; UV: 254 nm;
Analytical Chiral HPLC (method see Example 104): $R_t$=2.28 min.
$[a]_D$=−122.8° (from solution in DMSO, c=1.5 mg/mL)
LC-MS (Method 2): $R_t$=1.27 min; MS (ESIpos): m/z=566 [M+H]⁺
¹H-NMR (400 MHz, DMSO-$d_6$) δ [ppm]: 0.000 (11.92), 0.008 (0.40), 1.160 (5.52), 1.177 (5.61), 2.325 (0.64), 2.329 (0.93), 2.334 (0.65), 2.520 (3.89), 2.525 (2.50), 2.659 (1.35), 2.664 (1.55), 2.671 (1.38), 2.676 (0.96), 2.700 (1.46), 2.705 (1.35), 2.866 (16.00), 3.195 (0.81), 3.211 (0.98), 3.236 (0.84), 3.253 (0.76), 3.802 (0.53), 3.808 (0.59), 3.819 (0.84), 3.824 (0.84), 3.835 (0.59), 3.840 (0.53), 4.119 (0.65), 4.133 (0.76), 4.142 (0.76), 4.156 (0.60), 5.814 (0.59), 5.944 (0.53), 5.955 (1.18), 5.966 (0.56), 6.095 (0.53), 6.208 (0.70), 6.211 (0.76), 6.231 (1.38), 6.250 (0.78), 6.254 (0.76), 6.631 (0.79), 6.634 (0.76), 6.643 (0.79), 6.647 (0.79), 6.654 (0.59), 6.662 (0.60), 6.666 (0.53), 6.704 (0.98), 6.707 (1.04), 6.726 (1.47), 6.743 (0.60), 7.095 (0.93), 7.098 (0.91), 7.108 (2.00), 7.112 (2.16), 7.122 (2.28), 7.125 (2.71), 7.145 (0.84), 7.148 (0.84), 7.162 (2.11), 7.167 (0.78), 7.184 (4.57), 7.201 (0.82), 7.206 (2.53), 7.379 (2.54), 7.386 (3.10), 7.392 (1.21), 7.400 (2.48), 7.408 (2.22), 7.417 (0.88), 7.422 (1.89), 8.068 (2.65), 8.082 (2.54), 8.149 (2.34), 10.635 (2.91), 11.797 (2.20).

Example 105

(+)-4,4-difluoro-N-{4-[3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide (Enantiomer 2)

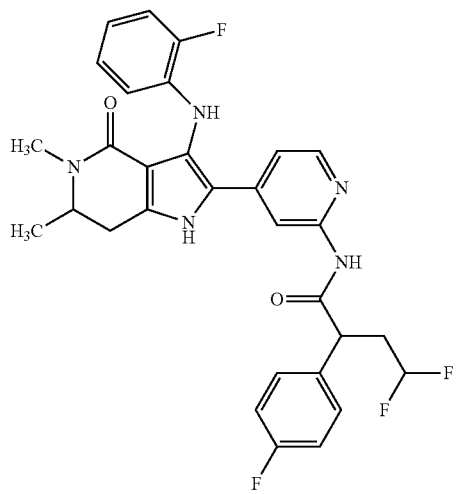 [SMILES: CC1Cc2[nH]c(-c3ccnc(NC(=O)C(CC(F)F)c4ccc(F)cc4)c3)c(Nc3ccccc3F)c2C(=O)N1C]

For the preparation of the mixture of two stereoisomers #1 see Example 103. Separation of the mixture of two stereoisomers #1 by preparative chiral HPLC (method see Example 104) gave the title compound (14 mg).

Analytical Chiral HPLC (method see Example 104): $R_t$=2.68 min.

$[a]_D$=+255.4° (from solution in DMSO, c=1.5 mg/mL)

¹H-NMR (400 MHz, DMSO-$d_6$) δ [ppm]=0.000 (11.52), 1.158 (5.93), 1.175 (6.10), 1.235 (0.73), 2.163 (0.41), 2.203 (0.43), 2.216 (0.43), 2.325 (0.75), 2.329 (1.05), 2.334 (0.75), 2.520 (4.65), 2.525 (2.97), 2.662 (1.71), 2.667 (2.12), 2.671 (1.74), 2.676 (1.17), 2.681 (0.68), 2.704 (1.51), 2.709 (1.44), 2.864 (16.00), 3.199 (0.87), 3.216 (1.05), 3.241 (0.89), 3.258 (0.82), 3.802 (0.57), 3.808 (0.66), 3.819 (0.91), 3.825 (0.91), 3.835 (0.64), 3.841 (0.57), 4.115 (0.71), 4.129 (0.84), 4.137 (0.84), 4.151 (0.68), 5.780 (0.61), 5.909 (0.55), 5.920 (1.21), 5.932 (0.57), 6.061 (0.55), 6.208 (0.75), 6.211 (0.82), 6.230 (1.53), 6.250 (0.84), 6.254 (0.82), 6.621 (0.43), 6.629 (0.85), 6.633 (0.85), 6.640 (0.85), 6.645 (0.87), 6.652 (0.64), 6.660 (0.62), 6.664 (0.57), 6.716 (1.10), 6.735 (1.60), 6.751 (0.68), 7.087 (0.96), 7.091 (0.98), 7.106 (2.69), 7.110 (2.83), 7.120 (2.79), 7.123 (2.28), 7.137 (0.94), 7.141 (0.89), 7.163 (2.28), 7.168 (0.89), 7.186 (4.86), 7.203 (0.94), 7.208 (2.67), 7.370 (2.46), 7.373 (2.51), 7.416 (2.38), 7.422 (1.17), 7.430 (2.63), 7.438 (2.40), 7.446 (0.96), 7.452 (2.05), 8.066 (2.79), 8.079 (2.67), 8.156 (2.55), 10.649 (3.10), 11.807 (2.38).

Example 106

(−)-(2RS)-4,4-difluoro-N-{4-[(6R*)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide (2 Stereoisomers #2)

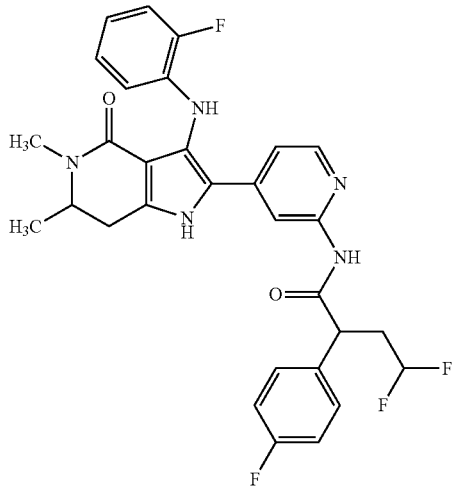 [SMILES: CC1Cc2[nH]c(-c3ccnc(NC(=O)C(CC(F)F)c4ccc(F)cc4)c3)c(Nc3ccccc3F)c2C(=O)N1C]

A solution of (−)-2-(2-aminopyridin-4-yl)-3-(2-fluoroanilino)-5,6-dimethyl-1,5,6,7-tetrahydro-4H-pyrrolo[3,2-c]pyridin-4-one (Enantiomer 2) (see Intermediate 102, 0.15 g, 0.41 mmol, 1 eq) in DMA (4 mL) was treated with N,N-diisopropylethylamine (0.43 mL, 6 eq; CAS-RN: [7087-68-5]), 4,4-difluoro-2-(4-fluorophenyl)butanoic acid (Racemate) (0.179 g, 2 eq, CAS 1538957-14-0, VCS 1835354, #3), and benzotriazol-1-yloxytripyrrolidinophosphonium hexafluorophosphate (1.07 g, 5 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column silica gel, 50 g, gradient dichloromethane/methanol, 0-25%) to give 240 mg of the title compound.

$[\alpha]_D = -13.4°$ (from solution in DMSO, c=2.40 mg/mL)

LC-MS (Method 2): $R_t$=1.27 min; MS (ESIpos): m/z=566 [M+H]$^+$ $^1$H-NMR (400 MHz, DMSO-d$_6$) δ [ppm]: 0.795 (0.64), 1.006 (0.48), 1.085 (0.79), 1.155 (8.24), 1.157 (6.97), 1.173 (15.09), 1.190 (4.70), 1.233 (0.88), 1.259 (1.03), 1.988 (15.52), 2.161 (0.45), 2.200 (0.52), 2.323 (1.27), 2.327 (1.79), 2.332 (1.24), 2.518 (6.39), 2.523 (4.36), 2.665 (2.61), 2.669 (2.55), 2.673 (1.70), 2.702 (1.64), 2.863 (16.00), 3.197 (0.76), 3.210 (0.85), 3.238 (0.76), 3.252 (0.73), 3.388 (0.61), 3.807 (0.79), 3.817 (1.09), 3.822 (1.09), 3.833 (0.76), 4.000 (1.12), 4.017 (3.24), 4.035 (3.12), 4.053 (1.00), 4.114 (0.73), 4.133 (0.91), 4.149 (0.70), 5.918 (0.76), 5.953 (0.79), 6.210 (1.00), 6.229 (1.82), 6.248 (1.03), 6.252 (1.00), 6.629 (0.97), 6.645 (1.00), 6.660 (0.61), 6.706 (0.82), 6.710 (0.79), 6.724 (1.12), 6.741 (0.52), 7.089 (0.70), 7.096 (0.79), 7.107 (2.48), 7.109 (2.58), 7.119 (2.61), 7.122 (2.64), 7.142 (0.70), 7.160 (2.48), 7.182 (5.36), 7.204 (2.94), 7.376 (2.00), 7.383 (2.52), 7.397 (1.73), 7.406 (1.70), 7.414 (2.03), 7.419 (1.94), 7.427 (1.76), 7.435 (1.58), 7.449 (1.33), 8.065 (3.36), 8.078 (3.12), 8.148 (2.15), 10.635 (1.88), 10.648 (1.76), 11.796 (1.61), 11.807 (1.61).

Example 107

(−)-4,4-difluoro-N-{4-[3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide (Enantiomer 3)

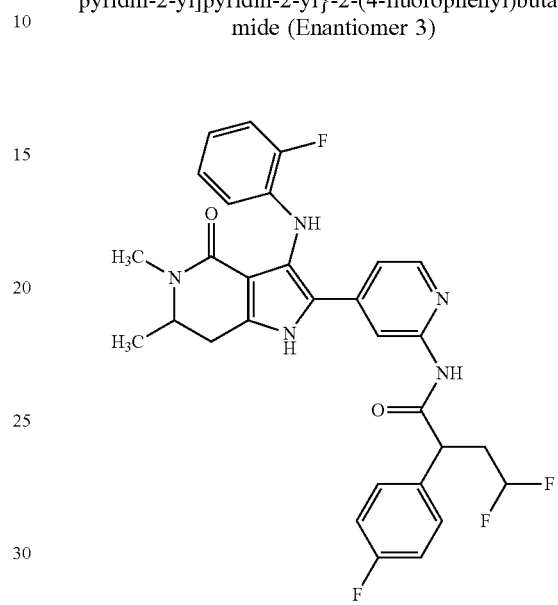

The mixture of two stereoisomers #2 (Example 106, 205 mg) was separated into the single stereoisomers by preparative chiral HPLC to give stereoisomer 3 (23 mg, 100% ee, see Example 107) and stereoisomer 4 (26 mg, 100% ee, see Example 108).

Preparative Chiral HPLC Method:
Instrument: PrepCon Labomatic HPLC; Column: YMC Cellulose SB 5μ, 250×30; eluent A: methyl tert-butyl ether+ 0.1 vol % diethylamine; eluent B: acetonitrile+0.1 vol % diethylamine; gradient: 0-10 min 2-30% B; flow: 50 mL/min; temperature: 25° C.; UV: 254 nm;

Analytical Chiral HPLC Method:
Instrument: Waters Alliance 2695; Column: YMC Cellulose SB 3μ, 100×4.6; eluent A: hexane+0.1 vol % diethylamine; eluent B: ethanol; gradient; flow: 1.4 mL/min; temperature: 25° C.; UV: 254 nm;

Analytical Chiral HPLC (method see Example 107): $R_t$=2.14 min.

$[\alpha]_D = -243.7°$ (from solution in DMSO, c=1.7 mg/mL)

LC-MS (Method 2): $R_t$=1.28 min; MS (ESIpos): m/z=566 [M+H]$^+$ $^1$H-NMR (400 MHz, DMSO-d6) δ [ppm]: −0.008 (0.73), 0.008 (0.81), 1.159 (6.27), 1.175 (6.59), 1.235 (1.03), 1.990 (0.67), 2.087 (2.78), 2.164 (0.45), 2.176 (0.41), 2.204 (0.47), 2.216 (0.47), 2.325 (0.55), 2.329 (0.76), 2.334 (0.55), 2.525 (1.97), 2.647 (0.41), 2.662 (1.76), 2.668 (2.09), 2.704 (1.60), 2.709 (1.55), 2.865 (16.00), 3.200 (0.94), 3.216 (1.13), 3.241 (0.96), 3.258 (0.88), 3.803 (0.63), 3.809 (0.69), 3.819 (0.97), 3.824 (0.96), 3.836 (0.68), 3.841 (0.60), 4.115 (0.78), 4.129 (0.91), 4.137 (0.91), 4.151 (0.72), 5.780 (0.62), 5.910 (0.58), 5.921 (1.24), 5.932 (0.59), 6.062 (0.58), 6.208 (0.79), 6.212 (0.86), 6.231 (1.64), 6.250 (0.87), 6.254 (0.86), 6.614 (0.41), 6.629 (0.92), 6.633 (0.90), 6.641 (0.91), 6.645 (0.94), 6.652 (0.65), 6.660 (0.63), 6.664 (0.58), 6.716 (1.19), 6.735

(1.76), 6.752 (0.73), 7.089 (1.00), 7.091 (1.01), 7.107 (2.72), 7.111 (2.94), 7.120 (2.91), 7.124 (2.40), 7.138 (0.96), 7.141 (0.91), 7.164 (2.27), 7.186 (4.79), 7.208 (2.65), 7.371 (2.71), 7.374 (2.71), 7.417 (2.45), 7.431 (2.73), 7.439 (2.47), 7.453 (2.08), 8.066 (3.00), 8.080 (2.87), 8.157 (2.83), 10.651 (3.33), 11.809 (2.60).

Example 108

(+)-4,4-difluoro-N-{4-[3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide (Enantiomer 4)

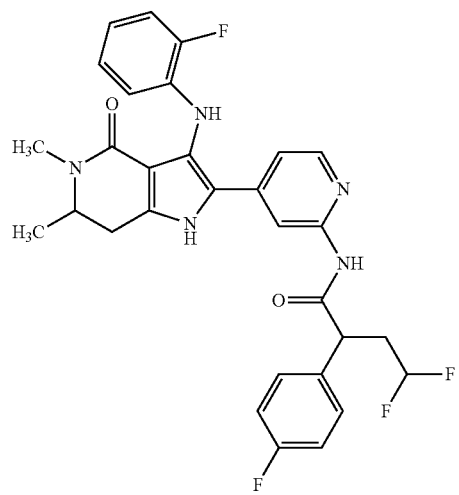 [SMILES: CC1Cc2[nH]c(-c3ccnc(NC(=O)C(CC(F)F)c4ccc(F)cc4)c3)c(Nc3ccccc3F)c2C(=O)N1C]

For the preparation of the mixture of two stereoisomers #2 see Example 106. Separation of the mixture of two stereoisomers #2 by preparative chiral HPLC (method see Example 107) gave the title compound (26 mg).

Analytical Chiral HPLC (method see Example 107): $R_t$=2.52 min.

$[\alpha]_D$=+131.6° (from solution in DMSO, c=1.8 mg/mL)

LC-MS (Method 2): $R_t$=1.27 min; MS (ESIpos): m/z=566 [M+H]$^+$ $^1$H-NMR (400 MHz, DMSO-d$_6$) δ [ppm]=−0.149 (0.40), −0.008 (3.57), 0.008 (3.28), 0.146 (0.43), 0.834 (0.79), 0.839 (0.50), 0.854 (0.83), 0.861 (0.54), 1.160 (5.69), 1.177 (5.77), 1.241 (1.30), 2.203 (0.40), 2.325 (1.51), 2.329 (2.16), 2.334 (1.55), 2.338 (0.68), 2.520 (8.29), 2.525 (5.44), 2.667 (2.38), 2.671 (2.67), 2.676 (1.87), 2.700 (1.48), 2.705 (1.41), 2.866 (16.00), 3.195 (0.83), 3.211 (1.01), 3.236 (0.86), 3.253 (0.79), 3.307 (0.72), 3.808 (0.61), 3.819 (0.86), 3.824 (0.83), 3.836 (0.61), 4.118 (0.68), 4.132 (0.79), 4.141 (0.79), 4.155 (0.65), 5.814 (0.61), 5.944 (0.58), 5.955 (1.23), 5.966 (0.54), 6.095 (0.54), 6.211 (0.79), 6.230 (1.44), 6.250 (0.79), 6.254 (0.79), 6.631 (0.83), 6.634 (0.83), 6.643 (0.83), 6.646 (0.86), 6.653 (0.61), 6.662 (0.65), 6.666 (0.61), 6.707 (1.12), 6.726 (1.55), 6.743 (0.68), 7.095 (0.94), 7.098 (1.01), 7.108 (2.05), 7.112 (2.16), 7.121 (2.27), 7.125 (2.85), 7.145 (0.86), 7.148 (0.90), 7.162 (2.13), 7.184 (4.65), 7.206 (2.63), 7.386 (3.21), 7.400 (2.59), 7.408 (2.34), 7.422 (1.98), 8.068 (2.81), 8.081 (2.63), 8.149 (2.49), 10.635 (3.03), 11.797 (2.31).

Example 109

N-{4-[3-(2-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl)butanamide (Racemate)

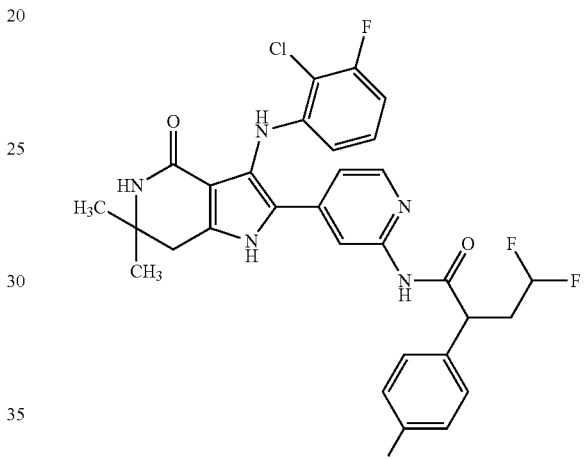

2-(2-Aminopyridin-4-yl)-3-(2-chloro-3-fluoroanilino)-6,6-dimethyl-1,5,6,7-tetrahydro-4H-pyrrolo[3,2-c]pyridin-4-one (see Intermediate 105, 500 mg), 4,4-difluoro-2-(4-fluorophenyl)butanoic acid (Racemate) (546 mg, 2.50 mmol, CAS-RN: [1538957-14-0], VCS 1835354), PyBOP (3.25 g, 6.25 mmol) and N,N-diisopropylethylamine (1.3 mL, 7.5 mmol) were dissolved in 7.3 mL DMF and it was stirred at r.t. under nitrogen atmosphere overnight. To the reaction mixture saturated aqueous sodium hydrogencarbonate solution was added and it was diluted with dichloromethane. The layers were separated and the aqueous layer was extracted with dichloromethane twice. The combined organic layers were dried using a water resistant filter. The clear filtrate was concentrated under reduced pressure. The crude product was purified by HPLC under basic conditions in two portions to provide the target compound in 98% purity: 462 mg.

LC-MS (Method 2): $R_t$=1.25 min; MS (ESIpos): m/z=600 [M+H]$^+$ $^1$H-NMR (400 MHz, DMSO-d$_6$) δ [ppm]=1.27 (s, 6H), 2.08-2.27 (m, 1H), 2.58-2.74 (m, 1H), 2.81 (s, 2H), 4.08-4.18 (m, 1H), 5.76-6.16 (m, 2H), 6.62 (td, 1H), 6.90 (td, 1H), 7.06-7.14 (m, 2H), 7.14-7.23 (m, 2H), 7.37-7.50 (m, 3H), 8.06-8.17 (m, 2H), 10.64 (s, 1H), 11.85 (s, 1H).

Example 110

(−)-N-{4-[3-(2-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl)butanamide (Enantiomer 1)

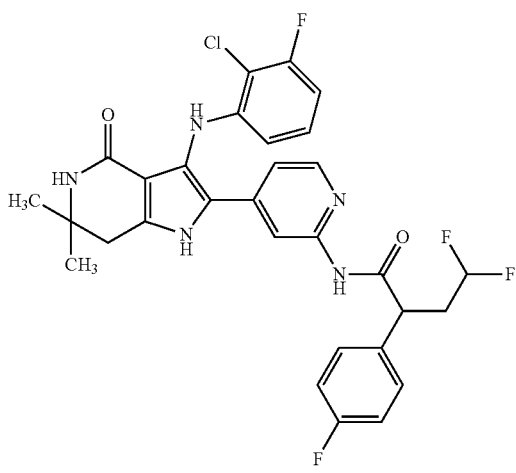 [SMILES: CC1(C)Cc2[nH]c(-c3ccnc(NC(=O)C(CC(F)F)c4ccc(F)cc4)c3)c(Nc3cccc(F)c3Cl)c2C(=O)N1]

The racemic compound (see Example 109, 410 mg) was separated into enantiomers by preparative chiral HPLC to give enantiomer 1 (141 mg, 100% ee, see Example 110) and enantiomer 2 (165 mg, 100% ee, see Example 111).

Preparative Chiral HPLC Method:

Instrument: PrepCon Labomatic HPLC; Column: YMC Cellulose SB 10μ, 250×50; eluent A: hexane+0.1 vol % diethylamine; eluent B: ethanol+0.1 vol % diethylamine; isocratic: 90% A+10% B; flow: 100 mL/min; temperature: 25° C.; UV: 254 nm;

Analytical Chiral HPLC Method:

Instrument: Waters Alliance 2695; Column: YMC Cellulose SB 3μ, 100×4.6; eluent A: hexane+0.1 vol % diethylamine; eluent B: ethanol; isocratic: 90% A+10% B; flow: 1.4 mL/min; temperature: 25° C.; UV: 254 nm;

Analytical Chiral HPLC (method see Example 110): $R_t$=3.01 min.

$[a]_D$=−136.1° (from solution in DMSO, c=8.9 mg/mL)

$^1$H-NMR (400 MHz, DMSO-$d_6$) δ [ppm]=1.27 (s, 6H), 2.19 (br d, 1H), 2.58-2.74 (m, 1H), 2.81 (s, 2H), 4.13 (dd, 1H), 5.74-6.15 (m, 2H), 6.55-6.70 (m, 1H), 6.90 (td, 1H), 7.06-7.13 (m, 2H), 7.15-7.23 (m, 2H), 7.36-7.43 (m, 2H), 7.46 (s, 1H), 8.04-8.19 (m, 2H), 10.64 (s, 1H), 11.85 (s, 1H).—minor impurities in the aliphatic range.

Example 111

(+)-N-{4-[3-(2-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl)butanamide (Enantiomer 2)

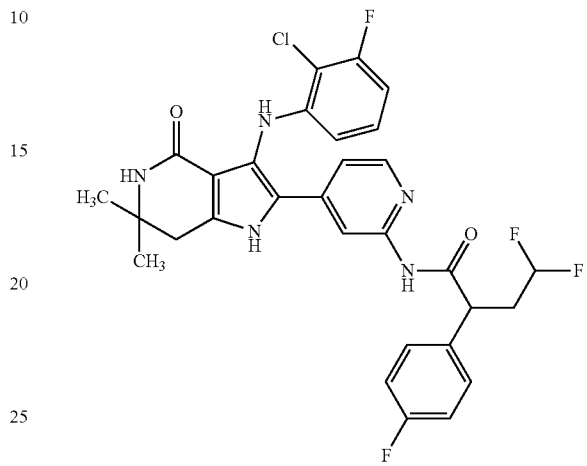

For the preparation of the racemic title compound see Example 109. Separation of enantiomers by preparative chiral HPLC (method see Example 110) gave the title compound (165 mg).

Analytical Chiral HPLC (method see Example 41): $R_t$=4.25 min.

$[a]_D$=+118.5° (from solution in DMSO, c=8.8 mg/mL)

$^1$H-NMR (400 MHz, DMSO-$d_6$) δ [ppm]=1.27 (s, 6H), 2.09-2.27 (m, 1H), 2.56-2.73 (m, 1H), 2.81 (s, 2H), 4.13 (dd, 1H), 5.75-6.16 (m, 2H), 6.58-6.69 (m, 1H), 6.90 (td, 1H), 7.06-7.13 (m, 2H), 7.14-7.23 (m, 2H), 7.36-7.44 (m, 2H), 7.46 (s, 1H), 8.04-8.17 (m, 2H), 10.64 (s, 1H), 11.85 (s, 1H).—minor impurities in the aliphatic range.

Example 112

N-{4-[3-(2-chloro-3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide

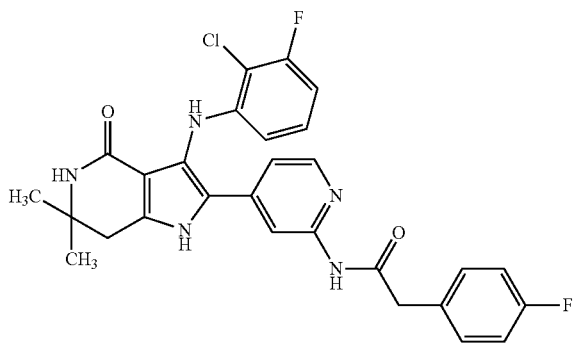 [SMILES: CC1(C)Cc2[nH]c(-c3ccnc(NC(=O)Cc4ccc(F)cc4)c3)c(Nc3cccc(F)c3Cl)c2C(=O)N1]

2-(2-Aminopyridin-4-yl)-3-(2-chloro-3-fluoroanilino)-6,6-dimethyl-1,5,6,7-tetrahydro-4H-pyrrolo[3,2-c]pyridin-4-one (see Intermediate 105, 260 mg), (4-fluorophenyl)acetic acid (200 mg, 1.30 mmol), PyBOP (1.69 g, 3.25 mmol) and N,N-diisopropylethylamine (680 μL, 3.9 mmol) were dissolved in 3.8 mL DMF and it was stirred at rt under nitrogen atmosphere overnight. To the reaction mixture saturated aqueous sodium hydrogencarbonate solution was added and it was diluted with dichloromethane. The layers were separated and the aqueous layer was extracted with dichloromethane twice. The combined organic layers were dried using a water resistant filter. The clear filtrate was concentrated under reduced pressure. The crude product was purified by HPLC under basic conditions to provide the target compound in 90% purity: 116 mg.

LC-MS (Method 2): R$_t$=1.18 min; MS (ESIpos): m/z=536 [M+H]$^+$ $^1$H-NMR (400 MHz, DMSO-d6) δ [ppm]: 1.26 (s, 6H), 2.78-2.82 (m, 2H), 3.67 (s, 2H), 6.09-6.17 (m, 1H), 6.58-6.69 (m, 1H), 6.91 (td, 1H), 7.04-7.23 (m, 4H), 7.30-7.39 (m, 2H), 7.46 (s, 1H), 8.08-8.20 (m, 2H), 10.58 (s, 1H), 11.84 (s, 1H).—minor impurities in the aliphatic range.

Example 113

N-{4-[6,6-dimethyl-3-(2-methylanilino)-4-oxo-4,5,6,7-tetrahydro-1H-pyrrolo[3,2-c]pyridin-2-yl]pyridin-2-yl}-2-(4-fluorophenyl)acetamide

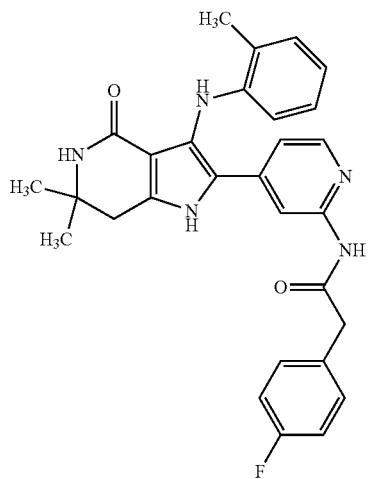 [SMILES: Cc1ccccc1Nc1c(-c2ccnc(NC(=O)Cc3ccc(F)cc3)c2)[nH]c2c1C(=O)NC(C)(C)C2]

2-(2-Aminopyridin-4-yl)-6,6-dimethyl-3-(2-methylanilino)-1,5,6,7-tetrahydro-4H-pyrrolo[3,2-c]pyridin-4-one (see Intermediate 108, 100 mg), (4-fluorophenyl)acetic acid (85.3 mg, 553 μmol), PyBOP (288 mg, 553 μmol) and N,N-diisopropylethylamine (290 μL, 1.7 mmol) were dissolved in 1.6 mL DMF and it was stirred at rt under nitrogen atmosphere over night To the reaction mixture aqueous saturated sodium hydrogencarbonate solution was added and it was diluted with dichloromethane and water. The layers were separated. The aqueous layer was extracted with dichoromethane three times. The combined organic layers were washed with water and brine once, filtered through a silicone coated filter and concentrated under reduced pressure. The crude product was purified by flash chromatography (10 g column, silica; ethyl acetate/ethanol 0%-10%). The product containing fractions were combined and purified by HPLC under basic conditions to provide the target compound in 95% purity: 9 mg.

LC-MS (Method 2): R$_t$=1.18 min; MS (ESIpos): m/z=499 [M+H]$^+$ $^1$H-NMR (400 MHz, DMSO-d6) δ [ppm]: 1.26 (s, 6H), 2.29 (s, 3H), 2.78 (s, 2H), 3.67 (s, 2H), 6.23 (d, 1H), 6.55-6.66 (m, 1H), 6.72-6.81 (m, 1H), 6.98 (dd, 1H), 7.00-7.11 (m, 3H), 7.11-7.21 (m, 2H), 7.27-7.44 (m, 2H), 8.02 (d, 1H), 8.14 (s, 1H), 10.52 (s, 1H), 11.70 (s, 1H).—contains ethanol.

Example 114

N-[4-(3-anilino-5-methyl-4-oxo-4,5,6,7-tetrahydro-1H-pyrrolo[3,2-c]pyridin-2-yl)pyridin-2-yl]-2-(pyrazin-2-yl)acetamide

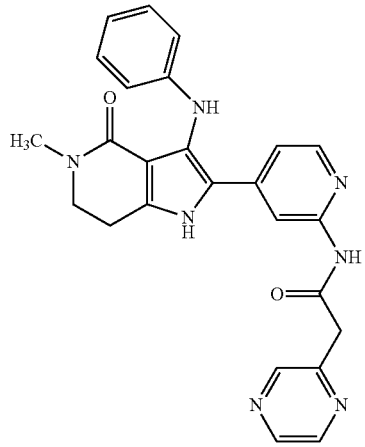 [SMILES: CN1CCc2[nH]c(-c3ccnc(NC(=O)Cc4cnccn4)c3)c(Nc3ccccc3)c2C1=O]

A solution of 2-(2-aminopyridin-4-yl)-3-anilino-5-methyl-1,5,6,7-tetrahydro-4H-pyrrolo[3,2-c]pyridin-4-one (see Intermediate 3, 0.2 g, 0.60 mmol, 1 eq) in DMA (4 mL) was treated with N,N-diisopropylethylamine (0.94 mL, 9 eq; CAS-RN: [7087-68-5]), (pyrazin-2-yl)acetic acid (0.414 g, 5 eq, CAS-RN: [140914-89-2]), and benzotriazol-1-yloxytripyrrolidinophosphonium hexafluorophosphate (1.56 g, 5 eq; CAS-RN: [128625-52-5]), and stirred for 18 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure. Silicagel chromatography (column NH-Biotage, 55 g, gradient dichloromethane/methanol, 0-12%) followed by preparative reverse phase HPLC (gradient of water and acetonitrile containing trifluoroacetic acid as additive) gave 32 mg of the title compound.

LC-MS (Method 2): R$_t$=0.97 min; MS (ESIpos): m/z=454 [M+H]$^+$

1H-NMR (400 MHz, DMSO-d$_6$) δ ppm 2.85 (s, 3H), 2.90 (br t, 2H), 3.52 (t, 2H), 4.01 (s, 2H), 6.55 (d, 2H), 6.62 (t, 1H), 7.01 (t, 2H), 7.14 (dd, 1H), 7.35 (s, 1H), 8.06 (d, 1H), 8.19 (br s, 1H), 8.54 (d, 1H), 8.56-8.61 (m, 1H), 8.66 (d, 1H), 10.69 (s, 1H), 11.74 (s, 1H).

Example 115

N-[4-(3-anilino-5-methyl-4-oxo-4,5,6,7-tetrahydro-1H-pyrrolo[3,2-c]pyridin-2-yl)pyridin-2-yl]-2-(pyridin-2-yl)acetamide

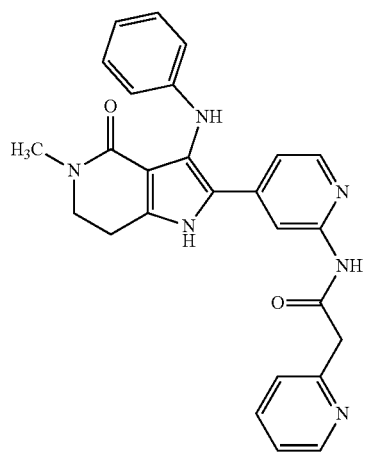 [SMILES: CN1CCc2[nH]c(-c3ccnc(NC(=O)Cc4ccccn4)c3)c(Nc3ccccc3)c2C1=O]

A solution of 2-(2-aminopyridin-4-yl)-3-anilino-5-methyl-1,5,6,7-tetrahydro-4H-pyrrolo[3,2-c]pyridin-4-one (see Intermediate 3, 0.1 g, 0.30 mmol, 1 eq) in DMA (2 mL) was treated with N,N-diisopropylethylamine (0.37 mL, 7 eq; CAS-RN: [7087-68-5]), (pyridin-2-yl)acetic acid (0.123 g, 3 eq, CAS-RN: [13115-43-0]), and benzotriazol-1-yloxytripyrrolidinophosphonium hexafluorophosphate (0.468 g, 3 eq; CAS-RN: [128625-52-5]), and stirred for 72 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure. Silicagel chromatography (column NH-Biotage, 28 g, gradient dichloromethane/ethanol, 0-12%) followed by preparative reverse phase HPLC (gradient of water and acetonitrile containing ammonium hydroxide as additive) gave 59 mg of the title compound as a yellow solid.

LC-MS (Method 2): $R_t$=1.05 min; MS (ESIneg): m/z=451 [M−H]⁻

¹H NMR (400 MHz, DMSO-$d_6$) δ ppm 2.86 (s, 3H), 2.90 (t, 2H), 3.53 (t, 2H), 3.92 (s, 2H), 6.52-6.58 (m, 2H), 6.59-6.66 (m, 1H), 7.02 (dd, 2H), 7.13 (dd, 1H), 7.27 (ddd, 1H), 7.34-7.40 (m, 2H), 7.76 (td, 1H), 8.05 (d, 1H), 8.22 (s, 1H), 8.50 (ddd, 1H), 10.59 (s, 1H), 11.75 (s, 1H).

Example 116

N-[4-(3-anilino-5-methyl-4-oxo-4,5,6,7-tetrahydro-1H-pyrrolo[3,2-c]pyridin-2-yl)pyridin-2-yl]-2-[3-(trifluoromethyl)phenyl]acetamide

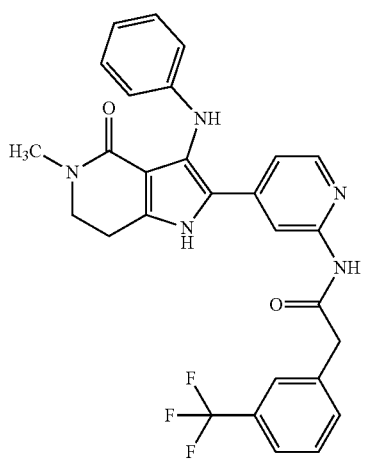 [SMILES: CN1CCc2[nH]c(-c3ccnc(NC(=O)Cc4cccc(C(F)(F)F)c4)c3)c(Nc3ccccc3)c2C1=O]

A solution of 2-(2-aminopyridin-4-yl)-3-anilino-5-methyl-1,5,6,7-tetrahydro-4H-pyrrolo[3,2-c]pyridin-4-one (see Intermediate 3, 0.1 g, 0.30 mmol, 1 eq) in DMA (2 mL) was treated with N,N-diisopropylethylamine (0.37 mL, 7 eq; CAS-RN: [7087-68-5]), [3-(trifluoromethyl)phenyl]acetic acid (184 mg, 3 eq, CAS-RN: [351-35-9]), and benzotriazol-1-yloxytripyrrolidinophosphonium hexafluorophosphate (0.468 g, 3 eq; CAS-RN: [128625-52-5]), and stirred for 42 h at r.t. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column NH-Biotage, 28 g, gradient dichloromethane/ethanol, 0-15%) followed by preparative reverse phase HPLC (gradient of water and acetonitrile containing ammonium hydroxide as additive) to give 6.7 mg of the title compound as a yellow solid.

LC-MS (Method 2): $R_t$=1.30 min; MS (ESIpos): m/z=520 [M+H]⁺

¹H NMR (400 MHz, DMSO-$d_6$) δ ppm 2.86 (s, 3H), 2.90 (t, 2H), 3.52 (t, 2H), 3.83 (s, 2H), 6.55 (d, 2H), 6.61 (t, 1H), 6.96-7.05 (m, 2H), 7.14 (dd, 1H), 7.36 (s, 1H), 7.55-7.66 (m, 3H), 7.72 (s, 1H), 8.05 (d, 1H), 8.19 (s, 1H), 10.64 (s, 1H), 11.73 (s, 1H).

Example 117 methyl 4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoate

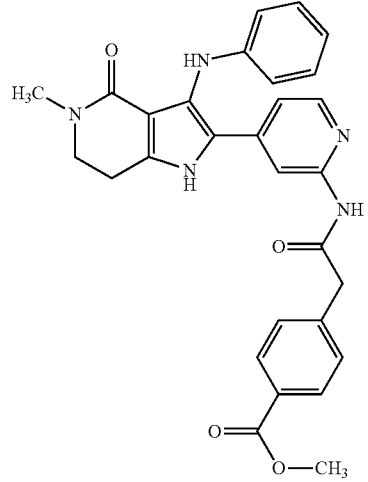 [SMILES: COC(=O)c1ccc(CC(=O)Nc2cc(-c3[nH]c4c(c3Nc3ccccc3)C(=O)N(C)CC4)ccn2)cc1]

A solution of 2-(2-aminopyridin-4-yl)-3-anilino-5-methyl-1,5,6,7-tetrahydro-4H-pyrrolo[3,2-c]pyridin-4-one (see Intermediate 3, 0.577 g, 1.73 mmol, 1 eq) in DMA (7.5 mL) was treated with N,N-diisopropylethylamine (1.80 mL, 6 eq; CAS-RN: [7087-68-5]), -(methoxycarbonyl)phenyl]acetic acid (0.672 g, 2 eq; CAS-RN: [22744-12-3]), and HATU (3.29 g, 5 eq; CAS-RN: [148893-10-1]), and stirred for 3.5 h at 60° C. Then a sodium bicarbonate solution in water was added, and the mixture was extracted with ethyl acetate. The organic phase was washed with saturated sodium chloride solution, dried (sodium sulfate), filtered, concentrated under reduced pressure, and purified by column chromatography (column silica gel, 25 g, gradient dichloromethane/ethanol, 0-20%, then NH-Biotage, 55 g, gradient hexane/ethyl acetate, 20-70%), and triturated with dichloromethane to give 185 mg of the title compound.

LC-MS (Method 2): $R_t$=1.07 min; MS (ESIpos): m/z=510 [M+H]$^+$ $^1$H NMR (400 MHz, DMSO-d$_6$) δ ppm 2.85 (s, 3H), 2.90 (t, 2H), 3.52 (t, 2H), 3.80 (s, 2H), 3.85 (s, 3H), 6.52-6.57 (m, 2H), 6.61 (t, 1H), 7.01 (dd, 2H), 7.13 (dd, 1H), 7.36 (s, 1H), 7.47 (d, 2H), 7.89-7.97 (m, 2H), 8.05 (d, 1H), 8.18 (s, 1H), 10.64 (s, 1H), 11.73 (s, 1H).

Example 118

N-[4-(3-anilino-6,6-dimethyl-4-oxo-4,5,6,7-tetrahydro-1H-pyrrolo[3,2-c]pyridin-2-yl)pyridin-2-yl]-4,4-difluoro-2-[4-(methanesulfonyl)phenyl]butanamide (Racemate)

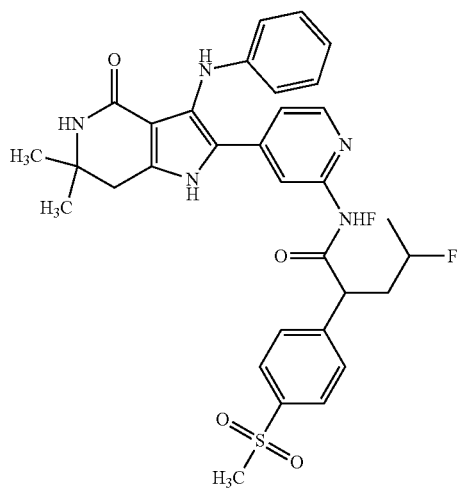

2-(2-Aminopyridin-4-yl)-3-anilino-6,6-dimethyl-1,5,6,7-tetrahydro-4H-pyrrolo[3,2-c]pyridin-4-one (see Intermediate 35, 100 mg, 288 µmol), 4,4-difluoro-2-[4-(methanesulfonyl)phenyl]butanoic acid (Racemate) (see Intermediate 110, 120 mg, 432 µmol), N,N-diisopropylethylamine (300 µl, 1.7 mmol) and PyBOP (300 mg, 576 µmol; CAS-RN: [128625-52-5]) were dissolved in 1.7 mL N,N-dimethylacetamide and stirred at rt under nitrogen atmosphere over night The reaction mixture was diluted with water and dichloromethane. The layers were separated. The aqueous layer was extracted with dichloromethane three times. The combined organic layers were washed with water and brine once, filtered through a silicone coated filter and concentrated under reduced pressure. The crude product was purified by HPLC under basic conditions to provide the target compound in 95% purity: 26 mg.

LC-MS (Method 2): $R_t$=1.05 min; MS (ESIpos): m/z=608 [M+H]$^+$ $^1$H-NMR (400 MHz, DMSO-d$_6$) δ [ppm]=1.26 (s, 6H), 2.19-2.30 (m, 1H), 2.70-2.77 (m, 1H), 2.79 (s, 2H), 3.20 (s, 3H), 4.28 (dd, 1H), 5.81-6.22 (m, 1H), 6.50-6.64 (m, 3H), 6.95-7.03 (m, 2H), 7.05 (s, 1H), 7.13 (dd, 1H), 7.35 (s, 1H), 7.67 (d, 2H), 7.90-7.95 (m, 2H), 8.03 (d, 1H), 8.14 (s, 1H), 10.74 (s, 1H), 11.70 (s, 1H).

Example 119

N-{4-[3-(3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide

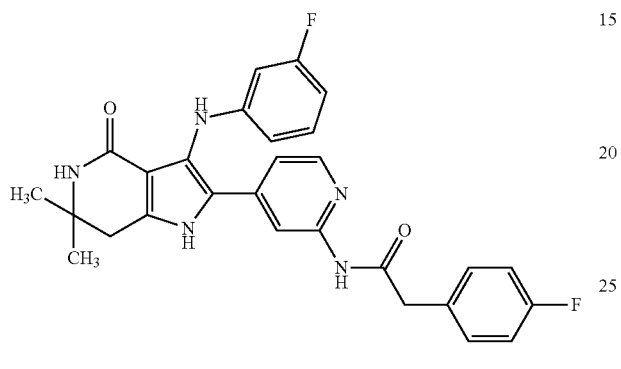

In a pressure resistant tube N-{4-[3-(4-chloro-3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide (see Intermediate 114, 24.0 mg) and triethylamine (6.6 µL, 47 µmol) were dissolved in 270 µL methanol and palladium on carbon (1.43 mg, 10% purity, 1.34 µmol) was added. The tube was evacuated and purged with hydrogen three times. It was stirred 1 hour at 100° C. The tube was evacuated and purged with hydrogen three times. It was stirred an additional hour at 100° C. and at rt overnight. New palladium on carbon (1.43 mg, 10% purity, 1.34 µmol) was added and the tube was evacuated and purged with hydrogen three times. It was stirred 1 hour at 100° C. Again pallidum on carbon (1.43 mg, 10% purity, 1.34 µmol) was added and the tube was evacuated and purged with hydrogen three times. It was stirred 2 hours at 100° C. Again pallidum on carbon (1.43 mg, 10% purity, 1.34 µmol) was added and the tube was evacuated and purged with hydrogen three times. It was stirred 2 hours at 100° C. The reaction mixture was directly loaded on the column and it was purified by flash chromatography (10 g silica ultra column, gradient dichloromethane/ethanol 2%-10%) to provide the target compound in 92% purity: 7.9 mg.

LC-MS (Method 2): $R_t$=1.12 min; MS (ESIpos): m/z=502 [M+H]$^+$ $^1$H-NMR (400 MHz, DMSO-d6) δ [ppm]: 1.057 (0.63), 1.235 (1.36), 1.253 (16.00), 2.522 (0.95), 2.526 (0.63), 2.781 (4.73), 3.695 (5.23), 6.229 (0.55), 6.234 (1.07), 6.240 (0.73), 6.259 (0.56), 6.265 (1.05), 6.270 (0.70), 6.320 (0.50), 6.324 (0.47), 6.340 (0.95), 6.346 (0.91), 6.362 (0.57), 6.369 (0.60), 6.374 (1.05), 6.378 (0.99), 6.394 (1.04), 6.398 (1.04), 6.979 (0.67), 6.999 (3.84), 7.017 (1.35), 7.037 (0.58), 7.130 (1.96), 7.135 (0.71), 7.146 (0.87), 7.152 (4.00), 7.158 (0.89), 7.169 (0.76), 7.174 (2.32), 7.182 (1.76), 7.187 (1.61), 7.196 (1.56), 7.200 (1.57), 7.340 (1.91), 7.346 (0.87), 7.354 (2.15), 7.361 (1.88), 7.370 (0.75), 7.376 (1.57), 7.600 (2.89), 8.102 (2.10), 8.115 (2.01), 8.196 (1.93), 10.589 (2.42), 11.775 (1.72).

Example 120

4,4-difluoro-N-{4-[3-(3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)butanamide (Enantiomer 1)

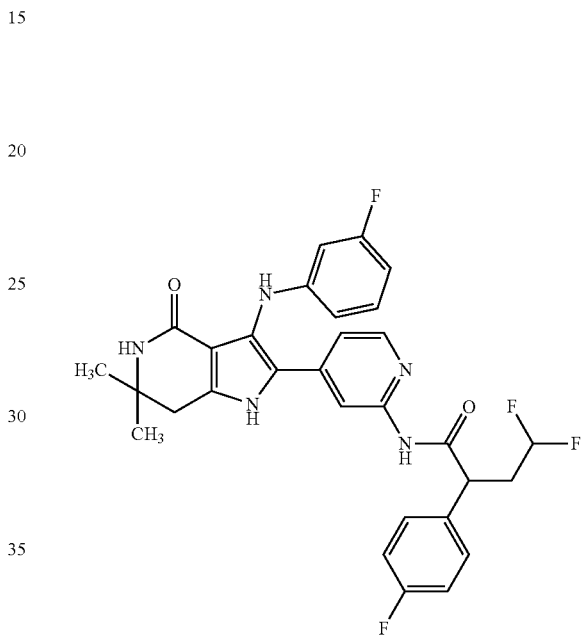

In a pressure resistant tube N-{4-[3-(4-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl)butanamide (Enantiomer 1) (Intermediate 116, 100 mg, 167 µmol) and triethylamine (24 µL, 170 µmol) were dissolved in 1 mL methanol and palladium on carbon (5.32 mg, 10% purity, 5.00 µmol) was added. The tube was evacuated and purged with hydrogen three times. It was stirred 1 hour at 100° C. The catalyst was filtered off using celite. The filtrate was concentrated under reduced pressure. The crude product was purified by flash chromatography (10 g silica ultra column, gradient dichloromethane/ethanol 2%-10%) to provide the target compound in 92% purity: 12.5 mg.

LC-MS (Method 2): $R_t$=1.25 min; MS (ESIpos): m/z=566 [M+H]$^+$ $^1$H-NMR (400 MHz, DMSO-d6) δ [ppm]=1.26 (s, 6H), 2.11-2.29 (m, 1H), 2.58-2.76 (m, 1H), 2.80 (s, 2H), 4.15 (dd, 1H), 5.77-6.14 (m, 1H), 6.25 (dt, 1H), 6.31-6.42 (m, 2H), 6.93-7.06 (m, 2H), 7.14-7.25 (m, 3H), 7.40-7.49 (m, 2H), 7.61 (s, 1H), 8.09 (d, 1H), 8.17 (s, 1H), 10.66 (s, 1H), 11.77 (s, 1H).

Example 121

4,4-difluoro-N-{4-[3-(3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)butanamide (Enantiomer 2)

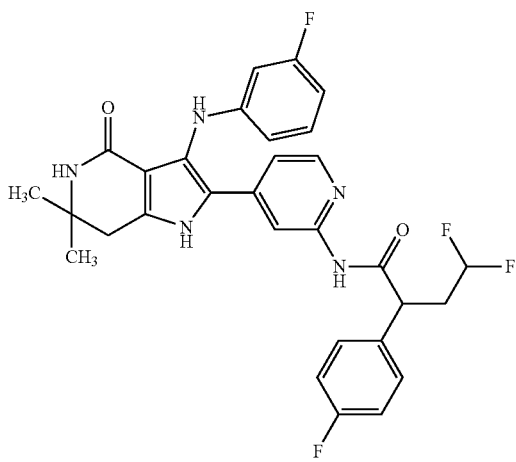 [SMILES: CC1(C)Cc2[nH]c(-c3ccnc(NC(=O)C(CC(F)F)c4ccc(F)cc4)c3)c(Nc3cccc(F)c3)c2C(=O)N1]

In a pressure resistant tube N-{4-[3-(4-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl)butanamide (Enantiomer 2) (see Intermediate 117, 100 mg) and triethylamine (24 μL, 170 μmol) were dissolved in 1 mL methanol and palladium on carbon (5.32 mg, 10% purity, 5.00 μmol) was added. The tube was evacuated and purged with hydrogen three times. It was stirred 1 hour at 100° C. The tube was evacuated and purged with hydrogen three times again. It was stirred an additional hour at 100° C. and at rt overnight. Palladium on carbon (5.32 mg, 10% purity, 5.00 μmol) was added and the tube was evacuated and purged with hydrogen three times. It was stirred 1 hour at 100° C. The catalyst was filtered off using celite. The filtrate was concentrated under reduced pressure. The crude product was purified by flash chromatography (10 g silica ultra column, gradient dichloromethane/ethanol 2%-10%) to provide the target compound in 92% purity: 17.3 mg.

LC-MS (Method 2): $R_t$=1.20 min; MS (ESIneg): m/z=564 [M−H]$^-$ $^1$H-NMR (400 MHz, DMSO-d6) δ [ppm]=1.26 (s, 6H), 2.11-2.28 (m, 1H), 2.59-2.70 (m, 1H), 2.80 (s, 2H), 4.15 (dd, 1H), 5.79-6.16 (m, 1H), 6.26 (dt, 1H), 6.31-6.41 (m, 2H), 6.92-7.05 (m, 2H), 7.15-7.22 (m, 3H), 7.40-7.49 (m, 2H), 7.61 (s, 1H), 8.09 (d, 1H), 8.17 (s, 1H), 10.66 (s, 1H), 11.77 (s, 1H).—contains DMF, ethanol and dichloromethane

Example 122

N-{4-[3'-(2-chloro-3-fluoroanilino)-4'-oxo-1',4',5',7'-tetrahydrospiro[cyclobutane-1,6'-pyrrolo[3,2-c]pyridin]-2'-yl]pyridin-2-yl}-2-(4-fluorophenyl)acetamide

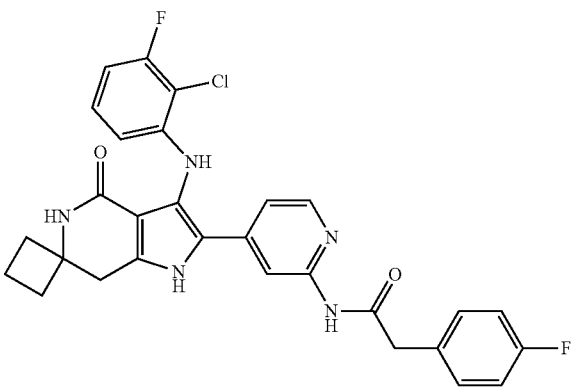 [SMILES: O=C(Cc1ccc(F)cc1)Nc1cc(-c2[nH]c3c(c2Nc2cccc(F)c2Cl)C(=O)NC2(CCC2)C3)ccn1]

2'-(2-Aminopyridin-4-yl)-3'-(2-chloro-3-fluoroanilino)-1',7'-dihydrospiro[cyclobutane-1,6'-pyrrolo[3,2-c]pyridin]-4'(5'H)-one (see Intermediate 120, 200 mg), (4-fluorophenyl)acetic acid (150 mg, 971 μmol), N,N-diisopropylethylamine (510 μL, 2.9 mmol) and PyBOP (1.26 g, 2.43 mmol) were dissolved in 4.5 mL N,N-dimethylacetamide and stirred at rt under nitrogen atmosphere overnight. To the reaction mixture aqueous saturated aqueous sodium hydrogencarbonate solution and dichloromethane were added. The layers were separated and the aqueous layer was extracted with dichloromethane once. The combined organic layers were dried using a water resistant filter. The clear filtrate was concentrated under reduced pressure. The crude product was purified by preparative HPLC and by flash chromatography (10 g silica ultra column, gradient dichloromethane/ethanol 2%-10%) to provide the target compound in 90% purity: 60 mg.

LC-MS (Method 2): $R_t$=1.25 min; MS (ESIpos): m/z=548 [M+H]$^+$ $^1$H-NMR (400 MHz, DMSO-d6) δ [ppm]=1.64-1.82 (m, 2H), 1.96-2.07 (m, 2H), 2.08-2.20 (m, 2H), 3.00 (s, 2H), 3.67 (s, 2H), 6.10 (d, 1H), 6.58-6.70 (m, 1H), 6.91 (td, 1H), 7.09 (dd, 1H), 7.11-7.20 (m, 2H), 7.30-7.38 (m, 2H), 7.45 (s, 1H), 7.56 (s, 1H), 8.12 (d, 1H), 8.15 (s, 1H), 10.59 (s, 1H), 11.92 (s, 1H)

Example 123

N-{4-[3'-(2-chloro-3-fluoroanilino)-4'-oxo-1',4',5',7'-tetrahydrospiro[cyclobutane-1,6'-pyrrolo[3,2-c]pyridin]-2'-yl]pyridin-2-yl}-4,4-difluoro-2-(4-fluorophenyl)butanamide (Racemate)

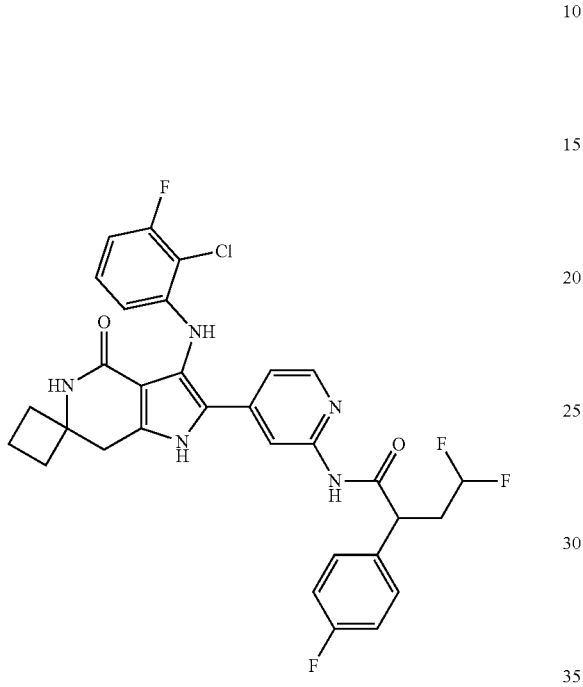

2'-(2-Aminopyridin-4-yl)-3'-(2-chloro-3-fluoroanilino)-1',7'-dihydrospiro[cyclobutane-1,6'-pyrrolo[3,2-c]pyridin]-4'(5'H)-one (see Intermediate 120, 400 mg), 4,4-difluoro-2-(4-fluorophenyl)butanoic acid (Racemate) (424 mg, 1.94 mmol), N,N-diisopropylethylamine (1.0 mL, 5.8 mmol) and PyBOP (2.53 g, 4.86 mmol) were dissolved in 9 mL N,N-dimethylacetamide and stirred at rt under nitrogen atmosphere overnight. To the reaction mixture saturated aqueous sodium hydrogencarbonate solution and dichloromethane were added. The layers were separated and the aqueous layer was extracted with dichloromethane once. The combined organic layers were dried using a water resistant filter. The clear filtrate was concentrated under reduced pressure. The crude product was purified by preparative HPLC to provide the target compound in 88% purity: 345 mg.

LC-MS (Method 2): $R_t$=1.29 min; MS (ESIpos): m/z=612 [M+H]$^+$ $^1$H-NMR (400 MHz, DMSO-d6) δ [ppm]: 1.67-1.80 (m, 2H), 1.97-2.08 (m, 2H), 2.09-2.26 (m, 3H), 2.58-2.76 (m, 1H), 2.95-3.09 (m, 2H), 4.13 (dd, 1H), 5.75-6.13 (m, 2H), 6.59-6.68 (m, 1H), 6.89 (td, 1H), 7.10 (dd, 1H), 7.15-7.23 (m, 2H), 7.38-7.47 (m, 3H), 7.58 (s, 1H), 8.07-8.16 (m, 2H), 10.65 (s, 1H), 11.93 (s, 1H)

Example 124

(−)-N-{4-[3'-(2-chloro-3-fluoroanilino)-4'-oxo-1',4',5',7'-tetrahydrospiro[cyclobutane-1,6'-pyrrolo[3,2-c]pyridin]-2'-yl]pyridin-2-yl}-4,4-difluoro-2-(4-fluorophenyl)butanamide (Enantiomer 1)

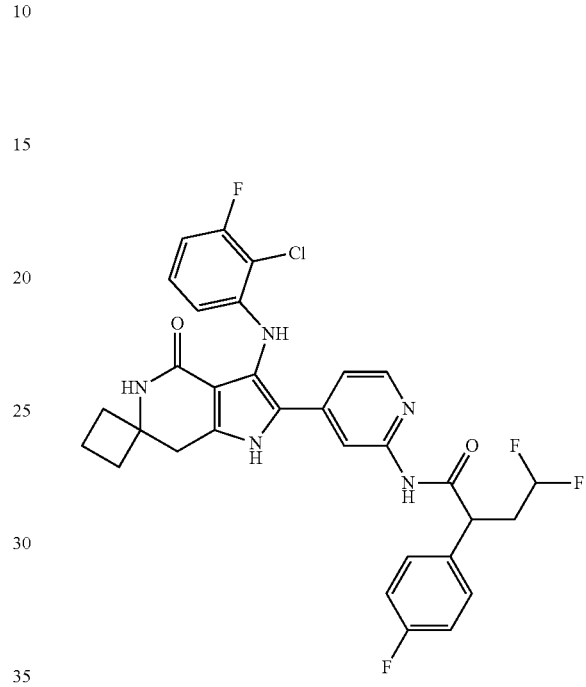

The racemic compound (see Example 123, 313 mg) was separated into enantiomers by preparative chiral HPLC to give enantiomer 1 (145 mg, 100% ee, see Example 124) and enantiomer 2 (155 mg, 100% ee, see Example 125).

Preparative Chiral HPLC Method:

Instrument: PrepCon Labomatic HPLC; Column: YMC Cellulose SB 10µ, 250×50; eluent A: hexane+0.1 vol % diethylamine; eluent B: ethanol+0.1 vol % diethylamine; isocratic: 90% A+10% B; flow: 150 mL/min; temperature: 25° C.; UV: 254 nm.

Analytical Chiral HPLC Method:

Instrument: Waters Alliance 2695; Column: YMC Cellulose SB 3µ, 100×4.6; eluent A: hexane+0.1 vol % diethylamine; eluent B: ethanol; isocratic: 90% A+10% B; flow: 1.4 mL/min; temperature: 25° C.; UV: 254 nm.

Analytical Chiral HPLC (method see Example 124): $R_t$=3.27 min.

$[α]_D$=−78.1° (from solution in methanol, c=6.9 mg/mL)

$^1$H-NMR (400 MHz, DMSO-d6) δ [ppm]=1.68-1.81 (m, 2H), 1.94-2.29 (m, 5H), 2.58-2.76 (m, 1H), 3.01 (s, 2H), 4.13 (dd, 1H), 5.72-6.16 (m, 2H), 6.57-6.67 (m, 1H), 6.89 (td, 1H), 7.10 (dd, 1H), 7.18 (t, 2H), 7.35-7.48 (m, 3H), 7.58 (s, 1H), 8.05-8.18 (m, 2H), 10.65 (s, 1H), 11.93 (s, 1H).— minor impurities in the aliphatic range.

Example 125

(+)-N-{4-[3'-(2-chloro-3-fluoroanilino)-4'-oxo-1',4',5',7'-tetrahydrospiro[cyclobutane-1,6'-pyrrolo[3,2-c]pyridin]-2'-yl]pyridin-2-yl}-4,4-difluoro-2-(4-fluorophenyl)butanamide (Enantiomer 2)

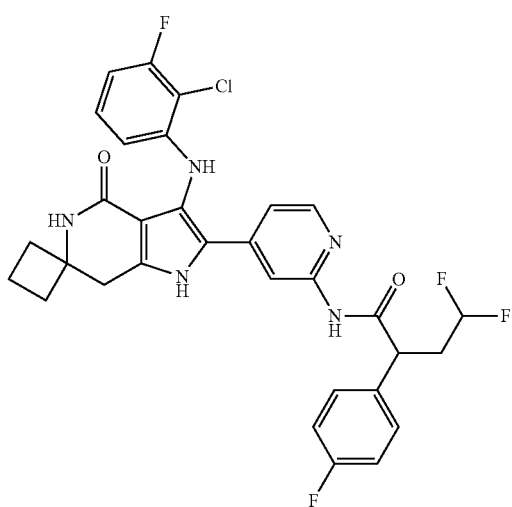 [SMILES: O=C1NC2(CCC2)Cc2[nH]c(-c3ccnc(NC(=O)C(CC(F)F)c4ccc(F)cc4)c3)c(Nc3cccc(F)c3Cl)c21]

For the preparation of the racemic title compound see Example 123. Separation of enantiomers by preparative chiral HPLC (method see Example 124) gave the title compound (155 mg).

Analytical Chiral HPLC (method see Example 124): $R_t$=5.29 min.

$[α]_D$=+82.9° (from solution in methanol, c=5.4 mg/mL)

$^1$H-NMR (400 MHz, DMSO-d6) δ [ppm]=1.67-1.82 (m, 2H), 1.97-2.08 (m, 2H), 2.09-2.29 (m, 3H), 2.58-2.75 (m, 1H), 3.01 (s, 2H), 4.13 (dd, 1H), 5.74-6.15 (m, 2H), 6.56-6.66 (m, 1H), 6.89 (td, 1H), 7.10 (dd, 1H), 7.14-7.24 (m, 2H), 7.38-7.50 (m, 3H), 7.58 (s, 1H), 8.05-8.18 (m, 2H), 10.65 (s, 1H), 11.93 (s, 1H).—minor impurities in the aliphatic range.

Example 126

2-(4-fluorophenyl)-N-(4-{3-[(6-fluoropyridin-2-yl)amino]-6,6-dimethyl-4-oxo-4,5,6,7-tetrahydro-1H-pyrrolo[3,2-c]pyridin-2-yl}pyridin-2-yl)acetamide

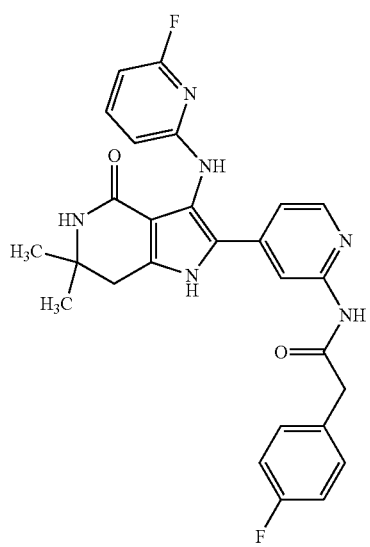 [SMILES: CC1(C)Cc2[nH]c(-c3ccnc(NC(=O)Cc4ccc(F)cc4)c3)c(Nc3cccc(F)n3)c2C(=O)N1]

2-(2-Aminopyridin-4-yl)-3-[(6-fluoropyridin-2-yl)amino]-6,6-dimethyl-1,5,6,7-tetrahydro-4H-pyrrolo[3,2-c]pyridin-4-one (see Intermediate 123, 150 mg), (4-fluorophenyl)acetic acid (94.7 mg, 614 μmol), N,N-diisopropylethylamine (430 μL, 2.5 mmol) and Pybop (426 mg, 819 μmol) were dissolved in 2.4 mL N,N-dimethylacetamide and stirred at rt under nitrogen atmosphere for 2 days. The reaction mixture was diluted with water and dichloromethane. Between both layers a precipitate was formed. It was filtered off. The aqueous layer was extracted with dichloromethane three times, and the combined organic layers were washed with water and brine once, filtered through a silicone coated filter and concentrated under reduced pressure. The crude product was purified by HPLC under basic conditions to provide the target compound in 94% purity: 15 mg.

LC-MS (Method 2): $R_t$=1.03 min; MS (ESIpos): m/z=504 [M+H]$^+$ $^1$H-NMR (400 MHz, DMSO-d6) δ [ppm]: 1.25 (s, 6H), 2.77 (s, 2H), 3.69 (s, 2H), 6.16 (dd, 2H), 6.93 (s, 1H), 7.09-7.20 (m, 2H), 7.24 (dd, 1H), 7.31-7.40 (m, 2H), 7.41-7.52 (m, 1H), 8.15 (d, 1H), 8.19 (d, 2H), 10.60 (s, 1H), 11.77 (s, 1H).—minor impurities in the aromatic and aliphatic range.

Example 127

2-(4-fluorophenyl)-N-(4-{3-[(6-fluoropyridin-2-yl)amino]-6,6-dimethyl-4-oxo-4,5,6,7-tetrahydro-1H-pyrrolo[3,2-c]pyridin-2-yl}pyridin-2-yl)acetamide-1,1',1"-phosphoryltripyrrolidine salt

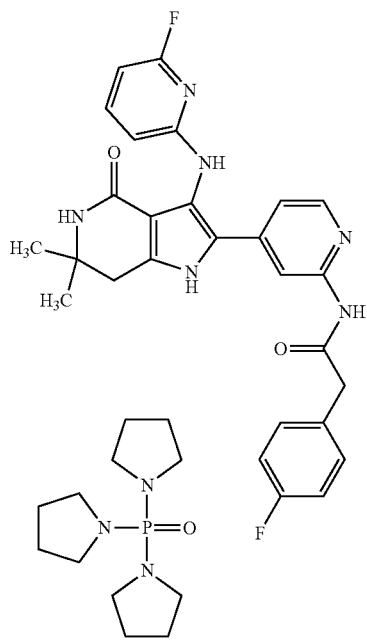 [SMILES: CC1(C)Cc2[nH]c(-c3ccnc(NC(=O)Cc4ccc(F)cc4)c3)c(Nc3cccc(F)n3)c2C(=O)N1 ; O=P(N1CCCC1)(N1CCCC1)N1CCCC1]

Repeating the beforehand reaction with 2-(2-aminopyridin-4-yl)-3-[(6-fluoropyridin-2-yl)amino]-6,6-dimethyl-1,5,6,7-tetrahydro-4H-pyrrolo[3,2-c]pyridin-4-one (see Intermediate 123, 57.0 mg) and (4-fluorophenyl)acetic acid (48.0 mg, 311 µmol) the target compound was provided in 90% purity: 11 mg.

LC-MS (Method 2): $R_t$=1.07 min; MS (ESIpos): m/z=504 [M+H]$^+$ $^1$H-NMR (400 MHz, DMSO-d6) δ [ppm]=1.25 (s, 6H), 2.77 (s, 2H), 3.69 (s, 2H), 6.16 (dd, 2H), 6.93 (s, 1H), 7.11-7.19 (m, 2H), 7.22-7.29 (m, 1H), 7.31-7.40 (m, 2H), 7.46 (q, 1H), 8.15 (d, 1H), 8.18 (s, 1H), 8.20 (s, 1H), 10.60 (s, 1H), 11.77 (s, 1H).

Example 128

4,4-difluoro-2-(4-fluorophenyl)-N-(4-{3-[(6-fluoropyridin-2-yl)amino]-6,6-dimethyl-4-oxo-4,5,6,7-tetrahydro-1H-pyrrolo[3,2-c]pyridin-2-yl}pyridin-2-yl)butanamide (Racemate)

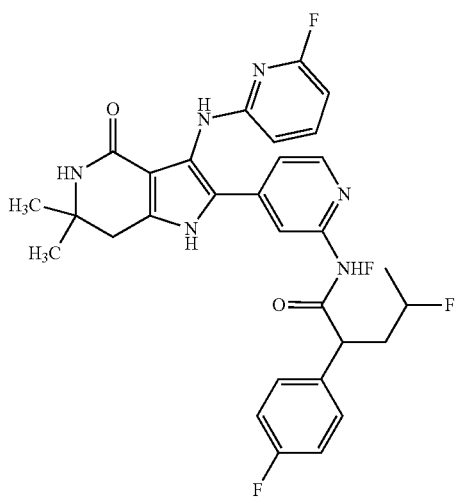

2-(2-Aminopyridin-4-yl)-3-[(6-fluoropyridin-2-yl)amino]-6,6-dimethyl-1,5,6,7-tetrahydro-4H-pyrrolo[3,2-c]pyridin-4-one (see Intermediate 123, 140 mg), 4,4-difluoro-2-(4-fluorophenyl)butanoic acid (Racemate) (125 mg, 573 µmol), N,N-diisopropylethylamine (400 µL, 2.3 mmol) and PyBOP (398 mg, 764 µmol) were dissolved in 2.2 mL N,N-dimethylacetamide and stirred at rt under nitrogen atmosphere over night. The reaction mixture was diluted with water and dichloromethane. The aqueous layer was extracted with dichloromethane three times. The combined organic layers were washed with water and brine once, filtered through a silicone coated filter and concentrated under reduced pressure. The crude product was purified by flash chromatography (11 g column, aminophase; dichloromethane/ethanol 0%-5%). The target compound containing fractions were concentrated under vacuum and the residue was triturated with dichloromethane and MTBE to provide the target compound in 90% purity: 70 mg.

LC-MS (Method 2): $R_t$=1.16 min; MS (ESIpos): m/z=567 [M+H]$^+$ $^1$H-NMR (400 MHz, DMSO-d6) δ [ppm]=1.26 (s, 6H), 2.09-2.28 (m, 1H), 2.59-2.75 (m, 1H), 2.79 (s, 2H), 4.15 (dd, 1H), 5.78-6.12 (m, 1H), 6.17 (dd, 2H), 6.95 (s, 1H), 7.12-7.21 (m, 2H), 7.24 (dd, 1H), 7.40-7.53 (m, 3H), 8.10-8.17 (m, 2H), 8.20 (s, 1H), 10.68 (s, 1H), 11.79 (s, 1H).—contains 1 eq 1,1',1"-phosphoryltripyrrolidine

Example 129

4,4-difluoro-2-(4-fluorophenyl)-N-(4-{3-[(6-fluoro-pyridin-2-yl)amino]-6,6-dimethyl-4-oxo-4,5,6,7-tetrahydro-1H-pyrrolo[3,2-c]pyridin-2-yl}pyridin-2-yl)butanamide (Enantiomer 1)

Example 130

4,4-difluoro-2-(4-fluorophenyl)-N-(4-{3-[(6-fluoro-pyridin-2-yl)amino]-6,6-dimethyl-4-oxo-4,5,6,7-tetrahydro-1H-pyrrolo[3,2-c]pyridin-2-yl}pyridin-2-yl)butanamide (Enantiomer 2)

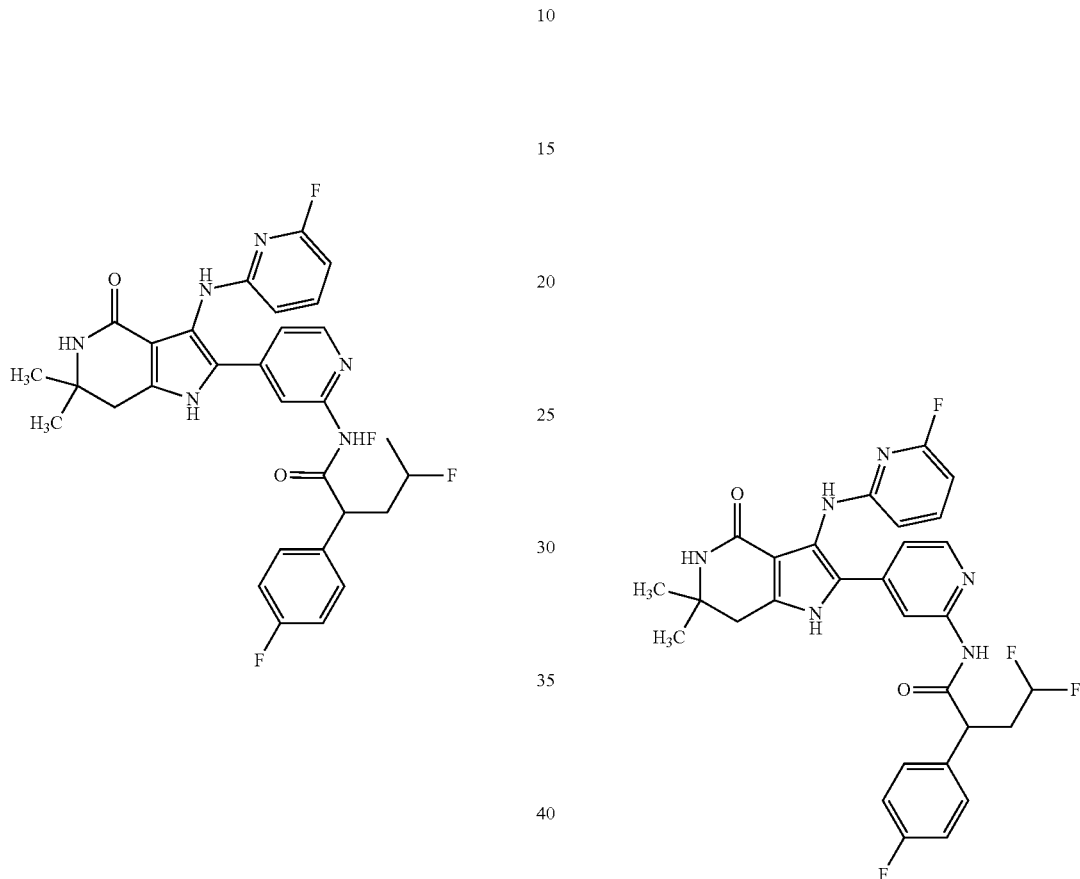

The racemic compound (see Example 128, 58 mg) was separated into enantiomers by preparative chiral HPLC to give enantiomer 1 (14 mg, >99.9% ee, see Example 129) and enantiomer 2 (15 mg, 98.1% ee, see Example 130).

Preparative Chiral HPLC Method:

Instrument: PrepCon Labomatic HPLC; Column: YMC Amylose SA 10μ, 250×50; eluent A: hexane+0.1 vol % diethylamine; eluent B: ethanol; flow: 100 mL/min; temperature: 25° C.; UV: 254 nm.

Analytical Chiral HPLC Method:

Instrument: Waters Alliance 2695; Column: YMC Amylose SA 3μ, 100×4.6; eluent A: hexane+0.1 vol % diethylamine; eluent B: ethanol; flow: 1.4 mL/min; temperature: 25° C.; UV: 254 nm.

Analytical Chiral HPLC (method see Example 129): $R_t$=8.53 min.

$^1$H-NMR (400 MHz, DMSO-d6) δ [ppm]=1.24-1.30 (m, 6H) 2.05-2.25 (m, 1H) 2.58-2.71 (m, 1H) 2.75-2.85 (m, 2H) 4.08-4.27 (m, 1H) 5.78-6.13 (m, 1H) 6.13-6.22 (m, 2H) 6.86-7.05 (m, 1H) 7.15-7.22 (m, 2H) 7.23-7.29 (m, 1H) 7.35-7.55 (m, 3H) 8.08-8.14 (m, 1H) 8.15-8.18 (m, 1H) 8.20-8.27 (m, 1H) 10.54-10.81 (m, 1H) 11.65-11.87 (m, 1H).

For the preparation of the racemic title compound see Example 128. Separation of enantiomers by preparative chiral HPLC (method see Example 129) gave the title compound (15 mg).

Analytical Chiral HPLC (method see Example 129): $R_t$=11.59 min.

$^1$H-NMR (400 MHz, DMSO-d6) δ [ppm]=1.24-1.30 (m, 6H) 2.05-2.25 (m, 1H) 2.58-2.71 (m, 1H) 2.75-2.85 (m, 2H) 4.08-4.27 (m, 1H) 5.78-6.13 (m, 1H) 6.13-6.22 (m, 2H) 6.86-7.05 (m, 1H) 7.15-7.22 (m, 2H) 7.23-7.29 (m, 1H) 7.35-7.55 (m, 3H) 8.08-8.14 (m, 1H) 8.15-8.18 (m, 1H) 8.20-8.27 (m, 1H) 10.54-10.81 (m, 1H) 11.65-11.87 (m, 1H).

Example 131

N-{4-[3-(3-fluoro-2-methylanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide

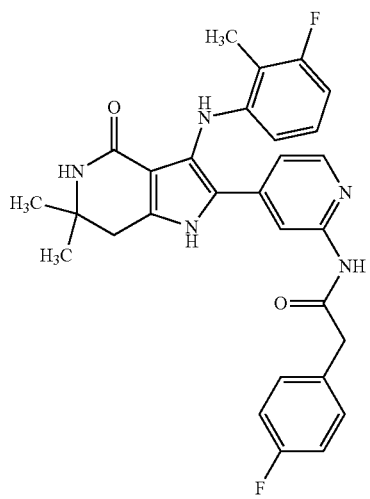 [SMILES: Cc1c(F)cccc1Nc1c(-c2ccnc(NC(=O)Cc3ccc(F)cc3)c2)[nH]c2c1C(=O)NC(C)(C)C2]

2-(2-Aminopyridin-4-yl)-3-(3-fluoro-2-methylanilino)-6,6-dimethyl-1,5,6,7-tetrahydro-4H-pyrrolo[3,2-c]pyridin-4-one (see Intermediate 126, 120 mg), (4-fluorophenyl)acetic acid (73.1 mg, 474 µmol), N,N-diisopropylethylamine (330 µL, 1.9 mmol) and PyBOP (494 mg, 949 µmol) were dissolved in 1.8 mL N,N-dimethylacetamide stirred at rt under nitrogen atmosphere over night. The reaction mixture was diluted with water and dichloromethane. The aqueous layer was extracted with dichloromethane three times. The combined organic layers were washed with water and brine once, filtered through a silicone coated filter and concentrated under reduced pressure. The crude product was purified by flash chromatography (11 g column, aminophase; dichloromethane/ethanol 0%-5%). The target compound containing fractions were concentrated under reduced pressure and tritiated with methanol and MTBE to provide the target compound in 96% purity: 40 mg.

LC-MS (Method 2): $R_t$=1.19 min; MS (ESIpos): m/z=517 [M+H]$^+$ $^1$H-NMR (400 MHz, DMSO-d6) δ [ppm]=1.26 (s, 6H), 2.18 (d, 3H), 2.79 (s, 2H), 3.67 (s, 2H), 6.05 (d, 1H), 6.45 (t, 1H), 6.70-6.83 (m, 1H), 7.01-7.09 (m, 3H), 7.11-7.20 (m, 2H), 7.31-7.40 (m, 2H), 8.07 (d, 1H), 8.17 (s, 1H), 10.52 (s, 1H), 11.74 (s, 1H).

Example 132

N-{4-[6,6-dimethyl-3-(2-methylanilino)-4-oxo-4,5,6,7-tetrahydro-1H-pyrrolo[3,2-c]pyridin-2-yl]pyridin-2-yl}-2-(4-fluorophenyl)propanamide (Racemate)

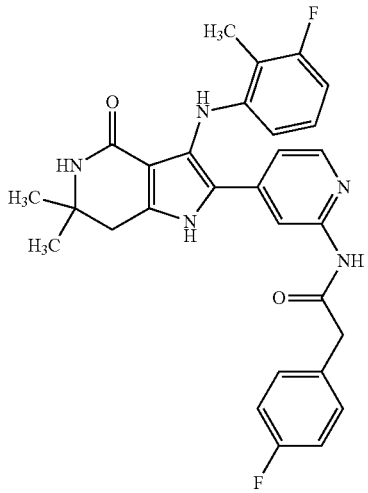

2-(2-Aminopyridin-4-yl)-6,6-dimethyl-3-(2-methylanilino)-1,5,6,7-tetrahydro-4H-pyrrolo[3,2-c]pyridin-4-one (see Intermediate 108, 120 mg), (2-(4-fluorophenyl)propanoic acid (Racemate) (83.7 mg, 498 µmol), N,N-diisopropylethylamine (350 µL, 2.0 mmol) and Pybop (346 mg, 664 µmol) were dissolved in 1.9 mL N,N-dimethylacetamide and stirred at rt under nitrogen atmosphere over night. The reaction mixture was diluted with water and dichloromethane. The aqueous layer was extracted with dichloromethane three times. The combined organic layers were washed with water and brine once, filtered through a silicone coated filter and concentrated under reduced pressure. The crude product was dissolved in dichloromethane and treated with half saturated brine. It was stirred for a few minutes, filtered through a silicone coated filter and concentrated under reduced pressure. The crude product 2 was used for the same reaction. The same amounts of all reagents were used. It was stirred for 2 days at rt. The reaction mixture was diluted with half saturated brine and dichloromethane and stirred for a few minutes, filtered through a silicone coated filter and concentrated under reduced pressure. The crude product 3 was purified by flash chromatography (11 g column, aminophase; dichloromethane/ethanol 0%-5%). The target compound containing fractions were concentrated under reduced pressure and purified by HPLC under basic conditions to provide the target compound in 94% purity: 47 mg.

LC-MS (Method 2): $R_t$=1.26 min; MS (ESIpos): m/z=513 [M+H]$^+$ $^1$H-NMR (400 MHz, DMSO-d6) δ [ppm]=1.27 (s, 6H), 1.38 (d, 3H), 2.30 (s, 3H), 2.80 (s, 2H), 3.99 (q, 1H), 6.21 (d, 1H), 6.59 (td, 1H), 6.71-6.80 (m, 1H), 6.96 (dd, 1H), 7.02 (s, 1H), 7.06 (d, 1H), 7.09 (s, 1H), 7.12-7.23 (m, 2H), 7.34-7.45 (m, 2H), 7.99 (d, 1H), 8.16 (d, 1H), 10.45 (s, 1H), 11.70 (s, 1H).

Example 133

(−)-N-{4-[6,6-dimethyl-3-(2-methylanilino)-4-oxo-4,5,6,7-tetrahydro-1H-pyrrolo[3,2-c]pyridin-2-yl]pyridin-2-yl}-2-(4-fluorophenyl)propanamide (Enantiomer 1)

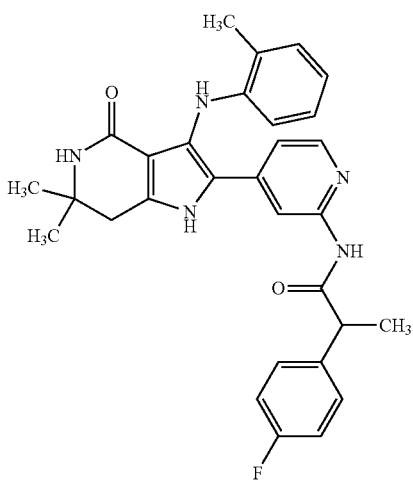 [SMILES: Cc1ccccc1Nc1c(-c2ccnc(NC(=O)C(C)c3ccc(F)cc3)c2)[nH]c2c1C(=O)NC(C)(C)C2]

The racemic compound (see Example 132, 41 mg) was separated into enantiomers by preparative chiral HPLC to give enantiomer 1 (12 mg, 96.8% ee, see Example 133) and enantiomer 2 (16 mg, >99.9% ee, see Example 134).

Preparative Chiral HPLC Method:

Instrument: PrepCon Labomatic HPLC; Column: YMC Cellulose SB 10μ, 250×50; eluent A: methyl tert-butyl ether+0.1 vol % diethylamine; eluent B: acetonitrile; isocratic: 90% A+10% B; flow: 150 mL/min; temperature: 25° C.; UV: 254 nm.

Analytical Chiral HPLC Method:

Instrument: Waters Alliance 2695; Column: YMC Cellulose SB 3μ, 100×4.6; eluent A: methyl tert-butyl ether+0.1 vol % diethylamine; eluent B: acetonitrile; isocratic: 90% A+10% B; flow: 1.4 mL/min; temperature: 25° C.; UV: 254 nm.

Analytical Chiral HPLC (method see Example 133): $R_t$=2.15/2.17 min.

$[α]_D$=−104.1° (from solution in methanol, c=8.6 mg/mL)

$^1$H-NMR (400 MHz, DMSO-d6) δ [ppm]=1.26 (s, 6H), 1.38 (d, 3H), 2.30 (s, 3H), 2.80 (s, 2H), 3.99 (q, 1H), 6.21 (d, 1H), 6.59 (td, 1H), 6.71-6.81 (m, 1H), 6.96 (dd, 1H), 7.00-7.12 (m, 3H), 7.12-7.22 (m, 2H), 7.35-7.46 (m, 2H), 7.99 (d, 1H), 8.16 (s, 1H), 10.45 (s, 1H), 11.70 (s, 1H).

Example 134

N-{4-[6,6-dimethyl-3-(2-methylanilino)-4-oxo-4,5,6,7-tetrahydro-1H-pyrrolo[3,2-c]pyridin-2-yl]pyridin-2-yl}-2-(4-fluorophenyl)propanamide (Enantiomer 2)

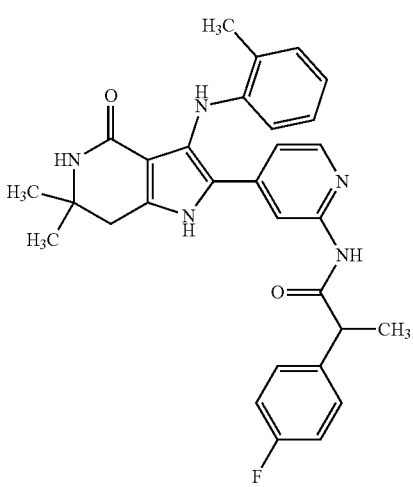 [SMILES: Cc1ccccc1Nc1c(-c2ccnc(NC(=O)C(C)c3ccc(F)cc3)c2)[nH]c2c1C(=O)NC(C)(C)C2]

For the preparation of the racemic title compound see Example 132. Separation of enantiomers by preparative chiral HPLC (method see Example 133) gave the title compound (16 mg).

Analytical Chiral HPLC (method see Example 133): $R_t$=3.44 min.

$^1$H-NMR (400 MHz, DMSO-d6) δ [ppm]=1.27 (s, 6H), 1.38 (d, 3H), 2.30 (s, 3H), 2.80 (s, 2H), 3.99 (q, 1H), 6.22 (d, 1H), 6.54-6.66 (m, 1H), 6.71-6.81 (m, 1H), 6.97 (dd, 1H), 7.00-7.07 (m, 2H), 7.11 (s, 1H), 7.12-7.25 (m, 2H), 7.33-7.45 (m, 2H), 7.99 (d, 1H), 8.17 (s, 1H), 10.46 (s, 1H), 11.71 (s, 1H).

Example 135

N-{4-[6,6-dimethyl-3-(2-methylanilino)-4-oxo-4,5,6,7-tetrahydro-1H-pyrrolo[3,2-c]pyridin-2-yl]pyridin-2-yl}-4,4-difluoro-2-(4-fluorophenyl)butanamide (Racemate)

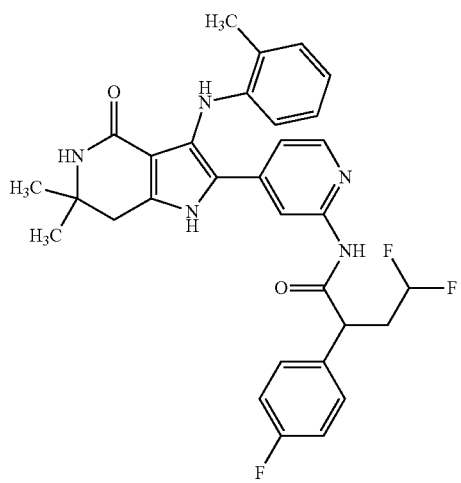 [SMILES: Cc1ccccc1Nc1c(-c2ccnc(NC(=O)C(CC(F)F)c3ccc(F)cc3)c2)[nH]c2c1C(=O)NC(C)(C)C2]

2-(2-Aminopyridin-4-yl)-6,6-dimethyl-3-(2-methylanilino)-1,5,6,7-tetrahydro-4H-pyrrolo[3,2-c]pyridin-4-one (see Intermediate 108, 120 mg), 4,4-difluoro-2-(4-fluorophenyl)butanoic acid (Racemate) (109 mg, 498 µmol), N,N-diisopropylethylamine (350 µL, 2.0 mmol) and PyBOP (346 mg, 664 µmol) were dissolved in 1.9 mL N,N-dimethylacetamide and stirred at rt under nitrogen atmosphere over night. The reaction mixture was diluted with water and dichloromethane. The aqueous layer was extracted with dichloromethane three times. The combined organic layers were washed with water and brine once, filtered through a silicone coated filter and concentrated under reduced pressure. The crude product was dissolved in dichloromethane and treated with half saturated brine. It was stirred for a few minutes, filtered through a silicone coated filter and concentrated under reduced pressure. The crude product 2 was used for the same reaction. The same amounts of all reagents were used. It was stirred for 2 days at rt. The reaction mixture was diluted with half saturated brine and dichloromethane and stirred for a few minutes, filtered through a silicone coated filter and concentrated under reduced pressure. The crude product 3 was purified by flash chromatography (11 g column, aminophase; dichloromethane/ethanol 0%-5%). The target compound containing fractions were concentrated under reduced pressure and purified by HPLC under basic conditions. To provide the target compound in 96% purity: 54 mg.

LC-MS (Method 2): $R_t$=1.27 min; MS (ESIpos): m/z=563 [M+H]$^+$ $^1$H-NMR (400 MHz, DMSO-d6) δ [ppm]=1.27 (s, 6H), 2.09-2.28 (m, 1H), 2.31 (s, 3H), 2.58-2.75 (m, 1H), 2.80 (s, 2H), 4.12 (dd, 1H), 5.77-6.11 (m, 1H), 6.20 (d, 1H), 6.59 (td, 1H), 6.71-6.79 (m, 1H), 6.97-7.03 (m, 2H), 7.06 (d, 1H), 7.10 (s, 1H), 7.16-7.26 (m, 2H), 7.36-7.50 (m, 2H), 8.00 (d, 1H), 8.12 (s, 1H), 10.58 (s, 1H), 11.70 (s, 1H).

Example 136

N-{4-[6,6-dimethyl-3-(2-methylanilino)-4-oxo-4,5,6,7-tetrahydro-1H-pyrrolo[3,2-c]pyridin-2-yl]pyridin-2-yl}-4,4-difluoro-2-(4-fluorophenyl)butanamide (Enantiomer 1)

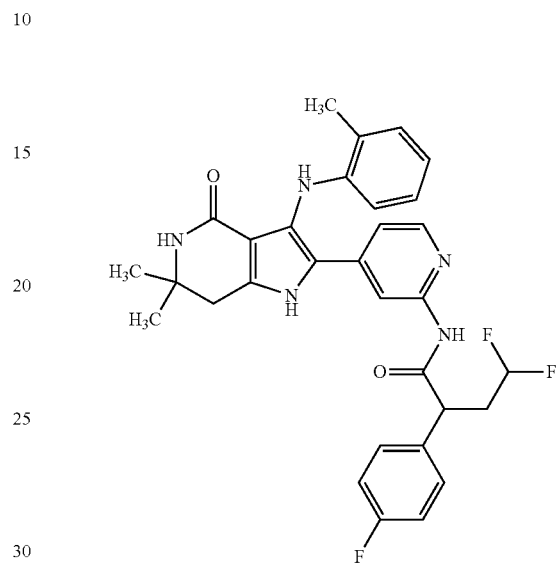

The racemic compound (see Example 135, 50 mg) was separated into enantiomers by preparative chiral HPLC to give enantiomer 1 (20 mg, 100% ee, see Example 136) and enantiomer 2 (18 mg, 97.9% ee, see Example 137). For further purification both fractions were treated with hexane and sonicated for 5 minutes. The undissolved precipitate was filtered off, washed with hexane and dried at 50° C. under vacuo to provide the both enantiomers: 5 mg each.

Preparative Chiral HPLC Method:

Instrument: PrepCon Labomatic HPLC; Column: Reprosil NR 8µ, 250×30; eluent A: hexane+0.1 vol % diethylamine; eluent B: 2-propanol+0.1 vol % diethylamine; gradient: 0-15 min 20-50% B; flow: 40 mL/min; temperature: 25° C.; UV: 280 nm.

Analytical Chiral HPLC Method:

Instrument: Waters Alliance 2695; Column: Reprosil NR 5µ, 100×4.6; eluent A: hexane+0.1 vol % diethylamine; eluent B: 2-propanol; gradient: 0-7 min 20-50% B; flow: 1.4 mL/min; temperature: 25° C.; UV: 280 nm.

Analytical Chiral HPLC (method Example 136): $R_t$=4.74 min.

$^1$H-NMR (400 MHz, DMSO-d6) δ [ppm]=1.27 (s, 6H), 2.08-2.26 (m, 1H), 2.31 (s, 3H), 2.59-2.75 (m, 1H), 2.80 (s, 2H), 4.12 (br dd, 1H), 5.74-6.12 (m, 1H), 6.20 (d, 1H), 6.52-6.65 (m, 1H), 6.69-6.80 (m, 1H), 6.94-7.07 (m, 3H), 7.08-7.14 (m, 1H), 7.19 (t, 2H), 7.37-7.53 (m, 2H), 8.00 (d, 1H), 8.12 (s, 1H), 10.58 (s, 1H), 11.70 (s, 1H).

Example 137

N-{4-[6,6-dimethyl-3-(2-methylanilino)-4-oxo-4,5,6,7-tetrahydro-1H-pyrrolo[3,2-c]pyridin-2-yl]pyridin-2-yl}-4,4-difluoro-2-(4-fluorophenyl)butanamide (Enantiomer 2)

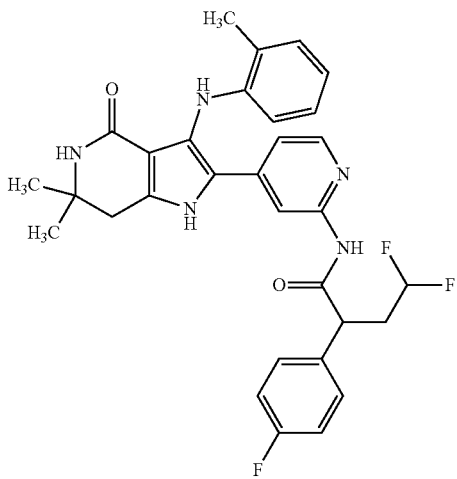 [SMILES: Cc1ccccc1Nc1c(-c2ccnc(NC(=O)C(CC(F)F)c3ccc(F)cc3)c2)[nH]c2c1C(=O)NC(C)(C)C2]

For the preparation of the racemic title compound see Example 135. Separation of enantiomers by preparative chiral HPLC (method see Example 136) and sonication from hexane gave the title compound (5 mg).

Analytical Chiral HPLC (method see Example 136: $R_t$=5.38 min.

$^1$H-NMR (400 MHz, DMSO-d6) δ [ppm]=1.27 (s, 6H), 2.06-2.25 (m, 1H), 2.31 (s, 3H), 2.58-2.74 (m, 1H), 2.80 (s, 2H), 4.12 (br dd, 1H), 5.74-6.12 (m, 1H), 6.20 (br d, 1H), 6.59 (t, 1H), 6.68-6.82 (m, 1H), 6.92-7.11 (m, 4H), 7.13-7.31 (m, 2H), 7.42 (br dd, 2H), 8.00 (d, 1H), 8.12 (s, 1H), 10.58 (s, 1H), 11.70 (s, 1H).

Example 138 tert-butyl [3-{[4-(3-anilino-6,6-dimethyl-4-oxo-4,5,6,7-tetrahydro-1H-pyrrolo[3,2-c]pyridin-2-yl)pyridin-2-yl]amino}-2-(4-fluorophenyl)-3-oxopropyl]carbamate (Racemate)

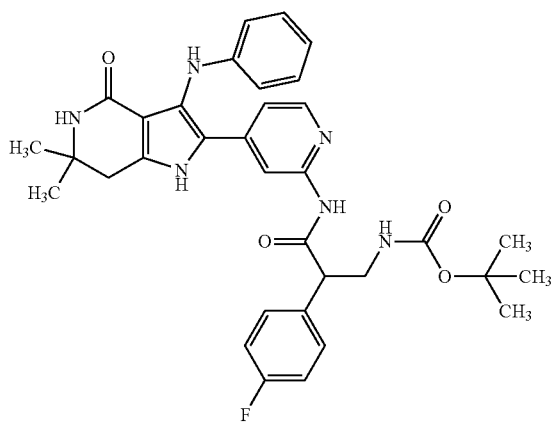 [SMILES: CC1(C)Cc2[nH]c(-c3ccnc(NC(=O)C(CNC(=O)OC(C)(C)C)c4ccc(F)cc4)c3)c(Nc3ccccc3)c2C(=O)N1]

2-(2-Aminopyridin-4-yl)-3-anilino-6,6-dimethyl-1,5,6,7-tetrahydro-4H-pyrrolo[3,2-c]pyridin-4-one (242 mg), 3-[(tert-butoxycarbonyl)amino]-2-(4-fluorophenyl)propanoic acid (Racemate) (see Intermediate 127, 296 mg), N,N-diisopropylethylamine (730 μL, 4.2 mmol) and PyBOP (725 mg, 1.39 mmol) were dissolved in 4 mL DMA and stirred at rt under nitrogen atmosphere for 2 days. The reaction mixture was diluted with water and dichloromethane and the layers were separated. The aqueous layer was extracted with dichloromethane three times. The combined organic layers were washed with water and brine, filtered through a silicone coated filter and concentrated under reduced pressure. The crude product was purified by flash chromatography (11 g column, aminophase; dichloromethane/ethanol 0%-5%). The target compound containing fractions were combined and purified by HPLC under basic conditions to provide the target compound in 85% purity: 39 mg.

LC-MS (Method 2): $R_t$=1.27 min; MS (ESIpos): m/z=613 [M+H]$^+$ $^1$H-NMR (400 MHz, DMSO-d6) δ [ppm]=1.26 (s, 6H), 1.33 (s, 9H), 2.79 (s, 2H), 3.22-3.31 (m, 1H), 3.44-3.52 (m, 1H), 4.12 (br t, 1H), 6.56 (d, 2H), 6.61 (t, 1H), 6.81-6.89 (m, 1H), 6.96-7.07 (m, 3H), 7.11 (dd, 1H), 7.16 (br t, 2H), 7.30-7.42 (m, 3H), 8.01 (d, 1H), 8.19 (s, 1H), 10.52 (s, 1H), 11.71 (s, 1H).

Example 139

3-amino-N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propanamide-hydrogen chloride salt (Racemate)

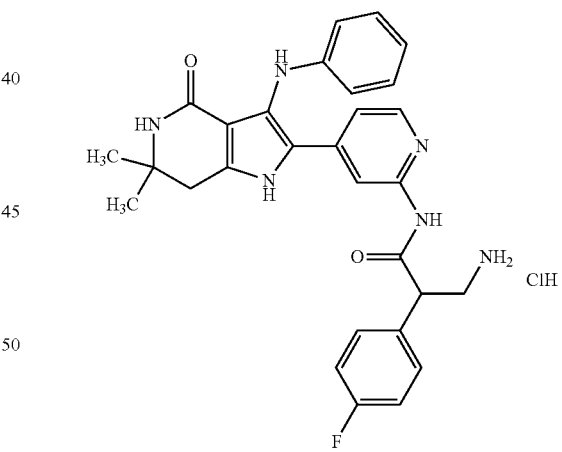

Tert-butyl [3-{[4-(3-anilino-6,6-dimethyl-4-oxo-4,5,6,7-tetrahydro-1H-pyrrolo[3,2-c]pyridin-2-yl)pyridin-2-yl]amino}-2-(4-fluorophenyl)-3-oxopropyl]carbamate (Racemate) (see Example 138, 100 mg) was dissolved in 3.5 mL dioxane and treated with hydrochloric acid in dioxane (200 μL, 4.0 M, 820 μmol). It was stirred at 40° C. for 2 hours under nitrogen atmosphere. The reaction mixture was concentrated under reduced pressure. The crude product was suspended in dichloromethane and sonicated. The undissolved precipitate was filtered off and dried at 50° C. under vacuum to provide the target compound in 69% purity: 74 mg.

LC-MS (Method 2): $R_t$=1.04 min; MS (ESIpos): m/z=514 [M+H]$^+$ $^1$H-NMR (400 MHz, DMSO-d6) δ [ppm]=1.27 (d, 6H), 2.82 (s, 2H), 2.98-3.10 (m, 1H), 3.42-3.53 (m, 1H), 4.20 (br dd, 1H), 6.59 (d, 2H), 6.62-6.69 (m, 1H), 7.03 (dd, 2H), 7.15 (s, 1H), 7.20-7.29 (m, 3H), 7.35-7.43 (m, 2H), 7.97 (br s, 4H), 8.08 (d, 1H), 10.72-11.34 (m, 1H), 11.78-12.04 (m, 1H).

Example 140

3-amino-N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propanamide (Enantiomer 1)

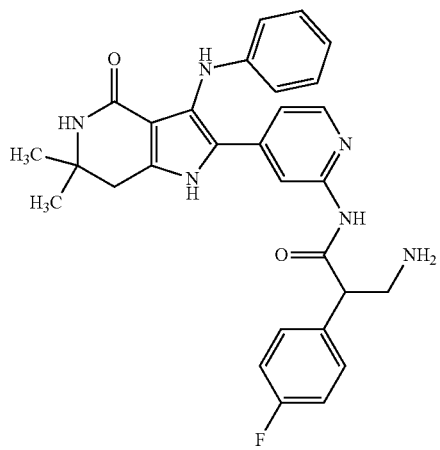 [SMILES: CC1(C)Cc2[nH]c(-c3ccnc(NC(=O)C(CN)c4ccc(F)cc4)c3)c(Nc3ccccc3)c2C(=O)N1]

The racemic compound (see Example 139, 70 mg) was separated into enantiomers by preparative chiral HPLC to give enantiomer 1 (32 mg, 99.5% ee, see Example 140) and enantiomer 2 (41 mg, see Example 141). Both enantiomers were further purified by HPLC under basic conditions to provide enantiomer 1 (84% purity, 12 mg) and enantiomer 2 (84% purity; 11 mg).

Preparative Chiral HPLC Method:

Instrument: PrepCon Labomatic HPLC; Column: YMC Amylose SA 10μ, 250×50; eluent A: hexane+0.1 vol % diethylamine; eluent B: ethanol; isocratic: 50% A+50% B; flow: 150 mL/min; temperature: 25° C.; UV: 254 nm.

Analytical Chiral HPLC Method:

Instrument: Waters Alliance 2695; Column: YMC Amylose SA 3μ, 100×4.6; eluent A: hexane+0.1 vol % diethylamine; eluent B: ethanol; isocratic: 50% A+50% B; flow: 1.4 mL/min; temperature: 25° C.; UV: 254 nm.

Analytical Chiral HPLC (method Example 140): $R_t$=3.04 min.

$^1$H-NMR (400 MHz, DMSO-d6) δ [ppm]=1.26 (s, 6H), 2.79 (s, 3H), 3.07-3.23 (m, 2H), 3.39-3.47 (m, 1H), 3.86 (br dd, 1H), 6.47-6.66 (m, 3H), 6.94-7.07 (m, 3H), 7.08-7.21 (m, 3H), 7.29-7.48 (m, 3H), 8.01 (d, 1H), 8.22 (s, 1H), 10.38-10.84 (m, 1H), 11.72 (br s, 1H).

Example 141

3-amino-N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propanamide (Enantiomer 2)

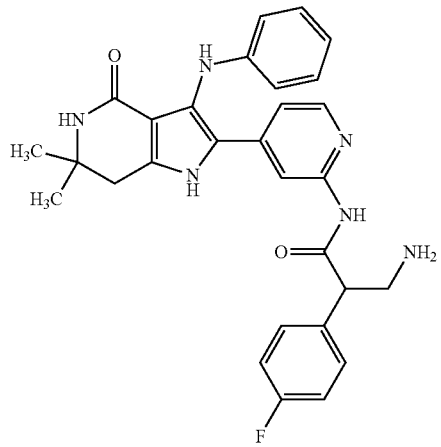 [SMILES: CC1(C)Cc2[nH]c(-c3ccnc(NC(=O)C(CN)c4ccc(F)cc4)c3)c(Nc3ccccc3)c2C(=O)N1]

For the preparation of the racemic title compound see Example 139. Separation of enantiomers by preparative chiral HPLC (method see Example 140) gave the title compound (41 mg), which was further purified by HPLC under basic conditions: enantiomer 2 (84% purity; 11 mg).

Analytical Chiral HPLC (method see Example 140: $R_t$=4.94 min.

$^1$H-NMR (400 MHz, DMSO-d6) δ [ppm]=1.26 (s, 6H), 2.80 (s, 3H), 3.10-3.23 (m, 1H), 3.25-3.49 (m, 2H), 3.86 (br dd, 1H), 6.50-6.66 (m, 3H), 6.93-7.07 (m, 3H), 7.07-7.22 (m, 3H), 7.28-7.51 (m, 3H), 8.01 (d, 1H), 8.22 (s, 1H), 10.57 (s, 1H), 11.72 (br s, 1H).

Example 142

2-(4-fluorophenyl)-N-{4-[3'-(2-methylanilino)-4'-oxo-1',4',5',7'-tetrahydrospiro[cyclobutane-1,6'-pyrrolo[3,2-c]pyridin]-2'-yl]pyridin-2-yl}acetamide

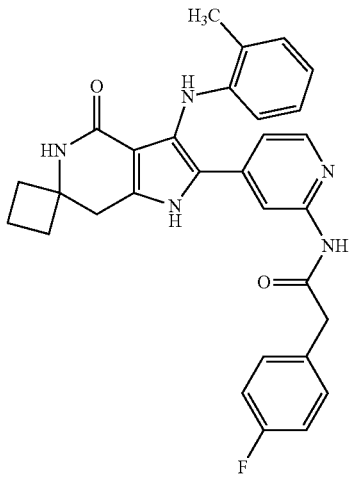 [SMILES: Cc1ccccc1Nc1c(-c2ccnc(NC(=O)Cc3ccc(F)cc3)c2)[nH]c2c1C(=O)NC1(CCC1)C2]

2'-(2-Aminopyridin-4-yl)-3'-(2-methylanilino)-1',7'-dihydrospiro[cyclobutane-1,6'-pyrrolo[3,2-c]pyridin]-4'(5'H)-one (see Intermediate 130, 150 mg), (4-fluorophenyl)acetic acid (92.9 mg, 602 μmol), N,N-diisopropylethylamine (420 μl, 2.4 mmol) and PyBOP (627 mg, 1.20 mmol) were dissolved in 2.3 mL DMA and stirred at 35° C. under nitrogen atmosphere over night. The reaction mixture was diluted with water and dichloromethane and the layers were separated. The aqueous layer was extracted with dichloromethane twice. The combined organic layers were washed with water and brine, filtered through a silicone coated filter and concentrated under reduced pressure. The crude product was purified by HPLC under basic conditions to provide the target compound in 90% purity: 51 mg.

LC-MS (Method 2): R$_t$=1.22 min; MS (ESIpos): m/z=511 [M+H]$^+$ $^1$H-NMR (400 MHz, DMSO-d6) δ [ppm]=1.65-1.79 (m, 2H), 1.95-2.07 (m, 2H), 2.08-2.19 (m, 2H), 2.28 (s, 3H), 2.99 (s, 2H), 3.68 (s, 2H), 6.20 (d, 1H), 6.59 (td, 1H), 6.71-6.81 (m, 1H), 6.92-7.02 (m, 2H), 7.05 (d, 1H), 7.10-7.25 (m, 2H), 7.29-7.41 (m, 2H), 7.57 (s, 1H), 8.02 (d, 1H), 8.15 (s, 1H), 10.53 (s, 1H), 11.77 (s, 1H).

Example 143

4,4-difluoro-2-(4-fluorophenyl)-N-{4-[3'-(2-methylanilino)-4'-oxo-1',4',5',7'-tetrahydrospiro[cyclobutane-1,6'-pyrrolo[3,2-c]pyridin]-2'-yl]pyridin-2-yl}butanamide (Racemate)

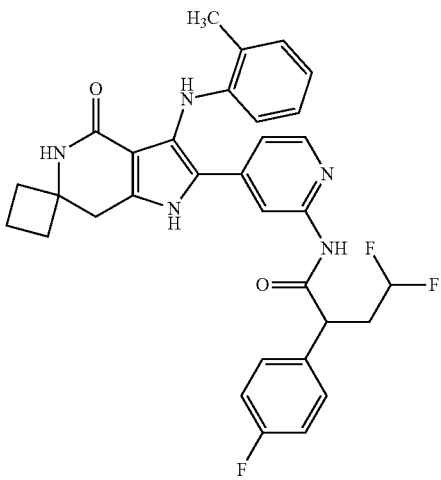 [SMILES: Cc1ccccc1Nc1c(-c2ccnc(NC(=O)C(CC(F)F)c3ccc(F)cc3)c2)[nH]c2c1C(=O)NC1(CCC1)C2]

2'-(2-Aminopyridin-4-yl)-3'-(2-methylanilino)-1',7'-dihydrospiro[cyclobutane-1,6'-pyrrolo[3,2-c]pyridin]-4'(5'H)-one (see Intermediate 130, 300 mg), 4,4-difluoro-2-(4-fluorophenyl)butanoic acid (racemate) (263 mg, 1.20 mmol), N,N-diisopropylethylamine (840 μl, 4.8 mmol) and PyBOP (1.25 g, 2.41 mmol) were dissolved in 4.7 mL DMA and stirred at rt under nitrogen atmosphere over night. The reaction mixture was diluted with water and dichloromethane and the layers were separated. The aqueous layer was extracted with dichloromethane twice. The combined organic layers were washed with water and brine, filtered through a silicone coated filter and concentrated under reduced pressure. The crude product was purified by HPLC under basic conditions in 2 portions to provide the target compound in 99% purity: 122 mg.

LC-MS (Method 2): R$_t$=1.29 min; MS (ESIpos): m/z=575 [M+H]$^+$ $^1$H-NMR (400 MHz, DMSO-d6) δ [ppm]=1.66-1.83 (m, 2H), 1.97-2.08 (m, 2H), 2.08-2.27 (m, 3H), 2.30 (s, 3H), 2.67 (dt, 1H), 3.01 (s, 2H), 4.12 (dd, 1H), 5.71-6.12 (m, 1H), 6.18 (d, 1H), 6.55-6.64 (m, 1H), 6.68-6.81 (m, 1H), 6.92-7.02 (m, 2H), 7.06 (d, 1H), 7.14-7.29 (m, 2H), 7.38-7.49 (m, 2H), 7.58 (s, 1H), 8.01 (d, 1H), 8.13 (s, 1H), 10.60 (s, 1H), 11.78 (s, 1H).

Example 144

(−)-4,4-difluoro-2-(4-fluorophenyl)-N-{4-[3'-(2-methylanilino)-4'-oxo-1',4',5',7'-tetrahydrospiro[cyclobutane-1,6'-pyrrolo[3,2-c]pyridin]-2'-yl]pyridin-2-yl}butanamide-(Enantiomer 1)

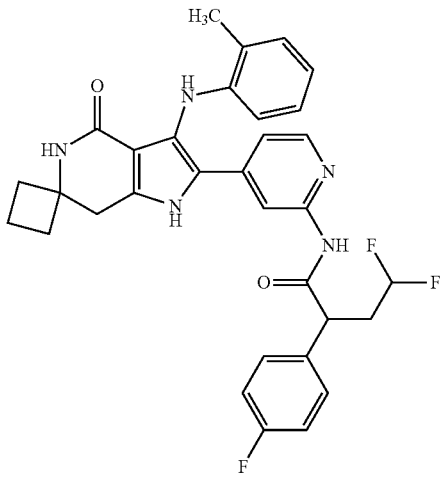 [SMILES: Cc1ccccc1Nc1c(-c2ccnc(NC(=O)C(CC(F)F)c3ccc(F)cc3)c2)[nH]c2c1C(=O)NC1(CCC1)C2]

The racemic compound (see Example 143, 120 mg) was separated into enantiomers by preparative chiral HPLC to give enantiomer 1 (51 mg, 100% ee, see Example 144) and enantiomer 2 (54 mg, 99.6% ee, see Example 145).

Preparative Chiral HPLC Method:

Instrument: Sepiatec: Prep SFC100; Column: Reprosil Chiral NR 8μ 250×30 mm; eluent A: carbon dioxide; eluent B: ethanol; isocratic: 30% B; flow: 100 mL/min; temperature: 40° C.; BPR: 150 bar; UV: 254 nm.

Analytical Chiral HPLC Method:

Instrument: Agilent: 1260, Aurora SFC-Modul; Column: Reprosil Chiral NR 5μ 100×4.6 mm; eluent A: carbon dioxide; eluent B: ethanol; isocratic: 30% B; flow: 4 mL/min; temperature: 37.5° C.; BPR: 100 bar; UV: 254 nm.

Analytical Chiral HPLC (method Example 144): R$_t$=3.20 min.

[a]$_D$=−142.3° (from solution in DMSO, c=4.5 mg/mL)

$^1$H-NMR (400 MHz, DMSO-d6) δ [ppm]=1.66-1.80 (m, 2H), 1.97-2.07 (m, 2H), 2.08-2.25 (m, 3H), 2.29 (s, 3H), 2.58-2.74 (m, 1H), 3.01 (s, 2H), 4.10 (dd, 1H), 5.74-6.11 (m, 1H), 6.16 (d, 1H), 6.57 (td, 1H), 6.69-6.76 (m, 1H), 6.94-7.02 (m, 2H), 7.05 (d, 1H), 7.12-7.25 (m, 2H), 7.36-7.47 (m, 2H), 7.56 (s, 1H), 8.00 (d, 1H), 8.10 (s, 1H), 10.57 (s, 1H), 11.79 (s, 1H).

Example 145

(+)-4,4-difluoro-2-(4-fluorophenyl)-N-{4-[3'-(2-methylanilino)-4'-oxo-1',4',5',7'-tetrahydrospiro[cyclobutane-1,6'-pyrrolo[3,2-c]pyridin]-2'-yl]pyridin-2-yl}butanamide-(Enantiomer 2)

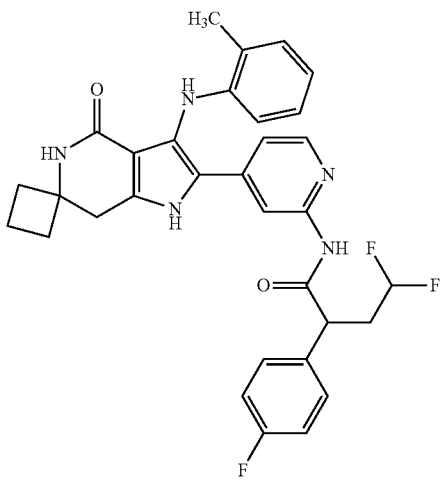 [SMILES: Cc1ccccc1Nc1c(-c2ccnc(NC(=O)C(CC(F)F)c3ccc(F)cc3)c2)[nH]c2c1C(=O)NC1(CCC1)C2]

For the preparation of the racemic title compound see Example 143. Separation of enantiomers by preparative chiral HPLC (method see Example 144) gave the title compound (54 mg).

Analytical Chiral HPLC (method see Example 144: $R_t$=3.93 min.

$[a]_D$=+160.4° (from solution in DMSO, c=5.3 mg/mL)

$^1$H-NMR (400 MHz, DMSO-d6) δ [ppm]=1.66-1.81 (m, 2H), 1.95-2.07 (m, 2H), 2.08-2.25 (m, 3H), 2.29 (s, 3H), 2.58-2.76 (m, 1H), 3.01 (s, 2H), 4.10 (dd, 1H), 5.73-6.11 (m, 1H), 6.16 (d, 1H), 6.57 (td, 1H), 6.68-6.77 (m, 1H), 6.93-7.02 (m, 2H), 7.05 (d, 1H), 7.13-7.25 (m, 2H), 7.35-7.46 (m, 2H), 7.56 (s, 1H), 8.00 (d, 1H), 8.10 (s, 1H), 10.57 (s, 1H), 11.79 (s, 1H).

Example 146

N-[4-(3'-anilino-4'-oxo-1',4',5',7'-tetrahydrospiro[cyclopropane-1,6'-pyrrolo[3,2-c]pyridin]-2'-yl)pyridin-2-yl]-2-(4-fluorophenyl)acetamide

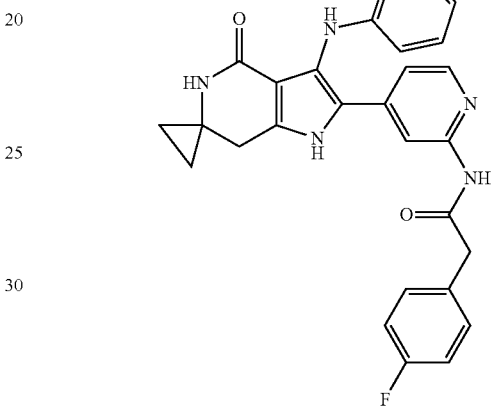

2'-(2-Aminopyridin-4-yl)-3'-anilino-1',7'-dihydrospiro[cyclopropane-1,6'-pyrrolo[3,2-c]pyridin]-4'(5'H)-one (see Intermediate 133, 150 mg), (4-fluorophenyl)acetic acid (73.6 mg, 478 μmol), N,N-diisopropylethylamine (450 μL, 2.6 mmol) and PyBOP (678 mg, 1.30 mmol; CAS-RN: [128625-52-5]) were dissolved in 2.5 mL DMA and stirred at rt under nitrogen atmosphere overnight. To the reaction mixture aqueous saturated sodium hydrogencarbonate solution was added and the layers were separated. The aqueous layer was extracted with dichloromethane three times. The combined organic layers were filtered through a silicone coated filter and concentrated under reduced pressure. The crude product was purified by HPLC to provide the analytically pure target compound: 62 mg.

LC-MS (Method 2): $R_t$=1.12 min; MS (ESIpos): m/z=482 [M+H]$^+$ $^1$H-NMR (400 MHz, DMSO-d6) δ [ppm]=0.60-0.70 (m, 2H), 0.71-0.79 (m, 2H), 2.80 (s, 2H), 3.69 (s, 2H), 6.50-6.68 (m, 3H), 7.02 (t, 2H), 7.10-7.19 (m, 3H), 7.23 (s, 1H), 7.31-7.41 (m, 3H), 8.05 (d, 1H), 8.18 (s, 1H), 10.57 (s, 1H), 11.75 (s, 1H).—contains DMF.

Example 147

N-[4-(3'-anilino-4'-oxo-1',4',5',7'-tetrahydrospiro[cyclopropane-1,6'-pyrrolo[3,2-c]pyridin]-2'-yl)pyridin-2-yl]-4,4-difluoro-2-(4-fluorophenyl)butanamide (Racemate)

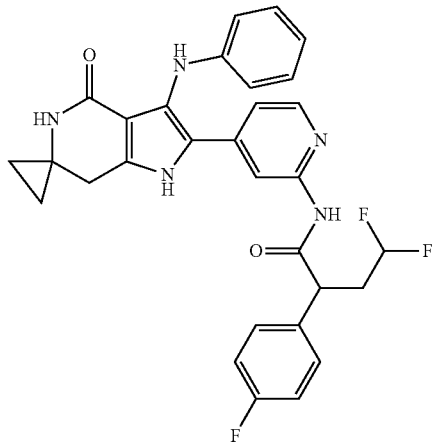 [SMILES: O=C1NC2(CC2)Cc2[nH]c(-c3ccnc(NC(=O)C(CC(F)F)c4ccc(F)cc4)c3)c(Nc3ccccc3)c21]

2'-(2-Aminopyridin-4-yl)-3'-anilino-1',7'-dihydrospiro[cyclopropane-1,6'-pyrrolo[3,2-c]pyridin]-4'(5'H)-one (see Intermediate 133, 300 mg), 4,4-difluoro-2-(4-fluorophenyl)butanoic acid (Racemate) (208 mg, 955 µmol; CAS-RN: [1538957-14-0]), N,N-diisopropylethylamine (910 µL, 5.2 mmol) and PyBOP (1.36 g, 2.61 mmol; CAS-RN: [128625-52-5]) were dissolved in 5 mL DMA and stirred at rt under nitrogen atmosphere overnight. To the reaction mixture aqueous saturated sodium hydrogencarbonate solution was added and the layers were separated. The aqueous layer was extracted with dichloromethane three times. The combined organic layers were filtered through a silicone coated filter and concentrated under reduced pressure. The crude product was purified by HPLC to provide the target analytically pure target compound: 102 mg.

LC-MS (Method 2): $R_t$=1.20 min; MS (ESIpos): m/z=546 [M+H]$^+$ $^1$H-NMR (400 MHz, DMSO-d6) δ [ppm]: =0.59-0.71 (m, 2H), 0.72-0.83 (m, 2H), 2.10-2.29 (m, 1H), 2.58-2.76 (m, 1H), 2.82 (s, 2H), 4.15 (dd, 1H), 5.75-6.14 (m, 1H), 6.51-6.70 (m, 3H), 6.99-7.08 (m, 2H), 7.09-7.22 (m, 3H), 7.25 (s, 1H), 7.36 (s, 1H), 7.40-7.51 (m, 2H), 8.03 (d, 1H), 8.16 (s, 1H), 10.64 (s, 1H), 11.76 (s, 1H).

Example 148

N-[4-(3'-anilino-4'-oxo-1',4',5',7'-tetrahydrospiro[cyclopropane-1,6'-pyrrolo[3,2-c]pyridin]-2'-yl)pyridin-2-yl]-4,4-difluoro-2-(4-fluorophenyl)butanamide (Enantiomer 1)

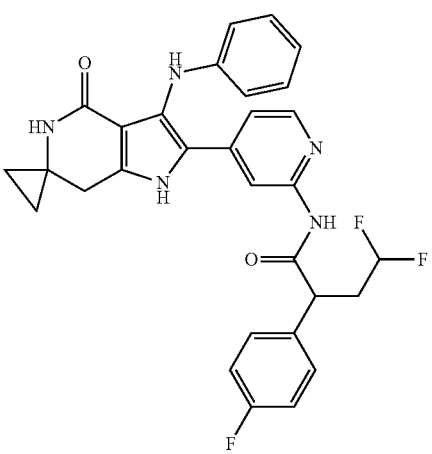 [SMILES: O=C1NC2(CC2)Cc2[nH]c(-c3ccnc(NC(=O)C(CC(F)F)c4ccc(F)cc4)c3)c(Nc3ccccc3)c21]

The racemic compound (see Example 147, 84 mg) was separated into enantiomers by preparative chiral HPLC to give enantiomer 1 (55 mg, 100% ee, see Example 148) and enantiomer 2 (75 mg, 96.8% ee, see Example 149). Enantiomer 1 was diluted with hexane and stirred over night at rt. The residue was filtered off and dried under vacuo at 50° C. to provide the target compound in 94% purity: 25 mg Preparative chiral HPLC method:

Instrument: Sepiatec: Prep SFC100; Column: Chiralpak IA 5µ 250×30 mm; eluent A: carbon dioxide; eluent B: 2-propanol+0.4 vol % diethylamin; isocratic: 35% B; flow: 100 mL/min; temperature: 40° C.; BPR: 150 bar; UV: 254 nm.

Analytical Chiral HPLC Method:

Instrument: Agilent: 1260, Aurora SFC-Modul; Column: Chiralpak IA 5µ 100×4.6 mm; eluent A: carbon dioxide; eluent B: ethanol+0.2 vol % aqueous ammonia (32%); isocratic: 35% B; flow: 4 mL/min; temperature: 37.5° C.; BPR: 100 bar; UV: 254 nm.

Analytical Chiral HPLC (method Example 148): $R_t$=4.53 min.

$^1$H-NMR (400 MHz, DMSO-d6) δ [ppm]=0.61-0.72 (m, 2H), 0.73-0.80 (m, 2H), 2.09-2.30 (m, 1H), 2.60-2.78 (m, 1H), 2.82 (s, 2H), 4.15 (dd, 1H), 5.77-6.14 (m, 1H), 6.52-6.69 (m, 3H), 6.95-7.04 (m, 2H), 7.09-7.22 (m, 3H), 7.25 (s, 1H), 7.36 (s, 1H), 7.40-7.51 (m, 2H), 8.03 (d, 1H), 8.16 (s, 1H), 10.64 (s, 1H), 11.76 (s, 1H).

Example 149

N-[4-(3'-anilino-4'-oxo-1',4',5',7'-tetrahydrospiro[cyclopropane-1,6'-pyrrolo[3,2-c]pyridin]-2'-yl)pyridin-2-yl]-4,4-difluoro-2-(4-fluorophenyl)butanamide (Enantiomer 2)

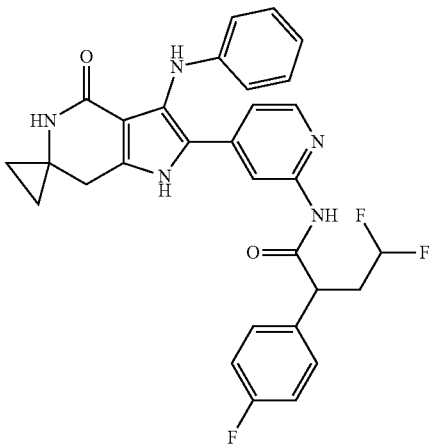 [SMILES: O=C1NC2(CC2)Cc2[nH]c(-c3ccnc(NC(=O)C(CC(F)F)c4ccc(F)cc4)c3)c(Nc3ccccc3)c21]

For the preparation of the racemic title compound see Example 147. Separation of enantiomers by preparative chiral HPLC (method see Example 148 gave the title compound (75 mg), which was diluted with hexane and stirred over night at rt. The residue was filtered off and dried under vacuo at 50° C. to provide the target compound in 96% purity: 31 mg.

Analytical Chiral HPLC (method see Example 148: $R_t$=6.48 min.

$^1$H-NMR (400 MHz, DMSO-d6) δ [ppm]=0.65-0.71 (m, 2H), 0.72-0.79 (m, 2H), 2.08-2.28 (m, 1H), 2.59-2.76 (m, 1H), 2.82 (s, 2H), 4.15 (dd, 1H), 5.77-6.14 (m, 1H), 6.51-6.68 (m, 3H), 6.97-7.07 (m, 2H), 7.10-7.22 (m, 3H), 7.25 (s, 1H), 7.36 (s, 1H), 7.41-7.51 (m, 2H), 8.03 (d, 1H), 8.16 (s, 1H), 10.64 (s, 1H), 11.76 (s, 1H).

Example 150

N-{4-[3-(2,5-difluoroanilino)-5-methyl-4-oxo-4,5,6,7-tetrahydro-1H-pyrrolo[3,2-c]pyridin-2-yl]pyridin-2-yl}-2-(4-fluorophenyl)acetamide

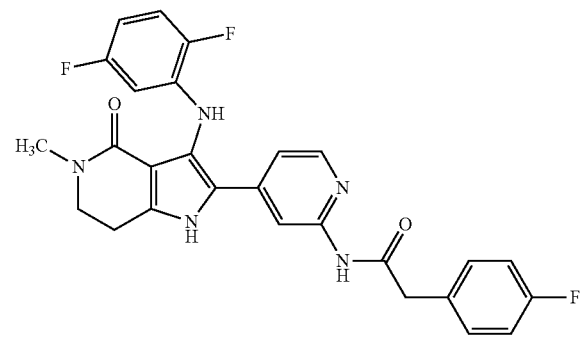 [SMILES: CN1CCc2[nH]c(-c3ccnc(NC(=O)Cc4ccc(F)cc4)c3)c(Nc3cc(F)ccc3F)c2C1=O]

A mixture of (4-fluorophenyl)acetic acid (41.7 mg, 271 μmol), 2-(7-Azabenzotriazol-1-yl)-N,N,N',N'-tetramethyl-uronium hexafluorophosphate (HATU) (154 mg, 406 μmol), N,N-diisopropylethylamine (190 μL, 1.1 mmol) in N,N-dimethylformamide (2.0 mL) was stirred at 25° C. for 0.5 hours, then 2-(2-aminopyridin-4-yl)-3-(2,5-difluoroanilino)-5-methyl-1,5,6,7-tetrahydro-4H-pyrrolo[3,2-c]pyridin-4-one (100 mg, Intermediate 136) was added into the mixture and stirred at 25° C. for 16 hours. The reactions mixture was adjusted to pH~3 with hydrochloric acid (1 M in water). The mixture was extracted with ethyl acetate, the combined organic layers were washed with brine, dried over anhydrous sodium sulfate, filtered and concentrated in vacuum. The residue was purified by preparative-HPLC [Instrument: ACSWH-GX-Q; Column: Shim-pack C18 150*25*10 um; eluent A: water (0.225% Formic acid)-water), eluent B: acetonitrile; gradient: 0-10 min 29-59% B; flow 25 ml/min; temperature: RT; Detector: UV 220/254 nm.] to give N-{4-[3-(2,5-difluoroanilino)-5-methyl-4-oxo-4,5,6,7-tetrahydro-1H-pyrrolo[3,2-c]pyridin-2-yl]pyridin-2-yl}-2-(4-fluorophenyl)acetamide (7.00 mg, 95% purity) as a white solid.

LC-MS (Method C, see Intermediate 135): $R_t$=0.84 min; MS (ESIpos): m/z=506 [M+H]$^+$ $^1$H NMR (400 MHz, DMSO-d$_6$): δ [ppm]=11.93 (s, 1H), 10.76 (s, 1H), 8.17 (d, J=6.0 Hz, 1H), 8.08 (s, 1H), 7.56 (s, 1H), 7.37-7.30 (m, 2H), 7.22 (d, 1H), 7.20-7.08 (m, 3H), 6.46-6.37 (m, 1H), 5.97-5.91 (m, 1H), 3.69 (s, 2H), 3.55 (t, 2H), 2.94 (t, 2H), 2.86 (s, 3H).

Example 151

4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoic acid

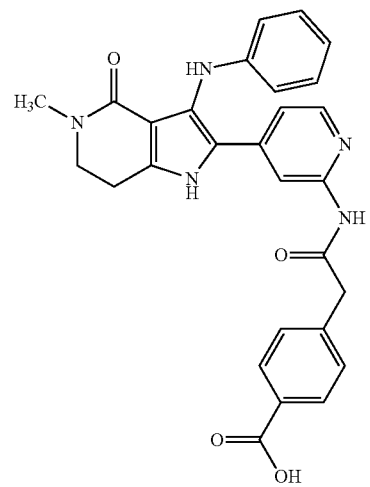 [SMILES: CN1CCc2[nH]c(-c3ccnc(NC(=O)Cc4ccc(C(=O)O)cc4)c3)c(Nc3ccccc3)c2C1=O]

To a stirred solution of methyl 4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoate (see Example 117, 185 mg, 0.363 mmol) in ethanol (3.0 mL) and tetrahydrofurane (6.0 mL) was added and aqueous solution of sodium hydroxide (72 mg, 1.8 mmol, 5.0 eq) in water (67 μL) and the mixture was stirred at r.t. for 2 h. Hydrochloric acid was added until pH 4 was reached, and the mixture was extracted with chloroform and methanol (10:1). The organic phase was dried (sodium sulfate), filtered and the solvent was removed in vacuum to give a solid that was triturated with hexane and then suspended with toluene and concentrated under reduced pressure to give 140 mg of the title compound.

LC-MS (Method 2): $R_t$=0.63 min; MS (ESIneg): m/z=494 [M−H]⁻

¹H-NMR (400 MHz, DMSO-$d_6$): δ [ppm]=13.32-12.49 (m, 1H), 11.95-11.68 (m, 1H), 11.03-10.62 (m, 1H), 8.11-7.99 (m, 2H), 7.96-7.85 (m, 2H), 7.49-7.42 (m, 2H), 7.22-7.17 (m, 1H), 7.07-6.97 (m, 2H), 6.64 (t, 1H), 6.60-6.54 (m, 2H), 3.81 (s, 2H), 3.54 (t, 2H), 2.92 (t, 2H), 2.86 (s, 3H), (one H not detected).

Example 152

4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)-N-(2-methoxyethyl)benzamide

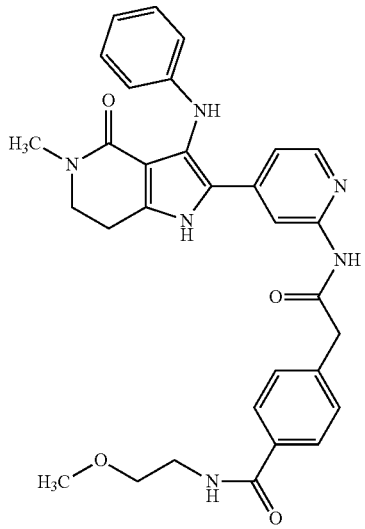 [SMILES: COCCNC(=O)c1ccc(CC(=O)Nc2cc(-c3[nH]c4c(c3Nc3ccccc3)C(=O)N(C)CC4)ccn2)cc1]

A solution of 4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoic acid (see Example 151, 90.0 mg, 182 µmol) in DMF (8.5 mL) was treated with potassium carbonate (62.8 mg, 454 µmol), 2-methoxyethan-1-amine (15.0 mg, 200 µmol), and HATU (276 mg, 726 µmol), and stirred for 64 h at r.t. Then a sodium bicarbonate solution in water was added, and the mixture was extracted with ethyl acetate. The organic phase was washed with saturated sodium chloride solution, dried (sodium sulfate), filtered, and concentrated under reduced pressure. Preparative reverse phase HPLC (gradient of water and acetonitrile containing ammonium hydroxide as additive) gave 32 mg of the title compound.

LC-MS (Method 2): $R_t$=0.96 min; MS (ESIpos): m/z=553 [M+H]⁺

¹H-NMR (400 MHz, DMSO-$d_6$): δ [ppm]=11.73 (s, 1H), 10.59 (s, 1H), 8.48 (t, 1H), 8.18 (s, 1H), 8.05 (d, 1H), 7.84-7.75 (m, 2H), 7.39 (d, 2H), 7.35 (s, 1H), 7.13 (dd, 1H), 7.01 (dd, 2H), 6.62 (t, 1H), 6.58-6.52 (m, 2H), 3.76 (s, 2H), 3.53 (t, 2H), 3.48-3.39 (m, 4H), 3.26 (s, 3H), 2.90 (t, 2H), 2.86 (s, 3H).

Example 153

N-[4-(3-anilino-5-methyl-4-oxo-4,5,6,7-tetrahydro-1H-pyrrolo[3,2-c]pyridin-2-yl)pyridin-2-yl]-2-[4-(piperazine-1-carbonyl)phenyl]acetamide

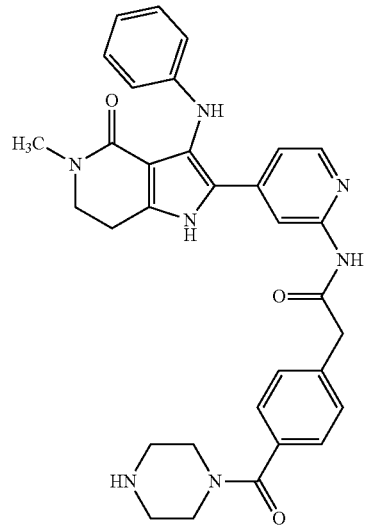 [SMILES: CN1CCc2[nH]c(-c3ccnc(NC(=O)Cc4ccc(C(=O)N5CCNCC5)cc4)c3)c(Nc3ccccc3)c2C1=O]

To a stirred solution of tert-butyl 4-[4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoyl]piperazine-1-carboxylate (see Intermediate 137, 748 mg, 1.13 mmol) in dichloromethane (40 mL) was added hydrogen chloride in dioxane (1.4 ml, 4.0 M, 5.6 mmol). The mixture was stirred at room temperature for 16 h. Further hydrogen chloride in dioxane (14 ml, 4.0 M, 56 mmol) was added and the mixture was stirred at room temperature for 96 h. The solvent was removed in vacuum. Then a potassium carbonate solution in water was added, and the mixture was extracted with chloroform and methanol (10:1). The organic phase was dried (sodium sulfate), filtered, concentrated under reduced pressure, and purified by column chromatography (column NH-Biotage, 100 g, gradient dichloromethane/ethanol, 1-7%) to give 220 mg of the title compound.

LC-MS (Method 2): $R_t$=0.89 min; MS (ESIpos): m/z=564 [M+H]⁺

¹H-NMR (400 MHz, DMSO-$d_6$) δ [ppm]: 0.904 (0.63), 1.037 (2.38), 1.055 (4.72), 1.072 (2.28), 1.173 (0.57), 1.234 (0.54), 2.068 (0.72), 2.324 (0.68), 2.329 (0.95), 2.334 (0.69), 2.520 (3.19), 2.524 (2.08), 2.632 (0.83), 2.662 (1.06), 2.666 (1.42), 2.671 (1.67), 2.676 (1.43), 2.680 (1.07), 2.857 (16.00), 2.889 (1.52), 2.906 (3.25), 2.923 (1.64), 3.236 (0.60), 3.380 (0.63), 3.424 (0.76), 3.437 (0.79), 3.442 (0.79), 3.455 (0.78), 3.459 (0.41), 3.472 (0.44), 3.510 (2.34), 3.527 (4.23), 3.545 (2.03), 3.737 (5.46), 4.359 (0.63), 5.760 (6.38), 6.542 (3.13), 6.561 (3.30), 6.563 (2.73), 6.598 (0.98), 6.616 (1.99), 6.634 (1.08), 6.992 (2.56), 7.011 (3.16), 7.013 (3.12), 7.032 (1.97), 7.122 (2.06), 7.126 (1.94), 7.135 (1.87), 7.139 (2.01), 7.318 (3.01), 7.322 (1.27), 7.334 (1.75), 7.338 (6.25), 7.355 (4.13), 7.373 (5.55), 7.393 (2.44), 8.044 (2.66), 8.059 (2.57), 8.190 (2.28), 10.610 (3.00), 11.727 (2.01).

Example 154

N-{4-[3-(2,3-difluoroanilino)-5-methyl-4-oxo-4,5,6,7-tetrahydro-1H-pyrrolo[3,2-c]pyridin-2-yl]pyridin-2-yl}-2-(4-fluorophenyl)acetamide formamide salt

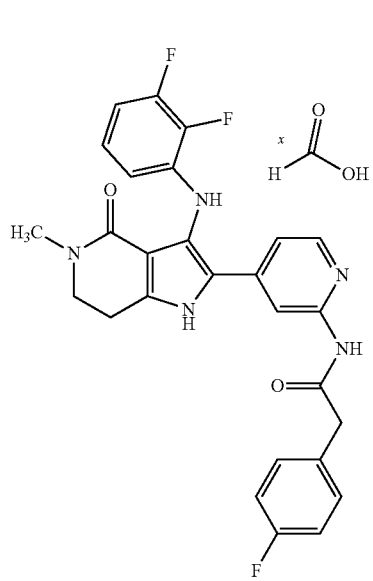 [SMILES: CN1CCc2[nH]c(-c3ccnc(NC(=O)Cc4ccc(F)cc4)c3)c(Nc3cccc(F)c3F)c2C1=O ; O=CO]

To a mixture of N-[4-(3-bromo-5-methyl-4-oxo-4,5,6,7-tetrahydro-1H-pyrrolo[3,2-c]pyridin-2-yl)pyridin-2-yl]-2-(4-fluorophenyl)acetamide (100 mg, Intermediate 140) and 2,3-difluoroaniline (36.7 mg, 284 μmol) in 1,4-dioxane (5.0 mL) was added methanesulfonato (2-dicyclohexylphosphino-3,6-dimethoxy-2',4',6'-tri-i-propyl-1,1'-biphenyl)(2'-amino-1,1'-biphenyl-2-yl) (5.0 mL) and cesium carbonate (18.1 mg, 546 μmol) in one portion at rt. The reaction mixture was stirred at 100° C. for 16 hours under nitrogen atmosphere. The mixture was purified by prep-TLC (petroleum ether/ethyl acetate=0/1, $R_f$=0.5) to give a residue. The residue was purified by preparative HPLC [Instrument: ACSWH-GX-P; Column: phenomenex Synergi C18 150*25*10 μm; eluent A: water (0.225% formic acid)-acetonitrile), eluent B: acetonitrile; gradient: 0-10 min 30-60% B; flow 25 mL/min; temperature: rt; Detector: UV 220/254 nm] to give N-{4-[3-(2,3-difluoroanilino)-5-methyl-4-oxo-4,5,6,7-tetrahydro-1H-pyrrolo[3,2-c]pyridin-2-yl]pyridin-2-yl}-2-(4-fluorophenyl)acetamide (4.00 mg, 98% purity) as a white solid.

LC-MS (Method C, see Intermediate 135): $R_t$=0.77 min; MS (ESIpos): m/z=506 [M+H]$^+$ $^1$H NMR (400 MHz, DMSO-d$_6$): δ [ppm]=11.85 (s, 1H), 10.55 (s, 1H), 8.35 (s, 1H), 8.19 (s, 1H), 8.14 (d, 1H), 7.46 (s, 1H), 7.34 (dd, 2H), 7.22-7.10 (m, 3H), 6.77-6.68 (m, 1H), 6.65-6.55 (m, 1H), 6.07 (t, 1H), 4.10-4.02 (m, 2H), 3.54 (t, 2H), 2.96-2.90 (m, 2H), 2.88-2.82 (m, 3H).

Example 155

4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)-N-[2-(dimethylamino)ethyl]benzamide

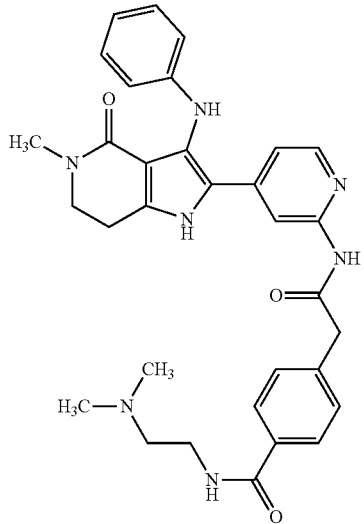 [SMILES: CN(C)CCNC(=O)c1ccc(CC(=O)Nc2cc(-c3[nH]c4c(c3Nc3ccccc3)C(=O)N(C)CC4)ccn2)cc1]

A solution of 4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoic acid (see Example 151, 90.0 mg, 182 μmol) in DMF (8.5 mL) was treated with potassium carbonate (62.8 mg, 454 μmol]), N$^1$,N$^1$-dimethylethane-1,2-diamine (17.6 mg, 200 μmol), and HATU (276 mg, 726 μmol), and stirred for 64 h at r.t. Then a sodium bicarbonate solution in water and sodium chloride were added, and the mixture was extracted with chloroform and ethanol (10:1). The organic phase was washed with saturated sodium chloride solution, dried (sodium sulfate), filtered, and concentrated under reduced pressure. Preparative reverse phase HPLC (gradient of water and acetonitrile containing ammonium hydroxide as additive) gave 31 mg of the title compound.

LC-MS (Method 2): $R_t$=0.96 min; MS (ESIpos): m/z=566 [M+H]$^+$ $^1$H-NMR (400 MHz, DMSO-d$_6$) δ [ppm]: −0.003 (1.14), 2.168 (16.00), 2.367 (0.84), 2.384 (1.53), 2.402 (0.89), 2.518 (1.39), 2.523 (0.90), 2.855 (5.87), 2.886 (0.57), 2.903 (1.24), 2.921 (0.62), 3.377 (0.64), 3.507 (0.70), 3.525 (1.38), 3.542 (0.63), 3.752 (1.99), 6.537 (1.16), 6.556 (1.23), 6.615 (0.73), 6.633 (0.40), 6.990 (0.95), 7.008 (1.19), 7.011 (1.15), 7.029 (0.75), 7.120 (0.71), 7.125 (0.71), 7.134 (0.71), 7.138 (0.69), 7.351 (1.48), 7.381 (1.36), 7.402 (1.48), 7.775 (1.76), 7.780 (0.61), 7.796 (1.47), 8.042 (0.95), 8.056 (0.91), 8.175 (0.83), 8.339 (0.61), 10.589 (1.06), 11.731 (0.72).

Example 156

N-[4-(3'-anilino-5'-methyl-4'-oxo-1',4',5',7'-tetrahydrospiro[cyclobutane-1,6'-pyrrolo[3,2-c]pyridin]-2'-yl)pyridin-2-yl]-2-(4-fluorophenyl)acetamide

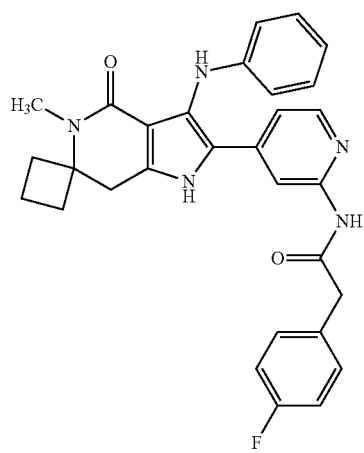 [SMILES: CN1C(=O)c2c([nH]c(-c3ccnc(NC(=O)Cc4ccc(F)cc4)c3)c2Nc2ccccc2)CC12CCC2]

2'-(2-Aminopyridin-4-yl)-3'-anilino-5'-methyl-1',7'-dihydrospiro[cyclobutane-1,6'-pyrrolo[3,2-c]pyridin]-4'(5'H)-one (see Intermediate 147, 100 mg), (4-fluorophenyl)acetic acid (61.9 mg, 402 µmol), N,N-diisopropylethylamine (280 µL, 1.6 mmol) and PyBOP (418 mg, 803 µmol) were dissolved in 1.6 mL DMA stirred at rt under nitrogen atmosphere for 2 days. The reaction mixture was diluted with dichloromethane, aqueous saturated sodium hydrogencarbonate solution and water were added. It was stirred for 10 minutes and the organic layer was filtered through a silicone coated filter and concentrated under reduced pressure. The crude product was purified by HPLC to provide the target compound in 98% purity: 51 mg.

LC-MS (Method 1): $R_t$=1.11 min; MS (ESIpos): m/z=511 [M+H]$^+$ $^1$H-NMR (400 MHz, DMSO-d6) δ [ppm]=1.70-1.84 (m, 2H), 1.86-1.98 (m, 2H), 2.39-2.48 (m, 2H), 2.96 (s, 3H), 3.11 (s, 2H), 3.69 (s, 2H), 6.53 (d, 2H), 6.61 (t, 1H), 6.97-7.05 (m, 2H), 7.09-7.23 (m, 3H), 7.32-7.44 (m, 3H), 8.05 (d, 1H), 8.19 (s, 1H), 10.57 (s, 1H), 11.77 (s, 1H).

Example 157

N-[4-(3'-anilino-5'-methyl-4'-oxo-1',4',5',7'-tetrahydrospiro[cyclobutane-1,6'-pyrrolo[3,2-c]pyridin]-2'-yl)pyridin-2-yl]-2-(4-fluorophenyl)propanamide (Racemate)

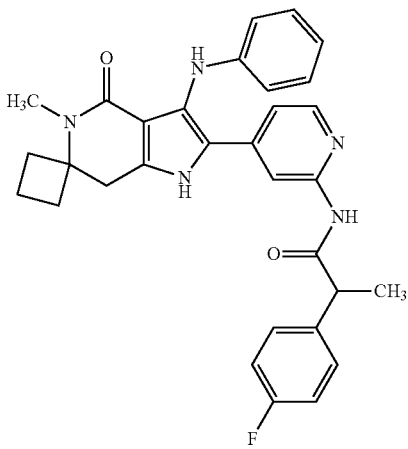 [SMILES: CC(C(=O)Nc1cc(-c2[nH]c3c(c2Nc2ccccc2)C(=O)N(C)C2(CCC2)C3)ccn1)c1ccc(F)cc1]

2'-(2-Aminopyridin-4-yl)-3'-anilino-5'-methyl-1',7'-dihydrospiro[cyclobutane-1,6'-pyrrolo[3,2-c]pyridin]-4'(5'H)-one (see Intermediate 147, 150 mg), 2-(4-fluorophenyl)propanoic acid (Racemate) (101 mg, 602 µmol), N,N-diisopropylethylamine (420 µL, 2.4 mmol) and PyBOP (627 mg, 1.20 mmol) were dissolved in 420 µL DMA and stirred at rt under nitrogen atmosphere for 2 days. The reaction mixture was diluted with dichloromethane and aqueous saturated sodium hydrogencarbonate solution and water was added. It was stirred for 10 minutes and the organic layer was filtered through a silicone coated filter and concentrated under reduced pressure. The crude product was purified by HPLC to provide the target compound in 96% purity: 69 mg.

LC-MS (Method 1): $R_t$=1.16 min; MS (ESIpos): m/z=525 [M+H]$^+$ $^1$H-NMR (400 MHz, DMSO-d6) δ [ppm]=1.39 (d, 3H), 1.69-1.86 (m, 2H), 1.92 (dt, 2H), 2.39-2.48 (m, 2H), 2.96 (s, 3H), 3.12 (s, 2H), 4.01 (q, 1H), 6.53 (d, 2H), 6.60 (t, 1H), 6.94-7.06 (m, 2H), 7.08-7.22 (m, 3H), 7.34-7.47 (m, 3H), 8.02 (d, 1H), 8.21 (s, 1H), 10.51 (s, 1H), 11.78 (s, 1H).

Example 158

(−)-N-[4-(3'-anilino-5'-methyl-4'-oxo-1',4',5',7'-tetrahydrospiro[cyclobutane-1,6'-pyrrolo[3,2-c]pyridin]-2'-yl)pyridin-2-yl]-2-(4-fluorophenyl)propanamide (Enantiomer 1)

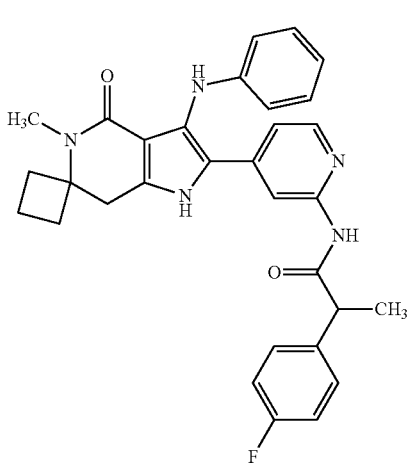 [SMILES: CC(C(=O)Nc1cc(-c2[nH]c3c(c2Nc2ccccc2)C(=O)N(C)C2(CCC2)C3)ccn1)c1ccc(F)cc1]

The racemic compound (see Example 157, 60 mg) was separated into enantiomers by preparative chiral HPLC to give enantiomer 1 (23 mg, 94.6% ee, see Example 158) and enantiomer 2 (25 mg, 100% ee, see Example 159).

Preparative Chiral HPLC Method:

Instrument: PrepCon Labomatic HPLC-2; Column: YMC Cellulose SB 10µ, 250×50; eluent A: hexane+0.1 vol % diethylamine; eluent B: ethanol+0.1 vol % diethylamine; isocratic: 50% A+50% B; flow: 120 mL/min; temperature: 25° C.; UV: 254 nm.

Analytical Chiral HPLC Method:

Instrument: Waters Alliance 2695; Column: YMC Cellulose SB 3µ, 100×4.6; eluent A: hexane+0.1 vol % diethylamine; eluent B: ethanol; isocratic: 50% A+50% B; flow: 1.4 mL/min; temperature: 25° C.; UV: 254 nm.

Analytical Chiral HPLC (method Example 158): $R_t$=1.18 min.

$[a]_D$=−138.86° (from solution in DMSO, c=5.1 mg/mL)

$^1$H-NMR (400 MHz, DMSO-d6) δ [ppm]=1.39 (d, 3H), 1.73-1.84 (m, 2H), 1.87-2.01 (m, 2H), 2.39-2.48 (m, 2H), 2.96 (s, 3H), 3.12 (s, 2H), 4.01 (q, 1H), 6.53 (d, 2H), 6.60 (t, 1H), 6.96-7.04 (m, 2H), 7.10 (dd, 1H), 7.13-7.22 (m, 2H), 7.33-7.46 (m, 3H), 8.02 (d, 1H), 8.21 (s, 1H), 10.51 (s, 1H), 11.78 (s, 1H).—minor impurities in the aliphatic range.

Example 159

(+)-N-[4-(3'-anilino-5'-methyl-4'-oxo-1',4',5',7'-tetrahydrospiro[cyclobutane-1,6'-pyrrolo[3,2-c]pyridin]-2'-yl)pyridin-2-yl]-2-(4-fluorophenyl)propanamide (Enantiomer 2)

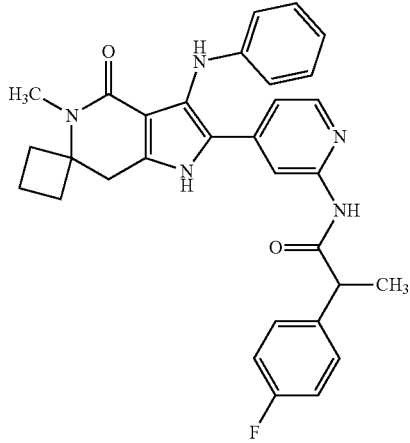 [SMILES: CC(C(=O)Nc1cc(-c2[nH]c3c(c2Nc2ccccc2)C(=O)N(C)C2(CCC2)C3)ccn1)c1ccc(F)cc1]

For the preparation of the racemic title compound see Example 157. Separation of enantiomers by preparative chiral HPLC (method see Example 158 gave the title compound (25 mg).

Analytical Chiral HPLC (method see Example 158: $R_t$=1.69 min.

$[a]_D$=+152.27° (from solution in DMSO, c=4.3 mg/mL)

$^1$H-NMR (400 MHz, DMSO-d6) δ [ppm]=1.39 (d, 3H), 1.72-1.85 (m, 2H), 1.93 (dt, 2H), 2.39-2.48 (m, 2H), 2.96 (s, 3H), 3.12 (s, 2H), 4.01 (q, 1H), 6.53 (d, 2H), 6.60 (t, 1H), 7.00 (t, 2H), 7.08-7.22 (m, 3H), 7.33-7.49 (m, 3H), 8.02 (d, 1H), 8.21 (s, 1H), 10.51 (s, 1H), 11.78 (s, 1H).—minor impurities in the aliphatic range.

Example 160

N-[4-(3'-anilino-5'-methyl-4'-oxo-1',4',5',7'-tetrahydrospiro[cyclobutane-1,6'-pyrrolo[3,2-c]pyridin]-2'-yl)pyridin-2-yl]-4,4-difluoro-2-(4-fluorophenyl)butanamide (Racemate)

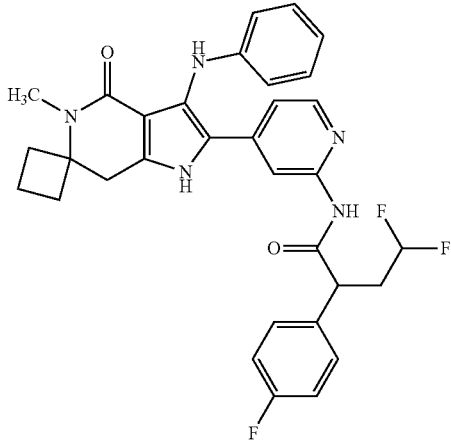 [SMILES: CN1C(=O)c2c([nH]c(-c3ccnc(NC(=O)C(CC(F)F)c4ccc(F)cc4)c3)c2Nc2ccccc2)CC12CCC2]

2'-(2-Aminopyridin-4-yl)-3'-anilino-5'-methyl-1',7'-dihydrospiro[cyclobutane-1,6'-pyrrolo[3,2-c]pyridin]-4'(5'H)-one (see Intermediate 147, 150 mg), 4,4-difluoro-2-(4-fluorophenyl)butanoic acid (Racemate) (131 mg, 602 μmol), N,N-diisopropylethylamine (420 μL, 2.4 mmol) and PyBOP (627 mg, 1.20 mmol) were dissolved in 2.3 mL DMA and stirred at rt under nitrogen atmosphere for 2 days. The reaction mixture was diluted with dichloromethane and aqueous saturated sodium hydrogencarbonate solution and water were added. It was stirred for 10 minutes and the organic layer was filtered through a silicone coated filter and concentrated under reduced pressure. The crude product was purified by HPLC to provide the analytically pure target compound: 120 mg.

LC-MS (Method 1): $R_t$=1.24 min; MS (ESIpos): m/z=575 [M+H]$^+$ $^1$H-NMR (400 MHz, DMSO-d6) δ [ppm]=1.71-1.86 (m, 2H), 1.92 (td, 2H), 2.09-2.30 (m, 1H), 2.39-2.48 (m, 2H), 2.60-2.79 (m, 1H), 2.97 (s, 3H), 3.13 (s, 2H), 4.15 (dd, 1H), 5.76-6.14 (m, 1H), 6.53 (dd, 2H), 6.58-6.66 (m, 1H), 7.00 (dd, 2H), 7.13 (dd, 1H), 7.15-7.25 (m, 2H), 7.39 (s, 1H), 7.41-7.48 (m, 2H), 8.03 (d, 1H), 8.17 (s, 1H), 10.64 (s, 1H), 11.78 (s, 1H).

Example 161

(−)-N-[4-(3'-anilino-5'-methyl-4'-oxo-1',4',5',7'-tetrahydrospiro[cyclobutane-1,6'-pyrrolo[3,2-c]pyridin]-2'-yl)pyridin-2-yl]-4,4-difluoro-2-(4-fluorophenyl)butanamide (Enantiomer 1)

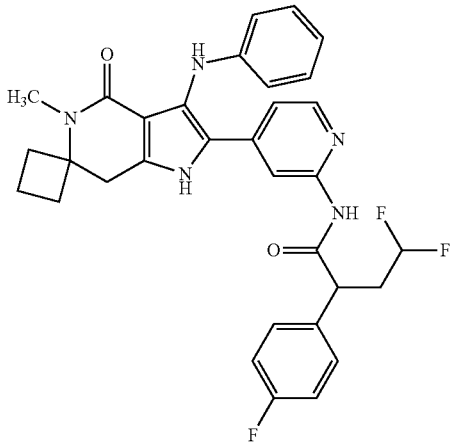 [SMILES: CN1C(=O)c2c([nH]c(-c3ccnc(NC(=O)C(CC(F)F)c4ccc(F)cc4)c3)c2Nc2ccccc2)CC12CCC2]

The racemic compound (see Example 160, 110 mg) was separated into enantiomers by preparative chiral HPLC to give enantiomer 1 (41 mg, 100% ee, see Example 161) and enantiomer 2 (40 mg, 100% ee, see Example 162).

Preparative Chiral HPLC Method:

Instrument: PrepCon Labomatic HPLC-2; Column: YMC Cellulose SB 10μ, 250×50; eluent A: hexane+0.1 vol % diethylamine; eluent B: ethanol+0.1 vol % diethylamine; isocratic: 80% A+20% B; flow: 120 mL/min; temperature: 25° C.; UV: 254 nm.

Analytical Chiral HPLC Method:

Instrument: Waters Alliance 2695; Column: YMC Cellulose SB 3μ, 100×4.6; eluent A: hexane+0.1 vol % diethylamine; eluent B: ethanol; isocratic: 80% A+20% B; flow: 1.4 mL/min; temperature: 25° C.; UV: 254 nm.

Analytical Chiral HPLC (method Example 161): $R_t$=2.22 min.

[a]$_D$=−180.20° (from solution in DMSO, c=0.48 mg/mL)

$^1$H-NMR (400 MHz, DMSO-d6) δ [ppm]=1.71-1.84 (m, 2H), 1.92 (td, 2H), 2.10-2.29 (m, 1H), 2.46 (br d, 2H), 2.63-2.76 (m, 1H), 2.97 (s, 3H), 3.13 (s, 2H), 4.10-4.21 (m, 1H), 5.76-6.14 (m, 1H), 6.50-6.56 (m, 2H), 6.60 (t, 1H), 6.96-7.04 (m, 2H), 7.12 (dd, 1H), 7.15-7.25 (m, 2H), 7.39 (s, 1H), 7.41-7.50 (m, 2H), 8.03 (d, 1H), 8.17 (s, 1H), 10.64 (s, 1H), 11.78 (s, 1H).—impurities in the aliphatic range.

Example 162

(+)-N-[4-(3'-anilino-5'-methyl-4'-oxo-1',4',5',7'-tetrahydrospiro[cyclobutane-1,6'-pyrrolo[3,2-c]pyridin]-2'-yl)pyridin-2-yl]-4,4-difluoro-2-(4-fluorophenyl)butanamide (Enantiomer 2)

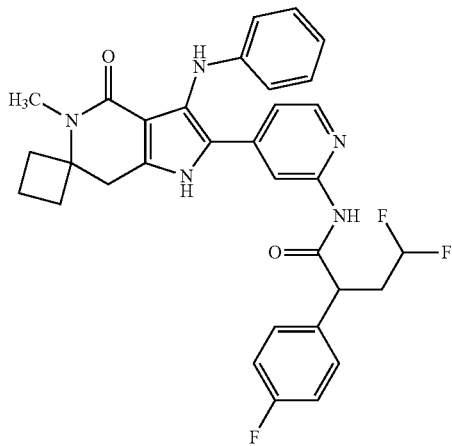 [SMILES: CN1C(=O)c2c([nH]c(-c3ccnc(NC(=O)C(CC(F)F)c4ccc(F)cc4)c3)c2Nc2ccccc2)CC12CCC2]

For the preparation of the racemic title compound see Example 160. Separation of enantiomers by preparative chiral HPLC (method see Example 161 gave the title compound (40 mg).

Analytical Chiral HPLC (method see Example 162: $R_t$=2.95 min.

[a]$_D$=+178.39° (from solution in DMSO, c=4.6 mg/mL)

$^1$H-NMR (400 MHz, DMSO-d6) δ [ppm]=1.70-1.84 (m, 2H), 1.87-2.01 (m, 2H), 2.11-2.30 (m, 1H), 2.37-2.48 (m, 2H), 2.62-2.78 (m, 1H), 2.97 (s, 3H), 3.13 (s, 2H), 4.15 (dd, 1H), 5.76-6.15 (m, 1H), 6.50-6.57 (m, 2H), 6.58-6.65 (m, 1H), 7.00 (dd, 2H), 7.12 (dd, 1H), 7.15-7.24 (m, 2H), 7.39 (s, 1H), 7.42-7.49 (m, 2H), 8.03 (d, 1H), 8.17 (s, 1H), 10.64 (s, 1H), 11.78 (s, 1H).—impurities in the aliphatic range.

Example 163

N-[4-(3'-anilino-5'-methyl-4'-oxo-1',4',5',7'-tetrahydrospiro[cyclopropane-1,6'-pyrrolo[3,2-c]pyridin]-2'-yl)pyridin-2-yl]-4,4-difluoro-2-(4-fluorophenyl)butanamide (Racemate)

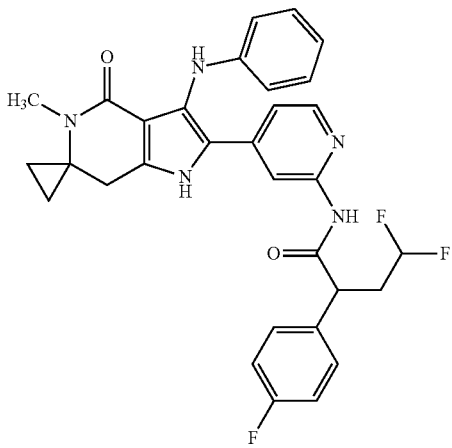 [SMILES: CN1C(=O)c2c([nH]c(-c3ccnc(NC(=O)C(CC(F)F)c4ccc(F)cc4)c3)c2Nc2ccccc2)CC12CC2]

2'-(2-Aminopyridin-4-yl)-3'-anilino-5'-methyl-1',7'-dihydrospiro[cyclopropane-1,6'-pyrrolo[3,2-c]pyridin]-4'(5'H)-one (see Intermediate 153, 139 mg), 4,4-difluoro-2-(4-fluorophenyl)butanoic acid (Racemate) (127 mg) N,N-diisopropylethylamine (400 µL, 2.3 mmol) and PyBOP (604 mg, 1.16 mmol) were dissolved in 2.2 mL DMA and stirred at rt under nitrogen atmosphere for 2 days. The reaction mixture was diluted with dichloromethane, and aqueous saturated sodium hydrogencarbonate solution and water were added. The reaction mixture was stirred for 10 minutes and the organic layer was filtered through a silicone coated filter and concentrated under reduced pressure. The crude product was purified by HPLC to provide the target compound in 92% purity: 136 mg.

LC-MS (Method 1): $R_t$=1.18 min; MS (ESIpos): m/z=561 [M+H]$^+$ $^1$H-NMR (400 MHz, DMSO-d6) δ [ppm]=0.69-0.80 (m, 2H), 1.01-1.15 (m, 2H), 2.11-2.28 (m, 1H), 2.60-2.76 (m, 4H), 2.83 (s, 2H), 4.15 (dd, 1H), 5.78-6.14 (m, 1H), 6.55 (d, 2H), 6.61 (t, 1H), 6.98-7.07 (m, 2H), 7.13-7.24 (m, 3H), 7.40-7.51 (m, 3H), 8.04 (d, 1H), 8.17 (s, 1H), 10.64 (s, 1H), 11.75 (s, 1H).

Example 164

N-[4-(3-anilino-5-methyl-4-oxo-4,5,6,7-tetrahydro-1H-pyrrolo[3,2-c]pyridin-2-yl)pyridin-2-yl]-2-(2,4,6-trifluorophenyl)acetamide

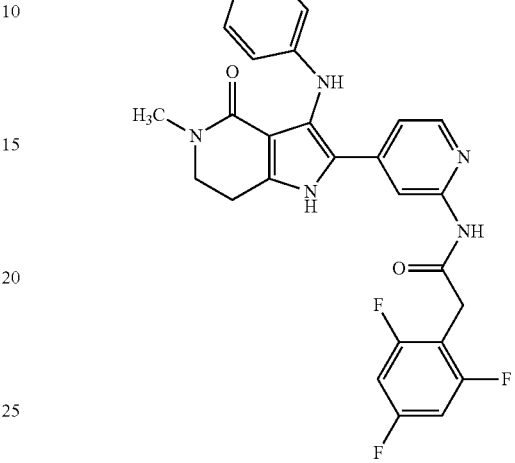

A solution of 2-(2-aminopyridin-4-yl)-3-anilino-5-methyl-1,5,6,7-tetrahydro-4H-pyrrolo[3,2-c]pyridin-4-one (see Intermediate 3, 0.12 g, 0.36 mmol, 1 eq) in DMA (4 mL) was treated with N,N-diisopropylethylamine (0.37 mL, 6 eq; CAS-RN: [7087-68-5]), (2,4,6-trifluorophenyl)acetic acid (137 mg, 2 eq), and benzotriazol-1-yloxytripyrrolidinophosphonium hexafluorophosphate (0.937 g, 5 eq; CAS-RN: [128625-52-5]), and stirred for 66 h at r.t. Then a sodium bicarbonate solution in water was added, and the mixture was extracted with ethyl acetate. The organic phase was, dried (sodium sulfate), filtered, concentrated under reduced pressure, and purified by column chromatography (column silica gel, 25 g, gradient: ethanol/dichloromethane 0-12%) to give a solid that was triturated with ethyl acetate to give 102 mg of the title compound.

LC-MS (Method 2): $R_t$=1.17 min; MS (ESIpos): m/z=506 [M+H]$^+$ $^1$H-NMR (400 MHz, DMSO-d$_6$): 0 [ppm]=11.73 (s, 1H), 10.71 (s, 1H), 8.18 (s, 1H), 8.05 (d, 1H), 7.36 (s, 1H), 7.26-7.16 (m, 2H), 7.13 (dd, 1H), 7.01 (t, 2H), 6.62 (t, 1H), 6.55 (d, 2H), 3.81 (s, 2H), 3.52 (t, 2H), 2.90 (t, 2H), 2.85 (s, 3H).

Co-Crystallization and Structure Determination of Casein Kinase Inhibitors with Casein Kinase 1D
Crystallization Crystals of Casein Kinase 1D (residues 1-294 with mutation Arg13Asn) in complex with Example 5 were obtained using hanging-drop vapor diffusion set-ups. Casein Kinase 1D at a concentration of 13.77 mg/mL (50 mM Hepes, 290 mM NaCl, 1 mM EDTA, 1 mM DTT, 5 mM β-OG, pH 7.5) was pre-incubated with 2 mM (5.0-fold molar excess) of Example 5 (150 mM in DMSO) for 1 h. 0.8 µL of the protein solution was then mixed with 0.8 µL of reservoir solution (0.10 M sodium citrate pH 4.90, 20% (w/v) PEG 3350) and equilibrated at 20° C. over 0.4 mL of reservoir solution. Well-diffracting plates grew within a week and data were collected from a single crystal cryo-protected with 20% (v/v) ethylene glycol.

Data Collection, Structure Determination and Refinement

A complete 1.8 Å data set of a Casein Kinase 1D/Example 5 crystal was collected at the ESRF (Grenoble, FR, beamline ID30a1) (Table 5). Molecular replacement was done using a previously determined model of Casein Kinase 1D as starting model. Several rounds of alternating manual re-building and refinement with REFMAC5 resulted in the final model (Table 5). The B-factors were modelled through a combination of an isotropic B-factor for each atom and a single TLS group for each of the four copies of Casein Kinase 1D in the asymmetric unit. Local NCS restraints as implemented in REFMAC5 were used throughout refinement.

TABLE 5

Data collection and refinement statistics

| | |
|---|---|
| Space group | P1 |
| Unit cell parameters, | |
| axes a, b, c [Å], | 48.9, 83.9, 89.9, |
| angles α, β, γ (°) | 69.3, β = 74.2, γ = 87.9 |
| Resolution [Å] | 80.75-1.80 (1.83-1.80) |
| Number of unique reflections | 115984 (5666) |
| Mean I/σ | 9.9 (3.1) |
| Completeness | 97.6 (96.3) |
| Multiplicity | 2.8 (2.9) |
| Rmeas | 0.065 (0.320) |
| Resolution [Å] | 80.75-1.80 (1.85-1.80) |
| $R_{work}$ | 0.186 (0.241) |
| $R_{free}$ | 0.232 (0.278) |
| Completeness | 97.5 (96.4) |
| r.m.s.d. bonds [Å] | 0.019 |
| r.m.s.d. angles | 1.932 |

Values in brackets refer to the highest resolution shell

Absolute Configuration of Example 5 (Bound to Casein Kinase 1D)

The complex of Casein Kinase 1D and Example 5 crystallized with four molecules of Casein Kinase 1D in the asymmetric unit. A single molecule of the Example 5 is present in the active site of all four molecules of Casein Kinase 1D. For co-crystallization, an enantiomer-pure batch of Example 5 was used for which the exact stereo-configuration was not known. The electron density maps allowed the deduction of the configuration at C6 of the stereoisomer bound in the crystal. The stereochemistry at the central carbon atom C6 of Example 5 (FIG. 1) is unambiguously defined by the knowledge of the stereochemistry of the protein Casein Kinase 1D. Example 5 unambiguously features the (S)-configuration on carbon atom C6 (FIG. 1).

EXPERIMENTAL SECTION—BIOLOGICAL ASSAYS

The following assays can be used to illustrate the commercial utility of the compounds according to the present invention.

Examples were tested in selected biological assays one or more times. When tested more than once, data are reported as either average values or as median values or single individual measurements, wherein
  the average value, also referred to as the arithmetic mean value, represents the sum of the values obtained divided by the number of times tested, and
  the median value represents the middle number of the group of values when ranked in ascending or descending order. If the number of values in the data set is odd, the median is the middle value. If the number of values in the data set is even, the median is the arithmetic mean of the two middle values.
  Individual measurements are shown when median or average values cannot be computed.

Examples were synthesized one or more times. When synthesized more than once, data from biological assays represent average values calculated utilizing data sets obtained from testing of one or more synthetic batch.

The in vitro activity of the compounds of the present invention can be demonstrated in the following assays:

CSNK1A1 Assay 1

CSNK1A1-inhibitory activity of compounds of the present invention in presence of 1 µM adenosine-tri-phosphate (ATP) was quantified employing the CSNK1A1 assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent"). Recombinant fusion protein of N-terminal Glutathion-S-Transferase (GST) and full-length human CSNK1A1, expressed by baculovirus infected insect cells and purified via Glutathion affinity chromatography, was purchased from Life Technologies (product no. PV4174) and used as enzyme. As substrate for the kinase reaction the biotinylated peptide Btn-Ahx-SGSEGDSESGEEEG (C-terminus in amide form) was used which can be purchased e.g. from the company Biosyntan (Berlin-Buch, Germany).

For the assay 50 nl of a 100 fold concentrated solution of the test compound in DMSO was pipetted into a white 1536-well microtiter plate (Greiner Bio-One, Frickenhausen, Germany), 2 µL of a solution of CSNK1A1 in aqueous assay buffer [50 mM HEPES pH 7.5, 10% (v/v) glycerol, 10 mM MgCl$_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 µL of a solution of ATP (1.67 µM=>final conc. in the 5 µL assay volume is 1 µM) and peptide substrate (50 µM=>final conc. in the 5 µL assay volume is 30 µM) in assay buffer and the resulting mixture was incubated for a reaction time of 30 min at 22° C. The concentration of CSNK1A1 was adjusted depending of the activity of the enzyme lot and was chosen appropriate to have the assay in the linear range, a typical concentration is 0.15 ng/µL. The reaction was stopped by the addition of 2.5 µL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 µL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1A1.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1A1 Assay 2

CSNK1A1-inhibitory activity of compounds of the present invention in presence of 1 μM adenosine-tri-phosphate (ATP) was quantified employing the CSNK1A1 assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent"). Recombinant fusion protein of N-terminal Glutathion-S-Transferase (GST) and full-length human CSNK1A1, expressed by baculovirus infected insect cells and purified via Glutathion affinity chromatography, was purchased from Life Technologies (product no. PV4174) and used as enzyme. As substrate for the kinase reaction the biotinylated peptide biotin-Ahx-KRRRAL-pS-VASLPGL (C-terminus in amide form) was used which can be purchased e.g. from the company Biosyntan (Berlin-Buch, Germany).

For the assay 50 nl of a 100 fold concentrated solution of the test compound in DMSO was pipetted into a white 1536-well microtiter plate (Greiner Bio-One, Frickenhausen, Germany), 2 μL of a solution of CSNK1A1 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 μM=>final conc. in the 5 μL assay volume is 1 μM) and peptide substrate (50 μM=>final conc. in the 5 μL assay volume is 30 μM) in assay buffer and the resulting mixture was incubated for a reaction time of 30 min at 22° C. The concentration of CSNK1A1 was adjusted depending of the activity of the enzyme lot and was chosen appropriate to have the assay in the linear range, a typical concentrations are about 0.0375 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1A1.

The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1A1 High ATP Assay

CSNK1A1-inhibitory activity of compounds of the present invention in presence of 1 mM adenosine-tri-phosphate (ATP) was quantified employing the CSNK1A1-high-ATP-assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1A1, expressed by baculovirus infected insect cells and purified via Glutathion affinity chromatography, was purchased from Life Technologies (product no. PV4174) and used as enzyme. As substrate for the kinase reaction the biotinylated peptide biotin-Ahx-KRRRAL-pS-VASLPGL (C-terminus in amide form) was used which can be purchased e.g. from the company Biosyntan (Berlin-Buch, Germany).

For the assay 50 nl of a 100 fold concentrated solution of the test compound in DMSO was pipetted into a white low volume 384-well microtiter plate (Greiner Bio-One, Frickenhausen, Germany), 2 μL of a solution of CSNK1A1 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 μL of a solution of ATP (1.67 mM=>final conc. in the 5 μL assay volume is 1 mM) and peptide substrate (167 μM=>final conc. in the 5 μL assay volume is 100 μM) in assay buffer and the resulting mixture was incubated for a reaction time of 30 min at 22° C. The concentration of CSNK1A1 was adjusted depending of the activity of the enzyme lot and was chosen appropriate to have the assay in the linear range, a typical concentration is about 0.4 ng/μL. The reaction was stopped by the addition of 2.5 μL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 μL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1A1.

The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1D Assay

CSNK1 D-inhibitory activity of compounds of the present invention in presence of 1 µM adenosine-tri-phosphate (ATP) was quantified employing the CSNK1D assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent"). Recombinant fusion protein of N-terminal Glutathion-S-Transferase (GST) and full-length human CSNK1D, expressed by baculovirus infected insect cells and purified via Glutathion affinity chromatography, was purchased from Life Technologies (product no. PV3665) and used as enzyme. As substrate for the kinase reaction the biotinylated peptide Btn-Ahx-SGSEGDSESGEEEG (C-terminus in amide form) was used which can be purchased e.g. from the company Biosyntan (Berlin-Buch, Germany).

For the assay 50 nl of a 100 fold concentrated solution of the test compound in DMSO was pipetted into a white 1536-well microtiter plate (Greiner Bio-One, Frickenhausen, Germany), 2 µL of a solution of CSNK1D in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 µL of a solution of ATP (1.67 µM=>final conc. in the 5 µL assay volume is 1 µM) and peptide substrate (50 µM=>final conc. in the 5 µL assay volume is 30 µM) in assay buffer and the resulting mixture was incubated for a reaction time of 30 min at 22° C. The concentration of CSNK1 D was adjusted depending of the activity of the enzyme lot and was chosen appropriate to have the assay in the linear range, a typical concentration is about 0.5 ng/µL. The reaction was stopped by the addition of 2.5 µL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 µL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1D.

The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

CSNK1G3 Assay

CSNK1G3-inhibitory activity of compounds of the present invention in presence of 1 µM adenosine-tri-phosphate (ATP) was quantified employing the CSNK1G3 assay as described in the following paragraphs. In essence, the enzyme activity is measured by quantification of the adenosine-di-phosphate (ADP), which is generated as a co-product of the enzyme reaction, via the "ADP-Glo™ Kinase Assay" kit from the company Promega. This detection system works as follows: In a first step the ATP not consumed in the kinase reaction is quantitatively converted to cAMP employing an adenylate cyclase ("ADP-Glo-reagent"), then the adenylate cyclase is stopped and the ADP generated in the kinase reaction converted to ATP which generates in a luciferase-based reaction a glow-luminescence signal ("Kinase Detection Reagent").

Recombinant fusion protein of N-terminal Glutathion-S-Transferase (GST) and full-length human CSNK1G3, expressed by baculovirus infected insect cells and purified via Glutathion affinity chromatography, was purchased from Life Technologies (product no. PV3838) and used as enzyme. As substrate for the kinase reaction the biotinylated peptide biotin-Ahx-KRRRAL-pS-VASLPGL (C-terminus in amide form) was used which can be purchased e.g. from the company Biosyntan (Berlin-Buch, Germany).

For the assay 50 nl of a 100 fold concentrated solution of the test compound in DMSO was pipetted into a white 1536-well microtiter plate (Greiner Bio-One, Frickenhausen, Germany), 2 µL of a solution of CSNK1G3 in aqueous assay buffer [50 mM HEPES pH 7.5, 10% (v/v) glycerol, 10 mM $MgCl_2$, 50 mM NaCl, 1 mM dithiothreitol, 0.01% (w/v) bovine serum albumin, 0.01% (v/v) Triton X-100] were added and the mixture was incubated for 15 min at 22° C. to allow pre-binding of the test compounds to the enzyme before the start of the kinase reaction. Then the kinase reaction was started by the addition of 3 µL of a solution of ATP (1.67 µM=>final conc. in the 5 µL assay volume is 1 µM) and peptide substrate (50 µM=>final conc. in the 5 µL assay volume is 30 µM) in assay buffer and the resulting mixture was incubated for a reaction time of 30 min at 22° C. The concentration of CSNK1G3 was adjusted depending of the activity of the enzyme lot and was chosen appropriate to have the assay in the linear range, a typical concentration is about 0.06 ng/µL. The reaction was stopped by the addition of 2.5 µL of "ADP-Glo-reagent" (1:1.5 fold diluted with water) and the resulting mixture was incubated at 22° C. for 1 h to convert the ATP not consumed in the kinase reaction completely to cAMP. Subsequently 2.5 µL of the "kinase detection reagent" (1.2 fold more concentrated than recommended by the producer) were added, the resulting mixture was incubated at 22° C. for 1 h and then the luminescence measured with a suitable measurement instrument (e.g. Viewlux™ from Perkin-Elmer). The amount of emitted light was taken as a measure for the amount of ADP generated and thereby for the activity of the CSNK1G3.

The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

WT-EGFR Kinase Assay

Inhibitory activity of compounds of the present invention against wild-type Epidermal Growth Factor Receptor (EGFR) was quantified employing the TR-FRET based EGFR assay as described in the following paragraphs.

Recombinant fusion protein of N-terminal Glutathion-S-Transferase (GST) and a fragment of human EGFR (amino acids R669 to A1210), expressed in Sf9 insect cells and purified via affinity chromatography using Glutathion Sepharose as described above, was used as kinase. As substrate for the kinase reaction the biotinylated peptide biotin-Ahx-AEEEEYFELVAKKK (C-terminus in amide form) was used which can be purchased e.g. form the company Biosynthan GmbH (Berlin-Buch, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 2 µL of a solution of EGFR in aqueous assay buffer [50 mM Hepes pH 7.0, 10 mM $MgCl_2$, 1 mM dithiothreitol, 0.5 mM EGTA, 0.3 mM activated sodium ortho-vanadate, 0.005% (w/v) bovine serum albumin, 0.005% (v/v) Tween-20] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 3.33 mM=>final conc. in the 5 µL assay volume is 2 mM) and substrate (1.67 µM=>final conc. in the 5 µL assay volume is 1 µM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration was 7.6 pg/µL. The reaction was stopped by the addition of 3 µL of a solution of HTRF detection reagents (83.3 nM streptavidine-XL665 [Cisbio Bioassays, Codolet, France] and 1.67 nM PT66-Tb-Cryptate, a terbium-cryptate labelled anti-phospho-tyrosine antibody from Cisbio Bioassays [instead of the PT66-Tb-cryptate PT66-Eu-Chelate from Perkin Elmer can also be used]) in an aqueous EDTA-solution (133.3 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated using Genedata Screener™ software.

Bub1 Kinase Assay

Bub1-inhibitory activity of compounds of the present invention was quantified employing the Bub1 TR-FRET assay as described in the following paragraphs.

N-terminally $His_6$-tagged recombinant catalytic domain of human Bub1 (amino acids 704-1085), expressed in insect cells (Hi5) and purified by Ni-NTA affinity chromatography and subsequent size exclusion chromatography, was used as enzyme. As substrate for the kinase reaction the biotinylated peptide biotin-Ahx-VLLPKKSFAEPG (C-terminus in amid form) was used which can be purchased e.g. form the company Biosyntan (Berlin, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 2 µL of a solution of Bub1 in aqueous assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (1.67 µM=>final conc. in the 5 µL assay volume is 1 µM) in assay buffer and the resulting mixture was incubated for a reaction time of 60 min at 22° C. The concentration of Bub1 was adjusted depending of the activity of the enzyme lot and was chosen appropriate to have the assay in the linear range, typical concentrations were in the range of 200 ng/mL. The reaction was stopped by the addition of 5 µL of a solution of TR-FRET detection reagents (0.2 µM streptavidine-XL665 [Cisbio Bioassays, Codolet, France] and 1 nM anti-phosho-Serine antibody [Merck Millipore, cat. #35-002] and 0.4 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (50 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar or Pherastar FS (both from BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). The test compounds were tested on the same microtiterplate, usually in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions, the exact concentrations and the number of tested concentrations may vary depending on the liquid handling instrumentation used for test sample preparation) in duplicate values for each concentration and $IC_{50}$ values were calculated by a 4 parameter fit.

Bub1 High ATP Kinase Assay

Bub1-inhibitory activity of compounds of the present invention at a high ATP concentration was quantified employing the Bub1 TR-FRET high ATP kinase assay as described in the following paragraphs.

N-terminally Hiss-tagged recombinant catalytic domain of human Bub1 (amino acids 704-1085), expressed in insect cells (Hi5) and purified by Ni-NTA affinity chromatography and subsequent size exclusion chromatography, was used as enzyme. As substrate for the kinase reaction the biotinylated peptide biotin-Ahx-VLLPKKSFAEPG (C-terminus in amid form) was used which can be purchased e.g. form the company Biosyntan (Berlin, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 3 µL of a solution of adenosine-tri-phosphate (ATP, 3.33 mM=>final conc. in the 5 µL assay volume is 2 mM) and substrate (1.67 µM=>final conc. in the 5 µL assay volume is 1 µM) in aqueous assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added. Then the kinase reaction was started by the addition of 2 µL of a solution of Bub1 in assay buffer and the resulting mixture was incubated for a reaction time of 60 min at 22° C. The concentration of Bub1 was adjusted depending on the activity of the enzyme lot and was chosen appropriate to have the assay in the linear range, a typical concentration is about 200 ng/mL. The reaction was stopped by the addition of 3 µL of a solution of TR-FRET detection reagents (0.167 µM streptavidine-XL665 [Cisbio Bioassays, Codolet, France] and 1.67 nM anti-phosho-Serine antibody [Merck Millipore, cat. #35-002] and 0.67 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (83.3 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar or Pherastar FS (both from BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.0.7 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated by a 4 parameter fit.

Cellular Mechanistic Assays

P-RPS6 (Ser244/247) Ribosomal Protein S6

The kinase CSNK1A phosphorylates Ribosomal protein S6 at Ser247. In-cell Western assay simultaneously detects two targets at 700 and 800 nm using two spectrally distinct near-infrared dyes. With a specific antibody, Ser244/247-phosphorylated RPS6 (Thermo Fisher 44-923) can be quantified and the samples can be normalized with cell stains Draq5 (Cell signaling, 4084L) and Sapphire700 (LiCor, 928-40022) in parallel.

2000 HCT 116 cells were seeded in growth medium (DMEM/Ham's F12, 10% FCS) in 96 well plate (Falcon 353075) over night at 37° C. Cells were treated with varying concentrations of test compounds at 37° C. for 4 h. Cells were fixed with 4% paraformaldehyde, washed (Sigma-Aldrich, AB351787, Tween 20, 1%) and blocked with buffer (Odyssey blocking buffer, LiCor, 927-40000) before incubating with the primary antibody (Ser244/247-phosphorylated RPS6 (Thermo Fisher 44-923) overnight at 2-8° C. After washing, secondary IRDye-labeled antibody mix with cell stains was added for 1 h and washed again. Plates were scanned with LiCor Odyssey Infrared Imager CLX at 800 nm for pRPS6 and at 700 nm for cell stains Draq5/Sapphire. The quotient of 800 nm and 700 nm for standard compound-treated cells was set as 0% and the quotient of 800 nm and 700 nm of DMSO treated cells was set as 100%. The results given as % reflecting the inhibition of Casein kinase activity compared to control and normalized according to cell number.

The $IC_{50}$ values were determined by means of a 4 parameter fit.

P-β-Catenin (Ser45)

50,000 DLD-1 cells were seeded in 96 well plates (nunc #161093) in RPMI 1640 (Biochrom; #FG 1215, 10% FCS, 2 mM L-Glutamine). After 24 h, cells were treated with varying concentrations of test compounds at 37° C. for 30 min. Cells were washed twice with ice-cold PBS buffer, treated with lysis buffer and all next steps were performed to the supplier's manual (β-Catenin pS45 ELISA Kit; ab205703). The content of pS45 was measured with ELISA at 450 nm, calculated with calibration curve and normalized to protein content. The normalized quotient of control compound-treated cells treated cells was set as 0% and the normalized quotient of untreated cells was set as 100%. The results given as % reflecting the content of β-Catenin pS45 compared to control. The $IC_{50}$ values were determined by means of a 4 parameter fit.

Proliferation Assays

HCT 116

400 HCT 116 cells/30 µL/well were plated in growth medium (DMEM/Ham's F12, 10% FCS) in a 384-well plate (CORNING #3571) at day 1. Reference plate was seeded for time zero determination. All plates were incubated overnight 37° C. Day 2: test compound was added in 7-step dilution and incubate at 37° C. for 96 h. Day 2: time zero plate: 30 µL/well CTG solution (Promega Cell Titer Glo solution; catalog #G755B and G756B) were added, incubated for 30 minutes, read luminescence on PheraStar. Day 6: compound treated plates: 30 µL/well CTG solution (Promega Cell Titer Glo solution; catalog #G755B and G756B) were added, incubated for 30 minutes, luminescence was read on PheraStar. Proliferation was calculated after subtracting time zero luminescence values from day 6 values and comparing to untreated wells.

The $IC_{50}$ values were determined using the four parameter fit.

A549

400 A549 cells/30 µL/well were plated in growth medium (DMEM/Ham's F12, 10% FCS) in a 384-well plate (CORNING #3571) at day 1. Reference plate was seeded for time zero determination. All plates were incubated overnight 37° C. Day 2: test compound was added in 7-step dilution and incubated at 37° C. for 96 h. Day 2: time zero plate: 30 µL/well CTG solution were added (Promega Cell Titer Glo solution; catalog #G755B and G756B), incubated for 30 minutes, luminescence was read on PheraStar. Day 6: compound treated plates: 30 µL/well CTG solution (Promega Cell Titer Glo solution; catalog #G755B and G756B) were added, incubated for 30 minutes, luminescence was read on PheraStar. Proliferation was calculated after subtracting time zero luminescence values from day 6 values and comparing to untreated wells. The $IC_{50}$ values were determined using the four parameter fit.

TMD8

400 TMD8 cells/30 µL/well were plated in growth medium (RPM11640, 20% FCS) in a 384-well plate (CORNING #3571) at day 1. Reference plate was seeded for time zero determination. All plates were incubated overnight 37° C. Day 2: test compound was added in 7-step dilution and incubated at 37° C. for 96 h. Day 2: time zero plate: 30 µL/well CTG solution (Promega Cell Titer Glo solution; catalog #G755B and G756B) were added, incubated 30 minutes, luminescence was read on PheraStar. Day 6: compound treated plates: 30 µL/well CTG solution (Promega Cell Titer Glo solution; catalog #G755B and G756B) were added, incubated 30 minutes, luminescence was read on PheraStar. Proliferation was calculated after subtracting time zero luminescence values from day 6 values and comparing to untreated wells.

The $IC_{50}$ values were determined using the four parameter fit.

Results:

Table 2 shows the results of the inhibition in the CSNK1A1 and CSNK1 D biochemical assays.

TABLE 2

| Example No | CSNK1A1 Assay 1 $IC_{50}$ [mol/l] (median) | CSNK1A1 Assay 2 $IC_{50}$ [mol/l] (median) | CSNK1D $IC_{50}$ [mol/l] (median) | CSNK1A1 high ATP assay $IC_{50}$ [mol/l] (median) |
|---|---|---|---|---|
| 1 | 2.54E−9 | 1.97E−9 | 5.64E−9 | 2.84E−8 |
| 2 | 3.95E−9 | | 5.41E−9 | 1.14E−7 |
| 3 | 4.28E−9 | | 5.66E−9 | 7.84E−8 |
| 4 | 1.12E−8 | 5.49E−9 | 1.51E−8 | 1.15E−7 |
| 5 | 3.62E−9 | 4.45E−9 | 1.21E−8 | 6.34E−8 |
| 6 | 3.33E−8 | 4.40E−8 | 4.96E−8 | 1.60E−6 |
| 7 | | 2.52E−9 | 8.48E−9 | 1.07E−7 |
| 8 | | 1.54E−8 | 3.79E−8 | 1.93E−6 |
| 9 | | | | |

TABLE 2-continued

| Example No | CSNK1A1 Assay 1 $IC_{50}$ [mol/l] (median) | CSNK1A1 Assay 2 $IC_{50}$ [mol/l] (median) | CSNK1D $IC_{50}$ [mol/l] (median) | CSNK1A1 high ATP assay $IC_{50}$ [mol/l] (median) |
|---|---|---|---|---|
| 10 | | 4.61E−9 | 1.40E−8 | 2.55E−8 |
| 11 | | 3.04E−8 | 3.08E−8 | 3.97E−6 |
| 12 | 2.32E−9 | | 1.02E−8 | 5.20E−9 |
| 13 | | 1.90E−9 | 7.06E−9 | 3.70E−8 |
| 14 | | 4.96E−9 | 1.40E−8 | 7.39E−8 |
| 15 | | 4.25E−8 | 3.86E−8 | 1.07E−5 |
| | | | | >5.71E−6 |
| 16 | | 2.57E−9 | 8.00E−9 | 1.02E−7 |
| 17 | | 1.09E−8 | 3.93E−8 | 6.65E−8 |
| 18 | | 2.04E−8 | 4.47E−8 | 1.79E−6 |
| 19 | | 1.70E−9 | 6.55E−9 | 1.06E−8 |
| 20 | | 9.72E−9 | 2.42E−8 | 1.66E−6 |
| 21 | | 7.67E−9 | 2.15E−8 | 3.44E−7 |
| 22 | | 4.23E−9 | 1.19E−8 | 5.47E−8 |
| 23 | | 2.67E−8 | 3.68E−8 | 2.62E−6 |
| 24 | | 3.92E−8 | 6.40E−8 | >5.71E−6 |
| | | | | 4.24E−6 |
| 25 | | 5.54E−8 | 8.86E−8 | 1.27E−5 |
| | | | | >2.00E−5 |
| 26 | | 4.05E−9 | 2.31E−8 | 2.88E−7 |
| 27 | | 7.70E−9 | 3.62E−8 | 1.57E−7 |
| 28 | | 1.14E−8 | 7.12E−8 | 1.98E−6 |
| 29 | | 3.19E−9 | | 1.38E−7 |
| 30 | | 8.01E−9 | 2.59E−8 | 4.85E−7 |
| 31 | | 3.85E−9 | | 2.49E−7 |
| 32 | | 7.22E−8 | | 4.56E−6 |
| 33 | | 6.15E−8 | 1.81E−8 | 7.22E−8 |
| 34 | | 2.68E−9 | | 1.65E−8 |
| 35 | | 2.05E−8 | | 7.05E−7 |
| 36 | | 1.13E−8 | | 1.08E−6 |
| 37 | | 2.26E−8 | | >1.63E−6 |
| | | | | >1.63E−6 |
| 38 | | 1.46E−8 | | 1.29E−6 |
| 39 | | 1.79E−7 | 2.14E−7 | 2.84E−6 |
| | | | | 2.90E−6 |
| | | | | >2.00E−5 |
| | | | | >2.00E−5 |
| 40 | | 4.59E−9 | 1.05E−8 | 5.17E−8 |
| 41 | | 2.26E−8 | 3.12E−8 | 3.53E−6 |
| 42 | | 2.40E−9 | 4.92E−9 | 5.72E−8 |
| 43 | | 3.52E−9 | 7.12E−9 | 6.75E−8 |
| 44 | | 4.82E−9 | 1.07E−8 | 6.71E−7 |
| 45 | | 1.63E−8 | 1.32E−8 | 2.73E−7 |
| 46 | | 6.64E−9 | 8.33E−9 | 1.19E−7 |
| 47 | | 1.63E−7 | 1.51E−7 | >2.00E−5 |
| | | | | >2.00E−5 |
| 48 | | 7.69E−9 | 1.34E−8 | 3.70E−8 |
| 49 | | 4.57E−9 | 7.30E−9 | 1.96E−6 |
| 50 | | 5.10E−8 | 6.82E−8 | 2.46E−6 |
| 51 | | 4.87E−9 | 6.67E−9 | 2.58E−8 |
| 52 | | 4.91E−9 | 6.78E−9 | 2.54E−8 |
| 53 | | 9.68E−9 | 1.50E−8 | 9.07E−7 |
| 54 | | 4.62E−9 | 5.50E−9 | 1.46E−8 |
| 55 | | 4.25E−9 | 4.38E−9 | 9.10E−9 |
| 56 | | 1.92E−8 | 2.79E−8 | 1.08E−6 |
| 57 | | 2.01E−9 | 3.10E−9 | 1.03E−8 |
| 58 | | 1.24E−8 | 4.06E−8 | 1.20E−6 |
| 59 | | 9.43E−8 | 8.62E−8 | 7.30E−6 |
| 60 | | 7.34E−9 | 1.18E−8 | 4.37E−7 |
| 61 | | 5.11E−9 | 7.68E−9 | 2.19E−8 |
| 62 | | 2.10E−8 | 2.97E−8 | 1.50E−6 |
| 63 | | 2.12E−9 | 4.00E−9 | 1.21E−8 |
| 64 | | 2.65E−9 | 5.51E−9 | 3.10E−8 |
| 65 | | 1.51E−9 | 5.46E−9 | 1.75E−8 |
| 66 | | 2.75E−9 | 5.57E−9 | 3.35E−8 |
| 67 | | 2.41E−9 | 3.79E−9 | 4.46E−8 |
| 68 | | 3.20E−9 | 3.63E−9 | 7.42E−8 |
| 69 | | 3.13E−9 | 4.68E−9 | 8.17E−8 |
| 70 | | 3.20E−9 | 3.66E−9 | 1.40E−7 |
| 71 | | 4.79E−9 | 6.47E−9 | 2.41E−7 |
| 72 | | 3.97E−9 | 6.09E−9 | 6.64E−8 |
| 73 | | 2.38E−9 | 4.46E−9 | 6.33E−8 |
| 74 | | 3.39E−8 | 5.51E−8 | 5.99E−7 |
| 75 | | 5.49E−9 | 8.28E−9 | 1.64E−7 |

TABLE 2-continued

| Example No | CSNK1A1 Assay 1 IC$_{50}$ [mol/l] (median) | CSNK1A1 Assay 2 IC$_{50}$ [mol/l] (median) | CSNK1D IC$_{50}$ [mol/l] (median) | CSNK1A1 high ATP assay IC$_{50}$ [mol/l] (median) |
|---|---|---|---|---|
| 76 |  | 1.44E−8 | 1.75E−8 | 5.06E−7 |
| 77 |  | 2.12E−9 | 4.43E−9 | 8.67E−8 |
| 78 |  | 2.95E−9 | 7.93E−9 | 9.55E−8 |
| 79 |  | 8.93E−9 | 1.95E−8 | 3.37E−7 |
| 80 |  | 2.41E−8 | 3.03E−8 | 2.84E−6 |
| 81 |  | 4.33E−9 | 8.47E−9 | 7.14E−8 |
| 82 |  | 2.26E−9 | 5.52E−9 | 1.62E−7 |
| 83 |  | 3.03E−9 | 7.30E−9 | 6.14E−8 |
| 84 |  | 2.64E−9 | 8.50E−9 | 2.17E−7 |
| 85 |  | 1.78E−9 | 3.36E−9 | 2.65E−8 |
| 86 |  | 4.44E−9 | 9.48E−9 | 1.10E−7 |
| 87 |  | 2.57E−9 | 6.02E−9 | 6.47E−8 |
| 88 |  | 2.33E−9 | 5.18E−9 | 6.51E−8 |
| 89 |  | 1.88E−9 | 5.72E−9 | 3.64E−7 |
| 90 |  | 1.43E−9 | 3.79E−9 | 6.24E−8 |
| 91 |  | 4.73E−9 | 8.83E−9 | 6.93E−7 |
| 92 |  | 4.66E−9 | 1.07E−8 | 2.30E−7 |
| 93 |  | 4.72E−8 | 4.73E−8 | 3.18E−6 |
| 94 |  | 4.33E−9 | 7.02E−9 | 1.54E−7 |
| 95 |  | 4.62E−8 | 4.53E−8 | 2.46E−6 |
| 96 |  | 5.37E−9 | 4.36E−9 | 3.58E−8 |
| 97 |  | 4.40E−9 | 5.73E−9 | 4.70E−8 |
| 98 |  | 4.16E−9 | 6.13E−9 | 1.49E−7 |
| 99 |  | 3.78E−9 | 5.10E−9 | 2.59E−8 |
| 100 |  | 3.97E−9 | 1.56E−8 | 2.54E−7 |
| 101 |  | 3.74E−9 | 7.42E−9 | 2.58E−7 |
| 102 |  | 3.60E−9 | 7.21E−9 | 5.10E−8 |
| 103 |  | 1.28E−8 | 1.73E−8 | 2.68E−7 |
| 104 |  | 6.79E−8 | 6.05E−8 | 4.49E−6 |
| 105 |  | 4.06E−9 | 5.45E−9 | 9.45E−8 |
| 106 |  | 1.78E−8 | 2.23E−8 | 5.62E−8 |
| 107 |  | 4.57E−8 | 5.92E−8 | 3.16E−6 |
| 108 |  | 3.27E−9 | 4.62E−9 | 8.33E−9 |
| 109 |  | 1.64E−8 | 1.41E−8 | 1.36E−7 |
| 110 |  | 2.62E−7 | 2.49E−7 | >2.00E−5 |
|  |  |  |  | >2.00E−5 |
| 111 |  | 1.09E−8 | 1.02E−8 | 1.35E−7 |
| 112 |  | 6.69E−9 | 8.41E−9 | 1.67E−7 |
| 113 |  | 1.37E−8 | 1.61E−8 | 1.66E−7 |
| 114 |  | 2.43E−9 | 4.70E−9 | 2.27E−7 |
| 115 |  | 2.41E−9 | 5.09E−9 | 2.48E−7 |
| 116 |  | 1.86E−8 | 5.44E−8 | 4.53E−7 |
| 117 |  | 1.46E−9 | 2.99E−9 | 9.62E−8 |
| 118 |  | 5.16E−9 | 1.29E−8 | 1.07E−7 |
| 119 |  | 5.65E−9 | 1.08E−8 | 3.54E−7 |
| 120 |  | 9.64E−9 | 1.10E−8 | 4.77E−7 |
| 121 |  | 7.01E−8 | 6.35E−8 | 1.02E−5 |
| 122 |  | 4.12E−9 | 4.71E−9 | 2.68E−8 |
| 123 |  | 1.35E−8 | 9.91E−9 | 2.91E−8 |
| 124 |  | 7.46E−8 | 5.87E−8 | >5.71E−6 |
|  |  |  |  | >5.71E−6 |
|  |  |  |  | >5.71E−6 |
|  |  |  |  | >5.71E−6 |
| 125 |  | 1.05E−8 | 9.39E−9 | 1.21E−8 |
| 126 |  | 4.44E−9 | 1.44E−8 | 4.78E−8 |
| 127 |  | 4.74E−9 | 1.46E−8 | 2.31E−8 |
| 128 |  | 7.16E−9 | 1.14E−8 | 3.14E−8 |
| 129 |  | 3.39E−9 | 5.40E−9 | 6.37E−9 |
| 130 |  | 2.67E−8 | 7.16E−8 | 1.34E−6 |
| 131 |  | 9.38E−9 | 1.16E−8 | 4.64E−7 |
| 132 |  | 2.43E−8 | 3.29E−8 | 9.15E−7 |
| 133 |  | 1.97E−7 | 2.80E−7 | >5.71E−6 |
|  |  |  |  | >5.71E−6 |
| 134 |  | 1.91E−8 | 4.59E−8 | 3.04E−7 |
| 135 |  | 2.58E−8 | 1.99E−8 | 3.65E−7 |
| 136 |  | 1.37E−8 | 4.53E−8 | 4.56E−8 |
| 137 |  | 4.22E−8 | 8.27E−8 | 4.51E−7 |
| 138 |  | 1.66E−8 | 2.24E−8 | 4.30E−7 |
| 139 |  | 3.21E−9 | 7.73E−9 | 4.14E−8 |
| 140 |  | 4.10E−9 | 9.95E−9 | 5.69E−8 |
| 141 |  | 5.78E−8 | 1.27E−7 | 5.99E−7 |
| 142 |  | 5.10E−9 | 9.35E−9 | 1.23E−8 |
| 143 |  | 1.67E−8 | 1.84E−8 | 3.20E−8 |
| 144 |  | 8.07E−8 | 8.20E−8 | 5.06E−6 |
| 145 |  | 1.07E−8 | 8.21E−9 | 1.48E−8 |
| 146 |  | 1.38E−8 | 6.28E−9 | 5.04E−9 |
| 147 |  | 6.20E−9 | 1.16E−8 | 1.92E−8 |
| 148 |  | 8.82E−9 | 8.31E−9 | 1.28E−8 |
| 149 |  | 4.04E−8 | 3.94E−8 | 4.73E−7 |
| 150 |  | 1.79E−8 | 2.66E−8 | 1.27E−6 |
| 151 |  |  |  |  |
| 152 |  | 2.45E−9 | 7.96E−9 | 3.70E−8 |
| 153 |  | 1.96E−9 | 9.28E−9 | 7.39E−8 |
| 154 |  | 3.33E−9 | 4.45E−9 | 1.19E−7 |
| 155 |  | 3.12E−9 | 7.01E−9 | 4.85E−8 |
| 156 |  | 6.09E−9 | 9.38E−9 | 2.97E−8 |
| 157 |  | 8.76E−9 | 1.58E−8 | 5.08E−8 |
| 158 |  | 2.39E−7 | 1.88E−7 | >1.63E−6 |
|  |  | 2.63E−7 |  | 5.57E−6 |
|  |  | 5.25E−8 |  |  |
|  |  | 6.77E−8 |  |  |
| 159 |  | 9.03E−8 | 9.07E−8 | 2.17E−7 |
| 160 |  | 1.33E−8 | 1.58E−8 | 2.72E−8 |
| 161 |  | 3.42E−7 | 3.60E−7 | >2.00E−5 |
|  |  | 3.68E−7 |  | 1.91E−5 |
|  |  | 1.04E−7 |  | 1.06E−5 |
|  |  | 1.58E−7 |  | 1.46E−5 |
| 162 |  | 6.02E−8 | 5.29E−8 | 6.14E−8 |
| 163 |  |  |  |  |
| 164 |  | 3.83E−9 | 3.08E−9 | 1.49E−7 |

Table 3 shows the results of the inhibition in the WT-EGFR assay.

TABLE 3

| Example No | EGFR Wildtyp- 2 mM ATP IC$_{50}$ [mol/l] (median) |
|---|---|
| 1 | 1.20E−6 |
| 2 | 1.17E−6 |
| 3 | 2.13E−6 |
| 4 | >2.00E−5 |
|  | >2.00E−5 |
|  | 1.26E−5 |
|  | 1.12E−5 |
| 5 | 1.44E−5 |
|  | 1.45E−5 |
|  | 1.15E−5 |
|  | >2.00E−5 |
|  | >2.00E−5 |
|  | >2.00E−5 |
|  | >2.00E−5 |
|  | >2.00E−5 |
|  | >2.00E−5 |
|  | 1.55E−5 |
|  | >2.00E−5 |
|  | >2.00E−5 |
|  | >2.00E−5 |
|  | 1.68E−5 |
|  | 1.76E−5 |
| 6 | 1.61E−5 |
|  | 1.56E−5 |
|  | 1.82E−5 |
|  | >2.00E−5 |
|  | >2.00E−5 |
|  | 1.59E−5 |
|  | 1.71E−5 |
| 7 | 2.74E−6 |
| 8 | >2.00E−5 |
| 9 |  |
| 10 | 1.24E−5 |
| 11 | 2.29E−6 |
| 12 | >2.00E−5 |

TABLE 3-continued

| Example No | EGFR Wildtyp- 2 mM ATP $IC_{50}$ [mol/l] (median) |
|---|---|
| 13 | 1.05E−6 |
| 14 | >2.00E−5 |
| 15 | >2.00E−5 |
| 16 | >2.00E−5 |
| 17 | >2.00E−5 |
|  | >2.00E−5 |
|  | 1.45E−5 |
|  | 1.43E−5 |
| 18 | 1.49E−5 |
| 19 | >2.00E−5 |
|  | >2.00E−5 |
|  | 1.61E−5 |
|  | >2.00E−5 |
|  | >2.00E−5 |
|  | >2.00E−5 |
| 20 | >2.00E−5 |
|  | 1.81E−5 |
| 21 | >2.00E−5 |
| 22 | 8.15E−7 |
| 23 | 7.28E−6 |
| 24 | >2.00E−5 |
| 25 | >2.00E−5 |
| 26 | >2.00E−5 |
| 27 | 1.80E−5 |
|  | >2.00E−5 |
| 28 | >2.00E−5 |
| 29 | >2.00E−5 |
| 30 | >2.00E−5 |
| 31 | >2.00E−5 |
| 32 | >2.00E−5 |
| 33 | >2.00E−5 |
| 34 | >2.00E−5 |
| 35 | 1.48E−5 |
| 36 | >2.00E−5 |
| 37 | >2.00E−5 |
| 38 | 6.69E−6 |
| 39 | >2.00E−5 |
| 40 | 1.41E−7 |
|  | 1.18E−7 |
|  | 3.45E−6 |
|  | 3.39E−6 |
|  | >2.00E−5 |
|  | >2.00E−5 |
| 41 | >2.00E−5 |
| 42 | >2.00E−5 |
| 43 | 2.00E−6 |
| 44 | 4.14E−6 |
| 45 | >2.00E−5 |
| 46 | >2.00E−5 |
| 47 | >2.00E−5 |
| 48 | 1.45E−5 |
| 49 | >2.00E−5 |
| 50 | >2.00E−5 |
| 51 | 5.63E−7 |
| 52 | 5.26E−7 |
| 53 | 6.03E−6 |
| 54 | >2.00E−5 |
| 55 | 1.17E−6 |
| 56 | 8.57E−7 |
| 57 | 8.70E−7 |
| 58 | >2.00E−5 |
| 59 | 1.63E−5 |
| 60 | 7.34E−6 |
| 61 | 8.02E−6 |
| 62 | >2.00E−5 |
| 63 | 6.68E−6 |
| 64 | 1.20E−6 |
| 65 | 4.90E−7 |
| 66 | 8.55E−6 |
| 67 | 9.97E−7 |
| 68 | 2.10E−6 |
| 69 | 5.10E−7 |
| 70 | 2.04E−6 |
| 71 | 7.43E−6 |
| 72 | 7.59E−6 |
| 73 | 6.78E−6 |
| 74 | >2.00E−5 |
| 75 | >2.00E−5 |
| 76 | >2.00E−5 |
| 77 | >2.00E−5 |
| 78 | 3.09E−6 |
| 79 | >2.00E−5 |
| 80 | >2.00E−5 |
| 81 | >2.00E−5 |
| 82 | 1.15E−6 |
| 83 | 2.92E−6 |
| 84 | 1.02E−6 |
| 85 | 9.37E−7 |
| 86 | 6.47E−6 |
| 87 | 1.58E−7 |
| 88 | 7.27E−7 |
| 89 | 6.05E−6 |
| 90 | 5.61E−7 |
| 91 | >2.00E−5 |
| 92 | >2.00E−5 |
| 93 | >2.00E−5 |
| 94 | 4.41E−6 |
| 95 | 6.31E−6 |
| 96 | 7.04E−6 |
| 97 | 5.29E−7 |
| 98 | 4.34E−6 |
| 99 | 3.29E−7 |
| 100 | 3.83E−6 |
| 101 | >2.00E−5 |
| 102 | 2.33E−6 |
| 103 | >2.00E−5 |
| 104 | >2.00E−5 |
| 105 | >2.00E−5 |
| 106 | >2.00E−5 |
| 107 | >2.00E−5 |
| 108 | >2.00E−5 |
| 109 | >2.00E−5 |
| 110 | 4.13E−6 |
| 111 | 1.14E−6 |
| 112 | 3.43E−6 |
| 113 | 7.71E−6 |
|  | >5.71E−6 |
| 114 | 2.06E−6 |
| 115 | 3.67E−6 |
| 116 | >2.00E−5 |
| 117 | 1.27E−6 |
| 118 | 7.26E−6 |
| 119 | 2.54E−6 |
| 120 | >2.00E−5 |
| 121 | >2.00E−5 |
| 122 | 2.15E−6 |
| 123 | 5.64E−8 |
| 124 | >2.00E−5 |
| 125 | >2.00E−5 |
| 126 |  |
| 127 | >2.00E−5 |
|  | 1.69E−5 |
| 128 | >2.00E−5 |
| 129 | >2.00E−5 |
| 130 | >2.00E−5 |
| 131 | 1.09E−6 |
| 132 | >2.00E−5 |
| 133 | 4.05E−7 |
| 134 | >2.00E−5 |
| 135 | >2.00E−5 |
| 136 | >2.00E−5 |
| 137 | >2.00E−5 |
| 138 | 1.11E−5 |
| 139 | 6.81E−7 |
| 140 | >2.00E−5 |
| 141 | >2.00E−5 |
| 142 | >2.00E−5 |
| 143 | >2.00E−5 |
| 144 | >2.00E−5 |
| 145 | >2.00E−5 |

TABLE 3-continued

| Example No | EGFR Wildtyp-<br>2 mM ATP<br>IC$_{50}$ [mol/l]<br>(median) |
|---|---|
| 146 | 6.67E−7 |
| 147 | 2.68E−7 |
| 148 | 3.40E−6 |
| 149 | 1.67E−5 |
| 150 | 1.83E−5 |
| 151 | >2.00E−5 |
| 152 | 1.66E−6 |
| 153 | 2.87E−7 |
| 154 | >2.00E−5 |
| 155 | 4.76E−7 |
| 156 | 6.66E−6 |
| 157 | >2.00E−5 |
| 158 | >2.00E−5 |
| 159 | >2.00E−5 |
| 160 | >2.00E−5 |
| 161 | >2.00E−5 |
| 162 | >2.00E−5 |
| 163 |  |
| 164 | 4.19E−7 |

Compounds of the present invention have surprisingly been found to show advantageous properties, such as effectively inhibiting CSNK1A1 kinase. In particular the exemplified compounds of the present invention display an IC$_{50}$ of below 100 nM in a CSNK1A1 kinase assay in the presence of 1 μM ATP. Furthermore it has been found that said compounds of the present invention additionally show low inhibition of wild type-EGFR kinase. In particular, the exemplified compounds of the present invention are less potent than 600 nM in a wild type-EGFR kinase assay in the presence of 2 mM ATP, which may be useful to reduce potential toxicity arising from excessive inhibition of wild-type EGFR.

In contrast to the claimed compounds of this invention the compounds claimed in the closest prior art WO 2016/120196 do not show the advantageous combined properties described above. This can be seen in Table 4.

TABLE 4

| WO 2016/120196<br>Example No. | CSNK1A1<br>Assay 1<br>IC$_{50}$ [mol/l]<br>(median) | CSNK1A1<br>Assay 2<br>IC$_{50}$ [mol/l]<br>(median) | EGFR Wildtyp-<br>2 mM ATP<br>IC$_{50}$ [mol/l]<br>(median) |
|---|---|---|---|
| 14 | 2.03E−8 |  | 1.04E−7 |
| 23 |  | 1.14E−8 | 1.50E−7 |
| 24 | <3.43E−9<br>9.32E−9<br>1.01E−8<br>5.57E−9<br>4.38E−9 | 4.51E−9 | 4.26E−8 |
| 25 | 6.25E−8 |  | 3.21E−7 |
| 40 | 2.41E−8 |  | 8.55E−8 |

The invention claimed is:

1. A compound of formula (I)

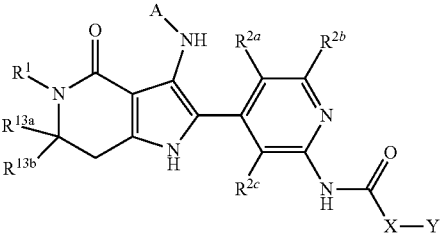

wherein:

R$^1$ represents hydrogen or a group selected from C$_1$-C$_4$-alkyl, C$_3$-C$_6$-cycloalkyl, C$_3$-C$_6$-cycloalkyl-C$_1$-C$_4$-alkyl-, C$_1$-C$_3$-alkoxy-C$_1$-C$_3$-alkyl-, and C$_1$-C$_5$-hydroxyalkyl, wherein said groups are each independently optionally substituted, one or more times, with halogen;

R$^{2a}$ represents hydrogen, hydroxy, halogen, cyano, —NH$_2$, —NHMe, —NMe$_2$, C$_1$-C$_2$-alkoxy, C$_1$-C$_2$-haloalkyl, or C$_1$-C$_2$-haloalkoxy;

R$^{2b}$ represents hydrogen, hydroxy, halogen, cyano, —NH$_2$, —NHR$^9$, or —NMe$_2$;

R$^{2c}$ represents hydrogen, halogen, cyano, —NMe$_2$, C$_1$-C$_2$-alkoxy, or C$_1$-C$_2$-haloalkoxy;

X represents methylene or ethylene,
  wherein said methylene and ethylene groups are each independently optionally substituted, one or more times, with R$^3$;

Y represents phenyl or a heteroaryl group,
  wherein said phenyl and heteroaryl groups are each independently optionally substituted, one or more times, with R$^4$;

R$^3$ represents hydroxy, halogen, cyano, C$_1$-C$_3$-alkyl, C$_1$-C$_3$-alkoxy, C$_1$-C$_3$-haloalkyl, C$_1$-C$_2$-haloalkoxy, C$_3$-C$_4$-cycloalkyl, —NHR$^6$, R$^5$O—C$_1$-C$_3$-alkyl, R$^6$R$^7$N—C$_1$-C$_5$-alkyl, or R$^6$R$^7$N—X'—C(R$^{10}$)(R$^{11}$)—C$_1$-C$_2$-alkyl-;

X' represents methylene or ethylene;

R$^4$ represents hydroxy, halogen, cyano, C$_1$-C$_4$-alkyl, C$_1$-C$_4$-alkoxy, C$_1$-C$_4$-haloalkyl, C$_1$-C$_4$-haloalkoxy, —NMe$_2$, —CO$_2$R$^{14}$, —CONR$^{15}$R$^{16}$, or —SO$_2$Me;

R$^5$ represents hydrogen, C$_1$-C$_2$-alkyl, C$_1$-C$_2$-haloalkyl, or C$_3$-C$_4$-cycloalkyl;

R$^6$ represents hydrogen, C$_1$-C$_2$-alkyl, C$_1$-C$_2$-haloalkyl, or C$_3$-C$_4$-cycloalkyl and R$^7$ represents hydrogen, C$_1$-C$_2$-alkyl, C$_1$-C$_2$-haloalkyl, C$_3$-C$_4$-cycloalkyl, or —CO$_2$-C$_1$-C$_4$-alkyl, or R$^6$ and R$^7$, together with the nitrogen atom to which they are attached, represent a 4- to 7-membered heterocyclic ring, wherein said heterocyclic ring optionally contains one or more further heteroatoms selected from N, O, S, C(═O), S(═O), and SO$_2$, and is independently optionally substituted, one or more times, with halogen, C$_1$-C$_3$-alkyl, C$_3$-cycloalkyl-C$_1$-C$_2$-alkyl-, —NH$_2$, —NHR$^9$, —NR$^9$R$^{9a}$, or hydroxy;

A represents a group selected from:

[Structures: substituted phenyl with $R^{8f}$, $R^{8a}$, $R^{8b}$; pyridyl with $R^{8g}$, $R^{8c}$; pyridazinyl with $R^{8d}$; pyrazinyl with $R^{8e}$]

and wherein * indicates the point of attachment of said group to the —NH— of formula (I);

$R^{8a}$ represents hydrogen, hydroxy, halogen, cyano, $C_1$-$C_2$-alkyl, or $C_1$-$C_2$-haloalkyl;

$R^{8b}$ represents hydrogen, hydroxy, halogen, cyano, $C_1$-$C_2$-alkyl, or $C_1$-$C_2$-haloalkyl;

$R^{8c}$ represents hydrogen, hydroxy, halogen, cyano, $C_1$-$C_2$-alkyl, or $C_1$-$C_2$-haloalkyl;

$R^{8d}$ represents hydrogen, hydroxy, halogen, cyano, $C_1$-$C_2$-alkyl, or $C_1$-$C_2$-haloalkyl;

$R^{8e}$ represents hydrogen, hydroxy, halogen, cyano, $C_1$-$C_2$-alkyl, or $C_1$-$C_2$-haloalkyl;

$R^{8f}$ represents hydrogen, hydroxy, halogen, cyano, $C_1$-$C_2$-alkyl, or $C_1$-$C_2$-haloalkyl;

$R^{8g}$ represents hydrogen or halogen;

$R^9$ represents $C_1$-$C_3$-alkyl or cyclopropyl;

$R^{9a}$ represents $C_1$-$C_3$-alkyl or cyclopropyl;

$R^{10}$ represents methyl, halogen, or hydroxy;

$R^{11}$ represents methyl, halogen, or hydroxy;

$R^{13a}$ represents hydrogen, or a group selected from $C_1$-$C_4$-alkyl, $C_1$-$C_4$-haloalkyl, $C_3$-$C_4$-cycloalkyl, $C_3$-$C_6$-cycloalkyl-$C_1$-$C_4$-alkyl-, and $C_1$-$C_3$-alkoxy-$C_1$-$C_3$-alkyl-, wherein said groups are each independently optionally substituted, one or more times, with halogen and $R^{13b}$ represents hydrogen, or a group selected from $C_1$-$C_4$-alkyl, $C_3$-$C_4$-cycloalkyl, $C_3$-$C_6$-cycloalkyl-$C_1$-$C_4$-alkyl-, and $C_1$-$C_3$-alkoxy-$C_1$-$C_3$-alkyl-, wherein said groups are each independently optionally substituted, one or more times, with halogen, or, $R^{13a}$ and $R^{13b}$, together with the carbon atom to which they are attached, form a $C_3$-$C_5$-cycloalkyl ring or a 4- to 5-membered heterocyclic ring;

$R^{14}$ represents hydrogen, methyl, or ethyl; and $R^{15}$ represents hydrogen, methyl, or ethyl and $R^{16}$ represents hydrogen, methyl, ethyl, methoxyethyl, or dimethylaminoethyl, or $R^{15}$ and $R^{16}$, together with the nitrogen atom to which they are attached, represent a 5- to 6-membered heterocyclic ring, wherein said heterocyclic ring optionally contains one or two further heteroatoms selected from N, O, S, C(=O), S(=O), and $SO_2$;

or an N-oxide, a salt, a tautomer, or a stereoisomer of said compound, or a salt of said N-oxide, tautomer, or stereoisomer.

2. The compound of formula (I) according to claim 1, wherein:

$R^1$ represents hydrogen or a group selected from $C_1$-$C_4$-alkyl, $C_3$-$C_6$-cycloalkyl, $C_3$-$C_6$-cycloalkyl-$C_1$-$C_4$-alkyl-, and $C_1$-$C_5$-hydroxyalkyl, wherein said groups are each independently optionally substituted, one or more times with halogen;

$R^{2a}$ represents hydrogen or halogen;

$R^{2b}$ represents hydrogen, halogen, —$NH_2$, or —$NHR^9$;

$R^2c$ represents hydrogen or halogen;

X represents methylene, wherein said methylene group is independently optionally substituted, one or more times, with $R^3$;

Y represents phenyl or a pyridyl group, wherein said phenyl and pyridyl groups are each independently optionally substituted, one or more times, with $R^4$;

$R^3$ represents hydroxy, $C_1$-$C_3$-alkyl, $C_1$-$C_3$-haloalkyl, —$NHR^6$, $R^5O$—$C_1$-$C_3$-alkyl, or $R^6R^7N$—$C_1$-$C_5$-alkyl;

$R^4$ represents halogen, $C_1$-$C_4$-alkyl, $C_1$-$C_4$-haloalkyl, methoxy, —$OCF_3$, —$NMe_2$, —$CO_2R^{14}$, —$CONR^{15}R^{16}$, or —$SO_2Me$;

$R^5$ represents hydrogen, methyl, or trifluoromethyl;

$R^6$ represents hydrogen, $C_1$-$C_2$-alkyl, $C_1$-$C_2$-haloalkyl, or $C_3$-$C_4$-cycloalkyl and $R^7$ represents hydrogen, $C_1$-$C_2$-alkyl, $C_1$-$C_2$-haloalkyl, $C_3$-$C_4$-cycloalkyl, or —$CO_2$-tert-butyl, or $R^6$ and $R^7$, together with the nitrogen atom to which they are attached, represent a 4- to 7-membered heterocyclic ring, wherein said heterocyclic ring optionally contains one or more further heteroatoms selected from N, O, and S, or a group C(=O), and is independently optionally substituted, one or more times, with halogen, $C_1$-$C_3$-alkyl, $C_3$-cycloalkyl-$C_1$-$C_2$-alkyl-, —$NH_2$, —$NHR^9$, or —$NR^9R^{9a}$;

A represents a group selected from:

[Structures: substituted phenyl with $R^{8f}$, $R^{8a}$, $R^{8b}$; pyridyl with $R^{8g}$, $R^{8c}$; pyridazinyl with $R^{8d}$; pyrazinyl with $R^{8e}$]

and wherein * indicates the point of attachment of said group to the —NH— of formula (I);

$R^{8a}$ represents hydrogen, hydroxy, halogen, or $C_1$-$C_2$-alkyl;

$R^{8b}$ represents hydrogen, hydroxy, halogen, or $C_1$-$C_2$-alkyl;

$R^{8c}$ represents hydrogen, hydroxy, halogen, or $C_1$-$C_2$-alkyl;

$R^{8d}$ represents hydrogen, hydroxy, halogen, or $C_1$-$C_2$-alkyl;

$R^{8e}$ represents hydrogen, hydroxy, halogen, or $C_1$-$C_2$-alkyl;

$R^{8f}$ represents hydrogen, hydroxy, halogen, or $C_1$-$C_2$-alkyl;
$R^{8g}$ represents hydrogen or halogen;
$R^9$ represents $C_1$-$C_3$-alkyl or cyclopropyl;
$R^{9a}$ represents $C_1$-$C_3$-alkyl or cyclopropyl;
$R^{13a}$ represents hydrogen or $C_1$-$C_2$-alkyl, wherein said $C_1$-$C_2$-alkyl is independently optionally substituted, one or more times, with halogen and
$R^{13b}$ represents hydrogen or $C_1$-$C_2$-alkyl, wherein said $C_1$-$C_2$-alkyl is independently optionally substituted, one or more times, with halogen, or
$R^{13a}$ and $R^{13b}$, together with the carbon atom to which they are attached, form a $C_3$-$C_5$-cycloalkyl ring;
$R^{14}$ represents hydrogen, methyl or ethyl; and
$R^{15}$ represents hydrogen or methyl and
$R^{16}$ represents methyl, ethyl, methoxyethyl, or dimethylaminoethyl, or
$R^{15}$ and $R^{16}$, together with the nitrogen atom to which they are attached, represent a 5- to 6-membered heterocyclic ring, wherein said heterocyclic ring optionally contains one or two further heteroatoms selected from N, O, and S;
or an N-oxide, a salt, a tautomer, or a stereoisomer of said compound, or a salt of said N-oxide, tautomer, or stereoisomer.

3. The compound of formula (I) according to claim 1, wherein:
$R^1$ represents hydrogen or a group selected from $C_1$-$C_2$-alkyl, cyclopropyl, and cyclopropylmethyl, wherein said $C_1$-$C_2$-alkyl is independently optionally substituted, one or more times, with halogen;
$R^{2a}$ represents hydrogen;
$R^{2b}$ represents hydrogen;
$R^{2c}$ represents hydrogen;
X represents methylene, wherein said methylene group is independently optionally substituted, one or two times, with $R^3$;
Y represents phenyl, wherein said phenyl is independently optionally substituted, one or two times, with $R^4$;
$R^3$ represents $C_1$-$C_3$-alkyl, $C_1$-$C_3$-haloalkyl, $R^5O$—$C_1$-$C_3$-alkyl, or $R^6R^7N$—$C_1$-$C_3$-alkyl;
$R^4$ represents halogen, $C_1$-$C_4$-alkyl, $C_1$-$C_4$-haloalkyl, —$NMe_2$, —$CO_2R^{14}$, —$CONR^{15}R^{16}$, or —$SO_2Me$;
$R^5$ represents hydrogen;
$R^6$ represents hydrogen or $C_1$-$C_2$-alkyl and
$R^7$ represents hydrogen, $C_1$-$C_2$-alkyl, or —$CO_2$-tert-butyl, or
$R^6$ and $R^7$, together with the nitrogen atom to which they are attached, represent a 4- to 6-membered heterocyclic ring, wherein said heterocyclic ring optionally contains further heteroatoms selected from N, O, and S, and is independently optionally substituted, one or more times, with halogen, $C_1$-$C_3$-alkyl, —$NH_2$, —$NHR^9$, or —$NR^9R^{9a}$;
A represents a group selected from:

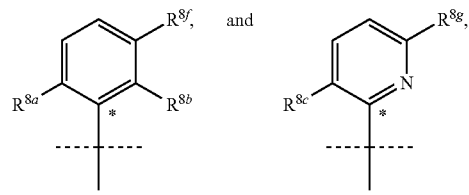

wherein * indicates the point of attachment of said group to the —NH— of formula (I);
$R^{8a}$ represents hydrogen, hydroxy, halogen, or $C_1$-$C_2$-alkyl;
$R^{8b}$ represents hydrogen, hydroxy, halogen, or $C_1$-$C_2$-alkyl;
$R^{8c}$ represents hydrogen, hydroxy, halogen, or $C_1$-$C_2$-alkyl;
$R^{8f}$ represents hydrogen or halogen;
$R^{8g}$ represents hydrogen or halogen;
$R^9$ represents $C_1$-$C_3$-alkyl;
$R^{9a}$ represents $C_1$-$C_3$-alkyl;
$R^{13a}$ represents hydrogen or methyl, wherein said methyl is independently optionally substituted, one or more times, with halogen and
$R^{13b}$ represents hydrogen or methyl, wherein said methyl is independently optionally substituted, one or more times, with halogen, or
$R^{13a}$ and $R^{13b}$, together with the carbon atom to which they are attached, form a $C_3$-$C_4$-cycloalkyl ring;
$R^{14}$ represents methyl; and
$R^{15}$ represents hydrogen and
$R^{16}$ represents methoxyethyl or dimethylaminoethyl, or
$R^{15}$ and $R^{16}$, together with the nitrogen atom to which they are attached, represent a 6-membered heterocyclic ring, wherein said heterocyclic ring optionally contains one or two further heteroatoms selected from N and O;
or an N-oxide, a salt, a tautomer, or a stereoisomer of said compound, or a salt of said N-oxide, tautomer, or stereoisomer.

4. The compound of formula (I) according to claim 1, which is selected from:
N-[4-(3-anilino-5-methyl-4-oxo-4,5,6,7-tetrahydro-1H-pyrrolo[3,2-c]pyridin-2-yl)pyridin-2-yl]-2-(4-fluorophenyl)acetamide,
N-[4-(3-anilino-5-methyl-4-oxo-4,5,6,7-tetrahydro-1H-pyrrolo[3,2-c]pyridin-2-yl)pyridin-2-yl]-2-phenylacetamide,
N-[4-(3-anilino-5-methyl-4-oxo-4,5,6,7-tetrahydro-1H-pyrrolo[3,2-c]pyridin-2-yl)pyridin-2-yl]-2-(4-fluoro-3-methylphenyl)acetamide,
N-[4-(3-anilino-5-methyl-4-oxo-4,5,6,7-tetrahydro-1H-pyrrolo[3,2-c]pyridin-2-yl)pyridin-2-yl]-2-(4-fluorophenyl)propanamide,
(2S)-N-[4-(3-anilino-5-methyl-4-oxo-4,5,6,7-tetrahydro-1H-pyrrolo[3,2-c]pyridin-2-yl)pyridin-2-yl]-2-(4-fluorophenyl)propanamide,
(2R)-N-[4-(3-anilino-5-methyl-4-oxo-4,5,6,7-tetrahydro-1H-pyrrolo[3,2-c]pyridin-2-yl)pyridin-2-yl]-2-(4-fluorophenyl)propanamide,
N-[4-(3-anilino-5-cyclopropyl-4-oxo-4,5,6,7-tetrahydro-1H-pyrrolo[3,2-c]pyridin-2-yl)pyridin-2-y1]-2-(4-fluorophenyl)acetamide,
(N-[4-(3-anilino-5-cyclopropyl-4-oxo-4,5,6,7-tetrahydro-1H-pyrrolo[3,2-c]pyridin-2-yl)pyridin-2-yl]-2-(4-fluorophenyl)propanamide,
N-[4-(3-anilino-4-oxo-4,5,6,7-tetrahydro-1H-pyrrolo[3,2-c]pyridin-2-yl)pyridin-2-yl]-2-(4-fluorophenyl)propanamide,
(2S)-N-[4-(3-anilino-4-oxo-4,5,6,7-tetrahydro-1H-pyrrolo[3,2-c]pyridin-2-yl)pyridin-2-yl]-2-(4-fluorophenyl)propanamide,
(2R)-N-[4-(3-anilino-4-oxo-4,5,6,7-tetrahydro-1H-pyrrolo[3,2-c]pyridin-2-yl)pyridin-2-yl]-2-(4-fluorophenyl)propanamide, 2-(4-fluorophenyl)-N-(4-{5-methyl-4-oxo-3-[(pyridin-2-yl)amino]-4,5,6,7-tetrahydro-1H-pyrrolo[3,2-c]pyridin-2-yl}pyridin-2-yl)acetamide, N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)acetamide, N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)propanamide, (2R)-N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)propanamide, (2S)-N-{4-[3-(2-chloroanilino)-4-oxo-4,5,6,7-tetrahydro-1H-pyrrolo[3,2-c]pyridin-2-yl]pyridin-2-yl}-2-(4-fluorophenyl)propanamide, N-[4-(3-anilino-5-methyl-4-oxo-4,5,6,7-tetrahydro-1H-pyrrolo[3,2-c]pyridin-2-yl)pyridin-2-yl]-2-(4-fluorophenyl)-3-hydroxypropanamide, (2R)-N-[4-(3-anilino-5-methyl-4-oxo-4,5,6,7-tetrahydro-1H-pyrrolo[3,2-c]pyridin-2-yl)pyridin-2-yl]-2-(4-fluorophenyl)-3-hydroxypropanamide, (2S)-N-[4-(3-anilino-5-methyl-4-oxo-4,5,6,7-tetrahydro-1H-pyrrolo[3,2-c]pyridin-2-yl)pyridin-2-yl]-2-(4-fluorophenyl)-3-hydroxypropanamide, N-{4-[3-anilino-5-(cyclopropylmethyl)-4-oxo-4,5,6,7-tetrahydro-1H-pyrrolo[3,2-c]pyridin-2-yl]pyridin-2-yl}-2-(4-fluorophenyl)acetamide, N-[4-(3-anilino-5-ethyl-4-oxo-4,5,6,7-tetrahydro-1H-pyrrolo[3,2-c]pyridin-2-yl)pyridin-2-yl]-2-(4-fluorophenyl)propanamide, N-[4-(3-anilino-6,6-dimethyl-4-oxo-4,5,6,7-tetrahydro-1H-pyrrolo[3,2-c]pyridin-2-yl)pyridin-2-y1]-2-(4-fluorophenyl)acetamide, N-{4-[3-anilino-5-(2-hydroxy-2-methylpropyl)-4-oxo-4,5,6,7-tetrahydro-1H-pyrrolo[3,2-c]pyridin-2-yl]pyridin-2-yl}-2-(4-fluorophenyl)acetamide, N-{4-[3-anilino-5-(2-hydroxy-2-methylpropyl)-4-oxo-4,5,6,7-tetrahydro-1H-pyrrolo[3,2-c]pyridin-2-yl]pyridin-2-yl}-2-(4-fluorophenyl)propanamide, (2R)-N-[4-(3-anilino-5-ethyl-4-oxo-4,5,6,7-tetrahydro-1H-pyrrolo[3,2-c]pyridin-2-yl)pyridin-2-y1]-2-(4-fluorophenyl)propanamide, (2S)-N-[4-(3-anilino-5-ethyl-4-oxo-4,5,6,7-tetrahydro-1H-pyrrolo[3,2-c]pyridin-2-yl)pyridin-2-y1]-2-(4-fluorophenyl)propanamide, N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propanamide, N-[4-(3-anilino-5-ethyl-4-oxo-4,5,6,7-tetrahydro-1H-pyrrolo[3,2-c]pyridin-2-yl)pyridin-2-yl]-2-(4-fluorophenyl)acetamide, N-{4-[3-(2-fluoroanilino)-5-methyl-4-oxo-4,5,6,7-tetrahydro-1H-pyrrolo[3,2-c]pyridin-2-yl]pyridin-2-yl}-2-(4-fluorophenyl)propanamide, N-[4-(3-anilino-5-methyl-4-oxo-4,5,6,7-tetrahydro-1H-pyrrolo[3,2-c]pyridin-2-yl)pyridin-2-yl]-4-(morpholin-4-yl)-2-phenylbutanamide, (2R)-N-[4-(3-anilino-5-methyl-4-oxo-4,5,6,7-tetrahydro-1H-pyrrolo[3,2-c]pyridin-2-yl)pyridin-2-yl]-4-(morpholin-4-yl)-2-phenylbutanamide, (2S)-N-[4-(3-anilino-5-methyl-4-oxo-4,5,6,7-tetrahydro-1H-pyrrolo[3,2-c]pyridin-2-yl)pyridin-2-yl]-4-(morpholin-4-yl)-2-phenylbutanamide, N-[4-(3-anilino-5-methyl-4-oxo-4,5,6,7-tetrahydro-1H-pyrrolo[3,2-c]pyridin-2-yl)pyridin-2-yl]-4,4-difluoro-2-phenylbutanamide, (2R)-N-[4-(3-anilino-5-methyl-4-oxo-4,5,6,7-tetrahydro-1H-pyrrolo[3,2-c]pyridin-2-yl)pyridin-2-yl]-4,4-difluoro-2-phenylbutanamide, (2S)-N-[4-(3-anilino-5-methyl-4-oxo-4,5,6,7-tetrahydro-1H-pyrrolo[3,2-c]pyridin-2-yl)pyridin-2-yl]-4,4-difluoro-2-phenylbutanamide, N-{4-[3-anilino-4-oxo-5-(2,2,2-trifluoroethyl)-4,5,6,7-tetrahydro-1H-pyrrolo[3,2-c]pyridin-2-yl]pyridin-2-yl}-2-(4-fluorophenyl)acetamide, N-{4-[3-anilino-4-oxo-5-(2,2,2-trifluoroethyl)-4,5,6,7-tetrahydro-1H-pyrrolo[3,2-c]pyridin-2-yl]pyridin-2-yl}-2-(4-fluorophenyl)propanamide, N-[4-(3-anilino-5-methyl-4-oxo-4,5,6,7-tetrahydro-1H-pyrrolo[3,2-c]pyridin-2-yl)pyridin-2-yl]-4-(dimethylamino)-2-phenylbutanamide, (2R)-N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propenamide, (2S)-N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propenamide, (2R)-N-{4-[3-(2-fluoroanilino)-5-methyl-4-oxo-4,5,6,7-tetrahydro-1H-pyrrolo[3,2-c]pyridin-2-yl]pyridin-2-yl}-2-(4-fluorophenyl)propenamide, (2S)-N-{4-[3-(2-fluoroanilino)-5-methyl-4-oxo-4,5,6,7-tetrahydro-1H-pyrrolo[3,2-c]pyridin-2-yl]pyridin-2-yl}-2-(4-fluorophenyl)propenamide, N-{4-[3-anilino-4-oxo-6-(trifluoromethyl)-4,5,6,7-tetrahydro-1H-pyrrolo[3,2-c]pyridin-2-yl]pyridin-2-yl}-2-(4-fluorophenyl)acetamide, N-[4-(3-anilino-5,6,6-trimethyl-4-oxo-4,5,6,7-tetrahydro-1H-pyrrolo[3,2-c]pyridin-2-yl)pyridin-2-yl]-2-(4-fluorophenyl)acetamide, 4,4-difluoro-N-{4-[3-(2-fluoroanilino)-5,6,6-trimethyl-4-oxo-4,5,6,7-tetrahydro-1H-pyrrolo[3,2-c]pyridin-2-yl]pyridin-2-yl}-2-(4-fluorophenyl)butanamide, (2R)-4,4-difluoro-N-{4-[3-(2-fluoroanilino)-5,6,6-trimethyl-4-oxo-4,5,6,7-tetrahydro-1H-pyrrolo[3,2-c]pyridin-2-yl]pyridin-2-yl}-2-(4-fluorophenyl)butanamide, (2S)-4,4-difluoro-N-{4-[3-(2-fluoroanilino)-5,6,6-trimethyl-4-oxo-4,5,6,7-tetrahydro-1H-pyrrolo[3,2-c]pyridin-2-yl]pyridin-2-yl}-2-(4-fluorophenyl)butanamide, N-[4-(3-anilino-6,6-dimethyl-4-oxo-4,5,6,7-tetrahydro-1H-pyrrolo[3,2-c]pyridin-2-yl)pyridin-2-y1]-4,4-difluoro-2-(4-fluorophenyl)butanamide, (2S)-N-[4-(3-anilino-6,6-dimethyl-4-oxo-4,5,6,7-tetrahydro-1H-pyrrolo[3,2-c]pyridin-2-yl)pyridin-2-yl]-4,4-difluoro-2-(4-fluorophenyl)butanamide, (2R)-N-[4-(3-anilino-6,6-dimethyl-4-oxo-4,5,6,7-tetrahydro-1H-pyrrolo[3,2-c]pyridin-2-yl)pyridin-2-yl]-4,4-difluoro-2-(4-fluorophenyl)butanamide, N-[4-(3-anilino-6,6-dimethyl-4-oxo-4,5,6,7-tetrahydro-1H-pyrrolo[3,2-c]pyridin-2-yl)pyridin-2-yl]-2-(pyridin-4-yl)acetamide, N-[4-(3-anilino-6,6-dimethyl-4-oxo-4,5,6,7-tetrahydro-1H-pyrrolo[3,2-c]pyridin-2-yl)pyridin-2-yl]-2-(pyridin-3-yl)acetamide, N-{4-[3-anilino-5-(2-methoxyethyl)-4-oxo-4,5,6,7-tetrahydro-1H-pyrrolo[3,2-c]pyridin-2-yl]pyridin-2-yl}-2-(4-fluorophenyl)acetamide, N-[4-(3'-anilino-4'-oxo-1',4',5',7'-tetrahydrospiro [cyclobutane-1,6'-pyrrolo[3,2-c]pyridin]-2'-yl)pyridin-2-yl]-4,4-difluoro-2-(4-fluorophenyl)butanamide, (2S)-N-[4-(3'-anilino-4'-oxo-1',4',5',7'-tetrahydrospiro [cyclobutane-1,6'-pyrrolo[3,2-c]pyridin]-2'-yl)pyridin-2-yl]-4,4-difluoro-2-(4-fluorophenyl)butanamide, (−)-N-[4-(3'-anilino-4'-oxo-1',4',5',7'-tetrahydrospiro [cyclobutane-1,6'-pyrrolo[3,2-c]pyridin]-2'-yl)pyridin-2-yl]-4,4-difluoro-2-(4-fluorophenyl)butanamide (Enantiomer 2), N-[4-(3'-anilino-4'-oxo-1',4',5',7'-tetrahydrospiro [cyclobutane-1,6'-pyrrolo[3,2-c]pyridin]-2'-yl)pyridin-2-yl]-2-(4-fluorophenyl)acetamide, N-[4-(3-anilino-5-methyl-4-oxo-4,5,6,7-tetrahydro-1H-pyrrolo[3,2-c]pyridin-2-yl)pyridin-2-yl]-5-(dimethylamino)-2-phenylpentanamide, (2R)-N-[4-(3-anilino-5-methyl-4-oxo-4,5,6,7-tetrahydro-1H-pyrrolo[3,2-c]pyridin-2-yl)pyridin-2-yl]-5-(dimethylamino)-2-phenylpentanamide, (2S)-N-[4-(3-anilino-5-methyl-4-oxo-4,5,6,7-tetrahydro-1H-pyrrolo[3,2-c]pyridin-2-yl)pyridin-2-yl]-5-(dimethylamino)-2-phenylpentanamide, N-[4-(3-anilino-5-methyl-4-oxo-4,5,6,7-tetrahydro-1H-pyrrolo[3,2-c]pyridin-2-yl)pyridin-2-yl]-4,4-difluoro-2-(4-fluorophenyl)butanamide, (2R)-N-[4-(3-anilino-5-methyl-4-oxo-4,5,6,7-tetrahydro-1H-pyrrolo[3,2-c]pyridin-2-yl)pyridin-2-yl]-4,4-difluoro-2-(4-fluorophenyl)butanamide, (2S)-N-[4-(3-anilino-5-methyl-4-oxo-4,5,6,7-tetrahydro-1H-pyrrolo[3,2-c]pyridin-2-yl)pyridin-2-yl]-4,4-difluoro-2-(4-fluorophenyl)butanamide, N-[4-(3-anilino-5-methyl-4-oxo-4,5,6,7-tetrahydro-1H-pyrrolo[3,2-c]pyridin-2-yl)pyridin-2-yl]-2-(pyridin-4-yl)acetamide, N-[4-(3-anilino-5-methyl-4-oxo-4,5,6,7-tetrahydro-1H-pyrrolo[3,2-c]pyridin-2-yl)pyridin-2-yl]-2-[4-(methanesulfonyl)phenyl]acetamide, N-[4-(3-anilino-5-methyl-4-oxo-4,5,6,7-tetrahydro-1H-pyrrolo[3,2-c]pyridin-2-yl)pyridin-2-yl]-2-[4-(trifluoromethyl)phenyl]acetamide, N-[4-(3-anilino-5-methyl-4-oxo-4,5,6,7-tetrahydro-1H-pyrrolo[3,2-c]pyridin-2-yl)pyridin-2-yl]-2-(pyridin-3-yl)acetamide, N-[4-(3-anilino-5-methyl-4-oxo-4,5,6,7-tetrahydro-1H-pyrrolo[3,2-c]pyridin-2-yl)pyridin-2-yl]-2-(4-methylphenyl)acetamide, N-[4-(3-anilino-5-methyl-4-oxo-4,5,6,7-tetrahydro-1H-pyrrolo[3,2-c]pyridin-2-yl)pyridin-2-yl]-2-[3-(methanesulfonyl)phenyl]acetamide, N-[4-(3-anilino-5-methyl-4-oxo-4,5,6,7-tetrahydro-1H-pyrrolo[3,2-c]pyridin-2-yl)pyridin-2-yl]-2-(3-methylphenyl)acetamide, N-[4-(3-anilino-5-methyl-4-oxo-4,5,6,7-tetrahydro-1H-pyrrolo[3,2-c]pyridin-2-yl)pyridin-2-yl]-2-(2-methylphenyl)acetamide, N-[4-(3-anilino-5-methyl-4-oxo-4,5,6,7-tetrahydro-1H-pyrrolo[3,2-c]pyridin-2-yl)pyridin-2-yl]-2-(pyridin-4-yl)propenamide, (2S)-N-[4-(3-anilino-5-methyl-4-oxo-4,5,6,7-tetrahydro-1H-pyrrolo[3,2-c]pyridin-2-yl)pyridin-2-yl]-2-(pyridin-4-yl)propenamide, (2R)-N-[4-(3-anilino-5-methyl-4-oxo-4,5,6,7-tetrahydro-1H-pyrrolo[3,2-c]pyridin-2-yl)pyridin-2-yl]-2-(pyridin-4-yl)propenamide, N-[4-(3-anilino-5-methyl-4-oxo-4,5,6,7-tetrahydro-1H-pyrrolo[3,2-c]pyridin-2-yl)pyridin-2-yl]-2-(4-fluorophenyl)butanamide, (2R)-N-[4-(3-anilino-5-methyl-4-oxo-4,5,6,7-tetrahydro-1H-pyrrolo[3,2-c]pyridin-2-yl)pyridin-2-yl]-2-(4-fluorophenyl)butanamide, (2S)-N-[4-(3-anilino-5-methyl-4-oxo-4,5,6,7-tetrahydro-1H-pyrrolo[3,2-c]pyridin-2-yl)pyridin-2-yl]-2-(4-fluorophenyl)butanamide, N-[4-(3-anilino-5-methyl-4-oxo-4,5,6,7-tetrahydro-1H-pyrrolo[3,2-c]pyridin-2-yl)pyridin-2-yl]-2-[4-(difluoromethyl)phenyl]acetamide, N-[4-(3-anilino-5-methyl-4-oxo-4,5,6,7-tetrahydro-1H-pyrrolo[3,2-c]pyridin-2-yl)pyridin-2-yl]-2-(4-chlorophenyl)propenamide, (2R)-N-[4-(3-anilino-5-methyl-4-oxo-4,5,6,7-tetrahydro-1H-pyrrolo[3,2-c]pyridin-2-yl)pyridin-2-yl]-2-(4-chlorophenyl)propenamide, (2S)-N-[4-(3-anilino-5-methyl-4-oxo-4,5,6,7-tetrahydro-1H-pyrrolo[3,2-c]pyridin-2-yl)pyridin-2-yl]-2-(4-chlorophenyl)propenamide, N-[4-(3-anilino-5-methyl-4-oxo-4,5,6,7-tetrahydro-1H-pyrrolo[3,2-c]pyridin-2-yl)pyridin-2-yl]-2-(2,4-difluorophenyl)acetamide, N-[4-(3-anilino-5-methyl-4-oxo-4,5,6,7-tetrahydro-1H-pyrrolo[3,2-c]pyridin-2-yl)pyridin-2-yl]-2-(3,4-difluorophenyl)acetamide, N-[4-(3-anilino-5-methyl-4-oxo-4,5,6,7-tetrahydro-1H-pyrrolo[3,2-c]pyridin-2-yl)pyridin-2-yl]-2-[4-(dimethylamino)phenyl]acetamide, N-[4-(3-anilino-5-methyl-4-oxo-4,5,6,7-tetrahydro-1H-pyrrolo[3,2-c]pyridin-2-yl)pyridin-2-yl]-2-(2-methylpyridin-4-yl)acetamide, N-{4-[3-(2-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide, N-{4-[3-(2-chloro-3-fluoroanilino)-4-oxo-4,5,6,7-tetrahydro-1H-pyrrolo[3,2-c]pyridin-2-yl]pyridin-2-yl}-2-(4-fluorophenyl)acetamide, N-{4-[3-anilino-5,6-dimethyl-4-oxo-4,5,6,7-tetrahydro-1H-pyrrolo[3,2-c]pyridin-2-yl]pyridin-2-y1}-2-(4-fluorophenyl)acetamide, N-{4-[(6R)-3-anilino-5,6-dimethyl-4-oxo-4,5,6,7-tetrahydro-1H-pyrrolo[3,2-c]pyridin-2-yl]pyridin-2-yl}-2-(4-fluorophenyl)acetamide, N-{4-[(6S)-3-anilino-5,6-dimethyl-4-oxo-4,5,6,7-tetrahydro-1H-pyrrolo[3,2-c]pyridin-2-yl]pyridin-2-yl}-2-(4-fluorophenyl)acetamide, (2RS)-N-{4-[(6S)-3-anilino-5,6-dimethyl-4-oxo-4,5,6,7-tetrahydro-1H-pyrrolo[3,2-c]pyridin-2-yl]pyridin-2-yl}-2-(4-fluorophenyl)propenamide, (2R)-N-{4-[(6S)-3-anilino-5,6-dimethyl-4-oxo-4,5,6,7-tetrahydro-1H-pyrrolo[3,2-c]pyridin-2-yl]pyridin-2-yl}-2-(4-fluorophenyl)propenamide, (2S)-N-{4-[(6S)-3-anilino-5,6-dimethyl-4-oxo-4,5,6,7-tetrahydro-1H-pyrrolo[3,2-c]pyridin-2-yl]pyridin-2-yl}-2-(4-fluorophenyl)propenamide, (2RS)-N-{4-[(6R)-3-anilino-5,6-dimethyl-4-oxo-4,5,6,7-tetrahydro-1H-pyrrolo[3,2-c]pyridin-2-yl]pyridin-2-yl}-2-(4-fluorophenyl)propenamide, (2R)-N-{4-[(6R)-3-anilino-5,6-dimethyl-4-oxo-4,5,6,7-tetrahydro-1H-pyrrolo[3,2-c]pyridin-2-yl]pyridin-2-yl}-2-(4-fluorophenyl)propenamide, (2S)-N-{4-[(6R)-3-anilino-5,6-dimethyl-4-oxo-4,5,6,7-tetrahydro-1H-pyrrolo[3,2-c]pyridin-2-yl]pyridin-2-yl}-2-(4-fluorophenyl)propenamide, N-{4-[3-anilino-5,6-dimethyl-4-oxo-4,5,6,7-tetrahydro-1H-pyrrolo[3,2-c]pyridin-2-yl]pyridin-2-y1}-2-(pyridin-4-yl)acetamide, N-{4-[(6R)-3-anilino-5,6-dimethyl-4-oxo-4,5,6,7-tetrahydro-1H-pyrrolo[3,2-c]pyridin-2-yl]pyridin-2-yl}-2-(pyridin-4-yl)acetamide, N-{4-[(6S)-3-anilino-5,6-dimethyl-4-oxo-4,5,6,7-tetrahydro-1H-pyrrolo[3,2-c]pyridin-2-yl]pyridin-2-yl}-2-(pyridin-4-yl)acetamide, N-{4-[3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)acetamide, N-{4-[(6R)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)acetamide, N-{4-[(6S)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)acetamide, (2RS)-4,4-difluoro-N-{4-[(6R)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide, (2S)-4,4-difluoro-N-{4-[(6R)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide, (2R)-4,4-difluoro-N-{4-[(6R)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide, (2RS)-4,4-difluoro-N-{4-[(6S)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide, (2S)-4,4-difluoro-N-{4-[(6S)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide, (2R)-4,4-difluoro-N-{4-[(6S)-3-(2-fluoroanilino)-5,6-dimethyl-4-oxo-4,5,6,7-tetrahydro-1H-pyrrolo[3,2-c]pyridin-2-yl]pyridin-2-yl}-2-(4-fluorophenyl)butanamide, N-{4-[3-(2-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl)butanamide, (2R)-N-{4-[3-(2-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl)butanamide, (2S)-N-{4-[3-(2-chloro-3-fluoroanilino)-6,6-dimethyl-4-oxo-4,5,6,7-tetrahydro-1H-pyrrolo[3,2-c]pyridin-2-yl]pyridin-2-yl}-4,4-difluoro-2-(4-fluorophenyl)butanamide, N-{4-[3-(2-chloro-3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide, N-{4-[6,6-dimethyl-3-(2-methylanilino)-4-oxo-4,5,6,7-tetrahydro-1H-pyrrolo[3,2-c]pyridin-2-yl]pyridin-2-yl}-2-(4-fluorophenyl)acetamide, N-[4-(3-anilino-5-methyl-4-oxo-4,5,6,7-tetrahydro-1H-pyrrolo[3,2-c]pyridin-2-yl)pyridin-2-yl]-2-(pyrazin-2-yl)acetamide, N-[4-(3-anilino-5-methyl-4-oxo-4,5,6,7-tetrahydro-1H-pyrrolo[3,2-c]pyridin-2-yl)pyridin-2-yl]-2-(pyridin-2-yl)acetamide, N-[4-(3-anilino-5-methyl-4-oxo-4,5,6,7-tetrahydro-1H-pyrrolo[3,2-c]pyridin-2-yl)pyridin-2-yl]-2-[3-(trifluoromethyl)phenyl]acetamide, methyl 4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoate, N-[4-(3-anilino-6,6-dimethyl-4-oxo-4,5,6,7-tetrahydro-1H-pyrrolo[3,2-c]pyridin-2-yl)pyridin-2-yl]-4,4-difluoro-2-[4-(methanesulfonyl)phenyl]butanamide, N-{4-[3-(3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide, (2S)-4,4-difluoro-N-{4-[3-(3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)butanamide, (2R)-4,4-difluoro-N-{4-[3-(3-fluoroanilino)-6,6-dimethyl-4-oxo-4,5,6,7-tetrahydro-1H-pyrrolo[3,2-c]pyridin-2-yl]pyridin-2-yl}-2-(4-fluorophenyl)butanamide, N-{4-[3'-(2-chloro-3-fluoroanilino)-4'-oxo-1',4',5',7'-tetrahydrospiro [cyclobutane-1,6'-pyrrolo[3,2-c]pyridin]-2'-yl]pyridin-2-yl}-2-(4-fluorophenyl)acetamide, N-{4-[3'-(2-chloro-3-fluoroanilino)-4'-oxo-1',4',5',7'-tetrahydrospiro [cyclobutane-1,6'-pyrrolo[3,2-c]pyridin]-2'-yl]pyridin-2-yl}-4,4-difluoro-2-(4-fluorophenyl)butanamide, (2R)-N-{4-[3'-(2-chloro-3-fluoroanilino)-4'-oxo-1',4',5',7'-tetrahydrospiro [cyclobutane-1,6'-pyrrolo[3,2-c]pyridin]-2'-yl]pyridin-2-yl}-4,4-difluoro-2-(4-fluorophenyl)butanamide, (2S)-N-{4-[3'-(2-chloro-3-fluoroanilino)-4'-oxo-1',4',5',7'-tetrahydrospiro [cyclobutane-1,6'-pyrrolo[3,2-c]pyridin]-2'-yl]pyridin-2-yl}-4,4-difluoro-2-(4-fluorophenyl)butanamide, 2-(4-fluorophenyl)-N-(4-{3-[(6-fluoropyridin-2-yl)amino]-6,6-dimethyl-4-oxo-4,5,6,7-tetrahydro-1H-pyrrolo[3,2-c]pyridin-2-yl}pyridin-2-yl)acetamide, 2-(4-fluorophenyl)-N-(4-{3-[(6-fluoropyridin-2-yl)amino]-6,6-dimethyl-4-oxo-4,5,6,7-tetrahydro-1H-pyrrolo[3,2-c]pyridin-2-yl}pyridin-2-yl)acetamide-1,1',1''-phosphoryltripyrrolidine complex, 4,4-difluoro-2-(4-fluorophenyl)-N-(4-{3-[(6-fluoropyridin-2-yl)amino]-6,6-dimethyl-4-oxo-4,5,6,7-tetrahydro-1H-pyrrolo[3,2-c]pyridin-2-yl}pyridin-2-yl)butanamide, (2S)-4,4-difluoro-2-(4-fluorophenyl)-N-(4-{3-[(6-fluoropyridin-2-yl)amino]-6,6-dimethyl-4-oxo-4,5,6,7-tetrahydro-1H-pyrrolo[3,2-c]pyridin-2-yl}pyridin-2-yl)butanamide, (2R)-4,4-difluoro-2-(4-fluorophenyl)-N-(4-{3-[(6-fluoropyridin-2-yl)amino]-6,6-dimethyl-4-oxo-4,5,6,7-tetrahydro-1H-pyrrolo[3,2-c]pyridin-2-yl}pyridin-2-yl)butanamide, N-{4-[3-(3-fluoro-2-methylanilino)-6,6-dimethyl-4-oxo-4,5,6,7-tetrahydro-1H-pyrrolo[3,2-c]pyridin-2-yl]pyridin-2-yl}-2-(4-fluorophenyl)acetamide, N-{4-[6,6-dimethyl-3-(2-methylanilino)-4-oxo-4,5,6,7-tetrahydro-1H-pyrrolo[3,2-c]pyridin-2-yl]pyridin-2-yl}-2-(4-fluorophenyl)propenamide, (2R)-N-{4-[6,6-dimethyl-3-(2-methylanilino)-4-oxo-4,5,6,7-tetrahydro-1H-pyrrolo[3,2-c]pyridin-2-yl]pyridin-2-yl}-2-(4-fluorophenyl)propenamide, (2S)-N-{4-[6,6-dimethyl-3-(2-methylanilino)-4-oxo-4,5,6,7-tetrahydro-1H-pyrrolo[3,2-c]pyridin-2-yl]pyridin-2-yl}-2-(4-fluorophenyl)propenamide, N-{4-[6,6-dimethyl-3-(2-methylanilino)-4-oxo-4,5,6,7-tetrahydro-1H-pyrrolo[3,2-c]pyridin-2-yl]pyridin-2-yl}-4,4-difluoro-2-(4-fluorophenyl)butanamide, (2R)-N-{4-[6,6-dimethyl-3-(2-methylanilino)-4-oxo-4,5,6,7-tetrahydro-1H-pyrrolo[3,2-c]pyridin-2-yl]pyridin-2-yl}-4,4-difluoro-2-(4-fluorophenyl)butanamide, (2S)-N-{4-[6,6-dimethyl-3-(2-methylanilino)-4-oxo-4,5,6,7-tetrahydro-1H-pyrrolo[3,2-c]pyridin-2-yl]pyridin-2-yl}-4,4-difluoro-2-(4-fluorophenyl)butanamide, tert-butyl [3-{[4-(3-anilino-6,6-dimethyl-4-oxo-4,5,6,7-tetrahydro-1H-pyrrolo[3,2-c]pyridin-2-yl)pyridin-2-yl]amino}-2-(4-fluorophenyl)-3-oxopropyl]carbamate, 3-amino-N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propanamide-hydrogen chloride salt, (2R)-3-amino-N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propenamide, (2S)-3-amino-N-[4-(3-anilino-6,6-dimethyl-4-oxo-4,5,6,7-tetrahydro-1H-pyrrolo[3,2-c]pyridin-2-yl)pyridin-2-yl]-2-(4-fluorophenyl)propenamide, 2-(4-fluorophenyl)-N-{4-[3'-(2-methylanilino)-4'-oxo-1',4',5',7'-tetrahydrospiro [cyclobutane-1,6'-pyrrolo[3,2-c]pyridin]-2'-yl]pyridin-2-yl}acetamide, 4,4-difluoro-2-(4-fluorophenyl)-N-{4-[3'-(2-methylanilino)-4'-oxo-1',4',5',7'-tetrahydrospiro [cyclobutane-1,6'-pyrrolo[3,2-c]pyridin]-2'-yl]pyridin-2-yl}butanamide, (2R)-4,4-difluoro-2-(4-fluorophenyl)-N-{4-[3'-(2-methylanilino)-4'-oxo-1',4',5',7'-tetrahydrospiro [cyclobutane-1,6'-pyrrolo[3,2-c]pyridin]-2'-yl]pyridin-2-yl}butanamide, (2R)-4,4-difluoro-2-(4-fluorophenyl)-N-{4-[3'-(2-methylanilino)-4'-oxo-1',4',5',7'-tetrahydrospiro [cyclobutane-1,6'-pyrrolo[3,2-c]pyridin]-2'-yl]pyridin-2-yl}butanamide, N-[4-(3'-anilino-4'-oxo-1',4',5',7'-tetrahydrospiro [cyclopropane-1,6'-pyrrolo[3,2-c]pyridin]-2'-yl)pyridin-2-yl]-2-(4-fluorophenyl)acetamide, N-[4-(3'-anilino-4'-oxo-1',4',5',7'-tetrahydrospiro [cyclopropane-1,6'-pyrrolo[3,2-c]pyridin]-2'-yl)pyridin-2-yl]-4,4-difluoro-2-(4-fluorophenyl)butanamide, (2R)-N-[4-(3'-anilino-4'-oxo-1',4',5',7'-tetrahydrospiro [cyclopropane-1,6'-pyrrolo[3,2-c]pyridin]-2'-yl)pyridin-2-yl]-4,4-difluoro-2-(4-fluorophenyl)butanamide, (2S)-N-[4-(3'-anilino-4'-oxo-1',4',5',7'-tetrahydrospiro [cyclopropane-1,6'-pyrrolo[3,2-c]pyridin]-2'-yl)pyridin-2-yl]-4,4-difluoro-2-(4-fluorophenyl)butanamide, N-{4-[3-(2,5-difluoroanilino)-5-methyl-4-oxo-4,5,6,7-tetrahydro-1H-pyrrolo[3,2-c]pyridin-2-yl]pyridin-2-yl}-2-(4-fluorophenyl)acetamide, 4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)benzoic acid, 4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)-N-(2-methoxyethyl)benzamide, N-[4-(3-anilino-5-methyl-4-oxo-4,5,6,7-tetrahydro-1H-pyrrolo[3,2-c]pyridin-2-yl)pyridin-2-yl]-2-[4-(piperazine-1-carbonyl)phenyl]acetamide, N-{4-[3-(2,3-difluoroanilino)-5-methyl-4-oxo-4,5,6,7-tetrahydro-1H-pyrrolo[3,2-c]pyridin-2-yl]pyridin-2-yl}-2-(4-fluorophenyl)acetamide formamide salt, 4-(2-{[4-(3-anilino-5-methyl-4-oxo-4,5,6,7-tetrahydro-1H-pyrrolo[3,2-c]pyridin-2-yl)pyridin-2-yl]amino}-2-oxoethyl)-N-[2-(dimethylamino)ethyl]benzamide, N-[4-(3'-anilino-5'-methyl-4'-oxo-1',4',5',7'-tetrahydrospiro [cyclobutane-1,6'-pyrrolo[3,2-c]pyridin]-2'-yl)pyridin-2-yl]-2-(4-fluorophenyl)acetamide, N-[4-(3'-anilino-5'-methyl-4'-oxo-1',4',5',7'-tetrahydrospiro [cyclobutane-1,6'-pyrrolo[3,2-c]pyridin]-2'-yl)pyridin-2-yl]-2-(4-fluorophenyl)propenamide, (2R)-N-[4-(3'-anilino-5'-methyl-4'-oxo-1',4',5',7'-tetrahydrospiro [cyclobutane-1,6'-pyrrolo[3,2-c]pyridin]-2'-yl)pyridin-2-yl]-2-(4-fluorophenyl)propenamide, (2S)-N-[4-(3'-anilino-5'-methyl-4'-oxo-1',4',5',7'-tetrahydrospiro [cyclobutane-1,6'-pyrrolo[3,2-c]pyridin]-2'-yl)pyridin-2-yl]-2-(4-fluorophenyl)propenamide, N-[4-(3'-anilino-5'-methyl-4'-oxo-1',4',5',7'-tetrahydrospiro [cyclobutane-1,6'-pyrrolo[3,2-c]pyridin]-2'-yl)pyridin-2-yl]-4,4-difluoro-2-(4-fluorophenyl)butanamide, (2R)-N-[4-(3'-anilino-5'-methyl-4'-oxo-1',4',5',7'-tetrahydrospiro [cyclobutane-1,6'-pyrrolo[3,2-c]pyridin]-2'-yl)pyridin-2-yl]-4,4-difluoro-2-(4-fluorophenyl)butanamide, (2S)-N-[4-(3'-anilino-5'-methyl-4'-oxo-1',4',5',7'-tetrahydrospiro [cyclobutane-1,6'-pyrrolo[3,2-c]pyridin]-2'-yl)pyridin-2-yl]-4,4-difluoro-2-(4-fluorophenyl)butanamide, N-[4-(3'-anilino-5'-methyl-4'-oxo-1',4',5',7'-tetrahydrospiro [cyclopropane-1,6'-pyrrolo[3,2-c]pyridin]-2'-yl)pyridin-2-yl]-4,4-difluoro-2-(4-fluorophenyl)butanamide, and N-[4-(3-anilino-5-methyl-4-oxo-4,5,6,7-tetrahydro-1H-pyrrolo[3,2-c]pyridin-2-yl)pyridin-2-yl]-2-(2,4,6-trifluorophenyl)acetamide;

or an N-oxide, a salt, a tautomer, or a stereoisomer of said compound, or a salt of said N-oxide, tautomer, or stereoisomer.

5. A method of preparing a compound of general formula (I) according to claim 1, said method comprising reacting an intermediate compound of general formula (1-3), or a salt thereof:

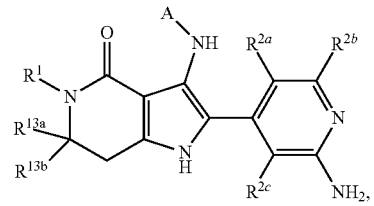

1-3 wherein $R^1$, $R^{2a}$, $R^{2b}$, $R^{2c}$, $R^{13a}$, $R^{13b}$, and A are as defined for the compound of general formula (I) according to claim 1, with an acylating reagent selected from:

a) a carboxylic acid of formula

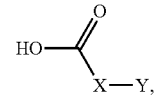

b) an acyl halide of formula

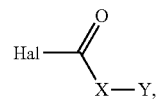

wherein Hal represents F, $C_1$, or Br, and c) an anhydride of formula

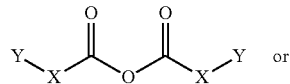 or

-continued

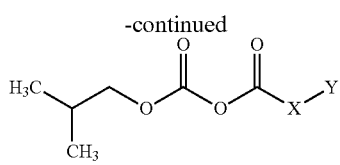

wherein X and Y are as defined for the compound of general formula (I) according to claim 1, to give a compound of general formula (I), or a salt thereof:

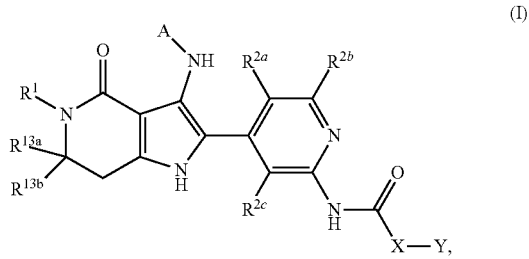

wherein $R^1$, $R^{2a}$, $R^{2b}$, $R^{2c}$, $R^{13a}$, $R^{13b}$, A, X, and Y are as defined for the compound of general formula (I) according to claim 1.

6. A method of treating a hyperproliferative disease selected from lymphoma, lung cancer, a colon tumor, and metastases thereof in a subject, comprising administering a compound according to claim 1 to the subject.

7. The method according to claim 6, wherein the hyperproliferative disease is selected from a lymphoma and metastases thereof.

8. The method according to claim 7, wherein the lymphoma is selected from diffuse large B-cell lymphoma and metastases thereof.

9. The method according to claim 6, wherein the hyperproliferative disease is selected from a lung tumour, a colon tumour, and metastases thereof.

10. The method according to claim 9, wherein the lung tumour is selected from a lung carcinoma and metastases thereof.

11. The method according to claim 9, wherein the colon tumour is selected from a colorectal carcinoma and metastases thereof.

12. A pharmaceutical composition comprising at least one compound of general formula (I) according to claim 1, together with at least one pharmaceutically acceptable auxiliary.

13. A method of treating a hyperproliferative disease selected from lymphoma, lung cancer, a colon tumor and metastases thereof in a subject, comprising administering a composition according to claim 12.

14. A combination comprising one or more first active ingredients selected from a compound of general formula (I) according to claim 1, and one or more second active ingredients selected from chemotherapeutic anti-cancer agents and target-specific anti-cancer agents.

15. An intermediate compound of general formula (1-3), or a salt thereof:

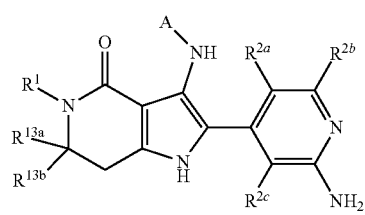

wherein $R^1$, $R^{2a}$, $R^{2b}$, $R^{2c}$, $R^{13a}$, $R^{13b}$, and A are as defined for the compound of general formula (I) according to claim 1, with the proviso that $R^1$ is not hydrogen or methyl.

* * * * *

UNITED STATES PATENT AND TRADEMARK OFFICE
CERTIFICATE OF CORRECTION

| | | |
|---|---|---|
| PATENT NO. | : 12,227,501 B2 | Page 1 of 1 |
| APPLICATION NO. | : 17/428730 | |
| DATED | : February 18, 2025 | |
| INVENTOR(S) | : Volker Schulze et al. | |

It is certified that error appears in the above-identified patent and that said Letters Patent is hereby corrected as shown below:

In the Claims

At Column 338, Claim number 5, Line number 60, please cancel the following text:
"wherein Hal represents F, $C_1$, or Br, and"
And insert the following:
--wherein Hal represents F, Cl, or Br, and--

Signed and Sealed this
Eleventh Day of November, 2025

John A. Squires
*Director of the United States Patent and Trademark Office*